(12) United States Patent
Du et al.

(10) Patent No.: US 8,785,468 B2
(45) Date of Patent: Jul. 22, 2014

(54) PHENYLALANINE AMIDE DERIVATIVES USEFUL FOR TREATING INSULIN-RELATED DISEASES AND CONDITIONS

(75) Inventors: Xiaohui Du, Belmont, CA (US); Zice Fu, Foster City, CA (US); Jonathan B. Houze, San Mateo, CA (US); XianYun Jiao, Belmont, CA (US); Yong-Jae Kim, Foster City, CA (US); Leping Li, Burlingame, CA (US); Jinqian Liu, Palo Alto, CA (US); Mike Elias Lizarzaburu, Pacifica, CA (US); Julio C. Medina, San Carlos, CA (US); Wang Shen, San Mateo, CA (US); Simon Turcotte, San Francisco, CA (US); Ming Yu, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 156 days.

(21) Appl. No.: 13/148,296

(22) PCT Filed: Feb. 12, 2010

(86) PCT No.: PCT/US2010/023988
§ 371 (c)(1),
(2), (4) Date: Jan. 24, 2012

(87) PCT Pub. No.: WO2010/093849
PCT Pub. Date: Aug. 19, 2010

(65) Prior Publication Data
US 2012/0115811 A1    May 10, 2012

Related U.S. Application Data

(60) Provisional application No. 61/152,647, filed on Feb. 13, 2009.

(51) Int. Cl.
*C07D 401/04*    (2006.01)
*A61K 31/444*    (2006.01)

(52) U.S. Cl.
USPC ........... 514/275; 514/256; 514/333; 514/336; 514/341; 514/342; 514/365; 544/332; 546/256; 546/268.7; 546/269.7; 546/270.4; 546/275.4; 546/204

(58) Field of Classification Search
None
See application file for complete search history.

(56) References Cited

FOREIGN PATENT DOCUMENTS

WO    WO 03/097047 A1    11/2003
WO    WO 2004/041813 A1    5/2004

OTHER PUBLICATIONS

Koopman, et al., "Changes in age at diagnosis of type 2 diabetes mellitus in the United States, 1988 to 2000," *Ann Fam Med*, 2005: 3:60-63.
Hoyt, et al., "Discovery of a novel class of benzazepinone . . . neuropathic pain," *Bioorganic & Medicinal Chemistry Letters* 17, (2007) 4630-4634.

*Primary Examiner* — Zinna Northington Davis
(74) *Attorney, Agent, or Firm* — Olga Mekhovich

(57) ABSTRACT

Provided herein are compounds of formula I: wherein A, B, X, $R^1$, $R^2$ and subscript n are as defined in the following disclosure. Compositions comprising the compounds are also provided, as well as methods for their use, for example, in treatment of type 2 diabetes and type 2 diabetes-related conditions.

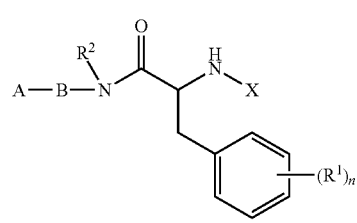

9 Claims, 6 Drawing Sheets

Mouse Islet Insulin secretion

Mouse Islet Insulin Secretion

Figure 1:
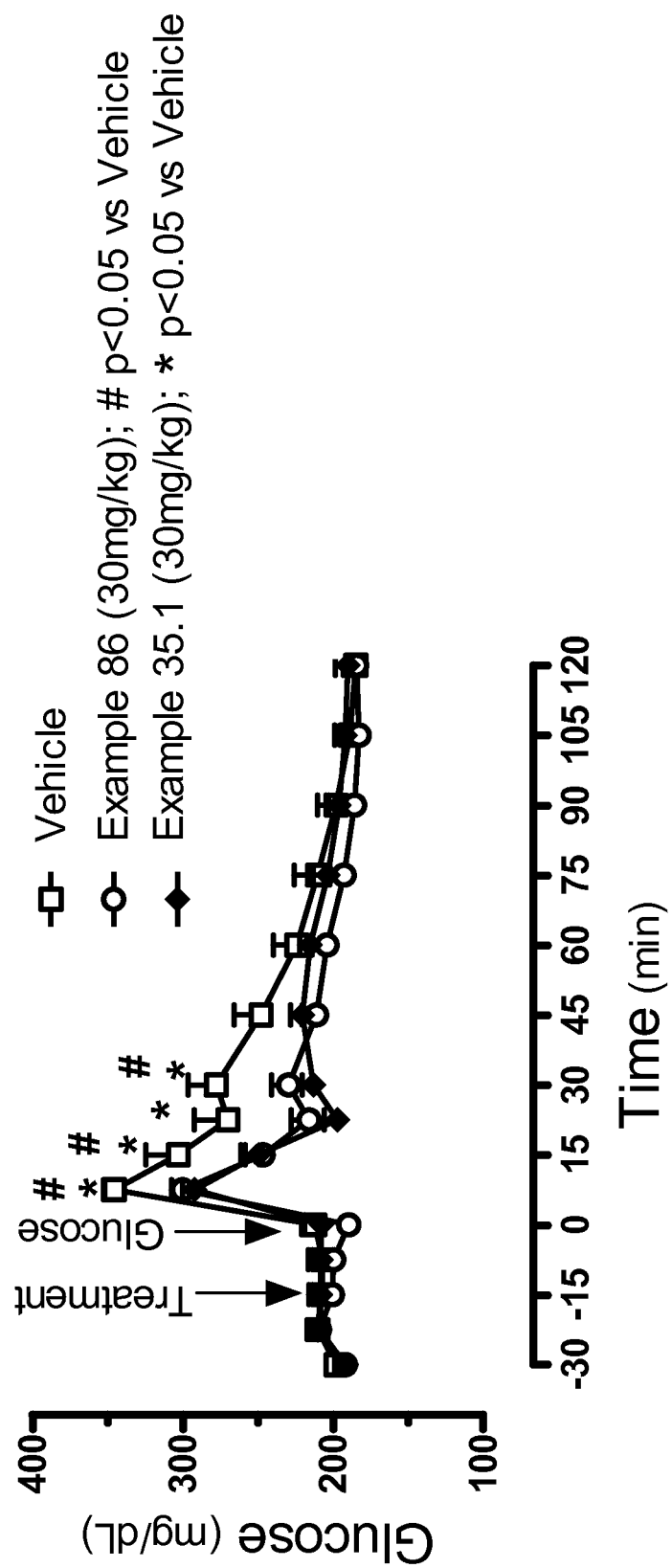

PHENYLALANINE AMIDE DERIVATIVES USEFUL FOR TREATING INSULIN-RELATED DISEASES AND CONDITIONS

1. CONTINUING DATA

This application is a 371 application of PCT/US2010/023988 filed Feb. 12, 2010 which claims the benefit of U.S. Provisional Application No. 61/152,647, filed Feb. 13, 2009, the content of which is hereby incorporated by reference in its entirety.

2. TECHNICAL FIELD

The present invention is directed to compounds, compositions and methods useful for treating insulin related diseases and conditions associated with insufficient insulin production, including diabetes and especially type 2 diabetes and type 2 diabetes-related conditions or symptoms thereof.

3. BACKGROUND

Type 2 diabetes is the most common form of diabetes, a condition in which the amount of glucose in the blood of a subject is not regulated properly. Diabetes can result when the body no longer responds adequately to insulin or when the production of insulin is inadequate. An estimated 135 million people worldwide are affected by type 2 diabetes. The number of Americans diagnosed with type 2 diabetes is estimated to range between 11.6 million to 14 million people. Although onset of type 2 diabetes is primarily observed in people over 40 years of age, the typical age at diagnosis of type 2 diabetes has decreased over the last decades as increasing numbers of youths and young adults have been affected. See Koopman et al., 2005, *Ann. Fam. Med.* 3:60-63.

Contributing factors to the rising incidence of type 2 diabetes include obesity and increasingly sedentary lifestyles. It is also recognized that insulin secretagogue therapy is appropriate for type 2 diabetes management when diet and lifestyle modifications fail. Typically, secretagogue therapy is intended to augment circulating insulin levels in patients with a moderate degree of β-cell dysfunction. Sulfonylureas, which stimulate insulin secretion and reduce hyperglycemia, have been used as insulin secretagogues when administered to patients with type 2 diabetes. Nevertheless, the long plasma half-life and the long-lasting effect of some sulfonylureas increase the risk of hypoglycemia, and new candidate insulin secretagogues are sought.

Therapies for treating type 2 diabetes and type 2 diabetes-related conditions or symptoms are sought because the prevalence of type 2 diabetes is increasing. Novel compounds that display desirable activity for treating type 2 diabetes and type 2 diabetes related conditions or symptoms are described herein.

4. SUMMARY

Provided herein are compounds, pharmaceutical compositions and methods useful for treating a disease or condition associated with insufficient insulin production, for instance, type 2 diabetes and type 2 diabetes-related diseases or conditions including diabetic ketoacidosis, hyperglycemia and diabetic neuropathy and related conditions or disorders such as obesity and metabolic syndrome; a disease or condition associated with inflammation, such as, for example, asthma, psoriasis, arthritis, rheumatoid arthritis, and inflammatory bowel disease; a disease or condition including cancer or neurologic disorder; or a symptom of any of the foregoing diseases or conditions.

In one aspect, the invention provides compounds of formula I:

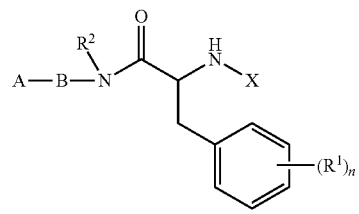

wherein A, B, X, $R^1$, $R^2$ and subscript n are as follows.

A is aryl, heteroaryl or heterocyclyl, each of which is optionally substituted.

B is cycloalkyl, heterocyclyl, aryl or heteroaryl, each of which is optionally substituted.

X is selected from hydrogen and -L-Z, where L is optionally substituted alkylene, and Z is amino, carboxy, optionally substituted alkyl, optionally substituted alkoxy, optionally substituted alkylamino, optionally substituted dialkylamino, optionally substituted cycloalkylamino, optionally substituted cycloalkyl, optionally substituted heterocyclyl, optionally substituted heteroaryl, —C(O)$OR^5$ or —C(O)$NR^9R^{10}$. In embodiments where Z is —C(O)$OR^5$, $R^5$ is hydrogen or ($C_1$-$C_5$)alkyl. In embodiments where Z is —C(O)$NR^9R^{10}$, $R^9$ and $R^{10}$ are independently selected from hydrogen and ($C_1$-$C_5$)alkyl, or optionally $R^9$ and $R^{10}$ together with the nitrogen atom to which $R^9$ and $R^{10}$ are attached form a 5-membered ring.

Each $R^1$ is independently halo.

Subscript n is 0, 1, 2 or 3.

$R^2$ is H, ($C_1$-$C_3$)alkyl, or, optionally, $R^2$ is a divalent radical that, together with two atoms adjacent to each other in ring B and the nitrogen atom to which $R^2$ is attached, forms a 5-membered ring fused to ring B, for example, as represented in formula II below.

In some embodiments, provided herein are compounds of formula II:

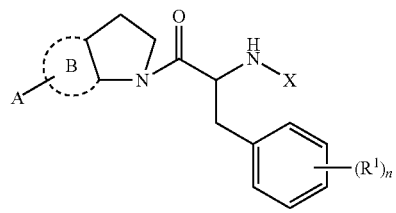

wherein A, ring B, X, $R^2$ and subscript n are as defined above in formula I.

In some embodiments, provided herein are compounds of formula IV:

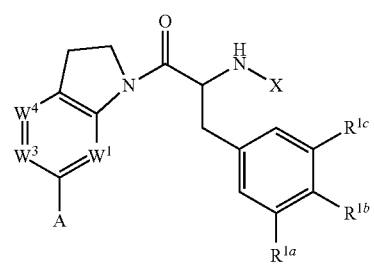

wherein A and X are as defined above with regard to formula I.

In formula IV, $R^{1a}$, $R^{1b}$ and $R^{1c}$ are each independently selected from —H, —Cl and —F; $W^1$ is —N= or —CH=; and $W^3$ and $W^4$ are each independently selected from —N= and —C($R^8$)=, where $R^8$ is selected from the group consisting of hydrogen, acyl, amino, carboxy, carboxyalkyl, halo, hydroxy, hydroxyalkyl, monosubstituted amino, optionally substituted ($C_1$-$C_5$)alkyl, optionally substituted ($C_1$-$C_5$)alkylamino, optionally substituted ($C_1$-$C_5$)alkoxy, optionally substituted heteroaryl, optionally substituted halo($C_1$-$C_5$)alkyl, optionally substituted heterocyclyl, and optionally substituted heterocyclylalkyl.

In other embodiments, provided herein are compounds of formula V:

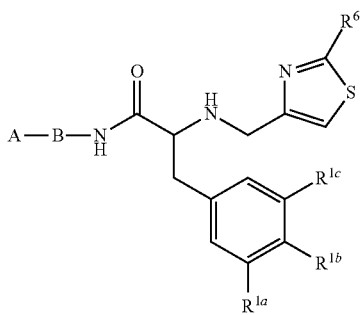

V wherein A and B are as defined above with regard to formula I.

In formula V, $R^{1a}$, $R^{1b}$ and $R^{1c}$ are each independently selected from —H, —Cl and —F; and $R^6$ is selected from amino or ($C_1$-$C_5$)alkyl.

In certain embodiments, provided herein are compounds of formula VI:

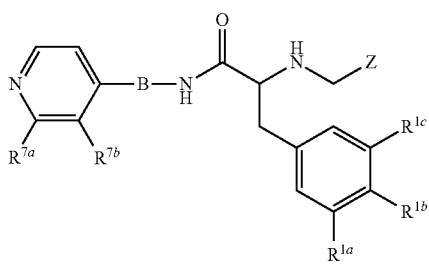

VI wherein B and Z are as defined with regard to formula I above.

In formula VI, $R^{1a}$, $R^{1b}$, $R^{1c}$ and $R^{7b}$ are each independently selected from —H, —Cl and —F; and $R^{7a}$ is selected from the group consisting of amino, monosubstituted amino, halo and optionally substituted ($C_1$-$C_5$)alkyl.

In certain embodiments, provided herein are compounds of formula VII:

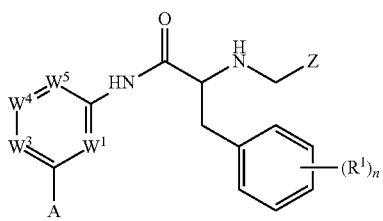

VII wherein A, Z, $R^1$ and subscript n are as defined above with regard to formula I.

In formula VII, $W^1$ is —N= or —CH=; and $W^3$, $W^4$ and $W^5$ are each independently selected from —N= and —C($R^8$)=, where $R^8$ is selected from the group consisting of hydrogen, acyl, amino, carboxy, carboxyalkyl, halo, hydroxy, hydroxyalkyl, monosubstituted amino, optionally substituted ($C_1$-$C_5$)alkyl, optionally substituted ($C_1$-$C_5$)alkylamino, optionally substituted ($C_1$-$C_5$)alkoxy, optionally substituted heteroaryl, optionally substituted halo($C_1$-$C_5$)alkyl, optionally substituted heterocyclyl and optionally substituted heterocyclylalkyl.

In yet other embodiments, provided herein are compounds of formula VIII:

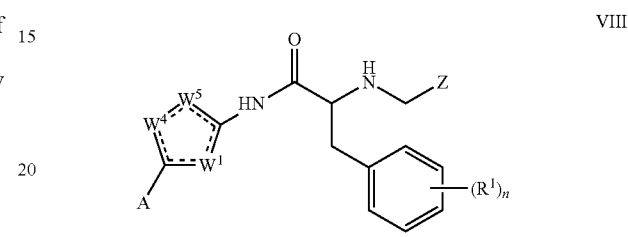

VIII wherein A, Z, $R^1$ and subscript n are as defined above with regard to formula I.

In formula VIII, $W^1$ selected from the group consisting of —CH=, —N=, —NH—, —O— and —S—.

$W^4$ and $W^5$ are independently selected from —C($R^8$)=, —C(O)—, —N=, —N($R^8$)—, —O— and —S—, where $R^8$ is selected from the group consisting of hydrogen, acyl, amino, carboxy, carboxyalkyl, halo, hydroxy, hydroxyalkyl, monosubstituted amino, optionally substituted ($C_1$-$C_5$)alkyl, optionally substituted ($C_1$-$C_5$)alkylamino, optionally substituted ($C_1$-$C_5$)alkoxy, optionally substituted heteroaryl, optionally substituted halo($C_1$-$C_5$)alkyl, optionally substituted heterocyclyl and optionally substituted heterocyclylalkyl.

In formula VIII, each ═ bond is a single bond or a double bond.

In certain embodiments, the group represented by

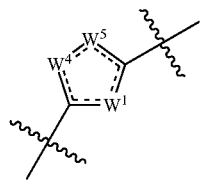

in formula VIII is aromatic. In other embodiments, the group represented by

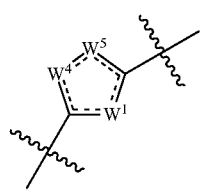

in formula VIII is not aromatic.

In another aspect, pharmaceutical compositions are provided herein comprising a compound of any one of formula I-VIII and a pharmaceutically acceptable carrier, excipient or diluent.

In one aspect, compounds of any one of formula I-VIII are provided for use in treatment of a disease or condition, or symptom thereof.

In yet another aspect, compounds of any one of formula I-VIII are provided for the manufacture of a medicament for the treatment of type 2 diabetes, diabetic ketoacidosis, hyperglycemia, diabetic neuropathy, obesity, metabolic syndrome, inflammation, asthma, psoriasis, arthritis, rheumatoid arthritis and/or inflammatory bowel disease.

In one aspect, methods are provided for treating a disease or condition in a subject in need thereof, comprising administering a therapeutically effective amount of a compound of any one of formula I-VIII to the subject. In certain embodiments, the disease or condition to be treated is type 2 diabetes, diabetic ketoacidosis, hyperglycemia, diabetic neuropathy, obesity, metabolic syndrome, inflammation, inflammatory disorders including asthma, psoriasis, arthritis, rheumatoid arthritis, and inflammatory bowel disease, cancer, neurologic disorder, or a symptom thereof. The methods include the treatment of a human. In certain embodiments, the subject, e.g., human, has the disease or condition.

In some embodiments of the methods provided, the compound is administered in combination with a second therapeutic agent useful for treating type 2 diabetes, diabetic ketoacidosis, hyperglycemia, diabetic neuropathy, or a symptom thereof.

In another aspect, methods are provided comprising administering an amount of a compound of any one of formula I-VIII to a subject wherein the amount of the compound is effective to a) reduce food intake; b) lower plasma glucagon; c) reduce gastric motility or delay gastric emptying; or d) stimulate insulin release in the subject in need thereof.

In yet another aspect, provided herein are methods for modulating insulin concentration in plasma in a subject, comprising administering an amount of a compound of any one of formula I-VIII to the subject to modulate insulin concentration in the subject's plasma. In certain embodiments, the methods are for increasing insulin concentration in plasma. In certain embodiments, the subject, e.g., human, is in need of increased plasma insulin concentrations. In some embodiments the subject, e.g., human, has low circulating insulin concentrations (e.g., equal to or less than 50-75 pmol/L), for instance, after consuming carbohydrates and/or starches.

In another aspect, methods are provided for modulating secretion by a pancreatic β-cell, in vitro or in vivo, comprising contacting the pancreatic β-cell with an amount of a compound of any one of formula I-VIII effective to modulate the pancreatic islet cell secretion under conditions wherein the pancreatic β-cell secretion is modulated.

Other objects, features and advantages of the invention will become apparent to those skilled in the art from the following description and claims.

5. BRIEF DESCRIPTION OF THE FIGURES

FIG. 1 provides results from glucose-challenged animal models demonstrating the decreases in blood glucose levels in animals treated with exemplary compound 35.1 or 86 relative to vehicle-treated control animals.

Figure 2:
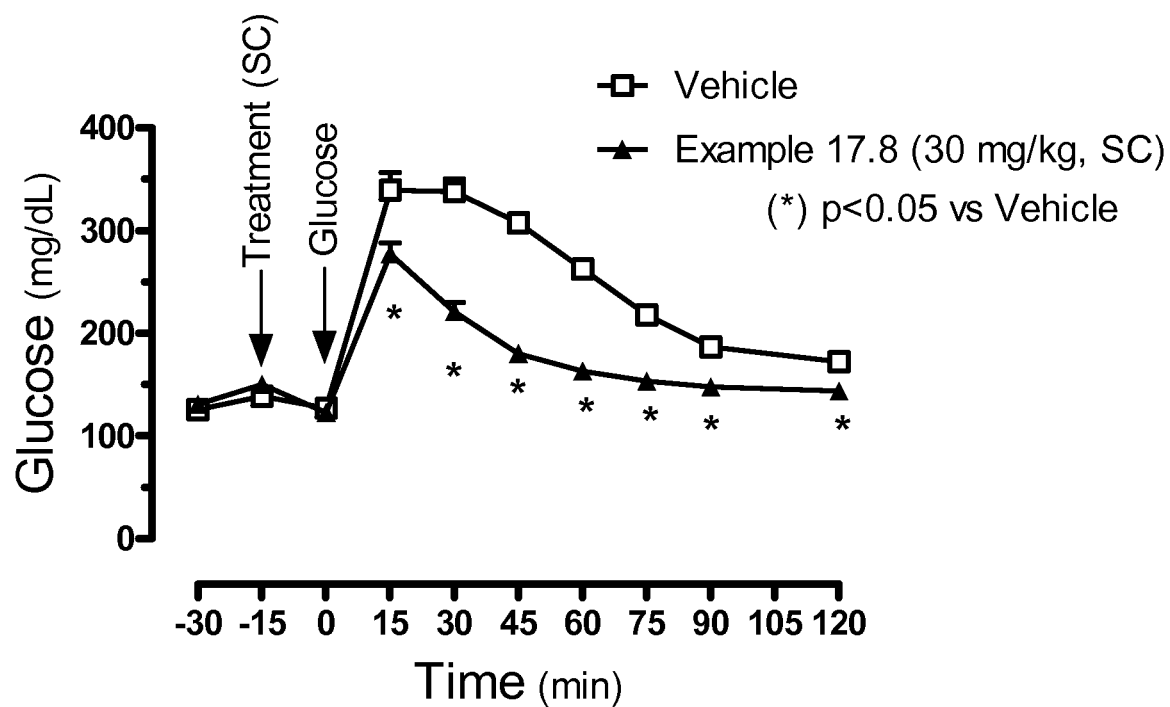

FIG. 2 provides results from glucose-challenged animal models demonstrating the decreases in blood glucose levels in animals treated with exemplary compound 17.8 relative to vehicle-treated control animals.

Figure 3:
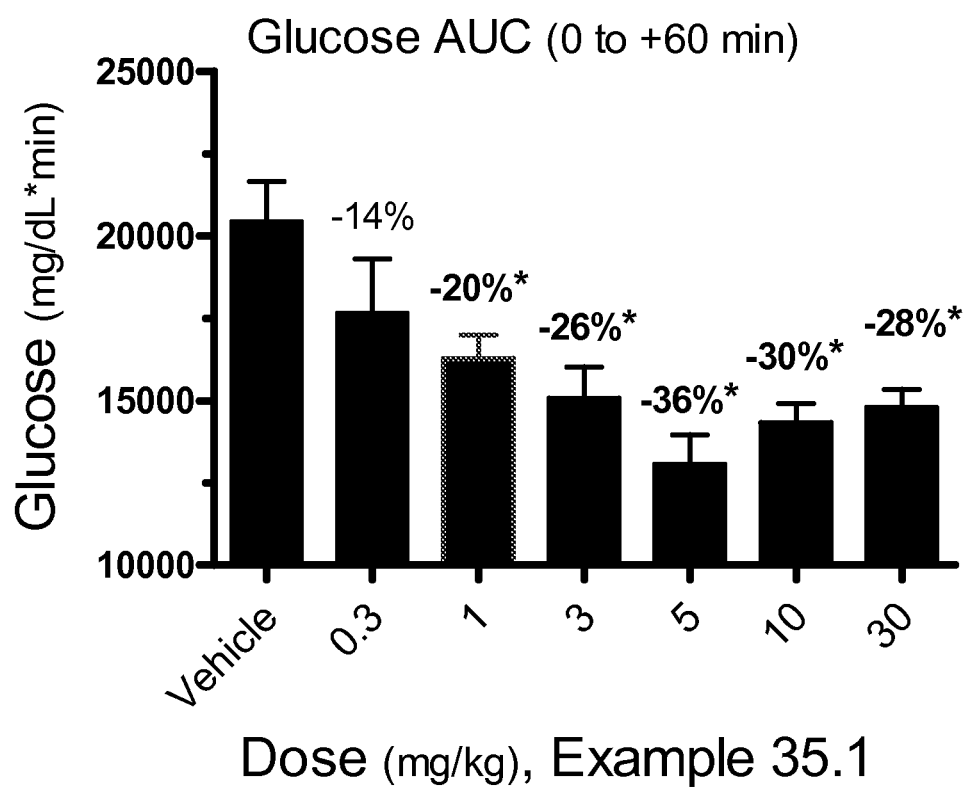

FIG. 3 provides results from glucose-challenged animal models demonstrating decreases in blood glucose levels in animals treated with 0.3, 1, 3, 5, 10 or 30 mg/kg exemplary compound 35.1 as compared to control animals.

Figure 4:
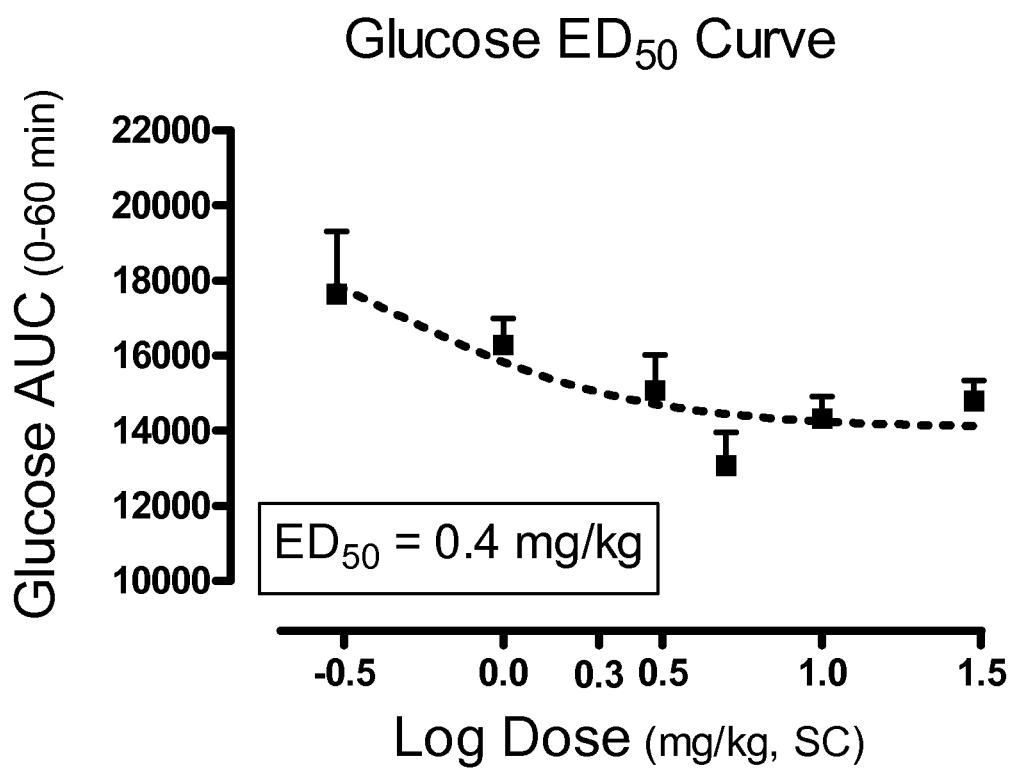

FIG. 4 provides a plot of the data represented in FIG. 3 for the $ED_{50}$ determination of the glucose lowering efficacy of compound 35.1.

Figure 5:
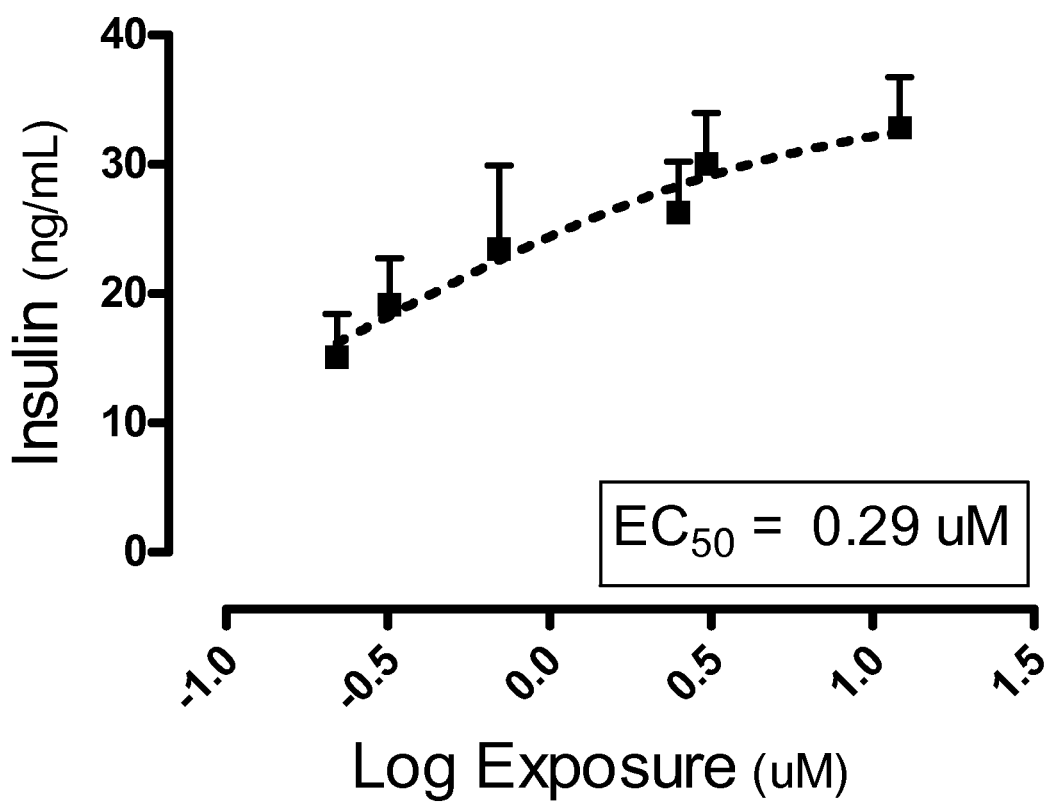

FIG. 5 provides results demonstrating that treating glucose-challenged mice with increasing amounts of exemplary compound 35.1 results in increasing amounts of blood insulin concentrations.

Figure 6A:
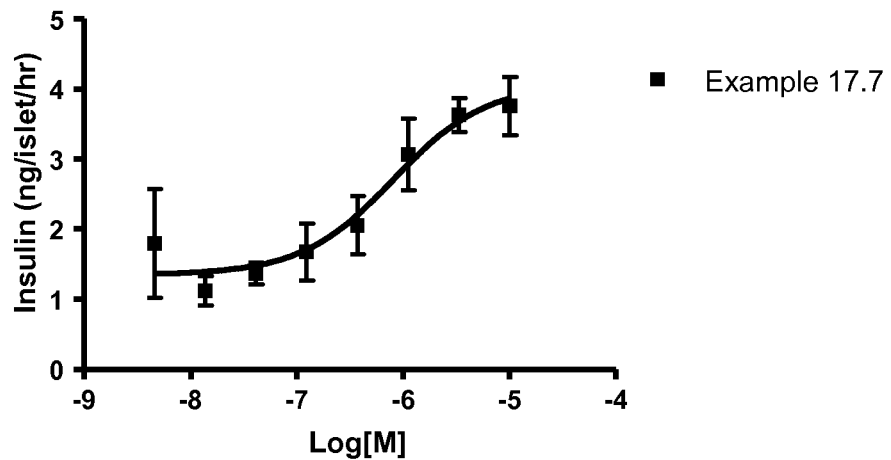
Figure 6B:
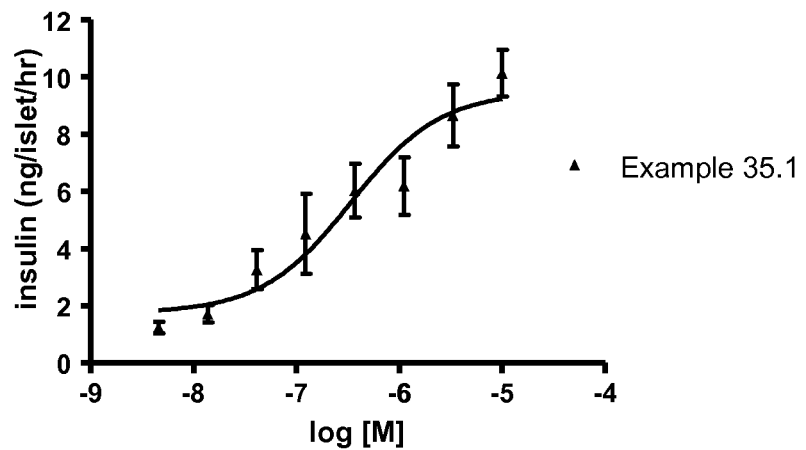

FIG. 6 provides results from mouse islet insulin secretion assays demonstrating that exemplary compound 17.7 (FIG. 6A) and 35.1 (FIG. 6B) increase secretion of insulin from mouse islets.

6. DETAILED DESCRIPTION

6.1 Terminology

Unless otherwise stated, the following terms used in the specification and claims are defined for the purposes of this application and have the following meanings.

Abbreviations used herein include the following: Boc, tert-butyl formate; DIPEA, N,N-diisopropylethylamine; DMF, dimethylformamide; GIP, gastric inhibitory peptide; HBTU, o-benzotriazole-N,N,N',N'-tetramethyl-uronium-hexafluoro-phosphate; $IP_3$, inositol trisphosphate.

"Alkyl" means, if not otherwise indicated, a linear saturated monovalent hydrocarbon radical of one to eight carbon atoms or a branched saturated monovalent hydrocarbon radical of three to eight carbon atoms. Exemplary alkyl groups include, for instance, methyl, ethyl, propyl, isopropyl, n-butyl, sec-butyl, isobutyl, tert-butyl, pentyl (including all isomeric forms) and hexyl (including all isomeric forms).

"Alkylene" means a linear saturated divalent hydrocarbon radical of one to eight carbon atoms or a branched saturated divalent hydrocarbon radical of three to eight carbon atoms, unless otherwise stated. Exemplary alkylene groups include, for instance, methylene, ethylene, propylene, 1-methylpropylene, 2-methylpropylene, butylene, pentylene, and the like.

"Alkenyl" means, unless otherwise indicated, a linear monovalent hydrocarbon radical of two to eight carbon atoms or a branched monovalent hydrocarbon radical of three to eight carbon atoms containing at least one double bond, e.g., ethenyl, propenyl, 2-propenyl, and the like.

"Acyl" means a —C(O)R radical, where R is alkyl, haloalkyl, cycloalkyl, cycloalkylalkyl, aryl, heteroaryl or heterocyclyl, each as defined herein. Exemplary acyl groups include, for instance, acetyl, propionyl, benzoyl, pyridinyl-carbonyl, and the like. When R in a —C(O)R radical is alkyl, the radical is also referred to herein as "alkylcarbonyl."

"Alkoxy" means an —OR radical, where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to eight carbon atoms or a branched monovalent hydrocarbon radical of three to eight carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Amidoalkyl" means a linear monovalent hydrocarbon radical of one to eight carbon atoms or a branched monovalent hydrocarbon radical of three to eight carbons substituted with a —C(O)NHR radical, where R is hydrogen or alkyl as defined above.

"Amino" means an —$NH_2$ radical. The term "monosubstituted amino" means an —NHR radical, and the term "disubstituted amino" means an —NRR' radical, where R and R' are independently alkyl, acyl, alkoxyalkyl, aminoalkyl, aryl, cycloalkyl, cycloalkylalkyl, dimethylaminoalkyl, haloalkyl, heterocyclyl, heterocyclylalkyl, hydroxyalkyl, methylaminoalkyl or sulfonyl, where such terms are as defined herein. When R is alkyl in a monosubstituted amino, the group is also termed an "alkylamino." Exemplary monosubstituted amino groups include, for instance, methylamino, ethylamino, hydroxyethylamino, and the like. Exemplary disubstituted amino groups include, for instance, dimethylamino, N-phenyl-N-methylamino, and the like.

"Aminoalkyl" means a linear monovalent hydrocarbon radical of one to eight carbon atoms or a branched monovalent hydrocarbon radical of three to eight carbons substituted with at least one amino, monosubstituted amino or disubstituted amino group, as each are defined above. Representative aminoalkyl groups include, for example, aminomethyl, methylaminoethyl, 2-ethylamino-2-methylethyl, 1,3-diaminopropyl, dimethylaminomethyl, diethylaminoethyl, acetylaminopropyl, and the like.

"Aryl" means a monocyclic or bicyclic polyunsaturated, typically aromatic, hydrocarbon radical of 6 to 12 ring atoms. Exemplary aryl groups include, for instance, phenyl or naphthyl. The term "heteroaryl" refers to aryl groups (or rings) in which one to four ring atoms are heteroatoms independently selected from the group consisting of N, O and S, wherein the nitrogen and sulfur atoms are optionally oxidized, and the nitrogen atom(s) are optionally quaternized. A heteroaryl can be attached to the remainder of a molecule through a heteroatom. Exemplary heteroaryl groups include, for instance, benzofuranyl, benzo[d]thiazolyl, furanyl, imidazolyl, isoquinolinyl, isoxazolyl, oxazolyl, oxadiazolyl, pyranyl, pyrazinyl, pyrazolyl, pyridinyl, pyrimidinyl, pyrrolyl, quinolinyl, tetrazolyl, thiadiazolyl, thiazolyl, thienyl, triazolyl, and the like.

"Carboxy" means —COOH.

"Carboxyalkyl" means a linear monovalent hydrocarbon radical of one to eight carbon atoms or a branched monovalent hydrocarbon radical of three to eight carbons substituted with at least one —COOR or —OC(O)R group, where R is hydrogen, alkyl, haloalkyl or hydroxyalkyl, as defined herein. Examples include, for instance, —$CH_2C(O)OC(CH_3)_3$, carboxymethyl, 2-carboxyethyl, —$CH_2CH_2OC(O)CH_2C(CH_3)_2$, and the like.

"Cycloalkyl," as used herein, means a saturated or partially unsaturated monocyclic hydrocarbon radical of three to eight carbon atoms, e.g., cyclopropyl, cyclobutyl, cyclopentyl, cyclohexyl, cyclohexenyl, and the like. The term "heterocyclyl" means cycloalkyl group in which one or two ring atoms are heteroatoms independently selected from N, O, S, S(O) and $S(O)_2$, the remaining ring atoms being carbon. Additionally, a heteroatom in a heterocyclyl group can occupy the position at which the heterocycle is attached to the remainder of the molecule. The term "heterocyclyl" includes, but is not limited to azetidinyl, 4,5-dihydro-1,3,4-oxadiazolyl, homopiperidinyl, imidazolidine, morpholinyl, piperazinyl, piperidinyl, pyranyl, pyrrolidinyl, tetrahydrofuranyl, tetrahydropyranyl, 1,2,5,6-tetrahydropyridyl, tetrahydrothienyl, thiomorpholino, and the like. When the cycloalkyl or heterocyclyl is unsaturated it can contain one or two ring double bonds, provided that the ring is not aromatic.

"Cycloalkylalkyl," means a linear monovalent hydrocarbon radical of one to eight carbon atoms or a branched monovalent hydrocarbon radical of three to eight carbons substituted with a cycloalkyl group as defined above. Exemplary cycloalkylalkyl groups include cyclopropylmethyl, 2-cyclopentylethyl, and the like.

"Halo" means fluoro, chloro, bromo, and iodo, preferably fluoro or chloro.

"Haloalkyl" means alkyl substituted with one or more halogen atoms, preferably one to five halogen atoms, preferably fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the halo atom is fluoro, it also referred to herein as fluoroalkyl.

"Heterocyclylalkyl," means a linear monovalent hydrocarbon radical of one to eight carbon atoms or a branched monovalent hydrocarbon radical of three to eight carbons substituted with a heterocyclyl group as defined above. Exemplary cycloalkylalkyl groups include azetidinylmethyl, pyrrolidinylethyl, and the like.

As used herein, the term "heteroatom" is meant to include oxygen (O), nitrogen (N), sulfur (S) and silicon (Si).

"Hydrogen" means —H.

"Hydroxy" means —OH.

"Hydroxyalkyl" means a linear monovalent hydrocarbon radical of one to eight carbon atoms or a branched monovalent hydrocarbon radical of three to eight carbons substituted with one or two hydroxy groups, provided that, if two hydroxy groups are present, they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, and the like.

As used herein, when the phrase "optionally substituted" is used in connection with "alkyl," "alkylene," "alkenyl," "aryl," "cycloalkyl," "cycloalkylalkyl," "heteroaryl," "heterocyclyl," "heterocyclylalkyl" or with specific examples of "alkyl," "alkylene," "alkenyl," "aryl," "cycloalkyl," "cycloalkylalkyl," "heteroaryl," "heterocyclyl" and "heterocyclylalkyl" provided herein, or with the alkyl portions of groups such as "acyl," "alkoxy," "alkoxyalkyl," "alkylamino," "aminoalkyl," "carboxyalkyl," "haloalkyl," "hydroxyalkyl" and "sulfonyl," as defined herein, it is meant that both substituted and unsubstituted forms of the indicated radical are included. Exemplary substituents for these groups are varied and are independently selected from —CN, —C(O)R', —$CO_2R'$, —C(O)NR'R", -halo, —$NO_2$, =NR', —NR'C($NH_2$)=NR", —NR'—C(O)NR"R''', —NR'C(O)R", —NR'C(O)OR", NR'R", —NR'S(O)$_2$R", =O, —OC(O)NR'R", —OC(O)R', —OR', —R', =S, —S(O)R', —S(O)$_2$R', —S(O)$_2$NR'R" and —SR', in a number ranging from zero to three, with those groups having zero, one or two substituents being particularly preferred. R', R" and R''' each independently refer to hydrogen, alkyl, amidoalkyl, aminoalkyl, aryl, carboxyalkyl, cycloalkyl, cycloalkylalkyl, haloalkyl, heteroaryl, heterocyclyl (optionally substituted with =O, =S, methyl, methoxy or —$NHCH_3$), heterocyclylalkyl (optionally substituted with =O, =S, methyl, methoxy or —$NHCH_3$) or hydroxyalkyl.

"Oxo" means the =O group.

"Sulfonyl" means a —$SO_2R$ radical, where R is alkyl, haloalkyl, aryl, heteroaryl, heterocyclyl, or heterocyclylalkyl, each as defined above, e.g., methylsulfonyl, phenylsulfonyl, benzylsulfonyl, pyridinylsulfonyl, and the like.

The terms "modulate," "modulation," and the like, when used in reference to a cell, e.g., a pancreatic β-cell or a cell made using recombinant technology, refer to the ability of a compound to increase or decrease the function of the cell leading to increased concentrations of insulin produced and/or secreted by a cell, where such function may include transcription regulatory activity, exocytosis, cell membrane excitability and/or protein binding. Modulation may occur in vitro or in vivo.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "therapeutically effective amount" refers to the amount of the subject compound that will elicit the biological or medical response of a cell, tissue, organ, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the disease or condition being treated, or to alleviate or ameliorate the disease or cause thereof. The therapeutically effective amount will vary depending on the compound, the disease and its severity and the age, weight, etc., of the mammal to be treated.

The terms "treat", "treating" and "treatment", as used herein, are meant to include alleviating or abrogating a disease and/or its attendant symptoms and/or alleviating or eradicating the cause of the disease itself.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al., 1977, *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The term "substantially pure" as used in connection with a isomer of a compound provided herein, such as, for example, a stereoisomer, enantiomer or diasteriomer, means that the compound comprises greater than about 70%, 75%, 80%, 85%, 90%, 93%, 95% or 97% by weight of one isomer. As used herein and unless otherwise indicated, the term "isolated" used in connection with a isomer of a compound provided herein, such as, for example, a stereoisomer, enantiomer or diasteriomer, means that the compound is in a form in which only one isomer is detectable using conventional techniques (e.g., NMR, polarimetry, chromatography, chiral resolution, etc.).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). As another example, the compounds provided herein can, for instance, be prepared to incorporate stable isotopes such as $^2H$ or $^{13}C$. All isotopic variations of the compounds of the invention, whether radioactive or not, are intended to be encompassed within the scope of the invention.

6.2 Embodiments

Provided herein are compounds that have utility as modulators of insulin levels. As such, the compounds find use as therapeutic agents for the treatment of type 2 diabetes and related conditions or symptoms thereof including diabetic ketoacidosis, hyperglycemia, diabetic neuropathy, obesity, metabolic syndrome, as well as a number of other uses described herein or apparent to those skilled in the art. In certain embodiments, the compounds provided herein can be used as therapeutic agents for the treatment of a disease or condition associated with inflammation, such as, for example, asthma, psoriasis, arthritis, rheumatoid arthritis, and inflammatory bowel disease; a disease or condition including cancer or neurologic disorder; or a symptom of any of the foregoing diseases or conditions.

Compounds contemplated by the invention include, but are not limited to, the exemplary compounds provided herein.

6.2.1 Compounds

In one aspect, provided herein are compounds of formula I:

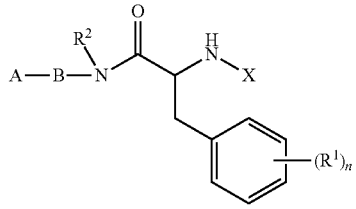

I wherein A, B, X, $R^1$, $R^2$ and subscript n are defined below.

A is aryl, heteroaryl or heterocyclyl, each of which is optionally substituted.

In some embodiments, A is furanyl, imidazolyl, isoxazolyl, oxazolyl, phenyl, piperidinyl, piperazinyl, pyrazolyl, pyridinyl, pyrimidinyl, pyrrolyl, thiadiazolyl, thiazolyl, thienyl and triazolyl, each of which is optionally substituted.

In certain embodiments, A is selected from the group consisting of phenyl, pyrazol-3-yl, pyrazol-4-yl, pyridine-4-yl and thiazol-5-yl, each of which is optionally substituted.

In certain embodiments, A is pyridin-2(1H)-one.

In certain embodiments, A is not substituted.

In some embodiments A is substituted. In subgroups of those embodiments where A is substituted, A can, for example, be monosubstituted, disubstituted or trisubstituted.

In some subgroups, A is substituted with one or more substituents above.

In certain subgroups, A is substituted with a substituent selected from the group consisting of amino, carboxy, halo, hydroxy, heterocyclyl, monosubstituted amino, optionally substituted ($C_1$-$C_5$)alkyl, optionally substituted ($C_1$-$C_5$)alkylamino, optionally substituted ($C_1$-$C_5$)alkoxy and optionally substituted halo($C_1$-$C_5$)alkyl.

In certain subgroups, A is substituted with amino, ethyl, fluoro, hydroxy, methyl, methylamino or methoxy.

B is cycloalkyl, heterocyclyl, aryl or heteroaryl, each of which is optionally substituted. In certain embodiments, ring B is aromatic. In other embodiments, ring B is not aromatic. In some embodiments, B is a 5- or 6-membered ring selected from cycloalkyl, heterocyclyl, aryl and heteroaryl.

In some embodiments, B is selected from the group consisting of furanyl, imidazolyl, isoxazolyl, oxazolyl, phenyl, piperidinyl, piperazinyl, pyrazolyl, pyridinyl, pyrimidinyl, pyrrolyl, thiadiazolyl, thiazolyl, thienyl and triazolyl, each of which is optionally substituted.

In some embodiments, B is a 5-membered heteroaryl or heterocyclyl, each of which is optionally substituted. Representative 5-membered B rings include, for example, 1,3,4-thiadiazolyl, 4H-1,2,4-triazolyl, isoxazolyl, thiazolyl and pyrazolyl, each of which is optionally substituted.

In other embodiments, B is a 6-membered aryl or heteroaryl. Representative 6-membered B rings include, for example, pyridinyl, pyrimidinyl and phenyl, each of which is optionally substituted.

In some embodiments, B is not substituted. In other embodiments, B is substituted.

In subgroups of those embodiments where B is substituted, B can, for example, be monosubstituted, disubstituted or trisubstituted.

In some subgroups, B is substituted with one or more substituents described above.

In certain subgroups, B is substituted with a substituent selected from the group consisting of acyl, amino, carboxy, carboxyalkyl, halo, hydroxy, hydroxyalkyl, monosubstituted amino, optionally substituted ($C_1$-$C_5$)alkyl, optionally substituted ($C_1$-$C_5$)alkylamino, optionally substituted ($C_1$-$C_5$)alkoxy, optionally substituted heteroaryl, optionally substituted halo($C_1$-$C_5$)alkyl, optionally substituted heterocyclyl, optionally substituted heterocyclylalkyl and oxo.

In certain subgroups, B is substituted with a substituent selected from amino, carboxy, ethyl, fluoro, hydroxy, 2-hydroxyethyl, isopropyl, methyl, methylamino, methoxy, oxo, propyl, trifluoromethyl, trifluoroethyl, —C(CH$_3$)$_2$COOH, —CF$_2$COOH, —CH$_2$-azetidine-C(O)OCH$_3$, —CH$_2$C(O)OCH$_2$CH$_3$, —CN, —C(O)CH$_3$, —C(O)NH$_2$, —C(O)NHCH$_3$, —C(O)N(CH$_3$)$_2$, —C(O)NHCH$_2$CH$_2$N(CH$_3$)$_2$, —C(O)NHCH$_2$C(O)NH$_2$, —C(O)NHCH$_2$C(O)OCH$_3$, —C(O)NHCH$_2$CH$_2$-(2-oxo-imidazolidine), —C(O)NHCH$_2$-cyclopropane, —COOCH$_3$, —NHS(O)$_2$CH$_3$, —OCH$_2$CH$_2$N(CH$_3$)$_2$, —OCH$_2$COOCH$_3$, —OCH$_2$C(O)OC(CH$_3$)$_3$, 2-oxo-1,3,4-oxadiazol, 2-thioxo-1,3,4-oxadiazol, 5-amino-1,3,4-oxadiazol, 5-methyl-1,3,4-oxadiazol, triazole and 5-methyl-1,2,4-triazol.

X is selected from hydrogen, carboxyalkyl and -L-Z, where L and Z are defined as follows.

L is optionally substituted alkylene.

In preferred embodiments, L is a divalent radical selected from the group consisting of —C($R^3$)($R^4$)—, —CH$_2$C($R^3$)($R^4$)—, —CH$_2$C($R^3$)($R^4$)CH$_2$—, —CH$_2$CH$_2$C($R^3$)($R^4$)— and —C($R^3$)($R^4$)CH$_2$CH$_2$—, where $R^3$ and $R^4$ are independently selected from H, methyl, ethyl and hydroxyl, or optionally $R^3$ and $R^4$ together with the carbon to which both $R^3$ and $R^4$ are attached form a cyclopropyl, cyclobutyl or oxiranyl ring.

In some embodiments, L is a divalent radical selected from the group consisting of —CH$_2$—, —CH(CH$_3$)—, —C(CH$_3$)$_2$—, —CH(CH$_2$CH$_3$)—,

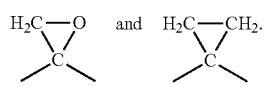

In certain embodiments, ring A is pyridin-2(1H)-one and L is cyclopropyl.

Z is amino, carboxy, optionally substituted alkyl, optionally substituted alkoxy, optionally substituted alkylamino, optionally substituted dialkylamino, optionally substituted cycloalkylamino, optionally substituted cycloalkyl, optionally substituted heterocyclyl, optionally substituted heteroaryl, —C(O)OR$^5$ or —C(O)OR$^9$R$^{10}$, wherein R$^5$ is hydrogen or optionally substituted (C$_1$-C$_5$)alkyl, and R$^9$ and R$^{10}$ are independently selected from hydrogen and optionally substituted (C$_1$-C$_5$)alkyl, or optionally R$^9$ and R$^{10}$ together with the nitrogen atom to which R$^9$ and R$^{10}$ are attached form a 5-membered ring.

In some embodiments, Z is amino, carboxy, methyl, —OCH$_2$CH$_3$, —C(O)OCH$_2$CH$_3$ or —C(O)OC(CH$_3$)$_3$.

In other embodiments, Z is cycloalkyl, heterocyclyl or heteroaryl, each of which is optionally substituted.

In certain embodiments, Z is cyclopropyl, tetrahydropyranyl, tetrahydrofuranyl, each of which is optionally substituted.

In certain embodiments, Z is pyridinyl, thiazolyl, pyrimidinyl, imidazolyl, triazolyl, pyrazolyl, oxazolyl, tetrazolyl, pyrazinyl, isooxazolyl. Within certain subgroups of these embodiments, Z can, for example, be selected from the group consisting of pyridin-2-yl, thiazol-2-yl, thiazol-4-yl, thiazol-5-yl, pyrimidin-2-yl, pyrimidin-4-yl, imidazol-2-yl, imidazol-4-yl, 1,2,3-triazol-4-yl, pyrazol-3-yl, tetrazol-5-yl, pyrazin-2-yl, 1,2,4-triazol-3-yl and isooxazol-3-yl.

In some embodiments, Z is not substituted. In other embodiments, Z is substituted.

In subgroups of those embodiments where Z is substituted, Z can, for example, be monosubstituted, disubstituted or trisubstituted.

In some subgroups, Z is substituted with one or more substituents described above.

In certain subgroups, Z is substituted with a substituent selected from the group consisting of acyl, amino, carboxy, carboxyalkyl, halo, hydroxy, hydroxyalkyl, monosubstituted amino, optionally substituted (C$_1$-C$_5$)alkyl, optionally substituted (C$_1$-C$_5$)alkoxy, optionally substituted halo(C$_1$-C$_5$)alkyl and oxo.

In certain subgroups, B is substituted with a substituent selected from amino, carboxy, ethyl, fluoro, hydroxy, 2-hydroxyethyl, isopropyl, methyl, methylamino, methoxy, oxo, propyl, trifluoromethyl or trifluoroethyl.

Returning to formula I, each R$^1$ is independently halo.
Subscript n is 0, 1, 2 or 3.
In some embodiments, subscript n=0.
In certain embodiments where subscript n=1, R$^1$ is para-fluoro. In certain embodiments where subscript n=1, R$^1$ is meta-fluoro. In certain embodiments where subscript n=2, each R$^1$ is chloro.

R$^2$ is H or (C$_1$-C$_3$)alkyl. Optionally, R$^2$ is a divalent radical with one bond attached directly to ring B which, together with adjacent ring atoms of ring B and the nitrogen to which R$^1$ is attached, forms a 5-membered ring (e.g., 2,3-dihydro-pyrrole, pyrrolidine or pyrrole) fused to ring B, as exemplified in formula II:

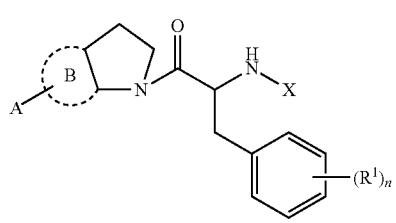

wherein A, ring B, X, R$^2$ and subscript n are as defined above.
Returning to formula I, In some embodiments, R$^2$ is H or methyl.

In those embodiments where R$^2$ forms a 5-membered fused ring with ring B, typically the B ring atoms common to both rings are carbon. In some embodiments, at least one ring atom common to both rings is a nitrogen atom.

In some embodiments where R$^2$ forms a 5-membered fused ring with ring B, ring B is a 5-membered ring. In other embodiments, ring B is a 6-membered ring.

It can be readily appreciated that certain compounds of the present disclosure exist in stereoisomers. In some embodiments, the compound of any one of formula I is a racemic compound. In some embodiments, the compound of formula I comprises a mixture of q(S) and (R) enantiomers. In some embodiments, the compound of formula I comprises a substantially pure or an isolated enantiomer. In certain embodiments, the compound of formula I comprises a mixture of diastereoisomers. In certain embodiments, the compound of formula I comprises a substantially pure or isolated diastereoisomer.

In some embodiments, the compound has the formula IIIa:

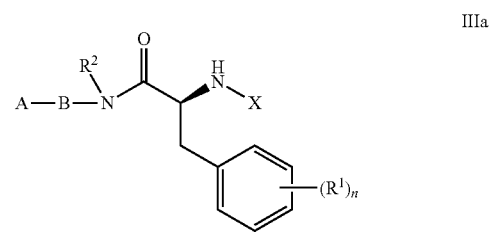

where A, B X, R', R$^2$ and subscript n are as defined above in formula I. In certain embodiments, the compound of formula IIIa is substantially pure or is isolated.

In other embodiments, the compound has the formula IIIb:

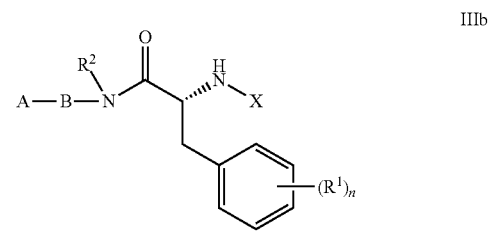

where A, B X, R$^1$, R$^2$ and subscript n are as defined above in formula I. In certain embodiments, the compound of formula IIIb is substantially pure or is isolated.

In certain embodiments, the compound provided has formula IV:

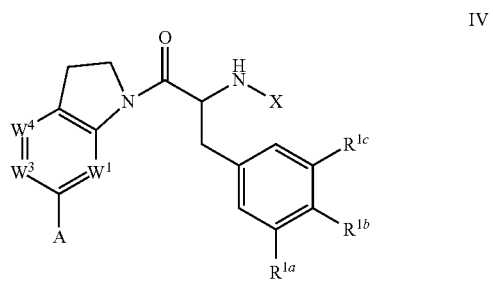

wherein A and X are as defined above with regard to formula I.

In formula IV, $R^{1a}$, $R^{1b}$ and $R^{1c}$ are each independently selected from —H, —Cl and —F.

$W^1$ is —N═ or —CH═.

$W^3$ and $W^4$ are each independently selected from —N═ and —C($R^8$)═.

$R^8$ is selected from the group consisting of hydrogen, acyl, amino, carboxy, carboxyalkyl, halo, hydroxy, hydroxyalkyl, monosubstituted amino, optionally substituted ($C_1$-$C_5$)alkyl, optionally substituted ($C_1$-$C_5$)alkylamino, optionally substituted ($C_1$-$C_5$)alkoxy, optionally substituted heteroaryl, optionally substituted halo($C_1$-$C_5$)alkyl, optionally substituted heterocyclyl and optionally substituted heterocyclylalkyl.

In certain subgroups, $R^8$ is selected from hydrogen, amino, carboxy, ethyl, fluoro, hydroxy, 2-hydroxyethyl, isopropyl, methyl, methylamino, methoxy, propyl, trifluoromethyl, trifluoroethyl, —C($CH_3$)$_2$COOH, —$CF_2$COOH, —$CH_2$-azetidine-C(O)O$CH_3$, —$CH_2$C(O)O$CH_2$$CH_3$, —CN, —C(O)$CH_3$, —C(O)$NH_2$, —C(O)NH$CH_3$, —C(O)N($CH_3$)$_2$, —C(O)NH$CH_2$$CH_2$N($CH_3$)$_2$, —C(O)NH$CH_2$C(O)$NH_2$, —C(O)NH$CH_2$C(O)O$CH_3$, —C(O)NH$CH_2$$CH_2$-(2-oxoimidazolidine), —C(O)NH$CH_2$-cyclopropane, —COO$CH_3$, —NHS(O)$_2$$CH_3$, —O$CH_2$$CH_2$N($CH_3$)$_2$, —O$CH_2$COO$CH_3$, —O$CH_2$C(O)OC($CH_3$)$_3$, 2-oxo-1,3,4-oxadiazol, 2-thioxo-1,3,4-oxadiazol, 5-amino-1,3,4-oxadiazol, 5-methyl-1,3,4-oxadiazol, triazole and 5-methyl-1,2,4-triazol.

In some embodiments of formula IV, $R^{1a}$, $R^{1b}$ and $R^{1c}$ are each —H. In other embodiments, $R^{1a}$ and $R^{1c}$ are each —H and $R^{1b}$ is —F. In yet other embodiments, $R^{1a}$ and $R^{1b}$ are each —H, and $R^{1c}$ is —F.

In certain embodiments of formula IV, one of $W^1$, $W^3$ and $W^4$ is —N═, the remainder of $W^1$, $W^3$ and $W^4$ being —CH═. In yet other embodiments, each of $W^1$, $W^3$ and $W^4$ is —CH═.

In certain embodiments, the compound provided has formula V:

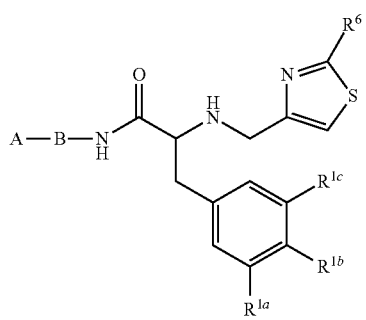

wherein A, B, $R^{1a}$, $R^{1b}$ and $R^{1c}$ are as defined above, and $R^6$ is selected from the group consisting of amino, monosubstituted amino, disubstituted amino and optionally substituted ($C_1$-$C_5$)alkyl.

In certain embodiments, provided herein is a compound of formula VI:

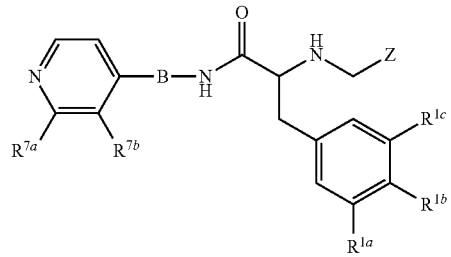

wherein B, Z, $R^{1a}$, $R^{1b}$ and $R^{1c}$ are as defined above, and $R^{7a}$ and $R^{7b}$ are as follows:

In formula VI, $R^{7a}$ is selected from the group consisting of amino, monosubstituted amino, halo and optionally substituted ($C_1$-$C_5$) alkyl.

In some embodiments, $R^{7a}$ is amino, methylamino, methyl or ethyl.

$R^{7b}$ is selected from the group consisting of —H and halo.

In certain embodiments, a compound is provided of formula VII:

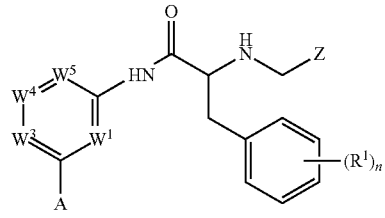

wherein A, Z, $R^1$ and subscript n are as defined above in formula I.

In formula VII, $W^1$ is —N═ or —CH═.

$W^3$, $W^4$ and $W^5$ are each independently selected from —N═ and —C($R^8$)═.

$R^8$ is selected from the group consisting of hydrogen, acyl, amino, carboxy, carboxyalkyl, halo, hydroxy, hydroxyalkyl, monosubstituted amino, optionally substituted ($C_1$-$C_5$)alkyl, optionally substituted ($C_1$-$C_5$)alkylamino, optionally substituted ($C_1$-$C_5$)alkoxy, optionally substituted heteroaryl, optionally substituted halo($C_1$-$C_5$)alkyl, optionally substituted heterocyclyl and optionally substituted heterocyclylalkyl.

In certain subgroups, $R^8$ is selected from hydrogen, amino, carboxy, ethyl, fluoro, hydroxy, 2-hydroxyethyl, isopropyl, methyl, methylamino, methoxy, propyl, trifluoromethyl, trifluoroethyl, —C($CH_3$)$_2$COOH, —$CF_2$COOH, —$CH_2$-azetidine-C(O)O$CH_3$, —$CH_2$C(O)O$CH_2$$CH_3$, —CN, —C(O)$CH_3$, —C(O)$NH_2$, —C(O)NH$CH_3$, —C(O)N($CH_3$)$_2$, —C(O)NH$CH_2$$CH_2$N($CH_3$)$_2$, —C(O)NH$CH_2$C(O)$NH_2$, —C(O)NH$CH_2$C(O)O$CH_3$, —C(O)NH$CH_2$$CH_2$-(2-oxoimidazolidine), —C(O)NH$CH_2$-cyclopropane, —COO$CH_3$, —NHS(O)$_2$$CH_3$, —O$CH_2$$CH_2$N($CH_3$)$_2$, —O$CH_2$COO$CH_3$, —O$CH_2$C(O)OC($CH_3$)$_3$, 2-oxo-1,3,4-oxadiazol, 2-thioxo-1,3,4-oxadiazol, 5-amino-1,3,4-oxadiazol, 5-methyl-1,3,4-oxadiazol, triazole and 5-methyl-1,2,4-triazol.

In certain embodiments of formula VII, one of $W^1$, $W^3$, $W^4$ and $W^5$ is —N═, the remainder of $W^1$, $W^3$, $W^4$ and $W^5$ being —CH═. In yet other embodiments, all of $W^1$, $W^3$, $W^4$ and $W^5$ are —CH═.

In some embodiments. Provided herein is a compound of formula VIII:

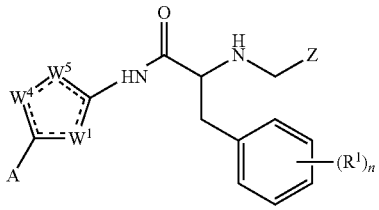

wherein A, Z, $R^1$ and subscript n are as defined above in formula I.

In formula VIII, $W^1$ is —CH═, —N═, —NH—, —O— or —S—.

$W^4$ and $W^5$ are independently selected from —C($R^8$)═, —C(O)—, —N═, —N($R^8$)—, —O— and —S—.

Each bond represented by ═══ is a single bond or a double bond according to requirements of the atoms at $W^1$, $W^4$ and $W^5$. In certain embodiments, the group represented by

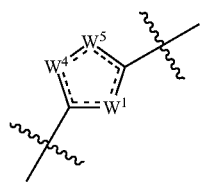

in formula VIII is aromatic. In other embodiments, the group represented by

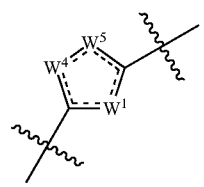

in formula VIII is not aromatic.

$R^8$ is selected from the group consisting of hydrogen, acyl, amino, carboxy, carboxyalkyl, halo, hydroxy, hydroxyalkyl, monosubstituted amino, optionally substituted ($C_1$-$C_5$)alkyl, optionally substituted ($C_1$-$C_5$)alkylamino, optionally substituted ($C_1$-$C_5$)alkoxy, optionally substituted heteroaryl, optionally substituted halo($C_1$-$C_5$)alkyl, optionally substituted heterocyclyl and optionally substituted heterocyclylalkyl.

In certain subgroups, $R^8$ is selected from hydrogen, amino, carboxy, ethyl, fluoro, hydroxy, 2-hydroxyethyl, isopropyl, methyl, methylamino, methoxy, propyl, trifluoromethyl, trifluoroethyl, —C($CH_3$)$_2$COOH, —$CF_2$COOH, —$CH_2$-azetidine-C(O)O$CH_3$, —$CH_2$C(O)O$CH_2$$CH_3$, —CN, —C(O)$CH_3$, —C(O)N$H_2$, —C(O)NH$CH_3$, —C(O)N($CH_3$)$_2$, —C(O)NH$CH_2$$CH_2$N($CH_3$)$_2$, —C(O)NH$CH_2$C(O)N$H_2$, —C(O)NH$CH_2$C(O)O$CH_3$, —C(O)NH$CH_2$$CH_2$-(2-oxo-imidazolidine), —C(O)NH$CH_2$-cyclopropane, —COO$CH_3$, —NHS(O)$_2$$CH_3$, —O$CH_2$$CH_2$N($CH_3$)$_2$, —O$CH_2$COO$CH_3$, —O$CH_2$C(O)OC($CH_3$)$_3$, 2-oxo-1,3,4-oxadiazol, 2-thioxo-1,3,4-oxadiazol, 5-amino-1,3,4-oxadiazol, 5-methyl-1,3,4-oxadiazol, triazole and 5-methyl-1,2,4-triazol.

In certain subgroups of formula VIII, $W^1$ is —S—, and $W^4$ and $W^5$ are each —N═. In some subgroups, $W^1$ is —NH—, and $W^4$ and $W^5$ are each —N═. In other subgroups, $W^1$ is —CH═, $W^4$ is —N═ and $W^5$ is —O—. In yet other subgroups, $W^1$ is —N═, $W^4$ is —S— and $W^5$ is —CH═. In some subgroups, $W^1$ is —S—, $W^4$ is —CH═ and $W^5$ is —N═. In some subgroups, $W^1$ is —CH═, and $W^4$ and $W^5$ are each —N═. In some subgroups, $W^1$ is —CH═, $W^4$ is —N═ and $W^5$ is —N($R^8$)—, where $R^8$ is ($C_1$-$C_3$)alkyl, ($C_1$-$C_3$)alkoxy, halo($C_1$-$C_3$)alkyl or hydroxy($C_1$-$C_3$)alkyl.

In certain embodiments, the compound of any one of formula IV-VIII is a racemic compound. In some embodiments, the compound of any one of formula IV-VIII comprises a mixture of (S) and (R) enantiomers. In some embodiments, the compound of any one of formula IV-VIII is in a substantially pure enantiomeric form, which can, for example, be in a (S) form or in a (R) form. In some embodiments, the compound of any one of formula IV-VIII is an isolated enantiomer. In certain embodiments, the compound of any one of formula IV-VIII comprises a mixture of diastereoisomers. In certain embodiments, the compound of any one of formula IV-VIII comprises a substantially pure or isolated diastereoisomer.

The compounds of formulas I-VIII include pharmaceutically acceptable salts, solvates or prodrugs thereof.

6.2.2 Preparation of Compounds

The compounds provided herein can be prepared by a variety of synthetic or semisynthetic techniques. Exemplary compounds of formula I can be prepared as shown in general Scheme A, where variables A, B and Z are rings as in formula I, and $R^1$ and subscript n are as defined in formula I. For example, BOC-1-phenylalanine can be coupled to an appropriately substituted amine using HBTU and DPIEA in DMF solution. Removal of the BOC protecting group under acidic conditions followed by reductive amination with the appropriate aldehyde and a mild reductant such as sodium triacetocyborohydride or sodium cyanoborohydride provides target compounds of the invention.

Scheme A

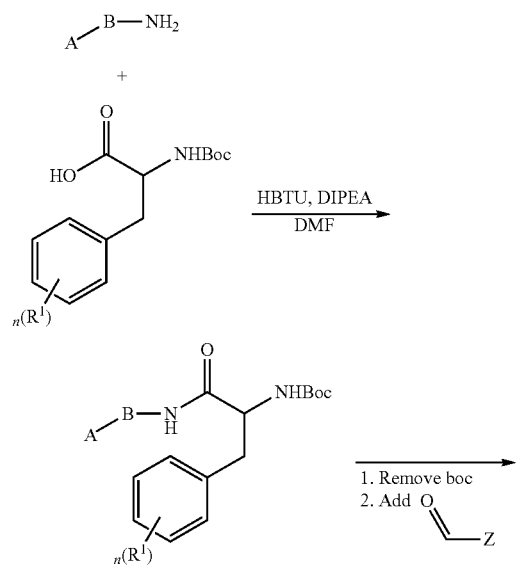

-continued

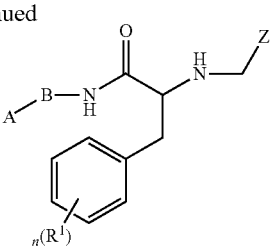

Additional exemplary synthesis routes to the compounds provided herein are described in the Examples below (see Section 7). Synthesis of appropriate starting materials can be prepared by techniques known or apparent to those of skill in the art or the starting materials may be commercially available. One of skill in the art will understand that the synthetic routes can be modified to use different starting materials and/or alternate reagents to accomplish the desired transformations, and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group. Accordingly, the methods and reagents described herein are all expressed as non-limiting embodiments.

6.2.3 Compositions

In one aspect, the invention provides pharmaceutical compositions suitable for pharmaceutical use comprising one or more compounds as provided herein and a pharmaceutically acceptable carrier, excipient or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

Formulation may improve one or more pharmacokinetic properties (e.g., oral bioavailabilty, membrane permeability) of a compound of the invention (herein referred to as the active ingredient).

The pharmaceutical compositions for the administration of the active ingredient may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form, particularly single unit dosage form, suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452 and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions can contain the active materials in an admixture with excipients suitable for the manufacture of aqueous suspensions. Such excipients include, for instance, suspending agents, dispersing or wetting agents and the like, as known to those skilled in the art. Suspending agents include, for example, sodium carboxymethylcellulose, methylcellulose, hydroxy-propylmethylcellulose, sodium alginate, polyvinyl-pyrrolidone, gum tragacanth and gum acacia. Dispersing or wetting agents can, for example, be a naturally-occurring phosphatide such as lecithin, or condensation products of an alkylene oxide with fatty acids, for example, polyoxy-ethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions can contain one or more preservatives, for example ethyl, or n-propyl, p-hydroxybenzoate, one or more coloring agents, one or more flavoring agents, and/or one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain demulcent, preservative, flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compounds of the invention are employed. As used herein, topical use is also meant to include the use of mouthwashes and gargles.

The pharmaceutical compositions and methods provided herein can further comprise other therapeutically active compounds, for example, as described in Section 6.2.4, useful in the treatment of diseases and conditions as described herein including type 2 diabetes, diabetic ketoacidosis, hyperglycemia, diabetic neuropathy, obesity, metabolic syndrome, inflammation, asthma, psoriasis, arthritis, rheumatoid arthritis, inflammatory bowel disease, cancer and neurologic disorder, or symptom thereof.

6.2.4 Methods of Use

In one aspect, methods are provided for treating a disease or condition associated with insufficient circulating insulin by administering to a subject having such a condition or disease, a therapeutically effective amount of a compound or composition of the invention. In one group of embodiments, diseases and conditions, including chronic diseases of humans or other species, can be treated with insulin secretagogoues. These diseases and conditions include type 2 diabetes, ketoacidosis, hyperglycemia and diabetic neuropathy.

In one aspect, methods are provided for treating a disease or condition, or symptom thereof, in a subject in need of treatment or prevention, comprising administering an amount of a compound or composition as provided herein effective to treat or prevent the disease or condition. In certain embodiments, the disease or condition or symptom thereof to be treated or prevented is type 2 diabetes, diabetic ketoacidosis, hyperglycemia, diabetic neuropathy, obesity, metabolic syndrome, inflammation, asthma, psoriasis, arthritis, rheumatoid arthritis, inflammatory bowel disease, cancer or neurologic disorder.

In another aspect, methods are provided comprising administering an amount of a compound of any one of formula I-VIII to a subject wherein the amount of the compound is effective to a) reduce food intake; b) lower plasma glucagon; c) reduce gastric motility or delay gastric emptying; or d) stimulate insulin release in the subject in need thereof.

In another aspect, the invention provides methods for modulating insulin concentration in plasma of a mammal, comprising administering an amount of a compound or composition as provided herein effective to modulate insulin concentration in plasma of the mammal.

In one aspect, the invention provides methods for increasing or augmenting insulin concentration in plasma of a mammal, comprising administering an amount of a compound or composition as provided herein effective to increase or augment insulin concentration in plasma of the mammal.

In certain embodiments of the methods provided, the mammal, e.g., human, is in need of increased plasma insulin concentrations. In some embodiments the mammal, e.g., human, has low circulating insulin concentrations (e.g., equal to or less than 50-75 µmol/L), for instance, after consuming carbohydrates and/or starches.

In one aspect, the invention provides methods for augmenting secretion by a pancreatic β-cell, comprising contacting the pancreatic β-cell with a composition or compound as provided herein.

In yet another aspect, the invention provides methods of treating or preventing a disease or condition responsive to insulin secretagogues, comprising administering to a subject having such a disease or condition, a therapeutically effective amount of one or more of the subject compounds or compositions.

Depending on the disease or symptom to be treated and the subject's condition, the compounds of the invention may be administered by oral, parenteral (e.g., intramuscular, intraperitoneal, intravenous, intracerebroventricular, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention of type 2 diabetes, ketoacidosis, hyperglycemia and diabetic neuropathy, or other diseases or conditions associated with insufficient circulating insulin, and diseases or conditions such as obesity, metabolic syndromes, inflammation, asthma, psoriasis, arthritis, rheumatoid arthritis, inflammatory bowel disease, cancer and neurologic disorders, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type 2 diabetes, ketoacidosis, hyperglycemia, diabetic neuropathy, obesity, metabolic syndrome, inflammation, asthma, psoriasis, arthritis, rheumatoid arthritis, inflammatory bowel disease, cancer or neurologic disorder. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

Examples of other therapeutic agents that may be combined with a compound of the invention, either administered separately or in the same pharmaceutical compositions, include, but are not limited to: sulfonylureas, for example, glibenclamide (DAONIL®), glimepiride (AMARYL®), glipizide (GLUCOTROL or MINODIAB), glyburide (MICRONASE®), and meglinitide; insulin and insulin mimetics; biguanides such as metformin (GLUCOPHAGE®); α-glucosidase inhibitors including acarbose (PRECOSE®) and miglitol (GLYSET®); meglitinides, for example, nateglinide (STARLIX®) and repaglinide (PRANDIN®); thiozolidinediones, for example, ciglitazone, englitazone, rosiglitazone (AVANDIA®), pioglitazone (ACTOS®) and troglitazone (REZULIN®); dipeptidyl-peptidase IV (DPP-IV) inhibitors, for example, sitagliptin (JANUVIA®), vildagliptin (GALVUS®), saxagliptin, denagliptin, and SYR-222; incretin mimetics such as exenatide (BYETTA™); cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin B3 (also known as nicotinic acid, or niacin), vitamin B6 (pyridoxine), vitamin B12 (cyanocobalamin), fibric acid derivatives (e.g., gemfibrozil, clofibrate, fenofibrate and benzafibrate), probucol, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat). The weight ratio of the compound of the invention to the second active ingredient may be varied and will depend upon the effective dose of each ingredient. Generally, an effective dose of each will be used. Thus, for example, when a compound of the invention is combined with a cholesterol lowering agent, the weight ratio of the compound of the invention to the cholesterol lowering agent will generally range from about 1000:1 to about 1:1000, preferably about 200:1 to about 1:200. Combinations of a compound of the invention and other active ingredients will generally also be within the aforementioned range, but in each case, an effective dose of each active ingredient should be used.

6.2.5 Assays

The antidiabetic effects of the compounds provided herein can be demonstrated using a variety of in vitro and in vivo assays including a number of animal models. Animal models for testing compounds include, for example, mouse strains in which type 2 diabetes characteristics have arisen spontaneously or were produced by selective breeding (see, e.g., Suzuki, 1999, *Exp. Anim.* 48:181-189 and citations therein; Hamada et al., 2001, *Metabolism* 50:1282-1285 (spontaneously diabetic Nagoya-Shibata-Yasuda mice); Kawano et al., 1992, *Diabetes* 41, 1422-1428 (Otsuka Long Evans Tokushima Fatty (OLETF) rats); Miura et al., 2006, *Biol. Pharm. Bull.* 29:585-587 (strain KK-Ay mice, available, for instance, from The Jackson Laboratory (Bar Harbor, Me.) (JAX® GEMM® strain mice)), or were produced by transgenic technology (see, e.g., Butler et al., 2004, *Diabetes* 53:1509-1516 (describing Human Islet Amyloid Polypeptide (HIP) rats)). Non-genetic-based or induced animal models of diabetes are also available, including, for example, animals with diet-induced diabetes (see, e.g., Leibowitz et al. 2001, *Diabetes* 50:S113-S117 (describing the gerbil Psammomys Obesus model of type 2 diabetes)), induced by a combination of high-fat diet and streptozotocin (STZ) injections or by neonatal STZ injections (see, e.g., Zhang et al., 2003, *Exp. Anim.* 52:401-407; Reed et al., 2000, *Metabolism* 49:1390-1394; Wang et al., 1996, *J. Pharmacol. Exp. Ther.* 278:82-89; Kergoat et al., 1986, *Diabete Metab.* 12:79-82; Portha et al., 1989, *Diabete Metab.* 15:61 75). Compounds can be evaluated using assays that, for example, measure levels of circulating glucose and/or insulin and/or other pertinent component, such as C-peptide, in an animal model, or that measure secretion from perfused pancreatic preparations or secretion from isolated pancreatic cells (e.g., (β or islet cells), as described, for example, in the references cited above and others including Portha et al., 1991, *Diabetes* 40:486-491; Latha et al., 2004, *Life Sci.* 75:2003-2014; Garcia-Lopez et al., 2004, *Eur. J. Pharmacol.* 504:139-142; Gunawardena et al., 2005, *BMC Endocr. Disord.* 5:9; Lupi et al., 1997, *Acta Diabetol.* 34:46-48; Gregario et al., 1992, *Diabetes Res. Clin. Pract.* 18:197-206. Additional examples of how compounds can be evaluated in isolated rodent islets, perfused and perifused islets and in a variety of diabetic animal models include Gotoh et al., 1987, *Transplantation* 43:725-730; Silvestre et al., 2001, *Horm. Metab. Res.* 33:379-381; and Young et al., 1999, *Diabetes* 48:1026-1034. In addition, modulation of secretion from isolated pancreatic cells can be assessed by measuring membrane voltage changes, second messenger activation (e.g., cAMP, $IP_3$ or $Ca^{2+}$) levels, ion flux, phosphorylation levels, transcription levels, and the like. Additional exemplary assays are described in the section below.

7. EXAMPLES

The following examples are offered by way of illustration and are not intended to limit the scope of the invention. Those of skill in the art will readily recognize a variety of noncritical parameters that could be modified to yield essentially similar results.

Reagents and solvents used below can be obtained from commercial sources such as Sigma Aldrich Co. (St. Louis, Mo., USA). 1H-NMR spectra were recorded on Varian Gemini 400 MHz or 500 MHz NMR spectrometers. Significant peaks are tabulated in the order: chemical shift, multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

7.1 Example 1

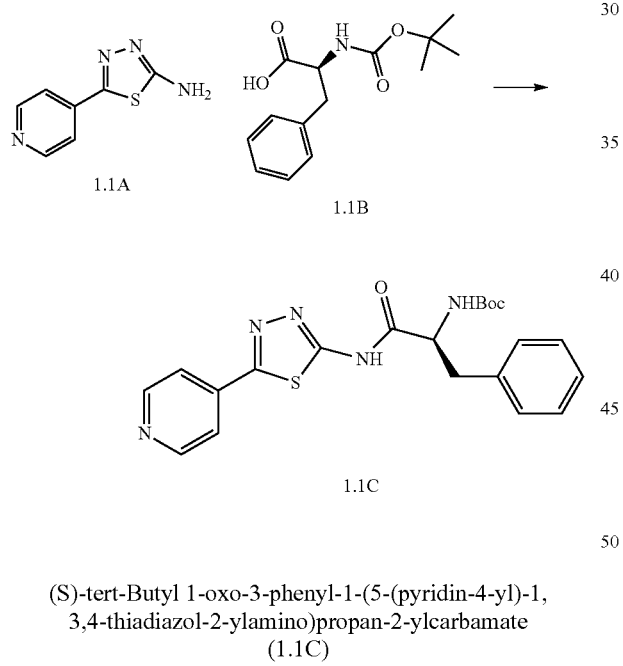

(S)-tert-Butyl 1-oxo-3-phenyl-1-(5-(pyridin-4-yl)-1, 3,4-thiadiazol-2-ylamino)propan-2-ylcarbamate (1.1C)

A solution of 5-(pyridin-4-yl)-1,3,4-thiadiazol-2-amine (0.216 g, 1.21 mmol), Boc-1-phenylalanine (0.354 g, 1.33 mmol), HBTU (0.919 g, 2.42 mmol) and DIEA (0.633 ml, 3.64 mmol) in DMF (10 mL) was stirred at room temperature for 16 h. The reaction was quenched with H$_2$O and extracted with EtOAc. The organics were combined and dried over MgSO$_4$, filtered and stripped. The residue was purified by silica gel flash chromatography (0-10% MeOH/CH$_2$Cl$_2$) to afford (S)-tert-butyl-1-oxo-3-phenyl-1-(5-(pyridin-4-yl)-1, 3,4-thiadiazol-2-ylamino)propan-2-ylcarbamate (0.426 g, 82.6% yield).

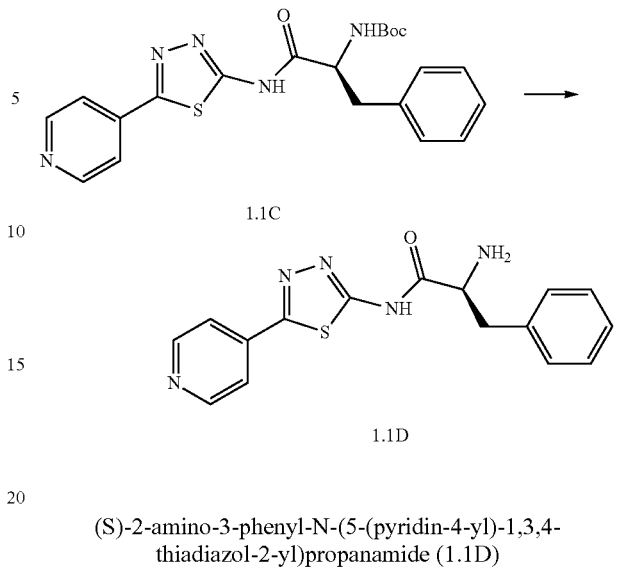

(S)-2-amino-3-phenyl-N-(5-(pyridin-4-yl)-1,3,4-thiadiazol-2-yl)propanamide (1.1D)

Into a solution of (S)-tert-butyl 1-oxo-3-phenyl-1-(5-(pyridin-4-yl)-1,3,4-thiadiazol-2-ylamino)propan-2-ylcarbamate (0.426 g, 1.00 mmol) in CH$_2$Cl$_2$ (5.0 mL) was injected trifluoroacetic acid (7.44 ml, 100 mmol) and let stir for 3 h. Reaction stripped of solvent. The residue was purified by silica gel flash chromatography (0-10% MeOH/CH$_2$Cl$_2$) to afford (S)-2-amino-3-phenyl-N-(5-(pyridin-4-yl)-1,3,4-thiadiazol-2-yl)propanamide (0.306 g. 93.9% yield)

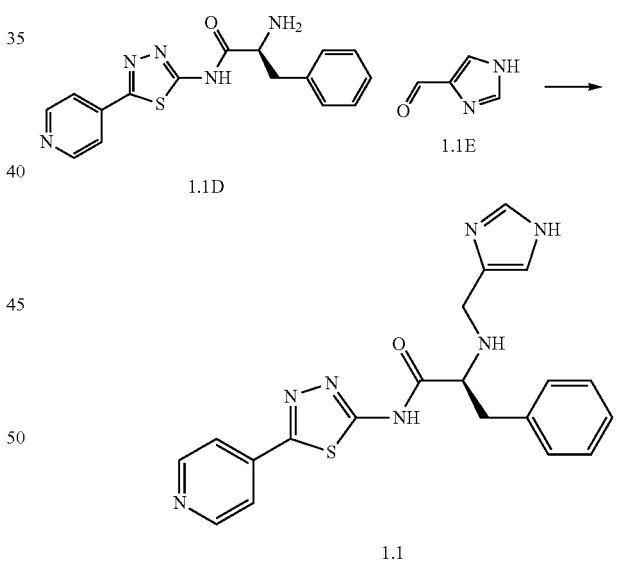

(S)-2-((1-methyl-1H-imidazol-4-yl)methylamino)-3-phenyl-N-(5-(pyridin-4-yl)-1,3,4-thiadiazol-2-yl) propanamide (1.1)

A solution of (S)-2-amino-3-phenyl-N-(5-(pyridin-4-yl)-1,3,4-thiadiazol-2-yl)propanamide (0.066 g, 0.20 mmol), 1H-imidazole-4-carbaldehyde (0.019 g, 0.20 mmol) in MeOH (2 mL) was heated to 55° C. for 15 min before addition of NaCNBH$_3$ (0.038 g, 0.61 mmol) and let stir for 4 h. The crude mixture was then purified by RPHPLC to afford (S)-2-

((1-methyl-1H-imidazol-4-yl)methylamino)-3-phenyl-N-(5-(pyridin-4-yl)-1,3,4-thiadiazol-2-yl)propanamide (47.0 mg, 55%).

The following compounds were prepared from methyl (S)-2-amino-3-phenyl-N-(5-(pyridin-4-yl)-1,3,4-thiadiazol-2-yl)propanamide and the appropriate aldehyde as shown above.

TABLE 1

| Compound | R | X |
|---|---|---|
| 1.1 | (1-methyl-1H-imidazol-4-yl)methyl | H |
| 1.2 | 1-(pyridin-2-yl)ethyl | H |
| 1.3 | (2-aminothiazol-4-yl)methyl | H |
| 1.4 | 1-(thiazol-4-yl)ethyl | H |
| 1.5 | thiazol-4-ylmethyl | H |
| 1.6 | thiazol-4-ylmethyl | F |

(S)-2-((1-methyl-1H-imidazol-4-yl)methylamino)-3-phenyl-N-(5-(pyridin-4-yl)-1,3,4-thiadiazol-2-yl)propanamide (1.1)

MS ESI (pos.) m/e: 406.1 (M+H). $^1$H NMR (400 MHz, MeOH) δ ppm 8.88-8.93 (2H, m) 8.85 (1H, d, J=1.56 Hz) 8.39-8.44 (2H, m) 7.56 (1H, d, J=1.17 Hz), 7.21-7.33 (5H, m) 4.34-4.26 (3H, m), 3.35 (1H, dd, J=13.69, 6.26 Hz), 3.26 (1H, dd, J=13.69, 7.83 Hz).

(S)-3-phenyl-2-((S)-1-(pyridin-2-yl)ethylamino)-N-(5-(pyridin-4-yl)-1,3,4-thiadiazol-2-yl)propanamide (1.2)

MS ESI (pos.) m/e: 431.1 (M+H). $^1$H NMR (400 MHz, MeOH) δ ppm 8.68-8.74 (2H, m), 8.38 (1H, d, J=4.30 Hz), 7.94-8.00 (2H, m), 7.66 (1H, td, J=7.73, 1.76 Hz), 7.13-7.31 (7H, m), 3.81 (1H, q, J=6.65 Hz), 3.50 (1H, dd, J=8.22, 5.87 Hz), 2.99-3.07 (1H, dd, J=13.69, 5.87 Hz), 2.91 (1H, dd, J=13.69, 8.61 Hz).

(S)-2-((2-aminothiazol-4-yl)methylamino)-3-phenyl-N-(5-(pyridin-4-yl)-1,3,4-thiadiazol-2-yl)propanamide (1.3)

MS ESI (pos.) m/e: 438.1 (M+H). $^1$H NMR (400 MHz, MeOH) δ ppm 8.87-8.91 (2H, m), 8.38-8.42 (2H, m), 7.21-7.34 (5H, m), 6.72 (1H, s), 4.29 (1H, dd, J=8.22, 6.65 Hz), 4.01-4.11 (2H, m), 3.35 (1H, dd), 3.36 (1H, dd, J=14.09, 6.65 Hz), 3.25 (1H, dd, J=13.69, 7.82 Hz).

(S)-3-phenyl-N-(5-(pyridin-4-yl)-1,3,4-thiadiazol-2-yl)-2-(S)-1-(thiazol-4-yl)ethylamino)propanamide (1.4)

MS ESI (pos.) m/e: 437.0 (M+H). $^1$H NMR (400 MHz, MeOH) δ ppm 8.89 (1H, d, J=1.96 Hz), 8.71 (2H, dd, J=4.70, 1.56 Hz), 7.98 (2H, dd, J=4.70, 1.56 Hz), 7.06-7.30 (6H, m), 3.99 (1H, q, J=6.65 Hz), 3.64 (1H, dd, J=8.02, 6.06 Hz), 3.04 (1H, dd, J=13.69, 6.26 Hz), 2.93 (1H, dd, J=13.30, 8.22 Hz), 1.42 (3H, d, J=6.65 Hz).

(S)-3-phenyl-N-(5-(pyridin-4-yl)-1,3,4-thiadiazol-2-yl)-2-(thiazol-4-ylmethylamino)propanamide (1.5)

MS ESI (pos.) m/e: 423.1 (M+H). $^1$H NMR (400 MHz, CD$_3$CN) δ ppm 8.90 (1H, d, J=2.0 Hz), 8.82-8.85 (2H, m), 8.65 (1H, d, J=3.1 Hz), 8.27 (2H, d, J=6.7 Hz), 7.61 (1H, d, J=2.0 Hz), 7.22-7.32 (6H, m), 4.51 (1H, t, J=7.0 Hz), 4.38 (2H, s), 3.31-3.43 (2H, m).

(S)-3-(3-fluorophenyl)-N-(5-(pyridin-4-yl)-1,3,4-thiadiazol-2-yl)-2-(thiazol-4-ylmethylamino)propanamide (1.6)

MS ESI (pos.) m/e: 441.1 (M+H). $^1$H NMR (400 MHz, CD$_3$OD) δ ppm 8.93 (1H, d, J=2.0 Hz), 8.70-8.73 (2H, m), 7.97-8.00 (2H, m), 7.36 (1H, d, J=2.2 Hz), 7.24-7.31 (1H, m), 6.93-7.05 (3H, m), 3.91-4.00 (2H, m), 3.82 (1H, dd, J=7.4, 6.7 Hz), 3.10-3.16 (1H, m), 3.03-3.09 (1H, m).

7.2 Example 2

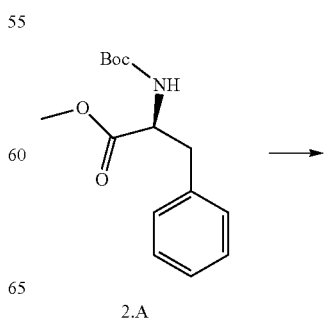

2.A

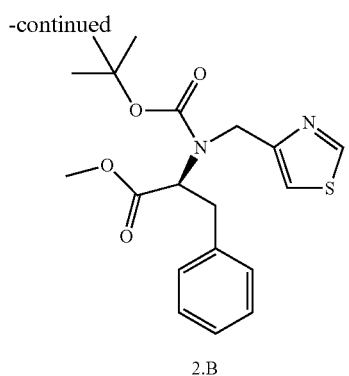

2.B

Methyl N-(((1,1-dimethylethyl)oxy)carbonyl)-N-(1,3-thiazol-4-ylmethyl)-L-phenylalaninate (2.B)

To a solution of 2.A (available from Aldrich) (627 mg, 2.3 mmol) in THF at 0° C. under $N_2$ atmosphere was added sodium hydride (88 mg, 60%, 2.3 mmol). When the gas formation ceased, to the mixture was added a solution of 4-(chloromethyl)thiazole (available from Combi-Blocks Inc.) (336 mg, 2.5 mmol) in DMF (1.0 mL). The reaction mixture was allowed to warm to rt over 30 mins and was then slowly poured into saturated aqueous $NH_4Cl$ (3.0 mL), diluted with water (15 mL), and extracted with EtOAc (3×10 mL). The combined organic solution was washed with brine (5 mL), and dried over $MgSO_4$. After removal of organic solvent under reduced pressure, purification of the residue by flash chromatography on silica gel using 0-100% EtOAc/Hexanes for elution gave 2.B as colorless solid (523, 61%).

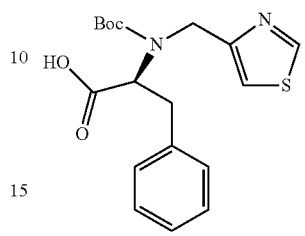

2.B

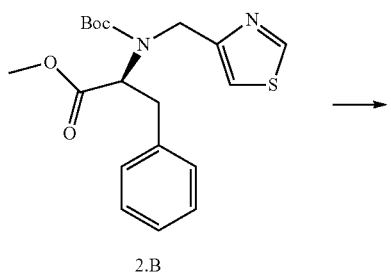

2.C

N-(((1,1-dimethylethyl)oxy)carbonyl)-N-(1,3-thiazol-4-ylmethyl)-L-phenylalanine (2.C)

To a solution of 2.B (374 mg, 1.0 mmol) in dioxane (1.5 mL) was added lithium hydroxide (70 µL, 1.5 mmol). After stirring at rt for 35 min, the reaction mixture was treated with HOAc (43 mg, 3.0 mmol), diluted with water (4 mL) and extracted with 40% $^iPrOH$/chloroform (3×7 mL). After removal of organic solvent under reduced pressure, purification of the residue by flash chromatography on silica gel using 0-15% MeOH/$CH_2Cl_2$ for elution gave 2.0 as yellow solid (290 mg, 81%).

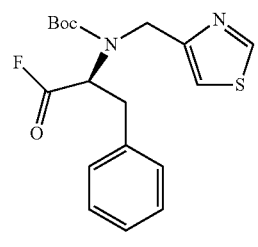

2.C

2.D

(S)-tert-Butyl 1-fluoro-1-oxo-3-phenylpropan-2-yl (thiazol-4-ylmethyl)carbamate (2.D)

To a solution of 2.0 (290 mg, 0.81 mmol) in $CH_2Cl_2$ at −20° C. was added pyridine (2.1 mL, 2.1 mmol) followed by cyanuric fluoride (available from Chem-Impex International, Inc.) (240 mg, 1.8 mmol). The resulting mixture was allowed to stir at <−10° C. for 1.0 hr, quenched with ice-$H_2O$ (5 mL), and extracted with $CH_2Cl_2$ (3×10 mL). After removal of organic solvent under reduced pressure at rt, the crude product 2.D was left on high vacuum for 3.0 hr before being directly used in the next step (280 mg, 95%).

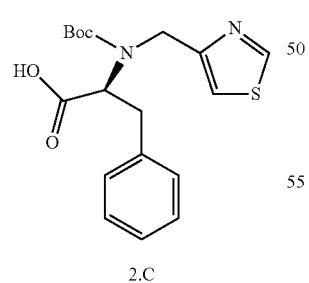

2.D

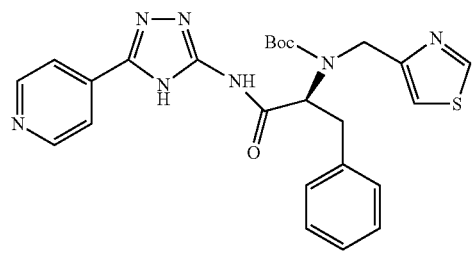

2.E

(S)-tert-Butyl 1-oxo-3-phenyl-1-(5-(pyridin-4-yl)-4H-1,2,4-triazol-3-ylamino)propan-2-yl(thiazol-4-ylmethyl)carbamate (2.E)

To a rt solution of 2.D (267 mg, 0.73 mmol) in DMF (2.5 mL) under $N_2$ was added 5-(pyridin-3-yl)-1,3,4-oxadiazol-2-amine (available from Chemical Block Ltd.) (143 mg, 0.88 mmol) followed by triethylamine (available from Alfa Aesar) (255 µl, 1.82 mmol). After stirring at rt for overnight, the reaction was quenched with saturated $NaHCO_3$, diluted with water, and extracted with EtOAc. After removal of organic solvent, purification by flash chromatography on silica gel using 0-10% MeOH/$CH_2Cl_2$ for elution to give 2.E as pale yellow syrup (159 mg, 43%).

(S)-3-Phenyl-N-(5-(pyridin-4-yl)-4H-1,2,4-triazol-3-yl)-2-(thiazol-4-ylmethylamino)propanamide (2)

To a rt solution of 2.E (147 mg, 0.29 mmol) in dioxane (3.0 mL) was added concentrated HCl (0.5 mL). After stirring at rt for 1.5 hr, the reaction mixture was poured into saturated $NaHCO_3$, diluted with water and extracted with 30% $^i$PrOH/chloroform. The organic solvent was removed under reduced pressure. After purification of the residue by preparative HPLC (10-90% $CH_3CN$/water, 45 min), the combined product fractions was treated with saturated $NaHCO_3$, and extracted with 30% $^i$PrOH/$CHCl_3$. After removal of solvent under reduced pressure, the title product 2 (40 mg, 37%) was obtained as colorless solid. MS ESI (positve.) m/e: 406.1 (M+H); $^1$H NMR (400 MHz, $CD_3OD$) δ ppm 3.22-3.43 (m, 3H), 3.47-(dd, J=13.50, 6.06 Hz, 1H), 4.40-4.63 (m, 3H), 7.21-7.41 (m, 5H), 7.80 (d, J=1.96 Hz, 1H), 8.50 (d, J=6.65 Hz, 2H), 8.86 (d, J=6.65 Hz, 2H), 9.10 (d, J=1.96 Hz, 1H).

7.3 Example 3

7.3.1 Example 3.1

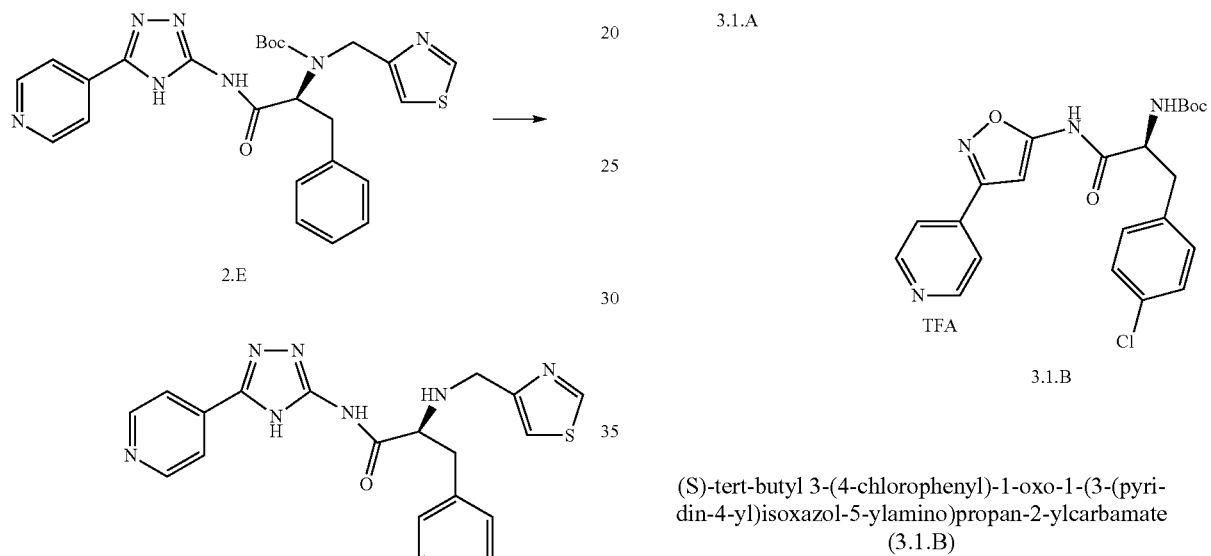

(S)-tert-butyl 3-(4-chlorophenyl)-1-oxo-1-(3-(pyridin-4-yl)isoxazol-5-ylamino)propan-2-ylcarbamate (3.1.B)

To a 100 ml flask was added 3-(pyridin-4-yl)isoxazol-5-amine (600 mg, 3.7 mmole, available from Betapharma) 2.1 g of HBTU (2.1 g, 5.6 mmole), (S)-2-(tert-butoxycarbonyl)-3-(4-chlorophenyl)propanoic acid (available from Chem-Impex, 1.3 g, 4.5 mmole), 20 ml of DMF and DIEA (2.0 ml, 11.7 mmole). The reaction was stirred at 50° C. for 6 hours, at which time the crude reaction was purified by reverse phase preparative HPLC to give (S)-tert-butyl 3-(4-chlorophenyl)-1-oxo-1-(3-(pyridin-4-yl)isoxazol-5-ylamino)propan-2-yl-carbamate TFA salt 3.1.B as an off white solid (200 mg, 12.1% yield).

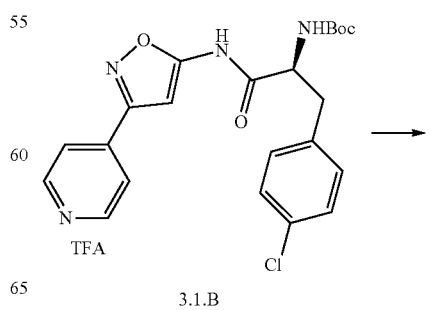

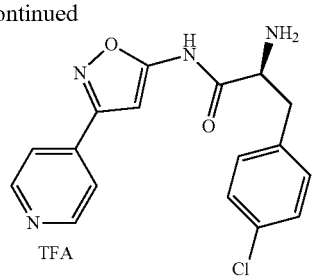

3.1.C

(S)-2-Amino-3-(4-chlorophenyl)-N-(3-(pyridin-4-yl)isoxazol-5-yl)propanamide (3.1.C)

(89426-13) To a 100 ml flask was (S)-tert-butyl 3-(4-chlorophenyl)-1-oxo-1-(3-(pyridin-4-yl)isoxazol-5-ylamino)propan-2-ylcarbamate TFA salt 3.1.B (200 mg, 0.54 mmole), 10 ml of CH$_2$Cl$_2$, and 10 ml of TFA. The reaction was stirred at room temperature for 4 hours at which time the solvent was removed to give (S)-2-amino-3-(4-chlorophenyl)-N-(3-(pyridin-4-yl)isoxazol-5-yl)propanamide TFA salt 3.1.C as a light yellow solid (250 mg, 100% yield).

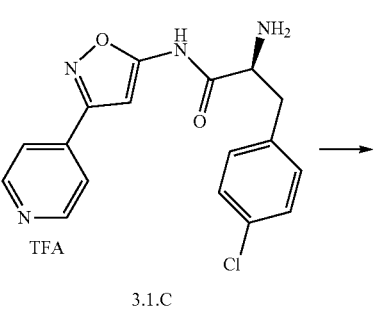

3.1.C

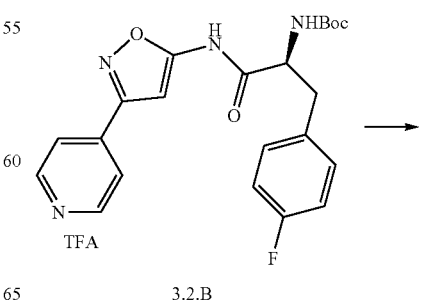

3.1

(S)-3-(4-Chlorophenyl)-N-(3-(pyridin-4-yl)isoxazol-5-yl)-2-(thiazol-4-ylmethylamino)propanamide (3.1)

To a 20 ml vial were added (S)-2-amino-3-(4-chlorophenyl)-N-(3-(pyridin-4-yl)isoxazol-5-yl)propanamide 3.1.C (50 mg, 0.15 mmole), thiazole-4-carbaldehyde (20 mg, 0.18 mmole), sodium triacetoxyborohydride (62 mg, 0.29 mmole), 5 ml of DCE, and DIEA (97 μl, 0.15 mmole). The reaction was stirred at 70° C. for 12 hours. The reaction was then partitioned between 10 ml of water and 20 ml of DCM and the solvent was removed by rotary evaporation. The crude was purified using reverse phase preparative HPLC to give 5.55 mg of (S)-3-(4-chlorophenyl)-N-(3-(pyridin-4-yl)isoxazol-5-yl)-2-(thiazol-4-ylmethylamino)propanamide TFA salt 3.1 as a clear film (5.6 mg, 9% yield). LCMS ESI (pos.) m/e: 440.1 (M+1): 1H NMR (500 MHz, MeOH) δ ppm 9.01 (d, J=1.71 Hz, 1H), 8.76-8.78 (m, 2H), 8.19 (d, J=6.60 Hz, 2H), 7.69 (dd, J=13.82, 8.68 Hz, 1H), 7.24 (d, J=1.96 Hz, 1H), 7.13 (d, J=8.31 Hz, 2H), 6.99 (d, J=8.31 Hz, 2H), 4.35-4.45 (s, 1H), 4.26 (m, 2H), 3.34 (dd, J=8.56, 5.87 Hz, 1H), 3.17 (dd, J=13.69, 5.87 Hz, 1H).

7.3.2 Example 3.2

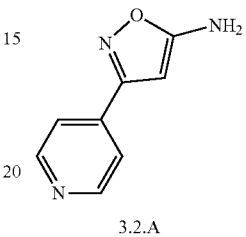

3.2.A

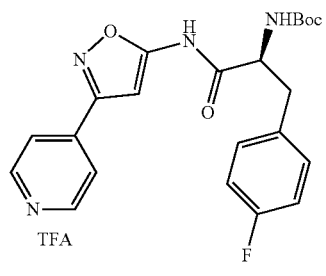

3.2.B

(S)-tert-Butyl 3-(4-chlorophenyl)-1-oxo-1-(3-(pyridin-4-yl)isoxazol-5-ylamino)propan-2-ylcarbamate (3.2.B)

To a 100 ml flask was added 3-(pyridin-4-yl)isoxazol-5-amine (890 mg, 5.5 mmole, available from Betapharma), (S)-2-(tert-butoxycarbonyl)-3-(4-fluorophenyl)propanoic acid (1877 mg, 6.6 mmole), EDC (2117 mg, 11 mmole), and 10 ml of pyridine. The reaction was stirred at room temperature for 4 hours at which time the excess pyridine was removed with a stream of nitrogen (50° C.) and the crude was partitioned between 500 ml of DCM 3×100 ml of water. The organic solvent was then removed by rotary evaporation and the crude purified by reverse phase preparative HPLC to give (S)-tert-butyl 3-(4-fluorophenyl)-1-oxo-1-(3-(pyridin-4-yl)isoxazol-5-ylamino)propan-2-ylcarbamate TFA 3.2.B as a white solid 620 mg, 26% yield)

3.2.B

-continued

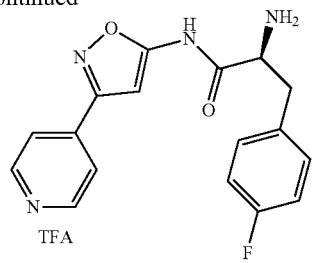

3.2.C

(S)-2-Amino-3-(4-fluorophenyl)-N-(3-(pyridin-4-yl)isoxazol-5-ylamino)propanamide (3.2.C)

To a 100 ml flask was (S)-tert-butyl 3-(4-fluorophenyl)-1-oxo-1-(3-(pyridin-4-yl)isoxazol-5-ylamino)propan-2-ylcarbamate TFA salt 3.2.B (620 mg, 0.54 mmole), 10 ml of CH$_2$Cl$_2$, and 10 ml of TFA. The reaction was stirred at room temperature for 4 hours at which time the solvent was removed to give (S)-2-amino-3-(4-fluorophenyl)-N-(3-(pyridin-4-yl)isoxazol-5-ylamino)propanamide diTFA salt 3.2.C as a light yellow solid (600 mg, 74% yield).

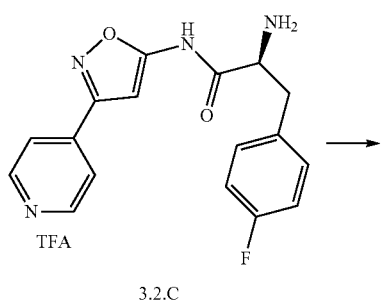

3.2.C

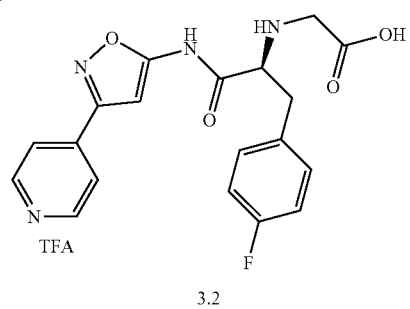

3.2

(S)-2-(3-(4-Fluorophenyl)-1-oxo-1-(3-(pyridin-4-yl)isoxazol-5-ylamino)propan-2-ylamino)acetic acid diTFA salt (3.2)

To a 500 ml flask was added (S)-2-amino-3-phenyl-N-(3-(pyridin-4-yl)isoxazol-5-ylamino)propanamide diTFA (120 mg, 0.22 mmole), 3 ml of DMF, 97 ul DIEA (97 ul, 0.56 mmole, make sure pH=7), 150 ul of AcOH and glyoxylic acid monohydrate (20.6 mg, 0.22 mmoles). The reaction was stirred at 70° C. for 5 minutes at which time sodium triacetoxyborohydride (190 mg, 0.90 mmole) was added and stirred at 70° C. for an additional 6 hours. The solvent was then removed and the crude purified by reverse phase preparative HPLC to give (S)-2-(3-(4-fluorophenyl)-1-oxo-1-(3-(pyridin-4-yl)isox- azol-5-ylamino)propan-2-ylamino)acetic acid diTFA as a light yellow solid (30 mg, 35% yield). LCMS ESI (pos.) m/e: 385.0 (M+1): 1H NMR (500 MHz, MeOH) δ ppm 8.88 (d, J=6.60 Hz, 2H), 8.27 (d, J=6.60 Hz, 2H), 7.33 (dd, J=8.56, 5.13 Hz, 2H), 7.01-7.15 (m, 3H), 4.45 (dd, J=8.19, 6.48 Hz, 1H), 3.92-4.06 (m, 2H), 3.43 (dd, J=13.94, 6.36 Hz, 1H), 3.31 (d, J=8.31 Hz, 1H).

7.3.3 Example 3.3

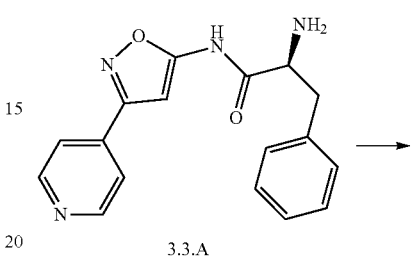

3.3.A

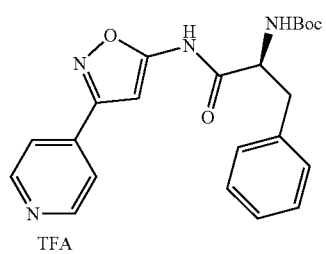

3.3.B

(S)-tert-Butyl 1-oxo-3-phenyl-1-(3-(pyridin-4-yl)isoxazol-5-ylamino)propan-2-ylcarbamate (3.3.B)

This example was made using the same procedure as example 3.1.B, with the substitution of n-(tert-butoxycarbonyl)-l-phenylalanine for (S)-2-(tert-butoxycarbonyl)-3-(4-chlorophenyl)propanoic acid.

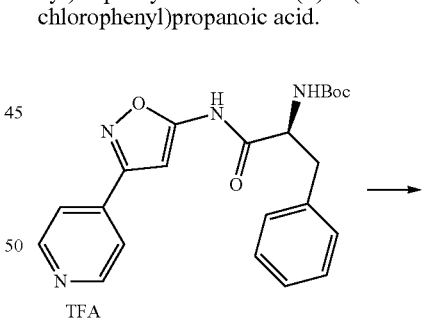

3.3.B

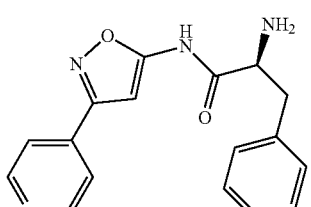

3.3.C

(S)-2-Amino-3-phenyl-N-(3-(pyridin-4-yl)isoxazol-5-yl)propanamide (3.3.C)

To a 25 ml flask was added (S)-tert-butyl 1-oxo-3-phenyl-1-(3-(pyridin-4-yl)isoxazol-5-ylamino)propan-2-ylcarbamate 3.3B (160 mg, 0.40 mmoles), 10 ml of CH$_2$Cl$_2$, and 5 ml of TFA. The reaction was stirred at room temperature for 3 hour at which time the solvent was removed with a stream of nitrogen. The crude material was then partitioned between 200 ml of DCM and 100 ml of saturated sodium bicarbonate. The organic solvent was removed by rotary evaporation to give (S)-2-amino-3-phenyl-N-(3-(pyridin-4-yl)isoxazol-5-yl)propanamide 3.3.C as a light yellow solid (100 mg, 81% yield).

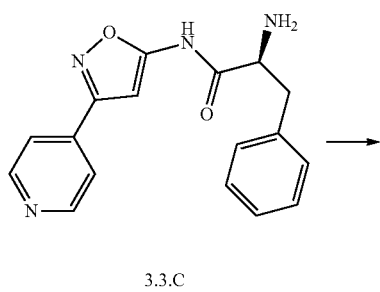

3.3.C

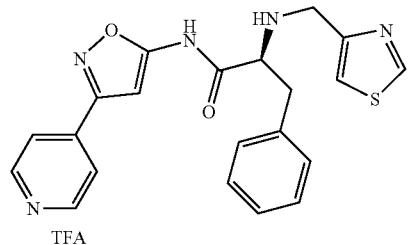

TFA 3.3

(S)-3-Phenyl-N-(3-(pyridin-4-yl)isoxazol-5-yl)-2-(thiazol-4-ylmethylamino)propanamide (3.3)

To a 20 ml vial were added (S)-2-amino-3-phenyl-N-(3-(pyridin-4-yl)isoxazol-5-yl)propanamide 3.3.C (40 mg, 0.13 mmole), thiazole-4-carbaldehyde (18 mg, 0.16 mmole), sodium triacetoxyborohydride (55 mg, 0.26 mmole) and 10 ml of DCE. The reaction was stirred at 70° C. for 12 hours. The crude material was partitioned between DCM and water and then purified by reverse phase preparative HLPC to give (S)-3-phenyl-N-(3-(pyridin-4-yl)isoxazol-5-yl)-2-(thiazol-4-ylmethylamino)propanamide TFA salt 3.3 as a white solid (14.2 mg, 27% yield). LCMS ESI (pos.) m/e: 406.1 (M+1): 1H NMR (500 MHz, MeOH-d) δ ppm 9.09 (d, J=1.96 Hz, 1H), 8.87 (br. s., 2H), 8.27 (d, J=5.38 Hz, 2H), 7.77 (d, J=1.96 Hz, 1H), 7.27-7.35 (m, 3H), 7.20-7.25 (m, 2H) 7.07 (s, 1H), 4.42-4.55 (m, 2H), 4.35 (dd, J=8.80, 5.87 Hz, 1H), 3.44 (dd, J=13.57, 5.99 Hz, 1H), 3.26 (dd, J=13.69, 8.80 Hz, 1H).

7.4 Example 4

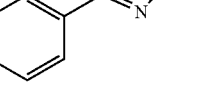

4.A

4.B

(S)-tert-Butyl 1-oxo-3-phenyl-1-(2-(pyridin-4-yl)thiazol-4-ylamino)propan-2-ylcarbamate (4.B)

To a rt solution of 4.A (available from J & W PharmLab) (250 mg, 1419 mmol), boc-1-phenylalanine (available from Aldrich) (452 mg, 1702 μmmol) in DMF (7.0 mL) was added Et$_3$N (592 μl, 4.3 mmol) followed by 2-(1h-benzotriazol-1-yl)-1,1,3,3-tetramethyluronium hexafluorophosphate (available from SynPep Corporation) (807 mg, 2128 μmol). After stirring at rt for 6.0 hr, and the reaction mixture was treated with H$_2$O (18 mL) and extracted with 30% $^i$PrOH/CHCl$_3$ (3×20 mL). The combined solution was washed with brine and dried over MgSO$_4$. After removal of organic solvent under reduced pressure, purification of the residue by flash chromatography on silica gel using 0-7% MeOH/CH$_2$Cl$_2$ for elution provided 4.B as a yellow solid (482 mg, 80%).

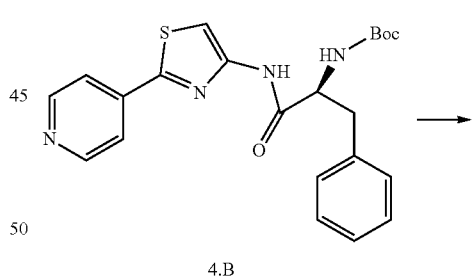

4.B

4.C

(S)-2-Amino-3-phenyl-N-(2-(pyridin-4-yl)thiazol-4-yl)propanamide (4.C)

To a rt solution of 4.B (163 mg, 384 μmol) in dioxane (2.5 mL) was added 6.0 N HCl (1 mL). After stirring at rt for 30 min, the reaction mixture was poured into saturated aqueous NaHCO$_3$ (5 m L), diluted with water (5 mL) and extracted by 30% $^i$PrOH/CHCl$_3$ (3×10 mL). The combined solution was washed with brine and dried over MgSO$_4$. After removal of organic solvent under reduced pressure, purification of the residue by flash chromatography on silica gel using 0-20% MeOH/CH$_2$Cl$_2$ for elution provided 4.C as a colorless solid (105 mg, 85%)

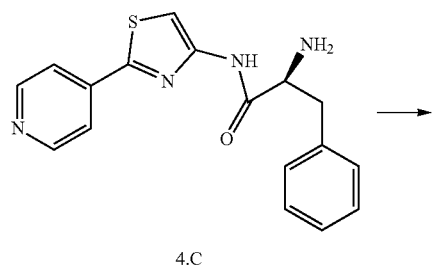

4.C

(S)-3-Phenyl-N-(2-(pyridin-4-yl)thiazol-4-yl)-2-(thiazol-4-ylmethylamino)propanamide (4)

To a rt solution of 4.C (100 mg, 0.31 mmol) and thiazole-4-carbaldehyde (available from Combi-Blocks Inc.) (34.9 mg, 0.31 mmol) in 1,2-dichloroethane was added sodium triacetoxyborohydride (available from Fluka Chemie GmbH) (196 mg, 0.93 mmol) followed by 5% HOAc/1,2-dichloroethane (50 μL). After stirring at 60° C. for 30 min, the reaction mixture was poured into saturated aqueous NaHCO$_3$ (1.0 mL), diluted with water (5 mL), and extracted with 30% $^i$PrOH/CHCl$_3$ (3×10 mL). The organic solvent was removed under reduced pressure. After purification of the residue by preparative HPLC (10-90% CH$_3$CN/water, 30 min), the title product 2 (30 mg, 23%) was obtained as colorless TFA salt. MS ESI (positve.) m/e: 422.0 (M+H); $^1$H NMR (400 MHz, CD$_3$OD) δ ppm 2.86-3.05 (m, 1H), 3.12 (dd, J=13.30, 6.26 Hz, 1H), 3.65 (dd, J=7.83, 6.26 Hz, 1H), 3.79-4.03 (m, 2H), 7.13-7.36 (m, 6H), 7.84 (s, 1H), 7.89-7.99 (m, 2H), 8.64 (dd, J=4.50, 1.76 Hz, 2H), 8.90 (d, J=2.35 Hz, 1H).

7.5 Example 5

7.5.1 Example 5.1

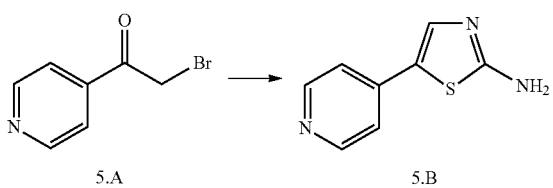 [SMILES: O=C(CBr)c1ccncc1 ; Nc1ncc(-c2ccncc2)s1]

2-(Pyridin-4-yl)thiazol-4-amine (5.B)

To a rt solution of 5.A (available from Oakwood Products, Inc.)(5.00 g, 17.8 mmol) and 2-thiourea (1.25 ml, 23.1 mmol) in EtOH was added triethylamine (2.5 mL, 17.8 mmol). The reaction solution was heated at 60° C. for 20 hr, and the resulting mixture was concentrated under reduced pressure. To the residue was added water (15 mL) and saturated aqueous NaHCO$_3$ (4 mL), the mixture was extracted with EtOAc (3×20 mL). After removal of organic solvent under reduced pressure, purification of the residue by flash chromatography on silica gel using 0-70% EtOAc/Hexanes for elution gave 5.B as yellow solid (2.71 g, 86%).

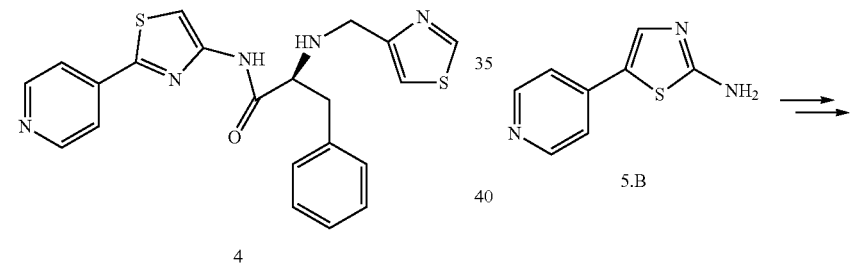

5.1

(S)-tert-Butyl 1-oxo-3-phenyl-1-(2-(pyridin-4-yl)thiazol-4-ylamino)propan-2-ylcarbamate (5.1)

This title product was prepared starting from 5.B (103 mg, 0.58 mmol) according the procedure described above for conversion of 4.A to 4. The crude product was purified by preparative HPLC (10-90% CH$_3$CN/water, 30 min) to provide 23.1 TFA salt (34.6 mg, 14%). MS ESI (positve.) m/e: 422.0 (M+H); $^1$H NMR (400 MHz, CD$_3$OD) δ ppm 3.40-3.25 (m, 1H), 3.48 (dt, J=3.42, 1.6 Hz, 1H), 4.40-4.49 (m, 3H), 7.30 (m, 5H), 7.75 (s, 1H), 8.27 (s, 1H), 8.34 (d, J=6.65 Hz, 2H), 8.75 (d, J=6.65 Hz, 2H), 9.10 (d, J=1.96 Hz, 1H).

7.5.2 Example 5.2

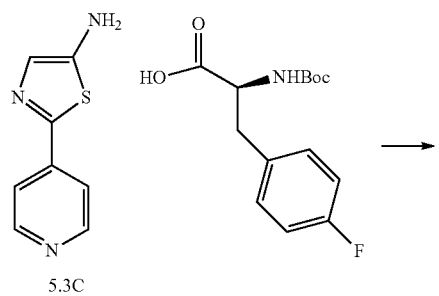

5.3C

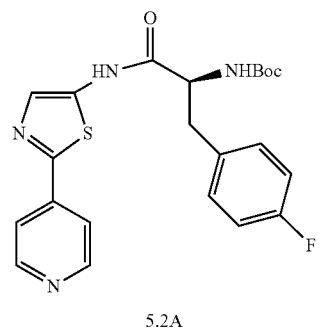

5.2A

(S)-tert-Butyl 3-(4-fluorophenyl)-1-oxo-1-(2-(pyridin-4-yl)thiazol-5-ylamino)propan-2-ylcarbamate (5.2A)

A mixture of 2-(pyridin-4-yl)thiazol-5-amine (0.987 g, 5.57 mmol), (S)-2-(tert-butoxycarbonyl)-3-(4-fluorophenyl)propanoic acid (1.58 g, 5.57 mmol), HBTU (2.11 g, 5.57 mmol) and N-ethyl-N-isopropylpropan-2-amine (2.43 ml, 13.9 mmol) in N,N-dimethylformamide (11.1 ml, 5.57 mmol) was allowed to stir at 80° C. for 4 hours. 20 mL of water was added and the resulting mixture was extracted with DCM (40 mL×4). The extract was dried and concentrated. The residue was purified by CombiFlash using 0-10% methanol/DCM to give 250 mg of (S)-tert-butyl 3-(4-fluorophenyl)-1-oxo-1-(2-(pyridin-4-yl)thiazol-5-ylamino)propan-2-ylcarbamate 5.2A. 400 MHz $^1$H NMR (CD$_3$OD) δ: 8.78 (d, 2H), 8.43 (d, J=8.0 Hz, 2H), 7.87 (s, 1H), 7.27 (dd, J=8.0, 4.0 Hz, 2H), 7.01 (dd, 2H), 4.50 (m, 1H), 3.15 (m, 1H), 2.99 (m, 1H), 1.40 (s, 9H). LCMS (ES+) m/z 443.

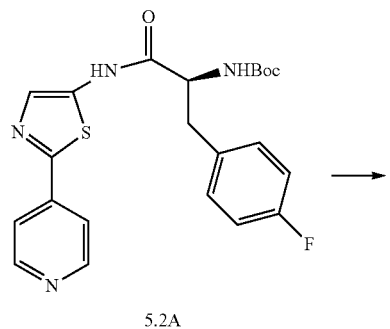

5.2A

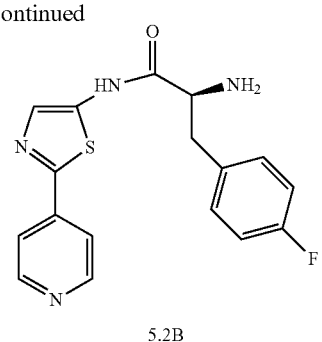

5.2B

(S)-2-Amino-3-(4-fluorophenyl)-N-(2-(pyridin-4-yl)thiazol-5-yl)propanamide (5.2B)

To a solution of (S)-tert-butyl 3-(4-fluorophenyl)-1-oxo-1-(2-(pyridin-4-yl)thiazol-5-ylamino)propan-2-ylcarbamate (0.250 g, 0.565 mmol) in DCM (10.0 ml, 155 mmol) was added TFA (2.50 ml, 32.4 mmol). The resulting mixture was allowed to stir at rt for 4 hours. The mixture was concentrated and the residue was purified by HPLC to give 145 mg of (S)-2-amino-3-(4-fluorophenyl)-N-(2-(pyridin-4-yl)thiazol-5-yl)propanamide 5.2B. 400 MHz $^1$H NMR (CD$_3$OD) δ: 8.79 (d, J=8.0 Hz, 2H), 8.37 (d, J=8.0 Hz, 2H), 7.86 (s, 1H), 7.30 (dd, J=8.0, 4.0 Hz, 2H), 7.08 (dd, J=12, 8.0 Hz, 2H), 4.37 (dd, J=8.0, 8.0 Hz, 1H), 3.34 (obscured dd, 1H), 3.23 (dd, J=12.0, 8.0 Hz, 1H), LCMS (ES+) m/z 343.

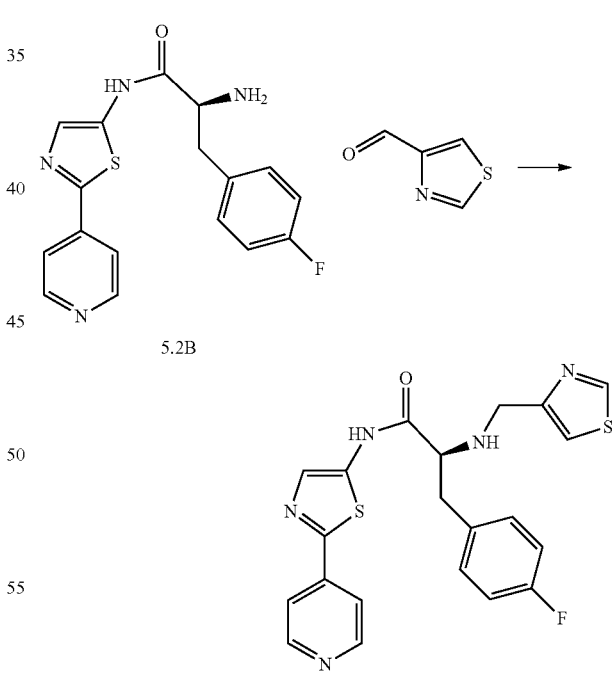

5.2

(S)-3-(4-Fluorophenyl)-N-(2-(pyridin-4-yl)thiazol-5-yl)-2-(thiazol-4-ylmethylamino)propanamide (5.2)

To a mixture of (S)-2-amino-3-(4-fluorophenyl)-N-(2-(pyridin-4-yl)thiazol-5-yl)propanamide (0.090 g, 0.20 mmol), thiazole-4-carbaldehyde (0.022 g, 0.20 mmol), N,N-dimethylformamide (0.014 g, 0.20 mmol) and 1,2-dichloroethane (0.020 g, 0.20 mmol) was added Reactant 3 (0.19 g, 0.89 mmol). The resulting mixture was allowed to stir at rt overnight. The mixture was directly purified HPLC to give 56 mg of (S)-3-(4-Fluorophenyl)-N-(2-(pyridin-4-yl)thiazol-5-yl)-2-(thiazol-4-ylmethylamino)propanamide 5.2. 400 MHz $^1$H NMR (CD$_3$OD) δ: 9.09 (d, J=4.0 Hz, 1H), 8.78 (d, 2H), 8.34 (d, J=8.0 Hz, 2H), 7.80 (d, 1H), 7.74 (s, 1H), 7.24 (dd, J=8.0, 4.0 Hz, 2H), 7.04 (, J=12, 8.0 hz, 2H), 4.54 (d, J=16 Hz, 1H), 4.50 (d, J=16 Hz, 1H), 4.40 (dd, J=12.0, 8.0 Hz, 1H), 3.47 (dd, J=16.0, 8.0 Hz, 1H), 3.26 (dd, J=16.0, 8.0 Hz, 1H). LCMS (ES+) m/z 440.

7.5.3 Example 5.3

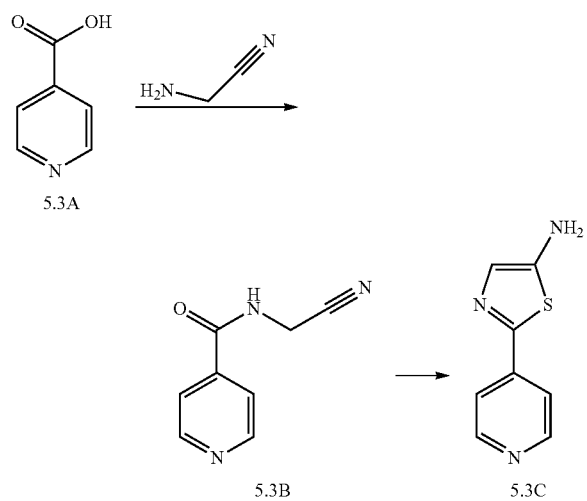

N-(cyanomethyl)isonicotinamide (5.3B)

A mixture of isonicotinic acid (1.00 g, 8.12 mmol), 2-aminoacetonitrile hydrochloride (0.902 g, 9.75 mmol), 1H-benzo[d][1,2,3]triazol-1-ol hydrate (1.24 g, 8.12 mmol), N1-((ethylimino)methylene)-N3,N3-dimethylpropane-1,3-diamine hydrochloride (1.71 g, 8.94 mmol) and N-ethyl-N-isopropylpropan-2-amine (4.95 ml, 28.4 mmol) in dichloromethane (20.3 ml, 8.12 mmol) was allowed to stir at room temperature for 24 hours. The mixture was concentrated and the residue was purified by CombiFlash using 0-10% methanol/DCM as the eluent to 1.31 g of N-(cyanomethyl)isonicotinamide 5.3B. 400 MHz $^1$H NMR (CDCl$_3$) δ: 9.62 (br s, 1H), 8.87 (d, J=8.0 Hz, 2H), 7.94 (d, J=8.0 Hz, 2H), 4.30 (d, J=2H). LCMS (ES+) m/z 162.

2-(Pyridin-4-yl)thiazol-5-amine (5.3C)

A mixture of N-(cyanomethyl)isonicotinamide (0.665 g, 4.1 mmol) and phosphorus pentasulfide (1.8 g, 8.3 mmol) in benzene (5.00 ml, 56 mmol) was allowed to refluxed for 24 hours. The mixture was concentrated and the residue was purified by CombiFlash using 0-10% methanol/DCM to give 730 mg of 2-(pyridin-4-yl)thiazol-5-amine 5.3C. 400 MHz $^1$H NMR (CD$_3$OD) δ: 8.51 (d, J=8.0 Hz, 2H), 7.72 (d, J=8.0 Hz, 2H), 7.07 (s, 1H). LCMS (ES+) m/z 178.

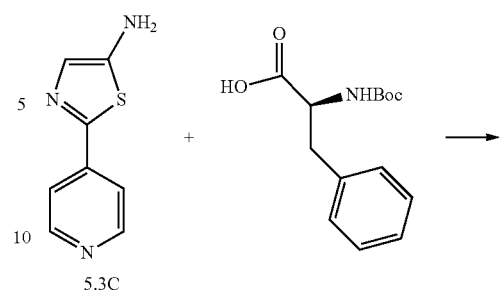

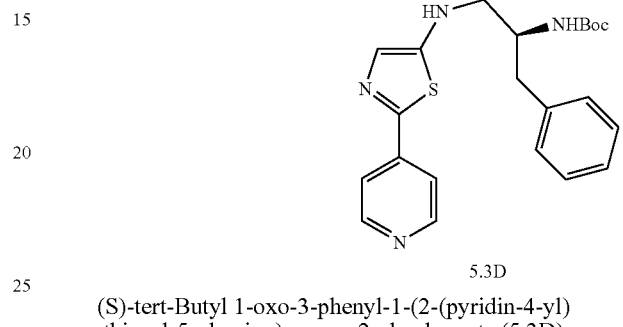

(S)-tert-Butyl 1-oxo-3-phenyl-1-(2-(pyridin-4-yl)thiazol-5-ylamino)propan-2-ylcarbamate (5.3D)

A mixture of 2-(pyridin-4-yl)thiazol-5-amine (0.730 g, 4.12 mmol), (S)-2-(tert-butoxycarbonyl)-3-phenylpropanoic acid (1.09 g, 4.12 mmol), Reactant 3 (1.57 g, 4.12 mmol) and N-ethyl-N-isopropylpropan-2-amine (1.79 ml, 10.3 mmol) in N,N-dimethylformamide (4.12 ml, 4.12 mmol) was allowed to stir at 80° C. for 3 hours. The mixture was directly subjected to HPLC purification to give 508 mg of (S)-tert-butyl 1-oxo-3-phenyl-1-(2-(pyridin-4-yl)thiazol-5-ylamino)propan-2-ylcarbamate 5.3D. 500 MHz $^1$H NMR (CD$_3$OD) δ: 8.78 (d, J=5.0 Hz, 2H), 8.43 (d, J=5.0 Hz, 2H), 7.83 (s, 1H), 7.21-7.30 (m, 5H), 4.51 (m, 1H), 3.17 (m, 1H), 3.01 (m, 1H), 1.42 (s, 9H). LCMS (ES+) m/z 425.

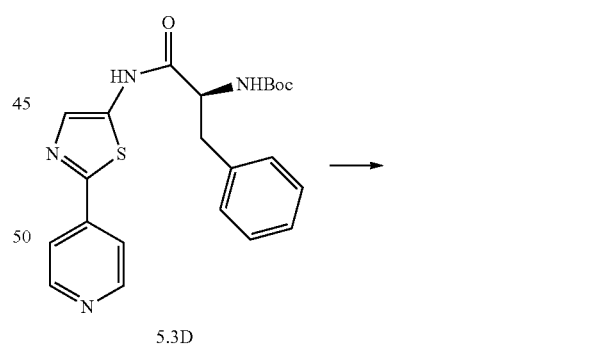

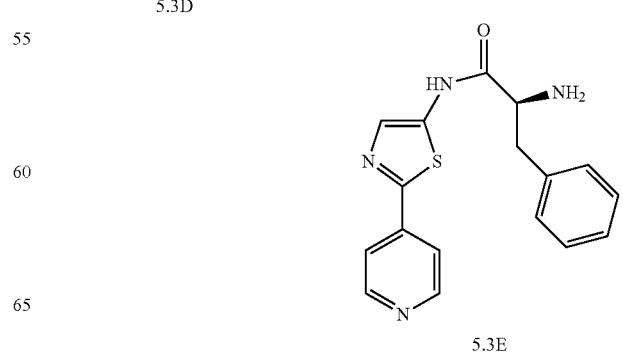

(S)-2-Amino-3-phenyl-N-(2-(pyridin-4-yl)thiazol-5-yl)propanamide (5.3E)

To a solution of (S)-tert-butyl 1-oxo-3-phenyl-1-(2-(pyridin-4-yl)thiazol-5-ylamino)propan-2-ylcarbamate (0.448 g, 1.1 mmol) in DCM (10 ml, 155 mmol) was added TFA (3.00 ml, 39 mmol). The resulting mixture was allowed to stir at rt for 3 hours. Upon completion, the mixture was concentrated and the residue was purified by HPLC to give 165 mg of (S)-2-amino-3-phenyl-N-(2-(pyridin-4-yl)thiazol-5-yl)propanamide 5.3E. 400 MHz $^1$H NMR (CD$_3$OD) δ: 8.80 (d, J=8.0 Hz, 2H), 8.40 (d, J=8.0 Hz, 2H), 7.84 (s, 1H), 7.28-7.37 (m, 5H), 4.40 (dd, J=8.0, 8.0 Hz, 1H), 3.35 (obscured dd, 1H), 3.24 (dd, J=16.0, 8.0 Hz, 1H). LCMS (ES+) m/z 325.

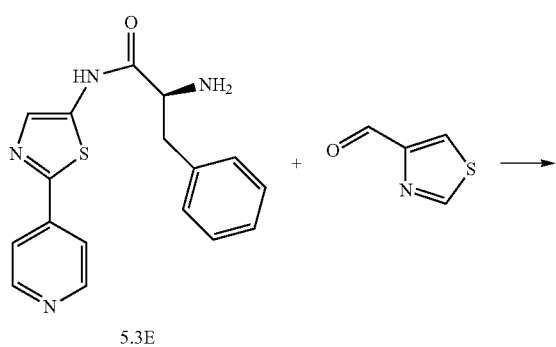

5.3E

(S)-3-Phenyl-N-(2-(pyridin-4-yl)thiazol-5-yl)-2-(thiazol-4-ylmethylamino)-propanamide (5.3)

To a mixture of (S)-2-amino-3-phenyl-N-(2-(pyridin-4-yl)thiazol-5-yl)propanamide (0.075 g, 0.23 mmol), thiazole-4-carbaldehyde (0.026 g, 0.23 mmol) and N,N-dimethylformamide (0.500 ml, 0.23 mmol) in 1,2-dichloroethane (1.000 ml, 0.23 mmol) was added sodium triacetoxyborohydride (0.17 g, 0.81 mmol). The resulting mixture was allowed to stir at room temperature for 4 hours. Upon completion, the mixture was directly subjected to HPLC purification give 10 mg of (S)-3-phenyl-N-(2-(pyridin-4-yl)thiazol-5-yl)-2-(thiazol-4-ylmethylamino)-propanamide 5.3. 400 MHz $^1$H NMR (CD$_3$OD) δ: 9.30 (d, 1H), 8.81 (d, 2H), 8.07 (d, 2H), 7.95 (d, 1H), 7.76 (s, 1H), 7.28-7.37 (m, 3H), 7.24 (dd, J=8.0, 4.0 Hz, 2H), 4.49 (d, J=16 Hz, 1H), 4.44 (d, J=16 Hz, 1H), 4.43 (dd, J=12, 8.0 Hz, 1H), 3.49 (dd, J=12, 4.0 Hz, 1H), 3.23 (dd, J=12, 8.0 Hz, 1H). LCMS (ES+) m/z 422.

7.6 Example 6

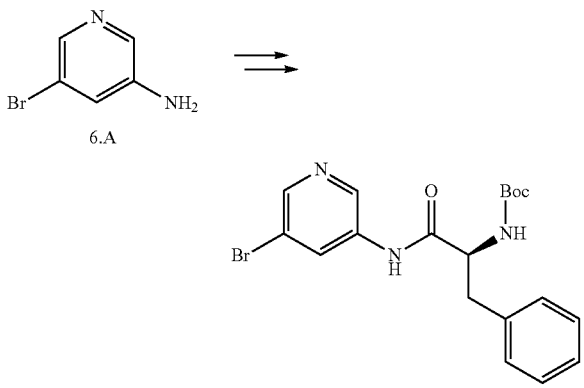

(S)-tert-butyl 1-(5-bromopyridin-3-ylamino)-1-oxo-3-phenylpropan-2-ylcarbamate (6.B)

This title product was prepared starting from 6.A (2.00 g, 11.6 mmol) according the procedure described above for conversion of 4.A to 4B. The crude product was purified by flash chromatography on silica gel using 0-55% EtOAc/Hexanes for elution to give 6.B as white solid (4.12 g, 85%).

tert-Butyl (S)-1-(5-(1H-pyrazol-5-yl)pyridin-3-ylamino)-1-oxo-3-phenylpropan-2-ylcarbamate (6.C)

To a rt solution of 6.B (850 mg, 2.02 mmol) in n-BuOH (10 mL) was added 14.1.B (619 mg, 2.23 mmol), potassium phosphate (available from Strem Chemicals, Inc.) (1.29 g, 6.07 mmol) and bis(triphenylphosphine)palladium(ii) chloride (available from Aldrich) (142 mg, 0.20 mmol). After being purged with N$_2$ for 15 mins, the mixture was stirred at 100° C. under N$_2$ atmosphere for 2.0 hrs and the resulting reaction solution was concentrated. The residue was re-dissolved in 30% $^i$PrOH/CHCl$_3$ (45 mL), washed with water and brine, and dried over MgSO$_4$. After removal of organic solvent under reduced pressure, purification of the residue by flash chromatography on silica gel using 0-80% EtOAc/Hexanes for elution gave the title product 6.0 as colorless solid (571 mg, 58%).

6.C

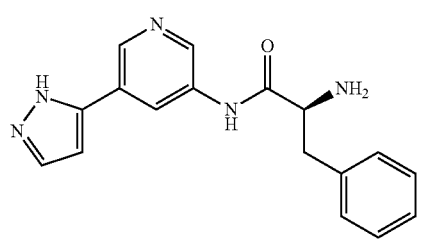

6.D (2S)—N-(5-(1H-pyrazol-5-yl)pyridin-3-yl)-2-amino-3-phenylpropanamide (6.D)

To a rt solution of 6.0 (571 mg, 1.16 mmol) in dioxane (6 mL) was added in aqueous 6.0N HCl (1 mL). After stirring at rt for 45 min, the reaction mixture was basified to PH=8 by saturated aqueous NaHCO$_3$, diluted with H$_2$O (7 mL) and extracted by $^i$PrOH/CHCl$_3$ (3×10 mL). After removal of organic solvents under reduced pressure, purification of the residue by flash chromatography on silica gel using 0-15% MeOH/CH$_2$Cl$_2$ for elution gave 6.D as colorless syrup (289 mg, 81%).

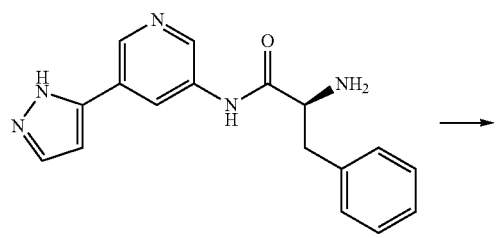

6.D

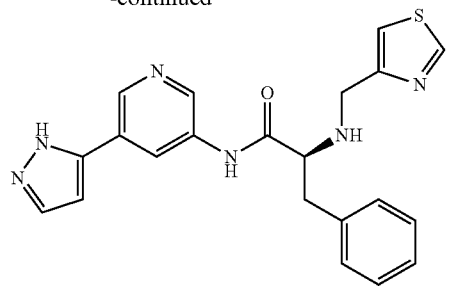

6

(2S)—N-(5-(1H-Pyrazol-5-yl)pyridin-3-yl)-3-phenyl-2-(thiazol-4-ylmethylamino)propanamide (6)

This title compound was prepared starting from 6.D (275 mg, 0.90 mmol) according the procedure described above for conversion of 4C to 4. The product 6 was purified by flash chromatography on silica gel using 0-10% MeOH/CH$_2$Cl$_2$ for elution (217 mg, 60%). MS ESI (positve.) m/e: 405.1 (M+H); $^1$H NMR (400 MHz, chloroform-d) δ ppm 2.82 (dd, J=14.09, 9.78 Hz, 1H), 3.29 (dd, J=14.09, 3.91 Hz, 1H), 3.58 (dd, J=9.78, 3.91 Hz, 2H), 3.87 (s, 2H) 6.67 (d, J=2.35 Hz, 1H), 6.99 (d, J=1.96 Hz, 1H), 7.17 (d, J=6.65 Hz, 2H), 7.19-7.33 (m, 3H), 7.65 (d, J=2.35 Hz, 1H), 8.61 (t, J=2.15 Hz, 1H), 8.72 (dd, J=4.89, 2.15 Hz, 2H), 8.81 (d, J=1.56 Hz, 1H), 9.92 (s, 1H).

7.7 Example 7

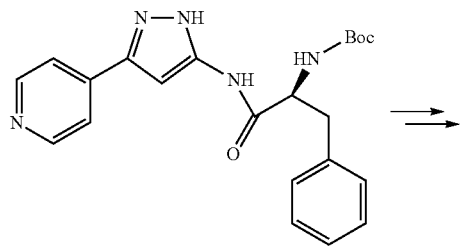

7.A

7.B

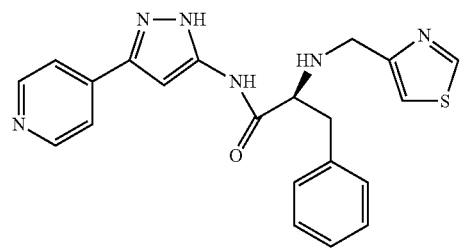

7

(S)-tert-Butyl 1-oxo-3-phenyl-1-(3-(pyridin-4-yl)-1H-pyrazol-5-ylamino)propan-2-ylcarbamate (7.B)

To a rt solution of 7.A (available from J & W PharmLab) (257 mg, 1.6 mmol) and boc-L-phenylalanine (available from Aldrich) (480 mg, 1.8 µmol) in pyridine (10 mL) was added 1-(3-dimethylaminopropyl)-3-ethylcarbodiimide hydrochloride (available from Chem-Impex International, Inc.) (403 mg, 2.1 mmol). After stirring at rt for 3.0 hr, the reaction mixture was treated with water and extracted with EtOAc. The organic solution was washed with water, brine and dried over $MgSO_4$. After removal of organic solvents under reduced pressure, purification of the residue by flash chromatography on silica gel using 0-10% $MeOH/CH_2Cl_2$ for elution gave 7.B as pale yellow solid (576 mg, 89%).

(S)-3-Phenyl-N-(3-(pyridin-4-yl)-1H-pyrazol-5-yl)-2-(thiazol-4-ylmethylamino)propanamide (7)

This title compound was prepared starting from 7.B according the procedure described above for conversion of 4.B to 4. The crude product was purified by preparative HPLC (20-70% $CH_3CN$/water, 30 min) to provide 7 as white TFA salt (20 mg, 32%). MS ESI (positve.) m/e: 405.1 (M+H); $^1$H NMR (500 MHz, $CD_3OD$) δ ppm 3.25 (m, 1H) 3.36 (dd, J=13.57, 5.75 Hz, 1H), 4.30 (dd, J=9.05, 5.87 Hz, 1H), 4.36-4.52 (m, 2H), 6.99 (s, 1H), 7.17-7.33 (m, 5H), 7.73 (d, J=1.47 Hz, 1H), 8.26 (d, J=6.60 Hz, 2H), 8.74 (d, J=6.60 Hz, 2H), 9.04 (d, J=1.71 Hz, 1H).

7.8 Example 8

7.8.1 Example 8.1

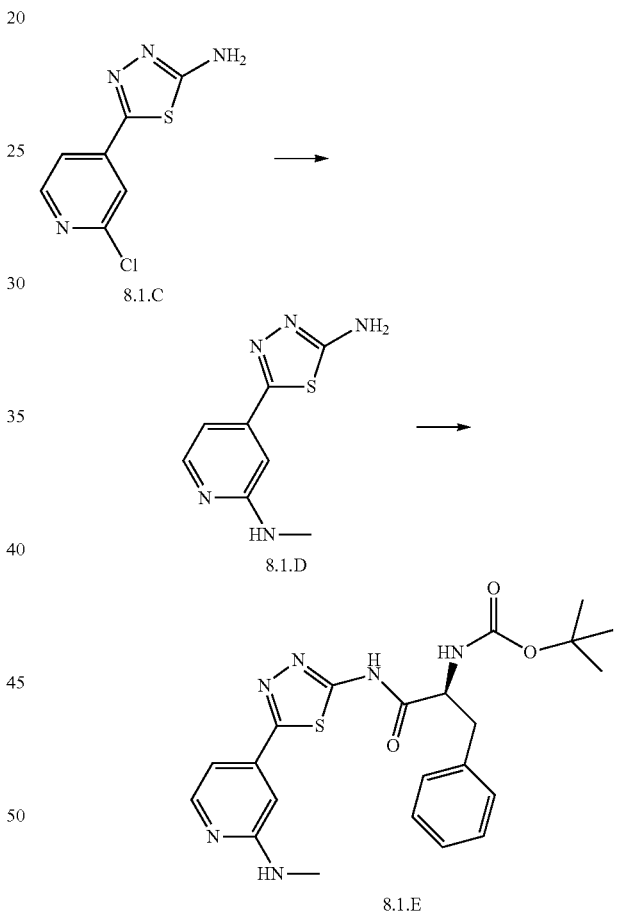

1-(2-Chloroisonicotinoyl)thiosemicarbazide (8.1.B)

2-chloroisonicotinic acid 8.1.A (5000 mg, 31735 µmol) was refluxed in $SOCl_2$ overnight under nitrogen. Another 4 mL of $SOCl_2$ was added in the morning. After 2 hr., solution cleared up. The rxn was then concentrated and added to a thiosemicarbazide (2892 mg, 31735 µmol)/pyridine solution at 0° C. After 4 hr., LC/MS showed product MS along with many side peaks. The reaction was stopped and concentrated. Water and a small amount of EtOAc were added, precipitates were generated. Filtered and washed the precipitates with water 4 times. The solids were dried. LC/MS and the NMR of the precipitates showed to be the pure product. 4.05 g of the product 8.1.B (55%) was generated as a yellow powder.

5-(2-Chloropyridin-4-yl)-1,3,4-thiadiazol-2-amine (8.1.C)

To a flask was weighed 42 g of PPA. Preheated the flask to 100° C. and then 2.4 g (10 mmol) of 8.1.B were added in portions into the flask. After an hour, ice water was added to dilute the reaction and the pH was adjusted to 7 with aqueous $NH_3$. Bright yellow precipitates were generated. Filtered and the precipitates were dried. LC/MS of the precipitates showed to be the product. 2.05 g of 8.1.C was generated with a yield of 93%.

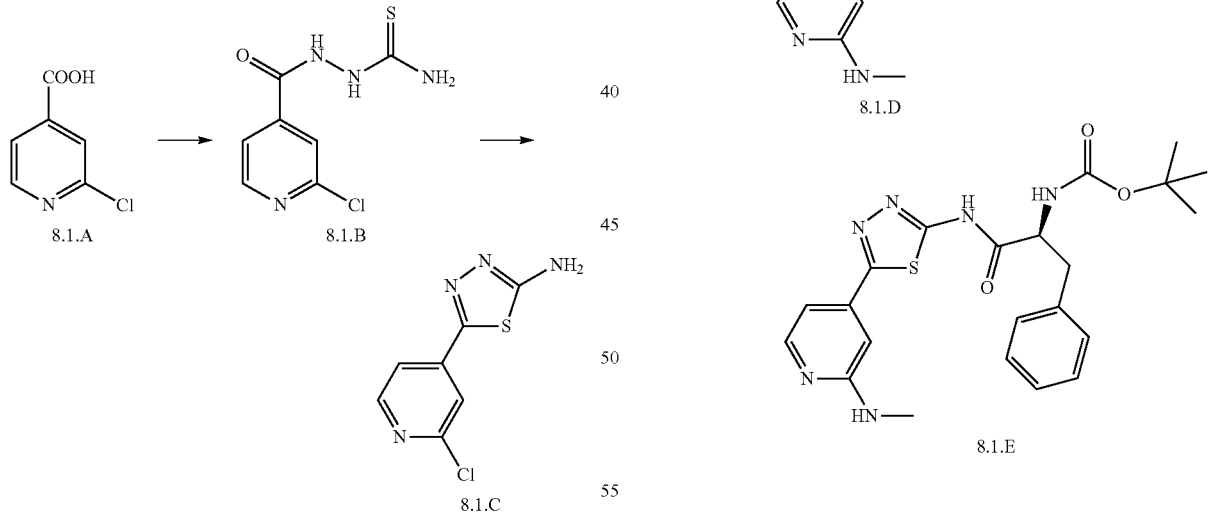

4-(5-Amino-1,3,4-thiadiazol-2-yl)-N-methylpyridin-2-amine (8.1.D)

To 5-(2-chloropyridin-4-yl)-1,3,4-thiadiazol-2-amine 8.1.C (1.03 g, 4843 µmol) in a pressure tube was added 16 mL of methylamine 40% in water. The reaction was heated at 130° C. for 3 hours. The pressure tube was cooled down and precipitates were generated. The precipitates were filtered and rinsed with water and dried to afford 476 mg of product 8.1.D (47%).

tert-Butyl (S)-1-(5-(2-methylamino)pyridine-4-yl)-1,3,4-thiadiazol-2-ylamino)-1-oxo-3-phenylpropan-2-ylcarbamate (8.1.E)

To a flask with 120 mg 8.1.D (0.579 mmol) was added HBTU (439 mg, 1.16 mmol) and (S)-2-(tert-butoxycarbonyl)-3-phenylpropanoic acid (161 mg, 0.61 mmol). DMF was added followed by N-ethyl-N-isopropylpropan-2-amine (0.4 mL, 2.3 mmol). The reaction was stirred overnight. LC/MS indicated that the desired product was major. Water was added and EtOAc was used to extract the product. The EtOAc layer was dried, concentrated and purified on silica gel with 0-75% EtOAc/DCM to afford 260 mg of 8.1.E (99% yield).

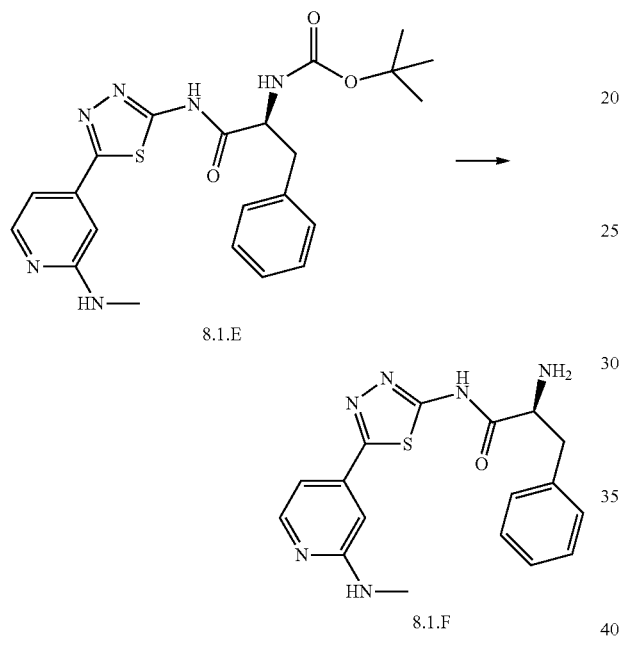

(2S)-2-amino-N-(5-(2-(methylamino)pyridine-4-yl)-1,3,4-thiadiazol-2-yl)-3-phenylpropanamide (8.1.F)

To a flask with 260 mg of 8.1.E (0.572 mmol) was added 3 mL of dichloromethane, followed by 1.5 mL of trifluoroacetic acid. The reaction was stirred for 2 hr. and concentrated. The crude reaction mixture was diluted with EtOAc and washed with saturated NaHCO$_3$. Silica gel chromatography using dichloromethane and methanol afforded 105 mg (52%) of product 8.1.F.

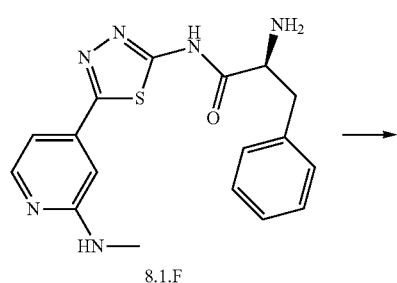

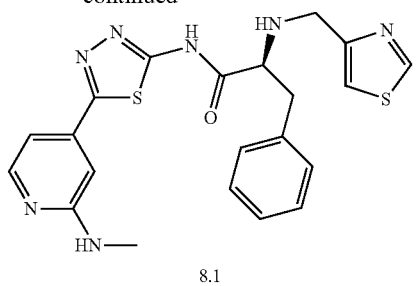

(2S)—N-(5-(2-methylamino)pyridine-4-yl)-1,3,4-thiadiazol-2-yl)-3-phenyl-2-(thiazol-4-ylmethylamino)propanamide (8.1)

To a flask with 69 mg of 8.1.F (0.19 mmol) was added thiazole-4-carbaldehyde (23 mg, 0.2 mmol), 2 mL MeOH and 1 mL dichloromethane. Then sodium cyanoborohydride (24 mg, 0.49 mmol) was added. The reaction mixture was heated at 50° C. for 1 hour. 2 drops of water were added and the reaction was concentrated and purified on reverse phase HPLC column to afford 32 mg of 8.1 (37% yield). 1H NMR (400 MHz, MeOH) δ ppm 8.90 (d, J=1.96 Hz, 1H) 8.06 (d, J=4.70 Hz, 1H) 7.31 (d, J=1.96 Hz, 1H) 7.16-7.28 (m, 5H) 7.03 (dd, J=5.48, 1.56 Hz, 1H) 6.96-7.00 (m, 1H) 3.92 (d, J=5.09 Hz, 2H) 3.78 (t, J=7.04 Hz, 1H) 3.10 (dd, J=12.00, 8.00 Hz, 1H) 3.01 (dd, J=12.00, 8.00 Hz, 1H) 2.92 (s, 3H).

7.8.2 Example 8.2

The following compound (2S)-3-(4-fluorophenyl)-N-(5-(2-(methylamine)pyridine-4-yl)-1,3,4-thiadiazol-2-yl)-2-(thiazol-4-ylmethylamino)propanamide (8.2) was prepared by the methods used for Example 8.1 using 4-fluorophenylalanine

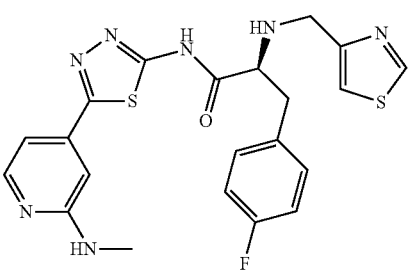

(2S)-3-(4-fluorophenyl)-N-(5-(2-(methylamine)pyridine-4-yl)-1,3,4-thiadiazol-2-yl)-2-(thiazol-4-ylmethylamino)propanamide (8.2)

1H NMR (400 MHz, MeOH) δ ppm 8.91 (d, J=1.96 Hz, 1H) 8.07 (d, J=5.48 Hz, 1H) 7.34 (d, J=1.96 Hz, 1H) 7.13-7.26 (m, 2H) 7.03 (dd, J=5.48, 1.56 Hz, 1H) 6.93-7.01 (m, 3H) 3.84-4.04 (m, 2H) 3.75 (t, J=7.04 Hz, 1H) 3.08 (dd, J=12.00, 8.00 Hz, 1H) 3.01 (dd, J=12.00, 8.00 Hz, 1H) 2.92 (s, 3H).

7.9 Example 9

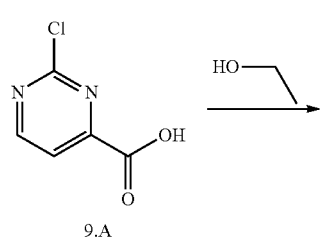

9.A

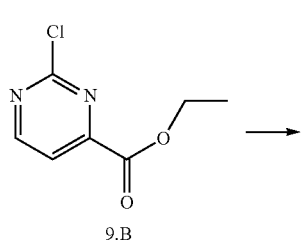

9.B

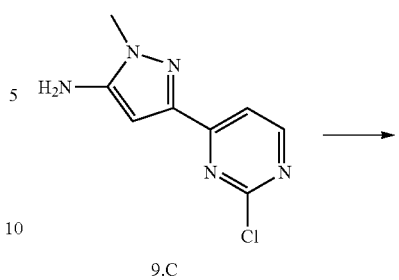

9.C

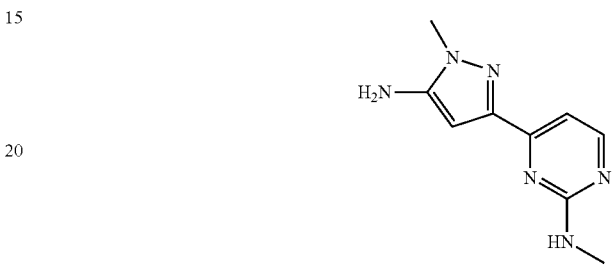

9.D

Ethyl 2-chloropyrimidine-4-carboxylate (9.B)

The reaction mixture of 2-chloropyrimidine-4-carboxylic acid, 9.A (avialable from Anichem LLC, 1.00 g, 6.3 mmol), 1,3-dicyclohexylcarbodiimide (1.4 g, 6.9 mmol) and ethanol (0.32 g, 6.9 mmol) in DCM (10 ml) was stirred at room temperature overnight. The solid was filtrated off. DCM (80 ml) was added and washed with brine (30 ml) and dried over MgSO$_4$. The solvent was evaporated. The crude product was purified by Cobi-Flash silica gel column to give 9.B. 0.74 g, yield, 63%. $^1$H NMR (400 MHz, chloroform-d) δ ppm 8.87 (1H, d, J=4.7 Hz), 7.95 (1H, d, J=4.7 Hz), 4.51 (2H, q, J=7.4 Hz), 1.45 (3H, t, J=7.0 Hz). MS ESI (pos.) m/e: 187.0 (M+H)$^+$.

3-(2-chloropyrimidin-4-yl)-1-methyl-1H-pyrazol-5-amine (9.C)

To a solution of acetonitrile (0.19 ml, 3.60 mmol) in THF 4.0 ml was slowly added butyllithium (1.5 ml, 2.5M solution in hexanes, 3.77 mmol) at −78° C. and the mixture was stirred at −78° C. for 50 min. Ethyl 2-chloropyrimidine-4-carboxylate, 9.B (0.64 g, 3.43 mmol) in THF (3.0 ml) was added dropwise at −78° C. The reaction mixture was continued to stirred at −78° C. for 1 h. The reaction mixture was allowed to warm up to room temperature and stirred for 1 h. The reaction was quenched by addition of water (15.0 ml). The aquouse layer was acidified to pH=5 with 1N HCl, and extracted with ethyl acetate (30×3 ml). The combined organic layer was washed with brine (20 ml) and dried over Na$_2$SO$_4$. The solvent was removed to give the intermediate ketonitrile as a dark brown solid. The crude ketonitrile was treated with methyl hydrazine (0.37 ml, 6.86 mmol) in methanol (6.0 ml) and 2N HCl (3.0 ml) at 80° C. for 6 h. LC-MS results indicated the product was formed. The crude mixture was purified by preperative HPLC to give 9.C. 0.23 g, yield 32%. MS ESI (pos.) m/e: 209.9 (M+H)$^+$.

4-(5-amino-1-methyl-1H-pyrazol-3-yl)-N-methylpyrimidin-2-amine (9.D)

The reaction mixture of 3-(2-chloropyrimidin-4-yl)-1-methyl-1H-pyrazol-5-amine, 9.C (74.0 mg, 353.0 µmol) and methanamine (394.7 mg, 1.0 ml, 40% in water, 1.27 mmol) in 1,4-dioxane (1.5 ml) in a seal tube was heated at 50° C. for 7 h. LCMS results showed the reaction was done. The solvent was removed. The crude product was used for next step. MS ESI (pos.) m/e: 205.0 (M+H)$^+$.

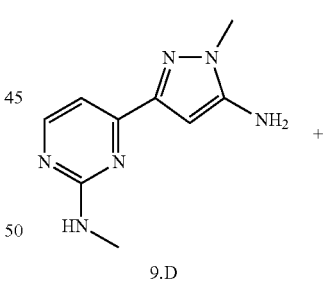

9.D

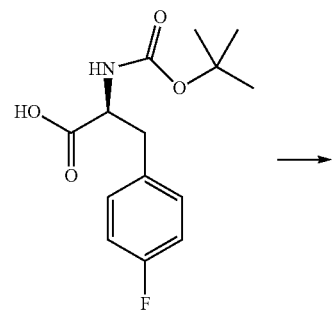

-continued

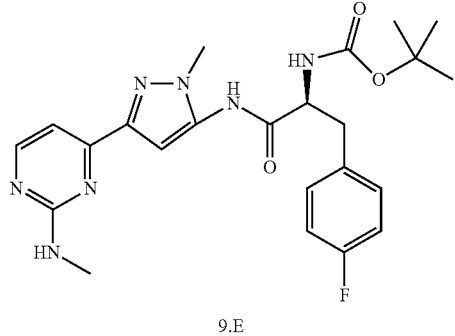

9.E tert-Butyl (S)-3-(4-fluorophenyl)-1-(1-methyl-3-(2-(methylamino) pyrimidin-4-yl)-1H-pyrazol-5-ylamino)-1-oxopropan-2-ylcarbamate (9.E)

The mixture of 4-(5-amino-1-methyl-1H-pyrazol-3-yl)-N-methylpyrimidin-2-amine, 9.D (72.0 mg, 353 μmol), boc-4-fluoro-1-phenylalanine (99.9 mg, 0.35 mmol) and N1-((ethylimino) methylene)-N3,N3-dimethylpropane-1,3-diamine hydrochloride (81.1 mg, 0.42 mmol) in pyridine (1.5 ml) was stirred at room temperature overnight. The LCMS results indicated the reaction was done. The mixture was purified by preperative HPLC to give 9.E. 0.125 g, yield 76%. ¹H NMR (500 MHz, acetonitrile-d₃) δ ppm 8.66 (1H, s), 7.26-7.42 (3H, m), 7.11 (2H, t, J=8.8 Hz), 6.96 (1H, s), 4.45 (1H, m), 3.77 (3H, s), 3.20 (1H, m), 3.12 (3H, s), 3.01 (1H, m), 1.41 (9H, s). MS ESI (pos.) m/e: 470.2 (M+H)⁺.

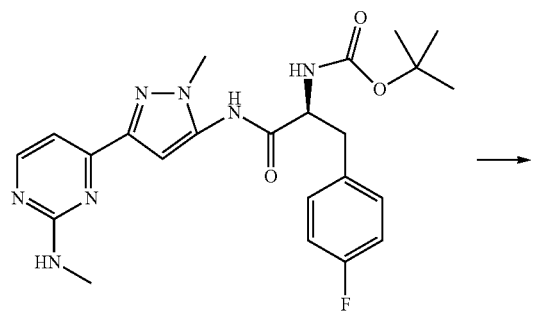

9.E

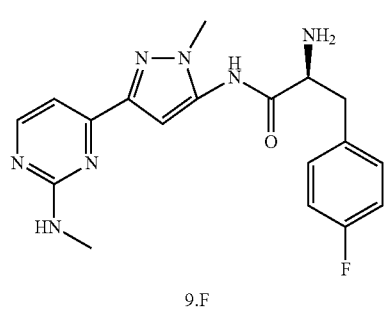

9.F (2S)-2-amino-3-(4-fluorophenyl)-N-(1-methyl-3-(2-(methylamino)pyrimidin-4-yl)-1H-pyrazol-5-yl)propanamide (9.F)

tert-Butyl (S)-3-(4-fluorophenyl)-1-(1-methyl-3-(2-(methylamino)pyrimidin-4-yl)-1H-pyrazol-5-ylamino)-1-oxopropan-2-ylcarbamate, 9.E (0.12 g, 0.26 mmol) was treated with hydrogen chloride, 4.0 M solution in 1,4-dioxane (9.32 mg, 0.256 mmol) in 1,4-dioxane (3.0 ml) at 50° C. for 1 h. LCMS showed that Boc group was removed from SM. The solvent was removed. The crude 9.F was used for next step without further purification. MS ESI (pos.) m/e: 370.1 (M+H)⁺.

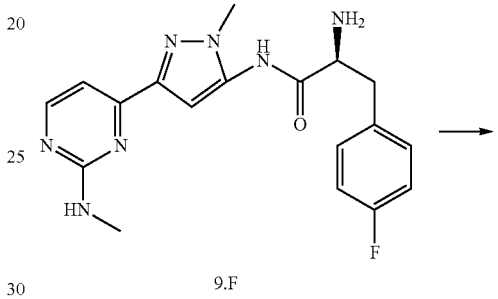

9.F

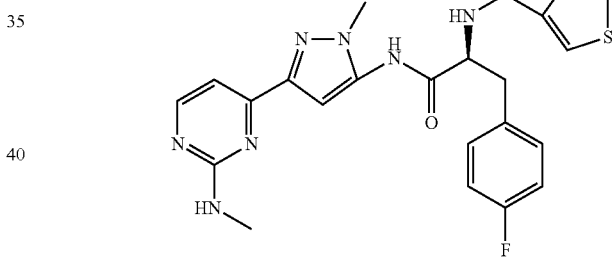

9

(2S)-3-(4-fluorophenyl)-N-(1-methyl-3-(2-(methylamino)pyrimidin-4-yl)-1H-pyrazol-5-yl)-2-(thiazol-4-ylmethylamino)propanamide (9)

The reaction mixture of (2S)-2-amino-3-(4-fluorophenyl)-N-(1-methyl-3-(2-(methylamino)pyrimidin-4-yl)-1H-pyrazol-5-yl)propanamide, 9.F (20.0 mg, 54.0 μmol), thiazole-4-carbaldehyde (7.4 mg, 65.0 μmol) and sodium triacetoxyborohydride (34.0 mg, 162.0 μmol) in DCE (1.0 ml), DMF (0.1 ml) and sodium acetate (3 eqv. 3.0 mg) was stirred at 25° C. overnight. The LCMS indicated compound 9 was formed. The crude mixture was purified by preperative HPLC to give the compound 9. ¹H NMR (500 MHz, MeOH) δ ppm 9.13 (1H, d, J=2.0 Hz), 8.23 (1H, d, J=5.0 Hz), 7.82 (1H, s), 7.35 (1H, d, J=5.0 Hz). 7.32-7.30 (2H, m), 7.13-7.11 (2H, m), 6.95 (1H, s), 4.53-4.46 (2H, m), 4.37-4.34 (1H, m), 3.62 (3H, s), 3.46-3.45 (1H, m), 3.23-3.21 (1H, m), 3.08 (3H, s). MS ESI (pos.) m/e: 467.2 (M+H)⁺.

7.10 Example 10

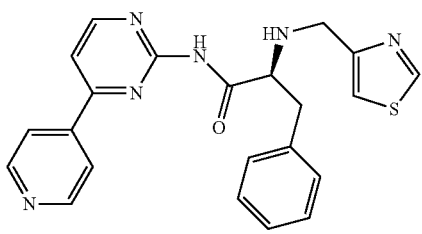 [SMILES: O=C(Nc1nccc(-c2ccncc2)n1)[C@H](Cc1ccccc1)NCc1cscn1]

(S)-3-phenyl-N-(4-(pyridin-4-yl)pyrimidin-2-yl)-2-(thiazol-4-ylmethylamino)propanamide (10)

The compound was prepared from 4-(pyridin-4-yl)pyrimidin-2-amine using procedures analagous to those in Example 3.1. LCMS ESI (pos.) m/e: 417.1 (M+1).

7.11 Example 11

7.11.1 Example 11.1

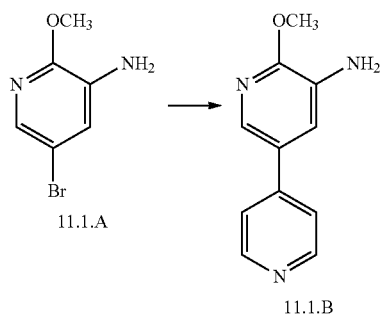 [SMILES: COc1ncc(Br)cc1N ; COc1ncc(-c2ccncc2)cc1N]

2-Methoxy-5-(pyridine-4-yl)pyridine-3-amine (11.1.B)

To a flask were weighed 5-bromo-2-methoxypyridin-3-amine, 11.1.A, (1 g, 4.9 mmol), pyridin-4-ylboronic acid (0.73 g, 5.9 mmol), X-Phos (0.47 g, 0.99 mmol), tris(dibenzylideneacetone)dipalladium (0) (0.22 g, 0.25 mmol), and Potassium phosphate tribasic (3.13 g, 14.8 mmol). N-butanol was added as a solvent and the reaction mixture was heated at 110° C. for 3 hr. The solids were filtered off through a pad of celite. The filtrate was concentrated and chromatographed by gradient EtOAc/DCM and then 10% MeOH/DCM to afford 730 mg of 11.1.B (74%).

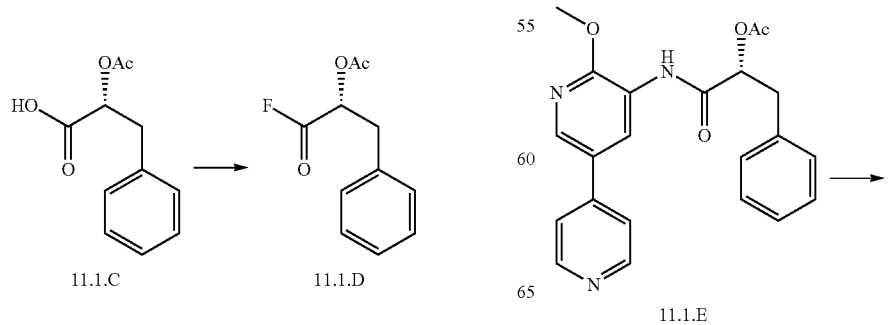

(R)-1-fluoro-1-oxo-3-phenylpropan-2-ylacetate (11.1.D)

(R)-2-acetoxy-3-phenylpropanoic acid 11.1.C (1170 mg, 5619 μmol) was azeotroped and dissolved in DCM under nitrogen. Pyridine (454 μl, 5619 μmol) was added followed by cyanuric fluoride (1423 μl, 16858 μmol) at −20° C. After 1 h, reaction was worked up with ice and DCM to afford 1.04 g (88%) crude (R)-1-fluoro-1-oxo-3-phenylpropan-2-yl acetate 11.1.D. The crude was directly used for next step.

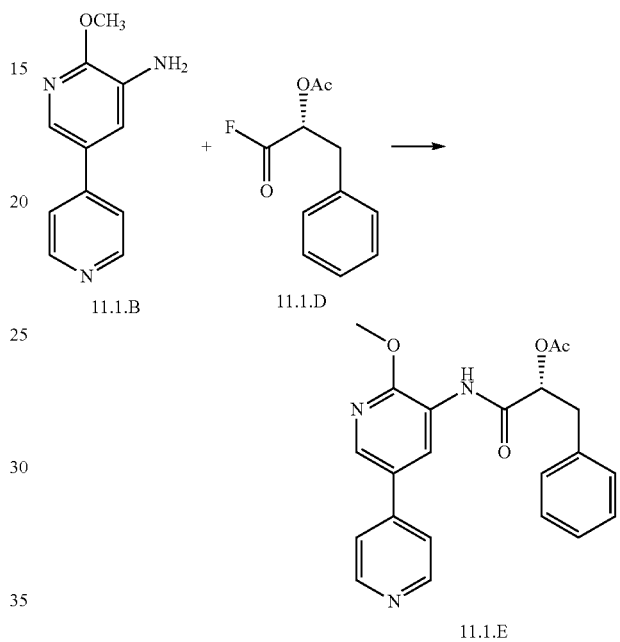

(R)-1-(2-methoxy-5-(pyridine-4-yl)pyridine-3-ylamino)-1-oxo-3-phenylpropan-2-1 acetate (11.1.E)

2-methoxy-5-(pyridin-4-yl)pyridin-3-amine 11.1.B (874 mg, 4343 μmol) was azeotroped, flushed with nitrogen and dissolved in DCM. Diisopropylethylamine (1513 μl, 8687 μmol) was added followed by a DCM solution of (R)-1-fluoro-1-oxo-3-phenylpropan-2-yl acetate 11.1.D (1004 mg, 4778 μmol). The reaction was stirred for about 6 hr., quenched with water. There was a small amount of unreacted starting material. Chromatograph with gradient MeOH/DCM did not separate it from the product. The mixture (1.5 g) was directly carried to the next step reaction.

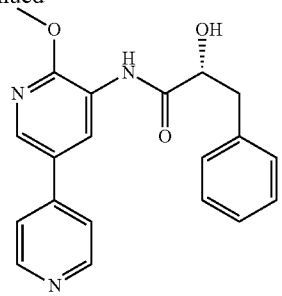

11.1.F

(R)-2-hydroxy-N-(2-methoxy-5-(pyridine-4-yl)pyridine-3-yl)-3-phenylpropanamide (11.1.F)

The mixture (R)-1-(2-methoxy-5-(pyridin-4-yl)pyridin-3-ylamino)-1-oxo-3-phenylpropan-2-yl acetate 11.1.E (1500 mg, 3832 µmol) was dissolved in 22 mL MeOH. Potassium carbonate (1059 mg, 7664 µmol) was added to the mix. The reaction was stirred for 1 hour. LC/MS showed the product and trace starting material. Filtered, concentrated and worked up between DCM and water to afford 1.4 g of crude mix. Used DCM to rinse and filtered. The solids are purer by TLC. 1.02 g of 11.1.F was obtained.

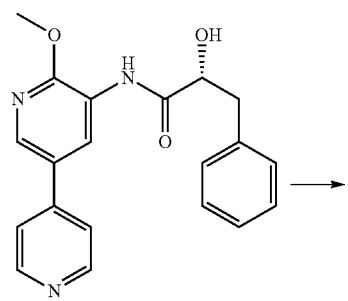

11.1.F

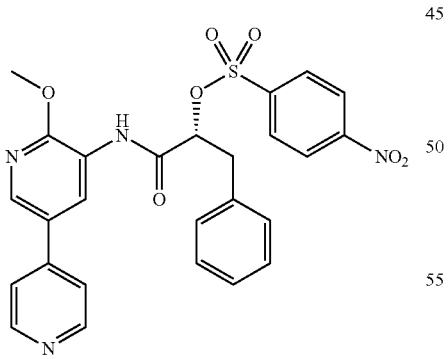

11.1.G

(R)-1-(2-methoxy-5-(pyridine-4-yl)pyridine-3-ylamino)-1-oxo-3-phenylpropan-2-yl-4-nitrobenzenesulfonate (11.1.G)

To a flask with 1.02 g (2.9 mmol) 11.1.F was added DCM, triethylamine (1.01 mL, 7.3 mmol), followed by 4-nitrobenzenesulfonyl chloride (0.97 g, 4.4 mmol). After 1 hr. 30 min, reaction was mostly completed. LC/MS showed product mass of 535.1. Another 100 mg 4-nitrobenzenesulfonyl chloride was added and the reaction was stirred for another 45 min. The reaction was worked-up with DCM and H$_2$O. Silica gel purification with EtOAc/DCM on a 40 g silica gel column separated the side spots. The product 11.1.G was obtained in 69% yield (1.08 g).

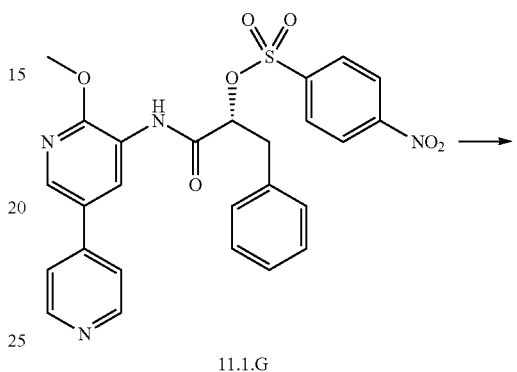

11.1.G 11.1

S)—N-(2-methoxy-5-(pyridin-4-yl)pyridin-3-yl)-3-phenyl-2-(1-(pyridin-2-yl)cyclopropylamino)propanamide (11.1)

1-(pyridin-2-yl)cyclopropanamine (75.3 mg, 561 µmol) and (R)-1-(2-methoxy-5-(pyridin-4-yl)pyridin-3-ylamino)-1-oxo-3-phenylpropan-2-yl-4-nitrobenzenesulfonate (150 mg, 281 µmol) were weighed into a 25 mL flask. 0.5 mL DMF was added. The reaction was heated to 100° C. for 15 hours. LC/MS showed the formation of (S)—N-(2-methoxy-5-(pyridin-4-yl)pyridin-3-yl)-3-phenyl-2-(1-(pyridin-2-yl)cyclopropylamino)propanamide 11.1 in a MS of 466.1 as major product. 50 mg fairly pure product was obtained by silica gel chromatography with 0-90% EtOAc/DCM gradient. 30 mg (23%) pure product 11.1 was produced after HPLC purification. 1H NMR (400 MHz, MeOH) δ ppm 8.79 (d, J=2.35 Hz, 1H) 8.59 (d, J=6.26 Hz, 2H) 8.30-8.33 (m, 1H) 8.28 (d, J=2.35 Hz, 1H) 7.69 (dd, J=4.50, 1.76 Hz, 2H) 7.57 (td, J=7.73, 1.76 Hz, 1H) 7.20-7.27 (m, 3H) 7.06-7.19 (m, 4H) 3.63 (dd, J=8.61, 4.70 Hz, 1H) 3.05 (dd, J=13.69, 5.09 Hz, 1H) 2.84

(dd, J=13.69, 5.09 Hz, 1H) 1.13-1.22 (m, 1H) 1.07-1.13 (m, 1H) 0.98-1.07 (m, 1H) 0.87-0.96 (m, 1H).

7.12 Example 12

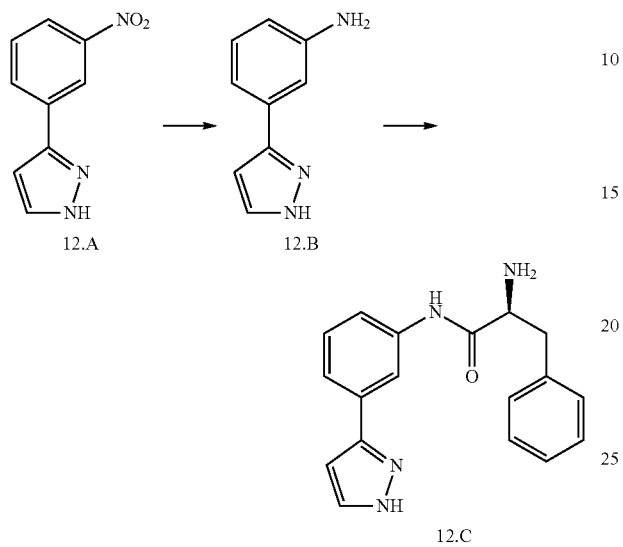

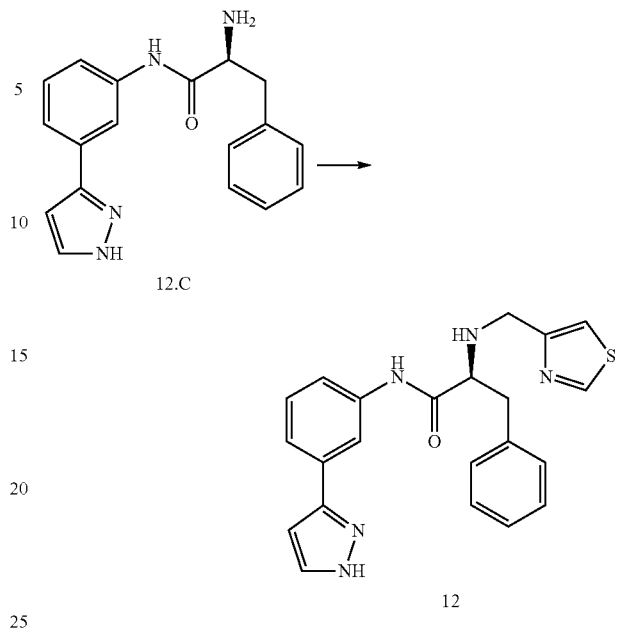

(2S)—N-(3-(1H-pyrazol-3-yl)phenyl)-3-phenyl-2-(thiazol-4-ylmethylamino)propanamide (12)

3-(1H-pyrazol-3-yl)benzenamine (12.B)

To a solution of 3-(3-nitrophenyl)-1H-pyrazole 12.A (490 mg, 2.59 mmol, available from Oakwood) in methanol (5 mL) was added 10% Pd on carbon by weight (100 mg). The air was evacuated from the reaction flask and was replaced with hydrogen. The resulting slurry was stirred overnight at room temperature. The reaction mixture was filtered, and the mother liquor condensed to afford 3-(1H-pyrazol-3-yl)benzenamine 12.B (397 mg, 96% yield).

(2S)—N-(3-(1H-pyrazol-3-yl)phenyl)-2-amino-3-phenylpropanamide (12.C)

To a solution of 3-(1H-pyrazol-3-yl)benzenamine 12.B (400 mg, 2.52 mmol) in DMF (5 mL) was added (S)-2-(tert-butoxycarbonyl)-3-phenylpropanoic acid (795 mg, 3.02 mmol, available from Aldrich), diisopropylethylamine (0.65 mL, 3.75 mmol) and 2-(1H-Benzotriazole-1-yl)-1,1,3,3-Tetramethyluronium hexafluorophosphate (1.14 g, 3.02 mmol). The resulting mixture was stirred overnight at room temperature. The mixture was then partitioned between water (50 mL) and EtOAc (50 mL). The layers were separated and the aqueous phase was extracted with additional EtOAc (2×50 mL). The combined organic layers were washed with water and brine, dried (MgSO₄), and concentrated.

The crude intermediate was then stirred in HCl solution (4M in dioxane, 5 mL) for 1 h. The mixture was then concentrated, the resulting white solid was neutralized with NaHCO₃ saturated solution (5 mL) and extracted with DCM (2×5 mL) to afford (2S)—N-(3-(1H-pyrazol-3-yl)phenyl)-2-amino-3-phenylpropanamide 12.C as a colorless film (200 mg, 26% yield).

To a solution of (2S)—N-(3-(1H-pyrazol-3-yl)phenyl)-2-amino-3-phenylpropanamide 12.C (200 mg, 0.65 mmol) in DCM (5 mL) was added thiazole-4-carbaldehyde (73 mg, 0.65 mmol, available from Combi-Blocks). The mixture was stirred for 1 h, then sodium triacetoxyborohydride (207 mg, 0.98 mmol) was added and the mixture stirred for an additional hour at room temperature. The mixture was then concentrated and the crude product purified by reverse phase chromatography (0-100% CH₃CN/water+0.5% TFA) to afford (2S)—N-(3-(1H-pyrazol-3-yl)phenyl)-3-phenyl-2-(thiazol-4-ylmethylamino)propanamide 12 as a white solid (66.7 mg, 25% yield). LCMS ESI (pos.) m/e: 404.0 (M+1): 1H NMR (500 MHz, MeOH-D4) δ ppm 9.11 (d, J=1.96 Hz, 1H), 7.82-7.87 (m, 1H), 7.80 (d, J=1.96 Hz, 1H), 7.74 (d, J=2.20 Hz, 1H), 7.51-7.60 (m, 1H), 7.21-7.38 (m, 7H), 6.68 (d, J=2.20 Hz, 1H), 4.50 (d, J=5.38 Hz, 2H), 4.29 (dd, J=9.29, 5.87 Hz, 1H), 3.43 (dd, J=13.45, 5.62 Hz, 1H), 3.27 (dd, J=13.45, 9.29 Hz, 1H).

7.13 Example 13

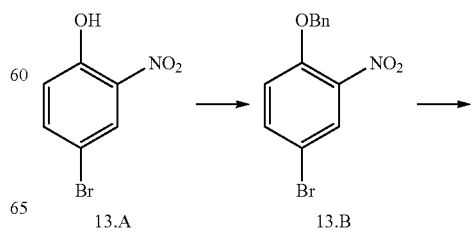

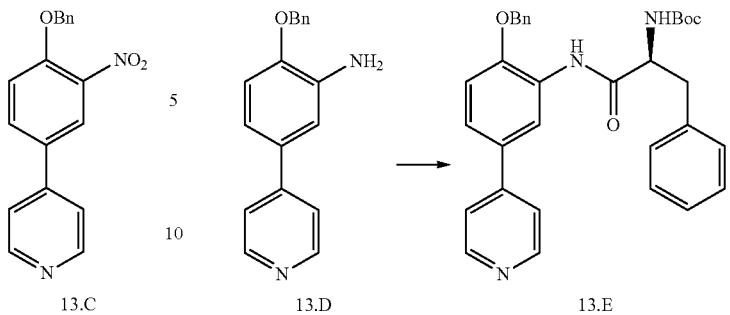

1-((4-Bromo-2-nitrophenoxy)methyl)benzene (13.B)

To a solution of 4-bromo-2-nitrophenol 13.A (1.00 g, 4.59 mmol, available from Aldrich) and benzyl bromide (0.55 mL, 5.05 mmol) in DMF (10 mL) was added cesium carbonate (2.2 g, 6.9 mmol). The mixture was stirred overnight at room temperature and then partitioned between AcOEt and water. The organic phase was concentrated to afford 1-((4-bromo-2-nitrophenoxy)methyl)benzene 13.B (1.40 g, 99% yield) which was used in the next step without any further purification.

4-(4-(Benzyloxy)-3-nitrophenyl)pyridine (13.C)

To a solution of 1-((4-bromo-2-nitrophenoxy)methyl)benzene 13.B (1.40 g, 4.55 mmol) and pyridin-4-ylboronic acid (665 mg, 5.45 mmol, available from Aldrich) in DMF (10 mL) was added cesium carbonate (2.93 g, 9.0 mmol). The mixture was stirred overnight at 80° C. and then partitioned between AcOEt and water. The organic phase was concentrated to afford 4-(4-(benzyloxy)-3-nitrophenyl)pyridine 13.0 (1.52 g, 109% yield) which was used in the next step without any further purification.

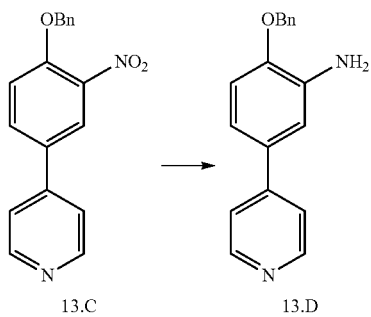 [SMILES: O=[N+]([O-])c1cc(-c2ccncc2)ccc1OCc1ccccc1 ; Nc1cc(-c2ccncc2)ccc1OCc1ccccc1]

2-(Benzyloxy)-5-(pyridin-4-yl)benzenamine (13.D)

To a solution of 4-(4-(benzyloxy)-3-nitrophenyl)pyridine 13.0 (1.52 g, 4.97 mmol) in ethyl acetate (20 mL) was added tin(II) chloride dihydrate (4.49 g, 19.87 mmol). The mixture was heated to reflux for 2 hours, then quenched with 100 ml 1N NaOH. The resulting mixture was stirred overnight at room temperature, then partitioned between AcOEt and water. The organic phase was dried on MgSO$_4$ and concentrated to afford 2-(benzyloxy)-5-bromobenzenamine 13.D (1.59 g, 115% yield) which was used in the next step without any further purification.

(S)-tert-butyl 1-(2-(benzyloxy)-5-(pyridin-4-yl)phenylamino)-1-oxo-3-phenylpropan-2-ylcarbamate (13.E)

To a solution of 2-(benzyloxy)-5-bromobenzenamine 13.D (1.59 g, 5.76 mmol) in DMF (20 mL) was added (S)-2-(tert-butoxycarbonyl)-3-phenylpropanoic acid (1.83 g, 6.91 mmol, available from Aldrich), diisopropylethylamine (1.50 mL, 8.64 mmol) and 2-(1H-Benzotriazole-1-yl)-1,1,3,3-Tetramethyluronium hexafluorophosphate (2.62 g, 6.91 mmol). The resulting mixture is stirred overnight at room temperature. The mixture was then partitioned between water and EtOAc, the organic layer was separated, and the aqueous phase was extracted with additional EtOAc. The combined organic layers were washed with water and brine, dried (MgSO$_4$), and concentrated. The residue was purified by silica gel flash chromatography (0-100% EtOAc/hexane) to afford tert-butyl (S)-1-(3-(1H-pyrazol-4-yl)phenylamino)-1-oxo-3-phenylpropan-2-ylcarbamate 13.E (1.25 g, 35% yield).

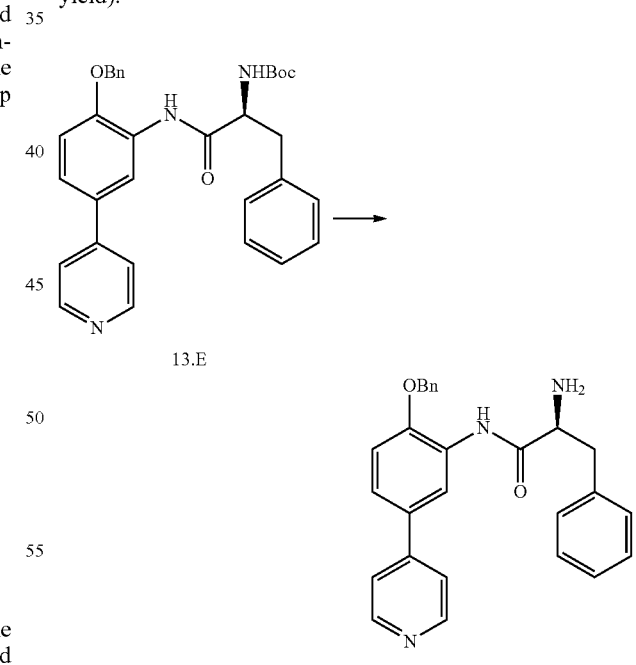

(S)-2-Amino-N-(2-(benzyloxy)-5-(pyridin-4-yl)phenyl)-3-phenylpropanamide (13.F)

To a solution of tert-butyl (S)-1-(3-(1H-pyrazol-4-yl)phenylamino)-1-oxo-3-phenylpropan-2-ylcarbamate 13.E (1.25 g, 2.39 mmol) in MeOH (10 mL) was added 4M HCl in dioxane solution (10 ml, 40 mmol). The resulting mixture was stirred for 2 hours at room temperature. The mixture was then concentrated to afford crude (S)-2-amino-N-(2-(benzyloxy)-5-(pyridin-4-yl)phenyl)-3-phenylpropanamide 13.F which was used in the next step without any further purification.

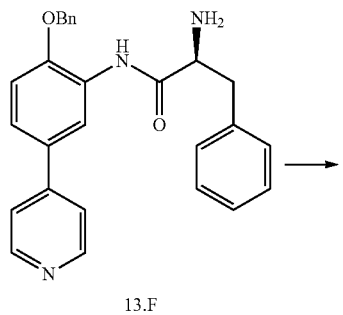

13.F

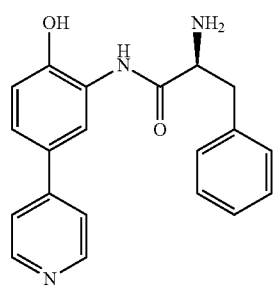

13.G

(S)-2-Amino-N-(2-hydroxy-5-(pyridin-4-yl)phenyl)-3-phenylpropanamide (13.G)

To a solution of (S)-2-amino-N-(2-(benzyloxy)-5-(pyridin-4-yl)phenyl)-3-phenylpropanamide 13.F (200 mg, 0.473 mmol) in methanol (2 mL) was added 10% Pd on carbon by weight (50 mg). The air was evacuated from the reaction flask and was replaced with hydrogen. The resulting slurry was stirred overnight at room temperature. The reaction mixture was filtered and the mother liquor condensed. The crude material was purified by reverse phase preparative HPLC to afford (S)-2-amino-N-(2-hydroxy-5-(pyridin-4-yl)phenyl)-3-phenylpropanamide 13.G (100 mg, 63% yield).

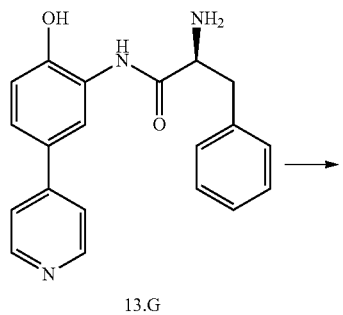

13.G

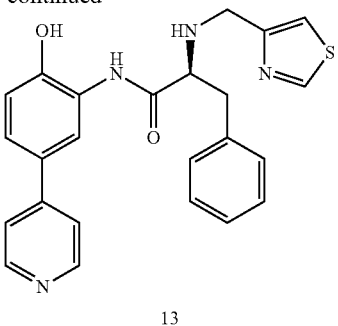

13

Synthesis of (S)—N-(2-hydroxy-5-(pyridin-4-yl)phenyl)-3-phenyl-2-(thiazol-4-ylmethylamino)propanamide (13)

The same procedure as example 12 was employed, replacing (2S)—N-(3-(1H-pyrazol-4-yl)phenyl)-2-amino-3-phenylpropanamide 12.0 with (S)-2-amino-N-(2-hydroxy-5-(pyridin-4-yl)phenyl)-3-phenylpropanamide 13.G to give (S)—N-(2-hydroxy-5-(pyridin-4-yl)phenyl)-3-phenyl-2-(thiazol-4-ylmethylamino)propanamide 13 as a white solid (6.0 mg, 32% yield). LCMS ESI (pos.) m/e: 431.0 (M+1): 1H NMR (400 MHz, MeOH-D4) δ ppm 7.59 (d, J=1.96 Hz, 1H), 7.20 (d, J=6.65 Hz, 2H), 6.94 (d, J=2.35 Hz, 1H), 6.61 (d, J=7.04 Hz, 2H), 6.25 (d, J=1.96 Hz, 1H), 6.16 (dd, J=8.61, 2.35 Hz, 1H), 5.74-5.85 (m, 5H), 5.51 (d, J=8.61 Hz, 1H), 2.97 (t, J=7.43 Hz, 1H), 2.93 (d, J=4.70 Hz, 2H), 1.84-1.91 (m, 1H), 1.70-1.76 (m, 1H).

7.14 Example 14

7.14.1 Example 14.1

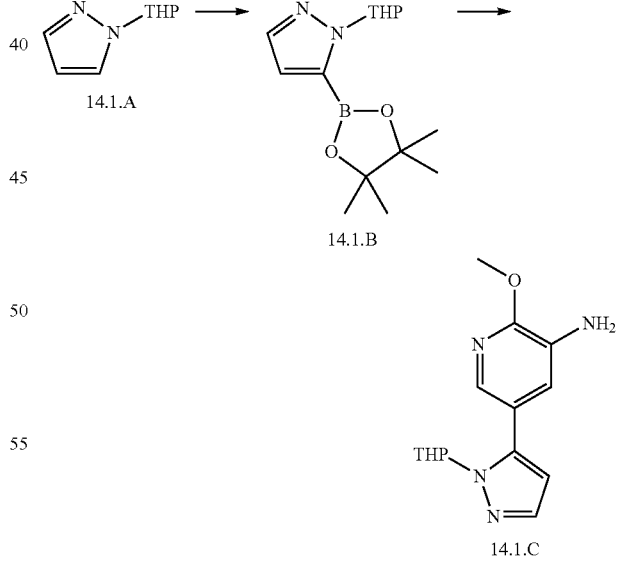

1-(Tetrahydro-2H-pyran-2-yl)-5-(4,4,5,5-tetramethyl-1,3,2-dioxaborolan-2-yl)-1H-pyrazole (14.B.A)

To a 500 ml flask was added 1-(tetrahydro-2H-pyran-2-yl)-1H-pyrazole 14.1.A and 100 ml of THF. The solution was cooled to −78° C. at which time butyllithium (52 ml, 83 mmole, 1.6M in hexanes) and pinacol (9.8 g, 83 mmole) were added. The reaction was stirred for 5 minutes at −78 C and then triisopropyl borate (19 g, 103 mmole) was added. The reaction was slowly warmed to room temperature over 90 minutes and then stirred at room temperature for an additional 16 hours at which time the reaction was quenched with NH₄Cl aq. (pH ~7-8), extracted with EtOAc, and purified by silica gel chromatography to give 1-(tetrahydro-2H-pyran-2-yl)-5-(4,4,5,5-tetramethyl-1,3,2-dioxaborolan-2-yl)-1H-pyrazole 14.1.B (7.2 g, 38% yield).

2-Methoxy-5-(1-(tetrahydro-2H-pyran-2-yl)-1H-pyrazol-5-yl)pyridin-3-amine (14.1.C)

To a 100 ml flask was added 1-(tetrahydro-2H-pyran-2-yl)-5-(4,4,5,5-tetramethyl-1,3,2-dioxaborolan-2-yl)-1H-pyrazole 14.1.B (6.0 g, 22 mmol), 5-bromo-2-methoxypyridin-3-amine (4 g, 20 mmol), 100 ml of DME, and 30 ml of water. Argon was then bubbled through the solution for 8 minutes at which time Pd(Ph₃)₄ (460 mg, 0.39 mmole) was added and argon was then bubbled through the solution for an additional 2 minutes. The reaction was then heated to 92° C. for 12 hours at which time the crude was quenched with brine and extracted with EtAc. The solvent was removed and the crude purifed on silica gel (eluting with 0-70% EtAc in Hexanes) to 2-methoxy-5-(1-(tetrahydro-2H-pyran-2-yl)-1H-pyrazol-5-yl)pyridin-3-amine 14.1.C (5.3 g, 97. % yield).

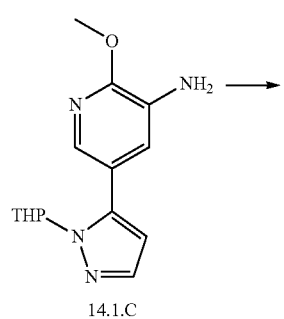

14.1.C

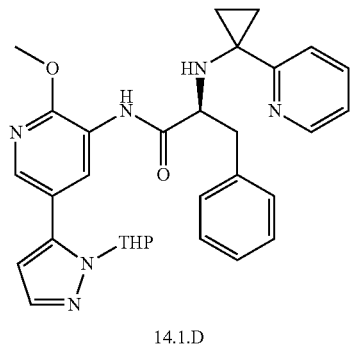

14.1.D (2S)—N-(2-methoxy-5-(1-(tetrahydro-2H-pyran-2-yl)-1H-pyrazol-5-yl)pyridin-3-yl)-3-phenyl-2-(1-(pyridin-2-yl)cyclopropylamino)propanamide (14.1.D)

This example was made using the same general procedure as the synthesis of 11.1 starting with 2-methoxy-5-(1-(tetrahydro-2H-pyran-2-yl)-1H-pyrazol-5-yl)pyridin-3-amine 14.1.C instead of 2-Methoxy-5-(pyridine-4-yl)pyridine-3-amine 11.1.B to give (2S)—N-(2-methoxy-5-(1-(tetrahydro-2H-pyran-2-yl)-1H-pyrazol-5-yl)pyridin-3-yl)-3-phenyl-2-(1-(pyridin-2-yl)cyclopropylamino)propanamide 14.1.D.

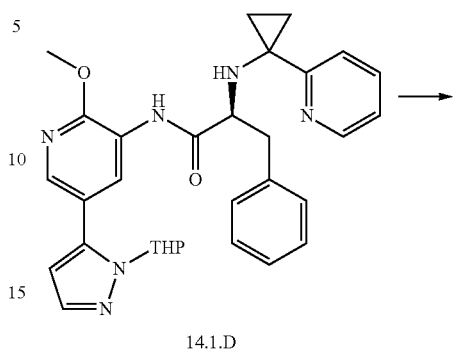

14.1.D

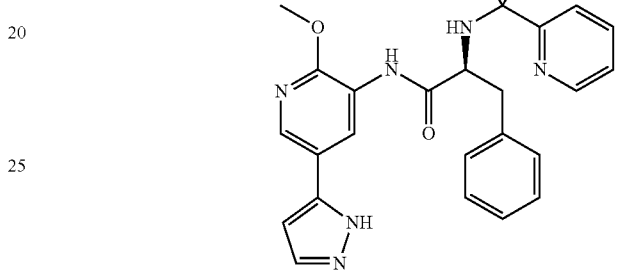

14.1.

(2S)—N-(2-methoxy-5-(1H-pyrazol-5-yl)pyridin-3-yl)-3-phenyl-2-(1-(pyridin-2-yl)cyclopropylamino)propanamide (14.1)

To a 20 ml vial was added (2S)—N-(2-methoxy-5-(1-(tetrahydro-2H-pyran-2-yl)-1H-pyrazol-5-yl)pyridin-3-yl)-3-phenyl-2-(1-(pyridin-2-yl)cyclopropylamino)propanamide 14.1.D (200 mg, 0.37 mmole), 8 ml of DCM and 2 ml of TFA. The reaction was stirred at room temperature for 2 hours then refluxed for 2 seconds at which time the solvent was removed with a stream of nitrogen. The crude was purified by reverse phase preparative HPLC to give (2S)—N-(2-methoxy-5-(1H-pyrazol-5-yl)pyridin-3-yl)-3-phenyl-2-(1-(pyridin-2-yl)cyclopropylamino)propanamide 14.1. (74 mg, 44% yield) LCMS ESI (pos.) m/e: 455.2 (M+1): 1H NMR (400 MHz, MeOH-d) δ ppm 8.59 (d, J=5.48 Hz, 1H), 8.56 (d, J=2.35 Hz, 1H,) 8.28 (d, J=2.35 Hz, 1H), 8.03-8.08 (m, 1H), 7.71 (d, J=2.35 Hz, 1H), 7.53-7.57 (m, 1H), 7.36 (d, J=8.22 Hz, 1H), 7.23-7.32 (m, 5H), 6.61 (d, J=2.35 Hz, 1H), 4.33 (t, J=7.63 Hz, 1H), 3.89 (s, 3H), 3.20 (d, J=7.83 Hz, 2H), 1.62-1.70 (m, 2H), 1.50-1.57 (m, 1H), 1.32 (ddd, J=10.17, 4.11, 2.15 Hz, 1H).

7.14.2 Example 14.2

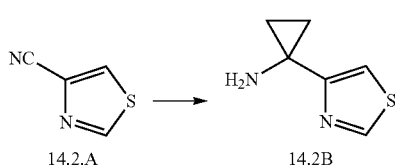 [SMILES: N#Cc1cscn1 ; NC1(c2cscn2)CC1]

14.2.A　　14.2B

1-(Thiazol-4-yl)cyclopropanamine (14.2.B)

Thiazole-4-carbonitrile (1035 mg, 9397 μmol) was azeotroped with toluene. Et₂O was added, and the clear solution was cooled to −70° C., followed by addition of titanium tetraisopropoxide (3025 μl, 10337 μmol), and ethylmagnesium bromide (6265 μl, 18795 μmol). The reaction mixture turned yellow. It remained yellow until about 15 min. The reaction was raised to RT, the solution changed into black. After 1 h., boron trifluoride diethyl etherate (2361 μl, 18795 μmol) was added and stirred for 1.5 hr. Then 1N HCl 27 mL was added, followed by 100 mL ether, 95 mL 10% NaOH. The reaction was extracted with Et2O×2 and 30% IPA/CHCl3×1. The organic layer was concentrated and purified with silica gel chromatography using 0-10% MeOH/DCM. 650 mg of product 14.2.B was obtained in 49% yield.

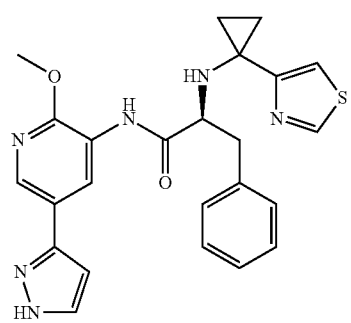

14.2

(2S)—N-(2-methoxy-5-(1H-pyrazol-3-yl)-3-phenyl-2-(1-(thiazol-4-yl)cyclopropylamino)propanamide (14.2)

This compound was synthesized following the synthesis of example 11.1. See 14.1 for the procedure for making 1-(tetrahydro-2H-pyran-2-yl)-5-(4,4,5,5-tetramethyl-1,3,2-dioxaborolan-2-yl)-1H-pyrazole. The necessary cyclopropylamine, 1-(thiazol-4-yl)cyclopropanamine, was prepared as shown above. ¹H NMR (400 MHz, MeOH) δ ppm 8.76-8.89 (m, 1H) 8.73 (d, J=1.96 Hz, 1H) 8.21-8.35 (m, 1H) 7.59-7.77 (m, 1H) 7.21-7.28 (m, 3H) 7.15-7.21 (m, 2H) 6.98 (d, J=1.96 Hz, 1H) 6.63 (d, J=1.96 Hz, 1H) 4.02 (s, 3H) 3.64 (dd, J=8.61, 4.70 Hz, 1H) 3.02 (dd, J=13.50, 4.50 Hz, 1H) 2.81 (dd, J=13.69, 8.61 Hz, 1H) 1.05-1.13 (m, 2H) 0.95-1.03 (m, 1H) 0.82-0.94 (m, 1H).

7.14.3 Example 14.3

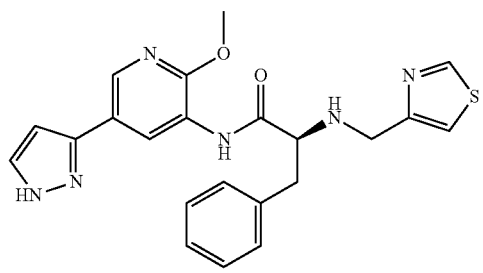 [SMILES: COc1ncc(-c2cc[nH]n2)cc1NC(=O)[C@H](Cc1ccccc1)NCc1cscn1]

(2S)—N-(2-methoxy-5-(1H-pyrazol-3-yl)pyridin-3-yl)-3-phenyl-2-(thiazol-4-ylmethylamino)propanamide (14.3)

Prepared from 1H-pyrazol-3-ylboronic acid using procedures analagous to those in Example 3.1. LCMS ESI (pos.) m/e: 435.1 (M+1).

7.15 Example 15

7.15.1 Example 15.1

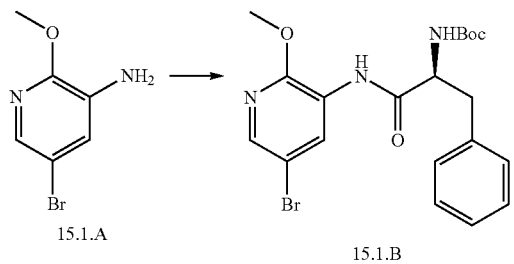

15.1.A → 15.1.B

(S)-tert-butyl 1-(5-bromo-2-methoxypyridin-3-ylamino)-1-oxo-3-phenylpropan-2-ylcarbamate (15.1.B)

To a 100 ml flask was added 5-bromo-2-methoxypyridin-3-amine 15.1.A (15 g, 74 mmole, available from Asymchem), HBTU (42 g, 111 mmoles), (S)-2-(tert-butoxycarbonyl)-3-phenylpropanoic acid (24 g, 89 mmole) of, 150 ml of DMF and 26 mL of DIEA. The reaction was stirred at 50° C. for 24 hours, at which time the reaction was quenched with water (500 ml) and extracted with EtAc (1000 ml). The organic layer was extracted three more times with water (200 mL) and the solvent was removed by rotary evaporation. The crude product was recrystallized in MeOH/H₂O (3/1) to give (S)-tert-butyl 1-(5-bromo-2-methoxypyridin-3-ylamino)-1-oxo-3-phenylpropan-2-ylcarbamate 15.1.B as white crystals (23.4 g, 70% yield).

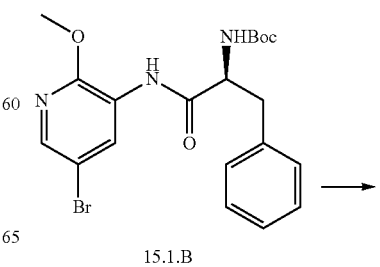

15.1.B

-continued

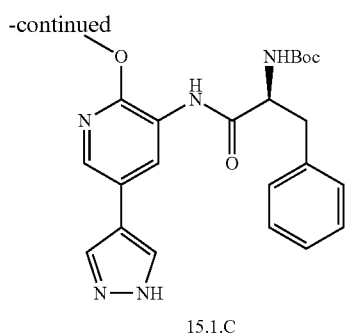
15.1.C

Tert-butyl (S)-1-(2-methoxy-5-(1H-pyrazol-4-yl)pyridin-3-ylamino)-1-oxo-3-phenylpropan-2-ylcarbamate (15.1.C)

To a solution of (S)-tert-butyl 1-(5-bromo-2-methoxypyridin-3-ylamino)-1-oxo-3-phenylpropan-2-ylcarbamate 15.1.B (1.00 g, 2.22 mmol) and 4-(4,4,5,5-tetramethyl-1,3,2-dioxaborolan-2-yl)-1h-pyrazole (0.52 g, 2.66 mmol, available from Aldrich) in t-amyl alcohol (20 mL) was added $K_3PO_4$ (1.41 g, 6.66 mmol), $Pd_2(dba)_3$ (102 mg, 0.111 mmol) and XPhos (212 mg, 0.444 mmol). The mixture was stirred for 4 hours at 100° C. and then was filtered over celite. The organic phase was concentrated and purified by flash chromatography on silica gel to afford tert-butyl (S)-1-(2-methoxy-5-(1H-pyrazol-4-yl)pyridin-3-ylamino)-1-oxo-3-phenylpropan-2-ylcarbamate 15.1.C.

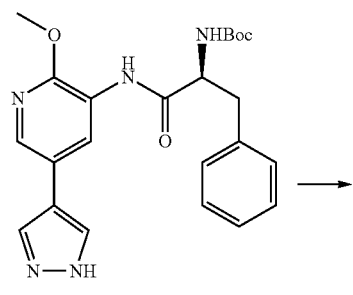
15.1.C

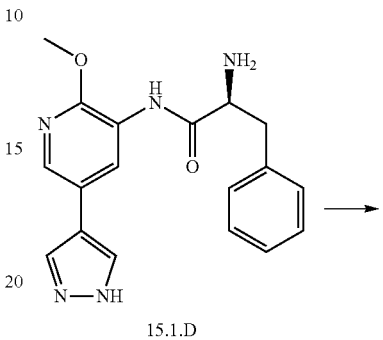
15.1.D

(2S)-2-Amino-N-(2-methoxy-5-(1H-pyrazol-4-yl)pyridin-3-yl)-3-phenylpropanamide (15.1.D)

To a solution of tert-butyl (S)-1-(2-methoxy-5-(1H-pyrazol-4-yl)pyridin-3-ylamino)-1-oxo-3-phenylpropan-2-ylcarbamate 15.1.C (302 mg, 0.67 mmol) in THF (5 mL) and water (5 mL) was added 4M HCl solution in dioxane (5 mL). The mixture was stirred overnight at room temperature, neutralized with saturated aqueous $NaHCO_3$ and extracted with 4:1 DCM/isopropanol. The organic layers were washed with brine, dried over $MgSO_4$ and concentrated to afford a 1:9 mixture of (2S)-2-amino-N-(2-methoxy-5-(1H-pyrazol-4-yl)pyridin-3-yl)-3-phenylpropanamide 15.1.D and (S)-2-amino-N-(2-oxo-5-(1H-pyrazol-4-yl)-1,2-dihydropyridin-3-yl)-3-phenylpropanamide (200 mg, 92%, yield) which were used as a mixture in the next step.

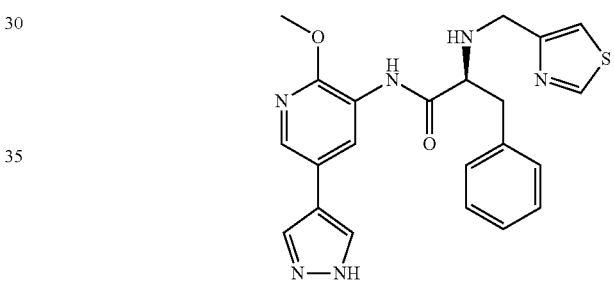
15.1

(2S)—N-(2-methoxy-5-(1H-pyrazol-4-yl)pyridin-3-yl)-3-phenyl-2-(thiazol-5-ylmethylamino)propanamide (15.1)

To a solution of a 1:9 mixture of (2S)-2-amino-N-(2-methoxy-5-(1H-pyrazol-4-yl)pyridin-3-yl)-3-phenylpropanamide 15.1.D and (S)-2-amino-N-(2-oxo-5-(1H-pyrazol-4-yl)-1,2-dihydropyridin-3-yl)-3-phenylpropanamide (90 mg, 0.28 mmol) in DCM (1 mL) was added thiazole-4-carbaldehyde (26 mg, 0.28 mmol) and was then stirred for 1 hour. Sodium triacetoxyborohydride (170 mg, 0.82 mmol) and acetic acid (16 μL, 0.28 mmol) was then added, the mixture was stirred for an additional 1 hour at room temperature, concentrated and the crude product purified by reverse phase chromatography (0-100% $CH_3CN$/water+0.5% TFA) to afford (2S)—N-(2-methoxy-5-(1H-pyrazol-4-yl)pyridin-3-yl)-3-phenyl-2-(thiazol-5-ylmethylamino)propanamide 15.1 (5.7 mg, 57%) as a white solid. LCMS ESI (pos.) m/e: 435.1 (M+1): 1H NMR (500 MHz, MeOH-D4) δ ppm 9.13 (d, J=1.83 Hz, 1H), 8.50 (d, J=1.83 Hz, 1H), 8.15 (d, J=1.83 Hz, 1H), 7.94 (s, 2H), 7.80 (d, J=1.83 Hz, 1H), 7.25-7.39 (m, 5H), 4.46-4.56 (m, 3H), 3.91 (s, 3H), 3.41 (dd, J=13.43, 6.10 Hz, 1H), 3.24 (dd, J=13.43, 9.16 Hz, 1H).

7.15.2 Example 15.2

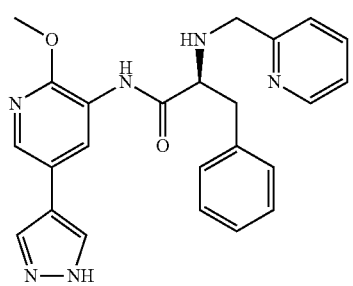 [SMILES: COc1ncc(-c2cn[nH]c2)cc1NC(=O)[C@H](Cc1ccccc1)NCc1ccccn1]

(2S)—N-(2-methoxy-5-(1H-pyrazol-4-yl)pyridin-3-yl)-3-phenyl-2-(pyridin-2-ylmethylamino)propanamide (15.2)

The compound was prepared in an analogous manner to Example 15.1. 1H NMR (500 MHz, MeOH) d ppm 3.29-3.32 (m, 1H) 3.44 (dd, J=13.43, 6.10 Hz, 1H) 3.91 (s, 3H) 4.36-4.53 (m, 2H) 4.60 (dd, J=9.16, 6.10 Hz, 1H) 7.28-7.40 (m, 5H) 7.44-7.52 (m, 2H) 7.89-7.93 (m, 1H) 7.94 (s, 2H) 8.15 (s, 1H) 8.52 (d, J=2.44 Hz, 1H) 8.68 (d, J=4.88 Hz, 1H).

7.16 Example 16

7.16.1 Example 16.1

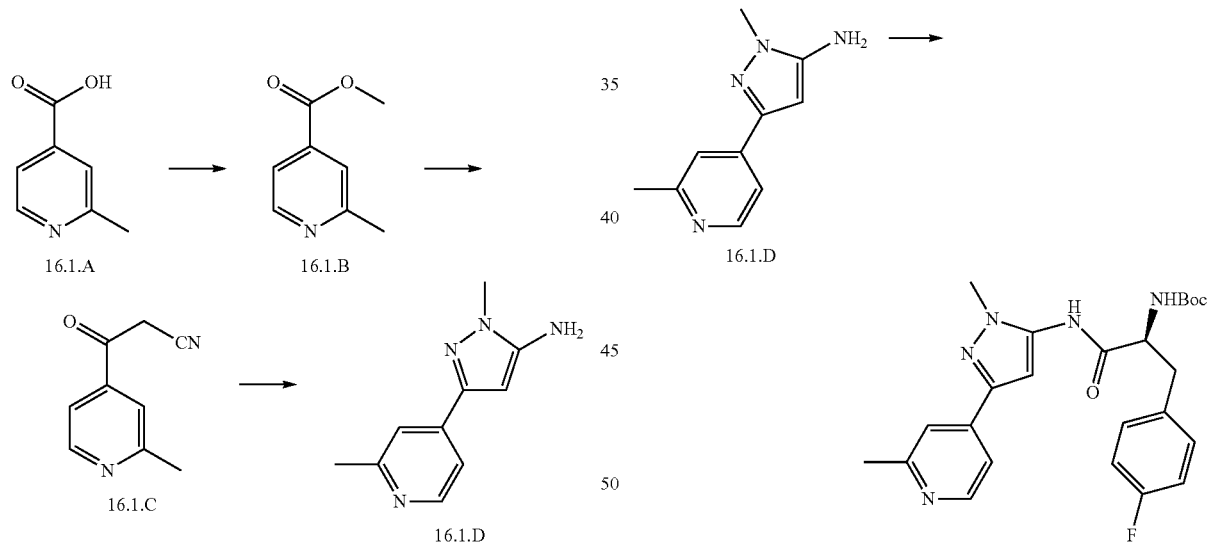

Methyl 2-methylisonicotinate (16.1.B)

To a 50 ml flask was added of 2-methylisonicotinic acid 16.1A (500 mg, 3.6 mmoles, available from Combiphos), 10 ml of MeOH and 500 ul of concentrated sulfuric acid. The reaction was refluxed for 4 hours at which time the reaction mixture was cooled, diluted with 500 ml of DCM and extracted with 100 ml of saturated sodium bicarbonate. The solvent was removed and the crude purified using a silica gel column (eluting with 5% MeOH in DCM) to give methyl 2-methylisonicotinate 16.1.B as a clear oil (290 mg, 53% yield).

3-(2-Methylpyridin-4-yl)-3-oxopropanenitrile (16.1.C)

To a 50 ml flask was added 8 ml of THF, acetonitrile (156 µl, 2.98 mmole), the mixture was cooled to −78° C. and then n-butyllithium (1191 µl, 2.98 mmole, 2.5 m in hexanes) was added. The reaction was stirred for 30 minutes at which time methyl 2-methylisonicotinate 16.1.B (150 mg, 0.99 mmoles) was added as a 2 ml THF solution. After 2 hour at −78° C., 500 µL of AcOH was added and the reaction was warmed to room temperature. The solvent was removed and the crude was purified on a silica gel column (eluting with 2% MeOH in DCM) to give 3-(2-methylpyridin-4-yl)-3-oxopropanenitrile 16.1.C as a light orange solid (170 mg 100% yield).

Methyl-3-(2-methylpyridin-4-yl)-1H-pyrazol-5-amine (16.1D)

To a 100 ml flask was added 3-(2-methylpyridin-4-yl)-3-oxopropanenitrile 16.1.C, (465 mg, 2.9 mmole), 10 ml of MeOH and methyl hydrazine (249 µl, 7.26 mmole). The reaction was stirred at 70° C. for 8 hours at which time the solvent was removed with a stream of nitrogen. The crude product was purified by using a silica gel column (eluting with 5% MeOH in DCM) to give of 1-methyl-3-(2-methylpyridin-4-yl)-1H-pyrazol-5-amine 16.1.D as a yellow film (317 mg 49% yield). (Note: converted to HCl salt).

Tert-butyl (S)-3-(4-fluorophenyl)-1-(1-methyl-3-(2-methylpyridin-4-yl)-1H-pyrazol-5-ylamino)-1-oxopropan-2-ylcarbamate (16.1.E)

To a 100 ml flask was added 1-methyl-3-(2-methylpyridin-4-yl)-1H-pyrazol-5-amine HCl 16.1.D, (310 mg, 1.65 mmole), boc-4-fluoro-1-phenylalanine (700 mg, 2.47 mmole), EDC (947 mg, 4.94 mmole) and 50 ml of pyridine. The reaction was stirred at room temperature for 4 hours at which time the solvent was removed with a stream of nitrogen (50° C.). The crude product was purified by reverse phase preparative HPLC to give tert-butyl (S)-3-(4-fluorophenyl)-1-(1-methyl-3-(2-methylpyridin-4-yl)-1H-pyrazol-5-ylamino)-1-oxopropan-2-ylcarbamate TFA 16.1.E as a light yellow solid (529 mg 56.6% yield).

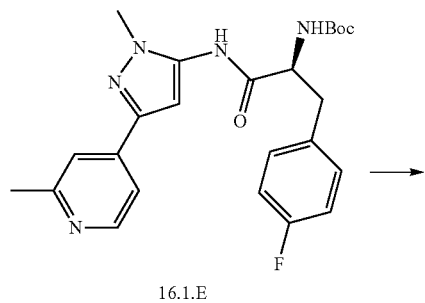

16.1.E

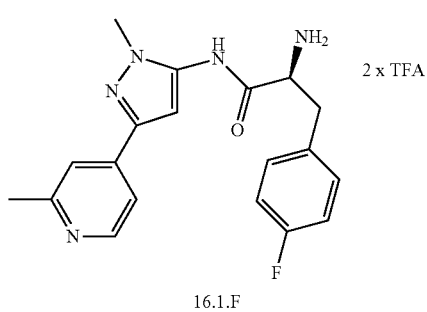

16.1.F (2S)-2-amino-3-(4-fluorophenyl)-N-(1-methyl-3-(2-methylpyridin-4-yl)-1H-pyrazol-5-yl)propanamide (16.1.F)

To a 100 flask was added tert-butyl (S)-3-(4-fluorophenyl)-1-(1-methyl-3-(2-methylpyridin-4-yl)-1H-pyrazol-5-ylamino)-1-oxopropan-2-ylcarbamate TFA 16.1.E (529 mg, 0.93 mmole), 20 ml of DCM, and 10 ml of TFA. The reaction was stirred at room temperature for 12 hours at which time the solvent was removed to give (2S)-2-amino-3-(4-fluorophenyl)-N-(1-methyl-3-(2-methylpyridin-4-yl)-1H-pyrazol-5-yl)propanamide diTFA 16.1F as a yellow solid (560 mg 100% yield). LCMS ESI (pos.) m/e: 354.1 (M+1).

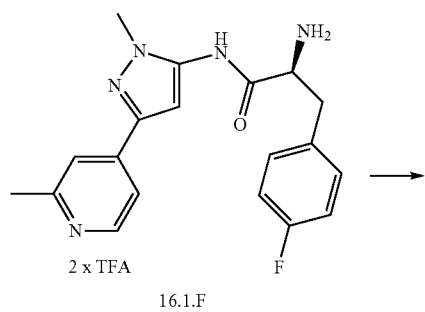

16.1.F

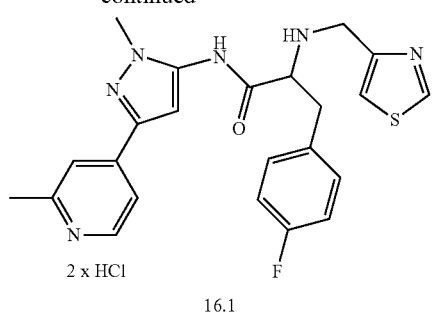

16.1

(2S)-3-(4-Fluorophenyl)-N-(1-methyl-3-(2-methylpyridin-4-yl)-1H-pyrazol-5-yl)-2-(thiazol-4-ylmethylamino)propanamide (16.1)

To a 100 ml flask was added (2S)-2-amino-3-(4-fluorophenyl)-N-(1-methyl-3-(2-methylpyridin-4-yl)-1H-pyrazol-5-yl)propanamide TFA (85 mg, 0.182 mmoles), 5 ml of DCE, DIEA (48 μl, 0.27 mmole, Make sure pH=7), 50 ul of AcOH and thiazole-4-carbaldehyde (16 mg, 0.15 mmole). The reaction was stirred at 65° C. for 5 minutes at which time sodium triacetoxyborohydride (116 mg, 0.55 mmoles) was added and stirred at 65° C. for an additional 30 minutes. The solvent was then removed and the crude purified by reverse phase preparative HPLC to give (2S)-2-amino-3-(4-fluorophenyl)-N-(1-methyl-3-(2-methylpyridin-4-yl)-1H-pyrazol-5-yl)propanamide HCl (27.8 mg, 34% yield) after salt exchange using 1 M HCl in ether (546 ul, 0.55 mmole). LCMS ESI (pos.) m/e: 451.1 (M+1): 1H NMR (500 MHz, MeOH-d) δ ppm 9.04 (d, J=1.22 Hz, 1H) 8.50 (d, J=6.11 Hz, 1H) 8.16 (s, 1H) 8.11 (d, J=6.11 Hz, 1H) 7.78 (s, 1H) 7.25 (dd, J=8.19, 5.26 Hz, 2H) 6.95-7.10 (m, 3H) 4.44 (s, 2H) 4.41 (dd, J=8.93, 5.99 Hz, 1H) 3.56 (s, 3H) 3.40 (dd, J=13.33, 5.50 Hz, 1H) 3.15 (dd, J=13.57, 9.41 Hz, 1H) 2.70 (s, 3H).

7.16.2 Example 16.2

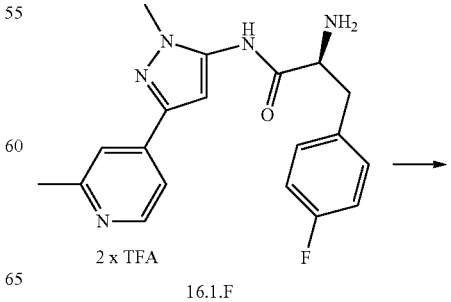

16.1.F

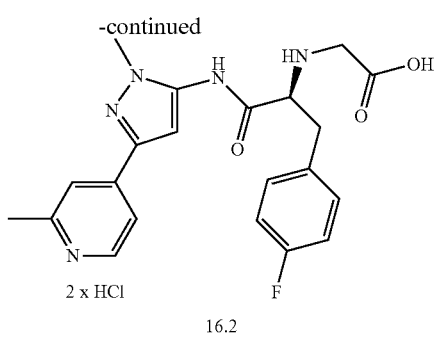

16.2

2-((S)-3-(4-Fluorophenyl)-1-(1-methyl-3-(2-methylpyridin-4-yl)-1H-pyrazol-5-ylamino)-1-oxopropan-2-ylamino)acetic acid dihydrochloride (16.2)

To a 100 ml flask was added (2S)-2-amino-3-(4-fluorophenyl)-N-(1-methyl-3-(2-methylpyridin-4-yl)-1H-pyrazol-5-yl)propanamide diTFA (120 mg, 0.21 mmole), 3 ml of DCE, DIEA (90 µl, 0.52 mmole, make sure pH=7), 75 µl of AcOH and glyoxylic acid monohydrate (19 mg, 0.21 mmole). The reaction was stirred at 65° C. for 5 minutes at which time was added sodium triacetoxyborohydride (131 mg, 0.62 mmole) and stirred at 65° C. for an additional 18 hours. The solvent was then removed and the crude purified by reverse phase preparative HPLC to give 2-((S)-3-(4-fluorophenyl)-1-(1-methyl-3-(2-methylpyridin-4-yl)-1H-pyrazol-5-ylamino)-1-oxopropan-2-ylamino)acetic acid dihydrochloride 16.2 as a yellow solid (20.7 mg, 21 mmol, yield) after salt exchange using 4 M HCl in dioxane (155 µl, 0.62 mmole). LCMS ESI (pos.) m/e: 412.1 (M+1): 1H NMR (400 MHz, MeOH) δ ppm 8.61 (d, J=6.26 Hz, 1H), 8.21 (d, J=6.65 Hz, 1H), 8.26 (s, 1H), 7.39 (dd, J=8.41, 5.28 Hz, 2H), 7.07-7.20 (m, 3H), 4.52 (br. s., 1H), 3.94-4.06 (m, 2H), 3.67-3.70 (m, 3H), 3.46 (m, 1H), 3.29 (m, 1H), 2.80 (s, 3H).

7.17 Example 17

7.17.1 Examples 17.1-17.6

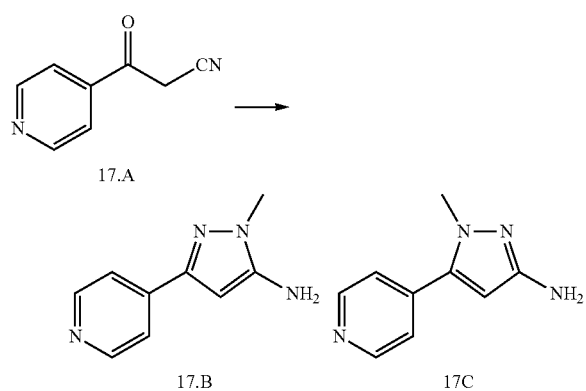

1-Methyl-3-(pyridin-4-yl)-1H-pyrazol-5-amine (17.B) and 1-methyl-5-(pyridin-4-yl)-1H-pyrazol-3-amine (17.C)

To a rt solution of 3-oxo-3-phenylpropanenitrile (available from Biofine International Inc.) (400 mg, 2.76 mmol) in MeOH (7 mL) was added methylhydrazine (367 µl, 6.89 µmol). The resulting mixture was stirred at 60° C. for 2.5 hr. After removal of organic solvent under reduced pressure, the residue was re-dissolved in 30% $^i$PrOH/chloroform. The solution was washed with brine, and dried over MgSO$_4$. After removal of organic solvent under reduced pressure, purification of the residue by flash chromatography on silica gel using 0-20% MeOH/CH$_2$Cl$_2$ for elution gave the title product 17.B (341 mg, 71%) and 17.C (86 mg, 18%) as white solids.

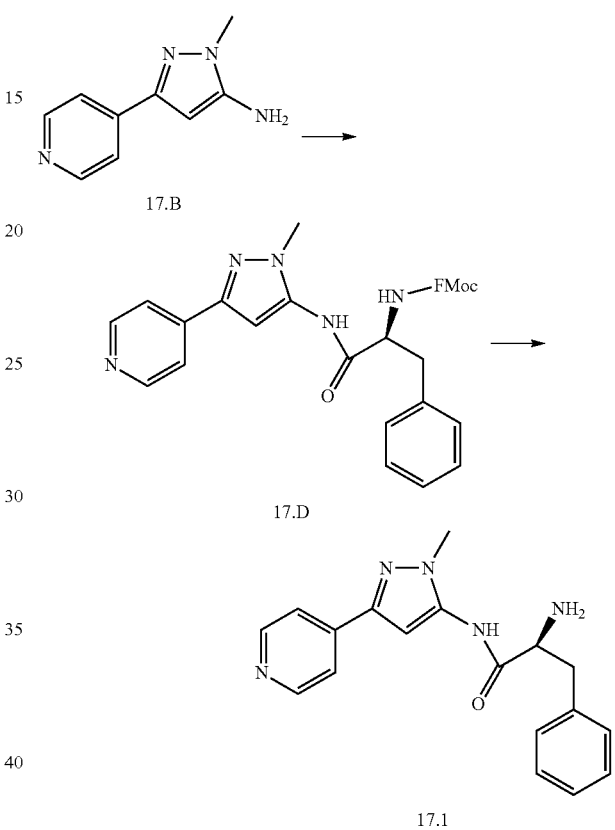

(S)-tert-Butyl 1-(1-methyl-3-(pyridin-4-yl)-1H-pyrazol-5-ylamino)-1-oxo-3-phenylpropan-2-ylcarbamate (17.1) (Method A)

To a −45° C. solution of 17.B (341 mg, 1.96 mmol) and (S)-2-(((9H-fluoren-9-yl)methoxy)carbonyl)-3-phenylpropanoic acid (available from Aldrich) (820 mg, 2.12 mmol) in chloroform was added pyridine (320 mL, 3.92 mmol) followed by drop wise addition of phosphoryl trichloride (available from Aldrich) (325 mg, 2.12 µmol) over 3 mins. The reaction mixture was stirred at −45—30° C. for 1.5 hr, poured into saturated aqueous NaHCO$_3$ (5 mL), diluted with water (12 mL), and extracted by CHCl$_3$ (3×15 mL). The combined organic solution was washed with brine and dried over MgSO$_4$. After removal of organic solvent under reduced pressure, purification of the residue by flash chromatography on silica gel using 0-50% EtOAc/Hexanes for elution gave 17.D as a white solid. The intermediate product 17.D was dissolved in 20% piperidine/DMF (8 mL). After stirring at rt for 2.0 hr, the resulting mixture was diluted with 30% $^i$PrOH/chloroform (20 mL) and washed with water. After removal of organic solvent under reduced pressure, purification of the residue by flash chromatography on silica gel using 0-15% MeOH/CH$_2$Cl$_2$ for elution gave 17.1 as a pale yellow solid (470 mg, 75%, two steps).

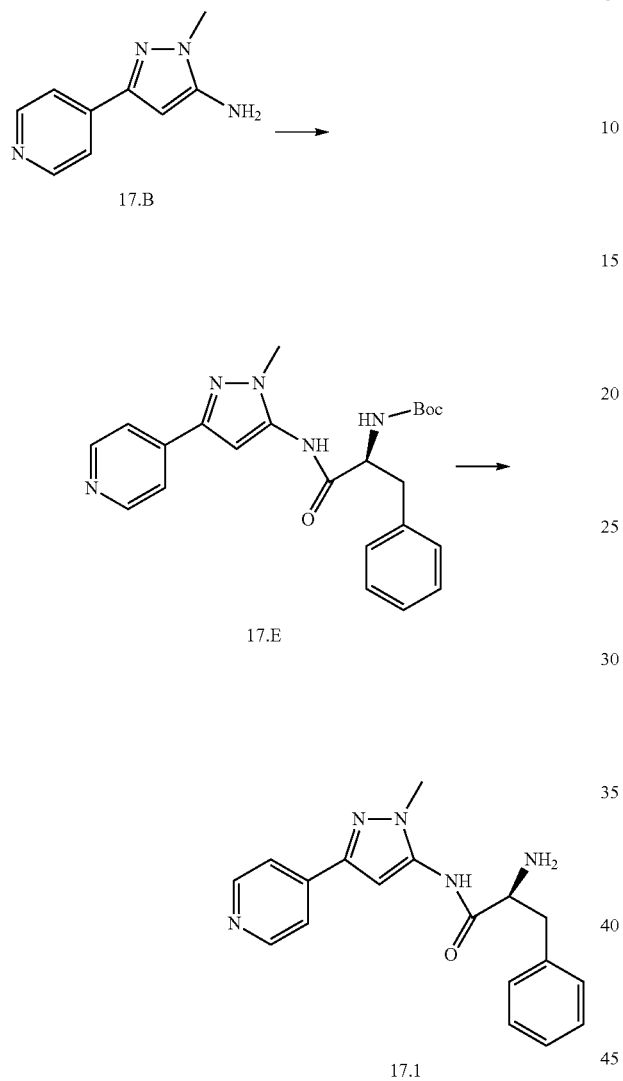

17.B

17.E 17.1

(S)-tert-Butyl 1-(1-methyl-3-(pyridin-4-yl)-1H-pyrazol-5-ylamino)-1-oxo-3-phenylpropan-2-ylcarbamate (17.1) (Method B)

To a rt solution of 17.B (524 mg, 3.01 mmol) and boc-1-phenylalanine (available from Aldrich) (954 mg, 3.60 mmol) in py (6.0 mL) was added 1-(3-dimethylaminopropyl)-3-ethylcarbodiimide hydrochloride (available from Chem-Impex International, Inc.) (860 mg, 4.5 mmol). After stirring at room temperature for 2.0 hr, the reaction mixture was diluted with water (20 mL) and extracted with EtOAc (3×20 mL). The organic solution was washed with brine and dried over MgSO$_4$. After removal of solvent under reduced pressure, purification of the residue by flash chromatography on silica gel using 0-80% EtOAc/Hexanes for elution gave 17.E as a white solid. The intermediate product 17.E was dissolved in 20% TFA/CH$_2$Cl$_2$ (12 mL). After stirring at rt for 1.5 hr, the reaction mixture was concentrated. The residue was re-dissolved in 30% $^i$PrOH/chloroform, the solution was washed with saturated aqueous NaHCO$_3$, water and brine. After removal of organic solvent under reduced pressure, purification of the residue by flash chromatography on silica gel using 0-15% MeOH/CH$_2$Cl$_2$ for elution gave 17.1 as a pale yellow solid (686 mg, 71%, two steps). MS ESI (positive.) m/e: 322.1 (M+H).

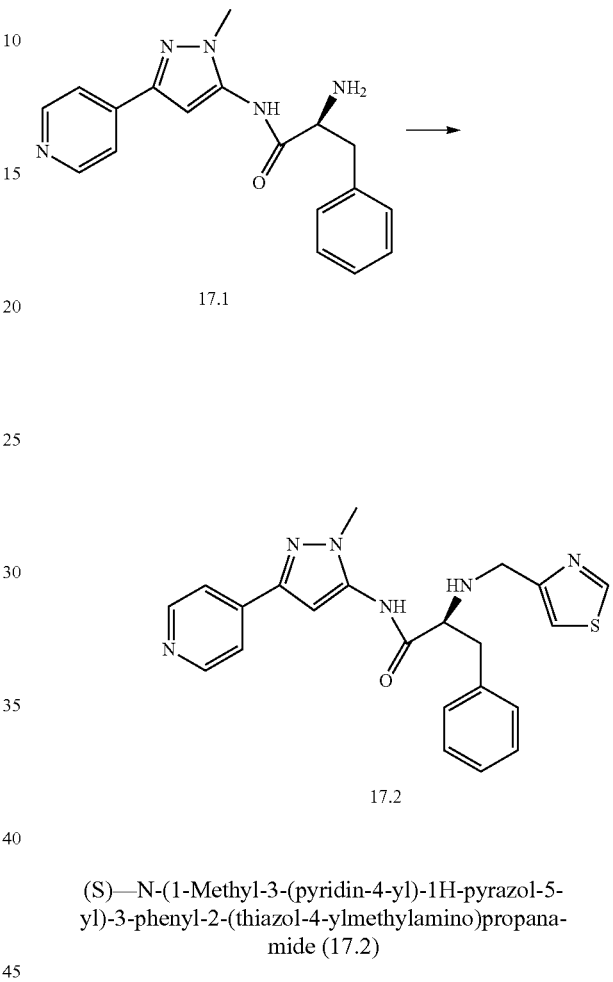

17.1

17.2

(S)—N-(1-Methyl-3-(pyridin-4-yl)-1H-pyrazol-5-yl)-3-phenyl-2-(thiazol-4-ylmethylamino)propanamide (17.2)

To a rt solution of 17.1 (150 mg, 0.47 mmol) and thiazole-4-carbaldehyde (available from Combi-Blocks Inc.) (48 mg, 0.42 mmol) in 1,2-dichloroethane (5.0 mL) was added 5% HOAc/1,2-dichloroethane (0.1 mL) followed by sodium triacetoxyborohydride (248 mg, 867 μmol). After stirring at 60° C. for 35 mins, the reaction mixture was quenched with saturated NaHCO$_3$ (4 mL), diluted with water (10 mL) and extracted by $^i$PrOH/CHCl$_3$ (1:1, 3×10 mL). The organic solvent was removed under reduced pressure. After purification of the residue by preparative HPLC (10-90% CH$_3$CN/water, 30 min), the combined product fractions was treated with saturated aqueous NaHCO$_3$, extracted with 30% $^i$PrOH/CHCl$_3$ and concentrated to provide the title product 17.2 (104 mg, 53%) as white solid. MS ESI (pos.) m/e: 419.1 (M+H); $^1$H NMR (400 MHz, CD$_3$OD) δ ppm 3.08 (s, 2H) 3.61 (s, 3H) 3.68 (s, 1H), 3.97 (s, 2H) 6.73 (s, 1H), 7.28 (m, 6H), 7.78 (m, 2H), 8.53 (m, 2H), 8.97 (s, 1H).

The following compounds were prepared according to the method described herein for 17.2 preparation using appropriate aldehydes, except that Boc-4-fluororo L-phenylalanine was used for 17.5 (X═F).

TABLE 2

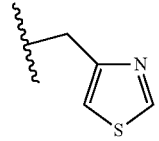 [SMILES: *Cc1cscn1]

| Compound | R | X |
|---|---|---|
| 17.2 | (thiazol-4-ylmethyl) | H |
| 17.3 | (pyridin-2-ylmethyl) | H |
| 17.4 | (5-fluoropyridin-2-ylmethyl) | H |
| 17.5 | (thiazol-4-ylmethyl) | F |
| 17.6 | (cyclopropylmethyl) | H |

(S)—N-(1-Methyl-3-(pyridin-4-yl)-1H-pyrazol-5-yl)-3-phenyl-2-(pyridin-2-ylmethylamino)propanamide (17.3)

MS ESI (pos.) m/e: 413.2 (M+H); $^1$H NMR (500 MHz, CD$_3$OD) δ ppm 3.20 (d, J=9.54 Hz, 1H), 3.43 (dd, J=13.33, 5.99 Hz, 1H), 3.47 (s, 3H) 4.41 (d, J=2.45 Hz, 2H), 4.45 (dd, J=9.41, 5.99 Hz, 1H), 7.03 (s, 1H), 7.14-7.34 (m, 5H), 7.35-7.46 (m, 2H), 7.83 (td, J=7.83, 1.71 Hz, 1H), 8.29 (d, J=6.85 Hz, 2H), 8.44-8.63 (m, 1H), 8.68 (d, J=7.09 Hz, 2H).

(S)-2-((5-Fluoropyridin-2-yl)methylamino)-N-(1-methyl-3-(pyridin-4-yl)-1H-pyrazol-5-yl)-3-phenyl-propanamide (17.4)

MS ESI (pos.) m/e: 432.2 (M+H); $^1$H NMR (400 MHz, CD$_3$OD) δ ppm 8.76 (d, J=7.04 Hz, 2H), 8.60 (d, J=2.74 Hz, 1H), 8.33 (d, J=6.65 Hz, 2H), 7.73 (td, J=8.51, 2.93 Hz, 1H), 7.58 (dd, J=8.61, 4.30 Hz, 1H), 7.30-7.49 (m, 5H), 7.10 (s, 1H), 4.39-4.58 (m, 3H), 3.47-3.63 (m, 4H), 3.22-3.34 (m, 1H).

(S)-3-(4-Fluorophenyl)-N-(1-methyl-3-(pyridin-4-yl)-1H-pyrazol-5-yl)-2-(thiazol-4-ylmethylamino)propanamide (17.5)

MS ESI (pos.) m/e: 437.0 (M+H); $^1$H NMR (400 MHz, CD$_3$OD) δ ppm 8.96 (d, J=1.96 Hz, 1H), 8.51-8.54 (m, 2H), 7.76-7.79 (m, 2H), 7.40 (d, J=1.96 Hz, 1H), 7.23-7.31 (m, 2H), 7.04 (t, J=8.80 Hz, 2H), 6.75 (s, 1H), 3.91-4.02 (m, 2H), 3.63-3.68 (m, 4H), 3.05 (qd, J=13.56, 7.04 Hz, 2H).

(S)-2-(Cyclopropylmethylamino)-N-(1-methyl-3-(pyridin-4-yl)-1H-pyrazol-5-yl)-3-phenylpropanamide (17.6)

MS ESI (pos.) m/e: 376.1.2 (M+H); $^1$H NMR (400 MHz, CD$_3$OD) δ ppm 8.77 (d, J=7.04 Hz, 2H), 8.36 (d, J=6.65 Hz, 2H), 7.28-7.43 (m, 5H), 7.11 (s, 1H), 4.45 (dd, J=9.98, 5.67 Hz, 1H), 3.42-3.62 (m, 4H), 3.08-3.27 (m, 2H), 2.86-3.03 (m, 1H), 1.11-1.34 (m, 1H), 0.70-0.89 (m, 2H), 0.47 (q, J=4.70 Hz, 2H).

7.17.2 Example 17.7

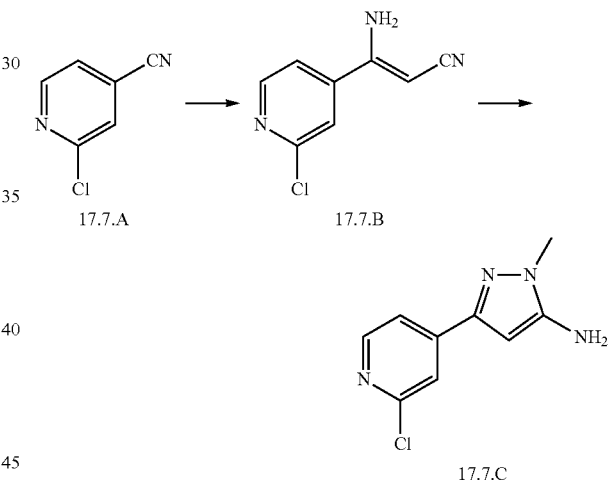

(Z)-3-Amino-3-(2-chloropyridin-4-yl)acrylonitrile (17.7.B)

To a 0° C. solution of 17.7.A (Combi-Blocks Inc.) (25.00 g, 180 mmol) in THF (300 mL) under N$_2$ atmosphere was added acetonitrile (25 ml, 469 mmol) followed by portion wise addition of potassium tert-butoxide (81 g, 722 mmol) over 30 minutes. The reaction solution was allowed to warm to room temperature over 30 minutes at which time the mixture was quenched with water (300 mL). The organic solvents were removed under reduced pressure, the dark brown solid was collected and then washed with cold CHCl$_3$. The solid was air dried to afford (Z)-3-amino-3-(2-chloropyridin-4-yl)acrylonitrile 17.7.B as a brown sold (28 g, 88%).

3-(2-Chloropyridin-4-yl)-1-methyl-1H-pyrazol-5-amine (17.7.C)

To 300 ml of MeOH at 0° C. was added (Z)-3-amino-3-(2-chloropyridin-4-yl)acrylonitrile 17.7.B (26 g, 145 mmol), 20 ml of concentrated HCl and anhydrous methyl hydrazine (9.24 ml, 174 mmol). After 10 minutes the reaction solution was warmed to room temperature, and then stirred at 80° C. for 1.5 hr. The solvent was then removed by rotary evaporation and the crude partitioned between 1500 ml of DCM and 500 ml of saturated aqueous sodium bicarbonate. The aqueous layer was extracted twice more with 400 ml of DCM, dried over sodium sulfate, and the solvent was removed by rotary evaporation to give 22.74 g of 3-(2-chloropyridin-4-yl)-1-methyl-1H-pyrazol-5-amine 17.7.C as a light brown solid.

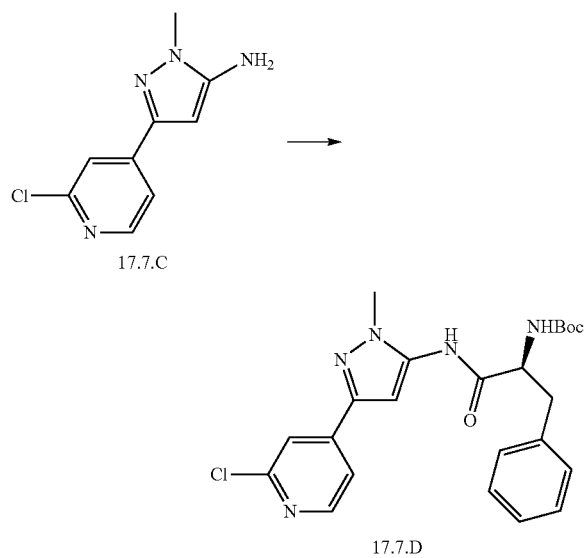

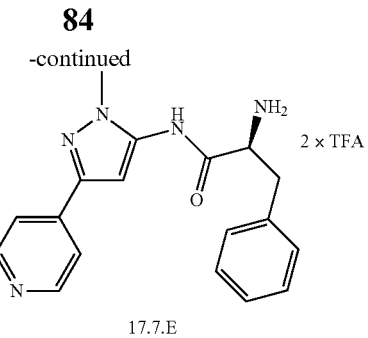

17.7.E (2S)-2-Amino-N-(3-(2-chloropyridin-4-yl)-1-methyl-1H-pyrazol-5-yl)-3-phenylpropanamide (17.7.E)

To a 250 ml flask was added 18.8 g of tert-butyl (S)-1-(3-(2-chloropyridin-4-yl)-1-methyl-1H-pyrazol-5-ylamino)-1-oxo-3-phenylpropan-2-ylcarbamate 1.D, 100 ml of DCM and 50 ml of TFA. The reaction was stirred at room temperature for 4 hours at which time the solvent was removed with a stream of nitrogen. The crude was partitioned between 2000 ml of DCM and 500 ml of saturated aqueous sodium bicarbonate. The organic layer was extracted twice more with 500 ml of water, dried over sodium sulfate and the organic solvent was removed by rotary evaporation. The crude was purified using a silica gel column (eluting with 5% MeOH in DCM) to give 8.6 g of (2S)-2-amino-N-(3-(2-chloropyridin-4-yl)-1-methyl-1H-pyrazol-5-yl)-3-phenylpropanamide 17.7.E as a light brown solid.

Tert-butyl (S)-1-(3-(2-chloropyridin-4-yl)-1-methyl-1H-pyrazol-5-ylamino)-1-oxo-3-phenylpropan-2-ylcarbamate (17.7.D)

To a 1000 ml flask was added 8.6 g 3-(2-chloropyridin-4-yl)-1-methyl-1H-pyrazol-5-amine 17.7.C, 13.1 g of (S)-2-(tert-butoxycarbonyl)-3-phenylpropanoic acid, 15.8 g of EDC, and 160 ml of pyridine. The reaction was stirred at room temperature for 4 hours at which time the reaction was partitioned between 2000 ml of DCM and 3×500 ml of 1N HCl. The organic layer was dried over sodium sulfate and the solvent removed by rotary evaporation to give 21.6 g of tert-butyl (S)-1-(3-(2-chloropyridin-4-yl)-1-methyl-1H-pyrazol-5-ylamino)-1-oxo-3-phenylpropan-2-ylcarbamate 17.7.D as a light brown thick oil.

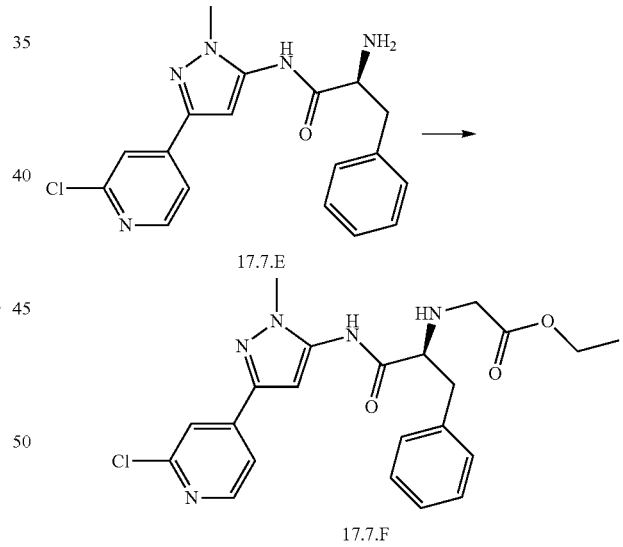

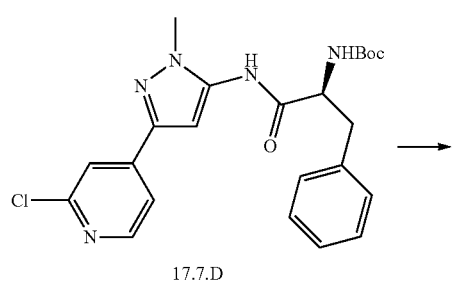

17.7.D

Ethyl 2-((S)-1-(3-(2-chloropyridin-4-yl)-1-methyl-1H-pyrazol-5-ylamino)-1-oxo-3-phenylpropan-2-ylamino)acetate (17.7.F)

To a 1000 ml flask was added 8.6 g of (2S)-2-amino-N-(3-(2-chloropyridin-4-yl)-1-methyl-1H-pyrazol-5-yl)-3-phenylpropanamide 1.E, 100 ml of DMF, 6.0 ml of DIEA and the reaction was cooled to 0° C. To the reaction was then added 2.8 ml of ethyl bromoacetate and the reaction was stirred at 22° C. for 16 hours at which time the crude was partitioned between 1500 ml EtAc, 2×400 ml of saturated brine, and 2×400 ml of water (Note: no product observed in aqueous layer). The organic solvent was removed by rotary evaporation and the crude purified with a silica gel column (eluting with 30% EtAc in Hexane) to give 6.3 g of ethyl 2-((S)-1-(3-(2-chloropyridin-4-yl)-1-methyl-1H-pyrazol-5-ylamino)-1-oxo-3-phenylpropan-2-ylamino)acetate 17.7.F as a white solid.

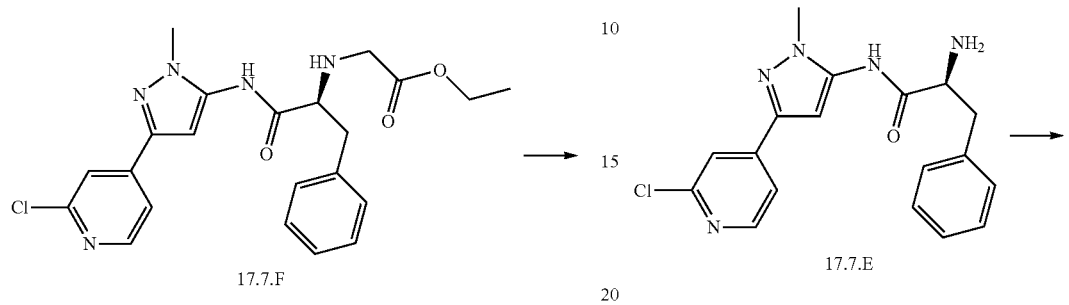

(S)-Ethyl 2-(1-(1-methyl-3-(pyridin-4-yl)-1H-pyrazol-5-ylamino)-1-oxo-3-phenylpropan-2-ylamino)acetate dihydrochloride (1.F)

To a 250 ml flask was added 6.3 g of (S)-ethyl 2-(1-(1-methyl-3-(pyridin-4-yl)-1H-pyrazol-5-ylamino)-1-oxo-3-phenylpropan-2-ylamino)acetate 1.F, 1.8 g of Pd on carbon, 150 ml of MeOH and 2.8 ml of DIEA. The air was removed from the flask and replaced with hydrogen gas. This process was repeated four more times and then the reaction was stirred at room temperature for 2 hours, at which time the reaction was filtered over a bed of celite. The solvent was then removed and the crude was purified with a silica gel column (eluting with 2-5% MeOH in DCM) to give 4.5 g of (S)-ethyl 2-(1-(1-methyl-3-(pyridin-4-yl)-1H-pyrazol-5-ylamino)-1-oxo-3-phenylpropan-2-ylamino)acetate as a sticky solid.

To a 250 ml flask containing the above purified material (1.8 g, 4.0 mmole) was added 20 ml of 20% EtOH in DCM, cooled to 0° C. and to the resulting solution was added 7 ml of a hydrogen chloride solution (2.0M in diethyl ether, 13 mmol). The solvent was removed by rotary evaporation and then placed on a high vacuum to give 17.7 as a light yellow solid. LCMS ESI (pos.) m/e: 408.3 (M+H): 1H NMR (500 MHz, MeOH) δ ppm 8.80 (d, J=6.85 Hz, 2H), 8.42 (d, J=7.09 Hz, 2H), 7.33-7.49 (m, 5H), 7.16 (s, 1H), 4.61 (dd, J=9.17, 6.24 Hz, 1H), 4.36 (q, J=7.09 Hz, 2H), 4.12 (s, 2H), 3.62 (s, 3H), 3.50 (dd, J=13.45, 6.36 Hz, 1H), 3.27-3.32 (m, 1H), 1.36 (t, J=7.21 Hz, 3H).

7.17.3 Example 17.8

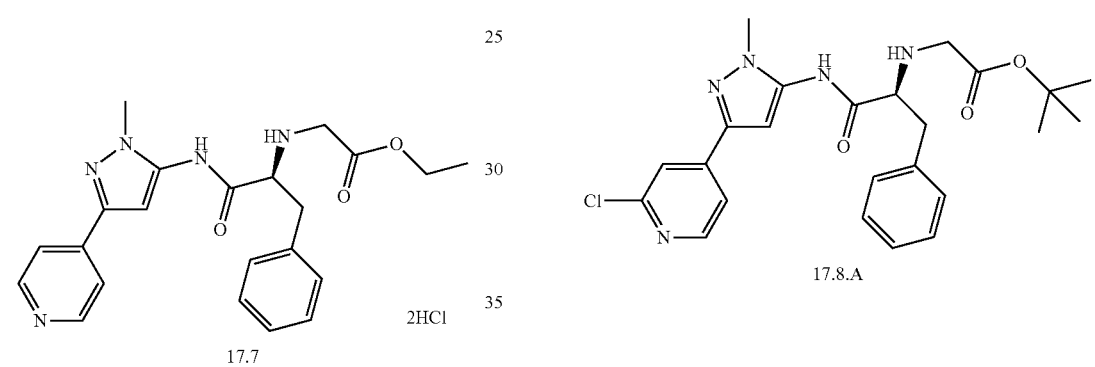

Tert-butyl 2-((S)-1-(3-(2-chloropyridin-4-yl)-1-methyl-1H-pyrazol-5-ylamino)-1-oxo-3-phenylpropan-2-ylamino)acetate as a white solid (17.8.A)

To a 500 ml flask was added 2000 mg of (2S)-2-amino-N-(3-(2-chloropyridin-4-yl)-1-methyl-1H-pyrazol-5-yl)-3-phenylpropanamide 17.7.E, 50 ml of DMF, 1.4 ml of DIEA and the reaction was cooled to 0° C. To the reaction was then added 953 µl of tert-butyl bromoacetate and the reaction was stirred at 22° C. for 16 hours at which time the crude was partitioned between 800 ml EtAc, 2×200 ml of saturated brine, and 2×200 ml of water. (Note: no product observed in aqueous layer). The organic solvent was removed by rotary evaporation and the crude purified with a silica gel column (eluting with 50% EtAc in Hexane) to give 1.8 g of 17.8.A as a white solid.

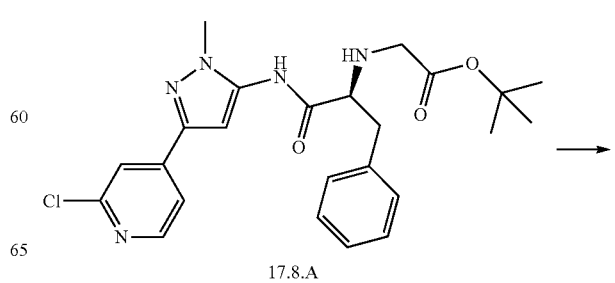

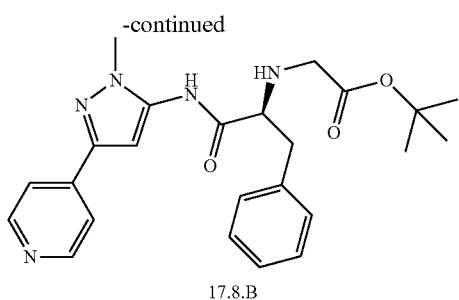

17.8.B (S)-Tert-butyl 2-(1-(1-methyl-3-(pyridin-4-yl)-1H-pyrazol-5-ylamino)-1-oxo-3-phenylpropan-2-ylamino)acetate (17.8.B)

To a 100 ml flask was added 1.4 g of 17.8.A, 500 mg of Pd on carbon, 150 ml of MeOH and 520 µl of diisopropylethylamine. The air was removed from the flask and replaced with hydrogen gas. This process was repeated four more times and then the reaction was stirred at room temperature for 2 hours, at which time the reaction was filtered over a bed of celite. The solvent was then removed and the crude was purified with a silica gel column (eluting with 2-5% MeOH in DCM) to give 800 mg of (S)-tert-butyl 2-(1-(1-methyl-3-(pyridin-4-yl)-1H-pyrazol-5-ylamino)-1-oxo-3-phenylpropan-2-ylamino)acetate 17.8.B as a solid. (Rf silica=0.27 in 5% MeOH in DCM).

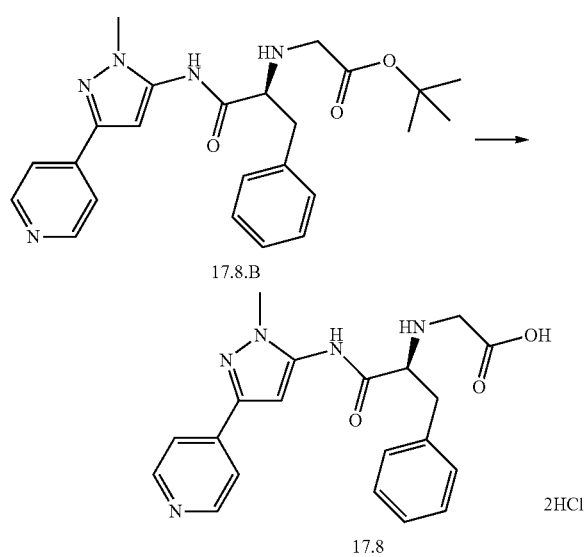

17.8

(S)-2-(1-(1-Methyl-3-(pyridin-4-yl)-1H-pyrazol-5-ylamino)-1-oxo-3-phenylpropan-2-ylamino)acetic acid dihydrochloride (17.8)

To a 20 ml vial was added 800 mg of 17.8.B, 15 ml of dioxane, 10 drops of water and 4.5 ml of hydrogen chloride (2.0 M solution in diethyl ether). After 16 hours 10 ml of concentrated HCl were added and stirred at room temperature for 16 hours. The solvent was removed with a stream of nitrogen (dried with MeOH) to give 740 mg of 2-((S)-1-(3-(2-chloropyridin-4-yl)-1-methyl-1H-pyrazol-5-ylamino)-1-oxo-3-phenylpropan-2-ylamino)acetic acid diHCl salt as a light yellow solid (Note: trace methyl ester was observed in final product).

The contaminated product was then purified by reverse phase preparative HPLC to give 655 mg of (S)-2-(1-(1-methyl-3-(pyridin-4-yl)-1H-pyrazol-5-ylamino)-1-oxo-3-phenylpropan-2-ylamino)acetic acid TFA salt.

To a 200 ml flask was added 640 mg of (S)-2-(1-(1-methyl-3-(pyridin-4-yl)-1H-pyrazol-5-ylamino)-1-oxo-3-phenylpropan-2-ylamino)acetic acid diTFA, 20 ml of dioxane, 20 drops of water and then slowly 3 ml of hydrogen chloride (2.0 M in diethyl ether). The solvent was then removed using a rotary evaporator and placed under high vacuum to give 565 mg (S)-2-(1-(1-methyl-3-(pyridin-4-yl)-1H-pyrazol-5-ylamino)-1-oxo-3-phenylpropan-2-ylamino)acetic acid dihydrochloride as an off white solid. The product was redissolved in 10% MeOH in DCM and the solvent was then removed using a rotary evaporator and placed under high vacuum to give 505 mg of 17.8 as a white solid. MS ESI (pos.) m/e: 380.2 (M+H); 1H NMR (400 MHz, CD3OD) δ ppm 8.52 (d, J=6.50 Hz, 2H), 7.72-7.89 (m, 2H), 7.25-7.47 (m, 5H), 6.65-6.81 (m, 1H), 4.17 (dd, J=8.80, 6.46 Hz, 1H), 3.51-3.57 (m, 4H), 3.41-3.51 (m, 1H), 3.28 (d, J=6.26 Hz, 1H), 3.10-3.23 (m, 1H).

7.18 Example 18

7.18.1 Example 18.1

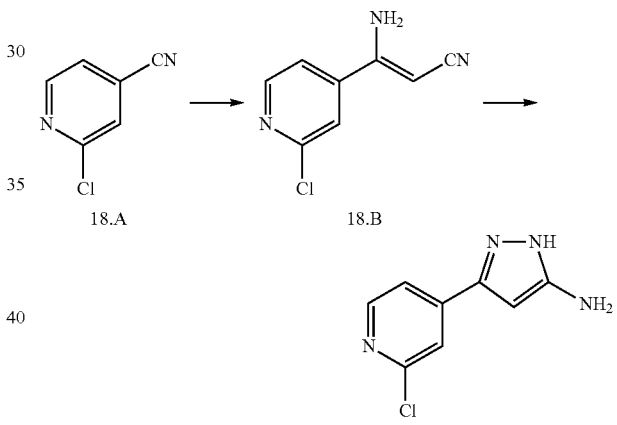

3-(2-Chloropyridin-4-yl)-1H-pyrazol-5-amine (18.B)

To a 0° C. solution of 18.A (Combi-Blocks Inc.) (25.00 g, 180 mmol) in THF (300 mL) under $N_2$ atmosphere was added acetonitrile (25 ml, 469 mmol) followed by portion wise addition of potassium tert-butoxide (81 g, 722 mmol) over 30 mins. The reaction solution was allowed to warm to rt over 30 min and the mixture was quenched with water (300 mL). Organic solvents were removed under reduced pressure, the dark brown solid was washed with $CHCl_3$ and cooled subsequently. The solid was collected and air dried to afford crude 18.B (28 g, 88%).

3-(2-Chloropyridin-4-yl)-1H-pyrazol-5-amine (18.C)

To a rt solution of 18.B (4.20 g, 23 mmol) in MeOH (20 mL) was added anhydrous hydrazine (3.72 g, 116 mmol) followed by concentrated HCl (3.0 mL). The reaction solution was stirred at 60° C. for 4.0 hr, and the resulting mixture was concentrated. The residue was re-dissolved in 30%

'PrOH/CHCl₃ and washed with saturated NaHCO₃, water, brine, and dried over MgSO₄. After removal of organic solvent under reduced pressure, purification of the residue by flash chromatography on silica gel using 0-12% MeOH/CH₂Cl₂ for elution gave title product 18.0 (3.91 g, 85%).

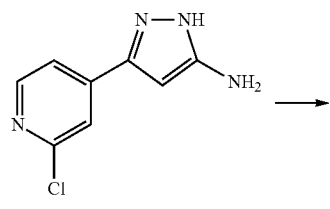

18.C 4-(5-Amino-1H-pyrazol-3-yl)-N-methylpyridin-2-amine (18.D)

A mixture of 18.0 (3.60 g, 18 mmol) in 40% aqueous MeNH₂ solution (25 mL) in sealed tube was heated at 135° C. for 15 hr. and the resulting mixture was allowed to cool to rt. After removal of solvents under reduced pressure, purification of the residue by flash chromatography on silica gel using 0-18% MeOH/CH₂Cl₂ for elution gave title product 18.D as brown solid (2.71 g, 79%).

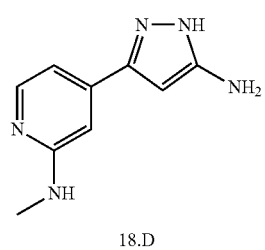

18.D

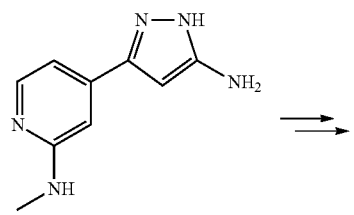

18.D

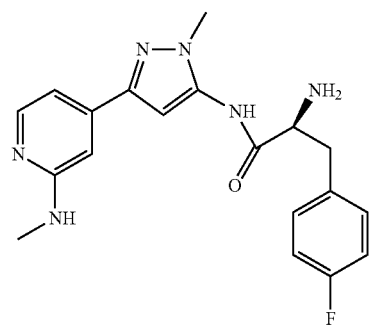

18.E (2S)-2-Amino-3-(4-fluorophenyl)-N-(3-(2-(methylamino)pyridin-4-yl)-1H-pyrazol-5-yl)propanamide (18.E)

This title intermediate was prepared starting from 18.D (2.30 g, 12.2 mmol) according the procedure (Method B) described above for conversion of 17.B to 17.1, except that boc-4-fluoro-1-phenylalanine was used. The product 18.E was purified by flash chromatography on silica gel using 0-8% MeOH/CH₂Cl₂ for elution (4.70 g, 85%).

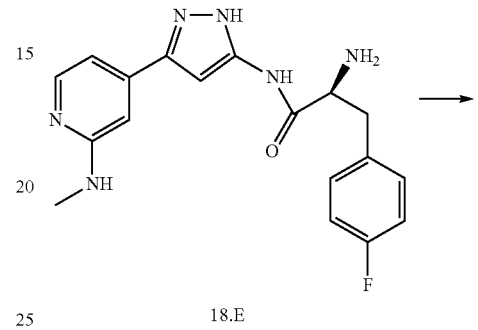

18.E

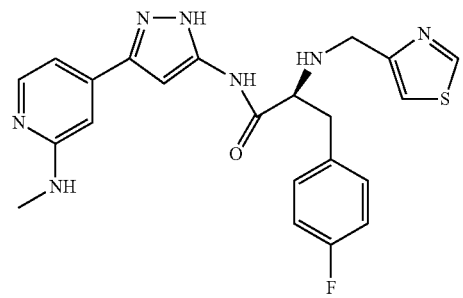

18.1

(2S)-3-(4-Fluorophenyl)-N-(3-(2-(methylamino)pyridin-4-yl)-1H-pyrazol-5-yl)-2-(thiazol-4-ylmethylamino)propanamide (18.1)

This title compound was prepared starting from 18.E (173 mg, 0.49 mmol) according the procedure described above for conversion of 4.C to 4. The product was purified by flash chromatography on silica gel using 0-8% MeOH/CH₂Cl₂ for elution to give 18.1 as colorless solid (119 mg, 54%). MS ESI (pos.) m/e: 452.1.0 (M+H); ¹H NMR (500 MHz, CD₃OD) δ ppm 8.88 (d, J=2.20 Hz, 1H), 7.98 (d, J=5.62 Hz, 1H), 7.29 (d, J=1.96 Hz, 1H), 7.13-7.23 (m, 2H), 6.89-7.04 (m, 3H), 6.85 (dd, J=5.38, 1.22 Hz, 1H), 6.79 (s, 1H), 3.89-4.00 (m, 1H), 3.78-3.89 (m, 1H), 3.57 (dd, J=7.58, 6.11 Hz, 1H), 3.07 (dd, J=13.69, 5.87 Hz, 1H), 2.82-2.98 (m, 4H).

7.18.2 Example 18.2

Compound 18.2 were prepared from 18.E using the appropriate aldehyde according to the method described herein for synthesis of 18.1.

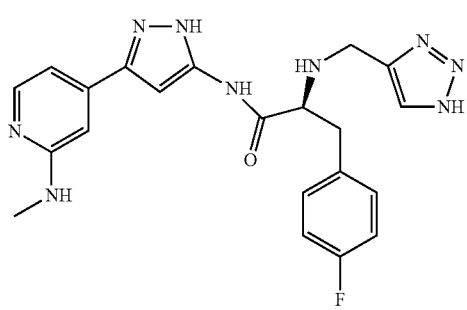

(2S)-2-((1H-1,2,3-triazol-4-yl)methylamino)-3-(4-fluorophenyl)-N-(3-(2-(methylamino)pyridin-4-yl)-1H-pyrazol-5-yl)propanamide (18.2)

MS ESI (pos.) MS ESI (pos.) m/e: 436.1.0 (M+H); $^1$H NMR (400 MHz, CD$_3$OD) δ ppm 8.00 (d, J=5.48 Hz, 1H), 7.64 (s, 1H), 7.25 (dd, J=8.61, 5.48 Hz, 2H), 6.94-7.07 (m, 2H), 6.87 (d, J=5.09 Hz, 1H), 6.81 (s, 1H), 3.89-4.00 (m, 1H), 3.78-3.89 (m, 1H), 3.56 (t, J=6.85 Hz, 1H), 3.37 (s, 1H), 3.04-3.13 (m, 1H), 2.89-3.01 (m, 4H).

7.19 Example 19

7.19.1 Example 19.1

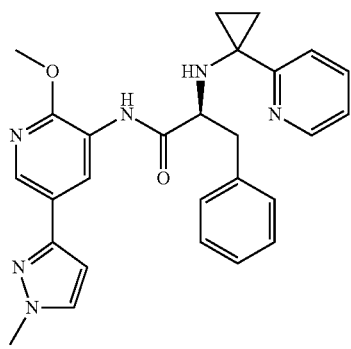

(2S)—N-(2-methoxy-5-(1-methyl-1H-pyrazol-3-yl)-3-phenyl-2-(1-(pyridin-2-yl)cyclopropylamino)propanamide (19.1)

This compound was synthesized following experimental procedures for example 11.1. 1H NMR (400 MHz, MeOH) δ ppm 8.54 (d, J=1.96 Hz, 1H) 8.30 (d, J=3.91 Hz, 1H) 8.05 (d, J=2.35 Hz, 1H) 7.92 (s, 1H) 7.77 (s, 1H) 7.56 (td, J=7.73, 1.76 Hz, 1H) 7.20-7.28 (m, 3H) 7.06-7.18 (m, 4H) 3.99 (s, 3H) 3.93 (s, 3H) 3.59 (dd, J=8.61, 4.69 Hz, 1H) 3.04 (dd, J=13.69, 5.09 Hz, 1H) 2.82 (dd, J=13.69, 8.61 Hz, 1H) 1.13-1.21 (m, 1H) 1.10 (dd, J=10.37, 4.11 Hz, 1H) 0.98-1.06 (m, 1H) 0.87-0.95 (m, 1H).

7.19.2 Example 19.2

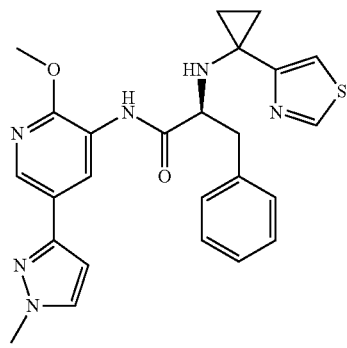

(2S)—N-(2-methoxy-5-(1-methyl-1H-pyrazol-3-yl)-3-phenyl-2-(1-(thiazol-4-yl)cyclopropylamino)propanamide (19.2)

This compound was synthesized following experimental procedures of example 11.1. 1H NMR (400 MHz, MeOH) δ ppm 8.73 (d, J=1.96 Hz, 1H) 8.56 (d, J=2.35 Hz, 1H) 8.05 (d, J=2.35 Hz, 1H) 7.88-7.96 (m, 1H) 7.77 (d, J=0.78 Hz, 1H) 7.21-7.29 (m, 3H) 7.13-7.19 (m, 2H) 6.98 (d, J=1.96 Hz, 1H) 3.99 (s, 3H) 3.93 (s, 3H) 3.63 (dd, J=8.61, 4.70 Hz, 1H) 3.02 (dd, J=13.69, 4.69 Hz, 1H) 2.80 (dd, J=13.69, 8.61 Hz, 1H) 1.03-1.13 (m, 2H) 0.96-1.03 (m, 1H) 0.85-0.93 (m, 1H).

7.20 Example 20

7.20.1 Example 20.1

(S)—N-(1-ethyl-3-(pyridine-4-yl)-1H-pyrazol-5-yl)-3-(4-fluorophenyl)-2-(thiazol-4-ylmethlamino)propanamide (20.1)

This compound was synthesized according to the method described in 17.2. 1H NMR (400 MHz, MeOH) δ ppm 8.95 (d, J=1.96 Hz, 1H) 8.52 (d, J=6.26 Hz, 2H) 7.68-7.83 (m, 2H) 7.40 (d, J=1.96 Hz, 1H) 7.27 (dd, J=8.61, 5.48 Hz, 2H) 7.04

(t, J=8.80 Hz, 2H) 6.73 (s, 1H) 3.89-3.98 (m, 4H) 3.66 (t, J=7.04 Hz, 1H) 3.05 (t, J=6.26 Hz, 2H) 1.32 (t, J=7.24 Hz, 4H).

7.20.2 Example 20.2

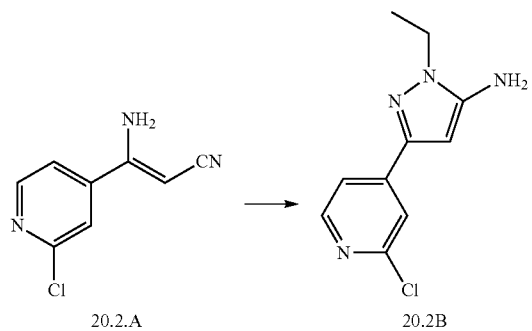

3-(2-Chloropyridin-4-yl)-1-ethyl-1H-pyrazol-5-amine (20.2.B)

To a solution of (Z)-3-amino-3-(2-chloropyridin-4-yl) acrylonitrile 20.2.A (2590 mg, 14420 μmol), and ethylhydrazine oxalate (3220 mg, 2144 μmol) in MeOH (70 mL) was added 2N HCl (18 mL). The reaction was stirred at 80° C. for 2 hr, when LC/MS indicated the completion of the reaction (m/e: 223). The reaction was concentrated and worked up between saturated NaHCO3. and iPrOH/CHCl$_3$. Silica gel chromatography afforded the desired product 20.2.B 1.96 g (61%).

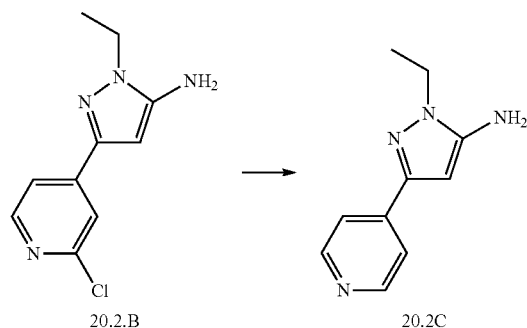

1-Ethyl-3-(pyridine-4-yl)-1H-pyrazol-5-amine (20.2C)

To a flask with 623 mg 20.2.B was added 15 ml MeOH) and 10% wet Palladium on carbon (257 mg, 40% weight of 20.2.B). The reaction was purged with hydrogen and stirred under a hydrogen balloon overnight. After filtering through a pad of celite, the crude was concentrated and purified on silica gel to afford 300 mg of product 20.2.0 (57%).

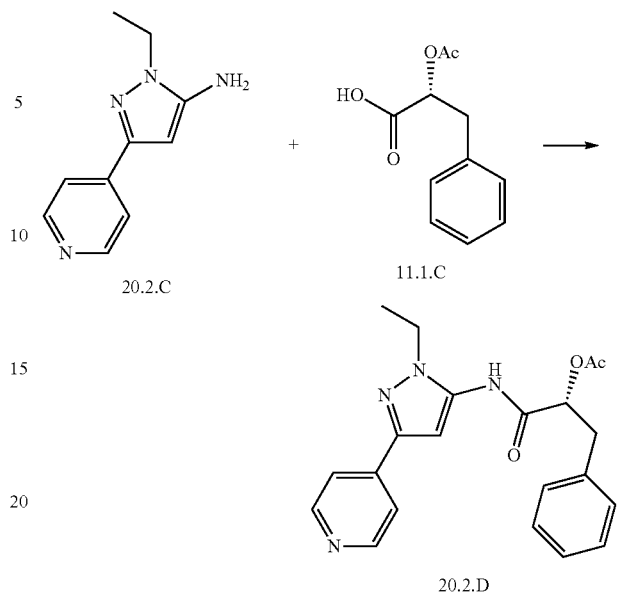

(R)-1-(1-Ethyl-3-(pyridine-4-yl)-1H-pyrazol-ylamino)-1-oxo-3-phenylpropan-2-yl acetate (20.2.D)

To a flask with 20.2.C (217 mg, 0.115 mmol) was added (R)-2-acetoxy-3-phenylpropanoic acid 11.1.C (442 mg, 2.1 mmol), N1-((ethylimino)methylene)-N3,N3-dimethylpropane-1,3-diamine hydrochloride (663 mg, 3.46 mmol). Then pyridine was added as a solvent. The reaction was stirred overnight at room temperature and was worked up with water and 30% isopropanol in chloroform. Silica gel chromatography afforded 438 mg of product 20.2.D (100%).

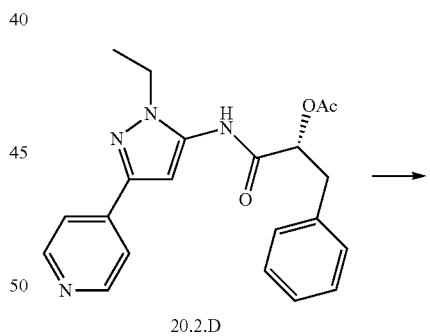

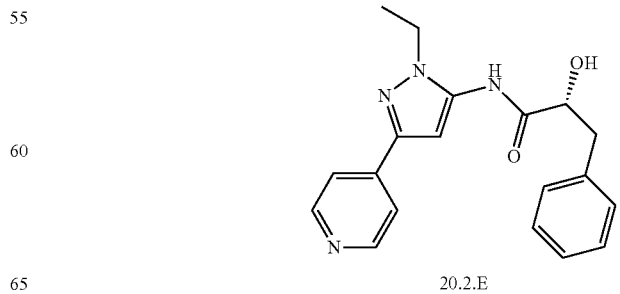

(R)—N-(1-Ethyl-3-(pyridine-4-yl)-1H-pyrazol-5-yl)-2-hydroxy-3-phenylpropanamide (20.2.E)

To (R)-1-(1-ethyl-3-(pyridin-4-yl)-1H-pyrazol-5-ylamino)-1-oxo-3-phenylpropan-2-yl acetate (438 mg, 1157 μmol) was added $K_2CO_3$ (320 mg, 2315 μmol), followed by MeOH. After 1 hr, the reaction was completed by LC/MS. The reaction was concentrated and worked up with brine and 30% isopropanol in CHCl3. The crude material was purified by trituration with dichloromethane followed by filtration.

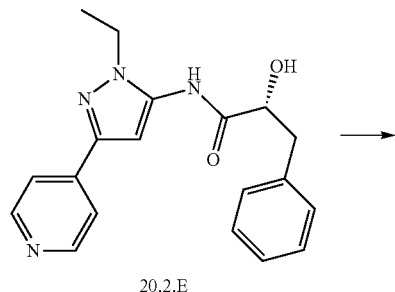

20.2.E

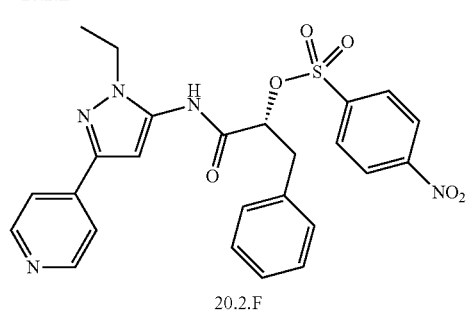

20.2.F

(R)-1-(1-Ethyl-3-(pyridin-4-yl)-1H-pyrazol-5-ylamino)-1-oxo-3-phenylpropan-2-yl-4-nitrobenzenesulfonate (20.2.F)

To (R)—N-(1-ethyl-3-(pyridin-4-yl)-1H-pyrazol-5-yl)-2-hydroxy-3-phenylpropanamide 20.2.E (95.8 mg, 285 μmol) and DMAP (3.48 mg, 28.5 μmol) were added pyridine 2 mL and the reaction was cooled to 0° C. 4-nitrobenzene-1-sulfonyl chloride (75.7 mg, 342 μmol) was then added and the reaction was stirred at 0° C. for 3 hr. The reaction was worked up with ice water and ethyl acetate followed by purification by chromatography on silica gel eluting with 0-8% MeOH/DCM to afford 103 mg (69%) of 20.2.F.

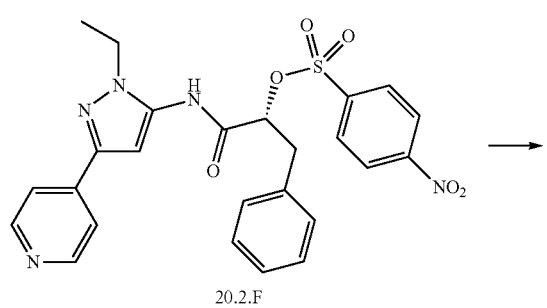

20.2.F

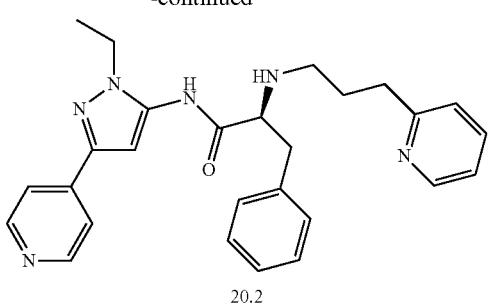

20.2

(S)—N-(1-Ethyl-3-(pyridine-4-yl)-1H-pyrazol-5-yl)-3-phenyl-2-(3-pyridin-2-yl)propylamino)propanamide (20.2)

To a flask with 66 mg of 20.2.F (0.13 mmol) was added 0.12 mL of DMF. The reaction was heated to 95° C. for 2 hours. Purification by reverse-phase HPLC afforded 2 mg (3%) of 20.2 as a TFA salt. 1H NMR (400 MHz, MeOH) δ ppm 8.75 (d, J=6.65 Hz, 2H) 8.54 (d, J=5.87 Hz, 1H) 8.31-8.40 (m, 2H) 8.08 (td, J=7.73, 1.76 Hz, 1H) 7.60 (d, J=7.83 Hz, 1H) 7.48-7.57 (m, 1H) 7.29-7.42 (m, 5H) 7.09 (s, 1H) 4.46 (dd, J=9.78, 5.48 Hz, 1H) 3.72-3.89 (m, 2H) 3.46 (dd, J=13.11, 5.67 Hz, 1H) 3.14-3.29 (m, 3H) 3.08 (t, J=7.43 Hz, 2H) 2.15-2.28 (m, 2H) 1.28 (t, J=7.24 Hz, 3H).

7.20.3 Example 20.3

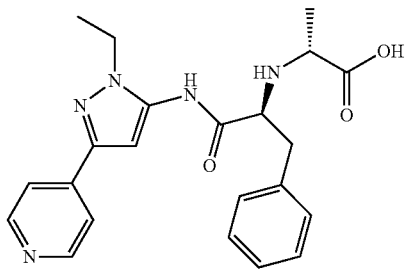

20.3

(R)-2-((S)-1-(1-Ethyl-3-(pyridin-4-yl)-1H-pyrazol-5-ylamino)-1-oxo-3-phenylpropan-2-ylamino)propanoic acid (20.3)

Compound 20.3 was prepared as the same procedures of preparing 20.2 with (S)-tert-butyl 2-aminopropanoate as the amine to displace 20.2.F. The t-butyl group was deprotected with trifluoroacetic acid at the last step. 1H NMR (400 MHz, MeOH) δ ppm 8.75 (d, J=7.04 Hz, 2H) 8.36 (d, J=7.04 Hz, 2H) 7.26-7.45 (m, 5H) 7.07 (s, 1H) 4.43 (dd, J=10.17, 5.87

Hz, 1H) 4.11 (q, J=7.30 Hz, 1H) 3.71-3.83 (m, 2H) 3.45 (dd, J=13.30, 6.26 Hz, 1H) 3.18-3.27 (m, 1H) 1.63 (d, J=7.43 Hz, 2H) 1.28 (t, J=7.24 Hz, 3H).

7.21 Example 21

7.21.1 Example 21.1

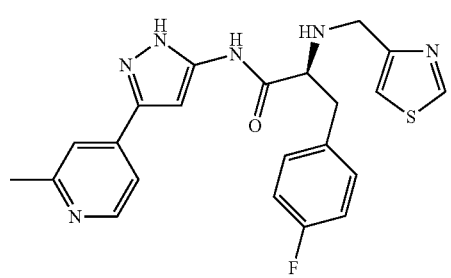 [SMILES: Cc1cc(-c2cc(NC(=O)[C@H](Cc3ccc(F)cc3)NCc3cscn3)[nH]n2)ccn1]

(2S)-3-(4-Fluorophenyl)-N-(3-(2-methylpyridin-4-yl)-1H-pyrazol-5-yl)-2-(thiazol-4-ylmethylamino)propanamide dihydrochloride (21.1)

The compound was prepared from compound 16.1.C using procedures analagous to those in Example 16.1. LCMS ESI (pos.) m/e: 437.2 (M+1): 1H NMR (500 MHz, MeOH) δ ppm 9.13 (d, J=1.71 Hz, 1H), 8.67 (d, J=6.36 Hz, 1H), 8.26 (s, 1H), 8.20 (d, J=5.87 Hz, 1H), 7.85 (d, J=1.47 Hz, 1H), 7.31 (dd, J=8.44, 5.26 Hz, 2H), 7.02-7.11 (m, 3H), 4.43-4.60 (m, 2H), 4.35 (dd, J=9.05, 5.62 Hz, 1H), 3.45 (dd, J=13.82, 5.75 Hz, 1H), 3.25-3.30 (m, 1H), 2.83 (s, 3H).

7.21.2 Example 21.2

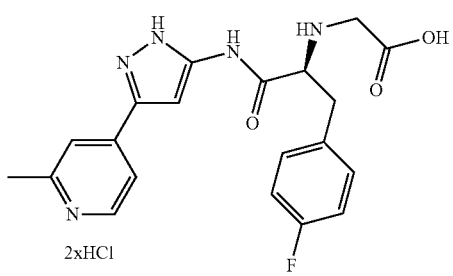 [SMILES: Cc1cc(-c2cc(NC(=O)[C@H](Cc3ccc(F)cc3)NCC(=O)O)[nH]n2)ccn1]

2-((S)-3-(4-Fluorophenyl)-1-(3-(2-methylpyridin-4-yl)-1H-pyrazol-5-ylamino)-1-oxopropan-2-ylamino)acetic acid dihydrochloride (21.2)

The compound was prepared from compound 16.1.C using procedures analagous to those in Example 16.1. LCMS ESI (pos.) m/e: 398.2 (M+1): 1H NMR (400 MHz, MeOH) δ ppm 8.66 (d, J=6.26 Hz, 1H), 8.24 (s, 1H), 8.19 (d, J=6.26 Hz, 1H), 7.34 (dd, J=8.41, 5.28 Hz, 2H), 7.08 (t, J=8.61 Hz, 3H), 4.41 (t, J=7.24 Hz, 1H), 3.93-4.08 (m, 2H), 3.55-3.80 (m, 1H), 3.36-3.44 (m, 1H), 2.82 (s, 3H).

7.22 Example 22

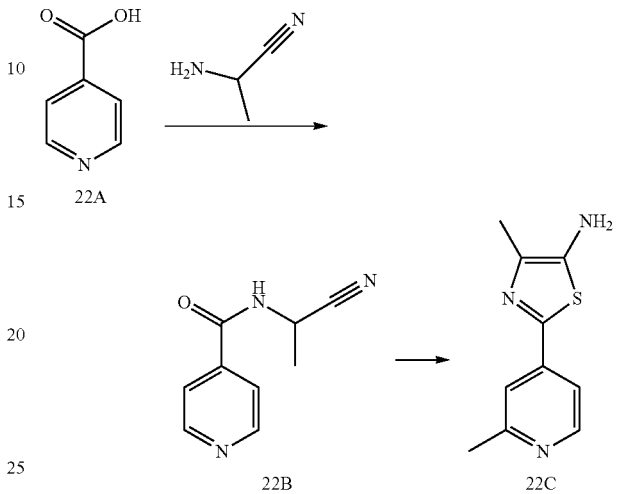

N-(1-Cyanoethyl)isonicotinamide (22B)

To a mixture of 2-methylisonicotinic acid (2.00 g, 15 mmol) and 2-aminopropanamide (3.7 g, 29 mmol) in pyridine (15 ml, 15 mmol) was added N1-((ethylimino)methylene)-N3,N3-dimethylpropane-1,3-diamine hydrochloride (5.6 g, 29 mmol). The resulting mixture was allowed to stir at rt overnight. The mixture was concentrated, to the residue was added 10% methanol/DCM (80 mL). The white precipitate was collected and the residue was purified by CombiFlash using 0-10% methanol/DCM as the eluent to give 2.14 g of N-(1-cyanoethyl)isonicotinamide 22B. LCMS (ES+) m/z 208.

4-Methyl-2-(2-methylpyridin-4-yl)thiazol-5-amine (22C)

A mixture of N-(1-amino-1-oxopropan-2-yl)-2-methylisonicotinamide (1.00 g, 4.83 mmol) and phosphorus pentasulfide (2.15 g, 9.65 mmol) in 10 mL of toluene was allowed to reflux overnight. The mixture was concentrated and the residue was purified by CombiFlash using 0-10% methanol/DCM to give 0.475 g of 4-methyl-2-(2-methylpyridin-4-yl)thiazol-5-amine 22C. LCMS (ES+) m/z 206.

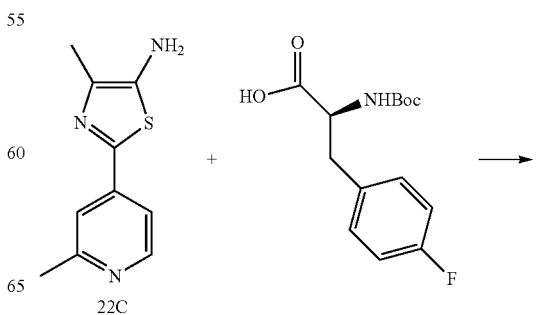

-continued

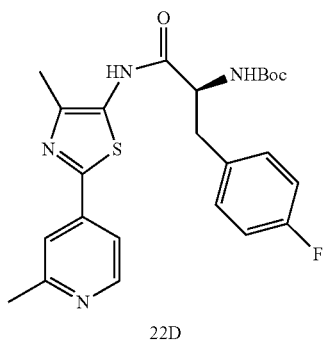

22D tert-Butyl (S)-3-(4-fluorophenyl)-1-(4-methyl-2-(2-methylpyridin-4-yl)thiazol-5-ylamino)-1-oxopropan-2-ylcarbamate (22D)

A mixture of 4-methyl-2-(2-methylpyridin-4-yl)thiazol-5-amine (0.475 g, 2.3 mmol), (S)-2-(tert-butoxycarbonyl)-3-(4-fluorophenyl)propanoic acid (0.66 g, 2.3 mmol), HBTU (0.88 g, 2.3 mmol) and N-ethyl-N-isopropylpropan-2-amine (1.2 ml, 6.9 mmol) in N,N-dimethylformamide (4.6 ml, 2.3 mmol) was allowed to stir at 80° C. for 3 hours. The mixture was directly subjected to HPLC purification to give 61 mg of tert-butyl (S)-3-(4-fluorophenyl)-1-(4-methyl-2-(2-methylpyridin-4-yl)thiazol-5-ylamino)-1-oxopropan-2-ylcarbamate 22D. 400 MHz $^1$H NMR (CDCl$_3$) δ: 8.51 (d, J=8.0 Hz, 1H), 7.84 (s, 1H), 7.69 (d, J=4.0 Hz, 1H), 7.19 (s, 1H), 7.17 (obscured dd, J=8.0, 4.0 Hz, 2H), 6.93 (dd, J=8.0, 8.0 Hz, 2H), 5.36 (d, J=8.0 Hz, 1H), 4.58 (m, 1H), 3.17 (dd, J=16.0, 8.0 Hz, 3.01 (dd, J=16.0, 8.0 Hz, 1H), 2.71 (s, 3H), 2.28 (s, 3H), 1.37 (s, 9H). LCMS (ES+) m/z 471.

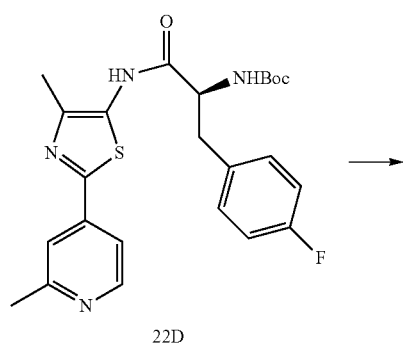

22D

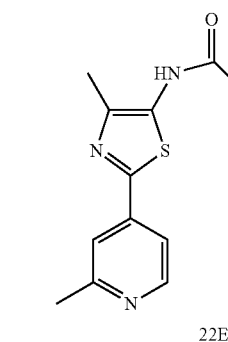

22E

(2S)-2-Amino-3-(4-fluorophenyl)-N-(4-methyl-2-(2-methylpyridin-4-yl)thiazol-5-yl)propanamide (22E)

To a solution of tert-butyl (S)-3-(4-fluorophenyl)-1-(4-methyl-2-(2-methylpyridin-4-yl)thiazol-5-ylamino)-1-oxopropan-2-ylcarbamate (0.061 g, 0.13 mmol) in DCM (0.0083 ml, 0.13 mmol) was added TFA (0.01 ml, 0.13 mmol). The resulting mixture was allowed to stir at rt overnight. The mixture was concentrated and the residue was purified by HPLC to give 40 mg of (2S)-2-Amino-3-(4-fluorophenyl)-N-(4-methyl-2-(2-methylpyridin-4-yl)thiazol-5-yl)propanamide 22E. 400 MHz $^1$H NMR (CD3OD) δ: 8.63 (d, J=8.0 Hz, 1H), 8.28 (br s, 1H), 8.22 (dd, J=8.0, 4.0 Hz, 1H), 7.31 (dd, J=8.0, 4.0 Hz, 2H), 7.09 (dd, J=8.0, 8.0 Hz, 2H), 4.51 (dd, J=8.0, 8.0 Hz, 1H), 3.30 (obscured dd, 1H), 3.23 (dd, J=16.0, 8.0 Hz, 1H), 2.80 (s, 3H), 2.43 (s, 3H). LCMS (ES+) m/z 371.

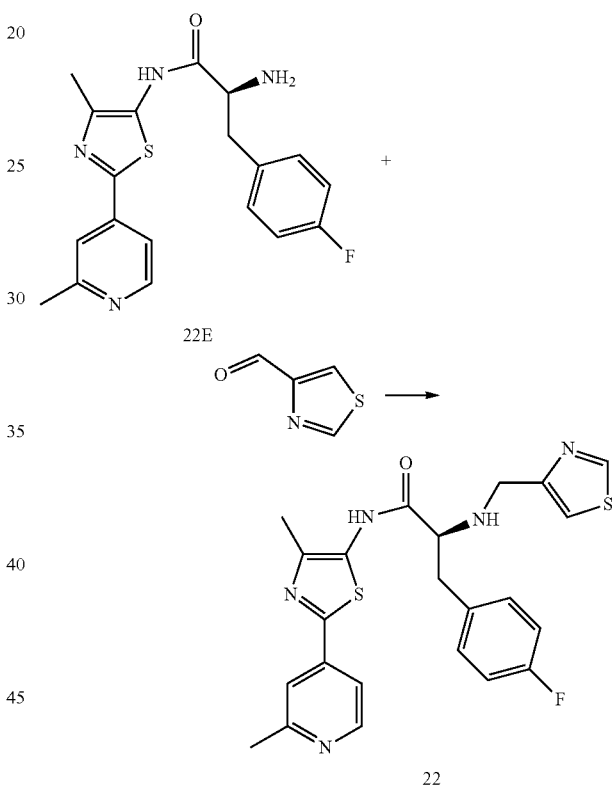

(2S)-3-(4-Fluorophenyl)-N-(4-methyl-2-(2-methylpyridin-4-yl)thiazol-5-yl)-2-(thiazol-4-ylmethylamino)propanamide (22)

A mixture of (2S)-2-amino-3-(4-fluorophenyl)-N-(4-methyl-2-(2-methylpyridin-4-yl)thiazol-5-yl)propanamide (0.0500 g, 0.13 mmol), thiazole-4-carbaldehyde (0.015 g, 0.13 mmol), reactant 3 (0.10 g, 0.47 mmol), N,N-dimethylformamide (0.50 ml, 0.13 mmol) and 1,2-dichloroethane (1.50 ml, 0.13 mmol) was allowed to stir at rt overnight. The mixture was directly subjected to HPLC purification to give 35.6 mg of (2S)-3-(4-Fluorophenyl)-N-(4-methyl-2-(2-methylpyridin-4-yl)thiazol-5-yl)-2-(thiazol-4-ylmethylamino)propanamide 22. 400 MHz $^1$H NMR (CD3OD) δ: 9.12 (d, 1H), 8.64 (d, J=4.0 Hz, 1H), 8.28 (d, 1H), 8.22 (dd, J=8.0, 4.0 Hz, 1H), 7.82 (d, 1H), 7.26 (dd, 1H), 7.06 (dd, J=8.0, 8.0 Hz, 2H), 4.56 (dd, J=12.0, 8.0 Hz, 1H), 3.50 (dd, J=16.0, 8.0 Hz, 1H), 3.23 (dd, J=12.0, 8.0 Hz, 1H), 2.80 (s, 3H), 2.31 (s, 3H). LCMS (ES+) m/z 468.

7.23 Example 23

7.23.1 Example 23.1

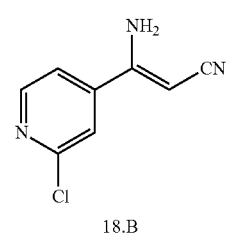

18.B

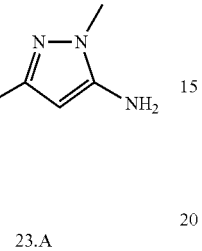

23.A

3-(2-Chloropyridin-4-yl)-1-methyl-1H-pyrazol-5-amine (23.A)

This title intermediate was prepared starting from 18.B (3.10 g, 17.3 mmol) according the procedure described above for conversion of 18.B to 18.C, except that methylhydrazine (3.5 equiv.) was used. The crude product was purified by flash chromatography on silica gel using 0-8% MeOH/CH$_2$Cl$_2$ for elution to provide 23.A (3.44 g mg, 89%) as a brown solid.

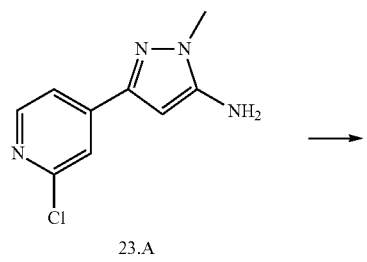

23.A

4-(5-Amino-1-methyl-1H-pyrazol-3-yl)-N-methylpyridin-2-amine (23.B)

This title intermediate was prepared starting from 23.A (2.10 g, 10.0 mmol) according the procedure described above for conversion of 18.0 to 18.D. The crude product was purified by flash chromatography using 0-10% MeOH/CH$_2$Cl$_2$ for elution to provide 23.B as white solid (1.61 g, 79%).

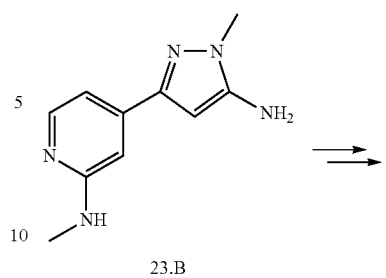

23.B

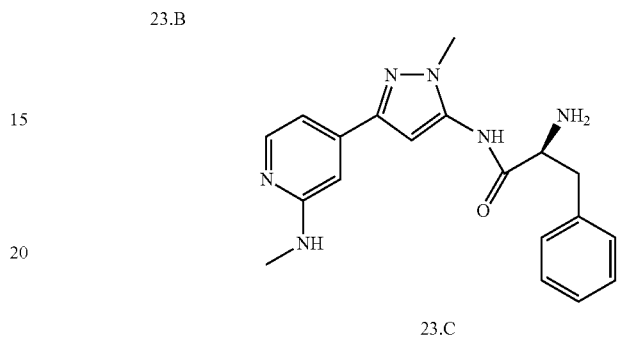

23.C

(2S)-2-Amino-N-(1-methyl-3-(2-(methylamino)pyridin-4-yl)-1H-pyrazol-5-yl)-3-phenylpropanamide (23.C)

This title intermediate was prepared starting from 23.B (101 mg, 0.48 mmol) according the procedure described above for conversion of 17.B to 17.1. The crude product was purified by flash chromatography on silica gel using 0-10% MeOH/CH$_2$Cl$_2$ for elution to provide 23.0 as colorless solid (132 mg, 76%).

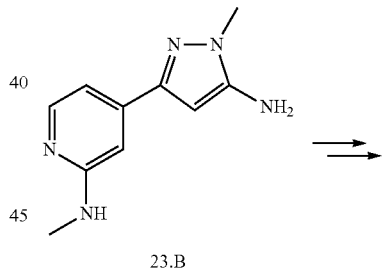

23.B

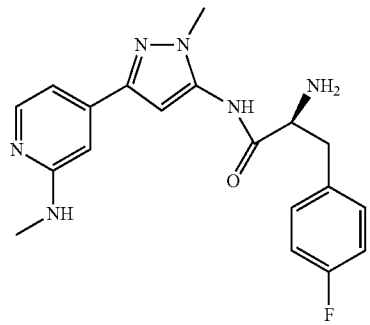

23.D

(2S)-2-Amino-3-(4-fluorophenyl)-N-(1-methyl-3-(2-(methylamino)pyridin-4-yl)-1H-pyrazol-5-yl)propanamide (23.D)

This title compound was prepared starting from 23.B (103 mg, 0.49 mmol) according the procedure (method B) described above for conversion of 17.B to 17.1, except that boc-4-fluoro-1-phenylalanine was used. The crude product was purified by flash chromatography on silica gel using 0-10% MeOH/CH$_2$Cl$_2$ for elution to provide 23.D as colorless solid (144 mg, 79%).

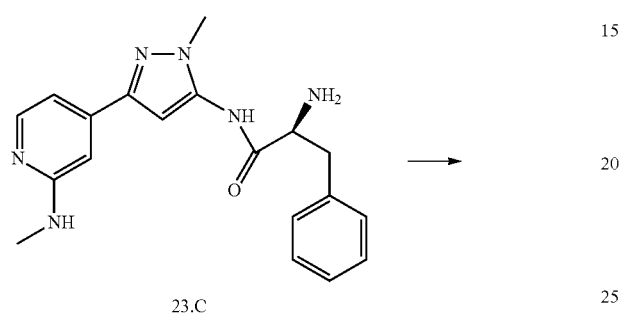

23.C

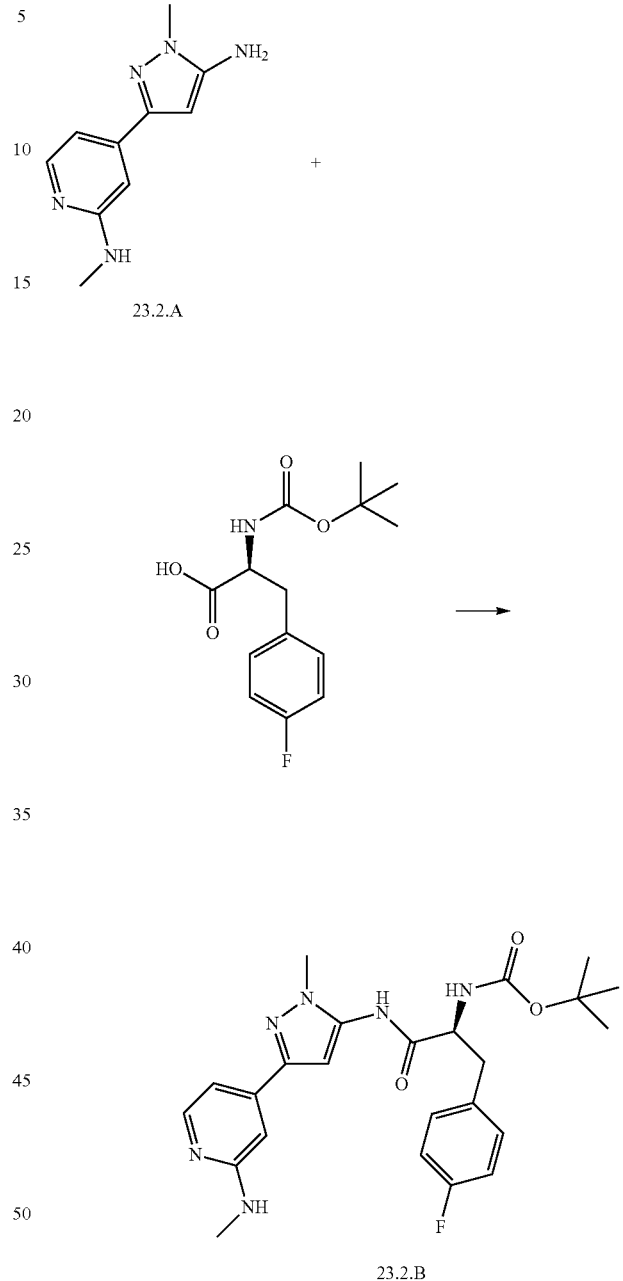

(2S)-2-((5-Fluoropyridin-2-yl)methylamino)-N-(1-methyl-3-(2-(methylamino)pyridin-4-yl)-1H-pyrazol-5-yl)-3-phenylpropanamide (23.1)

This title compound was prepared from 23.0 (82 mg, 0.23 mmol) according the procedure described above for conversion of 4.0 to 4, except that 5-fluoropicolinaldehyde (available from Atlantic SciTech Group, Inc.) (29 mg, 0.23 mmol) was used. After purification by preparative HPLC (10-90% CH$_3$CN/water, 30 min), the TFA salt of title product 23.1 (56 mg, 52%) was obtained as white solid. MS ESI (pos.) m/e: 460.1 (M+H); $^1$H NMR (400 MHz, CD$_3$OD) δ ppm 8.36 (d, J=2.74 Hz, 1H), 7.94 (d, J=5.48 Hz, 1H), 7.52 (td, J=8.51, 2.93 Hz, 1H), 7.38 (dd, J=8.61, 4.69 Hz, 1H), 7.21-7.35 (m, 5H), 6.91 (dd, J=5.48, 1.56 Hz, 1H), 6.85 (s, 1H), 6.59 (s, 1H), 3.90-3.99 (m, 1H), 3.81-3.90 (m, 1H), 3.63 (t, J=7.04 Hz, 1H), 3.57 (s, 3H) 2.99-3.14 (m, 2H), 2.89 (s, 3H).

7.23.2 Example 23.2

(S)-Tert-butyl 3-(4-fluorophenyl)-1-(1-methyl-3-(pyridine-4-yl)-1H-pyrazol-5-ylamino)-1-oxopropan-2-ylcarbamate (23.1.B)

To a flask with 23.2.A (999 mg, 4.9 mmol, prepared as in example 23.1) was added (S)-2-(tert-butoxycarbonyl)-3-(4-fluorophenyl)propanoic acid (1.46 g, 5.2 mmol) and N1-((ethylimino)methylene)-N3,N3-dimethylpropane-1,3-diamine hydrochloride (2.83 g, 14.7 mmol). Then pyridine was added as a solvent. The reaction was stirred overnight. Standard aqueous workup with water and ethyl acetate and silica gel chromatography afforded 1.58 g (69%) 23.2.B.

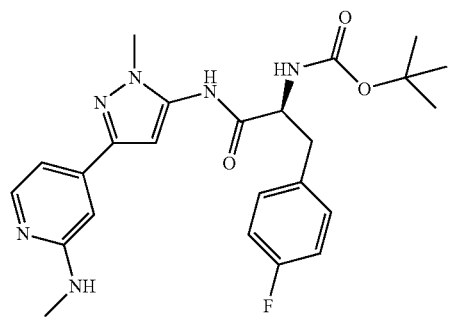

23.2.B

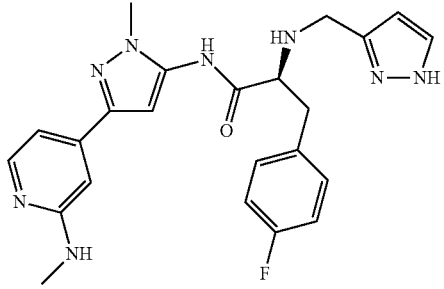

23.2

(2S)-2-((1H-Pyrazol-3-yl)methylamino)-3-(4-fluorophenyl)-N-(1-methyl-3-(2-(methylamino)pyridin-4-yl)-1H-pyrazol-5-yl)propanamide (23.2)

To (2S)-2-amino-3-(4-fluorophenyl)-N-(1-methyl-3-(2-(methylamino)pyridin-4-yl)-1H-pyrazol-5-yl)propanamide (79 mg, 214 μmol) was added 1H-pyrazole-3-carbaldehyde (29 mg, 300 μmol), then DCE and dioxane were added as solvents, followed by acetic acid (13 μl, 225 μmol) and NaBH(OAc)$_3$ (136 mg, 643 μmol). Heating was continued for 1 hr. 40 min. The reaction was concentrated and purified by reverse phase HPLC purification to afford 23.2 (27 mg, 28%) as a white solid. 1H NMR (400 MHz, MeOH) δ ppm 7.77-8.01 (m, 1H) 7.55 (br. s., 1H) 7.25 (dd, J=8.61, 5.48 Hz, 2H) 7.03 (t, J=8.80 Hz, 2H) 6.91 (dd, J=5.67, 1.37 Hz, 1H) 6.51-6.65 (m, 1H) 6.23 (d, J=1.96 Hz, 1H) 3.74-3.91 (m, 2H) 3.60-3.63 (m, 1H) 3.59 (s, 3H) 2.97-3.11 (m, 2H) 2.89 (s, 3H).

7.23.3 Examples 23.3-23.10

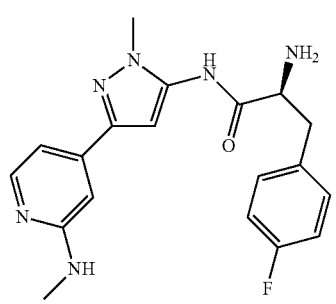

23.2.C (2S)-2-Amino-3-(4-fluorophenyl)-N-(1-methyl-3-(2-(methylamino)pyridin-4-yl)-1H-pyrazol-5-yl)propanamide (23.2.C)

To a flask with 23.2.B (1.58 g, 3.4 mmol) was added 12 mL DCM and 5.2 mL trifluoroacetic acid. The reaction was stirred for 2 hours and concentrated. The crude was bascified with saturated NaHCO$_3$ and extracted with 30% isopropanol in chloroform. Silica gel purification afforded 1.04 g (84%) of product 23.2.C.

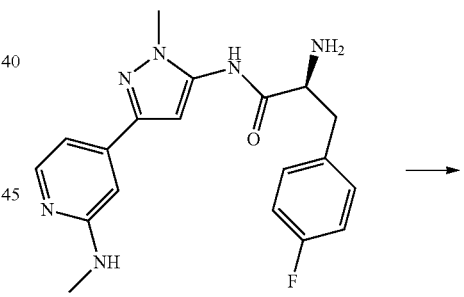

23.3.C

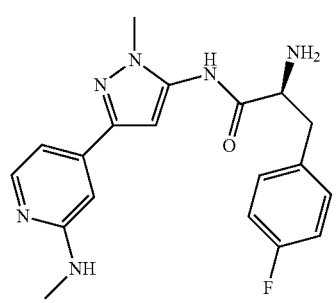

23.2.C

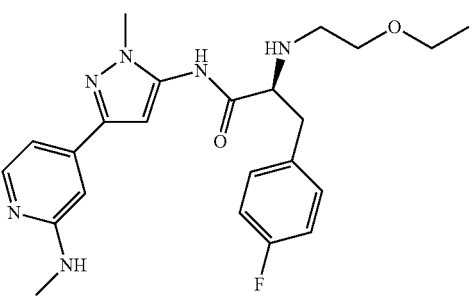

23.3

(2S)-2-(2-Ethoxyethylamino)-3-(4-fluorophenyl)-N-(1-methyl-3-(2-(methylamino)pyridin-4-yl)-1H-pyrazol-5-yl)propanamide (23.3)

To a pressure tube containing 23.1.C (50 mg, 0.136 mmol) was added K$_2$CO$_3$ (38 mg, 0.27 mmol), cesium iodide (71 mg, 0.27 mmol) and 2-bromoethyl ethyl ether (25 mg, 0.16 mmol). DMF (1.5 mL) was added and the reaction was heated overnight at 80° C. After aqueous workup, the crude was purified on reverse phase HPLC to afford 23.3 (4 mg, 7%). 1H NMR (400 MHz, MeOH) δ ppm 7.93 (d, J=5.48 Hz, 1H) 7.30 (dd, J=8.61, 5.48 Hz, 2H) 7.02-7.10 (m, 2H) 6.93 (dd, J=5.67, 1.37 Hz, 1H) 6.84-6.88 (m, 1H) 6.60 (s, 1H) 3.61 (s, 3H) 3.57-3.61 (m, 1H) 3.52 (t, J=5.28 Hz, 2H) 3.46 (qd, J=6.98, 3.33 Hz, 2H) 2.95-3.11 (m, 2H) 2.90 (s, 3H) 2.68-2.84 (m, 2H) 1.12-1.17 (m, 3H).

7.23.4 Example 23.4

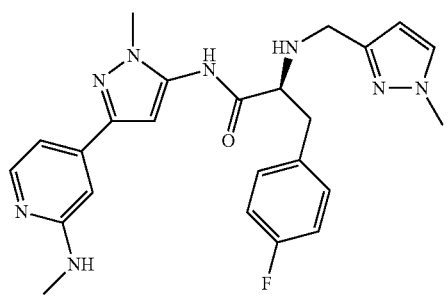

23.4

(2S)-3-(4-Fluorophenyl)-2-((1-methyl-1H-pyrazol-3-yl)methylamino)-N-(1-methyl-3-(2-(methylamino)pyridin-4-yl)-1H-pyrazol-5-yl)propanamide (23.4)

This compound was prepared according to the procedure to make 23.2. 1H NMR (400 MHz, MeOH) δ ppm 7.83 (dd, J=6.65, 0.78 Hz, 1H) 7.66 (d, J=1.96 Hz, 1H) 7.21-7.36 (m, 4H) 7.07-7.14 (m, 2H) 6.87 (s, 1H) 6.42 (d, J=2.35 Hz, 1H) 4.27-4.38 (m, 3H) 3.92 (s, 3H) 3.61 (s, 3H) 3.44 (dd, J=13.50, 5.67 Hz, 1H) 3.20 (dd, J=13.69, 9.39 Hz, 1H) 3.06 (s, 3H).

The following compounds were prepared from 23.0 using appropriate aldehydes according to the methods described herein for 23.1.

TABLE 3

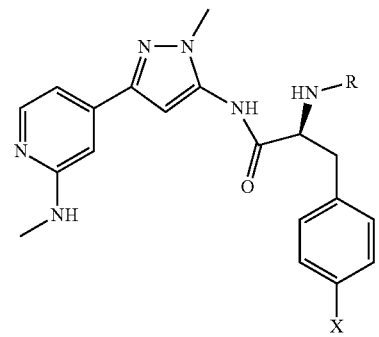

| Compound | R | X |
|---|---|---|
| 23.5 | ⸾CH$_2$-thiazol-4-yl | F |
| 23.6 | ⸾CH$_2$-(5-fluoropyridin-2-yl) | F |
| 23.7 | ⸾CH$_2$-(1H-1,2,3-triazol-4-yl) | F |
| 23.8 | ⸾CH$_2$C(O)OH | F |
| 23.9 | ⸾CH$_2$C(O)OH | H |
| 23.10 | ⸾CH$_2$-thiazol-4-yl | H |

(2S)-3-(4-Fluorophenyl)-N-(1-methyl-3-(2-methylamino) pyridin-4-yl)-1H-pyrazol-5-yl)-2-(thiazol-4-ylmethylamino)propanamide (23.5)

MS ESI (pos.) m/e: 466.2 (M+H); $^1$H NMR (400 MHz, CD$_3$OD) δ ppm 8.94 (d, J=2.35 Hz, 1H), 7.94 (d, J=5.48 Hz, 1H), 7.38 (d, J=1.96 Hz, 1H), 7.25 (dd, J=8.61, 5.09 Hz, 2H), 7.03 (t, J=8.80 Hz, 2H), 6.92 (dd, J=5.48, 1.56 Hz, 1H), 6.85 (s, 1H), 6.61 (s, 1H), 3.89-4.05 (m, 2H), 3.59-3.69 (m, 4H), 3.32 (t, J=1.56 Hz, 1H), 2.97-3.14 (m, J=13.89, 13.89, 13.69, 7.04 Hz, 2H), 2.90 (s, 3H).

(2S)-3-(4-Fluorophenyl)-2-((5-fluoropyridin-2-yl)methylamino)-N-(1-methyl-3-(2-(methylamino)pyridin-4-yl)-1H-pyrazol-5-yl)propanamide (23.6)

MS ESI (pos.) m/e: 478.1 (M+H); $^1$H NMR (400 MHz, CD$_3$OD) δ ppm 8.32 (d, J=4.69 Hz, 1H), 7.93 (d, J=5.48 Hz, 1H), 7.53 (t, J=8.41 Hz, 1H), 7.34 (ddd, J=8.51, 4.69, 4.40 Hz, 1H), 7.18-7.29 (m, 2H), 6.96-7.08 (m, 2H), 6.90 (dd, J=5.48, 1.57 Hz, 1H), 6.84 (s, 1H), 6.59 (s, 1H), 3.97 (s, 2H) 3.57-3.70 (m, 4H), 3.03-3.13 (m, 1H), 2.95-3.03 (m, 1H), 2.89 (s, 3H).

(2S)-2-((1H-1,2,3-triazol-4-yl)methylamino)-3-(4-fluorophenyl)-N-(1-methyl-3-(2-(methylamino)pyridin-4-yl)-1H-pyrazol-5-yl)propanamide (23.7)

MS ESI (pos.) m/e:450.1 (M+H); $^1$H NMR (400 MHz, CD$_3$OD) δ ppm 7.95 (d, J=5.48 Hz, 1H), 7.68 (s, 1H), 7.24-7.33 (m, 2H), 7.05 (t, J=8.80 Hz, 2H), 6.92 (d, J=4.30 Hz, 1H), 6.86 (s, 1H), 6.58 (s, 1H), 3.88-4.01 (m, 2H), 3.56-3.67 (m, 4H), 3.00-3.10 (m, 2H), 2.87-2.94 (m, 3H).

2-((S)-3-(4-Fluorophenyl)-1-(1-methyl-3-(2-(methylamino)pyridin-4-yl)-1H-pyrazol-5-ylamino)-1-oxopropan-2-ylamino)acetic acid (23.8)

MS ESI (pos.) m/e: 427.1 (M+H); $^1$H NMR (400 MHz, CD$_3$OD) δ ppm 7.84 (d, J=7.43 Hz, 1H), 7.36 (dd, J=8.61, 5.09 Hz, 2H), 7.26-7.33 (m, 2H), 7.08-7.20 (m, 2H), 6.90 (s, 1H), 4.41 (dd, J=9.00, 6.26 Hz, 1H), 3.83-4.03 (m, 2H), 3.63 (s, 3H) 3.36-3.47 (m, 1H), 3.25 (dd, J=13.30, 9.00 Hz, 1H), 3.07 (s, 3H).

2-((S)-1-(1-Methyl-3-(2-(methylamino)pyridin-4-yl)-1H-pyrazol-5-ylamino)-1-oxo-3-phenylpropan-2-ylamino)acetic acid (23.9)

MS ESI (pos.) m/e: 409.1 (M+H); $^1$H NMR (400 MHz, CD$_3$OD) δ ppm 7.84 (d, J=6.65 Hz, 1H), 7.34-7.45 (m, 5H), 7.27-7.34 (m, 2H), 6.90 (s, 1H), 4.61 (dd, J=9.39, 5.87 Hz, 1H), 4.05 (s, 2H) 3.55 (s, 3H) 3.50 (dd, J=13.50, 6.06 Hz, 1H), 3.27 (dd, J=13.30, 9.39 Hz, 1H), 3.08 (s, 3H).

(2S)—N-(1-methyl-3-(2-(methylamino)pyridin-4-yl)-1H-pyrazol-5-yl)-3-phenyl-2-(thiazol-4-ylmethylamino)propanamide (23.10)

MS ESI (pos.) m/e: 448.1 (M+H); $^1$H NMR (400 MHz, CD$_3$OD) δ ppm 8.94 (d, J=1.96 Hz, 1H), 7.94 (d, J=5.48 Hz, 1H), 7.36 (d, J=1.96 Hz, 1H), 7.21-7.35 (m, 5H), 6.91 (dd, J=5.48, 1.57 Hz, 1H), 6.85 (s, 1H), 6.60 (s, 1H), 3.96 (d, J=7.04 Hz, 2H), 3.66 (t, J=7.04 Hz, 1H), 3.57 (s, 3H), 3.01-3.15 (m, 2H), 2.89 (s, 3H).

7.23.5 Example 23.11

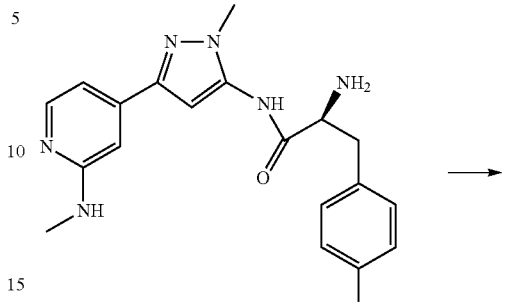

23.D

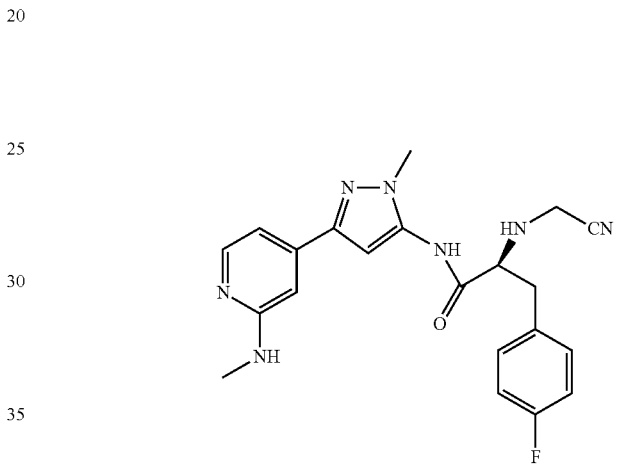

23.E

(2S)-2-(Cyanomethylamino)-3-(4-fluorophenyl)-N-(1-methyl-3-(2-(methylamino)pyridin-4-yl)-1H-pyrazol-5-yl)propanamide (23.E)

To a rt solution of 23.D (750 mg, 2036 μmol) and bromoacetonitrile (244 mg, 2036 μmol) in acetonitrile was added n,n-diisopropylethylamine (426 μl, 2443 μmol). After stirring at 60° C. for 2 hr, organic solvents were removed under reduced pressure. Purification of the residue by flash chromatography on silica gel using 0-12% MeOH/CH$_2$Cl$_2$ for elution gave the title product 23.E as yellow syrup (706 mg, 85%).

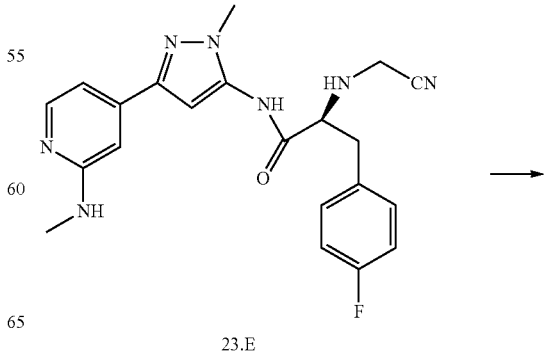

23.E

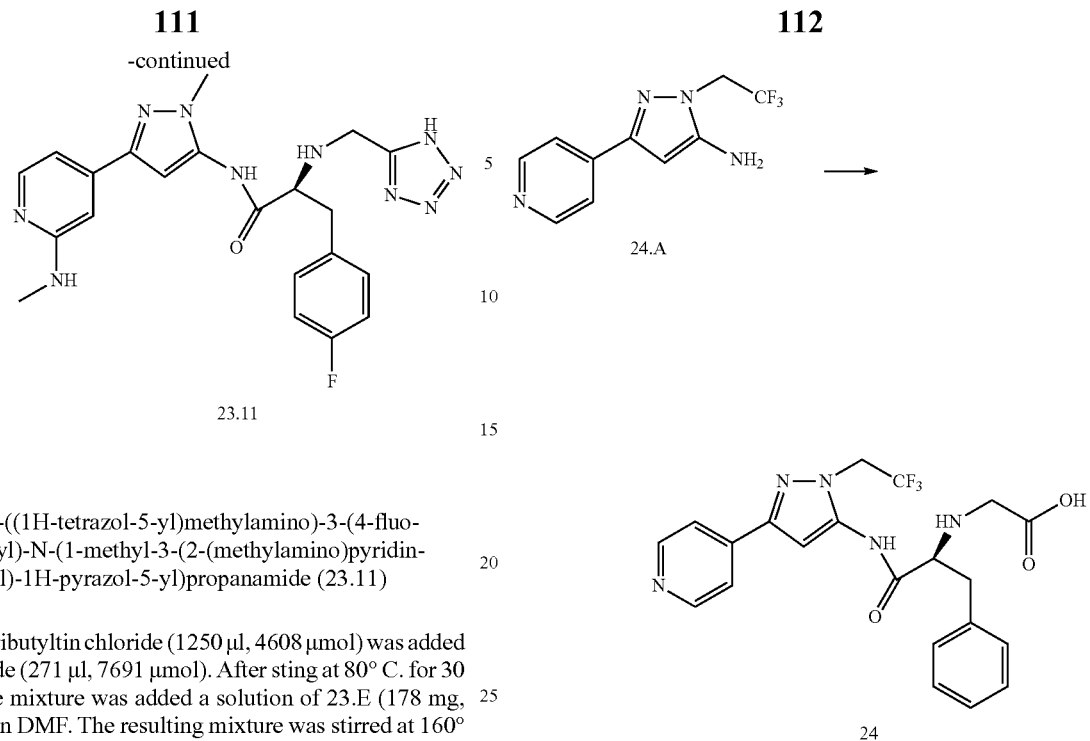

(2S)-2-((1H-tetrazol-5-yl)methylamino)-3-(4-fluorophenyl)-N-(1-methyl-3-(2-(methylamino)pyridin-4-yl)-1H-pyrazol-5-yl)propanamide (23.11)

To neat tributyltin chloride (1250 μl, 4608 μmol) was added sodium azide (271 μl, 7691 μmol). After sting at 80° C. for 30 mins, to the mixture was added a solution of 23.E (178 mg, 437 μmol) in DMF. The resulting mixture was stirred at 160° C. under N2 for 1.5 hr, cooled and diluted with water. The resulting mixture was extracted with 30% $^i$PrOH/CHCl$_3$ (3×10 mL), and organic solvents was removed under reduced pressure. After purification of the residue by preparative HPLC (10-90% CH$_3$CN/water, 30 min), the combined product fractions were treated with 1.0 N HCl (0.50 ml) and concentrated to provide 23.11 HCl salt colorless solid (121 mg, 57%) as. MS ESI (positve.) m/e: 451.1 (M+H), $^1$H NMR (400 MHz, CD$_3$OD) δ ppm 7.82 (d, J=6.65 Hz, 1H), 7.23-7.45 (m, 4H), 7.11 (t, J=8.61 Hz, 2H), 6.88 (s, 1H), 4.71 (s, 2H), 4.60 (br. s., 1H) 3.63 (s, 3H) 3.42-3.54 (m, 1H), 3.20-3.29 (m, 1H), 3.01-3.11 (m, 4H).

7.24 Example 24

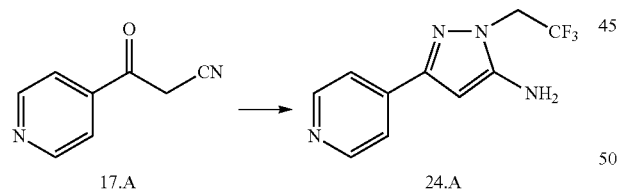

3-(Pyridin-4-yl)-1-(2,2,2-trifluoroethyl)-1H-pyrazol-5-amine (24.A)

This title intermediate was prepared from 17.A according the procedure described above for conversion of 17.A to 17.B, except that 1-(2,2,2-trifluoroethyl)hydrazine (available from Aldrich) (2.0 equiv.) was used. The crude product was purified by flash chromatography on silica gel using 0-8% MeOH/CH$_2$Cl$_2$ for elution to provide 24.A as colorless solid (741 mg,

(S)-2-(1-Oxo-3-phenyl-1-(3-(pyridin-4-yl)-1-(2,2,2-trifluoroethyl)-1H-pyrazol-5-ylamino)propan-2-ylamino)acetic acid (24)

This title compound was prepared starting from 24.A according the procedure described above for conversion of 17.B to 17.2, with method B for the amide formation, except that glyoxylic acid (1.2 equiv.) was used for reductive amination. After purification by preparative HPLC (5-45% CH$_3$CN/water, 45 in), the combined product fractions were treated with 1.0 N HCl, and concentrated to provide 24 HCl salt as a colorless solid. MS ESI (positve.) m/e: 448.1 (M+H); $^1$H NMR (400 MHz, CD$_3$OD) δ ppm 8.84 (d, J=5.09 Hz, 2H), 8.46 (d, J=6.26 Hz, 2H), 7.30-7.55 (m, 5H), 7.16-7.30 (m, 1H), 4.93-5.15 (m, 2H), 4.71-4.81 (m, 1H), 4.62 (t, J=7.43 Hz, 2H), 3.99 (br. s., 3H) 3.39-3.57 (m, 2H).

7.25 Example 25

7.25.1 Example 25.1

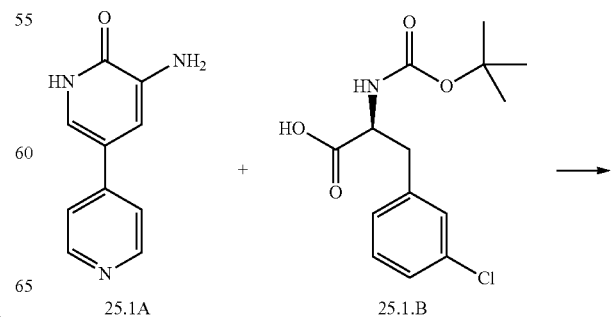

-continued

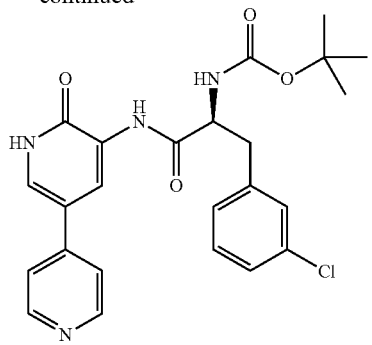

25.1.C

(S)-tert-butyl 3-(3-chlorophenyl)-1-oxo-1-(2-oxo-5-(pyridin-4-yl)-1,2-dihydropyridin-3-ylamino)propan-2-ylcarbamate (25.1.C)

Amrinone 25.1.A (Sigma, 250 mg, 1.33 mmol), (S)-2-(tert-butoxycarbonyl)-3-(3-chlorophenyl)propanoic acid 25.1.B (400 mg, 1.33 mmol), HBTU (608 mg, 1.60 mmol), and DIPEA (350 μL, 2.00 mmol) were stirred in DMF (10 ml) at room temperature for a week. The reaction mixture was diluted with water and filtered and the resulting solid was used in the next step without further purification.

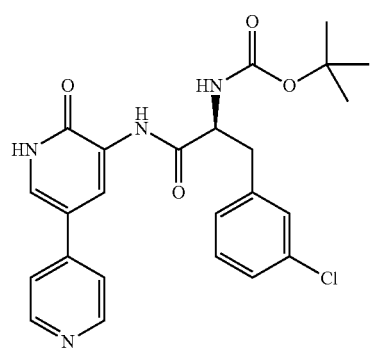

25.1.C

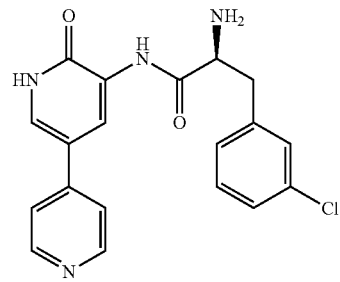

25.1.D

(S)-2-amino-3-(3-chlorophenyl)-N-(2-oxo-5-(pyridin-4-yl)-1,2-dihydropyridin-3-yl)propanamide (25.1.D)

Crude 25.1.C was stirred in DCM with HCl (4.0 M, dioxane) until the deprotection was complete. The reaction mixture was concentrated to a solid and partitioned with saturated NaHCO$_3$(aq)/CHCl$_3$:IPA (4:1). The aqueous layer was further extracted (2×) and the organics were combined, dried with sodium sulfate, filtered, and concentrated to give a light tan solid (230 mg, 47%).

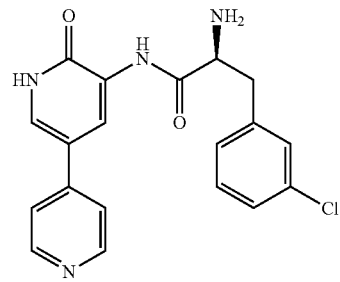

25.1.D

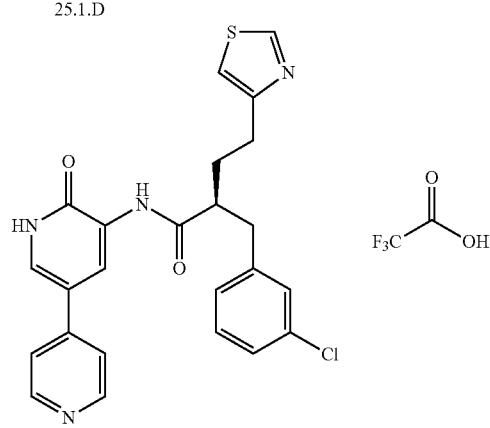

25.1

(S)-3-(3-Chlorophenyl)-N-(2-oxo-5-(pyridin-4-yl)-1,2-dihydropyridin-3-yl)-2-(thiazol-4-ylmethylamino)propanamide trifluoroacetate (25.1)

25.1 was prepared in an analogous manner to Example 12 to yield a light yellow powder (275 mg, 87%). LC-MS (+esi, M+H$^+$=466.1). 1H NMR (400 MHz, MeOH) δ ppm 9.10 (d, J=1.96 Hz, 1H) 8.85 (d, J=2.35 Hz, 1H) 8.72 (d, J=7.04 Hz, 2H) 8.05 (d, J=6.65 Hz, 2H) 8.02 (d, J=2.35 Hz, 1H) 7.76 (d, J=1.96 Hz, 1H) 7.27-7.33 (m, 3H) 7.19-7.23 (m, 1H) 4.50-4.56 (m, 1H) 4.39-4.48 (m, 2H) 3.31 (2H).

7.25.2 Example 25.2

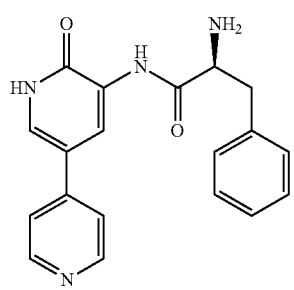

25.2

(S)-2-amino-N-(2-oxo-5-(pyridin-4-yl)-1,2-dihydro-pyridin-3-yl)-3-phenylpropanamide diTFA (25.2)

Prepared from 3-amino-5-(pyridin-4-yl)pyridin-2(1H)-one (available from Aldrich) according to procedures analogous to those in Example 3.1. LCMS ESI (pos.) m/e: 335.0 (M+1).

7.26 Example 26

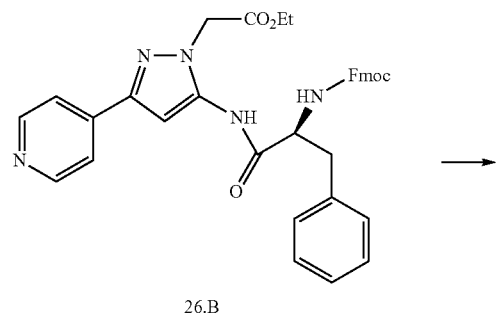

Methyl 2-(5-amino-3-(pyridin-4-yl)-1H-pyrazol-1-yl)acetate (26.A)

This title intermediate was prepared according the procedure described above for conversion of 17.A to 17.B, except that ethyl 2-hydrazinylacetate hydrochloride (available from Aldrich) (1.8 equiv.) was used. The crude product was purified by flash chromatography on silica gel using 0-20% MeOH/$CH_2Cl_2$ for elution to provide 26.A as colorless solid (304 mg, 57%).

(S)-Ethyl 2-(5-(2-(((9H-fluoren-9-yl)methoxy)carbonyl)-3-phenylpropanamido)-3-(pyridin-4-yl)-1H-pyrazol-1-yl)acetate (26.B)

This title intermediate was prepared from 26.A according the procedure described above for conversion of 17.B to 17.D. The crude product was purified by flash chromatography on silica gel using 0-10% MeOH/$CH_2Cl_2$ for elution to provide 26.B as white solid (407 mg, 56%).

(S)-Ethyl 2-(5-(2-amino-3-phenylpropanamido)-3-(pyridin-4-yl)-1H-pyrazol-1-yl)acetate (26.C)

To a rt solution of 26.B (341 mg, 0.63 mmol) in $CH_2Cl_2$ (5 mL) was added TBAF (available from Aldrich) (1.0 M, 3.2 mL, 3.2 mmol). The resulting mixture was stirred at rt for 12 hr, treated with water (15), and extracted with 30% $^iPrOH$/$CHCl_3$ (3×15 mL). The combined organic layers were washed with water, brine and dried over $MgSO_4$. After removal of organic solvent under reduced pressure, purification of the residue by flash chromatography on silica gel using 0-10% MeOH/$CH_2Cl_2$ for elution gave the title product 26.C as colorless solid (141 mg, 71%).

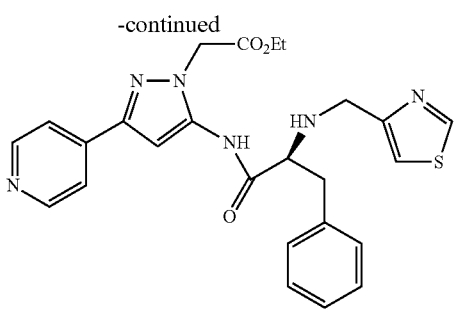

26.D

(S)-Ethyl 2-(5-(3-phenyl-2-(thiazol-4-ylmethylamino)propanamido)-3-(pyridin-4-yl)-1H-pyrazol-1-yl)acetate (26. D)

This title compound was prepared from 26.C according the procedure described above for conversion of 4.0 to 4. The crude product 26.D was purified by flash chromatography on silica gel using 0-10% MeOH/CH$_2$Cl$_2$ for elution to provide 26.D as colorless solid (46 mg, 43%).

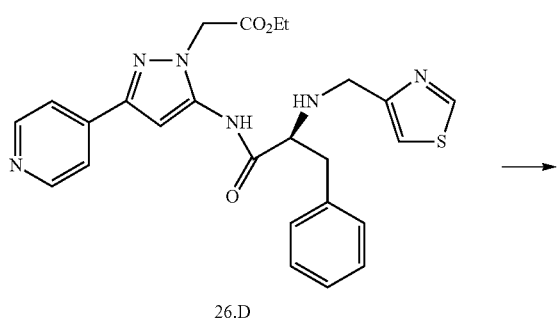

(S)-2-(5-(3-Phenyl-2-(thiazol-4-ylmethylamino)propanamido)-3-(pyridin-4-yl)-1H-pyrazol-1-yl)acetic acid (26)

To a rt solution of 26.D (35 mg, 73 μmol) in dioxane (1.0 mL) was added lithium hydroxide monohydrate (6 mg, 147 μmol) followed by water (0.3 mL). After stirring at rt for 1.0 hr, the reaction mixture was diluted with water (2 mL), neutralized to pH ~7 by 10% HOAc and extracted with 30% $^i$PrOH/CHCl$_3$ (3×4 mL). The combined organic solution was concentrated under reduced pressure. Purification of the residue by preparative HPLC (10-90% CH$_3$CN/water, 30 min) provided the title product 26 TFA salt as white solid (7 mg, 21%). MS ESI (positve.) m/e: 463.1 (M+H); $^1$H NMR (400 MHz, CD$_3$OD) δ ppm 9.13 (d, J=1.56 Hz, 1H), 8.81 (d, J=6.65 Hz, 2H), 8.44 (d, J=7.04 Hz, 2H), 7.82 (d, J=1.96 Hz, 1H), 7.35-7.44 (m, 3H), 7.25-7.35 (m, 2H), 7.19 (s, 1H), 4.69 (d, J=18.00 Hz, 1H), 4.39-4.57 (m, 3H), 3.45 (dd, J=13.69, 5.87 Hz, 1H), 3.26 (dd, J=13.69, 9.00 Hz, 1H).

7.27 Example 27

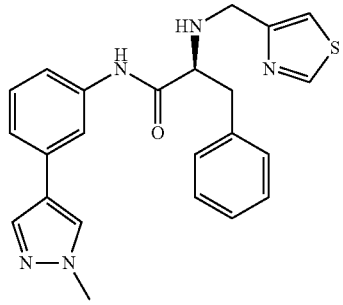 [SMILES: Cn1cc(-c2cccc(NC(=O)[C@H](Cc3ccccc3)NCc3cscn3)c2)cn1]

(2S)—N-(3-(1-Methyl-1H-pyrazol-4-yl)phenyl)-3-phenyl-2-(thiazol-4-ylmethylamino)propanamide (27)

The compound was prepared using the procedures analagous to those in Example 33. 1H NMR (500 MHz, MeOH-D4) δ ppm 3.28-3.30 (m, 2H) 3.93-4.03 (m, 3H) 4.23 (dd, J=9.29, 5.62 Hz, 1H) 4.50 (q, J=13.94 Hz, 2H) 5.51 (s, 1H) 7.16-7.26 (m, 1H) 7.26-7.42 (m, 7H) 7.58 (t, J=1.83 Hz, 1H) 7.74-7.86 (m, 2H) 7.93 (s, 1H) 9.14 (d, J=1.96 Hz, 1H).

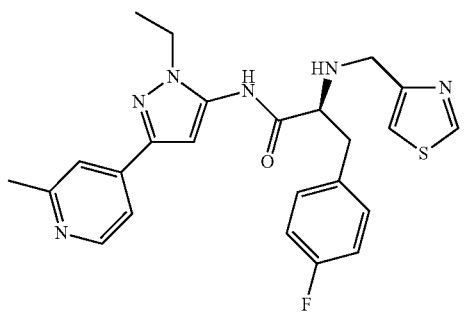 [SMILES: CCn1nc(-c2ccnc(C)c2)cc1NC(=O)[C@H](Cc1ccc(F)cc1)NCc1cscn1]

7.28 Example 28

(2S)—N-(1-ethyl-3-(2-methylpyridin-4-yl)-1H-pyrazol-5-yl)-3-(4-fluorophenyl)-2-(thiazol-4-ylmethylamino)propanamide dihydrochloride (28)

The compound was prepared from compound 16.1.C using procedures analagous to those in Example 16.1. LCMS ESI (pos.) m/e: 4465.1 (M+1): NMR (500 MHz, MeOH) δ ppm 9.04 (s, 1H), 8.50 (d, J=6.11 Hz, 1H), 8.17 (s, 1H), 8.12 (d, J=5.87 Hz, 1H), 7.79 (s, 1H), 7.26 (dd, J=8.07, 5.13 Hz, 2H), 7.03 (t, J=8.56 Hz, 3H), 4.42-4.47 (m, 3H), 3.75-3.86 (m,

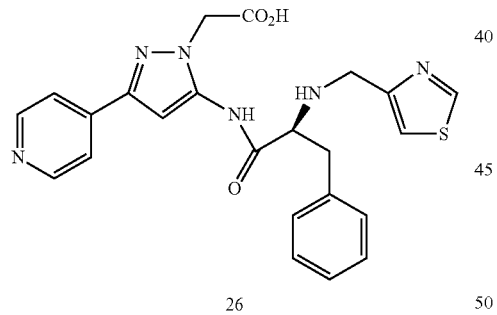

2H), 3.41 (dd, J=13.45, 5.14 Hz, 1H), 3.14 (dd, J=13.20, 9.54 Hz, 1H), 2.70 (s, 3H), 1.22 (t, J=7.09 Hz, 3H).

7.29 Example 29

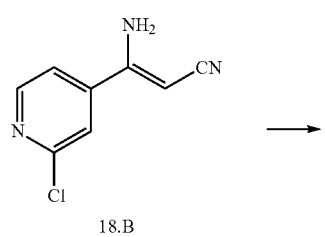

18.B

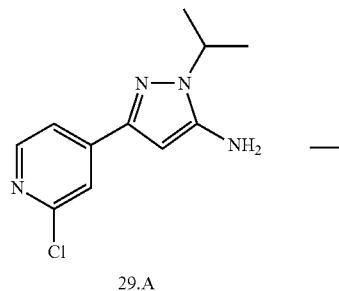

29.A

1-Isopropyl-3-(pyridin-4-yl)-1H-pyrazol-5-amine (29.A)

The title intermediate was prepared according the procedure described above for conversion of 18.B to 18.C, except that 1-tert-butylhydrazine hydrochloride (available from Aldrich) (1.0 equiv.) was used. The crude product 29.A was directly carried to the next step.

1-Isopropyl-3-(pyridin-4-yl)-1H-pyrazol-5-amine (29.B)

To a rt solution of 29.A (850 mg, 3591 μmol) in MeOH was added 5% Pd/C. The heterogeneous solution was stirred at 50° C. under H$_2$ for 1.0 hr. To the resulting mixture was added celite, solid was filtered off and washed with MeOH. The organic solution was concentrated under reduced pressure to provide the title product 29.B as colorless syrup (681 mg, 94%).

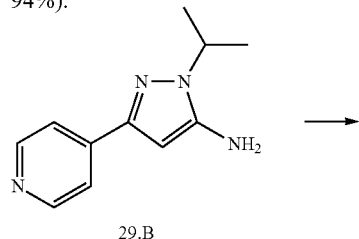

29.B

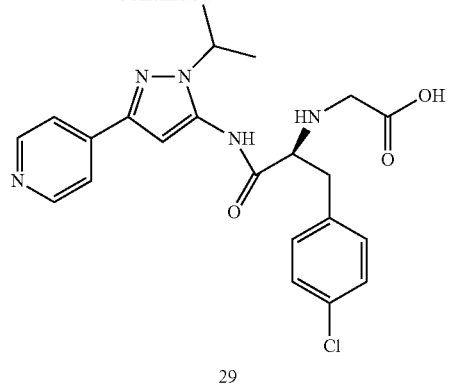

29

(S)-2-(3-(4-Chlorophenyl)-1-(1-isopropyl-3-(pyridin-4-yl)-1H-pyrazol-5-ylamino)-1-oxopropan-2-ylamino)acetic acid (29)

This title compound was prepared starting from 29.B (169 mg, 0.84 mmol) and Boc-4-chloro L-phenylalanine (available from Chem-Impex International, Inc. (305 mg, 1.0 mmol) according the procedure described above for conversion of 17.B to 17.2, except that glyoxylic acid (1.0 equiv.) was used in the last step. After purification by preparative HPLC (5-40% CH$_3$CN/water, 45 min), product fractions were collected, treated with 1.0 N HCl, and concentrated to provided 29 HCl salt as colorless solid (52 mg, 14%). MS ESI (positve.) m/e: 442.1 (M+H); $^1$H NMR (400 MHz, CD$_3$OD) δ ppm 8.77 (d, J=7.04 Hz, 2H), 8.40 (d, J=7.04 Hz, 2H), 7.39-7.49 (m, 2H), 7.32-7.39 (m, 2H), 7.08 (s, 1H), 4.58 (dd, J=10.17, 5.87 Hz, 1H), 4.06 (s, 2H) 3.99 (quin, J=6.55 Hz, 1H), 3.49 (dd, J=13.30, 5.87 Hz, 1H), 3.23 (dd, J=13.30, 9.78 Hz, 1H), 2.32 (s, 1H), 1.38 (dd, J=10.96, 6.26 Hz, 6H).

7.30 Example 30

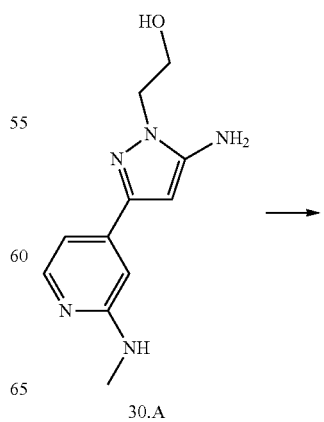

30.A

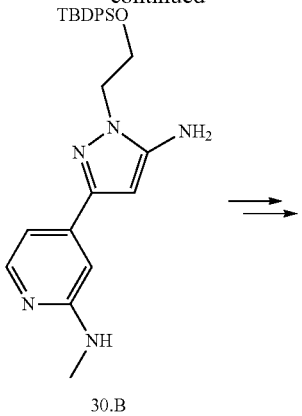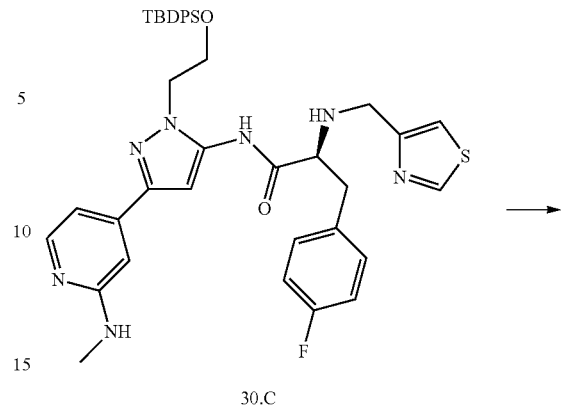

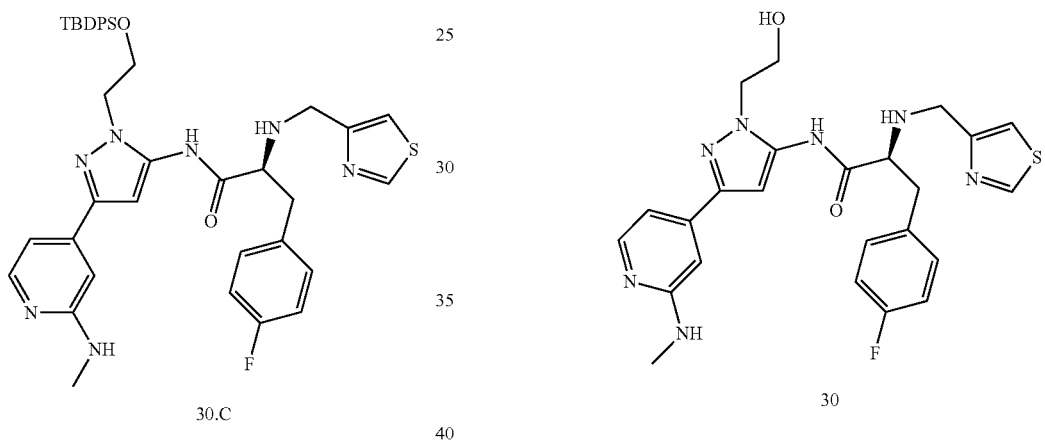

4-(5-Amino-1-(2-(tert-butyldiphenylsilyloxy)ethyl)-1H-pyrazol-3-yl)-N-methylpyridin-2-amine (30.B)

Starting material 2-(5-amino-3-(2-(methylamino)pyridin-4-yl)-1H-pyrazol-1-yl)ethanol 30.A was prepared analagously to example 23.1. To a flask with 30.A (306 mg, 1.3 mmol) was added DMAP (16 mg, 0.13 mmol), 1H-imidazole (268 mg, 3.9 mmol). Then DMF 1.5 mL was added, followed by tert-butylchlorodiphenylsilane (505 mg, 1.8 mmol). The reaction was stirred overnight. Standard aqueous workup and silica gel chromatography afforded 618 mg (100%) 30.B.

(2S)—N-(1-(2-(tert-butyldiphenylsilyloxy)ethyl)-3-(2-(methylamino)pyridin-4-yl)-1H-pyrazol-5-yl)-3-(4-fluorophenyl)-2-(thiazol-4-ylmethylamino)propanamide (30.C)

Synthesis of 30.0 followed the procedure to prepare 23.2 from 23.2.A.

(2S)-3-(4-Fluorophenyl)-N-(1-(2-hydroxyethyl)-3-(2-(methylamino)pyridin-4-yl)-1H-pyrazol-5-yl)-2-(thiazol-4-ylmethylamino)propanamide (30)

To a flask with 30.C (110 mg, 0.15 mmol) was added THF 1.2 mL, and 0.2 mL TBAF (1M, 0.3 mmol). After 2 hours, the reaction was concentrated and worked up with water and 30% isopropanol in chloroform. The organic phase was washed with water and brine, dried and concentrated. Reverse phase HPLC purification 5-40% afforded product 30 (32 mg, 43%). 1H NMR (400 MHz, MeOH) δ ppm 8.93 (d, J=1.96 Hz, 1H) 7.94 (d, J=5.48 Hz, 1H) 7.39 (d, J=1.96 Hz, 1H) 7.23 (dd, J=8.61, 5.48 Hz, 2H) 6.98-7.05 (m, 2H) 6.93-6.97 (m, 1H) 6.89 (s, 1H) 6.76 (s, 1H) 4.12 (td, J=5.09, 1.96 Hz, 2H) 3.84-4.01 (m, 4H) 3.57 (dd, J=7.82, 5.87 Hz, 1H) 3.10 (dd, J=13.69, 7.80 Hz, 1H) 2.95 (dd, J=13.69, 7.83 Hz, 1H) 2.91 (s, 3H).

7.31 Example 31

The following compounds were prepared according to the methods described for the preparation of example 23.2 with appropriate aldehydes.

TABLE 4

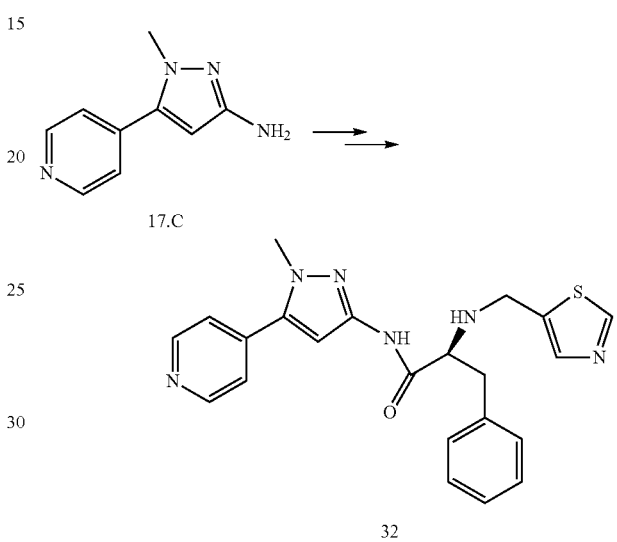

| Compound | R group |
|---|---|
| 31.1 | thiazol-4-ylmethyl |
| 31.2 | (1H-1,2,3-triazol-4-yl)methyl |
| 31.3 | (5-fluoropyridin-2-yl)methyl |
| 31.4 | -CH2-C(=O)-OH |

(2S)—N-(1-Ethyl-3-(2-(methylamino)pyridin-4-yl)-1H-pyrazol-5-yl)-3-(4-fluorophenyl)-2-(thiazol-4-ylmethylamino)propanamide (31.1)

1H NMR (400 MHz, MeOH) δ ppm 8.95 (d, J=1.96 Hz, 1H) 7.82-8.01 (m, 1H) 7.40 (d, J=1.96 Hz, 1H) 7.18-7.31 (m, 2H) 6.99-7.09 (m, 2H) 6.93 (dd, J=5.48, 1.37 Hz, 1H) 6.87 (s, 1H) 6.59 (s, 1H) 3.90-3.98 (m, 4H) 3.60-3.71 (m, 1H) 3.04 (dd, J=6.94, 4.99 Hz, 2H) 2.90 (s, 3H) 1.30 (t, J=7.24 Hz, 3H).

(2S)-2-((1H-1,2,3-triazol-4-yl)methylamino)-N-(1-ethyl-3-(2-(methylamino)pyridin-4-yl)-1H-pyrazol-5-yl)-3-(4-fluorophenyl)propanamide (31.2)

1H NMR (400 MHz, MeOH) δ ppm 7.93 (d, J=5.48 Hz, 1H) 7.68 (s, 1H) 7.20-7.34 (m, 2H) 7.01-7.09 (m, 2H) 6.91-6.97 (m, 1H) 6.88 (s, 1H) 6.57 (s, 1H) 3.80-3.97 (m, 4H) 3.63 (t, J=7.04 Hz, 1H) 3.03 (d, J=7.04 Hz, 2H) 2.91 (s, 3H) 1.30 (t, J=7.24 Hz, 3H).

(2S)—N-(1-Ethyl-3-(2-(methylamino)pyridin-4-yl)-1H-pyrazol-5-yl)-3-(4-fluorophenyl)-2-((5-fluoropyridin-2-yl)methylamino)propanamide (31.3)

1H NMR (400 MHz, MeOH) δ ppm 8.39 (d, J=3.13 Hz, 1H) 7.95 (d, J=6.26 Hz, 1H) 7.56 (td, J=8.51, 2.93 Hz, 1H) 7.44 (dd, J=8.80, 4.50 Hz, 1H) 7.20-7.32 (m, 2H) 7.01-7.10 (m, 2H) 6.91-6.97 (m, 1H) 6.87 (s, 1H) 6.59 (s, 1H) 3.81-4.00 (m, 4H) 3.61-3.66 (m, 1H) 3.06 (dd, J=7.04, 1.96 Hz, 2H) 2.91 (s, 3H) 1.31 (t, J=7.24 Hz, 3H).

2-((S)-1-(1-Ethyl-3-(2-(methylamino)pyridin-4-yl)-1H-pyrazol-5-ylamino)-3-(4-fluorophenyl)-1-oxo-propan-2-ylamino)acetic acid (31.4)

1H NMR (400 MHz, MeOH) δ ppm 7.82 (d, J=7.43 Hz, 1H) 7.24-7.44 (m, 4H) 7.05-7.20 (m, 2H) 6.89 (s, 1H) 4.44 (dd, J=9.39, 5.87 Hz, 1H) 3.91 (d, J=4.30 Hz, 2H) 3.82-3.90 (m, 2H) 3.40 (dd, J=13.69, 6.26 Hz, 1H) 3.23 (dd, J=13.69, 9.39 Hz, 1H) 3.06 (s, 3H) 1.29 (t, J=7.24 Hz, 3H).

7.32 Example 32

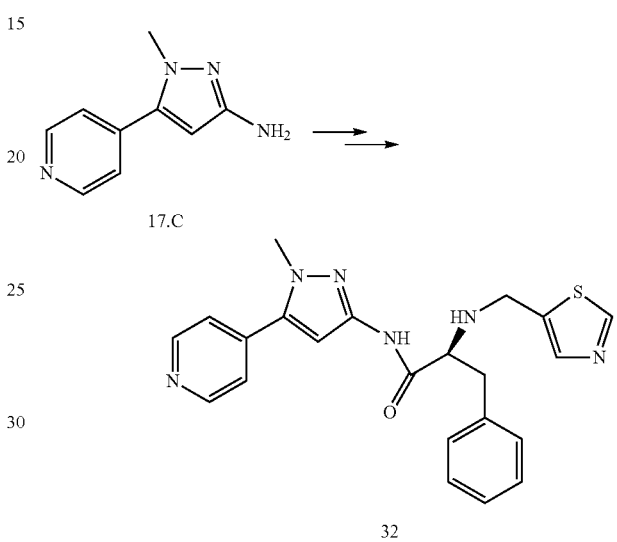

(S)—N-(1-Methyl-5-(pyridin-4-yl)-1H-pyrazol-3-yl)-3-phenyl-2-(thiazol-5-ylmethylamino)propanamide (32)

The title compound was prepared starting from 17.0 according the procedure described above for conversion of 17.B. to 17.2 (method B). The product was purified by flash chromatography on silica gel using 0-80% EtOAc/Hexanes for elution. MS ESI (positve.) m/e: 419.1 (M+H); ¹H NMR (400 MHz, CD₃OD) δ ppm 8.91 (d, J=1.96 Hz, 1H), 8.64-8.72 (m, 2H), 7.59-7.66 (m, 2H), 7.18-7.35 (m, 6H), 6.86 (s, 1H), 3.91-3.99 (m, 1H), 3.81 (s, 3H), 3.71-3.91 (m, 1H), 3.58 (dd, J=7.83, 5.87 Hz, 1H), 3.05-3.17 (s, 1H), 2.94 (dd, J=13.69, 7.83 Hz, 1H).

7.33 Example 33

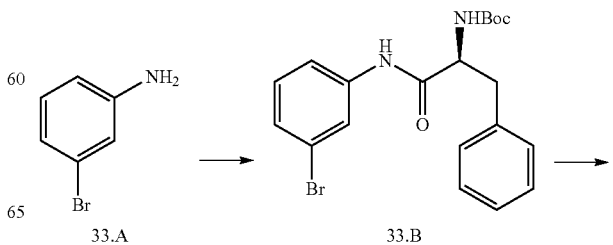

-continued

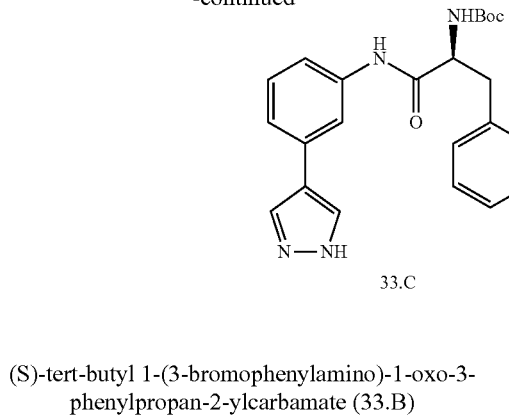

33.C (S)-tert-butyl 1-(3-bromophenylamino)-1-oxo-3-phenylpropan-2-ylcarbamate (33.B)

The same procedure as in example 13.E was employed for this example, replacing 2-(benzyloxy)-5-bromobenzenamine 13.D with 3-bromoaniline 33.A (available from Aldrich) to give (S)-tert-butyl 1-(3-bromophenylamino)-1-oxo-3-phenylpropan-2-ylcarbamate 33.B.

Tert-butyl (S)-1-(3-(1H-pyrazol-4-yl)phenylamino)-1-oxo-3-phenylpropan-2-ylcarbamate (33.C)

The same procedure as in example 13.0 was employed for this example, replacing tert-butyl (S)-1-(3-(1H-pyrazol-4-yl)phenylamino)-1-oxo-3-phenylpropan-2-ylcarbamate 13.B with 1-((4-bromo-2-nitrophenoxy)methyl)benzene 33.B and replacing pyridin-4-ylboronic acid with 4-(4,4,5,5-tetramethyl-1,3,2-dioxaborolan-2-yl)-1H-pyrazole to give tert-butyl (S)-1-(3-(1H-pyrazol-4-yl)phenylamino)-1-oxo-3-phenylpropan-2-ylcarbamate 33.C.

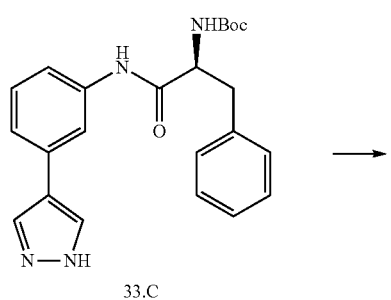

33.C

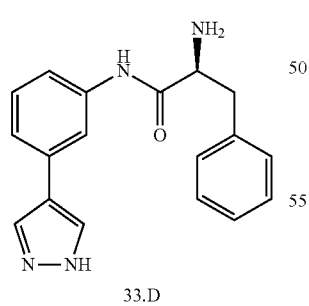

33.D (2S)—N-(3-(1H-Pyrazol-4-yl)phenyl)-2-amino-3-phenylpropanamide (33.D)

The same procedure as in example 13.F was employed for this example, replacing tert-butyl (S)-1-(3-(1H-pyrazol-4-yl)phenylamino)-1-oxo-3-phenylpropan-2-ylcarbamate 13.E with (S)-tert-butyl 1-(3-bromophenylamino)-1-oxo-3-phenylpropan-2-ylcarbamate 33.0 to give (2S)—N-(3-(1H-pyrazol-4-yl)phenyl)-2-amino-3-phenylpropanamide 33.D.

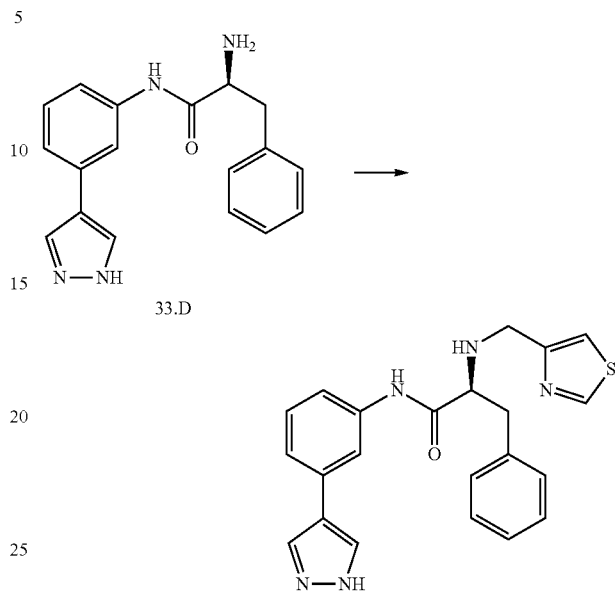

(2S)—N-(3-(1H-Pyrazol-4-yl)phenyl)-3-phenyl-2-(thiazol-4-ylmethylamino)propanamide (33)

The same procedure as in example 12 was employed for this example, replacing (2S)—N-(3-(1H-pyrazol-3-yl)phenyl)-2-amino-3-phenylpropanamide 12.C with (2S)—N-(3-(1H-pyrazol-4-yl)phenyl)-2-amino-3-phenylpropanamide 33.D to give (2S)—N-(3-(1H-pyrazol-4-yl)phenyl)-3-phenyl-2-(thiazol-5-ylmethylamino)propanamide 33 (8.7 mg, 29% yield) as a light yellow solid. LCMS ESI (pos.) m/e: 404.2 (M+1): 1H NMR (500 MHz, MeOH-D4) δ ppm 9.13 (d, J=1.96 Hz, 1H), 7.95 (s, 2H), 7.81 (d, J=1.96 Hz, 1H), 7.61 (t, J=1.83 Hz, 1H), 7.24-7.42 (m, 7H), 7.16-7.24 (m, 1H), 4.41-4.57 (m, 2H), 4.25 (dd, J=9.29, 5.87 Hz, 1H), 3.42 (dd, J=13.20, 5.87 Hz, 1H), 3.26 (dd, J=13.45, 9.29 Hz, 1H).

7.34 Example 34

7.34.1 Examples 34.1-34.3, 34.5-34.7 and 34.10-34.19

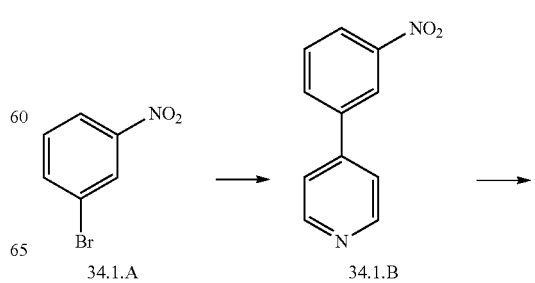

34.1.A     34.1.B

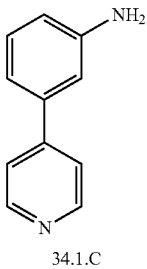
34.1.C

4-(3-Nitrophenyl)pyridine (34.1.B)

To a 250 ml flask was added 1-bromo-3-nitrobenzene 34.1.A (500 mg, 2.5 mmol), pyridin-4-ylboronic acid (665 mg, 5.45 mmol), and Pd(Ph$_3$)$_4$ (578 mg, 0.5 mmole), 40 ml of DMF, 10 ml of saturated aqueous sodium bicarbonate and cesium carbonate (1.63 g, 5.0 mmol). The resulting mixture was stirred overnight at 70° C., at which time the reaction mixture was partitioned between 500 ml of EtOAc and 100 ml of water. The organic layer was extracted twice more with 100 ml of water and the organic phase was concentrated to afford 34.1.B which was used in the next step without any further purification.

3-(Pyridin-4-yl)benzenamine (34.1.C)

To a solution of 4-(3-nitrophenyl)pyridine 34.1.B. (500 mg, 2.9 mole) in 5 ml of methanol was added 1 g of 10% Pd on carbon by weight. The air was evacuated from the reaction flask and was replaced with hydrogen. The resulting slurry was stirred overnight at room temperature, at which time the reaction mixture was filtered over a bed of celite and the mother liquor concentrated to afford 3-(pyridin-4-yl)benzenamine 34.1.C (500 mg, 100% yield).

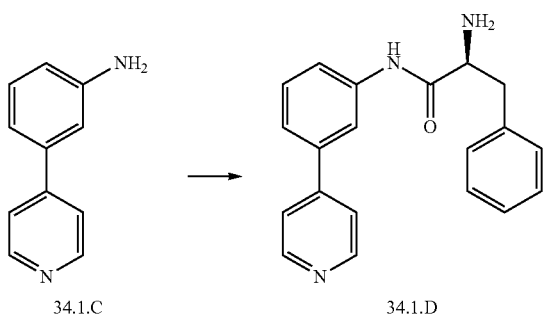 [SMILES: Nc1cccc(-c2ccncc2)c1 ; N[C@@H](Cc1ccccc1)C(=O)Nc1cccc(-c2ccncc2)c1]

(S)-2-Amino-3-phenyl-N-(3-(pyridin-4-yl)phenyl) propanamide (34.1.D)

To a 100 ml flask was added 3-(pyridin-4-yl)benzenamine 34.1.C. (500 mg, 2.9 mole), HBTU (1300 mg, 3.5 mmole), n-(tert-butoxycarbonyl)-1-phenylalanine (858 g, 3.2 mmole), 20 ml of DMF and DIEA (756 ul, 4.35 mmole). The reaction was stirred at room temperature for 6 hours, at which time the crude reaction was purified with a silica gel column (eluting with 10% MeOH in DCM) to give (S)-2-amino-3-phenyl-N-(3-(pyridin-4-yl)phenyl)propanamide.

The intermediate was then resuspended in 5 ml of MeOH and then 15 ml of 1N HCl in ether was added. The reaction was then stirred at room temperature for 6 hours at which time the solvent was removed to give the hydrochloride salt of (S)-2-amino-3-phenyl-N-(3-(pyridin-4-yl)phenyl)propanamide 34.1.D. LCMS ESI (pos.) m/e: 318.1 (M+1): 1H NMR (500 MHz, MeOH) δ ppm 8.56-8.60 (m, 2H), 7.93 (dd, J=3.67, 1.96 Hz, 1H), 7.68 (td, J=4.03, 1.71 Hz, 2H), 7.52-7.58 (m, 1H), 7.41-7.51 (m, 2H), 7.19-7.31 (m, 5H), 3.73-3.79 (m, 1H), 3.14 (dt, J=7.34, 3.67 Hz, 1H), 2.98 (d, J=7.34 Hz, 1H).

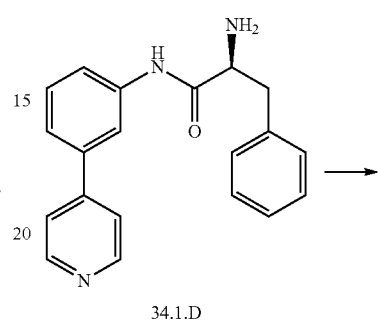
34.1.D

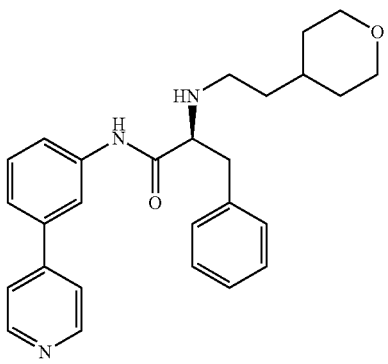
34.1

(S)-3-Phenyl-N-(3-(pyridin-4-yl)phenyl)-2-(2-(tetrahydro-2H-pyran-4-yl)ethylamino)propanamide (34.1)

To a 20 ml vial were added (S)-2-amino-3-phenyl-N-(3-(pyridin-4-yl)phenyl)propanamide 34.1.D (75 mg, 0.19 mmole), thiazole-4-carbaldehyde (20 mg, 0.18 mmole), sodium triacetoxyborohydride (60 mg, 2.9 mmole), 5 ml of DCE, and DIEA (99 µl, 0.57 mmole). The reaction was stirred at room temperature for 1 hour. The reaction was then partitioned between 10 ml of water and 20 ml of DCM and the solvent was removed by rotary evaporation. The crude was purified using reverse phase preparative HPLC to give 34.8 mg of (S)-3-phenyl-N-(3-(pyridin-4-yl)phenyl)-2-(2-(tetrahydro-2H-pyran-4-yl)ethylamino)propanamide 34.1 as a light yellow solid. LCMS ESI (pos.) m/e: 430.3 (M+1): 1H NMR (500 MHz, MeOH) δ ppm 8.89 (d, J=6.85 Hz, 2H), 8.32 (d, J=6.85 Hz, 2H), 8.11 (t, J=1.83 Hz, 1H), 7.67-7.79 (m, 1H), 7.50-7.64 (m, 2H), 7.22-7.34 (m, 5H), 4.29 (dd, J=9.41, 5.99 Hz, 1H), 3.81-3.94 (m, 2H), 3.34-3.43 (m, 3H), 3.21-3.27 (m, 1H), 3.05-3.18 (m, 2H), 1.57-1.75 (m, 5H), 1.29 (br. s., 2H).

The following compounds were prepared by reductive amination using intermediate 34.1.D and the appropriate aldehyde or ketone.

TABLE 5

| Compound | R group |
|---|---|
| 34.2 | 1-(pyridin-2-yl)ethyl |
| 34.3 | 1-(pyridin-2-yl)propyl |
| 34.5 | thiazol-4-ylmethyl |
| 34.6 | thiazol-4-ylmethyl |
| 34.7 | thiazol-2-ylmethyl |
| 34.10 | 1-(pyrazin-2-yl)ethyl |
| 34.11 | (tetrahydrofuran-3-yl)methyl |
| 34.12 | cyclopropylmethyl |
| 34.13 | isobutyl |
| 34.14 | thiazol-4-ylmethyl |
| 34.15 | oxazol-5-ylmethyl |
| 34.16 | thiazol-2-ylmethyl |
| 34.17 | thiazol-5-ylmethyl |
| 34.18 | (2-methylthiazol-4-yl)methyl |
| 34.19 | 1-(thiazol-4-yl)ethyl |

(2S)-3-Phenyl-2-(1-(pyridin-2-yl)ethylamino)-N-(3-(pyridin-4-yl)phenyl)propanamide (34.2)

1H NMR (400 MHz, MeOH) δ ppm 8.59 (dd, J=4.50, 1.76 Hz, 2H) 8.39-8.44 (m, 1H) 7.79-7.82 (m, 1H) 7.65-7.72 (m, 3H) 7.39-7.49 (m, 4H) 7.15-7.32 (m, 6H) 3.85 (q, J=6.65 Hz, 1H) 3.51 (t, J=6.85 Hz, 1H) 3.09-3.18 (m, 1H) 2.95-3.04 (m, 1H) 1.33 (d, J=6.65 Hz, 3H).

(2S)-3-Phenyl-2-(1-(pyridin-2-yl)propylamino)-N-(3-(pyridin-4-yl)phenyl)propanamide (34.3)

1H NMR (400 MHz, MeOH) δ ppm 8.53-8.69 (m, 2H) 8.36 (d, J=4.30 Hz, 1H) 7.96-8.03 (m, 1H) 7.71 (dd, J=4.50, 1.76 Hz, 2H) 7.64 (td, J=7.73, 1.76 Hz, 1H) 7.57-7.61 (m, 1H) 7.44-7.54 (m, 2H) 7.20-7.31 (m, 4H) 7.12-7.17 (m, 2H) 7.09 (d, J=7.83 Hz, 1H) 3.58 (t, J=6.85 Hz, 1H) 3.22 (dd, J=8.61, 5.48 Hz, 1H) 3.00 (dd, J=13.30, 5.48 Hz, 1H) 2.80-2.89 (m, 1H) 1.61-1.83 (m, 2H) 0.86 (t, J=7.43 Hz, 3H).

(R)-3-Phenyl-N-(3-(pyridin-4-yl)phenyl)-2-(thiazol-4-ylmethylamino)propanamide trifluoroacetate (34.5)

LC-MS (+esi, M+H⁺=415.1). 1H NMR (500 MHz, DICHLOROMETHANE-d₂) δ ppm 10.03 (s, 1H) 8.81 (d, J=1.96 Hz, 1H) 8.75 (d, J=6.60 Hz, 2H) 8.01 (s, 1H) 7.96 (d, J=6.60 Hz, 2H) 7.55 (d, J=1.71 Hz, 2H) 7.47 (d, J=4.89 Hz, 2H) 7.26 (s, 5H) 4.65-4.69 (m, 1H) 4.53 (q, J=13.69 Hz, 2H) 3.45-3.51 (m, 1H) 3.36-3.42 (m, 1H).

(R)-3-Phenyl-N-(3-(pyridin-4-yl)phenyl)-2-(thiazol-5-ylmethylamino)propanamide trifluoroacetate (34.6)

LC-MS (+esi, M+H+=415.1). 1H NMR (500 MHz, DICHLOROMETHANE-$d_2$) δ ppm 9.48 (s, 1H) 8.85 (s, 1H) 8.80 (d, J=6.85 Hz, 2H) 8.07 (s, 1H) 8.01 (d, J=6.60 Hz, 2H) 7.87 (s, 1H) 7.53-7.58 (m, 1H) 7.49-7.53 (m, 2H) 7.26-7.33 (m, 3H) 7.22-7.26 (m, 2H) 4.29-4.44 (m, 2H) 4.16-4.22 (m, 1H) 3.30-3.33 (m, 1H) 3.23-3.29 (m, 1H).

(R)-3-Phenyl-N-(3-(pyridin-4-yl)phenyl)-2-(thiazol-2-ylmethylamino)propanamide trifluoroacetate (34.7)

LC-MS (+esi, M+H+=415.1). 1H NMR (500 MHz, DICHLOROMETHANE-$d_2$) δ ppm 9.32 (s, 1H) 8.83 (d, J=6.60 Hz, 2H) 8.09 (s, 1H) 8.05 (d, J=6.85 Hz, 2H) 7.82 (d, J=3.42 Hz, 1H) 7.51-7.58 (m, 3H) 7.49 (d, J=3.42 Hz, 1H) 7.27-7.35 (m, 3H) 7.23-7.27 (m, 2H) 4.50-4.67 (m, 2H) 4.46 (t, J=7.46 Hz, 1H) 3.34 (d, J=7.09 Hz, 2H).

(2S)-3-Phenyl-2-(1-(pyrazin-2-yl)ethylamino)-N-(3-(pyridin-4-yl)phenyl)propanamide (34.10)

1H NMR (400 MHz, MeOH) δ ppm 8.63 (d, J=1.17 Hz, 1H) 8.59 (dd, J=4.50, 1.76 Hz, 2H) 8.46-8.49 (m, 1H) 8.35 (d, J=2.74 Hz, 1H) 7.74-7.78 (m, 1H) 7.65-7.69 (m, 2H) 7.45-7.49 (m, 1H) 7.38-7.42 (m, 2H) 7.26-7.30 (m, 4H) 7.21-7.24 (m, 1H) 3.94 (q, J=6.65 Hz, 1H) 3.56 (t, J=7.04 Hz, 1H) 3.08-3.14 (m, 1H) 2.96-3.03 (m, 1H) 1.39 (d, J=6.65 Hz, 3H).

(2S)-3-Phenyl-N-(3-(pyridin-4-yl)phenyl)-2-((tetrahydrofuran-3-yl)methylamino)propanamide TFA salt (34.11)

LCMS ESI (pos.) m/e: 402.2 (M+1).

(S)-2-(Cyclopropylmethylamino)-3-(3-fluorophenyl)-N-(3-(pyridin-4-yl)phenyl)propanamide (34.12)

LCMS ESI (pos.) m/e: 390.1 (M+1).
(S)-2-(Isopropylamino)-3-phenyl-N-(3-(pyridin-4-yl)phenyl)propanamide (34.13)
LCMS ESI (pos.) m/e: 360.3 (M+1).

(S)-3-Phenyl-N-(3-(pyridin-4-yl)phenyl)-2-(thiazol-4-ylmethylamino)propanamide (34.14)

1H NMR (500 MHz, MeOH-D4) δ ppm 1.92-1.99 (m, 1H) 2.14 (dd, J=13.45, 5.62 Hz, 1H) 3.00 (dd, J=9.29, 5.87 Hz, 1H) 3.16-3.26 (m, 2H) 5.94-6.06 (m, 5H) 6.21 (t, 1H) 6.24-6.31 (m, 1H) 6.43 (d, J=7.58 Hz, 1H) 6.50 (d, J=1.71 Hz, 1H) 6.79 (s, 1H) 6.96 (d, J=6.60 Hz, 2H) 7.57 (d, J=6.85 Hz, 2H) 7.82 (d, J=1.47 Hz, 1H).

(S)-2-(Oxazol-5-ylmethylamino)-3-phenyl-N-(3-(pyridin-4-yl)phenyl)propanamide (34.15)

1H NMR (500 MHz, MeOH-D4) δ ppm 3.20-3.27 (m, 1H) 3.36-3.38 (m, 1H) 3.43 (dd, J=13.45, 5.62 Hz, 1H) 4.26-4.33 (m, 1H) 4.55 (s, 1H) 7.26-7.40 (m, 6H) 7.53-7.64 (m, 2H) 7.73-7.78 (m, 1H) 8.08 (t, J=1.71 Hz, 1H) 8.26-8.37 (m, 3H) 8.90 (d, J=6.85 Hz, 2H).

(S)-3-Phenyl-N-(3-(pyridin-4-yl)phenyl)-2-(thiazol-2-ylmethylamino)propanamide (34.16)

1H NMR (500 MHz, MeOH-D4) δ ppm 3.24-3.28 (m, 1H) 3.31-3.43 (m, 1H) 4.12 (dd, J=5.62, 2.69 Hz, 1H) 4.36-4.42 (m, 1H) 4.64 (d, J=4.16 Hz, 3H) 7.17-7.24 (m, 5H) 7.45-7.50 (m, 2H) 7.66 (d, J=3.18 Hz, 2H) 7.84 (d, J=3.18 Hz, 1H) 8.04 (s, 1H) 8.26 (d, J=6.11 Hz, 2H) 8.81 (d, J=5.87 Hz, 2H).

(S)-3-Phenyl-N-(3-(pyridin-4-yl)phenyl)-2-(thiazol-5-ylmethylamino)propanamide (34.17)

1H NMR (500 MHz, MeOH-D4) δ ppm 3.28 (dd, J=13.45, 9.05 Hz, 1H) 3.43 (dd, J=13.45, 6.11 Hz, 1H) 4.30 (dd, J=9.17, 5.99 Hz, 1H) 4.69 (s, 2H) 7.27-7.37 (m, 5H) 7.54-7.63 (m, 2H) 7.76 (dt, J=7.40, 1.68 Hz, 1H) 8.06-8.11 (m, 2H) 8.33 (d, J=6.85 Hz, 2H) 8.91 (d, J=6.85 Hz, 2H) 9.17 (s, 1H).

(S)-2-((2-Methylthiazol-5-yl)methylamino)-3-phenyl-N-(3-(pyridin-4-yl)phenyl)propanamide (34.18)

1H NMR (500 MHz, MeOH-D4) δ ppm 2.73 (s, 3H) 3.28 (dd, J=13.45, 9.29 Hz, 1H) 3.45 (dd, J=13.45, 5.87 Hz, 1H) 4.33 (dd, J=9.05, 5.87 Hz, 1H) 4.41 (d, J=3.18 Hz, 2H) 7.25-7.36 (m, 5H) 7.52-7.61 (m, 3H) 7.76 (dt, J=6.17, 2.17 Hz, 1H) 8.09-8.15 (m, 1H) 8.34 (d, J=6.85 Hz, 2H) 8.91 (d, J=6.85 Hz, 2H).

(2S)-3-Phenyl-N-(3-(pyridin-4-yl)phenyl)-2-(1-(thiazol-4-yl)ethylamino)propanamide (34.19)

1H NMR (500 MHz, MeOH-D4) δ ppm 1.59-1.74 (m, 3H) 3.08 (dd, J=12.96, 10.76 Hz, 1H) 3.38 (dd, J=12.84, 5.01 Hz, 1H) 3.94 (dd, J=10.51, 5.14 Hz, 1H) 4.65-4.72 (m, 1H) 7.05-7.11 (m, 2H) 7.11-7.22 (m, 3H) 7.27-7.33 (m, 1H) 7.42 (t, J=7.95 Hz, 1H) 7.55-7.63 (m, 1H) 7.73 (d, J=1.96 Hz, 1H) 7.87 (t, J=1.83 Hz, 1H) 8.11-8.17 (m, 2H) 8.74-8.79 (m, 2H) 9.00 (d, J=1.71 Hz, 1H).

7.34.2 Example 34.4

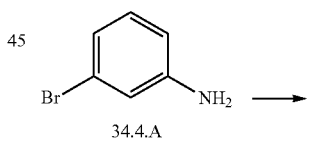

34.4.A

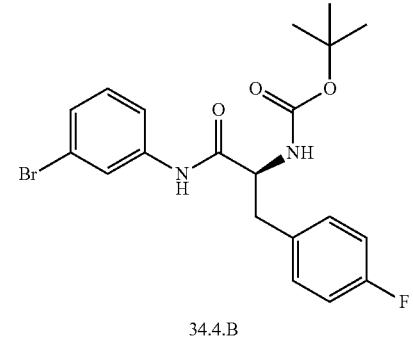

34.4.B

(S)-tert-Butyl 1-(3-bromophenylamino)-3-(4-fluorophenyl)-1-oxopropan-2-ylcarbamate (34.4B)

To a flask were weighed in 3-bromobenzenamine 34.4.A (513 mg, 3 mmol), (S)-2-(tert-butoxycarbonyl)-3-(4-fluorophenyl)propanoic acid (0.89 g, 3.1 mmol), and N1-((ethylimino)methylene)-N3,N3-dimethylpropane-1,3-diamine hydrochloride (1.7 g, 8.9 mmol). Pyridine was added as a solvent. The reaction was stirred for 1.5 hours and worked up with ethyl acetate and water. Silica gel chromatography afforded 1.2 g (92%) of 34.4.B.

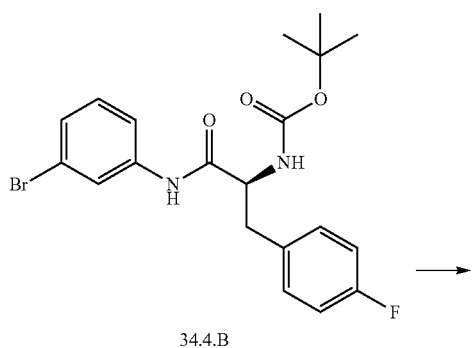

34.4.B

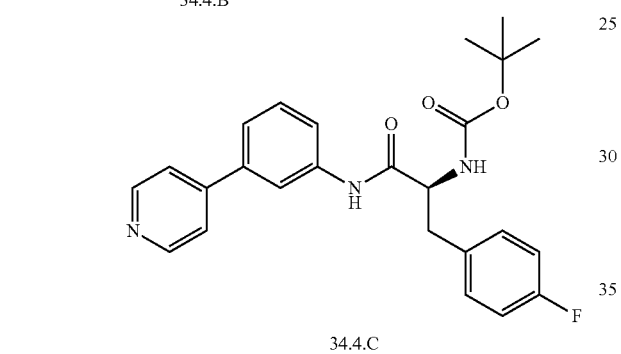

34.4.C

(S)-tert-Butyl 3-(4-fluorophenyl)-1-oxo-1-(3-(pyridin-4-yl)phenylamino)propan-2-ylcarbamate (34.4.C)

To a flask were weighed (5)-tert-butyl 1-(3-bromophenylamino)-3-(4-fluorophenyl)-1-oxopropan-2-ylcarbamate 34.4.B (800 mg, 1.8 mmol), potassium phosphate (1.16 g, 5.5 mmol), pyridin-4-ylboronic acid (270 mg, 2.2 mmol), and PdCl2dppf (134 mg, 0.18 mmol). The flask was flushed with N2. t-amyl alcohol was purged with N2 before adding into the flask. The reaction was heated to 82 degree overnight. Filtered and concentrated. Silica gel chromatography afforded 530 mg (67%) of 34.4C.

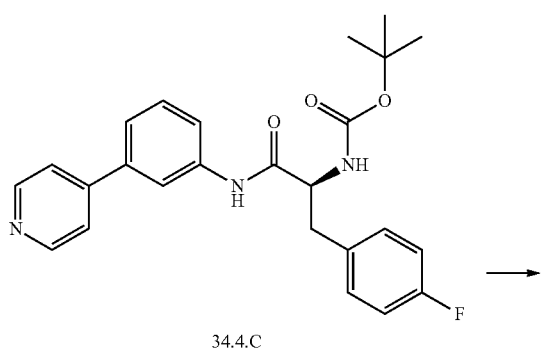

34.4.C

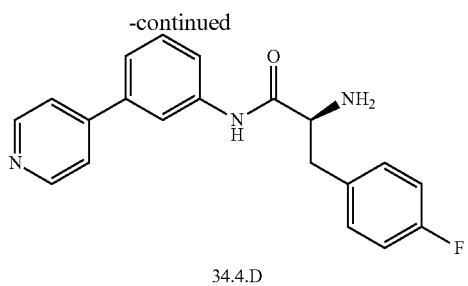

34.4.D

(S)-2-Amino-3-(4-fluorophenyl)-N-(3-(pyridin-4-yl)phenyl)propanamide (34.4D)

To a flask with (S)-tert-butyl 3-(4-fluorophenyl)-1-oxo-1-(3-(pyridin-4-yl)phenylamino)propan-2-ylcarbamate 34.4.C (530 mg, 1.2 mmol) was added 4 mL DCM and 1.8 mL trifluoroacetic acid. The reaction was stirred a few hours, concentrated and bascified by saturated NaHCO3. Silica gel chromatography afforded 345 mg (85%) of 34.4.D.

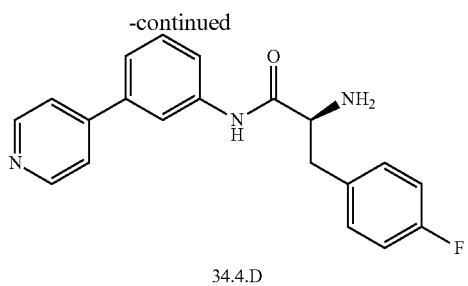

34.4.D

34.4

(S)-tert-Butyl 2-(1-oxo-3-phenyl-1-(3-(pyridin-4-yl)phenylamino)propan-2-ylamino)acetate (34.4)

To a flask with (S)-2-amino-3-(4-fluorophenyl)-N-(3-(pyridin-4-yl)phenyl)propanamide (200 mg, 0.6 mmol) was added CH3CN as solvent, N-ethyl-N-isopropylpropan-2-amine (0.15 mL, 0.89 mmol) and tert-butyl 2-bromoacetate (0.097 mL, 0.66 mmol) and was heated at 55 degree for 5 hours. Reverse phase purification on HPLC followed by silica gel purification afforded 39 mg (15%) 34.4. 1H NMR (400 MHz, MeOH) δ ppm 8.50-8.68 (m, 2H) 7.88-7.99 (m, 1H) 7.61-7.75 (m, 2H) 7.55-7.60 (m, 1H) 7.42-7.52 (m, 2H) 7.23-

7.31 (m, 2H) 6.97-7.04 (m, 2H) 3.53 (t, J=6.85 Hz, 1H) 3.29 (s, 2H) 3.05-3.12 (m, 1H) 2.95-3.03 (m, 1H) 1.43 (s, 9H)

7.34.3 Example 34.8

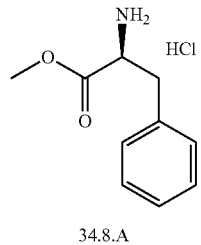 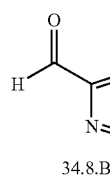

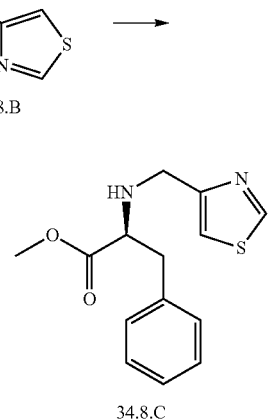

(S)-Methyl 3-phenyl-2-(thiazol-4-ylmethylamino)propanoate (34.8.C)

L-Phenylalanine methyl ester HCl 34.8.A (2.15 g, 10.0 mmol) was partitioned with DCM and saturated NaHCO₃. The aqueous layer was extracted with DCM (2×). The organic layers were combined, dried with sodium sulfate, filtered, and concentrated. The residue was dissolved in DCM (30 ml) and AcOH (571 µL, 10 mmol), thiazole-4-carboxaldehyde 34.8.B (1.13 g, 10 mmol), and NaBH(OAc)₃ (4.24 g, 20 mmol) were added and the reaction mixture was stirred at room temperature for 3 h. The reaction mixture was quenched with NaHCO₃(sat) and extracted with DCM. The organic extracts were dried with sodium sulfate, filtered, and concentrated. The resulting residue was partially purified on a silica gel column (120 g, 0-8% MeOH:DCM) to yield 34.8.0 as a crude oil (2.25 g).

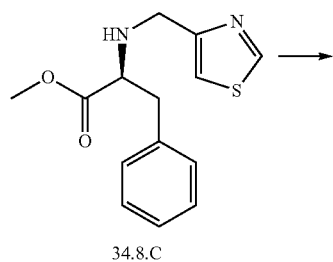

Methyl N-(tert-butoxycarbonyl)-N-(1,3-thiazol-4-ylmethyl)-L-phenylalaninate (34.8.D)

Amine 34.8.0 (2.13 g, 7.70 mmol) was heated with Boc₂O (1.68 g, 7.70 mmol) at 50° C. for 1 h. The reaction mixture was purified on a silica gel column (120 g, 0-50% EtOAc: Hex) to yield 34.8.D as an oil (2.75 g).

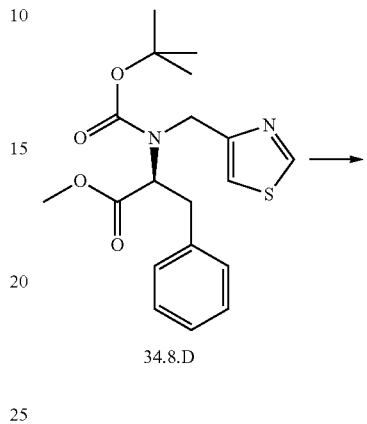

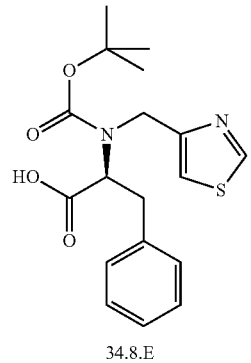

N-(tert-Butoxycarbonyl)-N-(1,3-thiazol-4-ylmethyl)-L-phenylalanine (34.8.E)

Ester 34.8.D (2.75 g, 7.3 mmol) was dissolved in THF/H₂O. LiOH hydrate (646 mg, 15.4 mmol) was added and the mixture was stirred at room temperature. The THF was removed on a rotavap and the resulting aqueous layer was acidified with 1.0 N HCl and then conc. HCl. A white sticky solid formed which was extracted with EtOAc. The organic layers were dried with sodium sulfate, filtered, and concentrated to yield 34.8.E as a sticky foam (2.20 g).

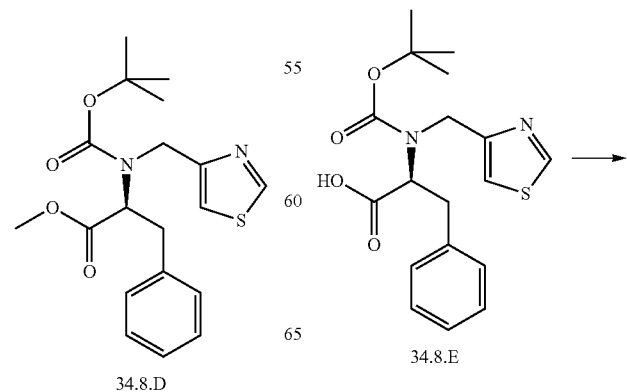

-continued

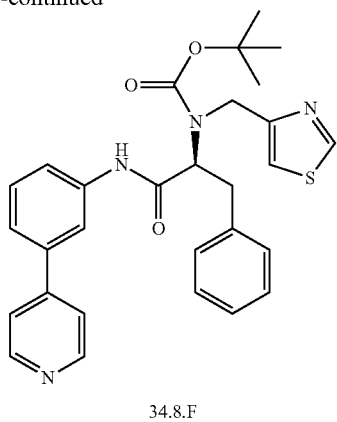
34.8.F (S)-tert-Butyl 1-oxo-3-phenyl-1-(3-(pyridin-4-yl)phenylamino)propan-2-yl(thiazol-4-ylmethyl)carbamate (34.8.F)

34.8.F was prepared analogous to 34.1. LC-MS (+esi, M+H$^+$=515.2). 1H NMR (500 MHz, DICHLOROMETHANE-d$_2$, rotamers) δ ppm 10.72 (br. s., 1H) 8.83-8.93 (m, 1H) 8.65 (d, J=5.87 Hz, 1H) 8.13 (t, J=1.96 Hz, 1H) 7.62-7.72 (m, 1H) 7.58 (d, J=5.87 Hz, 2H) 7.48 (t, J=7.83 Hz, 1H) 7.32-7.42 (m, 3H) 7.21-7.31 (m, 4H) 6.98-7.06 (m, 1H) 4.65-4.74 (m, 1H) 4.31-4.40 (m, 1H) 4.00-4.06 (m, 1H) 3.15-3.68 (m, 2H) 1.38 (s, 7H) 1.24 (s, 2H).

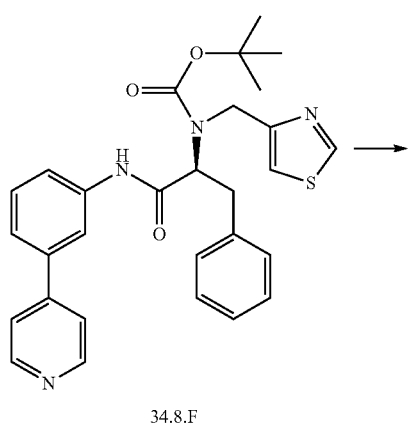
34.8.F

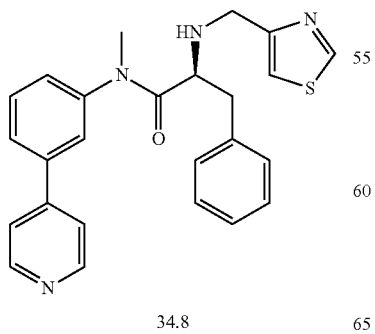
34.8

(S)—N-Methyl-3-phenyl-N-(3-(pyridin-4-yl)phenyl)-2-(thiazol-4-ylmethylamino)propanamide (34.8)

Amide 34.8.F (40 mg, 0.08 mmol) was dissolved in DMF, treated with NaH (3 mg, 0.08 mmol) and then MeI (5 μl, 0.08 mmol). The reaction mixture was partitioned with H$_2$O/EtOAc. The organic layer was dried with sodium sulfate, filtered, and concentrated. The residue was purified on a prepHPLC (C18, ACN:H$_2$O:0.1% TFA, gradient). The desired fractions were combined and partitioned with NaHCO$_3$ (sat)/EtOAc. The organic layer was dried with sodium sulfate, filtered, and concentrated to yield 22 mg. The residue was treated with HCl (4.0 M, dioxane) and concentrated to dryness. The solid was partitioned with NaHCO$_3$ (sat)/EtOAc. The organic layer was dried with sodium sulfate, filtered, and concentrated to yield 34.8 (15 mg). LC-MS (+esi, M+H$^+$=429.1).

7.34.4 Example 34.9

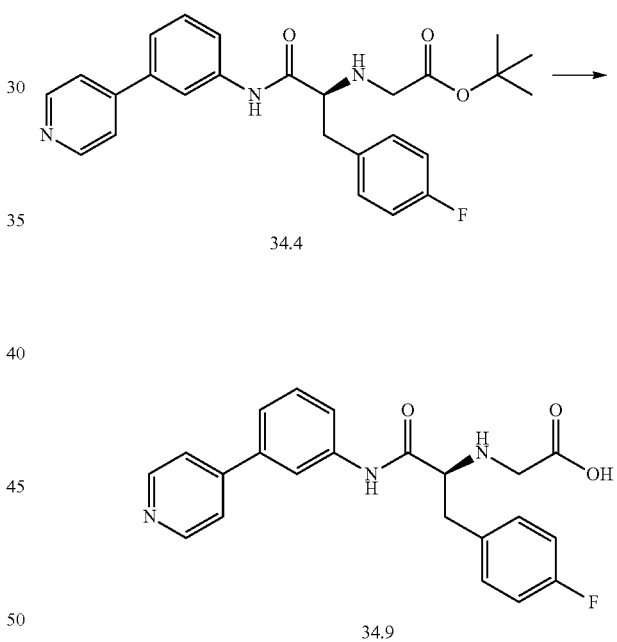

(S)-2-(1-Oxo-3-phenyl-1-(3-(pyridin-4-yl)phenylamino)propan-2-ylamino)acetic acid (34.9)

To a flask with (S)-tert-butyl 2-(3-(4-fluorophenyl)-1-oxo-1-(3-(pyridin-4-yl)phenylamino)propan-2-ylamino)acetate 34.4 36 mg, was added 20% trifluoroacetic acid (0.12 mL) in DCM. After 6 hours, the reaction was concentrated and added a small amount of 0.1% TFA in water. The solution was lyophilized and afforded 40 mg of the TFA salt of 34.9. 1H NMR (400 MHz, MeOH) δ ppm 8.85 (d, J=7.04 Hz, 2H) 8.24 (d, J=6.65 Hz, 2H) 8.13 (s, 1H) 7.72 (td, J=4.40, 1.76 Hz, 1H) 7.48-7.64 (m, 2H) 7.22-7.39 (m, 2H) 7.00-7.11 (m, 2H) 4.35 (dd, J=8.80, 6.06 Hz, 1H) 3.88-4.05 (m, 2H) 3.36-3.44 (m, 1H) 3.24-3.30 (m, 1H).

7.34.5 Example 34.20

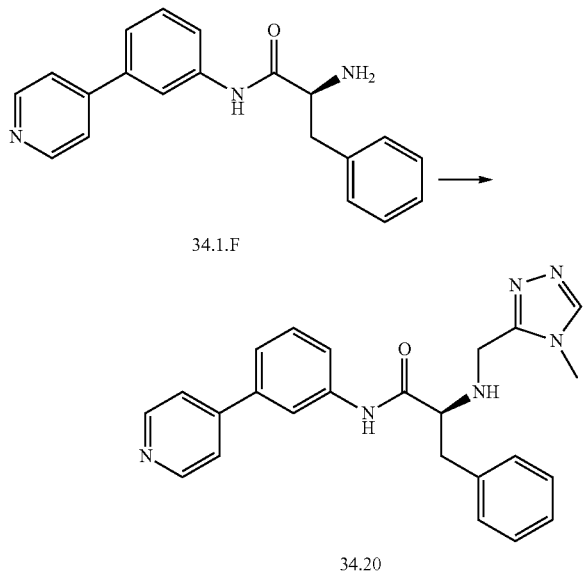

34.1.F 34.20

(S)-2-((4-Methyl-4H-1,2,4-triazol-3-yl)methylamino)-3-phenyl-N-(3-(pyridin-4-yl)phenyl)propanamide (34.20)

To a mixture of 34.1.F (225 mg, 0.71 mmol) and 3-(chloromethyl)-4-methyl-4H-1,2,4-triazole hydrochloride (187 mg, 1.42 mmol) in DMF (2 mL) was added potassium carbonate (245 mg, 1.78 mmol). The resulting mixture was stirred at 90° C. for 6.0 hr, cooled to rt, diluted with $H_2O$ (8 mL), and extracted with EtOAc (3×10 mL). The combined organic layers were washed with brine and dried over $MgSO_4$. After removal of organic solvent under reduced pressure, purification of the residue by flash chromatography on silica gel using 0-6% MeOH/$CH_2Cl_2$ for elution gave the title product 34.20 as colorless solid (14 mg, 6%). MS ESI (positve.) m/e: 413.1 (M+H), $^1$H NMR (400 MHz, CHLOROFORM-d) δ ppm 9.73 (s, 1H), 8.66 (d, J=5.48 Hz, 2H), 7.96-8.08 (m, 1H), 7.89 (s, 1H), 7.68 (d, J=7.82 Hz, 1H), 7.54 (d, J=6.26 Hz, 2H), 7.41-7.49 (m, 1H), 7.35-7.41 (m, 1H), 7.29-7.35 (m, 2H), 7.22-7.29 (m, 2H), 3.74-4.02 (m, 5H), 3.57-3.71 (m, 1H), 3.26-3.45 (m, 1H), 2.76-3.02 (m, 1H).

7.34.6 Example 34.21

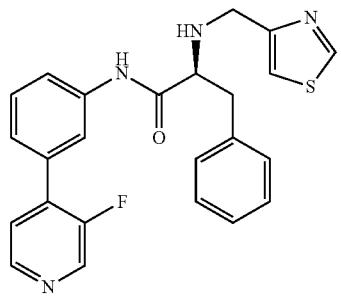 [SMILES: O=C(Nc1cccc(-c2ccncc2F)c1)[C@H](Cc1ccccc1)NCc1cscn1]

(2S)—N-(3-(3-Fluoropyridin-4-yl)phenyl)-3-phenyl-2-(thiazol-4-ylmethylamino)propanamide TFA salt (34.21)

LCMS ESI (pos.) m/e: 433.0 (M+1).

7.35 Example 35

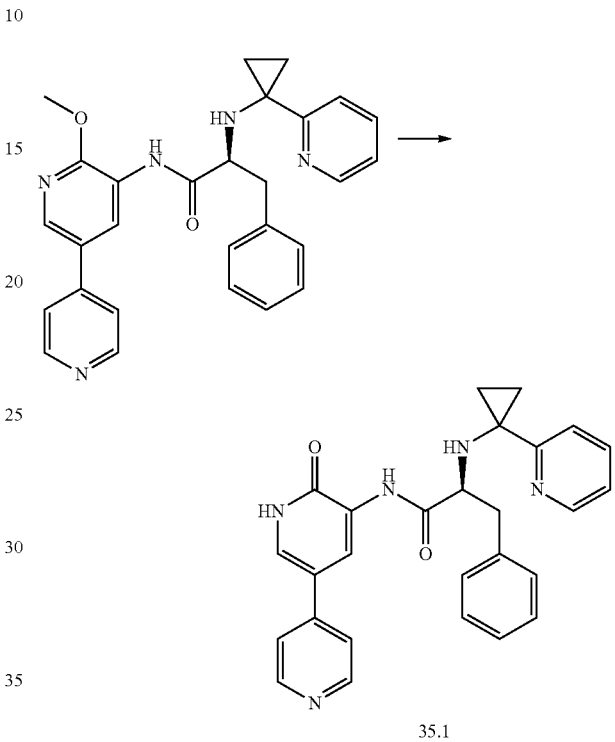

35.1

(S)—N-(2-Oxo-5-(pyridin-4-yl)-1,2-dihydropyridin-3-yl)-3-phenyl-2-(1-(pyridin-2-yl)cyclopropylamino)propanamide (35.1)

(S)—N-(2-methoxy-5-(pyridin-4-yl)pyridin-3-yl)-3-phenyl-2-(1-(pyridin-2-yl)cyclopropylamino)propanamide 11.1 (38.5 mg, 83 μmol) was dissolved in 4.5 mL dioxane. Concentrated HCl (0.5 ml, 16456 μmol) was added. The reaction was heated to 50° C. for 2.5 h. LC/MS showed the completion of the reaction. The reaction was concentrated, neutralized with saturated $NaHCO_3$, then extracted with 30% IPA/$CHCl_3$ once. The organic layer was concentrated and purified by silica gel chromatography to afford 33 mg (89%) of (S)—N-(2-oxo-5-(pyridin-4-yl)-1,2-dihydropyridin-3-yl)-3-phenyl-2-(1-(pyridin-2-yl)cyclopropylamino)propanamide (35.1). 1H NMR (400 MHz, MeOH) δ ppm 8.82 (d, J=2.74 Hz, 1H) 8.48-8.63 (m, 2H) 8.19-8.36 (m, 1H) 7.68 (d, J=2.74 Hz, 1H) 7.61-7.65 (m, 2H) 7.52-7.59 (m, 1H) 7.20-7.26 (m, 3H) 7.08-7.16 (m, 4H) 3.58 (dd, J=8.61, 4.70 Hz, 1H) 3.04 (dd, J=13.69, 4.69 Hz, 1H) 2.83 (dd, J=13.69, 9.00 Hz, 1H) 1.06-1.21 (m, 3H) 0.82-0.91 (m, 1H).

The following compounds were prepared according to the methods described for the preparation of example 11.1 with appropriate amines.

TABLE 6

[Structure: 2-methoxy-5-(pyridin-4-yl)pyridin-3-yl propanamide scaffold with HN-R substituent on α-carbon and benzyl group]

| Compound | R group |
|---|---|
| 35.2 | [1-(pyridin-2-yl)ethyl] |
| 35.3 | [1-(2-methylthiazol-4-yl)cyclopropyl] |
| 35.4 | [(oxazol-4-yl)methyl] |
| 35.5 | [1-(pyrimidin-2-yl)cyclopropyl] |

(S)—N-(2-Methoxy-5-(pyridin-4-yl)pyridin-3-yl)-3-phenyl-2-((S)-1-(pyridin-2-yl)ethylamino)propanamide (35.2)

1H NMR (400 MHz, MeOH) δ ppm 8.92 (d, J=2.35 Hz, 1H) 8.60 (dd, J=4.50, 1.76 Hz, 2H) 8.23-8.41 (m, 2H) 7.68-7.76 (m, 2H) 7.63 (td, J=7.73, 1.76 Hz, 1H) 7.18-7.30 (m, 4H) 7.10 (dd, J=6.46, 2.93 Hz, 2H) 7.03 (d, J=7.83 Hz, 1H) 4.09 (s, 3H) 3.75 (q, J=6.65 Hz, 1H) 3.25 (dd, J=9.39, 4.30 Hz, 1H) 3.07 (dd, J=13.69, 4.30 Hz, 1H) 2.77 (dd, J=13.69, 9.39 Hz, 1H) 1.40 (d, J=7.04 Hz, 3H).

(S)—N-(2-Methoxy-5-(pyridin-4-yl)pyridin-3-yl)-2-(1-(2-methylthiazol-4-yl)cyclopropylamino)-3-phenylpropanamide (35.3)

1H NMR (400 MHz, MeOH) δ ppm 8.83 (d, J=2.35 Hz, 1H) 8.59 (dd, J=4.69, 1.96 Hz, 2H) 8.29 (d, J=2.35 Hz, 1H) 7.59-7.78 (m, 2H) 7.20-7.28 (m, 3H) 7.12-7.18 (m, 2H) 6.85 (s, 1H) 4.07 (s, 3H) 3.65 (dd, J=9.19, 4.50 Hz, 1H) 3.04 (dd, J=13.69, 4.30 Hz, 1H) 2.75 (dd, J=13.69, 9.39 Hz, 1H) 2.48 (s, 3H) 0.90-1.05 (m, 3H) 0.77-0.87 (m, 1H).

(S)-2-(Isoxazol-3-ylmethylamino)-N-(2-methoxy-5-(pyridin-4-yl)pyridin-3-yl)-3-phenylpropanamide (35.4)

1H NMR (400 MHz, MeOH) δ ppm 8.87 (d, J=1.96 Hz, 1H) 8.60 (d, J=6.26 Hz, 2H) 8.53 (d, J=1.56 Hz, 1H) 8.29 (d, J=2.35 Hz, 1H) 7.70 (d, J=5.09 Hz, 2H) 7.20-7.32 (m, 5H) 6.33 (d, J=1.57 Hz, 1H) 4.03 (s, 3H) 3.83 (s, 2H) 3.59 (dd, J=8.22, 5.48 Hz, 1H) 3.19 (dd, J=13.69, 5.48 Hz, 1H) 2.93 (dd, J=13.69, 8.22 Hz, 1H).

(S)—N-(2-Methoxy-5-(pyridin-4-yl)pyridin-3-yl)-3-phenyl-2-(1-(pyrimidin-2-yl)cyclopropylamino)propanamide (35.5)

1H NMR (400 MHz, MeOH) δ ppm 8.84 (d, J=2.35 Hz, 1H) 8.49-8.65 (m, 4H) 8.29 (d, J=2.35 Hz, 1H) 7.56-7.77 (m, 2H) 7.19-7.30 (m, 5H) 7.17 (t, J=4.89 Hz, 1H) 4.02 (s, 3H) 3.69 (t, J=6.26 Hz, 1H) 3.27-3.35 (m, 1H) 3.15 (dd, J=13.50, 6.46 Hz, 1H) 1.43-1.54 (m, 1H) 1.17-1.26 (m, 2H) 1.09-1.17 (m, 1H).

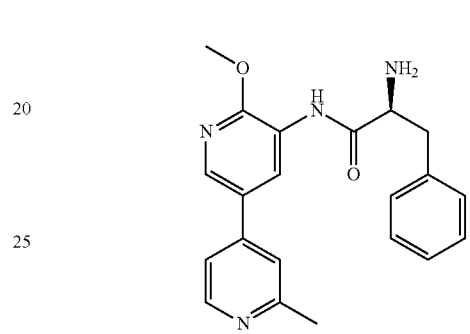

(2S)-2-Amino-N-(2-methoxy-5-(2-methylpyridin-4-yl)pyridin-3-yl)-3-phenylpropanamide (35.6)

LCMS ESI (pos.) m/e: 363.1 (M+1).

7.36 Example 36

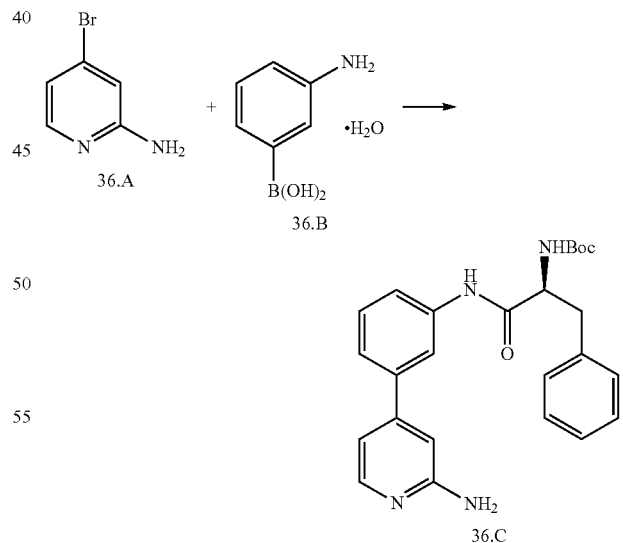

Tert-butyl (S)-1-(3-(2-aminopyridin-4-yl)phenylamino)-1-oxo-3-phenylpropan-2-ylcarbamate (36.C)

To a 100 ml flask was added 4-bromopyridin-2-amine 36.A (432 mg, 2.50 mmol, available from Apollo), 3-aminophenylboronic acid hydrate 36.B (465 mg, 3.00 mmol, available from Oakwood), tetrakis(triphenylphosphine)palladium(0) (288 mg, 0.25 mmol), DMF (5 mL) and saturated aqueous K₂CO₃ (5 mL). The reaction mixture was stirred at 80° C. overnight. The reaction was then extracted with DCM (2×50 mL), the organic layers combined, washed with brine and dried on MgSO₄. The DCM was removed under vacuum, leaving a crude solution of 4-(3-aminophenyl)pyridin-2-amine in DMF to which was added more DMF (10 mL), (S)-2-(tert-butoxycarbonyl)-3-phenylpropanoic acid (662 mg, 2.5 mmol, available from Aldrich), diisopropylethylamine (1.74 mL, 10 mmol) and 2-(1H-Benzotriazole-1-yl)-1,1,3,3-Tetramethyluronium hexafluorophosphate (1.90 g, 5.0 mmol). The resulting mixture was stirred overnight at room temperature. The mixture was then partitioned between water (50 mL) and EtOAc (100 mL). The layers were separated, and the aqueous phase was extracted with additional EtOAc (2×50 mL). The combined organic layers were washed with water and brine, dried (MgSO₄), and concentrated. The residue was purified by silica gel flash chromatography to afford tert-butyl (S)-1-(3-(2-aminopyridin-4-yl)phenylamino)-1-oxo-3-phenylpropan-2-ylcarbamate 36.C (200 mg, 15% yield).

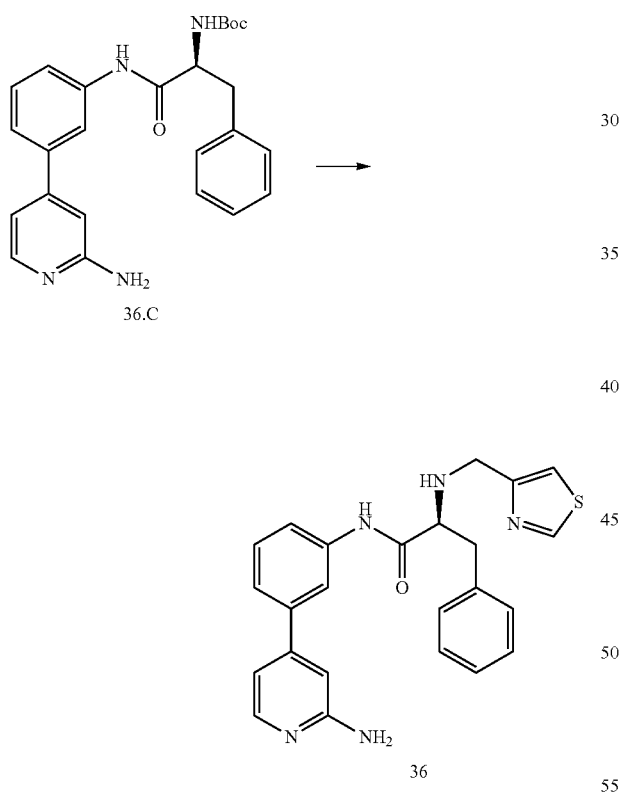

(2S)—N-(3-(2-Aminopyridin-4-yl)phenyl)-3-phenyl-2-(thiazol-4-ylmethylamino)propanamide (36)

To a solution of tert-butyl (S)-1-(3-(2-aminopyridin-4-yl)phenylamino)-1-oxo-3-phenylpropan-2-ylcarbamate (36.C) (200 mg, 0.46 mmol) in THF (2 mL) was added 4M HCl in dioxane (2 mL, 8 mmol). The mixture was stirred at room temperature for 2 hours and then was concentrated. The residue was neutralized with saturated aqueous NaHCO₃ and extracted with 4:1 DCM/isopropanol. The organic layers were combined, washed with brine, dried on MgSO₄ and concentrated. The residue was dissolved in DCM and then thiazole-4-carbaldehyde (56 mg, 0.50 mmol) was added. The mixture was stirred for 1 h at room temperature at which time acetic acid (28 μL, 0.46 mmol) and sodium triacetoxyborohydride (293 mg, 1.38 mmol) were added. The mixture was stirred at room temperature for additional 2 hours, concentrated and the residue purified by reverse phase preparative HPLC to afford (2S)—N-(3-(2-aminopyridin-4-yl)phenyl)-3-phenyl-2-(thiazol-4-ylmethylamino)propanamide 36 (58 mg, 29% yield) as a white solid. LCMS ESI (pos.) m/e: 430.1 (M+1): 1H NMR (400 MHz, MeOH-D4) δ ppm 9.12 (d, J=1.96 Hz, 1H), 7.91-7.97 (m, 2H), 7.79 (d, J=1.96 Hz, 1H), 7.42-7.57 (m, 3H), 7.25-7.36 (m, 5H), 7.18-7.21 (m, 1H), 7.13-7.17 (m, 1H), 4.42-4.54 (m, 2H), 4.25 (dd, J=9.39, 5.87 Hz, 1H), 3.42 (dd, J=13.30, 5.87 Hz, 1H), 3.25 (dd, J=13.30, 9.00 Hz, 1H).

7.37 Example 37

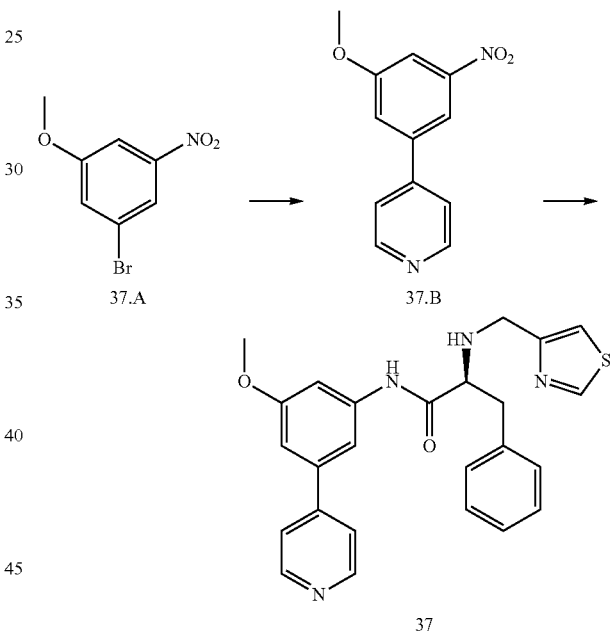

4-(3-Methoxy-5-nitrophenyl)pyridine (37.B)

The title compound was prepared from 1-bromo-3-methoxy-5-nitrobenzene 37.A employing the procedure of example 13.C. to give 4-(3-methoxy-5-nitrophenyl)pyridine 37.B (128 mg, 30% yield).

(S)—N-(4-Methoxy-3-(pyridin-4-yl)phenyl)-3-phenyl-2-(thiazol-4-ylmethylamino)propanamide 1H (37)

Title compound was prepared from 37.B by methods analogous to those described in Example 12. 1H NMR (500 MHz, MeOH-D4) δ ppm 3.21-3.27 (m, 1H) 3.38-3.51 (m, 1H) 3.80-3.95 (m, 3H) 4.24-4.38 (m, 1H) 4.52 (d, J=4.89 Hz, 2H) 7.16-7.26 (m, 2H) 7.26-7.39 (m, 5H) 7.61 (d, J=1.47 Hz, 1H) 7.82 (s, 1H) 8.31 (d, J=6.85 Hz, 2H) 8.81-8.92 (m, 2H) 9.12 (d, J=1.96 Hz, 1H).

7.38 Example 38

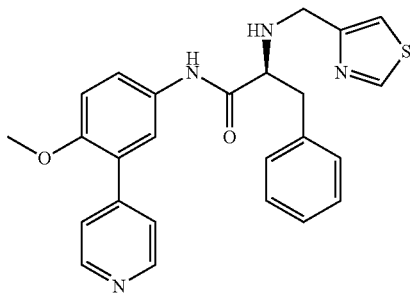 [SMILES: COc1ccc(NC(=O)[C@H](Cc2ccccc2)NCc2cscn2)cc1-c1ccncc1]

(S)—N-(4-Methoxy-3-(pyridin-4-yl)phenyl)-3-phenyl-2-(thiazol-4-ylmethylamino)propanamide (38)

The title compound was prepared by methods analogous to those described in Example 37. 1H NMR (500 MHz, MeOH-D4) δ ppm 3.18-3.29 (m, 1H) 3.40-3.50 (m, 1H) 3.82-3.97 (m, 3H) 4.15-4.33 (m, 1H) 4.51 (d, J=7.09 Hz, 2H) 7.22 (d, J=9.05 Hz, 1H) 7.24-7.40 (m, 5H) 7.47 (dd, J=9.05, 2.69 Hz, 1H) 7.72 (d, J=2.69 Hz, 1H) 7.81 (d, J=1.96 Hz, 1H) 8.19-8.29 (m, 2H) 8.81-8.88 (m, 2H) 9.12 (d, J=1.96 Hz, 1H).

7.39 Example 39

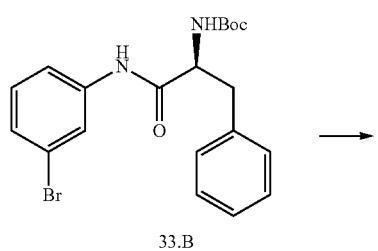

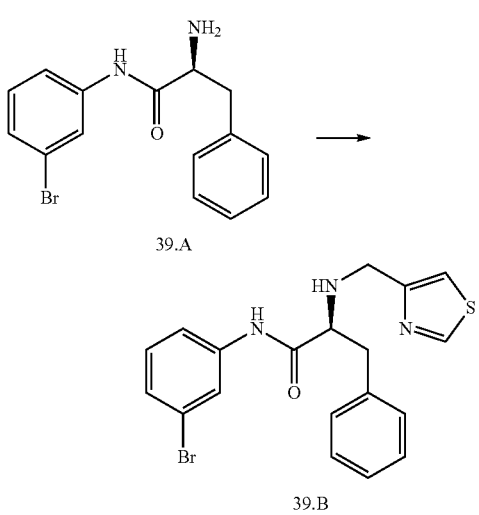

(S)-2-Amino-N-(3-bromophenyl)-3-phenylpropanamide (39.A)

The same procedure as in example 13.F was employed for this example, replacing tert-butyl (S)-1-(3-(1H-pyrazol-4-yl)phenylamino)-1-oxo-3-phenylpropan-2-ylcarbamate 13.E with (S)-tert-butyl 1-(3-bromophenylamino)-1-oxo-3-phenylpropan-2-ylcarbamate 33.B to give (S)-2-amino-N-(3-bromophenyl)-3-phenylpropanamide 39.A.

(S)—N-(3-bromophenyl)-3-phenyl-2-(thiazol-4-ylmethylamino)propanamide (39.B)

The same procedure as example 12 was employed, replacing (2S)—N-(3-(1H-pyrazol-4-yl)phenyl)-2-amino-3-phenylpropanamide 12.C with (S)-2-amino-N-(3-bromophenyl)-3-phenylpropanamide 39.A to give (S)—N-(3-bromophenyl)-3-phenyl-2-(thiazol-4-ylmethylamino)propanamide 39.B.

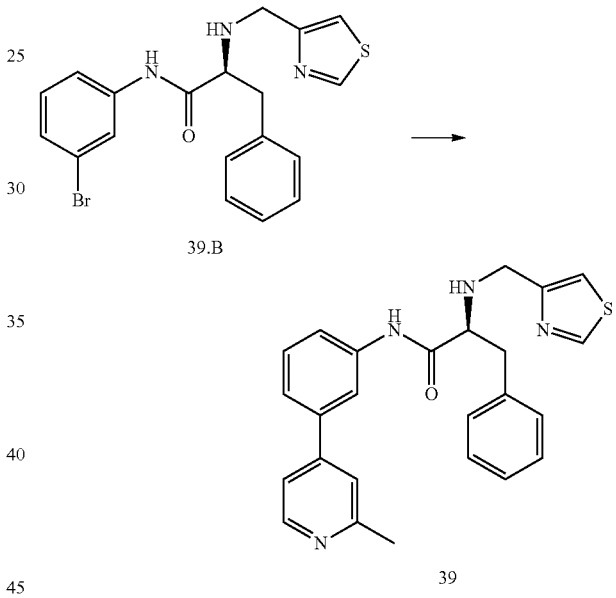

(2S)—N-(3-(2-methylpyridin-4-yl)phenyl)-3-phenyl-2-(thiazol-4-ylmethylamino)propanamide (39)

To a 5 mL flask was added (S)—N-(3-bromophenyl)-3-phenyl-2-(thiazol-4-ylmethylamino)propanamide 39.B (50 mg, 0.12 mmol), 2-methylpyridin-4-yl boronic acid (21 mg, 0.16 mmol, available from Combi-Phos), tetrakis(triphenylphosphine)palladium(0) (28 mg, 0.024 mmol), DMF (0.5 mL) and saturated aqueous K$_2$CO$_3$ (0.5 mL). The reaction mixture was stirred at 100° C. for 2 hours. The mixture was diluted with methanol (3 mL), filtered and purified directly on reverse phase preparative HPLC to afford (2S)—N-(3-(2-methylpyridin-4-yl)phenyl)-3-phenyl-2-(thiazol-4-ylmethylamino)propanamide 39 (27.2 mg, 53% yield) as a white solid. LCMS ESI (pos.) m/e: 429.1. (M+1). 1H NMR (500 MHz, MeOH-D4) δ ppm 9.12 (d, J=1.96 Hz, 1H), 8.74 (d, J=6.36 Hz, 1H), 8.19 (s, 1H), 8.12 (dd, J=6.36, 1.96 Hz, 1H), 8.11 (t, J=1.71 Hz, 1H), 7.82 (d, J=1.96 Hz, 1H), 7.68-7.75 (m, 1H), 7.58 (t, J=7.83 Hz, 1H), 7.52-7.56 (m, 1H), 7.23-

7.37 (m, 5H), 4.53 (d, J=4.65 Hz, 2H), 4.35 (dd, J=9.29, 5.87 Hz, 1H), 3.46 (dd, J=13.45, 5.87 Hz, 1H), 3.28 (dd, J=13.45, 9.29 Hz, 1H), 2.88 (s, 3H).

7.40 Example 40

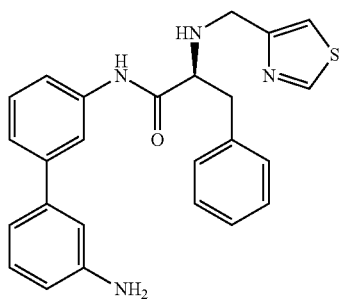 [SMILES: Nc1cccc(-c2cccc(NC(=O)[C@H](Cc3ccccc3)NCc3cscn3)c2)c1]

(S)—N-(3'-aminobiphenyl-3-yl)-3-phenyl-2-(thiazol-4-ylmethylamino)propanamide (40)

The title compound was prepared by methods analogous to those described in Example 33. 1H NMR (500 MHz, MeOH-D4) δ ppm 3.15-3.22 (m, 1H) 3.43 (dd, J=13.08, 5.75 Hz, 1H) 4.27 (dd, J=9.29, 5.62 Hz, 1H) 4.50 (d, J=11.00 Hz, 2H) 7.24-7.40 (m, 7H) 7.40-7.47 (m, 2H) 7.51-7.55 (m, 1H) 7.57-7.65 (m, 2H) 7.77 (d, J=0.98 Hz, 1H) 7.81 (d, J=1.96 Hz, 1H) 9.14 (d, J=1.96 Hz, 1H).

7.41 Example 41

7.41.1 Examples 41.1-41.5

The following compounds were prepared from methyl (R)-1-(2-methoxy-5-(2-methylpyridin-4-yl)pyridin-3-ylamino)-1-oxo-3-phenylpropan-2-yl 4-nitrobenzenesulfonate and the appropriate amine, or with (2S)-2-amino-N-(2-methoxy-5-(2-methylpyridin-4-yl)pyridin-3-yl)-3-phenylpropanamide and the appropriate aldehyde as shown elsewhere in this application.

TABLE 7

| Compound | R |
|---|---|
| 41.1 | cyclopropyl-pyridin-2-yl |
| 41.2 | (S)-1-(pyridin-2-yl)ethyl |
| 41.3 | pyridin-2-ylmethyl |
| 41.4 | (1-methyl-imidazol-4-yl)methyl |
| 41.5 | thiazol-4-ylmethyl |

(2S)—N-(2-Methoxy-5-(2-methylpyridin-4-yl)pyridin-3-yl)-3-phenyl-2-(1-(pyridin-2-yl)cyclopropylamino)propanamide (41.1)

MS ESI (pos.) m/e: 480.2 (M+H). ¹H NMR (400 MHz, CD₃OD) δ ppm 8.77 (1H, d, J=2.35 Hz), 8.46 (1H, d, J=5.28 Hz), 8.32 (1H, ddd, J=4.89, 1.86, 0.88 Hz), 8.25 (1H, d, J=2.35 Hz), 7.55-7.61 (2H, m), 7.48 (1H, dd, J=5.18, 1.47 Hz), 7.08-7.27 (7H, m), 4.05 (3H, s), 3.64 (1H, dd, J=8.51, 4.99 Hz), 3.06 (1H, dd, J=13.69, 4.89 Hz), 2.86 (1H, dd, J=13.69, 8.61 Hz), 2.61 (3H, s), 1.09-1.22 (2H, m), 1.04 (1H, ddd, J=9.98, 6.65, 4.11 Hz), 0.94 (1H, ddd, J=10.12, 6.21, 4.21 Hz).

(S)—N-(2-Methoxy-5-(2-methylpyridin-4-yl)pyridin-3-yl)-3-phenyl-2-((S)-1-(pyridin-2-yl)ethylamino)propanamide (41.2)

MS ESI (pos.) m/e: 468.2 (M+H). ¹H NMR (400 MHz, CD₃OD) δ ppm 8.92 (1H, d, J=2.35 Hz), 8.71 (1H, d, J=6.26 Hz), 8.60 (1H, dd, J=5.87, 1.56 Hz), 8.55 (1H, d, J=2.35 Hz), 8.22 (1H, d, J=1.17 Hz), 8.14 (1H, dd, J=6.46, 1.76 Hz), 7.85-7.93 (1H, m), 7.43-7.49 (2H, m), 7.29-7.35 (3H, m), 7.21-7.29 (2H, m), 4.66 (1H, q, J=6.91 Hz), 4.35 (1H, dd, J=8.22, 7.04 Hz), 3.95 (3H, s), 3.36 (1H, dd, J=13.30, 7.04 Hz), 3.27 (1H, dd, J=13.30, 8.22 Hz), 2.86 (3H, s), 1.68 (3H, d, J=6.65 Hz).

(2S)—N-(2-Methoxy-5-(2-methylpyridin-4-yl)pyridin-3-yl)-3-phenyl-2-(pyridin-2-ylmethylamino)propanamide (41.3)

MS ESI (pos.) m/e: 454.2 (M+H). ¹H NMR (400 MHz, CD₃OD) δ ppm 8.93 (1H, d, J=2.74 Hz), 8.70 (1H, d, J=6.26

Hz), 8.65 (1H, ddd, J=5.09, 1.56, 0.78 Hz), 8.55 (1H, d, J=2.35 Hz), 8.21 (1H, d, J=1.96 Hz), 8.13 (1H, dd, J=6.26, 1.96 Hz), 7.90 (1H, td, J=7.73, 1.76 Hz), 7.43-7.50 (2H, m), 7.34-7.30 (5H, m), 4.65 (1H, dd, J=9.00, 6.26 Hz), 4.46-4.52 (1H, m), 4.41-4.46 (1H, m), 3.99 (3H, s), 3.45 (1H, dd, J=13.50, 6.46 Hz), 3.26-3.35 (1H, m), 2.85 (3H, s).

(2S)—N-(2-Methoxy-5-(2-methylpyridin-4-yl)pyridin-3-yl)-2-((1-methyl-1H-imidazol-4-yl)methylamino)-3-phenylpropanamide (41.4)

MS ESI (pos.) m/e: 457.2 (M+H). $^1$H NMR (400 MHz, CD$_3$OD) δ ppm 8.95 (1H, d, J=2.35 Hz), 8.71 (1H, d, J=6.26 Hz), 8.57 (1H, d, J=2.35 Hz), 8.50 (1H, s), 8.23 (1H, d, J=1.96 Hz), 8.15 (1H, dd, J=6.26, 1.96 Hz), 7.46 (1H, s), 7.25-7.36 (5H, m), 4.30 (1H, dd, J=7.82, 6.65 Hz), 4.22-4.27 (1H, m), 4.16-4.22 (1H, m), 4.04 (3H, s), 3.87 (3H, s), 3.18-3.30 (2H, m), 2.86 (3H, s).

(2S)—N-(2-Methoxy-5-(2-methylpyridin-4-yl)pyridin-3-yl)-3-phenyl-2-(thiazol-4-ylmethylamino)propanamide TFA salt (41.5)

LCMS ESI (pos.) m/e: 460.1 (M+1): 1H NMR (500 MHz, MeOH) δ ppm 9.14 (d, J=1.96 Hz, 1H), 8.91 (d, J=2.20 Hz, 1H), 8.70 (d, J=6.11 Hz, 1H), 8.56 (d, J=2.45 Hz, 1H), 8.17 (d, J=0.98 Hz, 1H), 8.09 (dd, J=6.11, 1.71 Hz, 1H), 7.80 (d, J=1.96 Hz, 1H), 7.31-7.35 (m, 3H), 7.28-7.30 (m, 2H), 4.57 (dd, J=8.93, 5.99 Hz, 1H), 4.46-4.54 (m, 2H), 4.01 (s, 3H), 3.43 (dd, J=13.57, 5.99 Hz, 1H), 3.25 (dd, J=13.45, 9.05 Hz, 1H), 2.85 (s, 3H).

7.41.2 Example 41.6

2-Chloro-6-methoxypyridin-4-amine (41.6.B)

A solution of 2,6-dichloropyridin-4-amine 41.6.A (available from Aldrich) (3.10 g, 19.0 mmol) in 20% NaOMe/MeOH (15 mL) was refluxed for 72 hr. The reaction mixture was diluted with H$_2$O (40 mL) and extracted with 30% $^i$PrOH/CHCl$_3$ (3×30 mL). The combined organic layers were washed with water (2×20 mL), brine (15 mL) and dried over MgSO$_4$. After removal of organic solvents under reduced pressure, purification of the residue by flash chromatography on silica gel using 0-10% MeOH/CH$_2$Cl$_2$ for elution gave title product 41.6.B as white solid (2.45 g, 81.2%).

2-Methoxy-6-(2-methylpyridin-4-yl)pyridin-4-amine (41.6.C)

To a mixture of 41.6.B (719 mg, 4.53 mmol), 2-methylpyridin-4-ylboronic acid (available from CombiPhos Catalysts, Inc.) (931 mf, 6.80 mmol) and potassium phosphate (2.89 g, 13.6 mmol) in n-BuOH (10 mL) was added Pd(PPh$_3$)$_4$ (available from Aldrich) (318 mg, 0.45 mmol). After being purged with N$_2$ for 15 min, the mixture was stirred at 100° C. under N$_2$ atmosphere for 8.0 hrs. The resulting reaction solution was concentrated, re-dissolved in 30% $^i$ PrOH/CHCl$_3$ (25 mL), washed with water and brine, and dried over MgSO$_4$. After removal of organic solvent under reduced pressure, purification of the residue by flash chromatography on silica gel using 0-4% MeOH/CH$_2$Cl$_2$ for elution gave the title product 41.6.C as colorless solid (721 mg, 74%).

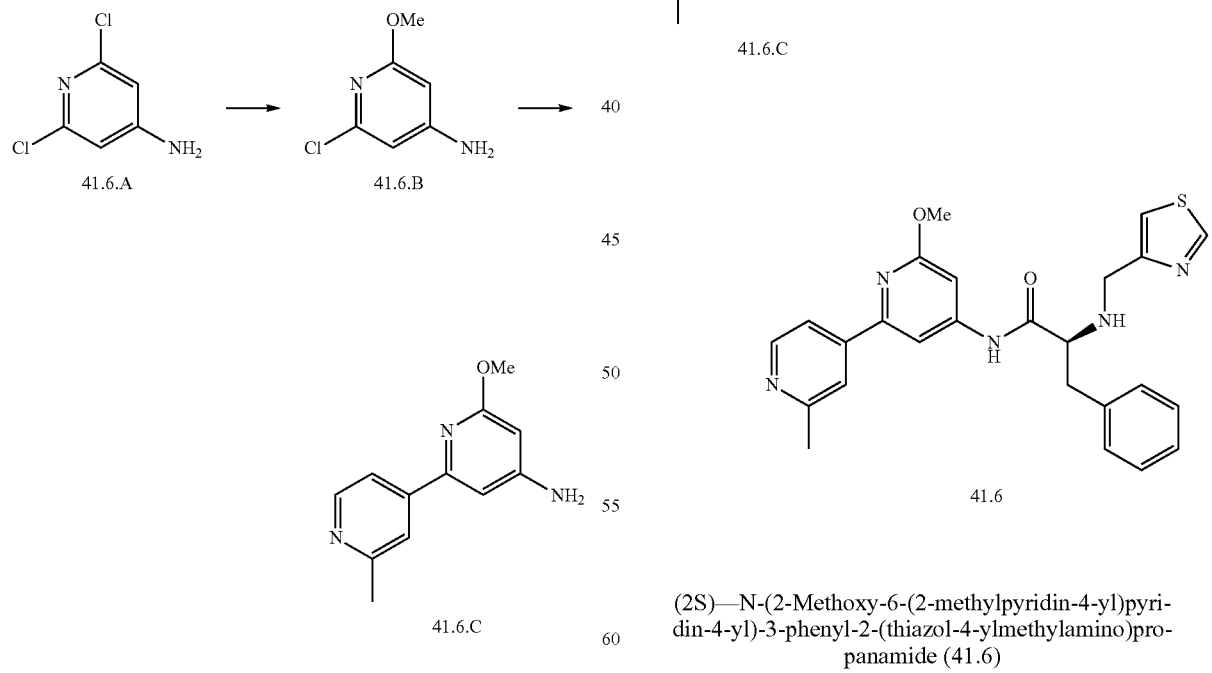

41.6.C

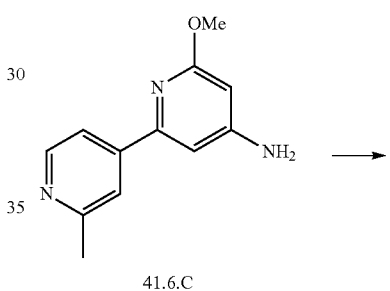

41.6.A → 41.6.B

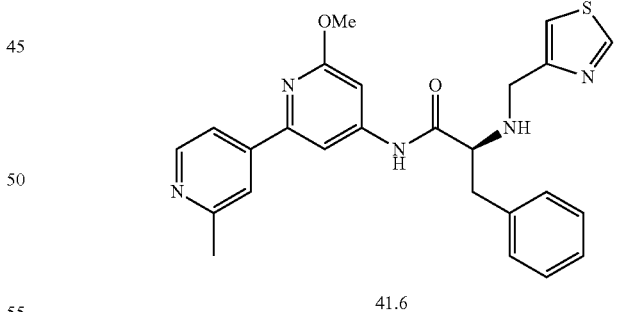

41.6

(2S)—N-(2-Methoxy-6-(2-methylpyridin-4-yl)pyridin-4-yl)-3-phenyl-2-(thiazol-4-ylmethylamino)propanamide (41.6)

This title compound was prepared starting from 41.6.0 according the procedure described above for conversion of 4.A to 4. The crude product 41.6 was purified by flash chromatography on silica gel using 0-6% MeOH/CH$_2$Cl$_2$ for elution. MS ESI (positive.) m/e: 460.1 (M+H).

7.42 Example 42

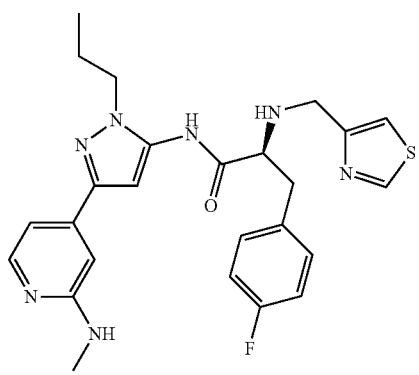 [SMILES: CCCn1nc(-c2ccnc(NC)c2)cc1NC(=O)[C@H](Cc1ccc(F)cc1)NCc1cscn1]

(2S)-3-(4-fluorophenyl)-N-(3-(2-(methylamino)pyridin-4-yl)-1-propyl-1H-pyrazol-5-yl)-2-(thiazol-4-ylmethylamino)propanamide (42)

This compound was synthesized according to the experimental procedures for example 23.2. 1H NMR (400 MHz, MeOH) δ ppm 8.95 (d, J=1.96 Hz, 1H) 7.93 (d, J=5.48 Hz, 1H) 7.39 (d, J=1.96 Hz, 1H) 7.26 (dd, J=8.61, 5.09 Hz, 2H) 6.99-7.07 (m, 2H) 6.93 (dd, J=5.48, 1.56 Hz, 1H) 6.87 (s, 1H) 6.63 (s, 1H) 3.82-3.98 (m, 4H) 3.65 (t, J=6.85 Hz, 1H) 3.04 (tt, J=14.28, 6.85 Hz, 2H) 2.90 (s, 3H) 1.72 (sxt, J=7.36 Hz, 2H) 0.83 (t, J=7.43 Hz, 3H).

7.43 Example 43

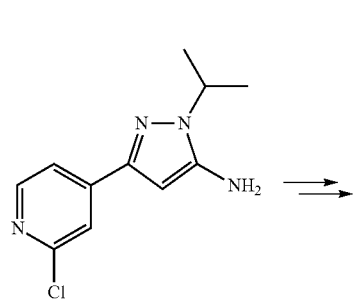

29.A

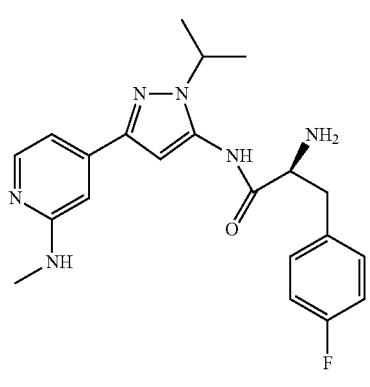

43.1

(2S)-2-Amino-3-(4-fluorophenyl)-N-(1-isopropyl-3-(2-(methylamino)pyridin-4-yl)-1H-pyrazol-5-yl)propanamide (43.1)

This title compound was prepared starting from 29.A according the procedure described above for conversion of 18.0 to 18.E. The crude product was purified by flash chromatography on silica gel using 0-15% MeOH/CH$_2$Cl$_2$ for elution to provide 43.1 (510 mg, 75%). MS ESI (positive.) m/e: 397.1 (M+H).

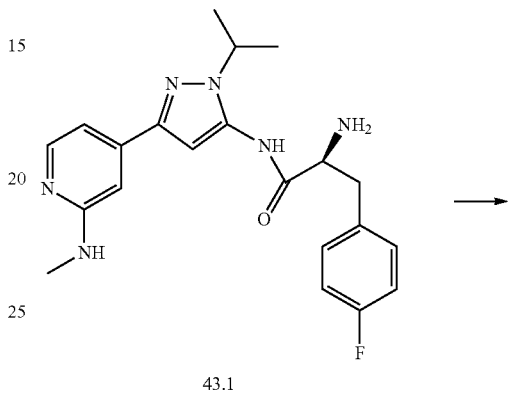

43.1

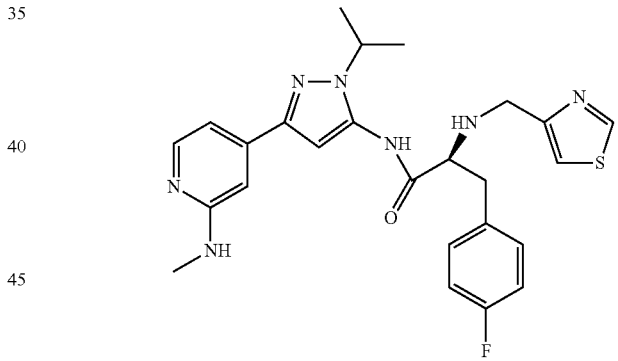

43.2

(2S)-3-(4-Fluorophenyl)-N-(1-isopropyl-3-(2-methylamino)pyridin-4-yl)-1H-pyrazol-5-yl)-2-(thiazol-4-ylmethylamino)propanamide (43.2)

This title compound was prepared from 43.1 according the procedure described above for conversion of 4.0 to 4. The crude product was purified by preparative HPLC (0-60% CH$_3$CN/water, 45 min) to provide 43.2 (20 mg). MS ESI (positve.) m/e: 494.2 (M+H), $^1$H NMR (400 MHz, CD$_3$OD) δ ppm 8.97 (d, J=1.96 Hz, 1H), 7.94 (d, J=5.48 Hz, 1H), 7.42 (d, J=1.96 Hz, 1H), 7.23-7.34 (m, 2H), 7.00-7.11 (m, 2H), 6.95 (d, J=5.48 Hz, 1H), 6.89 (s, 1H), 6.53 (s, 1H), 4.02-4.13 (m, 1H), 3.95-4.02 (m, 1H), 3.68 (t, J=7.04 Hz, 1H), 3.36 (s, 1H), 3.01-3.12 (m, 2H), 2.90 (s, 3H) 1.31-1.45 (m, 6H).

7.44 Example 44

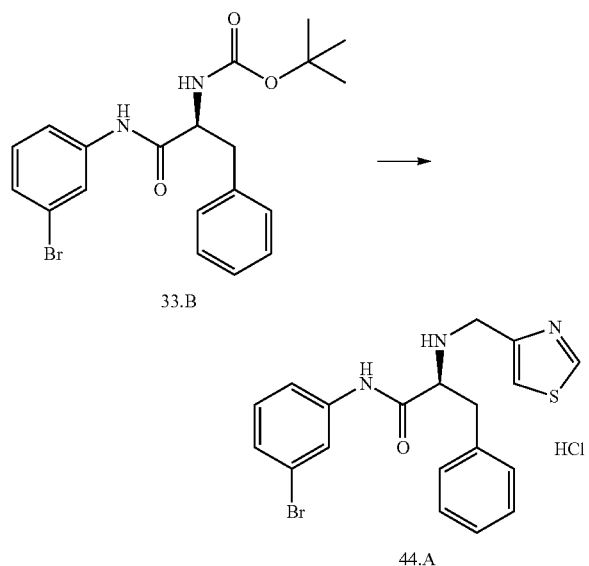

N-(3-Bromophenyl)-N-(1,3-thiazol-4-ylmethyl)-L-phenylalaninamide HCl (44.A)

44.A was prepared analogous to 33 and obtained as an HCl salt by dissolving the product in DCM, adding HCl (4.0 M, dioxane), and filtering. LC-MS (+esi, M+H$^+$=416.0).

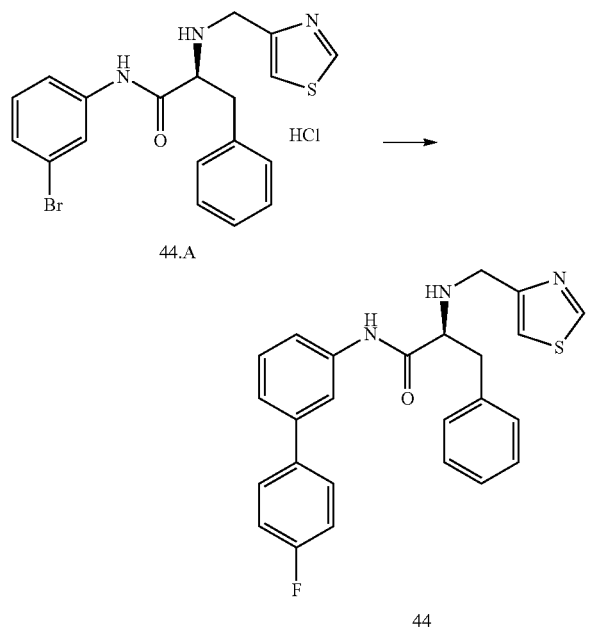

N-(4'-fluoro-1,1'-biphenyl-3-yl)-N-(1,3-thiazol-4-ylmethyl)-L-phenylalaninamide (44)

Bromide 44.A (200 mg, 0.44 mmol), 4-fluorophenylboronic acid (68 mg, 0.49 mmol), and Pd(dppf)Cl$_2$ were mixed in THF and Na$_2$CO$_3$ (2 M). The resulting mixture was heated in a sealed tube in a microwave at 135° C. for 10 minutes. The organic layer was concentrated and the residue was partially purified on a silica gel column (12 g, 0-10% MeOH:DCM). The fractions containing desired product were combined, concentrated, and purified again on a prepHPLC (C18, ACN:H$_2$O:0.1% TFA, gradient). The desired fractions were combined and concentrated on a rotavap to remove ACN and then partitioned with NaHCO$_3$ (sat)/EtOAc. The organic layer was dried with sodium sulfate, filtered, and concentrated to yield 44 (18 mg). LC-MS (+esi, M+H$^+$=432.1). 1H NMR (500 MHz, DICHLOROMETHANE-d$_2$) δ ppm 9.63 (br. s., 1H) 8.71 (d, J=1.96 Hz, 1H) 7.86 (t, J=1.96 Hz, 1H) 7.54-7.64 (m, 3H) 7.40 (t, J=7.82 Hz, 1H) 7.28-7.33 (m, 3H) 7.24-7.28 (m, 1H) 7.22 (d, J=6.85 Hz, 2H) 7.12-7.18 (m, 2H) 7.04 (d, J=1.71 Hz, 1H) 3.84-3.94 (m, 2H) 3.54 (dd, J=9.41, 4.28 Hz, 1H) 3.27 (dd, J=13.94, 4.16 Hz, 1H) 2.85 (dd, J=14.06, 9.41 Hz, 1H).

7.45 Example 45

7.45.1 Example 45.1

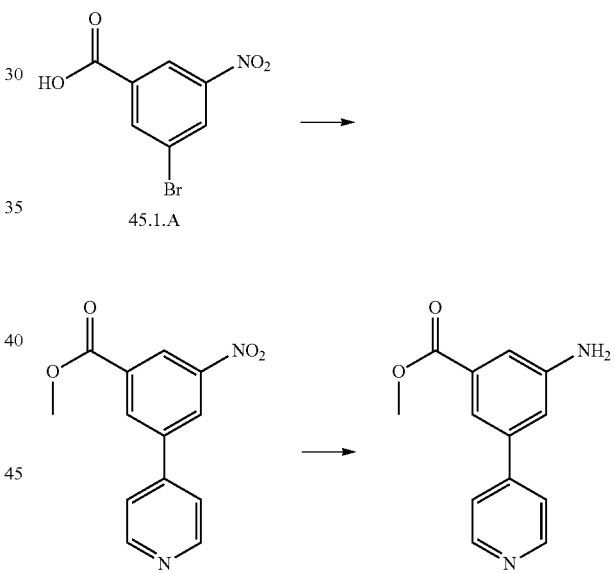

Methyl 3-nitro-5-(pyridin-4-yl)benzoate (45.1.B)

To a suspension of 3-bromo-5-nitrobenzoic acid 45.1.A (10.0 g, 40.7 mmol, available from Apollo) and pyridin-4-ylboronic acid (7.40 g, 60.9 mmol) in toluene (100 mL) was added 1,1'-Bis(diphenylphosphino)ferrocene-palladium(II) dichloride dichloromethane complex (3.3 g, 4.07 mmol), and 2M Na$_2$CO$_3$ aqueous (100 mL). The mixture was stirred for 3 hours at 90° C. at which time the mixture was condensed. The residue was dissolved in water (200 mL) and washed with EtOAc (50 mL). The water layer was then condensed, the residue was triturated with methanol (200 mL), and then filtered. Sulfuric acid (5 mL) was then added to the mother liquor and stirred at reflux overnight. The mixture was then concentrated, neutralized with saturated aqueous NaHCO₃ (100 mL), and extracted with DCM (2×100 mL). The combined organic layers were then concentrated to afford methyl 3-nitro-5-(pyridin-4-yl)benzoate 45.1.B (5.60 g, 53% yield) which was used in the next step without any further purification.

Methyl 3-amino-5-(pyridin-4-yl)benzoate (45.1.C)

To a solution of methyl 3-nitro-5-(pyridin-4-yl)benzoate (45.1.B) (5.60 g, 21.62 mmol) in methanol (50 mL) was added 10% Pd on carbon by weight (2.50 g). The air was evacuated from the reaction flask and was replaced with hydrogen. The resulting slurry was stirred overnight at room temperature. The reaction mixture was then filtered and the mother liquor condensed to afford methyl 3-amino-5-(pyridin-4-yl)benzoate (45.1.C) (4.70 g, 95% yield) which was used in the next step without any further purification.

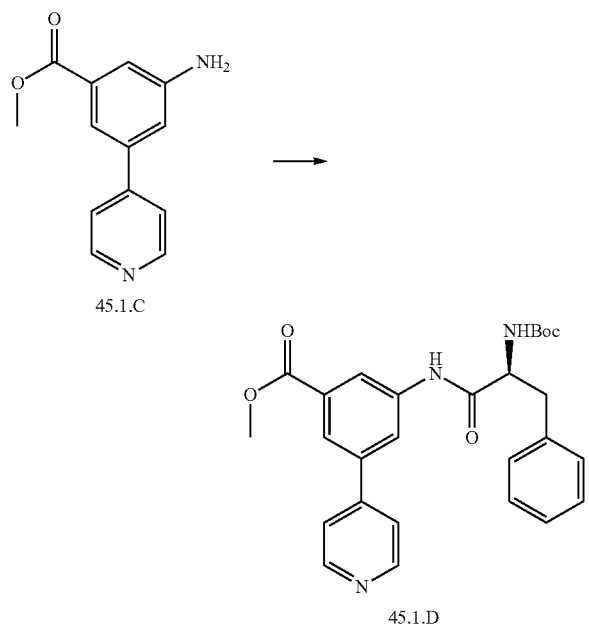

(S)-Methyl 3-(2-(tert-butoxycarbonyl)-3-phenylpropanamido)-5-(pyridin-4-yl)benzoate (45.1.D)

To a solution of methyl 3-amino-5-(pyridin-4-yl)benzoate 45.1.C (4.70 g, 20.6 mmol) in DMF (50 mL) was added (S)-2-(tert-butoxycarbonyl)-3-phenylpropanoic acid (6.56 g, 24.7 mmol, available from Aldrich), diisopropylethylamine (5.40 mL, 30.9 mmol) and 2-(1H-Benzotriazole-1-yl)-1,1,3,3-Tetramethyluronium hexafluorophosphate (9.36 g, 24.7 mmol). The resulting mixture is stirred overnight at room temperature. The mixture was then partitioned between water and EtOAc. The layers were separated, and the aqueous phase was extracted with additional EtOAc. The combined organic layers were washed with water and brine, dried (MgSO₄), and concentrated. The residue was purified by silica gel flash chromatography (0-100% EtOAc/hexane) to afford (S)-methyl 3-(2-(tert-butoxycarbonyl)-3-phenylpropanamido)-5-(pyridin-4-yl)benzoate 45.1.D (3.00 g, 31% yield).

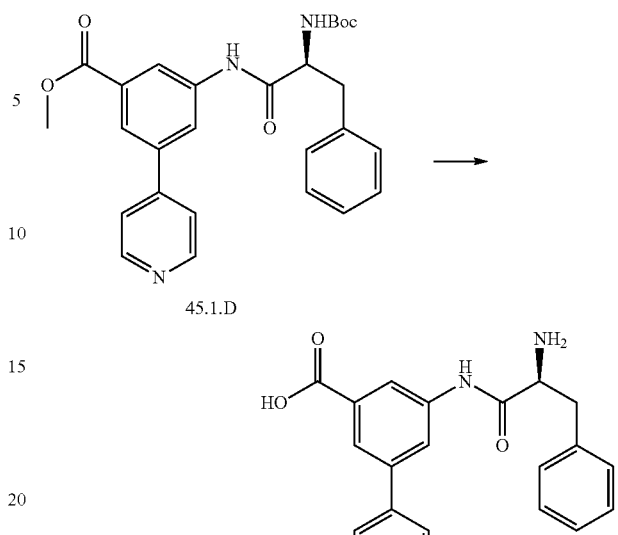

(S)-3-(2-Amino-3-phenylpropanamido)-5-(pyridin-4-yl)benzoic acid (45.1)

To a solution of (S)-methyl 3-(2-(tert-butoxycarbonyl)-3-phenylpropanamido)-5-(pyridin-4-yl)benzoate 45.1.D (3.0 g, 6.3 mmol) in THF (10 mL) was added LiOH (0.6 g, 25 mmol) and water (10 ml). The mixture was stirred at room temperature for 2 hours, the THF layer was then collected and the aqueous layer extracted with THF (5 mL). The THF layers were combined and 4M HCl in dioxane (10 mL, 40 mmol) was added. The mixture is stirred at room temperature for 1 hour and then concentrated. The residue was purified by reverse phase preparative HPLC to afford (S)-3-(2-amino-3-phenylpropanamido)-5-(pyridin-4-yl)benzoic acid 45.1 as a white solid. 1H NMR (500 MHz, MeOH-D4) δ ppm 8.82 (d, J=6.11 Hz, 2H), 8.31 (s, 1H), 8.20-8.28 (m, 4H), 7.18-7.30 (m, 5H), 4.21 (t, J=7.34 Hz, 1H), 3.53-3.58 (m, 2H).

7.45.2 Examples 45.2-45.6

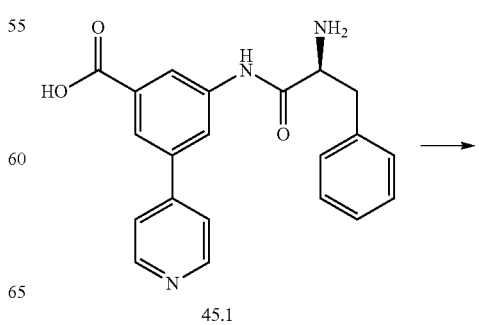

-continued

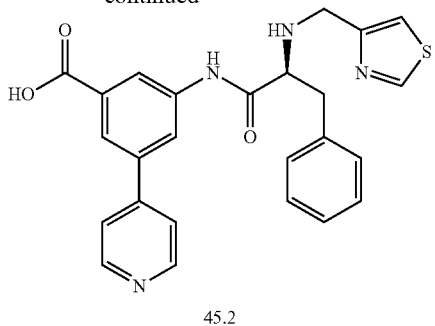

45.2

(S)-3-(3-Phenyl-2-(thiazol-5-ylmethylamino)propanamido)-5-(pyridin-4-yl)benzoic acid (45.2)

To a solution of (S)-3-(2-amino-3-phenylpropanamido)-5-(pyridin-4-yl)benzoic acid (45.1) (181 mg, 0.50 mmol) in DCM (5 mL) was added thiazole-4-carbaldehyde (56 mg, 0.50 mmol). The mixture was stirred for 1 h, sodium triacetoxyborohydride (212 mg, 1.00 mmol) was then added and the mixture stirred for an additional 1 hour at room temperature. The reaction mixture was then concentrated and the crude product purified by reverse phase chromatography (0-100% CH$_3$CN/water+0.5% TFA) to afford (S)-3-(3-phenyl-2-(thiazol-5-ylmethylamino)propanamido)-5-(pyridin-4-yl)benzoic acid (45.2) as a white solid (82 mg, 36% yield). LCMS ESI (pos.) m/e: 459.0 (M+1). 1H NMR (500 MHz, MeOH-D4) δ ppm 9.13 (d, J=1.96 Hz, 1H), 8.93 (d, J=6.85 Hz, 2H), 8.35 (d, J=1.22 Hz, 1H), 8.32-8.34 (m, 2H), 8.31 (t, J=1.83 Hz, 1H), 8.18-8.23 (m, 1H), 7.82 (d, J=1.96 Hz, 1H), 7.23-7.37 (m, 5H), 4.48-4.58 (m, 2H), 4.35 (dd, J=9.29, 5.87 Hz, 1H), 3.41-3.51 (m, 1H), 3.24-3.30 (m, 1H).

TABLE 8

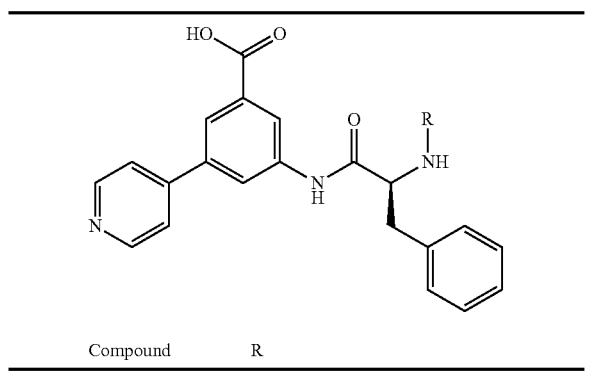

| Compound | R |
|---|---|
| 45.3 | 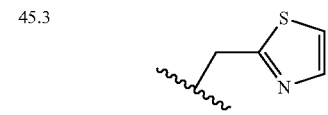 |
| 45.4 | 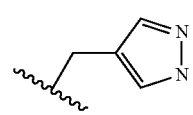 |
| 45.5 | 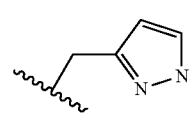 |

TABLE 8-continued

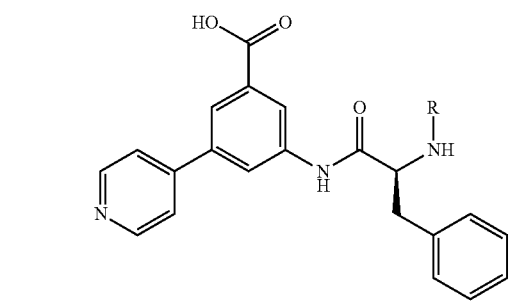

| Compound | R |
|---|---|
| 45.6 | 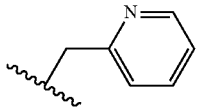 [SMILES: *Cc1ccccn1] |

(S)-3-(3-Phenyl-2-(thiazol-2-ylmethylamino)propanamido)-5-(pyridin-4-yl)benzoic acid (45.3)

1H NMR (500 MHz, MeOH-D4) δ ppm 3.18-3.20 (m, 1H) 3.45-3.53 (m, 1H) 3.89-3.99 (m, 2H) 4.38 (t, J=7.09 Hz, 1H) 7.26-7.40 (m, 5H) 7.78 (d, J=3.18 Hz, 1H) 7.97 (d, J=3.18 Hz, 1H) 8.15-8.22 (m, 1H) 8.32-8.37 (m, 2H) 8.39 (d, J=7.09 Hz, 2H) 8.95 (d, J=6.60 Hz, 2H).

(S)-3-(2-((1H-Pyrazol-4-yl)methylamino)-3-phenylpropanamido)-5-(pyridin-4-yl)benzoic acid (45.4)

LCMS ESI (pos.) m/e: 442.1 (M+1).

(S)-3-(2-((1H-Pyrazol-3-yl)methylamino)-3-phenylpropanamido)-5-(pyridin-4-yl)benzoic acid (45.5)

1H NMR (500 MHz, MeOH) δ ppm 3.45-3.51 (m, 1H) 4.33-4.45 (m, 2H) 6.50 (d, J=2.20 Hz, 1H) 7.23-7.39 (m, 5H) 7.77 (d, J=2.20 Hz, 1H) 8.11-8.20 (m, 3H) 8.27 (dd, J=14.55, 1.83 Hz, 2H) 8.80-8.90 (m, 2H).

(S)-3-(3-Phenyl-2-(pyridin-2-ylmethylamino)propanamido)-5-(pyridin-4-yl)benzoic acid (45.6)

1H NMR (500 MHz, MeOH-D4) δ ppm 3.23-3.26 (m, 1H) 3.45-3.53 (m, 1H) 4.40 (dd, J=8.93, 6.24 Hz, 1H) 4.44-4.57 (m, 2H) 7.25-7.39 (m, 5H) 7.42-7.55 (m, 2H) 7.91 (td, J=7.70, 1.71 Hz, 1H) 8.20 (t, J=1.71 Hz, 1H) 8.28-8.32 (m, 2H) 8.33 (d, J=1.71 Hz, 2H) 8.58-8.74 (m, 1H) 8.86-8.95 (m, 2H).

7.46 Example 46

Synthesis of (2S)—N-(3-chloro-5-(2-methylpyridin-4-yl)phenyl)-3-phenyl-2-(pyridin-2-ylmethylamino)propanamide (1)

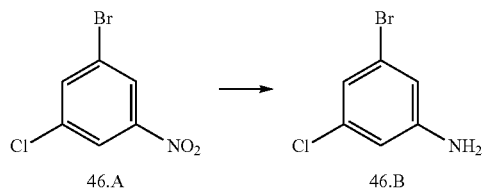 [SMILES: O=[N+]([O-])c1cc(Cl)cc(Br)c1 ; Nc1cc(Cl)cc(Br)c1]

3-Bromo-5-chlorobenzenamine (46.B)

1-bromo-3-chloro-5-nitrobenzene (4.27 g, 18.0 mmol) was dissolved in acetic acid (24.1 mL μl, 18.0 mmol) then zinc dust (11.82 g, 180 mmol) was added. After 4 h the reaction was filtered and concentrated to afford 3-bromo-5-chlorobenzenamine (3.7 g, 99% yield).

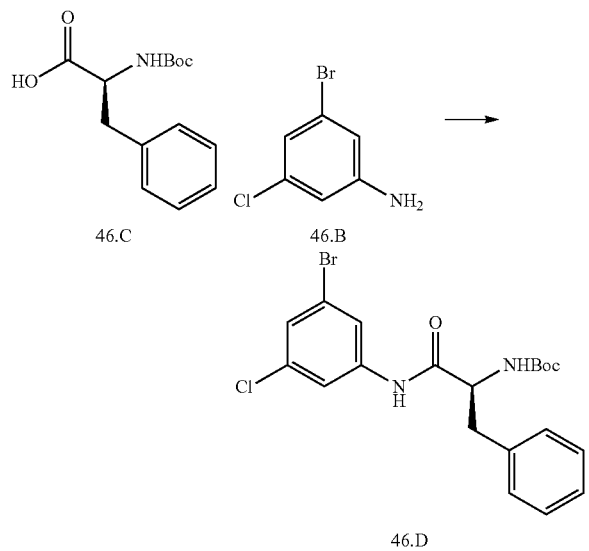

(S)-tert-Butyl 1-(3-bromo-5-chlorophenylamino)-1-oxo-3-phenylpropan-2-ylcarbamate (46.D)

3-bromo-5-chlorobenzenamine (3.73 g, 18 mmol) and (S)-2-(tert-butoxycarbonyl)-3-phenylpropanoic acid (4.8 g, 18 mmol) were dissolved in DMF (100 mL, 1291 mmol) then triethylmine (5 mL, 36 mmol) and HBTU (14 g, 36 mmol) were added and the mixture was stirred for 14 h. After 14 hours the reaction was diluted with 500 mL EtOAc and the organic was washed with 1N HCl and saturated bicarbonate solution. The extract was concentrated under reduced pressure on a rotary evaporator to afford a residue. The residue was purified on silica eluting with EtOAc/Hex in a linear gradient.

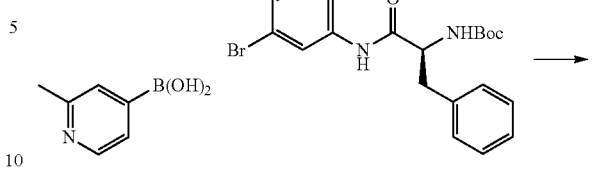

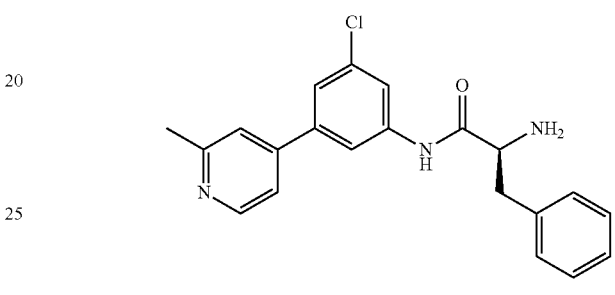

(2S)-2-Amino-N-(3-chloro-5-(2-methylpyridin-4-yl)phenyl)-3-phenylpropanamide (46.F)

2-methylpyridin-4-ylboronic acid (327 mg, 2.39 mmol), (S)-tert-butyl 1-(3-bromo-5-chlorophenylamino)-1-oxo-3-phenylpropan-2-ylcarbamate (542 mg, 1.19 mmol), tetrakis(triphenylphosphine)palladium (345 mg, 0.30 mmol), cesium fluoride (544 mg, 3.58 mmol) were added to a vial then DME (4778 μl, 1194 μmol) was added and the mixture was heated to 85° C. for 8 h. The reaction was loaded and purified on Phenomenex Geminni C18 HPLC 50 mm×250 mm running ACN/Water/0.1% TFA in a linear gradient. The fractions containing the desired product were combined and concentrated to afford tert-butyl (S)-1-(3-chloro-5-(2-methylpyridin-4-yl)phenylamino)-1-oxo-3-phenylpropan-2-ylcarbamate (367 mg, 66% yield). tert-butyl (S)-1-(3-chloro-5-(2-methylpyridin-4-yl)phenylamino)-1-oxo-3-phenylpropan-2-ylcarbamate (367 mg, 0.78 mmol) was dissolved in DCM (3 mL) and TFA (1 mL) add stirred for 3 h. The solution was concentrated to afford (2S)-2-amino-N-(3-chloro-5-(2-methylpyridin-4-yl)phenyl)-3-phenylpropanamide (280 mg, 99%).

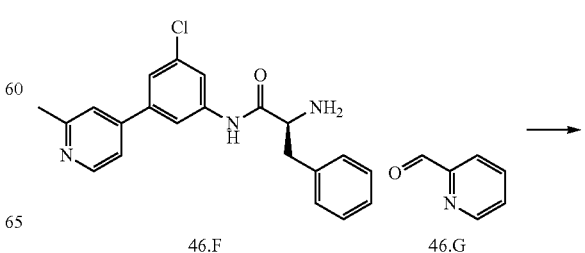

-continued

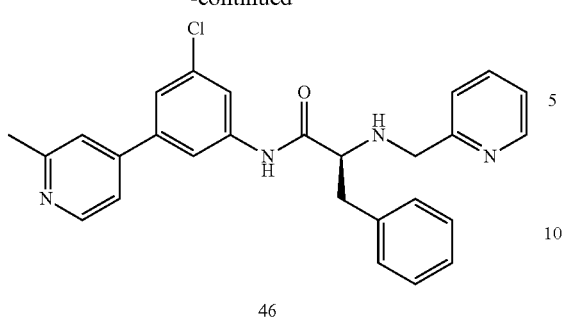

46

(2S)—N-(3-chloro-5-(2-methylpyridin-4-yl)phenyl)-3-phenyl-2-(pyridin-2-ylmethylamino)propanamide (46)

(2S)-2-amino-N-(3-chloro-5-(2-methylpyridin-4-yl)phenyl)-3-phenylpropanamide (32 mg, 87 μmol) was dissolved in trimethyl thoformate (1 ml) and acetic acid (0.25 ml, 4367 μmol). To this was added picolinaldehyde (94 mg, 875 mmol). After 30 min sodium cyanoborohydride (82 mg, 1312 μmol) dissolved in trimethyl orthoformate (1 ml). After 1 h the reaction mixture was poured onto 1N HCl and water was added, the mixture was concentrated under reduced pressure. The resulting crude solid was dissolved in AcOH/DMSO and purified on Phenomenex Geminni C18 HPLC 50 mm×250 mm running ACN/Water/0.1% TFA in a linear gradient. The fractions containing the desired product were combined and concentrated to afford (2S)—N-(3-chloro-5-(2-methylpyridin-4-yl)phenyl)-3-phenyl-2-(pyridin-2-ylmethylamino)propanamide (46) (30 mg, 75% yield). MS ESI (pos.) m/e: 457.1 (M+H). $^1$H NMR (500 MHz) (CDCl$_3$) δ 10.13 (1H, s), 8.68 (1H, d, J=6.1 Hz), 8.50 (1H, d, J=5.4 Hz), 7.99 (1H, dt, J=1.2, 9.0 Hz), 7.88 (1H, s), 7.72-7.77 (3H, m), 7.47-7.53 (2H, m), 7.34 (1H, m), 7.16-7.24 (6H, m), 4.28-4.36 (3H, m), 3.30 (1H, dd, J=5.8, 13.9 Hz), 3.14 (1H, dd, J=7.8, 13.7 Hz).

7.47 Example 47

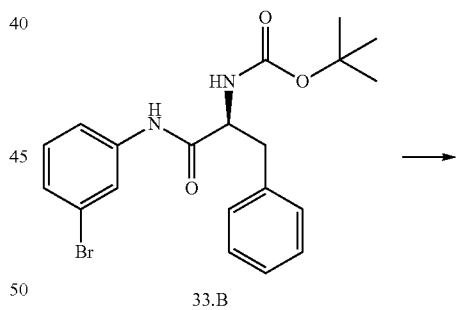

45.2

-continued

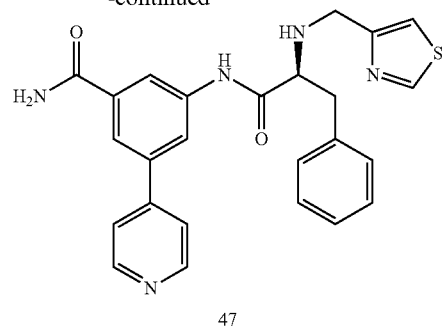

47

(S)-3-(3-phenyl-2-(thiazol-4-ylmethylamino)propanamido)-5-(pyridin-4-yl)benzamide (47)

To a solution of (S)-3-(3-phenyl-2-(thiazol-5-ylmethylamino)propanamido)-5-(pyridin-4-yl)benzoic acid 45.2 (15 mg, 0.033 mmol) in DMF (0.5 mL) was added ammonium chloride (7.6 mg, 0.050 mmol), diisopropylethylamine (23 μL, 0.13 mmol) and HBTU (25 mg, 0.066 mmol). The resulting mixture is stirred overnight at room temperature. The reaction mixture was purified directly on reverse phase preparative HPLC to afford (S)-3-(3-phenyl-2-(thiazol-4-ylmethylamino)propanamido)-5-(pyridin-4-yl)benzamide 47 as a white solid (5.2 mg, 35% yield). LCMS ESI (pos.) m/e: 458.1 (M+1). 1H NMR (400 MHz, MeOH-D4) δ ppm 9.12 (d, J=1.96 Hz, 1H), 7.91-7.97 (m, 2H), 7.79 (d, J=1.96 Hz, 1H), 7.48-7.57 (m, 2H), 7.43-7.48 (m, 1H), 7.25-7.36 (m, 5H), 7.19 (d, J=1.17 Hz, 1H), 7.13-7.17 (m, 1H), 4.48 (d, J=7.43 Hz, 2H), 4.25 (dd, J=9.39, 5.87 Hz, 1H), 3.42 (dd, J=13.30, 5.87 Hz, 1H), 3.25 (dd, J=13.30, 9.00 Hz, 1H).

7.48 Example 48

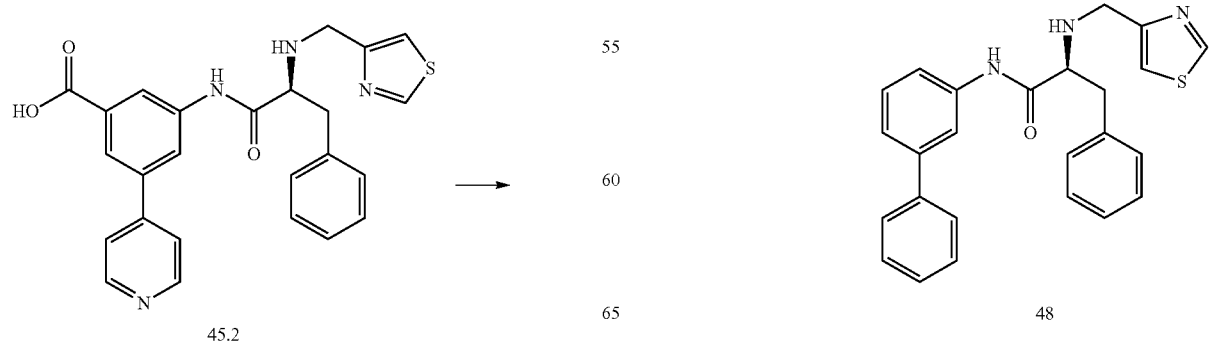

33.B → 48

N-(4'-fluoro-1,1'-biphenyl-3-yl)-N-(1,3-thiazol-4-ylmethyl)-L-phenylalaninamide (48)

48 was prepared analogously to 33. LC-MS (+esi, M+H+= 414.1). 1H NMR (500 MHz, DICHLOROMETHANE-d₂) δ ppm 9.64 (br. s., 1H) 8.71 (d, J=1.96 Hz, 1H) 7.86 (t, J=1.83 Hz, 1H) 7.61-7.66 (m, 3H) 7.43-7.48 (m, 2H) 7.41 (t, J=7.82 Hz, 1H) 7.34-7.38 (m, 2H) 7.28-7.33 (m, 2H) 7.25-7.28 (m, 1H) 7.20-7.25 (m, 2H) 7.06 (d, J=1.96 Hz, 1H) 3.85-3.95 (m, 2H) 3.55 (dd, J=9.41, 4.28 Hz, 1H) 3.27 (dd, J=13.94, 4.16 Hz, 1H) 2.87 (dd, J=14.06, 9.41 Hz, 1H).

7.49 Example 49

7.49.1 Example 49.1

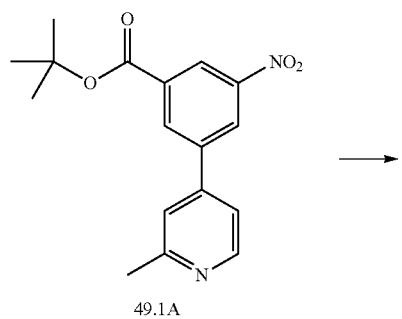

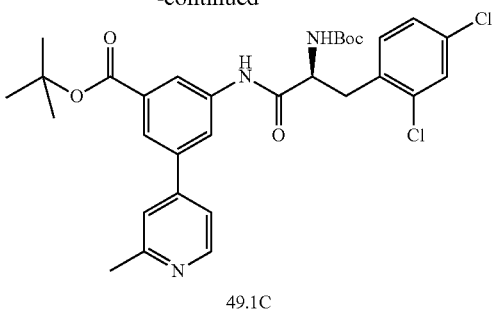

tert-Butyl 3-((S)-2-(tert-butoxycarbonyl)-3-(2,4-dichlorophenyl)propanamido)-5-(2-methylpyridin-4-yl)benzoate (49.1C)

A mixture of tert-butyl 3-amino-5-(2-methylpyridin-4-yl)benzoate (100 mg, 0.35 mmol), (S)-2-(tert-butoxycarbonyl)-3-(2,4-dichlorophenyl)-propanoic acid (152 mg, 0.45 mmol), HBTU (174 mg, 0.45 mmol) and N-ethyl-N-isopropylpropan-2-amine (92 µl, 0.53 mmol) in N,N-dimethylformamide (0.70 mL) was allowed to stir at 80° C. for 4 hours. Upon completion, the mixture was directly purified by HPLC to give 206 mg of tert-butyl 3-((S)-2-(tert-butoxycarbonyl)-3-(2,4-dichlorophenyl)propanamido)-5-(2-methylpyridin-4-yl)benzoate 49.1C. LCMS (ES+) m/z 601.

tert-Butyl 3-amino-5-(2-methylpyridin-4-yl)benzoate (49.1B)

A mixture of tert-butyl 3-(2-methylpyridin-4-yl)-5-nitrobenzoate (1.5 g, 4.8 mmol) and 300 mg of 10% wet Pd/C (~50% H2O) in 25 mL of methanol under a balloon of hydrogen was allowed to stir at room temperature overnight. Upon completion, the mixture was concentrated and the residue was dried to give 1.31 g of tert-Butyl 3-amino-5-(2-methylpyridin-4-yl)benzoate 49.1B. LCMS (ES+) m/z 285.

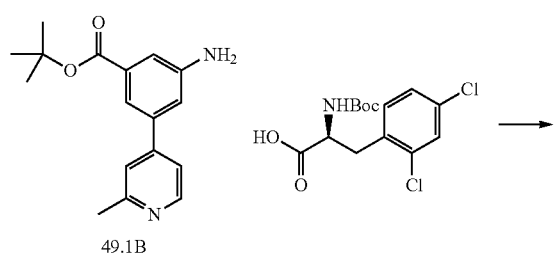

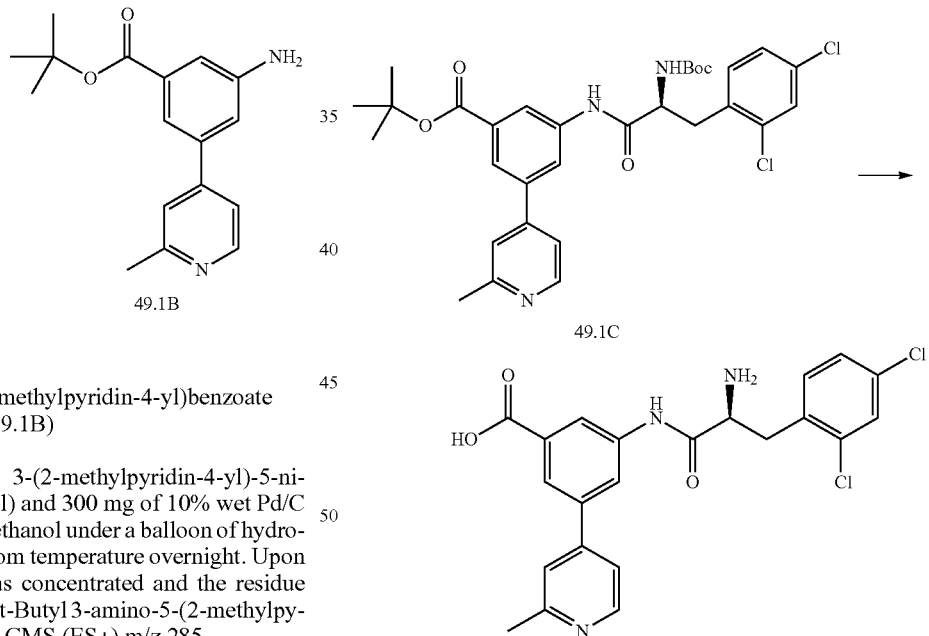

3-((S)-2-Amino-3-(2,4-dichlorophenyl)propanamido)-5-(2-methylpyridin-4-yl)benzoic acid (49.1)

To a solution of tert-butyl 3-((S)-2-(tert-butoxycarbonyl)-3-(2,4-dichlorophenyl)propanamido)-5-(2-methylpyridin-4-yl)benzoate (206 mg, 0.30 mmol) in 5.0 mL of DCM was added 1.5 mL of TFA. The resulting mixture was allowed to stir at room temperature overnight. Upon completion, the mixture was concentrated and the residue was purified by HPLC to give 90 mg of 3-((S)-2-amino-3-(2,4-dichlorophenyl)propanamido)-5-(2-methylpyridin-4-yl)benzoic acid 49.1. 400 MHz $^1$H NMR (CD3OD) δ: 7.19 (d, J=8.0 Hz, 1H), 6.77 (obscured d, 1H), 6.76 (s, 1H), 6.61 9d, J=4.0 Hz, 1H), 6.53 (dd, J=8.0, 4.) Hz, 1H), 6.01 (d, 1H), 5.82 (d, J=12.0 Hz, 1H), 5.76 (dd, J=8.0, 4.0 Hz, 1H), 2.76 (dd, 8.0, 8.0 Hz, 1H), 1.92 (dd, J=16.0, 8.0 Hz, 1H), 1.86 (dd, 16.0, 8.0 Hz, 1H), 1.31 (s, 3H). LCMS (ES+) m/z 445.

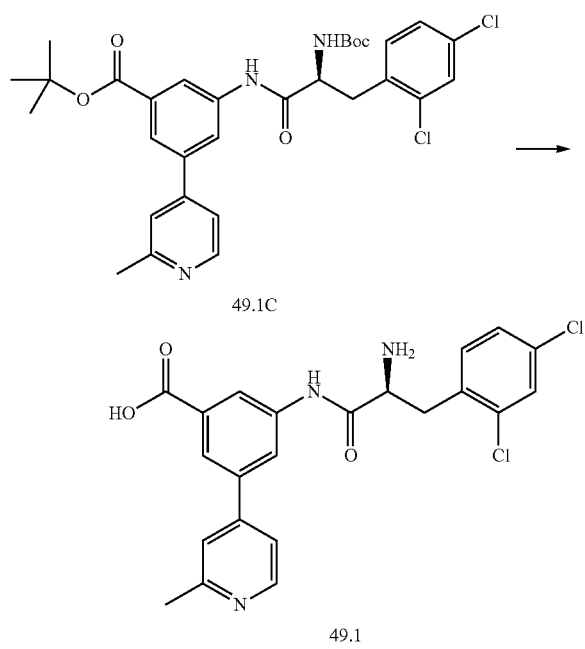

3-(2-Methylpyridin-4-yl)-5-(S)-3-phenyl-2-(thiazol-4-ylmethylamino)propanamido)benzoic acid TFA salt (49.2)

LCMS ESI (pos.) m/e: 473.1 (M+1): 1H NMR (400 MHz, MeOH) δ ppm 9.12 (d, J=1.96 Hz, 1H), 8.74 (d, J=6.26 Hz, 1H), 8.28 (dd, J=4.89, 1.76 Hz, 2H), 8.16 (d, J=10.96 Hz, 2H), 8.09 (d, J=6.26 Hz, 1H), 7.80 (d, J=1.96 Hz, 1H), 7.20-7.40 (m, 5H), 4.40-4.61 (m, 2H), 4.31 (dd, J=9.19, 5.67 Hz, 1H), 3.45 (dd, J=13.69, 5.87 Hz, 1H), 3.26 (dd, J=13.50, 9.19 Hz, 1H), 2.85 (s, 3H).

7.49.2 Example 49.2

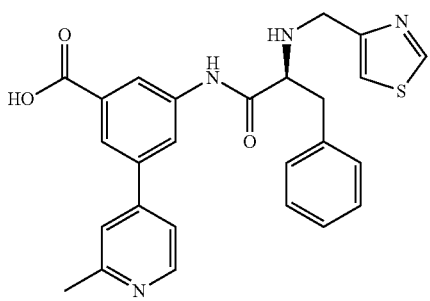 [SMILES: Cc1cc(-c2cc(NC(=O)[C@H](Cc3ccccc3)NCc3cscn3)cc(C(=O)O)c2)ccn1]

3-(2-Methylpyridin-4-yl)-5-((S)-3-phenyl-2-(thiazol-4-ylmethylamino)propanamido)benzoic acid TFA salt (49.2)

LCMS ESI (pos.) m/e: 473.1 (M+1): 1H NMR (400 MHz, MeOH) δ ppm 9.12 (d, J=1.96 Hz, 1H), 8.74 (d, J=6.26 Hz, 1H), 8.28 (dd, J=4.89, 1.76 Hz, 2H), 8.16 (d, J=10.96 Hz, 2H), 8.09 (d, J=6.26 Hz, 1H), 7.80 (d, J=1.96 Hz, 1H), 7.20-7.40 (m, 5H), 4.40-4.61 (m, 2H), 4.31 (dd, J=9.19, 5.67 Hz, 1H), 3.45 (dd, J=13.69, 5.87 Hz, 1H), 3.26 (dd, J=13.50, 9.19 Hz, 1H), 2.85 (s, 3H).

7.50 Example 50

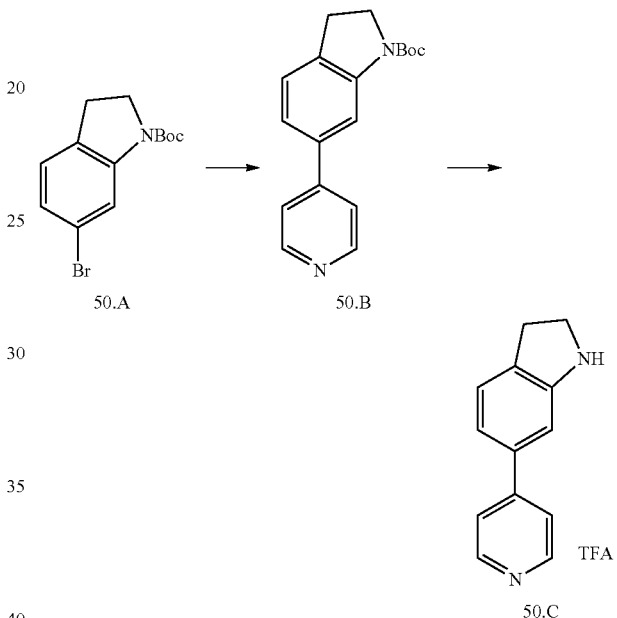

tert-Butyl 6-(pyridin-4-yl)indoline-1-carboxylate (50.B)

To a 20 ml vial was added tert-butyl 6-bromoindoline-1-carboxylate 50.A (500 mg, 1.7 mmole), 4-pyridylboronic acid (309 mg, 2.5 mmol), tetrakis(triphenylphosphine) palladium(388, 0.34 mmol), DMF and 3 ml of saturated sodium carbonate. The reaction was stirred at 70° C. for 6 hours at which time the reaction mixture was partitioned between 300 ml EtAc and 200 ml of water. The organic solvent was removed by rotary evaporation and the crude product purified by reverse phase preparative HPLC to give tert-butyl 6-(pyridin-4-yl)indoline-1-carboxylate 50.B as a yellow solid (202 mg, 41% yield).

tert-Butyl 6-(pyridin-4-yl)indoline-1-carboxylate (50.C)

To a 100 ml flask was added tert-butyl 6-(pyridin-4-yl)indoline-1-carboxylate 50.B (202 mg, 0.68), 10 ml of CH$_2$Cl$_2$, and 5 ml of TFA. The reaction was stirred at room temperature for 2 hours at which time the solvent was removed to give 6-(pyridin-4-yl)indoline TFA salt 50.0 as a light yellow solid (300 mg, 100% yield).

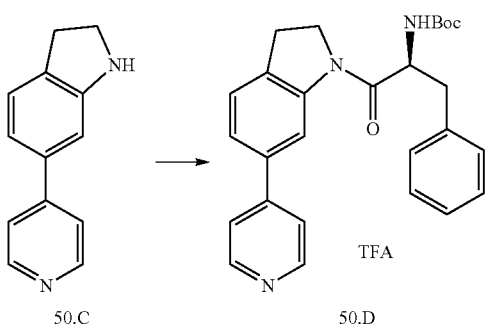 [SMILES: c1cc(-c2ccc3c(c2)NCC3)ccn1 ; CC(C)(C)OC(=O)N[C@@H](Cc1ccccc1)C(=O)N1CCc2ccc(-c3ccncc3)cc21]

(S)-tert-Butyl 1-oxo-3-phenyl-1-(6-(pyridin-4-yl)indolin-1-yl)propan-2-ylcarbamate (50.D)

To a 25 ml vial was added 6-(pyridin-4-yl)indoline 50.0 (200 mg, 1.2 mmole), HBTU (580 mg, 1.5 mmole), n-(tert-butoxycarbonyl)-1-phenylalanine (324 mg, 1.2 mmole, available from Aldrich), 5 ml of DMF and DIEA (533 ul, 3.0 mmole). The reaction was stirred at 22° C. for 12 hours, at which time the crude mixture was purified by reverse phase preparative HLPC with no work up performed to give (S)-tert-butyl 1-oxo-3-phenyl-1-(6-(pyridin-4-yl)indolin-1-yl)propan-2-ylcarbamate 50.D as a yellow solid (205 mg, 45.4% yield).

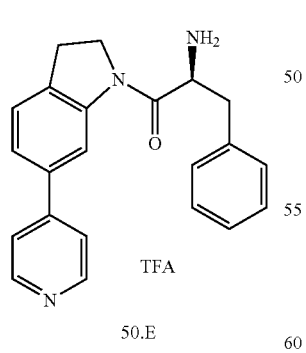

(S)-2-Amino-3-phenyl-1-(6-(pyridin-4-yl)indolin-1-yl)propan-1-one (50.E)

To a 25 ml flask was added (S)-tert-butyl 1-oxo-3-phenyl-1-(6-(pyridin-4-yl)indolin-1-yl)propan-2-ylcarbamate 50.D (300 mg, 0.68 mmole) 10 ml of $CH_2Cl_2$, and 5 ml of TFA. The reaction was stirred at room temperature for 3 hour at which time the solvent was removed with a stream of nitrogen. The crude was resuspended and the solvent was removed as before. This procedure was repeated one more time to give (S)-2-amino-3-phenyl-1-(6-(pyridin-4-yl)indolin-1-yl)propan-1-one 50.E of as a light yellow oil (300 mg, 21% yield).

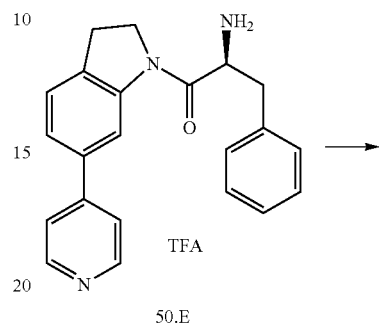

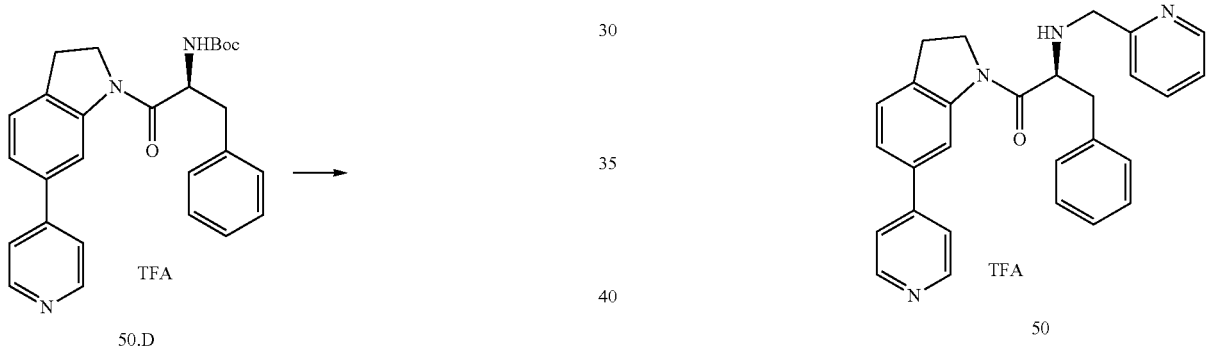

(S)-3-Phenyl-2-(pyridin-2-ylmethylamino)-1-(6-(pyridin-4-yl)indolin-1-yl)propan-1-one TFA Salt (50)

To a 20 ml vial were added (S)-2-amino-3-phenyl-1-(6-(pyridin-4-yl)indolin-1-yl)propan-1-one 50.E (60 mg, 0.18), 2-pyridaldehyde (17 ul, 0.18 mmole), sodium triacetoxyborohydride (81 mg, 0.35), DIEA (46 ul, 0.26) and 10 ml of DCE. The reaction was stirred at 70° C. for 12 hours at which time the reaction mixture was partitioned between $CH_2Cl_2$ and water and the solvent was removed from the organic layer by rotary evaporation. The crude product was purified by reverse phase preparative HPLC(S)-3-phenyl-2-(pyridin-2-ylmethylamino)-1-(6-(pyridin-4-yl)indolin-1-yl)propan-1-one 50 as a light brown solid (11 mg, 11% yield). LCMS ESI (pos.) m/e: 435.2 (M+1): 1H NMR (500 MHz, MeOH) δ ppm 7.50 (d, J=6.71 Hz, 2H), 7.41 (d, J=1.83 Hz, 1H), 7.26 (d, J=4.27 Hz, 1H), 6.98 (d, J=6.71 Hz, 2H), 6.51 (td, J=7.78, 1.53 Hz, 1H), 6.35 (dd, J=7.93, 1.83 Hz, 1H), 6.02-6.17 (m, 3H), 5.84-6.00 (m, 5H), 3.38 (dd, J=10.07, 5.19 Hz, 1H), 3.13

(d, J=3.05 Hz, 2H), 2.61 (d, J=6.71 Hz, 1H), 2.14 (dd, J=13.12, 5.19 Hz, 1H), 1.92 (m, 1H), 1.65-1.80 (m, 2H), 1.38 (s, 1H).

7.51 Example 51

7.51.1 Examples 51.1 and 51.2

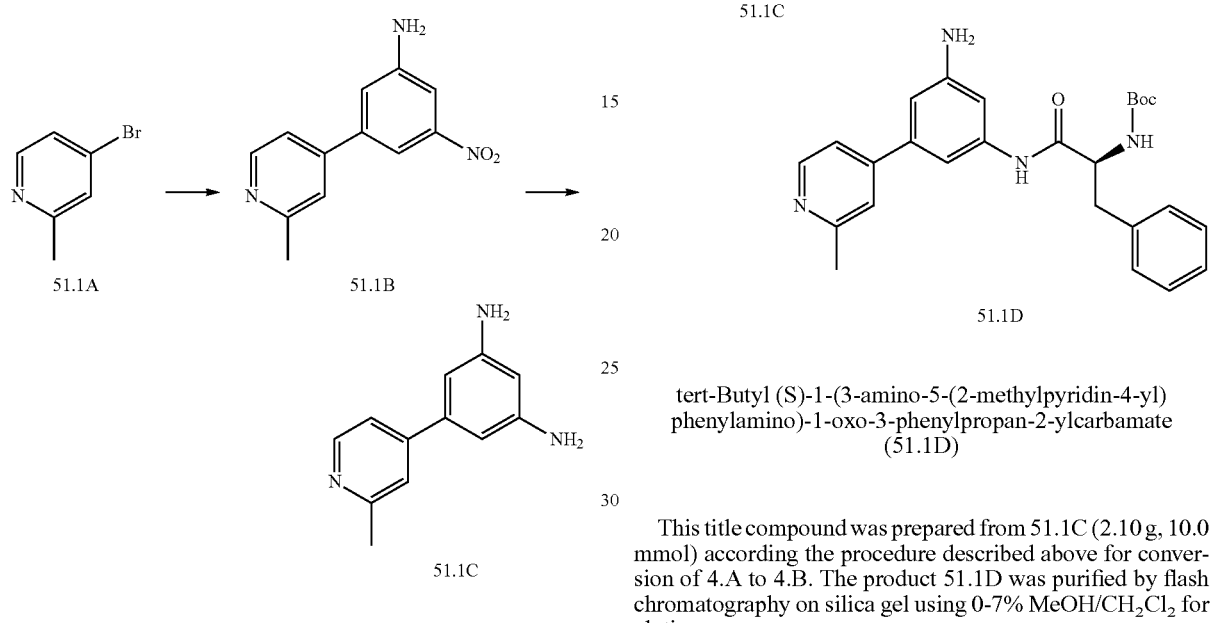

3-(2-Methylpyridin-4-yl)-5-nitrobenzenamine (51.1B)

To a rt solution of 51.1A (available from Frontier Scientific, Inc.) (3.00 g, 17.0 mmol) in n-BuOH (40 mL) was added 3-amino-5-nitrophenylboronic acid hydrochloride (available from Combi-Blocks Inc.) (3.50 g, 19.0 mmol), potassium phosphate (available from Strem Chemicals, Inc.) (11.0 g, 52.0 mmol) and bis(triphenylphosphine)palladium(ii) chloride (available from Aldrich) (0.64 g, 0.85 mmol). After being purge with $N_2$ for 15 mins, the mixture was stirred at 100° C. under $N_2$ atmosphere for 1.5 hrs. The reaction solution was concentrated. The residue was re-dissolved in 30% $^i$PrOH/CHCl$_3$ (45 mL), washed with $H_2O$ and brine, and dried over MgSO$_4$. After removal of organic solvent under reduced pressure, purification of the residue by flash chromatography on silica gel using 0-70% EtOAc/Hexanes for elution gave the title product 51.1B as yellow solid (3.21 g, 80%).

5-(2-Methylpyridin-4-yl)benzene-1,3-diamine (51.1C)

To a rt solution of 51.1B (1.10 mg, 4.8 mol) in MeOH (10 mL) was added 5% Pd/C. The heterogeneous solution was stirred at 50° C. under $H_2$ for 4.0 hr. To the resulting mixture was added celite, solid was filtered off and washed with MeOH. The combined liquid was concentrated under reduced pressure to provide the title product 51.1C as colorless solid (865 mg, 91%).

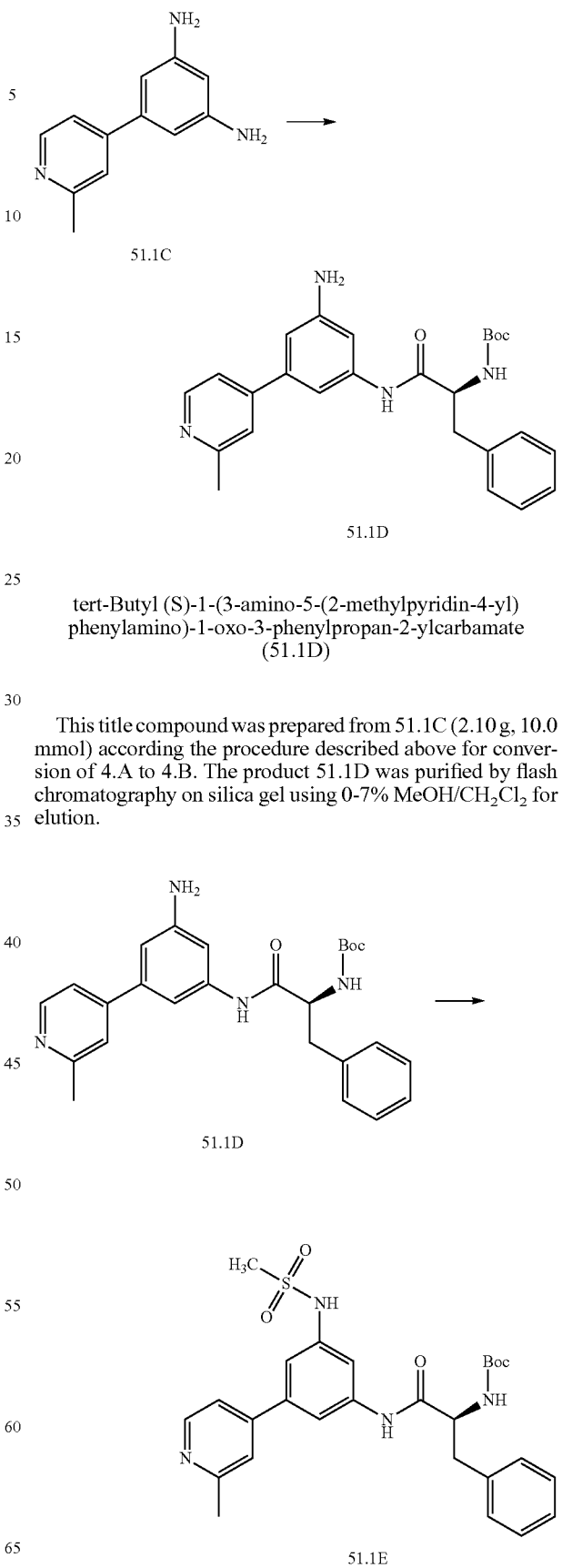

tert-Butyl (S)-1-(3-amino-5-(2-methylpyridin-4-yl)phenylamino)-1-oxo-3-phenylpropan-2-ylcarbamate (51.1D)

This title compound was prepared from 51.1C (2.10 g, 10.0 mmol) according the procedure described above for conversion of 4.A to 4.B. The product 51.1D was purified by flash chromatography on silica gel using 0-7% MeOH/CH$_2$Cl$_2$ for elution.

tert-Butyl (S)-1-(3-(2-methylpyridin-4-yl)-5-(methylsulfonamido)phenylamino)-1-oxo-3-phenylpropan-2-ylcarbamate (51.1E)

To a 0° C. solution of 51.1D (512 mg, 1.16 mmol) and triethylamine (478 μl, 3.44 mmol) in CH$_2$Cl$_2$ (10 mL) under N$_2$ was added methanesulfonyl chloride (available from Aldrich) (84.3 μl, 1.08 mmol) drop wise over 10 min. After stirring at 0° C. for 30 min, the reaction mixture was treated with saturated aqueous NaHCO$_3$ (1 mL), diluted with water (10 mL), and extracted with CH$_2$Cl$_2$ (3×10 mL). Organic layers were combined, dried over MgSO$_4$, and concentrated under reduced pressure. Purification of the residue by flash chromatography on silica gel using 0-70% EtOAc/CH$_2$Cl$_2$ provided title product 51.1E as white solid (268 mg, 43%).

The following compounds were prepared starting from 51.1E using appropriate aldehyde according to the method described above for conversion of 4.B to 4.

TABLE 9

| Compound | R |
|---|---|
| 51.1 | thiazol-4-ylmethyl |
| 51.2 | pyridin-2-ylmethyl |

(2S)—N-(3-(2-Methylpyridin-4-yl)-5-(methylsulfonamido)phenyl)-3-phenyl-2-(thiazol-4-ylmethylamino)propanamide (51.1)

MS ESI (positve.) m/e: 522.1 (M+H), $^1$H NMR (400 MHz, CHLOROFORM-d) δ ppm 10.01 (s, 1H), 8.68 (d, J=1.96 Hz, 1H), 8.47 (d, J=5.48 Hz, 1H), 7.93 (s, 1H), 7.55 (s, 1H), 7.33 (d, J=12.52 Hz, 2H), 7.09-7.29 (m, 5H), 6.98 (d, J=1.96 Hz, 1H), 3.74-3.89 (m, 2H), 3.58-3.69 (m, 1H), 3.28 (dd, J=14.09, 3.52 Hz, 1H), 2.89-3.07 (s, 3H), 2.71 (dd, J=14.09, 10.17 Hz, 1H), 2.51 (s, 3H).

(2S)—N-(3-(2-Methylpyridin-4-yl)-5-(methylsulfonamido)phenyl)-3-phenyl-2-(pyridin-2-ylmethylamino)propanamide (51.2)

MS ESI (positve.) m/e: 516.2 (M+H); $^1$H NMR (400 MHz, CHLOROFORM-d) δ ppm 10.24 (s, 1H), 8.42-8.52 (m, 2H), 8.12 (br. s., 1H), 7.86-7.98 (m, 1H), 7.44-7.61 (m, 2H), 7.32 (d, J=15.26 Hz, 2H), 7.14-7.28 (m, 5H), 7.06-7.14 (m, 1H), 6.95-7.04 (m, 1H), 3.70-3.84 (m, 2H), 3.56-3.69 (m, 1H), 3.26-3.37 (m, 1H), 2.93-3.05 (s, 3H), 2.68-2.84 (m, 1H), 2.49-2.62 (s, 3H).

7.52 Example 52

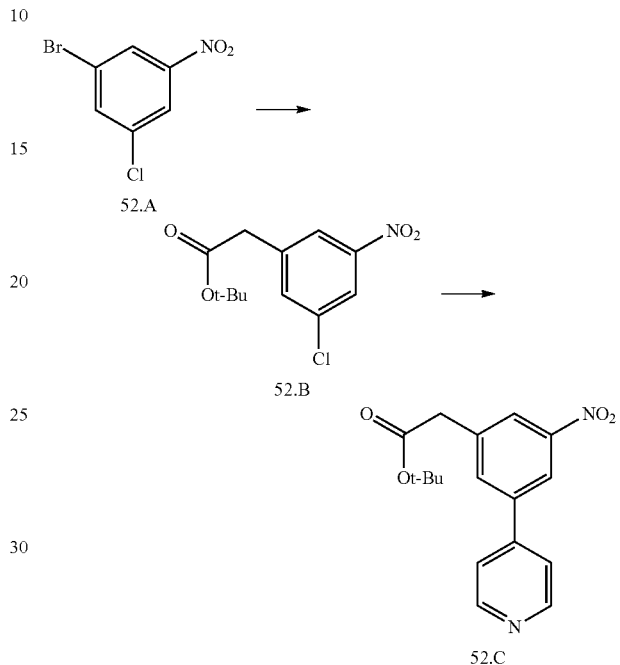

tert-Butyl 2-(3-chloro-5-nitrophenyl)acetate (52.B)

To a solution of 1-bromo-3-chloro-5-nitrobenzene 52.A (10.23 g, 43 mmol, available from Synchem Inc), Pd$_2$(dba)$_3$ (0.79 g, 0.87 mmol) and CTC-QPhos (1.20 g, 1.40 mmol) in THF (100 mL) was added 2-tert-Butoxy-2-oxoethylzinc chloride (95 mL, 0.5M solution in diethyl ether, 48 mmol, available from Rieke Metals). The mixture was stirred for 3 hours at room temperature. The reaction was then quenched by adding water (100 mL), washed with 1N HCl solution (2×100 mL), concentrated and purified by using flash chromatography on silica gel (0-10% AcOEt/Hexanes) to afford tert-butyl 2-(3-chloro-5-nitrophenyl)acetate 52.B (9.60 g, 82% yield) as a light pink oil.

tert-Butyl 2-(3-nitro-5-(pyridin-4-yl)phenyl)acetate (52.C)

To a solution of tert-butyl 2-(3-chloro-5-nitrophenyl)acetate 52.B (2.00 g, 7.36 mmol) and pyridin-4-ylboronic acid (1.09 g, 8.83 mmol) in t-amyl alcohol (20 mL) was added K$_3$PO$_4$ (4.69 g, 22.1 mmol), Pd$_2$(dba)$_3$ (337 mg, 0.368 mmol) and XPhos (702 mg, 1.47 mmol). The mixture was stirred for 3 hours at 100° C. and then was filtered over Celite. The liquid phase was concentrated and partitioned between water and AcOEt. The organic phase was then washed with brine, dried over MgSO$_4$, concentrated and purified by flash chromatography on silica gel to afford tert-butyl 2-(3-nitro-5-(pyridin-4-yl)phenyl)acetate 52.0 (2.03 g, 72% yield).

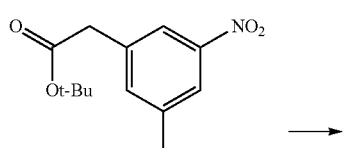

52.C

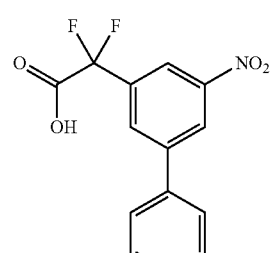

52.D

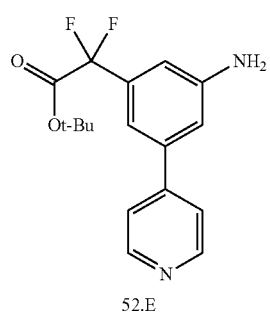

52.E

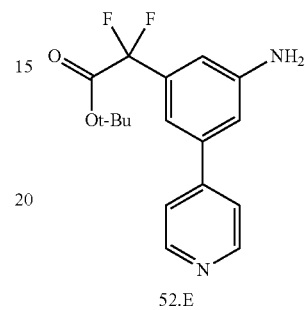

52.E was added n,n-dimethylformamide di-tert-butyl acetal (1.47 mL, 6.12 mmol). The mixture was stirred at 50° C. for 1 hour, then concentrated and dried under vacuum. The residue was then dissolved in EtOAc (10 mL), to which was added 10% Pd/C (150 mg). The air was then evacuated out of the flask and replaced by hydrogen. The mixture was stirred at room temperature for 2 hours, filtered over celite and then concentrated to afford tert-butyl 2-(3-amino-5-(pyridin-4-yl)phenyl)-2,2-difluoroacetate 52.E (473 mg, 96% yield) which is used in the next step with no further purification.

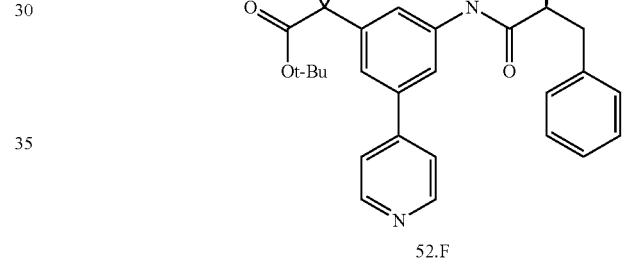

52.F

(S)-tert-Butyl 2-(3-(2-amino-3-phenylpropanamido)-5-(pyridin-4-yl)phenyl)-2,2-difluoroacetate (52.F)

To a solution of (S)-2-(tert-butoxycarbonyl)-3-phenylpropanoic acid (1.96 g, 7.38 mmol) 52.E in DCM (10 mL) and pyridine (4 mL) was added 2,4,6-trifluoro-1,3,5-triazine (1.20 g, 8.86 mmol) and was stirred at −10° C. for 1 hour. Crushed ice was then added to the reaction mixture and the mixture was extracted with DCM (2×50 mL), washed with ice cold water (50 mL), dried on MgSO$_4$ and concentrated to afford (S)-tert-butyl 1-fluoro-1-oxo-3-phenylpropan-2-yl-carbamate. The crude mixture was stirred at 50° C. overnight, then was dissolved in AcOEt (100 mL) and then washed with saturated aqueous NaHCO$_3$ (4×50 mL), brine (50 mL), dried over MgSO$_4$ and concentrated. The residue was dissolved in THF (5 mL), and then a 4M solution of HCl in dioxane (5 mL, 20 mmol) was added. The mixture was stirred at room temperature for 2 hours and then was concentrated. The residue was neutralized with saturated aqueous NaHCO$_3$ (10 mL) and extracted with DCM (3×10 mL). The organic layers were combined and concentrated to afford (S)-tert-butyl 2-(3-(2-amino-3-phenylpropanamido)-5-(pyridin-4-yl)phenyl)-2,2-difluoroacetate 52.F (300 mg, 43% yield) as a yellow oil, which is used in the next step without any further purification.

2,2-Difluoro-2-(3-nitro-5-(pyridin-4-yl)phenyl)acetic acid (52.D)

To a solution cooled to −78° C. of tert-butyl 2-(3-nitro-5-(pyridin-4-yl)phenyl)acetate 52.0 (2.00 g, 6.36 mmol) in THF (30 mL), was added drop wise a 0.5M solution of KHMDS in toluene (19 mL, 19 mmol). The mixture was then stirred for 15 minutes at which time 2-Fluoro-3,3-dimethyl-2,3-dihydro-1,2-benzisothiazole 1,1-dioxide (4.1 g, 19 mmol, available from Fluka) was added. The mixture was stirred at −78° C. for 1 hour and then allowed to warm to room temperature. Water was then added (100 mL) and the resulting mixture was extracted with DCM (3×100 mL). The organic layers were combined and washed with brine, dried on MgSO$_4$ and concentrated. The residue was purified by reverse phase preparative HPLC to afford 2,2-difluoro-2-(3-nitro-5-(pyridin-4-yl)phenyl)acetic acid 52.D as a white solid (700 mg, 37% yield).

tert-Butyl 2,2-difluoro-2-(3-nitro-5-(pyridin-4-yl)phenyl)acetate (52.E)

To a solution of 2-difluoro-2-(3-nitro-5-(pyridin-4-yl)phenyl)acetic acid 52.D (450 mg, 1.53 mmol) in toluene (5 mL)

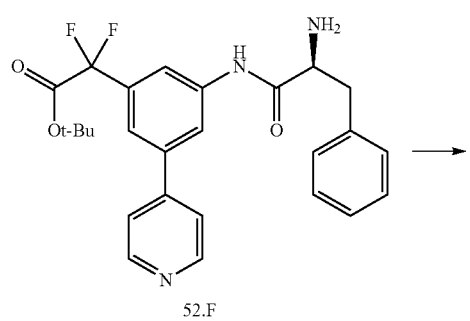

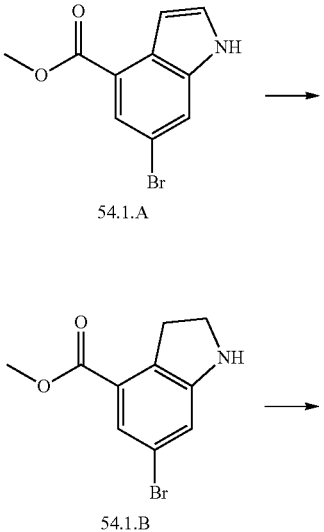

(S)-2,2-difluoro-2-(3-(3-phenyl-2-(thiazol-4-ylm-ethylamino)propanamido)-5-(pyridin-4-yl)phenyl) acetic acid (52)

To a solution of (S)-tert-butyl 2-(3-(2-amino-3-phenylpropanamido)-5-(pyridin-4-yl)phenyl)-2,2-difluoroacetate 52.F (300 mg, 0.64 mmol) in DCM (5 mL) was added thiazole-4-carbaldehyde (73 mg, 0.64 mmol). The mixture was stirred for 1 h at room temperature, then acetic acid (30 μL, 0.64 mmol) and sodium triacetoxyborohydride (408 mg, 1.93 mmol) were added and the mixture stirred at room temperature for an additional 2 hours. The mixture was then concentrated and the residue was stirred in THF (5 mL) and concentrated HCl (5 mL) at 50° C. overnight. The mixture was then concentrated and the crude product purified by reverse phase chromatography (0-100% CH$_3$CN/water+0.5% TFA) to afford (S)-2,2-difluoro-2-(3-(3-phenyl-2-(thiazol-4-ylm-ethylamino)propanamido)-5-(pyridin-4-yl)phenyl)acetic acid 52 as a white solid (140 mg, 43% yield). LCMS ESI (pos.) m/e: 509.0. (M+1). 1H NMR (500 MHz, MeOH-D4) δ ppm 9.14 (d, J=1.96 Hz, 1H), 8.81-8.87 (m, 2H), 8.16 (t, J=1.83 Hz, 1H), 8.12-8.15 (m, 2H), 7.88 (s, 1H), 7.81 (d, J=1.96 Hz, 1H), 7.72 (s, 1H), 7.24-7.37 (m, 5H), 4.46-4.59 (m, 2H), 4.27 (dd, J=9.29, 5.87 Hz, 1H), 3.40-3.51 (m, 1H), 3.27 (dd, J=13.45, 9.29 Hz, 1H).

7.53 Example 53

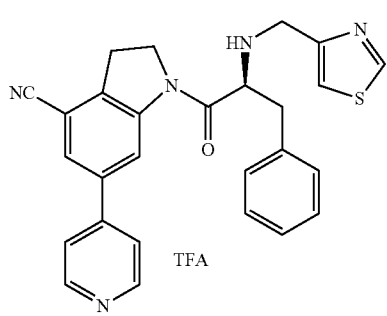 [SMILES: N#Cc1cc(-c2ccncc2)cc2c1CCN2C(=O)[C@H](Cc1ccccc1)NCc1cscn1]

(S)-1-(3-Phenyl-2-(thiazol-4-ylmethylamino)propanoyl)-6-(pyridin-4-yl)indoline-4-carbonitrile (53)

The title compound was prepared by methods analogous to those described in Example 50. LCMS ESI (pos.) m/e: 466.1 (M+1).

7.54 Example 54

7.54.1 Example 54.1

Methyl 6-bromoindoline-4-carboxylate (54.1.B)

To a 2000 ml flask were added of methyl 6-bromo-1H-indole-4-carboxylate 54.1.A (20.0 g, 78.7 mmole), 500 ml of DCM, 100 ml of TFA and triethylsilane (19 ml, 236 mmole). The reaction was stirred at room temperature for 16 hours at which time the reaction was partitioned between 1500 ml of DCM and 500 ml of saturated sodiumbicarbonate and the solvent was removed. The crude solid was resuspended in a 1 to 1 mixture 300 ml of EtAc/hexane and then HCl added (24 ml of 4N in Dioxane, 94.4 mmole), at which time the product crashed out. The solid was collected and dried to give of methyl 6-bromoindoline-4-carboxylate HCl 54.1.B as an off white solid (19.1 g, 85% yield).

Methyl 6-(pyridin-4-yl)indoline-4-carboxylate (54.1.C)

To a 100 ml flask was added methyl 6-bromoindoline-4-carboxylate 54.1.B (2000 mg, 7.8 mmole), 4-pyridylboronic acid (1152 mg, 9.4 mmole, available from Maybridge), tetrakis(triphenylphosphine)palladium (1805 mg, 1.6 mmole, available from Strem), 30 ml of DMF and 10 ml of saturated sodiumcarbonate. The reaction was stirred at 70° C. for 18 hours at which time additional tetrakis(triphenylphosphine) palladium (900 mg, 0.8 mmole) was added. After an additional 12 hours, the reaction mixture was partitioned between 1000 ml EtAc and 300 ml of water. The organic solvent was removed by rotary evaporation to give methyl 6-(pyridin-4-yl)indoline-4-carboxylate 54.1.C (1986 mg, 100% yield) which was used with no further purification.

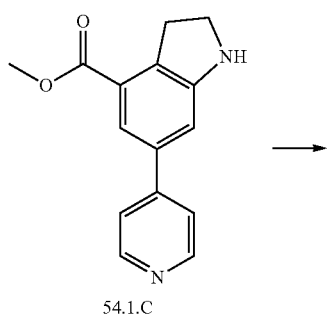

54.1.C

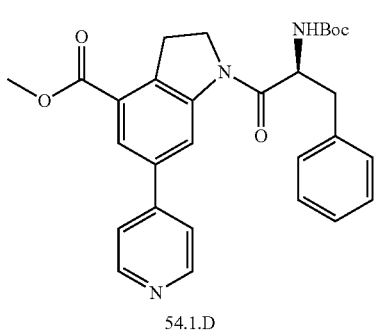

54.1.D

(S)-Methyl 1-(2-(tert-butoxycarbonyl)-3-phenylpropanoyl)-6-(pyridin-4-yl)indoline-4-carboxylate (54.1.D)

To a 500 ml flask was added methyl 6-(pyridin-4-yl)indoline-4-carboxylate 54.1.C (1.98 g, 7.81 mmole), of HBTU (5.92 g, 15.6 mmole), (S)-2-(tert-butoxycarbonyl)-3-phenylpropanoic acid 3.11 g, 11.7 mmole, available from Aldrich) 50 ml of DMF and DIEA (4.08 ml, 23.4 mmole). The reaction was stirred at 60° C. for 6 hours, at which time the crude reaction was partitioned between 1000 ml of EtAc and 500 ml of water. The solvent was removed and the crude purified using a silica gel column (Elutent; 50/50 EtAc/Hex) to give (S)-methyl 1-(2-(tert-butoxycarbonyl)-3-phenylpropanoyl)-6-(pyridin-4-yl)indoline-4-carboxylate 54.1.D as a yellow solid (2.05 g, 52.3% yield).

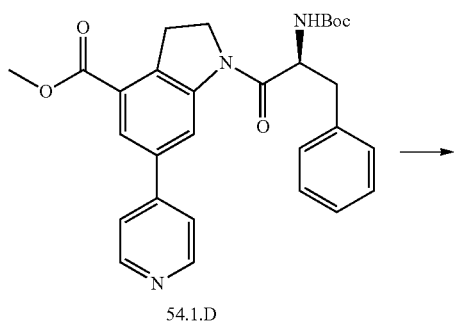

54.1.D

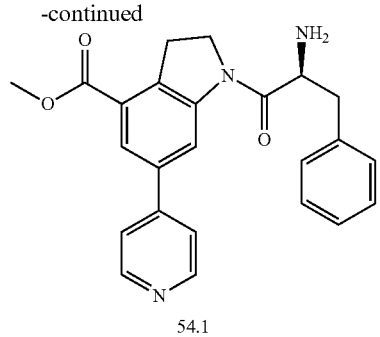

54.1

(S)-Methyl 1-(2-amino-3-phenylpropanoyl)-6-(pyridin-4-yl)indoline-4-carboxylate (54.1)

To a 100 ml flask was added (S)-methyl 1-(2-(tert-butoxycarbonyl)-3-phenylpropanoyl)-6-(pyridin-4-yl)indoline-4-carboxylate 54.1.D (500 mg, 1.0 mmole), 10 ml of DCM and 5 ml of TFA. The reaction was stirred at room temperature for 12 hours at which time the solvent was removed with a stream of nitrogen. The crude was partitioned between 400 ml of DCM and 100 ml of saturated sodium carbonate. The organic layer was washed once more with 100 ml of water, dried over sodium sulfate and the solvent removed by rotary evaporation to give (S)-methyl 1-(2-amino-3-phenylpropanoyl)-6-(pyridin-4-yl)indoline-4-carboxylate 54.1 as a light yellow film (185 mg, 46% yield). LCMS ESI (pos.) m/e: 402.1 (M+1).

7.54.2 Examples 54.2-54.7

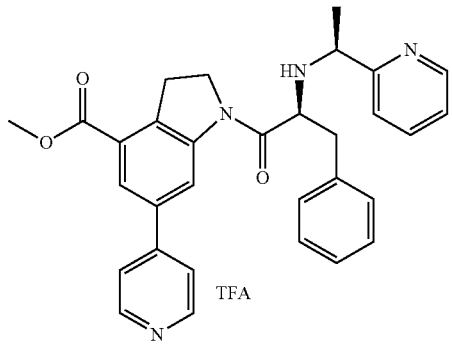

54.1

TFA 54.2

Methyl 1-((S)-3-phenyl-2-((S)-1-(pyridin-2-yl)ethylamino)propanoyl)-6-(pyridin-4-yl)indoline-4-carboxylate TFA salt (54.2)

To a 20 ml vial was added (S)-methyl 1-(2-amino-3-phenylpropanoyl)-6-(pyridin-4-yl)indoline-4-carboxylate 54.1 (185 mg of, 0.46 mmole), 1-(pyridin-2-yl)ethanone (52 ul, 0.46 mmole) 6 ml of MeOH. The reaction was stirred at 60° C. for 1 hour at which time sodium cyanoborohydride (47 mg, 1.4 mmole) was added and stirred an additional 18 hours. The reaction was partitioned between DCM and water, the solvent removed by rotary evaporation and the crude purified by reverse phase preparative HPLC to give methyl 1-((S)-3-phenyl-2-((R)-1-(pyridin-2-yl)ethylamino)propanoyl)-6-(pyridin-4-yl)indoline-4-carboxylate TFA salt (50.5 mg, 22% yield) and methyl 1-((S)-3-phenyl-2-((S)-1-(pyridin-2-yl)ethylamino)propanoyl)-6-(pyridin-4-yl)indoline-4-carboxylate 54.2 (16.5 mg, 7% yield) as off white solids. LCMS ESI (pos.) m/e: 507.2 (M+1): 1H NMR (500 MHz, MeOH) δ ppm 9.05 (d, J=1.47 Hz, 1H), 8.93 (d, J=6.60 Hz, 2H), 8.69 (d, J=4.89 Hz, 1H), 8.38 (d, J=6.85 Hz, 2H), 8.29 (d, J=1.22 Hz, 1H), 7.89 (td, J=7.70, 1.71 Hz, 1H), 7.41-7.56 (m, 2H), 7.20-7.36 (m, 5H), 4.69 (q, J=6.68 Hz, 1H), 4.32 (dd, J=9.78, 5.87 Hz, 1H), 3.85-3.97 (m, 3H), 3.34-3.44 (m, 2H), 3.17-3.30 (m, 2H), 2.81-3.01 (m, 2H), 1.73 (d, J=6.85 Hz, 3H).

TABLE 10

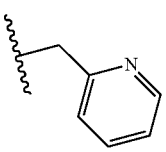 [SMILES: *Cc1ccccn1]

| Compound | R | X |
|---|---|---|
| 54.3 | thiazol-4-ylmethyl | H |
| 54.4 | (1H-pyrazol-3-yl)methyl | H |
| 54.5 | thiazol-4-ylmethyl | F |
| 54.6 | (1H-pyrazol-3-yl)methyl | F |
| 54.7 | pyridin-2-ylmethyl | F |

(S)-Methyl 1-(3-phenyl-2-(thiazol-4-ylmethylamino)propanoyl)-6-(pyridin-4-yl)indoline-4-carboxylate (54.3)

1H NMR (400 MHz, MeOH-D4) δ ppm 1.45-1.58 (m, 2H) 1.71-1.79 (m, 1H) 1.87-2.00 (m, 2H) 2.43 (s, 3H) 2.46-2.55 (m, 1H) 3.01 (d, J=1.57 Hz, 2H) 3.17-3.24 (m, 1H) 5.79 (s, 5H) 6.30 (d, J=1.96 Hz, 1H) 6.63 (d, J=6.65 Hz, 2H) 6.71 (d, J=1.96 Hz, 1H) 7.27-7.34 (m, 2H) 7.42 (d, J=1.96 Hz, 1H) 7.58 (d, J=1.96 Hz, 1H).

(S)-Methyl 1-(2-((1H-pyrazol-3-yl)methylamino)-3-phenylpropanoyl)-6-(pyridin-4-yl)indoline-4-carboxylate (54.4)

1H NMR (500 MHz, MeOH-D4) δ ppm 2.92-3.07 (m, 2H) 3.25 (dd, J=13.08, 10.15 Hz, 1H) 3.38-3.52 (m, 2H) 3.88-4.00 (m, 4H) 4.39 (q, J=13.94 Hz, 2H) 4.58 (dd, J=10.27, 5.14 Hz, 1H) 6.50 (d, J=2.20 Hz, 1H) 7.22-7.34 (m, 5H) 7.73 (d, J=2.20 Hz, 1H) 8.06-8.14 (m, 2H) 8.21 (t, J=1.71 Hz, 1H) 8.77-8.84 (m, 2H) 8.93 (t, J=1.59 Hz, 1H).

(S)-Methyl 1-(3-(4-fluorophenyl)-2-(thiazol-4-ylmethylamino)propanoyl)-6-(pyridin-4-yl)indoline-4-carboxylate (54.5)

1H NMR (500 MHz, MeOH-D4) δ ppm 3.15-3.30 (m, 3H) 3.42-3.63 (m, 2H) 3.97 (s, 3H) 4.08-4.22 (m, 1H) 4.54 (d, J=2.93 Hz, 2H) 4.76 (dd, J=9.54, 5.38 Hz, 1H) 7.06 (t, J=8.68 Hz, 2H) 7.34 (dd, J=8.68, 5.26 Hz, 2H) 7.83 (d, J=1.96 Hz, 1H) 8.25 (dt, J=4.46, 2.29 Hz, 2H) 8.28 (d, J=1.71 Hz, 1H) 8.84-8.90 (m, 2H) 8.96 (d, J=1.71 Hz, 1H) 9.10 (d, J=1.96 Hz, 1H).

(S)-Methyl 1-(2-((1H-pyrazol-3-yl)methylamino)-3-(4-fluorophenyl)propanoyl)-6-(pyridin-4-yl)indoline-4-carboxylate (54.6)

1H NMR (500 MHz, MeOH-D4) δ ppm 3.13-3.21 (m, 2H) 3.26 (dd, J=13.45, 9.78 Hz, 1H) 3.39-3.45 (m, 1H) 3.46-3.55 (m, 1H) 3.96 (s, 3H) 3.99-4.09 (m, 1H) 4.39 (q, J=13.94 Hz, 2H) 4.60 (dd, J=9.66, 5.50 Hz, 1H) 6.49 (d, J=2.45 Hz, 1H)

7.05 (t, J=8.68 Hz, 2H) 7.32 (dd, J=8.56, 5.14 Hz, 2H) 7.73 (d, J=2.45 Hz, 1H) 8.19 (d, J=6.60 Hz, 2H) 8.25 (d, J=1.71 Hz, 1H) 8.85 (d, J=6.60 Hz, 2H) 8.94 (d, J=1.71 Hz, 1H).

(S)-Methyl 1-(3-(4-fluorophenyl)-2-(pyridin-2-ylmethylamino)propanoyl)-6-(pyridin-4-yl)indoline-4-carboxylate (54.7)

1H NMR (500 MHz, MeOH-D4) δ ppm 3.17-3.27 (m, 1H) 3.34-3.39 (m, 2H) 3.41-3.59 (m, 2H) 3.97 (s, 3H) 4.03-4.19 (m, 1H) 4.51 (s, 2H) 4.80 (dd, J=9.54, 5.62 Hz, 1H) 7.08 (t, J=8.68 Hz, 2H) 7.38 (dd, J=8.68, 5.26 Hz, 2H) 7.46 (dd, J=6.85, 4.89 Hz, 1H) 7.50 (d, J=7.83 Hz, 1H) 7.91 (td, J=7.70, 1.71 Hz, 1H) 8.24-8.27 (m, 2H) 8.28 (d, J=1.71 Hz, 1H) 8.66 (d, J=4.89 Hz, 1H) 8.87 (d, J=6.85 Hz, 2H) 8.98 (d, J=1.71 Hz, 1H).

7.54.3 Example 54.8

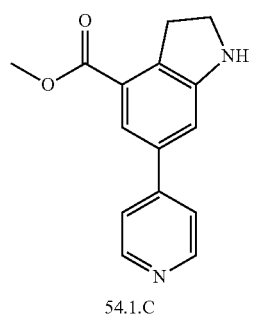

54.1.C

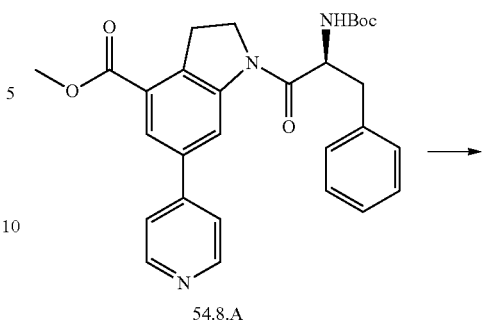

54.8.A

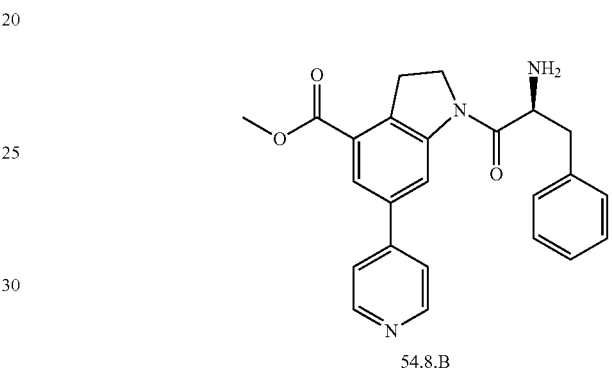

54.8.A

(S)-Methyl 1-(2-(tert-butoxycarbonyl)-3-phenylpropanoyl)-6-(pyridin-4-yl)indoline-4-carboxylate (54.8.A)

To a 500 ml flask was added methyl 6-(pyridin-4-yl)indoline-4-carboxylate 54.1.C (2.0 g, 7.9 mmole), of HBTU (4.5 g, 12.0 mmole), (S)-2-(tert-butoxycarbonyl)-3-phenylpropanoic acid (2.5 g, 9.4 mmole) 50 ml of DMF and DIEA (2.7 ml, 16.0 mmole). The reaction was stirred at 60° C. for 22 hours, at which time the crude reaction was partitioned between 700 ml of EtAc and 200 ml of water. The solvent was removed and the crude purified using a silica gel column (Elutent; 50/50 EtAc/Hex) to give (S)-methyl 1-(2-(tert-butoxycarbonyl)-3-phenylpropanoyl)-6-(pyridin-4-yl)indoline-4-carboxylate 54.8.A as a yellow solid (2.9 g, 74% yield).

54.8.B

(R)-Methyl 1-(2-amino-3-phenylpropanoyl)-6-(pyridin-4-yl)indoline-4-carboxylate (54.8.B)

To a 100 ml flask was added (S)-methyl 1-(2-(tert-butoxycarbonyl)-3-phenylpropanoyl)-6-(pyridin-4-yl)indoline-4-carboxylate 54.8.A (500 mg, 1.0 mmole), 20 ml of DCM and 10 ml of TFA. The reaction was stirred at room temperature for 6 hours at which time the solvent was removed with a stream of nitrogen. The crude was partitioned between 400 ml of DCM and 100 ml of saturated sodium carbonate. The organic layer was washed once more with 100 ml of water, dried over sodium sulfate and the solvent removed by rotary evaporation to give (S)-methyl 1-(2-amino-3-phenylpropanoyl)-6-(pyridin-4-yl)indoline-4-carboxylate 54.8.B as a light orange solid (370 mg, 93% yield).

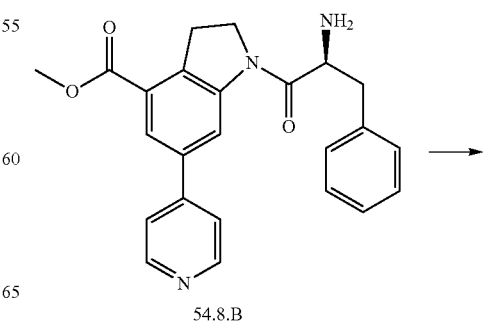

54.8.B

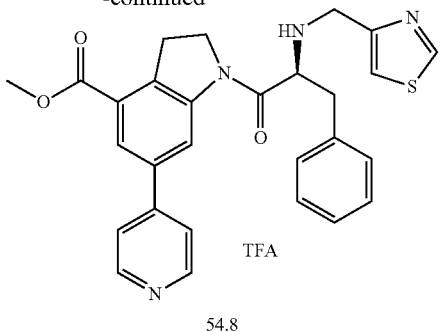

54.8

Methyl 1-((S)-3-phenyl-2-((S)-1-(pyridin-2-yl)ethylamino)propanoyl)-6-(pyridin-4-yl)indoline-4-carboxylate TFA salt (54.8)

To a 20 ml flask were added (S)-methyl 1-(2-amino-3-phenylpropanoyl)-6-(pyridin-4-yl)indoline-4-carboxylate 54.8.B (80 mg, 2.0 mmole, fresh from prep. HPLC), DIEA (52 μl, 3.0 mmole), thiazole-5-carbaldehyde (14 mg, 0.12 mmole), sodium triacetoxyborohydride (53 mg, 2.0 mmole) and 10 ml of DCE. The reaction was stirred at 70° C. for 1 hour, at which time the reaction was partitioned between DCM and water. The solvent was removed by rotary evaporation and the crude purified by reverse phase HPLC to give (S)-methyl 1-(3-phenyl-2-(thiazol-4-ylmethylamino)propanoyl)-6-(pyridin-4-yl)indoline-4-carboxylate TFA salt 54.8 as a light yellow film (35 mg, 35% yield). LCMS ESI (pos.) m/e: 499.2 (M+1): 1H NMR (500 MHz, MeOH) δ ppm 9.11 (d, J=1.96 Hz, 1H), 8.99 (d, J=1.71 Hz, 1H), 8.91 (d, J=6.85 Hz, 2H), 8.33 (d, J=6.85 Hz, 2H), 8.29 (d, J=1.71 Hz, 1H), 7.83 (d, J=1.96 Hz, 1H), 7.32 (s, 5H), 4.75 (dd, J=10.03, 5.14 Hz, 1H), 4.54 (d, J=3.18 Hz, 2H), 4.01-4.07 (m, 1H), 3.96 (s, 3H), 3.40-3.54 (m, 2H), 3.28 (m, 1H), 2.99-3.10 (m, 2H).

7.55 Example 55

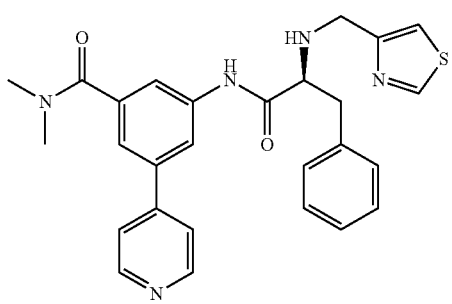 [SMILES: CN(C)C(=O)c1cc(NC(=O)[C@H](Cc2ccccc2)NCc2cscn2)cc(-c2ccncc2)c1]

(S)—N,N-Dimethyl-3-(3-phenyl-2-(thiazol-4-ylmethylamino)propanamido)-5-(pyridin-4-yl)benzamide (55)

The title compound was prepared according to a method analogous to that shown in Example 47. 1H NMR (400 MHz, MeOH-D4) δ ppm 3.05 (s, 3H) 3.16 (s, 3H) 3.26 (dd, J=13.30, 9.39 Hz, 1H) 4.29 (dd, J=9.39, 5.87 Hz, 1H) 4.52 (d, J=8.22 Hz, 2H) 7.25-7.36 (m, 5H) 7.60-7.62 (m, 1H) 7.72 (t, J=1.57 Hz, 1H) 7.81 (d, J=1.96 Hz, 1H) 8.02 (t, J=1.76 Hz, 1H) 8.10 (d, J=6.65 Hz, 2H) 8.83 (d, J=7.04 Hz, 2H) 9.13 (d, J=1.96 Hz, 1H).

7.56 Example 56

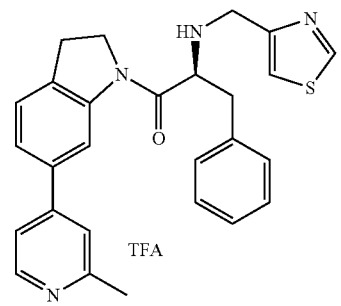 [SMILES: Cc1cc(-c2ccc3c(c2)N(C(=O)[C@H](Cc2ccccc2)NCc2cscn2)CC3)ccn1]

(2S)-1-(6-(2-Methylpyridin-4-yl)indolin-1-yl)-3-phenyl-2-(thiazol-4-ylmethylamino)propan-1-one (56)

The title compound was prepared according to a method analogous to that shown in Example 50. LCMS ESI (pos.) m/e: 455.2.

7.57 Example 57

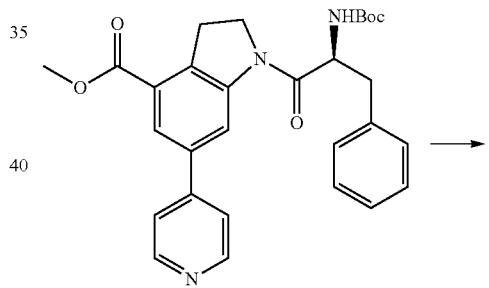

54.8.A

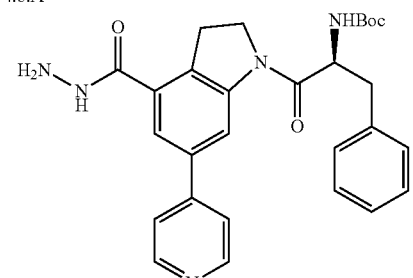

57.1.B

(S)-tert-Butyl 1-(4-hydrazide-6-(pyridin-4-yl)indolin-1-yl)-1-oxo-3-phenylpropan-2-ylcarbamate (57.1.B)

To a 100 ml flask was added (S)-methyl 1-(2-(tert-butoxycarbonyl)-3-phenylpropanoyl)-6-(pyridin-4-yl)indoline-4-carboxylate 54.8.A (1.30 g, 2.6 mmole), 15 ml of Dioxane, and hydrazine (161 μl, 5.2 mmole). The reaction was refluxed for 10 hours at which time the crude reaction was partitioned between EtAc and brine. The organic layer was dried and the solvent removed to give 1.3 g of (S)-tert-butyl 1-(4-hydrazide-6-(pyridin-4-yl)indolin-1-yl)-1-oxo-3-phenylpropan-2-ylcarbamate 57.1.B, which was used in the next step with no further purification.

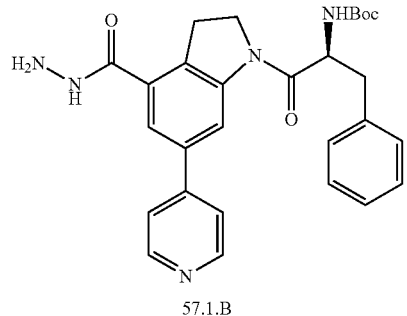

57.1.B

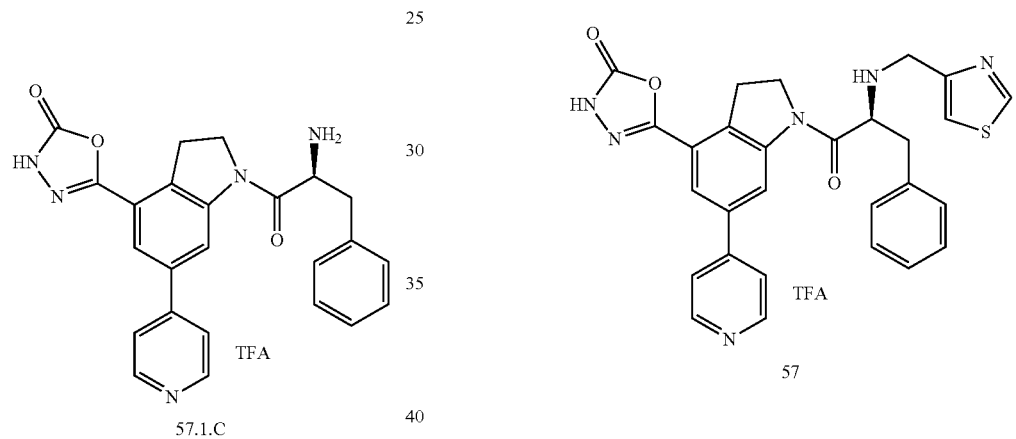

57.1.C

(S)-5-(1-(2-Amino-3-phenylpropanoyl)-6-(pyridin-4-yl)indolin-4-yl)-1,3,4-oxadiazol-2(3H)-one TFA salt (57.1.C)

To a 25 ml flask was added (S)-tert-butyl 1-(4-hydrazide-6-(pyridin-4-yl)indolin-1-yl)-1-oxo-3-phenylpropan-2-ylcarbamate 57.1.B (120 mg, 0.24 mmole), 5 ml of THF, triethylamine (48 mg, 0.48 mmole), cooled to 0° C., and 1,1'-carbonylbisimidazole (54.3 mg, 0.34 mmole) was then added. The reaction was slowly warmed to room temperature over 16 hours at which time the crude reaction was partitioned between EtAc and brine. The organic layer was dried (Na₂SO₄) and the solvent removed to give the intermediate (S)-tert-butyl 1-oxo-1-(4-(5-oxo-4,5-dihydro-1,3,4-oxadiazol-2-yl)-6-(pyridin-4-yl)indolin-1-yl)-3-phenylpropan-2-ylcarbamate, which was used in the next step with no further purification.

To a 100 ml flask containing (S)-tert-butyl 1-oxo-1-(4-(5-oxo-4,5-dihydro-1,3,4-oxadiazol-2-yl)-6-(pyridin-4-yl)indolin-1-yl)-3-phenylpropan-2-ylcarbamate was added 20 ml of DCM and 10 ml of TFA. The reaction was stirred at room temperature for 6 hours at which time the solvent was removed with a stream of nitrogen to give (S)-5-(1-(2-amino-3-phenylpropanoyl)-6-(pyridin-4-yl)indolin-4-yl)-1,3,4- oxadiazol-2(3H)-one TFA salt 57.1.C (97 mg, 100% yield), which was used in the next step with no further purification.

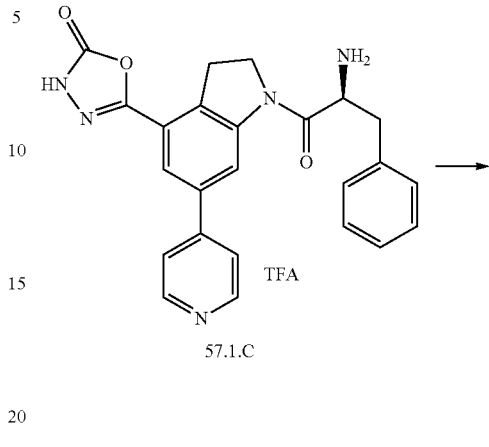

(S)-5-(1-(3-Phenyl-2-(thiazol-4-ylmethylamino)propanoyl)-6-(pyridin-4-yl)indolin-4-yl)-1,3,4-oxadiazol-2(3H)-oneTFA salt (57)

To a 20 ml flask were added (S)-5-(1-(2-amino-3-phenylpropanoyl)-6-(pyridin-4-yl)indolin-4-yl)-1,3,4-oxadiazol-2(3H)-one TFA salt 57.1.C (80 mg, 0.19 mmole), 10 ml of DCE, DIEA (To pH=7), thiazole-4-carbaldehyde (21 mg, 0.19 mmole). The reaction was stirred for 2 hour at which time sodium triacetoxyborohydride (119 mg, 0.56 mmole) was added and stirred for an additional 16 hours. The reaction was partitioned between DCM and water. The solvent was removed by rotary evaporation and the crude purified by reverse phase HPLC to (S)-5-(1-(3-phenyl-2-(thiazol-4-ylmethylamino)propanoyl)-6-(pyridin-4-yl)indolin-4-yl)-1,3,4-oxadiazol-2(3H)-oneTFA salt 57 as a white solid (7.4 mg, 8% yield). 1H NMR (400 MHz, MeOH) δ ppm 9.10 (d, J=1.96 Hz, 1H), 8.81-8.87 (m, 3H), 8.17 (d, J=5.09 Hz, 2H), 8.03 (d, J=1.56 Hz, 1H), 7.82 (d, J=1.96 Hz, 1H), 7.31 (s, 5H), 4.73 (dd, J=10.17, 5.48 Hz, 1H), 4.49-4.58 (m, 2H), 4.07 (td, J=10.17, 6.26 Hz, 1H), 3.47 (dd, J=12.91, 5.09 Hz, 1H), 3.35-3.43 (m, 1H), 3.28 (dd, J=13.11, 9.98 Hz, 1H), 3.07-3.16 (m, 1H), 2.93-3.05 (m, 1H).

7.58 Example 58

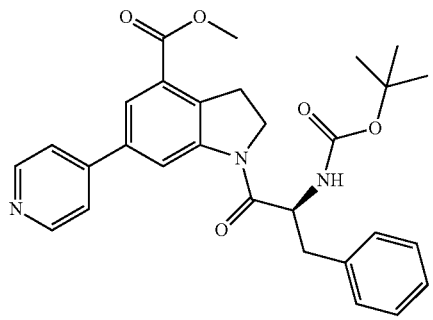

58.A

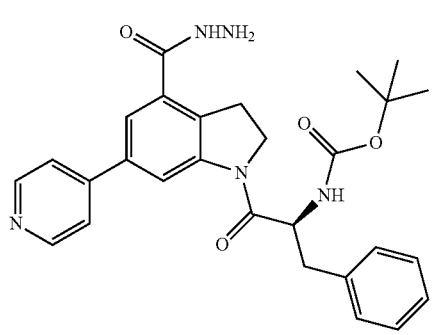

(S)-1-(2-(tert-Butoxycarbonyl)-3-phenylpropanoyl)-6-(pyridin-4-yl)indoline-4-carbohydrazide (58.B)

To (S)-methyl 1-(2-(tert-butoxycarbonyl)-3-phenylpropanoyl)-6-(pyridin-4-yl)indoline-4-carboxylate 58.A (339 mg, 0.68 mmol, prepared as in example 54.1) was added 4 mL EtOH and hydrazine (0.3 mL, 0.96 mmol). The reaction was refluxed overnight and concentrated. Silica gel purification afforded 250 mg (74%) product 58.B.

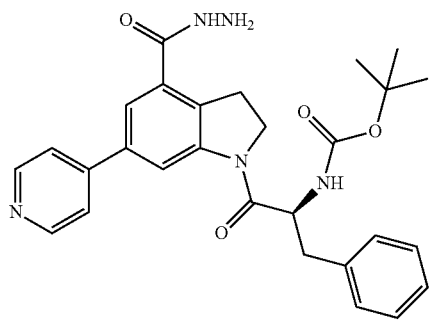

58.B

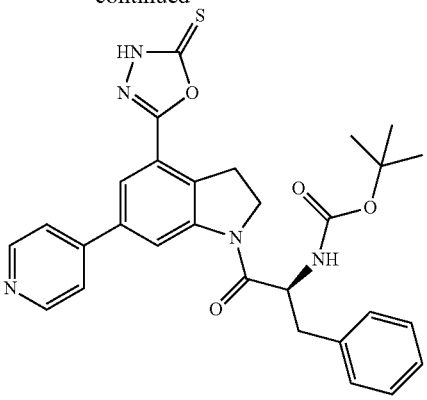

58.C (S)-tert-Butyl 1-oxo-3-phenyl-1-(6-(pyridin-4-yl)-4-(5-thioxo-4,5-dihydro-1,3,4-oxadiazol-2-yl)indolin-1-yl)propan-2-ylcarbamate (58.C)

To a flask with 58.B (142 mg, 0.28 mmol) was added KOH (27 mg) and EtOH. After a few minutes, $CS_2$ (26 μL, 0.43 mmol) was added. The reaction was heated to reflux for 3.5 hours and then concentrated and diluted with water. Saturated $NaHCO_3$ was added to adjust to basic pH. The reaction was extracted with 30% isopropanol in $CHCl_3$. The organic phase was dried and concentrated to afford 58.0 as a white solid 130 mg (84%).

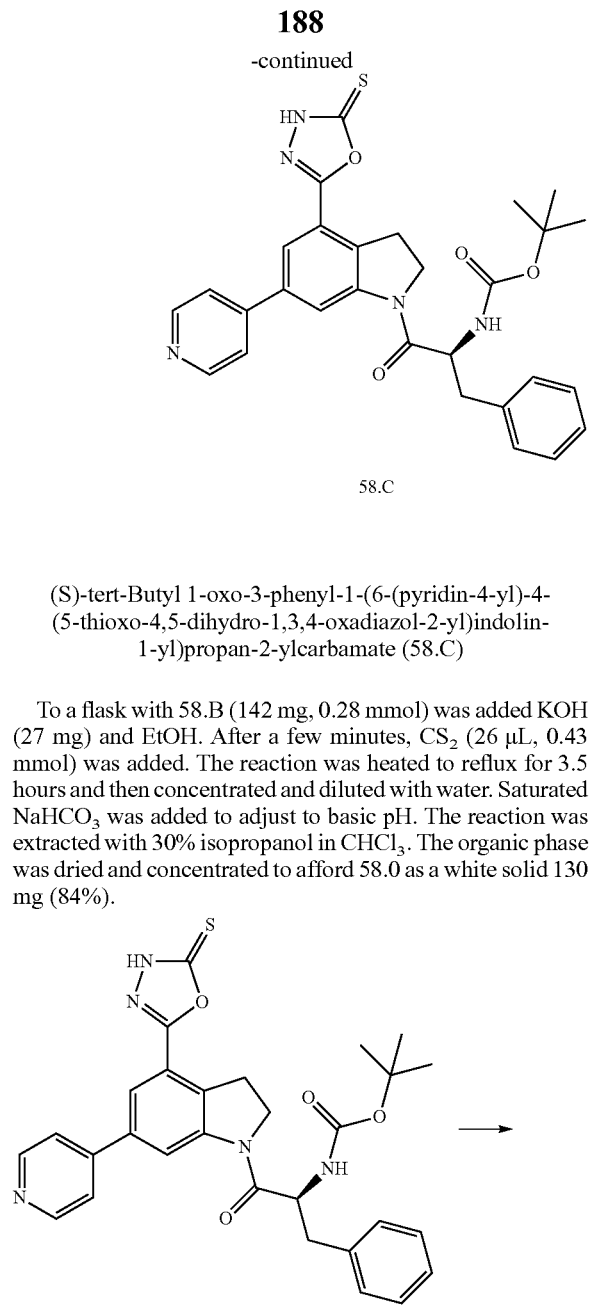

58.C

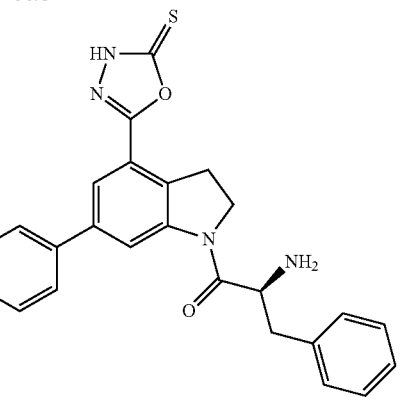

58.D

(S)-2-Amino-3-phenyl-1-(6-(pyridin-4-yl)-4-(5-thioxo-4,5-dihydro-1,3,4-oxadiazol-2-yl)indolin-1-yl)propan-1-one (58.D)

To (S)-tert-butyl 1-oxo-3-phenyl-1-(6-(pyridin-4-yl)-4-(5-thioxo-4,5-dihydro-1,3,4-oxadiazol-2-yl)indolin-1-yl)propan-2-ylcarbamate 58.C (80 mg) was added 3 mL dichloromethane and 1.5 mL trifluoroacetic acid. Stirring was continued for a few hours until deprotection was complete. Reaction was concentrated, basified with NaHCO3 and extracted with 30% isopropanol in chloroform six times to afford 41 mg (63%) 58.D.

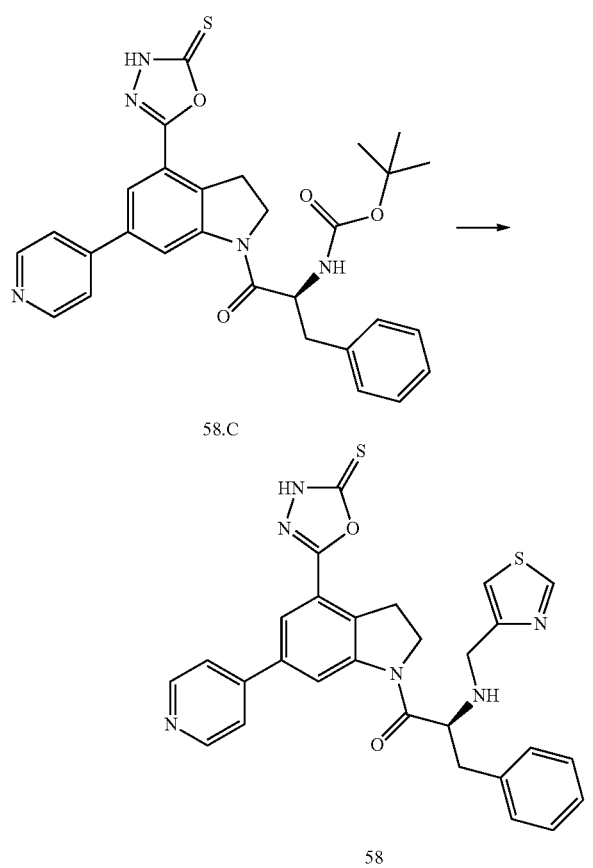

(S)-3-Phenyl-1-(6-(pyridin-4-yl)-4-(5-thioxo-4,5-dihydro-1,3,4-oxadiazol-2-yl)indolin-1-yl)-2-(thiazol-4-ylmethylamino)propan-1-one (58)

To a flask with (S)-2-amino-3-phenyl-1-(6-(pyridin-4-yl)-4-(5-thioxo-4,5-dihydro-1,3,4-oxadiazol-2-yl)indolin-1-yl)propan-1-one 58.0 (41 mg, 0.092 mmol) was added thiazole-4-carbaldehyde (13 mg, 0.111 mmol). Then 1 mL MeOH and 0.8 mL dichloromethane were added followed by sodium cyanoborohydrre (17.5 mg, 0.28 mmol). The reaction was heated to 55 degree for 1 hour. Two drops of water was added and reaction was concentrated and purified on reverse phase HPLC to afford 30 mg (42%) TFA salt of 58. 1H NMR (400 MHz, MeOH) δ ppm 9.08 (d, J=1.96 Hz, 1H) 8.81-8.91 (m, 3H) 8.21 (d, J=6.65 Hz, 2H) 8.11 (d, J=1.56 Hz, 1H) 7.81 (d, J=1.96 Hz, 1H) 7.26-7.34 (m, 5H) 4.73 (dd, J=10.17, 5.09 Hz, 1H) 4.47-4.59 (m, 2H) 4.08 (td, J=10.07, 6.46 Hz, 1H) 3.47 (dd, J=12.91, 5.48 Hz, 1H) 3.35-3.44 (m, 1H) 3.22-3.30 (m, 1H) 3.12 (td, J=9.88, 5.67 Hz, 1H) 2.93-3.07 (m, 1H).

7.59 Example 59

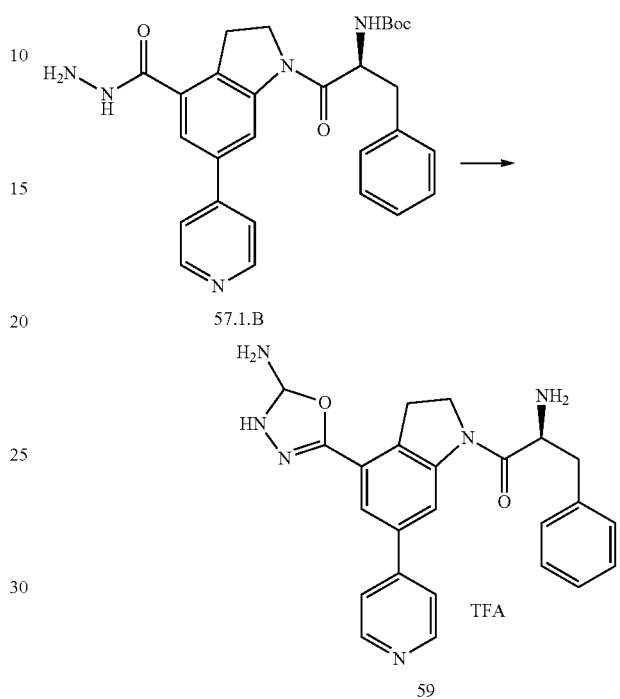

(2S)-2-Amino-1-(4-(5-amino-1,3,4-oxadiazol-2-yl)-6-(pyridin-4-yl)indolin-1-yl)-3-phenylpropan-1-one (59)

To a 25 ml flask was added (S)-tert-butyl 1-(4-hydrazide-6-(pyridin-4-yl)indolin-1-yl)-1-oxo-3-phenylpropan-2-ylcarbamate 57.1.B (120 mg, 0.20 mmole), 10 ml of Dioxane, monosodium hydrogen bicarbonate (42 mg, 0.50 mmole), cooled to 0° C., and bromoformonitrile (23.2 mg, 0.22 mmole) was then added. The reaction was slowly warmed to room temperature over 16 hours at which time the crude reaction was partitioned between EtAc and brine. The organic layer was dried (Na2SO4) and the solvent removed to give the intermediate tert-butyl (S)-1-(4-(5-amino-1,3,4-oxadiazol-2-yl)-6-(pyridin-4-yl)indolin-1-yl)-1-oxo-3-phenylpropan-2-ylcarbamate, which was used in the next step with no further purification.

To a 100 ml flask containing (S)-1-(4-(5-amino-1,3,4-oxadiazol-2-yl)-6-(pyridin-4-yl)indolin-1-yl)-1-oxo-3-phenylpropan-2-ylcarbamate was added 20 ml of DCM and 10 ml of TFA. The reaction was stirred at room temperature for 6 hours at which time the solvent was removed with a stream of nitrogen to give (2S)-2-amino-1-(4-(5-amino-1,3,4-oxadiazol-2-yl)-6-(pyridin-4-yl)indolin-1-yl)-3-phenylpropan-1-one 59 (98 mg, 100% yield) as a white solid LCMS ESI (pos.) m/e: 427.1 (M+1): 1H NMR (400 MHz, DMSO-d6) δ ppm 8.76 (d, J=6.26 Hz, 2H), 8.58 (d, J=1.56 Hz, 1H), 8.36 (br. s., 3H), 7.71-7.81 (m, 3H), 7.22-7.41 (m, 7H), 4.55 (br. s., 1H), 4.31 (td, J=10.37, 6.65 Hz, 1H), 3.68 (td, J=10.27, 6.46 Hz, 1H), 3.33-3.50 (m, 1H), 3.08-3.28 (m, 3H).

7.60 Example 60

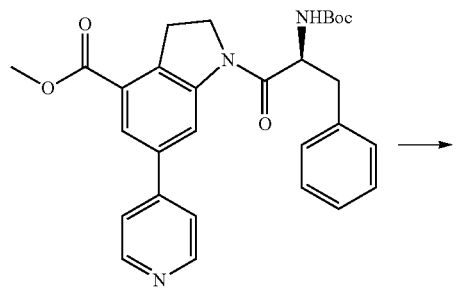
54.8.A

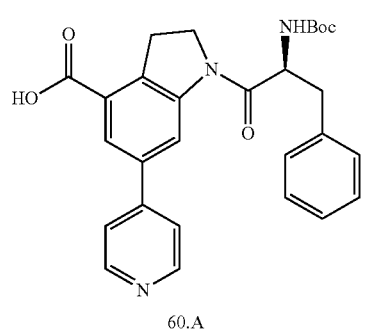
60.A

(S)-1-(2-(tert-Butoxycarbonyl)-3-phenylpropanoyl)-6-(pyridin-4-yl)indoline-4-carboxylic acid (60.A)

To a 20 ml vial were added (S)-methyl 1-(2-(tert-butoxycarbonyl)-3-phenylpropanoyl)-6-(pyridin-4-yl)indoline-4-carboxylate 54.8.A (900 mg, 1.8 mmole), LiOH)(376 mg, 9.0 mmole), 40 ml of THF, and 10 ml of water. The reaction was stirred at 50° C. for 3 hour at which time the solvent was removed by a stream of nitrogen. The crude product was purified using a silica gel column (eluting with 10% MeOH in DCM) to give (S)-1-(2-(tert-butoxycarbonyl)-3-phenylpropanoyl)-6-(pyridin-4-yl)indoline-4-carboxylic acid 60.A as a yellow solid (403 mg, 46% yield).

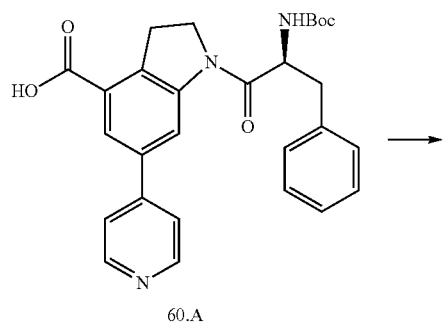
60.A

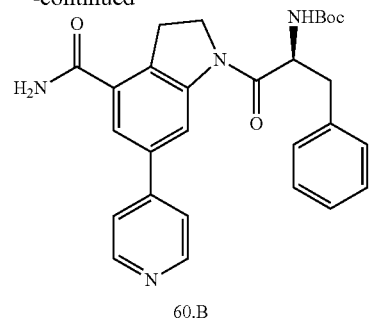
60.B

(S)-tert-Butyl 1-(4-carbamoyl-6-(pyridin-4-yl)indolin-1-yl)-1-oxo-3-phenylpropan-2-ylcarbamate (60.B)

To a 100 ml flask was added (S)-1-(2-(tert-butoxycarbonyl)-3-phenylpropanoyl)-6-(pyridin-4-yl)indoline-4-carboxylic acid 60.A (430 mg, 0.88 mmole), HBTU (669 mg, 1.8 mmole), 20 ml of DMF, DIEA (461 ul, 2.6 mmole) and 2.0 m ammonia solution in 2-propanol (3 ml, 5.3 mmole). The reaction was stirred at 22° C. for 2 hours, at which time the crude reaction was partitioned between 600 ml of EtAc and 200 ml of water. The solvent was removed and the crude purified on a silica gel column (eluting with 10% MeOH in DCM) to give (S)-tert-butyl 1-(4-carbamoyl-6-(pyridin-4-yl)indolin-1-yl)-1-oxo-3-phenylpropan-2-ylcarbamate 60.B as a white solid (228 mg, 53% yield).

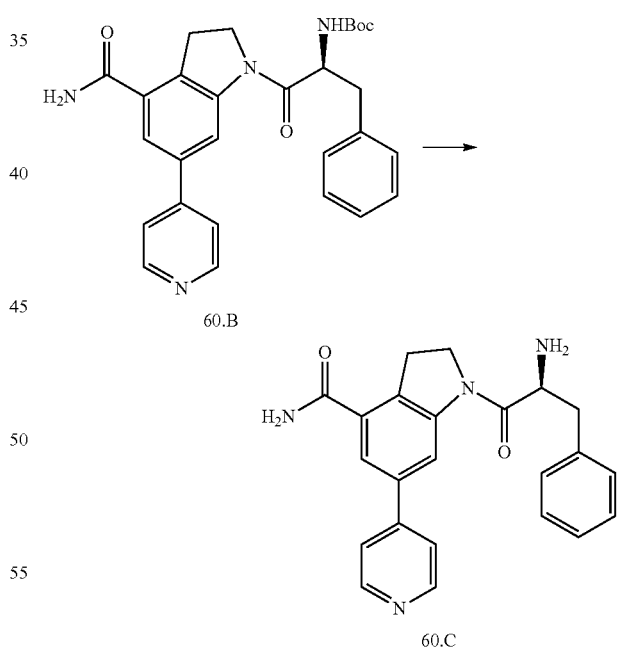
60.B

60.C

(S)-1-(2-Amino-3-phenylpropanoyl)-6-(pyridin-4-yl)indoline-4-carboxamide (60.C)

To a 20 ml vial was added crude (S)-tert-butyl 1-(4-carbamoyl-6-(pyridin-4-yl)indolin-1-yl)-1-oxo-3-phenylpropan-2-ylcarbamate 60.B (75 mg, 0.1 mmole), 20 ml of DCM and 10 ml of TFA. The reaction was stirred at room temperature for 12 hours at which time the crude was partitioned between 600 ml DCM and 100 ml saturated sodium carbonate. The organic layer was extracted once more with 100 ml of water, the organic layer dried with sodium sulfate and the solvent removed to give (S)-1-(2-amino-3-phenylpropanoyl)-6-(pyridin-4-yl)indoline-4-carboxamide 60.0 as an off white solid. (49 mg, 82% yield).

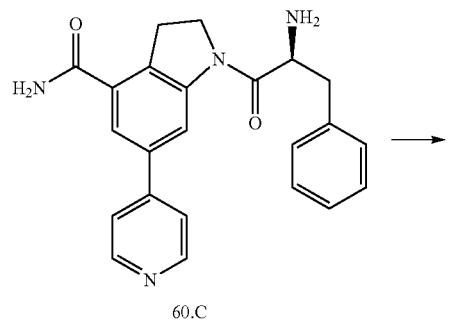

60.C

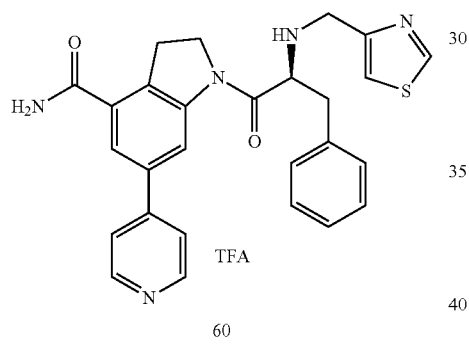

60

(S)-1-(3-Phenyl-2-(thiazol-4-ylmethylamino)propanoyl)-6-(pyridin-4-yl)indoline-4-carboxamide (60)

To a 100 ml flask were added (S)-1-(2-amino-3-phenylpropanoyl)-6-(pyridin-4-yl)indoline-4-carboxamide 61.0 (49 mg, 0.13 mmole), thiazole-5-carbaldehyde (16 mg, 0.14 mmole), sodium triacetoxyborohydride (49 mg, 0.23 mmole), 20 ml of DCE, and DIEA (30 µl, 0.17 mmole). The reaction was stirred at 70° C. for 4 hours at which time an additional 50 mg of sodium triacetoxyborohydride was added and stirred for an additional 72 hours. The reaction mixture was then partitioned between CH$_2$Cl$_2$ and water and the solvent was removed from the organic layer by rotary evaporation. The crude product was purified by reverse phase preparative HPLC to give (S)-1-(3-phenyl-2-(thiazol-4-ylmethylamino)propanoyl)-6-(pyridin-4-yl)indoline-4-carboxamide TFA salt 60 as light yellow solid (6.6 mg, 12% yield). LCMS ESI (pos.) m/e: 484.1 (M+1) 1H NMR (500 MHz, MeOH) 1H NMR (500 MHz, MeOH), 6 ppm 9.10 (d, J=1.96 Hz, 1H), 8.87-8.96 (m, 3H), 8.37 (d, J=6.85 Hz, 2H), 8.03 (d, J=1.71 Hz, 1H), 7.83 (d, J=1.96 Hz, 1H), 7.24-7.37 (m, 5H), 4.74 (dd, J=10.27, 5.14 Hz, 1H), 4.46-4.60 (m, 2H), 3.96-4.07 (m, 1H), 3.48 (dd, J=12.96, 4.89 Hz, 1H), 3.35-3.41 (m, 1H), 3.28 (dd, J=12.96, 10.27 Hz, 1H), 2.97-3.07 (m, 2H).

7.61 Example 61

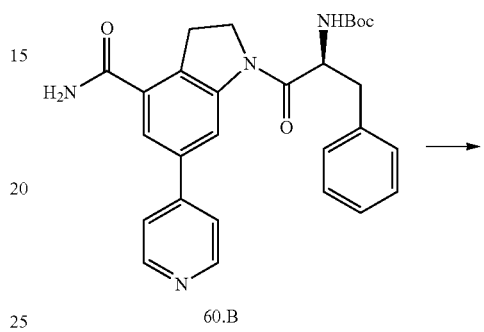

60.B

61.A tert-Butyl (S)-1-(4-(2-methyl-2H-1,2,4-triazol-3-yl)-6-(pyridin-4-yl)indolin-1-yl)-1-oxo-3-phenylpropan-2-ylcarbamate (61.A)

To a 20 ml vial was added (S)-tert-butyl 1-(4-carbamoyl-6-(pyridin-4-yl)indolin-1-yl)-1-oxo-3-phenylpropan-2-ylcarbamate 60.B (100 mg, 0.21 mmole), 2 ml of dimethylformamide dimethyl acetal, and 2 ml of DMF. The reaction was stirred at 80° C. for 1 hour at which time the solvent was removed via a stream of nitrogen and placed under high vacuum. The crude was resuspended in 5 ml of AcOH, anhydrous methyl hydrazine (200 µl, 1.4 mmoles) was slowly added and the reaction was stirred at 80° C. for 13 hours. The solvent was removed with a stream of nitrogen and the crude purified by reverse phase preparative to give tert-butyl (S)-1-(4-(2-methyl-2H-1,2,4-triazol-3-yl)-6-(pyridin-4-yl)indolin-1-yl)-1-oxo-3-phenylpropan-2-ylcarbamate TFA salt 61.A (40 mg of, 37% yield) as a light yellow solid.

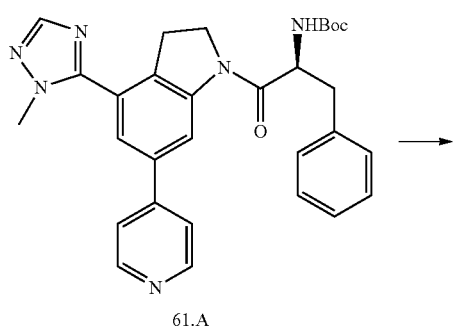

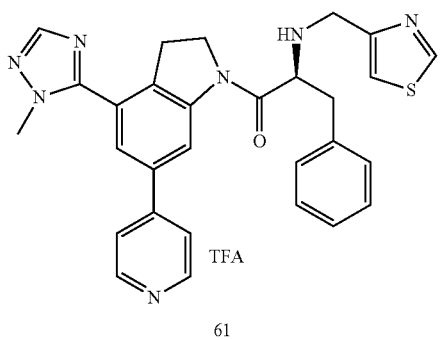

(2S)-1-(4-(2-Methyl-2H-1,2,4-triazol-3-yl)-6-(pyridin-4-yl)indolin-1-yl)-3-phenyl-2-(thiazol-4-ylmethylamino)propan-1-one (68)

The title compound was prepared from 61.A by methods analogous to those described in Example 60. LCMS ESI (pos.) m/e: 522.2. (M+1).

7.62 Example 62

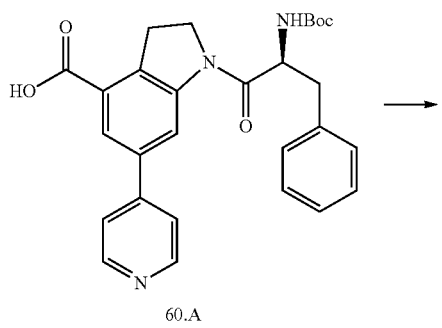

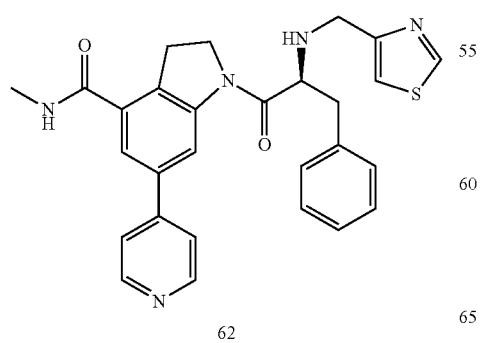

(S)—N-Methyl-1-(3-phenyl-2-(thiazol-4-ylmethylamino)propanoyl)-6-(pyridin-4-yl)indoline-4-carboxamide (62)

The carboxylic acid 60.A was converted to the methyl amide by standard methods known to those with skill in the art and then taken on to compound 62 according to methods analagous to those described in Example 60. LCMS ESI (pos.) m/e: 498.1 (M+1) 1H NMR (500 MHz, MeOH) δ ppm 9.10 (d, J=1.96 Hz, 1H), 8.82-9.00 (m, 3H), 8.27-8.44 (m, 2H), 7.95 (d, J=1.47 Hz, 1H), 7.83 (d, J=1.96 Hz, 1H), 7.24-7.37 (m, 5H), 4.73 (dd, J=10.27, 5.14 Hz, 1H), 4.44-4.59 (m, 2H), 3.94-4.08 (m, 1H), 3.48 (dd, J=13.08, 5.01 Hz, 1H), 3.20-3.32 (m, 2H), 2.96-3.06 (m, 2H), 2.95 (s, 3H).

7.63 Example 63

7.63.1 Example 63.1

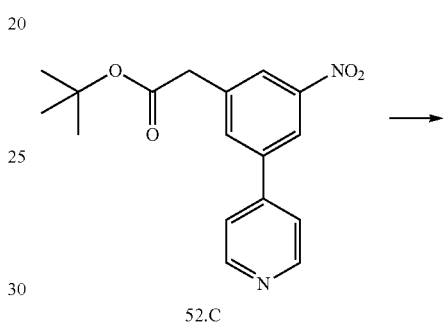

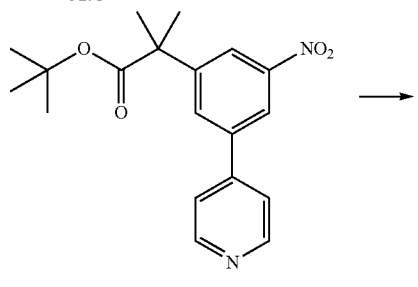

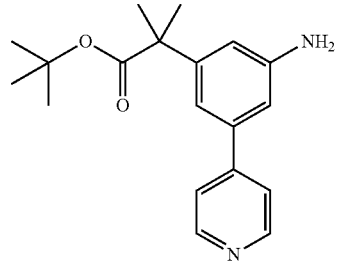

tert-Butyl 2-methyl-2-(3-nitro-5-(pyridin-4-yl)phenyl)propanoate (63.1.A)

To a 250 ml flask was added tert-butyl 2-(3-nitro-5-(pyridin-4-yl)phenyl)acetate 52.0 (2.7 g, 8.5 mmole) 100 ml of DMF, the reaction was cooled to 0° C. and sodium tert-butoxide (1.8 g, 19 mmole) was added slowly. The reaction mixture was warmed to room temperature at which time iodomethane (1.6 ml, 25.5 mmole) was added and the reaction was stirred at room temperature for an additional 2 hours. The crude reaction was partitioned between EtAc (400 ml)

and water (200 ml). The organic layer was extracted two more times with water (100 ml) and the organic solvent was removed by rotary evaporation. The crude reaction was purified by normal phase chromatography, eluting with 2% MeOH in DCM, to provide tert-butyl 2-methyl-2-(3-nitro-5-(pyridin-4-yl)phenyl)propanoate 63.1.A as a dark red oil (1.9 g, 65.3% yield).

tert-Butyl 2-(3-amino-5-(pyridin-4-yl)phenyl)-2-methylpropanoate (63.1.B)

To a 250 ml was added tert-butyl 2-methyl-2-(3-nitro-5-(pyridin-4-yl)phenyl)propanoate 63.1.A (1.9 g, 5.5 mmole) 4 g 10% of Pd/C and 50 ml of MeOH. The air from the reaction vessel was removed and purged with hydrogen gas via a balloon. This was repeated three times to ensure all air was removed from the reaction vessel. The reaction was stirred at room temperature under an atmosphere of hydrogen for 6 hours. The reaction mixture was filtered over a pad of celite (elute with MeOH) and the solvent removed to give tert-butyl 2-(3-amino-5-(pyridin-4-yl)phenyl)-2-methylpropanoate 63.1.B as a light brown solid (1.15 g, 66% yield).

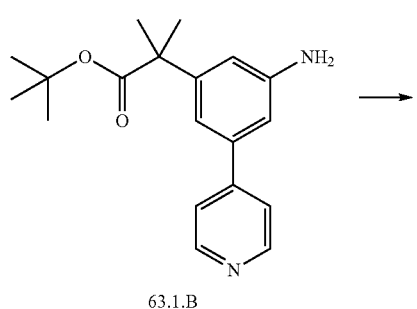

63.1.B

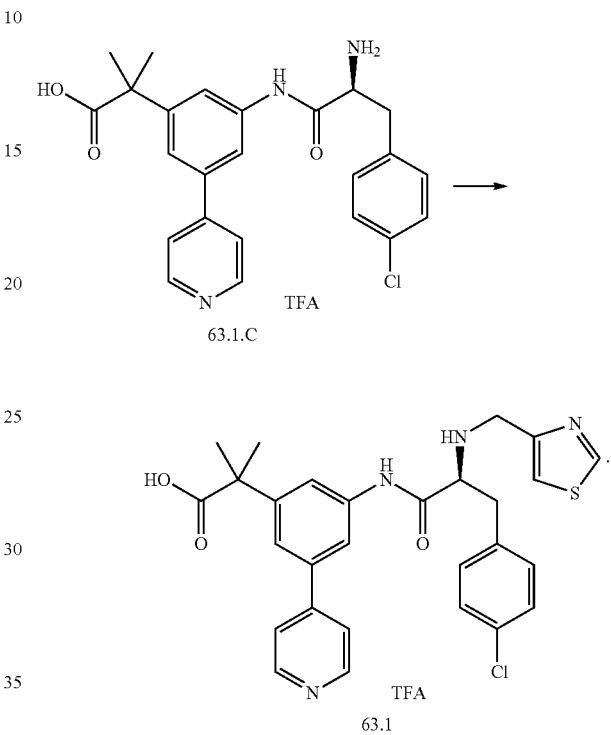

(S)-2-(3-(2-amino-3-(4-chlorophenyl)propanamido)-5-(pyridin-4-yl)phenyl)-2-methylpropanoic acid (63.1.C)

To a 25 ml vial was added tert-butyl 2-(3-amino-5-(pyridin-4-yl)phenyl)-2-methylpropanoate (200 mg, 0.64 mmole), HBTU (364 mg, 0.96 mmole), (S)-2-(tert-butoxycarbonyl)-3-(4-chlorophenyl)propanoic acid (230 mg, 0.77 mmole), 5 ml of DMF and DIEA (335 µl, 1.9 mmole). The reaction was stirred at 50° C. for 6 hours and then partitioned between 200 ml of EtAc and 100 ml of water. The organic layer was extracted two more times with water and the organic solvent was removed by rotary evaporation. The Intermediate was then resuspended in 20 ml of DCM, 20 ml of TFA was added and the reaction was stirred at room temperature for 4 hours. The solvent was removed to give (S)-2-(3-(2-amino-3-(4-chlorophenyl)propanamido)-5-(pyridin-4-yl)phenyl)-2-methylpropanoic acid TFA salt 63.1.C as a light yellow solid (600 mg, 120% yield).

(S)-2-(3-(3-(4-Chlorophenyl)-2-(thiazol-4-ylmethylamino)propanamido)-5-(pyridin-4-yl)phenyl)-2-methylpropanoic acid (63.1)

To a 100 ml flask were added (S)-2-(3-(2-amino-3-(4-chlorophenyl)propanamido)-5-(pyridin-4-yl)phenyl)-2-methylpropanoic acid TFA salt 63.1.C (200 mg, 0.36 mmole), thiazole-4-carbaldehyde (33 mg, 0.21 mmole), sodium triacetoxyborohydride (154 mg, 0.73 mmole), 20 ml of DCE, 1 ml MeOH and DIEA (95 µl, 0.54 mmole). The reaction was stirred at 70° C. for 2 hours at which time sodium cyanotrihydroborate (46 mg, 0.73 mmole) was added and stirred at 70° C. for an additional 1 hour. The reaction mixture was then partitioned between $CH_2Cl_2$ and water and the solvent was removed from the organic layer by rotary evaporation. The crude product was purified by reverse phase preparative HPLC to give (S)-2-(3-(3-(4-chlorophenyl)-2-(thiazol-4-ylmethylamino)propanamido)-5-(pyridin-4-yl)phenyl)-2-methylpropanoic acid TFA salt 63.1 as an off white solid (72.5 mg, 60% yield). LCMS ESI (pos.) m/e: 535.2 (M+1): 1H NMR (500 MHz, MeOH) δ ppm 9.14 (d, J=1.96 Hz, 1H), 8.79-8.91 (m, 2H), 8.14-8.25 (m, 2H), 7.99 (t, J=1.71 Hz, 1H), 7.82 (d, J=1.96 Hz, 1H), 7.69 (t, J=1.59 Hz, 1H), 7.52 (t, J=1.71 Hz, 1H), 7.35 (m, 2H), 7.27 (m, 2H), 4.43-4.63 (m, 2H), 4.28 (dd, J=9.29, 5.87 Hz, 1H), 3.45 (dd, J=13.45, 5.62 Hz, 1H), 3.24 (dd, J=13.33, 9.41 Hz, 1H), 1.65 (d, J=6.85 Hz, 6H).

7.63.2 Example 63.2

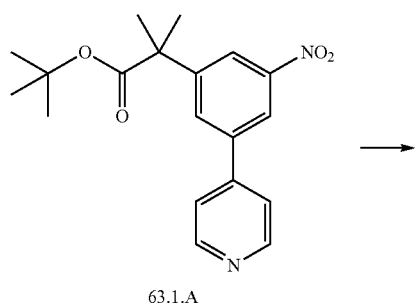

63.1.A

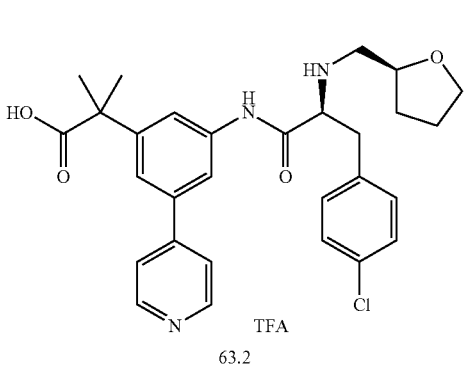

63.2

2-Methyl-2-(3-(S)-3-phenyl-2-(((R)-tetrahydrofuran-2-yl)methylamino)propanamido)-5-(pyridin-4-yl)phenyl)propanoic acid (63.2)

The title compound was prepared from 63.1.A by the methods analogous to those described in example 14.1. LCMS ESI (pos.) m/e: 524.2. (M+1).

7.64 Example 64

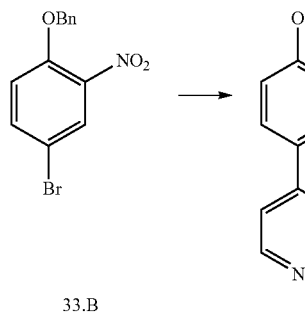
33.B

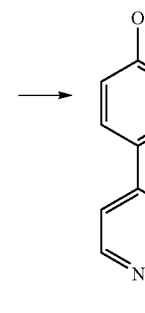
64.A

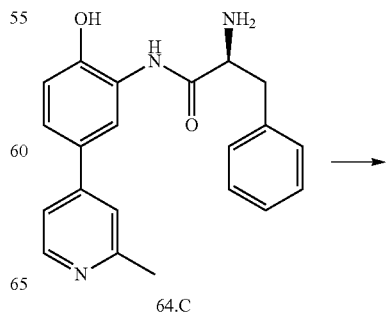
64.C

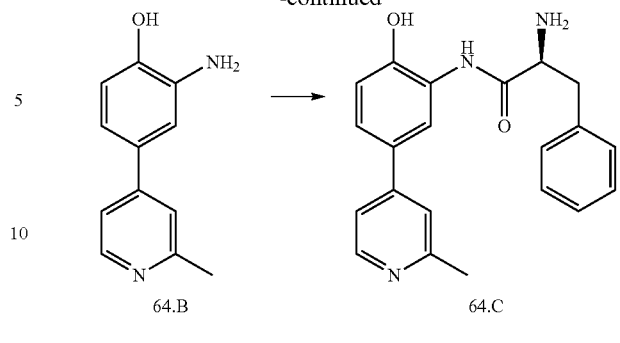

64.B      64.C

4-(4-(Benzyloxy)-3-nitrophenyl)-2-methylpyridine (64.A)

Bromide 13.B (9.00 g, 29.2 mmol), 2-methylpyridine-4-yl-boronic acid (4.40 g, 32.1 mmol), $K_3PO_4$ (15.5 g, 73.0 mmol), $Pd_2(dba)_3$ (669 mg, 0.73 mmol), and S-Phos (600 mg, 1.46 mmol), were heated in n-butanol (0.2 L) at 100° C. overnight. The reaction mixture was partitioned with $H_2O$/EtOAc. The organic layer was washed with $H_2O$ (2×), dried with sodium sulfate, filtered, and concentrated. The crude product was chromatographed on silica gel (330 g, 0-100% EtOAc:DCM). The desired fractions were concentrated to yield 64.A as a yellow solid (4.70 g, 50%). LC-MS (+esi, $M+H^+$=321.1).

2-Amino-4-(2-methylpyridin-4-yl)phenol (64.B)

Nitroarene 64.A (2.65 g, 8 mmol) was hydrogenated (10 psi) with Pd/C (500 mg, 10% Pd/C, 50% water) in EtOAc. The reaction mixture was filtered and concentrated to yield crude 64.B (1.85 g).

(2S)-2-Amino-N-(2-hydroxy-5-(2-methylpyridin-4-yl)phenyl)-3-phenylpropanamide (64.C)

64.0 was prepared from 64.B analogous to the preparation of 13.F. LC-MS (+esi, $M+H^+$=348.1).

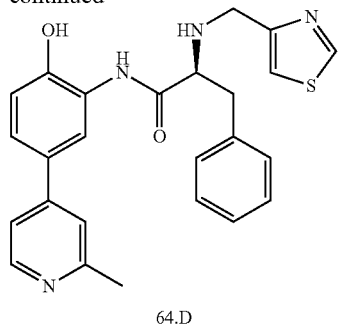

(2S)—N-(2-hydroxy-5-(2-methylpyridin-4-yl)phenyl)-3-phenyl-2-(thiazol-4-ylmethylamino)propanamide (64.D)

Amine 64.0 (310 mg, 0.9 mmol), thiazole-4-carboxaldehyde (101 mg, 0.9 mmol), AcOH (51 μL, 0.9 mmol), and NaBH(OAc)$_3$ were stirred in DCM (10 ml) overnight. The reaction mixture was diluted with DCM and neutralized with NaHCO$_3$ (sat). The organic layer was dried with sodium sulfate, filtered, and concentrated to yield 64.D (330 mg, 83%). LC-MS (+esi, M+H$^+$=445.1). 1H NMR (400 MHz, DMSO-d6) δ ppm 10.43 (br. s., 1H) 9.88 (s, 1H) 8.99 (d, J=1.96 Hz, 1H) 8.53 (d, J=2.45 Hz, 1H) 8.44 (d, J=5.38 Hz, 1H) 7.41 (s, 1H) 7.33-7.40 (m, 3H) 7.18-7.31 (m, 5H) 6.97 (d, J=8.31 Hz, 1H) 3.74-3.89 (m, 2H) 3.53-3.62 (m, 1H) 3.10 (dd, J=13.69, 4.89 Hz, 1H) 2.87 (dd, J=13.69, 8.31 Hz, 1H) 2.68 (d, J=6.36 Hz, 1H) 2.51 (s, 3H).

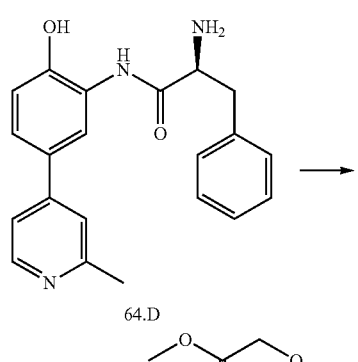

Methyl 2-(4-(2-methylpyridin-4-yl)-2-((S)-3-phenyl-2-(thiazol-4-ylmethylamino)propanamido)phenoxy)acetate (64)

Phenol 64.D (248 mg, 0.56 mmol), methyl 2-bromoacetate (85 mg, 0.56 mmol), and Cs$_2$CO$_3$ (182 mg, 0.56 mmol) were mixed in DMF (1 ml) and stirred at room temperature for 1 h. The reaction mixture was partitioned with EtOAc/H$_2$O and the aqueous layer was exctracted with EtOAc (3×). The organic layers were combined, dried with sodium sulfate, filtered, and concentrated. The crude product was first purified on a silica gel column (12 g, 0-10% MeOH:DCM) and then by prepHPLC(C18, ACN:H2O:0.1% TFA, gradient). The desired fractions were combined, partially concentrated on a rotavap, neutralized with NaHCO$_3$ (sat), and extracted with DCM (2×). The organic layers were combined, dried with sodium sulfate, filtered, and concentrated to yield 64 (190 mg, 66%). LC-MS (+esi, M+H$^+$=517.2). 1H NMR (400 MHz, MeOH) δ ppm 8.86 (d, J=1.96 Hz, 1H) 8.59 (d, J=2.35 Hz, 1H) 8.42 (d, J=5.09 Hz, 1H) 7.56 (s, 1H) 7.46-7.51 (m, 2H) 7.34 (d, J=1.96 Hz, 1H) 7.19-7.30 (m, 5H) 7.09 (d, J=8.61 Hz, 1H) 4.84 (s, 2H) 3.85-4.02 (m, 2H) 3.78 (s, 3H) 3.59 (dd, J=8.41, 4.89 Hz, 1H) 3.19 (dd, J=13.69, 5.09 Hz, 1H) 2.92 (dd, J=13.69, 8.61 Hz, 1H) 2.60 (s, 3H).

7.65 Example 65

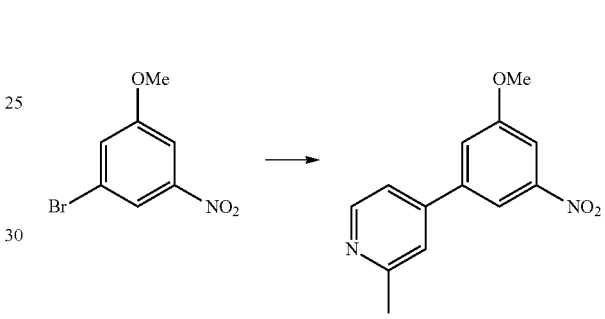

3-(2-Methylpyridin-4-yl)-5-nitrobenzenamine (65.B)

To a rt solution of 65.A (available from GLSynthesis Inc.) (5.00 g, 22.0 mmol) and 2-methylpyridin-4-ylboronic acid (available from CombiPhos Catalysts, Inc.) (2.71 g, 21.4 mmol) in n-BuOH (38 mL) was added potassium phosphate (available from Strem Chemicals, Inc.) (7.00 g, 33.0 mmol) and tris(dibenzylideneacetone)dipalladium (o) (available from Strem Chemicals, Inc.) (1.01 g, 1.2 mmol). After being purged with N$_2$ for 15 mins, the mixture was stirred at 110° C. under N$_2$ atmosphere for 12 hrs and resulting solution was concentrated. The residue was re-dissolved in EtOAc (60 mL), washed with water and brine, and dried over MgSO$_4$. After removal of organic solvent under reduced pressure, purification of the residue by flash chromatography on silica gel using 0-9% MeOH/CH$_2$Cl$_2$ for elution gave the title product 65.B as yellow solid (4.80 g, 91%).

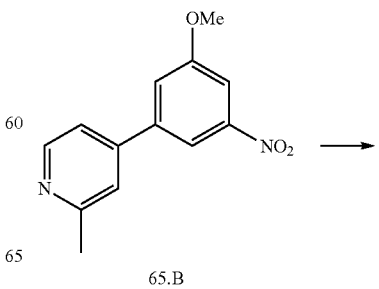

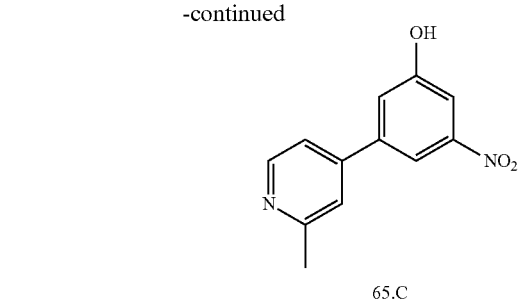

65.C

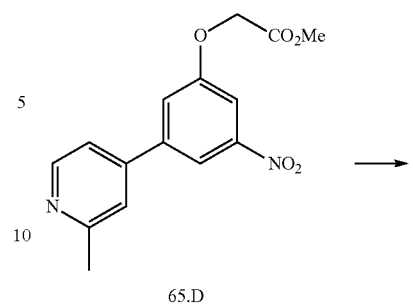

65.D

3-(2-Methylpyridin-4-yl)-5-nitrophenol (65.C)

To 0° C. flask charged with 65.B (2.85 g, 11.7 mmol) was added a solution of BBr$_3$/CH$_2$Cl$_2$ (1.0 M, 25 mL). The solution was allowed to warm to rt and stirred for 45 mins. The resulting mixture was treated with MeOH (7 mL), neutralized with solid NaHCO$_3$ to PH=7 and concentrated under reduced pressure. Purification of the residue by flash chromatography on silica gel using 0-10% of MeOH/CH$_2$Cl$_2$ for elution gave the title product 65.C as solid (1.83 g, 68%).

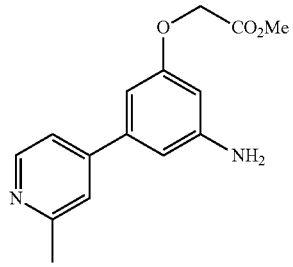

65.E

Methyl 2-(3-amino-5-(2-methylpyridin-4-yl)phenoxy)acetate (65.E)

To a rt solution of 65.D (476 mg, 1.58 mmol) in EtOAc (9 mL) was added SnCl$_2$-2H$_2$O (1.88 g, 7.93 mmol). The reaction solution was refluxed for 2.0 hr, cooled to rt, and treated with concentrated NH$_4$OH (2.5 mL). To the resulting mixture was added MeOH (10 mL) followed by celite. Solid was filtered off and washed with MeOH, the liquid layers was collected and concentrated. Purification of the residue by flash chromatography on silica gel using 0-20% MeOH/CH$_2$Cl$_2$ for elution gave title product 65.E as colorless syrup (282 mg, 65%).

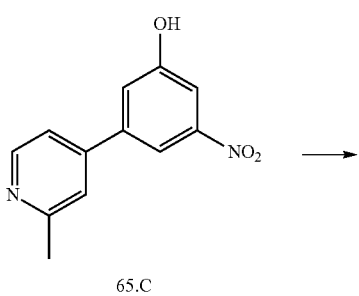

65.C

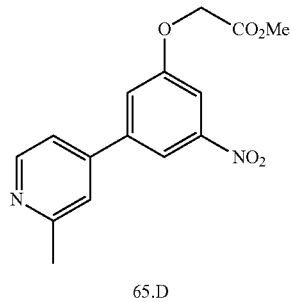

65.D

Methyl 2-(3-(2-methylpyridin-4-yl)-5-nitrophenoxy)acetate (65.D)

To a rt solution of 65.0 (715 mg, 3.11 mmol), and cesium carbonate (available from Alfa Aesar, A Johnson Matthey Company) (2.02 g, 6.21 mmol) in DMF (8 mL) was added methyl 2-bromoacetate (available from Aldrich) (618 mg, 4.04 mmol). After stirring at 110° C. for 12 hr, the reaction mixture was treated with saturated aqueous NaHCO$_3$, diluted with water (15 mL) and extracted with EtOAc (3×15 mL). The combined organic layers were washed with brine, dried over MgSO$_4$. After removal of organic solvent under reduced pressure, purification of the residue by flash chromatography on silica gel using 0-80% EtOAc/Hexanes for elution gave the title compound 65.D as yellow solid (630 mg, 67%).

65.E

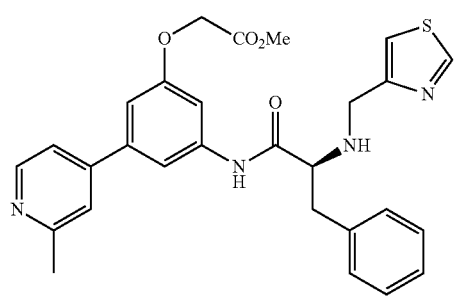

65

Methyl 2-(3-(2-methylpyridin-4-yl)-5-((S)-3-phenyl-2-(thiazol-4-ylmethylamino)propanamido)phenoxy)acetate (65)

The title compound was prepared starting from 65.E according the procedure described above for conversion of 4.A to 4. The final crude product was purified by flash chromatography on silica gel using 0-5% MeOH/CH$_2$Cl$_2$ for elution to provided 65 as colorless solid. MS ESI (positive) m/e: 517.2 (M+H).

7.66 Example 66

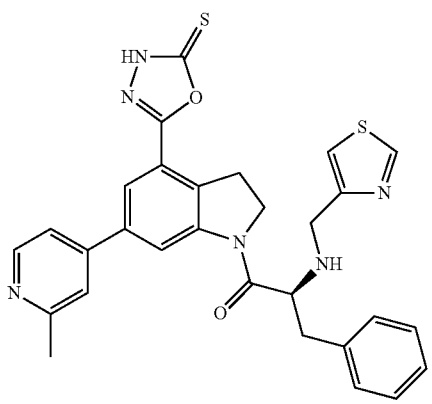 [SMILES: Cc1cc(-c2cc(-c3n[nH]c(=S)o3)c3c(c2)N(C(=O)[C@H](Cc2ccccc2)NCc2cscn2)CC3)ccn1]

(2S)-1-(6-(2-Methylpyridin-4-yl)-4-(5-thioxo-4,5-dihydro-1,3,4-oxadiazol-2-yl)indolin-1-yl)-3-phenyl-2-(thiazol-4-ylmethylamino)propan-1-one (66)

The title compound was prepared by methods analagous to those described in example 58. 1H NMR (400 MHz, MeOH) δ ppm 9.08 (d, J=1.96 Hz, 1H) 8.89 (d, J=1.76 Hz, 1H) 8.75 (d, J=6.26 Hz, 1H) 8.25 (d, J=1.56 Hz, 1H) 8.07-8.20 (m, 2H) 7.82 (d, J=1.76 Hz, 1H) 7.18-7.37 (m, 5H) 4.74 (dd, J=9.98, 5.09 Hz, 1H) 4.46-4.60 (m, 2H) 4.10 (td, J=10.07, 6.46 Hz, 1H) 3.45-3.52 (m, 1H) 3.36-3.45 (m, 1H) 3.22-3.30 (m, 1H) 3.07-3.16 (m, 1H) 2.96-3.06 (m, 1H) 2.87 (s, 3H).

7.67 Example 67

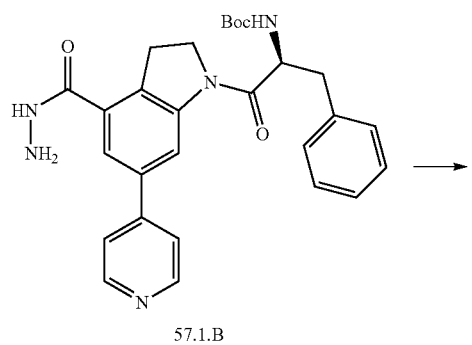

57.1.B

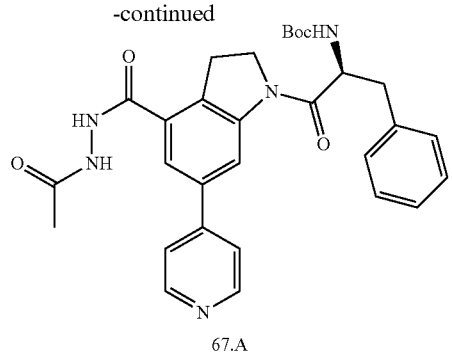

67.A

(S)-tert-Butyl 1-(4-N-acetylhydrazide-6-(pyridin-4-yl)indolin-1-yl)-1-oxo-3-phenylpropan-2-ylcarbamate (67.A)

To a solution of (5)-tert-butyl 1-(4-hydrazide-6-(pyridin-4-yl)indolin-1-yl)-1-oxo-3-phenylpropan-2-ylcarbamate 57.1.B (250 mg, 0.50 mmol) and triethylamine (174 μL, 1.25 mmol) in THF (2 mL) was added acetyl chloride (53 μL, 0.75 mmol). The mixture was stirred at room temperature overnight and concentrated. The residue was neutralized with saturated NaHCO$_3$ aqueous solution, extracted with DCM. The organic layer is concentrated to afford (5)-tert-butyl 1-(4-N-acetylhydrazide-6-(pyridin-4-yl)indolin-1-yl)-1-oxo-3-phenylpropan-2-ylcarbamate 67.A which is used in the next step without any further purification.

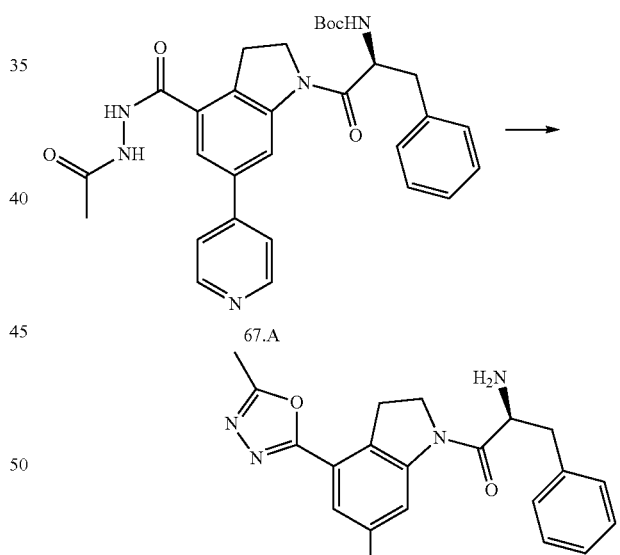

(2S)-2-amino-1-(4-(5-methyl-1,3,4-oxadiazol-2-yl)-6-(pyridin-4-yl)indolin-1-yl)-3-phenylpropan-1-one (67.B)

A solution of (S)-tert-butyl 1-(4-N-acetylhydrazide-6-(pyridin-4-yl)indolin-1-yl)-1-oxo-3-phenylpropan-2-ylcarbamate 67.A (20 mg, 0.037 mmol) in phosphorous oxychloride (1 mL) was heated to 50° C. for 1 hour. The reaction was quenched with crushed ice, neutralized with saturated aqueous NaHCO₃, and extracted with DCM. The organic layer was concentrated and the residue purified on reverse phase preparative HPLC to afford (2S)-2-amino-1-(4-(5-methyl-1,3,4-oxadiazol-2-yl)-6-(pyridin-4-yl)indolin-1-yl)-3-phenyl-propan-1-one 67.B.

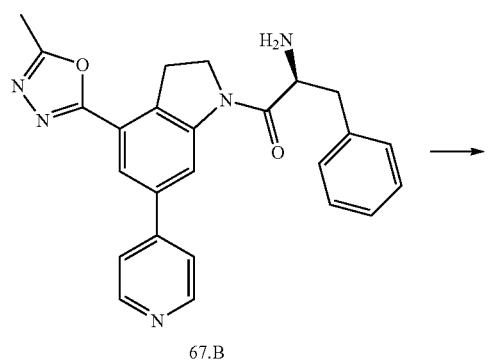

67.B

(2S)-1-(4-(5-Methyl-1,3,4-oxadiazol-2-yl)-6-(pyridin-4-yl)indolin-1-yl)-3-phenyl-2-(thiazol-4-ylmethylamino)propan-1-one (67)

The title compound was prepared from 67.B by methods analagous to those described in example 54.2. 1H NMR (500 MHz, MeOH-D4) δ ppm 2.67 (s, 3H) 3.04-3.16 (m, 2H) 3.25-3.31 (m, 1H) 3.45-3.52 (m, 2H) 4.04-4.15 (m, 1H) 4.55 (d, J=2.69 Hz, 2H) 4.75 (dd, J=10.15, 5.26 Hz, 1H) 7.27-7.38 (m, 5H) 7.83 (d, J=1.96 Hz, 1H) 8.09 (d, J=6.60 Hz, 2H) 8.19 (d, J=1.71 Hz, 1H) 8.81 (d, J=6.36 Hz, 2H) 8.89 (d, J=1.71 Hz, 1H) 9.11 (d, J=1.96 Hz, 1H).

7.68 Example 68

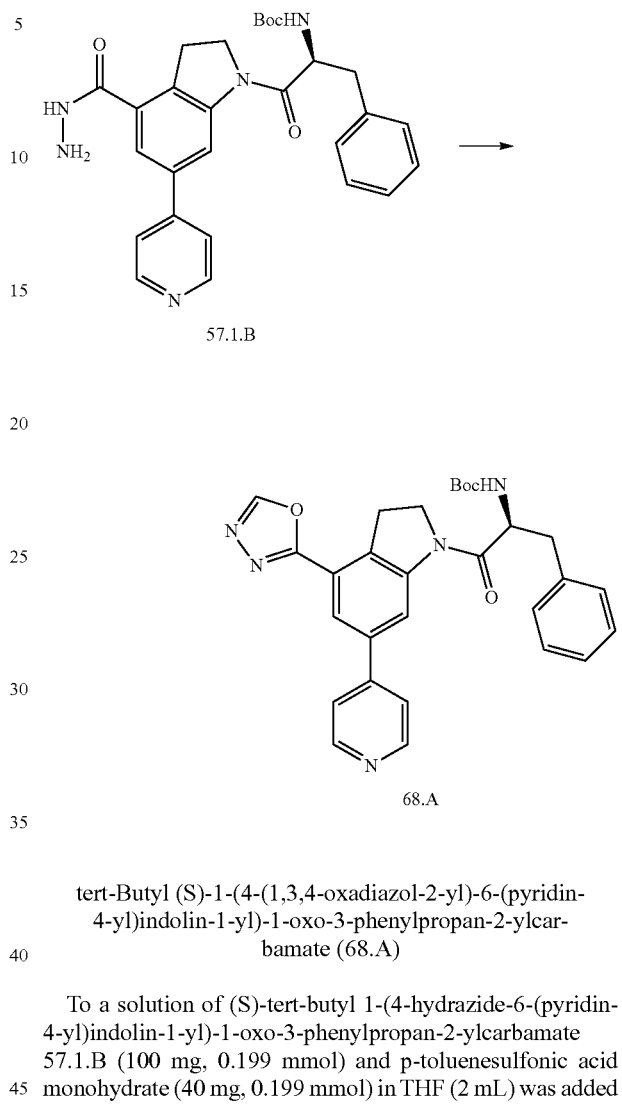

tert-Butyl (S)-1-(4-(1,3,4-oxadiazol-2-yl)-6-(pyridin-4-yl)indolin-1-yl)-1-oxo-3-phenylpropan-2-ylcarbamate (68.A)

To a solution of (S)-tert-butyl 1-(4-hydrazide-6-(pyridin-4-yl)indolin-1-yl)-1-oxo-3-phenylpropan-2-ylcarbamate 57.1.B (100 mg, 0.199 mmol) and p-toluenesulfonic acid monohydrate (40 mg, 0.199 mmol) in THF (2 mL) was added ethyl orthoformate (33 µL, 0.199 mmol). The mixture was stirred at 50° C. overnight, concentrated and the residue was directly purified on reverse phase preparative HPLC to afford tert-butyl (S)-1-(4-(1,3,4-oxadiazol-2-yl)-6-(pyridin-4-yl)indolin-1-yl)-1-oxo-3-phenylpropan-2-ylcarbamate 59.A (34 mg, 33% yield).

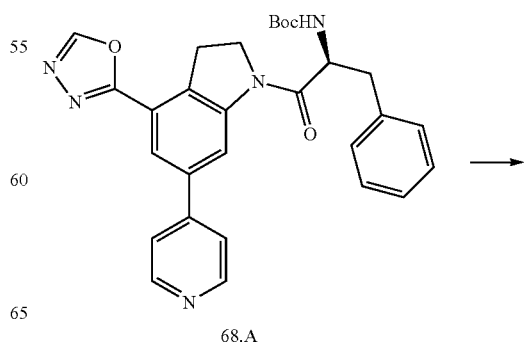

68.A

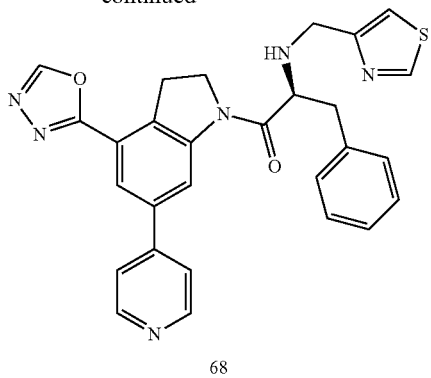

68

(2S)-1-(4-(1,3,4-Oxadiazol-2-yl)-6-(pyridin-4-yl)
indolin-1-yl)-3-phenyl-2-(thiazol-4-ylmethylamino)
propan-1-one (68)

The title compound was prepared from 68.A by methods analagous to those described in example 54.2. 1H NMR (400 MHz, MeOH-D4) δ ppm 1.57-1.65 (m, 2H) 1.73-1.78 (m, 1H) 1.92-2.02 (m, 2H) 2.54-2.63 (m, 1H) 3.02 (d, J=1.57 Hz, 2H) 3.23 (dd, J=9.98, 5.28 Hz, 1H) 5.80 (d, J=1.96 Hz, 5H) 6.31 (d, J=1.96 Hz, 1H) 6.58 (d, J=6.65 Hz, 2H) 6.73 (d, J=1.56 Hz, 1H) 7.29 (d, J=6.65 Hz, 2H) 7.38 (d, J=1.57 Hz, 1H) 7.58 (d, J=1.96 Hz, 1H) 7.59 (s, 1H).

7.69 Example 69

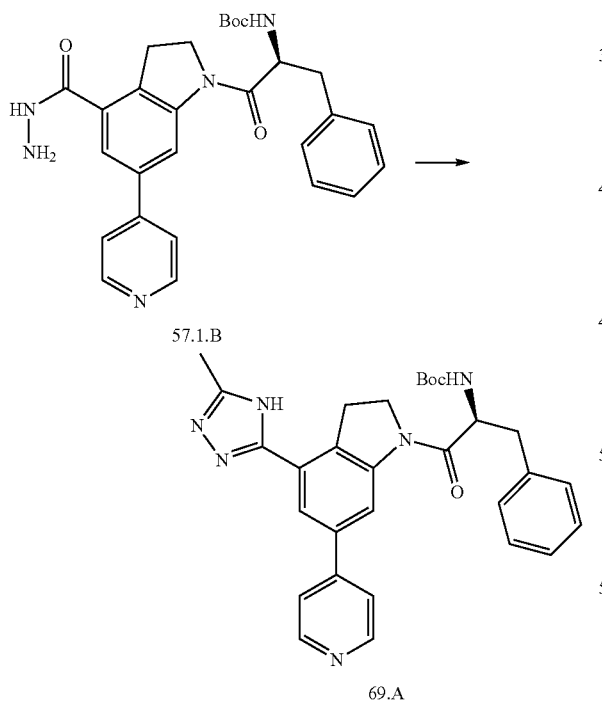

tert-Butyl (S)-1-(4-(5-methyl-4H-1,2,4-triazol-3-yl)-
6-(pyridin-4-yl)indolin-1-yl)-1-oxo-3-phenylpropan-
2-ylcarbamate (69.A)

To a solution of ethyl acetimidate hydrochloride (12 mg, 0.10 mmol) in methanol (0.5 mL) was added a 1M solution of NaOH in methanol (0.10 mL, 0.10 mmol). The mixture was stirred at room temperature ten minutes then was added (S)-tert-butyl 1-(4-hydrazide-6-(pyridin-4-yl)indolin-1-yl)-1-oxo-3-phenylpropan-2-ylcarbamate 57.1.B (50 mg, 0.10 mmol). The mixture was stirred in a sealed vial at 70° C. overnight and purified directly on reverse phase preparative HPLC to afford tert-butyl (S)-1-(4-(5-methyl-4H-1,2,4-triazol-3-yl)-6-(pyridin-4-yl)indolin-1-yl)-1-oxo-3-phenylpropan-2-ylcarbamate 69.A (26 mg, 50% yield).

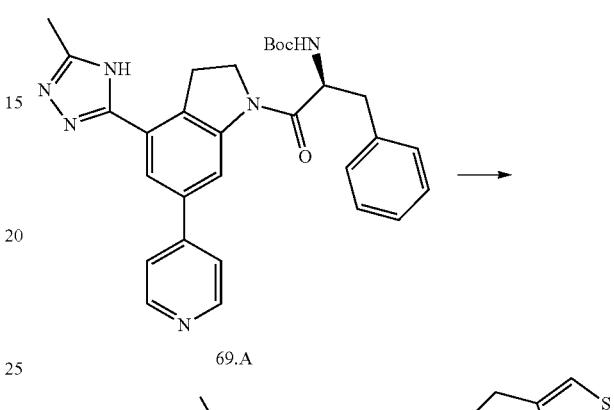

69.A

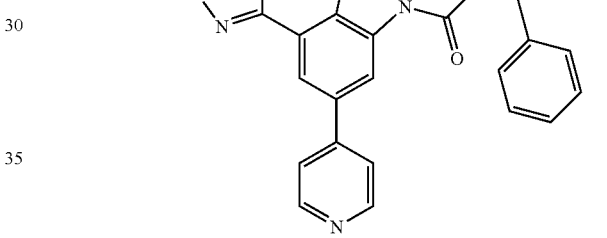

69

(2S)-1-(4-(5-Methyl-4H-1,2,4-triazol-3-yl)-6-(pyri-
din-4-yl)indolin-1-yl)-3-phenyl-2-(thiazol-4-ylm-
ethylamino)propan-1-one (69)

The title compound was prepared from 69.A by the methods analagous to those described in example 54.2.

7.70 Example 70

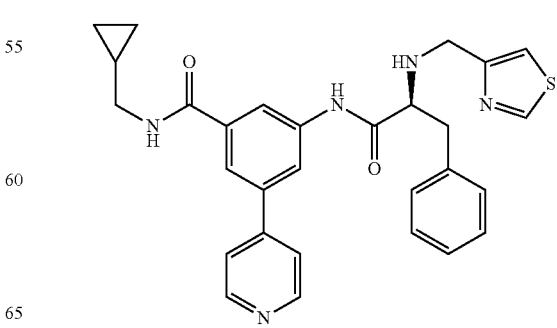

(S)—N-(Cyclopropylmethyl)-3-(3-phenyl-2-(thiazol-4-ylmethylamino)propanamido)-5-(pyridin-4-yl)benzamide (70)

The title compound was prepared by methods analagous to those described in example 47. 1H NMR (400 MHz, MeOH) δ ppm 0.28-0.37 (m, 2H) 0.51-0.62 (m, 2H) 1.06-1.23 (m, 1H) 3.23-3.28 (m, 1H) 3.30 (d, J=7.04 Hz, 2H) 3.44 (dd, J=13.30, 5.87 Hz, 1H) 4.29 (dd, J=9.19, 5.67 Hz, 1H) 4.51 (d, J=8.22 Hz, 2H) 7.26-7.37 (m, 5H) 7.81 (d, J=1.96 Hz, 1H) 7.99-8.00 (m, 1H) 8.03 (d, J=6.65 Hz, 2H) 8.05 (t, J=1.76 Hz, 1H) 8.08 (t, J=1.76 Hz, 1H) 8.80 (d, J=6.65 Hz, 2H) 9.14 (d, J=1.96 Hz, 1H).

7.71 Example 71

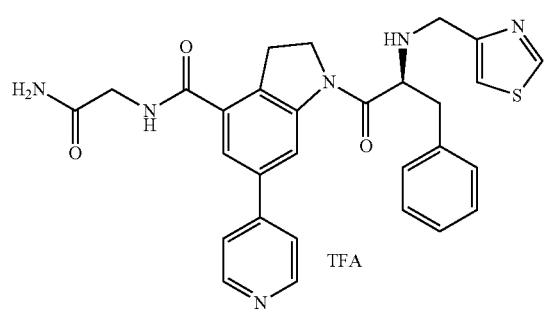 [SMILES: NC(=O)CNC(=O)c1cc(-c2ccncc2)cc2c1CCN2C(=O)[C@H](Cc1ccccc1)NCc1cscn1]

(S)—N-(2-Amino-2-oxoethyl)-1-(3-phenyl-2-(thiazol-4-ylmethylamino)propanoyl)-6-(pyridin-4-yl)indoline-4-carboxamide (71)

The title compound was prepared from compound 60.A by methods analagous to those described in example 60. LCMS ESI (pos.) m/e: 541.2. (M+1).

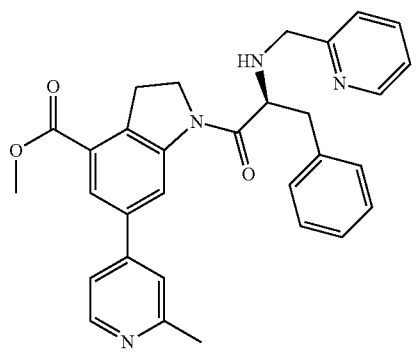 [SMILES: COC(=O)c1cc(-c2ccnc(C)c2)cc2c1CCN2C(=O)[C@H](Cc1ccccc1)NCc1ccccn1]

7.72 Example 72

Methyl 6-(2-methylpyridin-4-yl)-1-((S)-3-phenyl-2-(pyridin-2-ylmethylamino)propanoyl)indoline-4-carboxylate (72)

The title compound was prepared by methods analagous to those described in example 54.2. 1H NMR (500 MHz, MeOH-D4) δ ppm 2.82-2.90 (m, 3H) 3.04-3.22 (m, 2H) 3.34-3.38 (m, 1H) 3.39-3.50 (m, 1H) 3.53 (dd, J=13.08, 5.26 Hz, 1H) 3.96 (s, 3H) 3.99-4.08 (m, 1H) 4.52 (s, 2H) 4.79 (dd, J=10.15, 5.50 Hz, 1H) 7.28-7.38 (m, 5H) 7.46 (dd, J=7.58, 4.89 Hz, 1H) 7.50 (d, J=7.83 Hz, 1H) 7.91 (td, J=7.64, 1.59 Hz, 1H) 8.15 (br. s., 1H) 8.27 (t, J=1.59 Hz, 1H) 8.67 (d, J=4.89 Hz, 1H) 8.75 (dd, J=5.99, 1.59 Hz, 1H) 8.99 (t, J=1.47 Hz, 1H).

7.73 Example 73

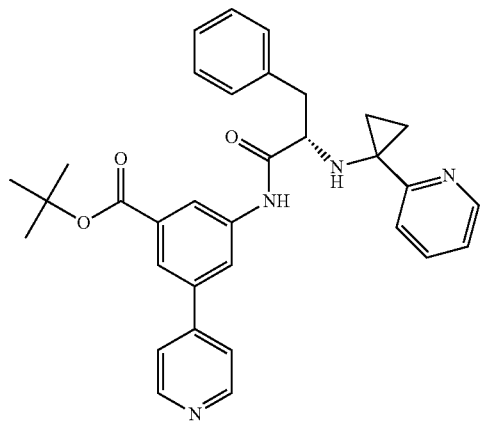 [SMILES: CC(C)(C)OC(=O)c1cc(NC(=O)[C@H](Cc2ccccc2)NC2(c3ccccn3)CC2)cc(-c2ccncc2)c1]

(S)— tert-Butyl 3-(3-phenyl-2-(1-(pyridin-2-yl)cyclopropylamino)propanamido)-5-(pyridin-4-yl)benzoate (73)

The title compound was prepared by methods analagous to those described in example 11.1. $^1$H NMR (400 MHz, MeOH) δ ppm 8.63 (dd, J=4.50, 1.76 Hz, 2H) 8.33 (d, J=5.09 Hz, 1H) 8.03-8.08 (m, 2H) 8.01 (d, J=1.56 Hz, 1H) 7.66-7.73 (m, 2H) 7.56 (td, J=7.73, 1.76 Hz, 1H) 7.18-7.29 (m, 6H) 7.03-7.12 (m, 1H) 3.60 (dd, J=8.02, 6.46 Hz, 1H) 2.91-3.05 (m, 1H) 2.81-2.91 (m, 1H) 1.63 (s, 9H) 1.05-1.20 (m, 2H) 0.93-1.04 (m, 2H).

7.74 Example 74

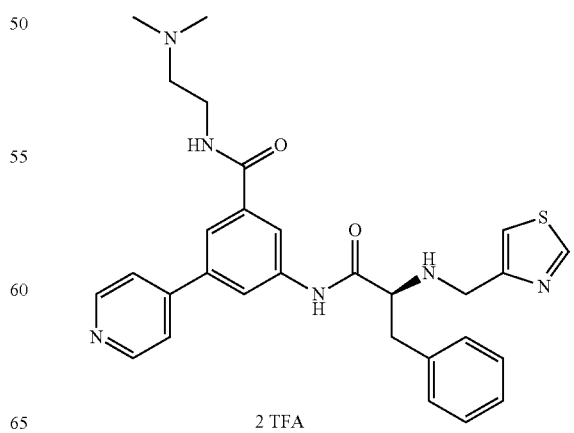

(S)—N-(2-(dimethylamino)ethyl)-3-(3-phenyl-2-(thiazol-4-ylmethylamino)propanamido)-5-(pyridin-4-yl)benzamide bis trifluoroacetate salt (74)

The title compound was prepared by methods analagous to those described in example 47. LCMS ESI (pos.) m/e: 529.2 (M+1).

7.75 Example 75

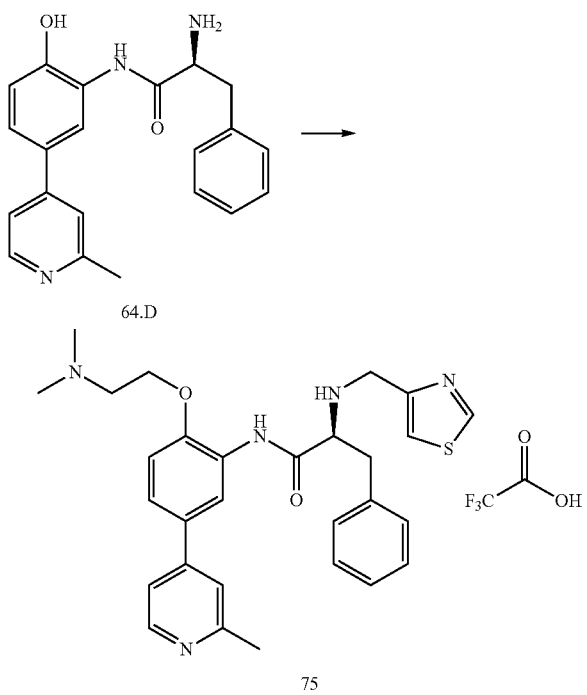

(2S)—N-(2-(2-(Dimethylamino)ethoxy)-5-(2-methylpyridin-4-yl)phenyl)-3-phenyl-2-(thiazol-4-ylmethylamino)propanamide trifluoroacetate (75)

Phenol 64.D (28 mg, 63 μmol), 2-dimethylaminoethyl chloride hydrochloride (9 mg, 63 μmol), and $Cs_2CO_3$ (41 mg, 126 μmol) were mixed in DMF (1 ml) and heated at 70° C. overnight. The reaction mixture was diluted with MeOH, filtered, and purified by prepHPLC(C18, ACN:$H_2O$:0.1% TFA, gradient). The desired fractions were combined and lyophilized to yield 75 (8 mg, 21%). LC-MS (+esi, M+H$^+$= 516.1). $^1$H NMR (500 MHz, MeOH) δ ppm 9.10 (d, J=1.83 Hz, 1H) 8.67 (d, J=6.10 Hz, 1H) 8.55 (d, J=2.44 Hz, 1H) 8.16 (d, J=1.83 Hz, 1H) 8.09 (dd, J=6.71, 1.83 Hz, 1H) 7.84 (dd, J=8.54, 2.44 Hz, 1H) 7.81 (d, J=1.83 Hz, 1H) 7.28-7.36 (m, 6H) 4.74 (dd, J=9.16, 5.49 Hz, 1H) 4.47-4.57 (m, 3H) 4.34 (dt, J=12.21, 4.27 Hz, 1H) 3.48-3.61 (m, 2H) 3.42 (dd, J=13.43, 6.10 Hz, 1H) 3.27-3.30 (m, 1H) 2.96 (s, 6H) 2.84 (s, 3H).

7.76 Example 76

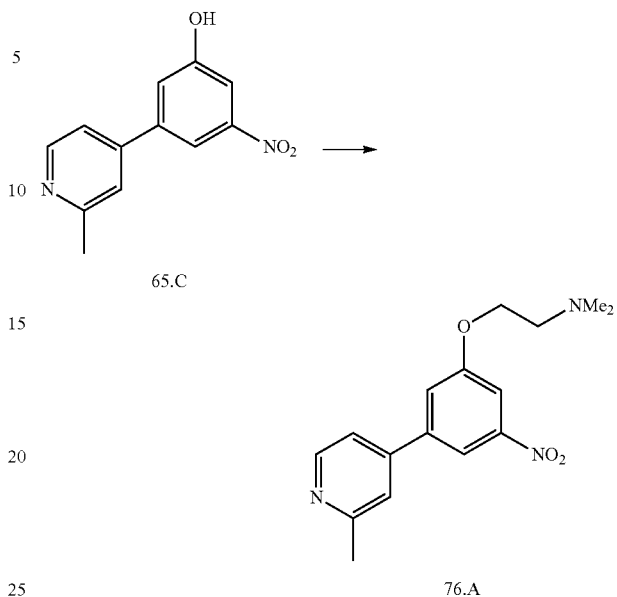

N,N-Dimethyl-2-(3-(2-methylpyridin-4-yl)-5-nitrophenoxy)ethanamine (76.A)

To a rt solution of 65.0 (805 mg, 3.50 mmol), and 2-dimethylaminoethyl chloride hydrochloride (available from Sigma) (756 mg, 5.26 mmol) in DMF (10 mL) was added $K_2CO_3$ (1.93 g, 14.0 mmol). After stirring at 110° C. for 18 hr, the reaction mixture was treated with saturated aqueous $NaHCO_3$ (2.0 mL), diluted with water and extracted with EtOAc (3×15 mL). The combined organic layers were washed with brine and dried over $MgSO_4$. After removal of organic solvent under reduced pressure, purification of the residue by flash chromatography on silica gel using 0-80% EtOAc/Hexanes for elution gave the title compound 76.A as yellow solid (725 mg, 69%).

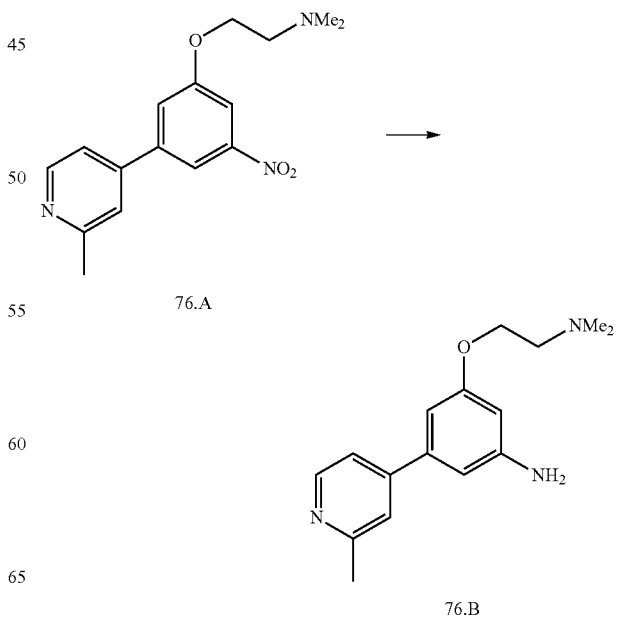

3-(2-(Dimethylamino)ethoxy)-5-(2-methylpyridin-4-yl)benzenamine (76.B)

This title intermediate was prepared starting from 76.A (694 mg, 2.30 mmol) according the procedure described above for conversion of 65.D to 65.E. The crude product was purified by flash chromatography on silica gel using 0-10% MeOH/CH$_2$Cl$_2$ for elution to provide 76.B as colorless syrup (582 mg, 93%).

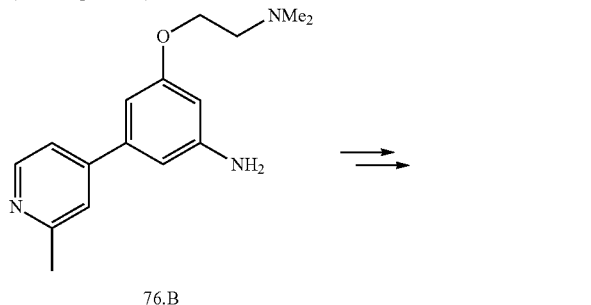

76.B

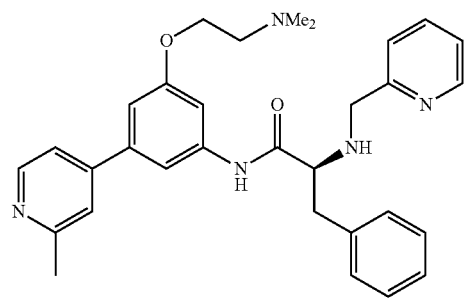

(2S)—N-(3-(2-(Dimethylamino)ethoxy)-5-(2-methylpyridin-4-yl)phenyl)-3-phenyl-2-(pyridin-2-ylmethylamino)propanamide (76)

This title compound was prepared starting from 76.B according the procedure described above for conversion of 4.A to 4, except that picolinaldehyde was used for reduction amination. The final crude product was purified by flash chromatography on silica gel using 0-6% MeOH/CH$_2$Cl$_2$ for elution to provide 76 as pale yellow solid. MS ESI (positve.) m/e: 510.2 (M+H), $^1$H NMR (400 MHz, CHLOROFORM-d) δ ppm 9.79 (s, 1H), 8.36-8.53 (m, 2H), 7.51 (td, J=7.63, 1.96 Hz, 1H), 7.34-7.44 (m, 2H), 7.27-7.34 (m, 1H), 7.12-7.27 (m, 5H), 7.05-7.12 (m, 1H), 6.98 (d, J=7.43 Hz, 1H), 6.86-6.93 (m, 1H), 4.08 (t, J=5.48 Hz, 2H), 3.66-3.85 (m, J=14.72, 14.72, 14.38, 7.04 Hz, 2H), 3.46 (ddd, J=9.78, 3.91, 1.96 Hz, 1H), 3.26 (dd, J=13.69, 3.91 Hz, 1H), 2.74-2.84 (m, 1H), 2.63-2.74 (m, 2H), 2.50-2.61 (s, 3H), 2.22-2.36 (m, 6H).

7.77 Example 77

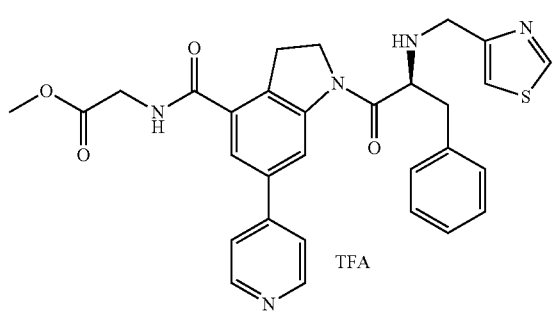 [SMILES: COC(=O)CNC(=O)c1cc(-c2ccncc2)cc2c1CCN2C(=O)[C@H](Cc1ccccc1)NCc1cscn1]

(S)-Methyl 2-(1-(3-phenyl-2-(thiazol-4-ylmethylamino)propanoyl)-6-(pyridin-4-yl)indoline-4-carboxamido)acetate (77)

The title compound was prepared from compound 60.A by methods analagous to those described in example 60. LCMS ESI (pos.) m/e: 556.2 (M+1).

7.78 Example 78

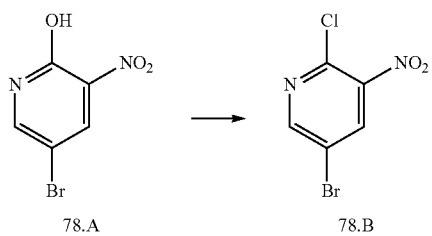 [SMILES: O=[N+]([O-])c1cc(Br)cnc1O ; O=[N+]([O-])c1cc(Br)cnc1Cl]

5-Bromo-2-chloro-3-nitropyridine (78.B)

To 5-bromo-3-nitropyridin-2-ol (78.A)(1 g, 5 mmol) was added 10 mL of phosphorus oxychloride. The reaction was heated at 100° C. for 1 hr., concentrated and worked up between EtOAc and saturated NaHCO3. The organic layer was concentrated, redissolved in DCM, filtered off the solids. The DCM layer was concentrated again to afford 450 mg (45%) of 78.B.

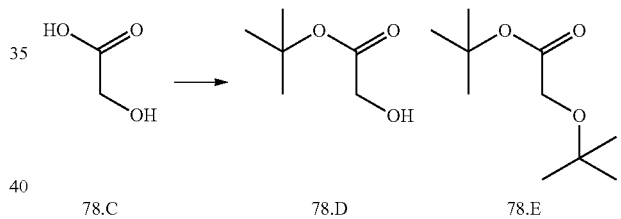

tert-Butyl 2-hydroxyacetate (78.D)

Di-tert-butoxy-N,N-dimethylmethanamine (1.62 g, 0.8 mmol) was added to a heated toluene solution of 2-hydroxyacetic acid 78.0 (152 mg, 2 mmol) dropwise. The reaction was heated at 80° C. for 2.5 hr. Water was added. The organic layer was washed with NaHCO3, brine and concentrated to afford 261 mg of mixture. It had 2.6:1 ratio of 78.D:78.E.

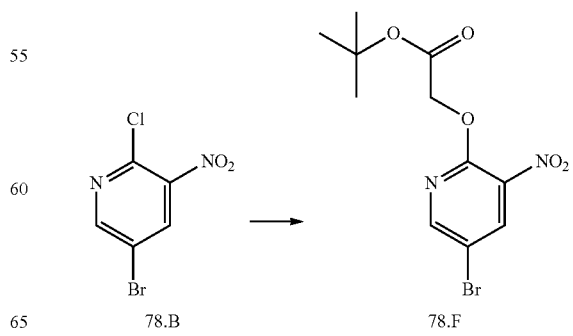

tert-Butyl 2-(5-bromo-3-nitropyridin-2-yloxy)acetate (78.F)

To a flask with 5-bromo-2-chloro-3-nitropyridine (73.B) (800 mg, 3.4 mmol) was added 78.D (mixed with 78.E, 445 mg, 3.4 mmol), cesium carbonate (2.2 g, 6.7 mmol) and N,N-dimethylpyridin-4-amine (82 mg, 0.67 mmol). DMF was used as the solvent. The reaction was heated for 2.5 hours. Standard aqueous workup with EtOAc as solvent and silica gel purification afforded 700 mg of 78.F mixed with some 78.E.

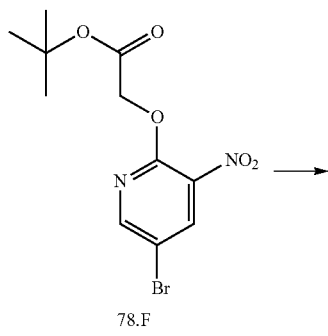

tert-Butyl 2-(5-(2-methylpyridin-4-yl)-3-nitropyridin-2-yloxy)acetate (78.G)

To a flask with tert-butyl 2-(5-bromo-3-nitropyridin-2-yloxy)acetate (78.F) (700 mg from last step, about 406 mg of estimated pure 78.F by NMR) was added tris(dibenzylideneacetone)dipalladium (o) (67 mg, 0.073 mmol), 2-methylpyridin-4-ylboronic acid (250 mg, 1.8 mmol), X-phos (139 mg, 0.29 mmol), potassium phosphate (1.04 g, 4.9 mmol). The solids were purged with nitrogen. Degassed t-amyl alcohol was added as a solvent. The reaction was heated at 100° C. for 2 hr. 40 min.s. The solids were filtered off. Silica gel purification afforded 280 mg (67%) 78.G.

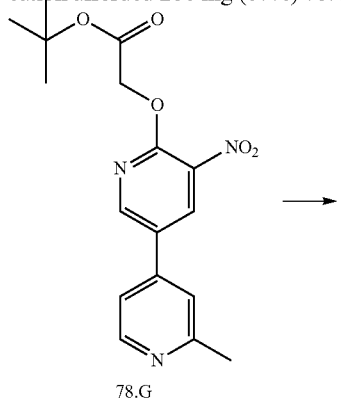

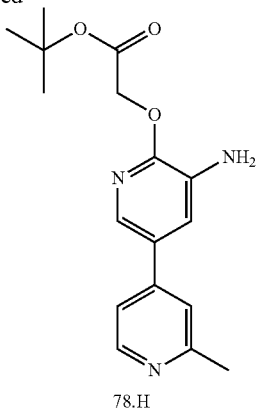

tert-Butyl 2-(3-amino-5-(2-methylpyridin-4-yl)pyridin-2-yloxy)acetate (78.H)

To a flask with 78.G (280 mg, 0.81 mmol) was added 112 mg 10% Pd/C. The reaction was purged with hydrogen and stirred under hydrogen for 4 hrs. After filtering through a pad of celite, silica gel purification afforded 78.H 134 mg (52%).

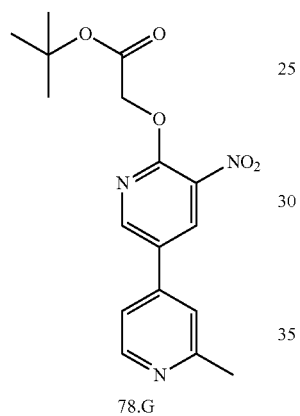

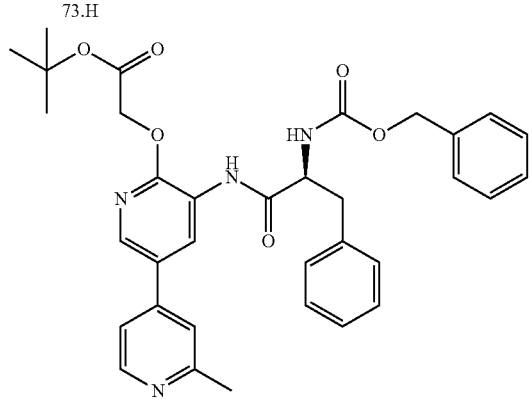

tert-Butyl 2-(3-((S)-2-(benzyloxycarbonyl)-3-phenylpropanamido)-5-(2-methylpyridin-4-yl)pyridin-2-yloxy)acetate (78.I)

To a flask with tert-butyl 2-(3-amino-5-(2-methylpyridin-4-yl)pyridin-2-yloxy)acetate (78.H) (134 mg, 0.43 mmol) was added HBTU (242 mg, 0.24 mmol), z-1-phenylalanine (134 mg, 0.45 mmol), N-ethyl-N-isopropylpropan-2-amine (0.22 mL, 1.3 mmol). DMF was added as the solvent and reaction was stirred overnight. Standard aqueous workup with EtOAc as extraction followed by silica gel chromatography afforded 78.I 250 mg (99%).

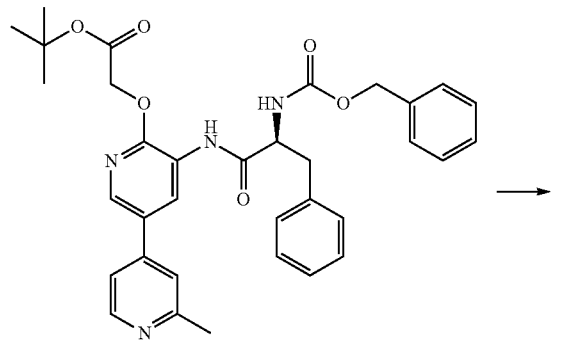

78.I

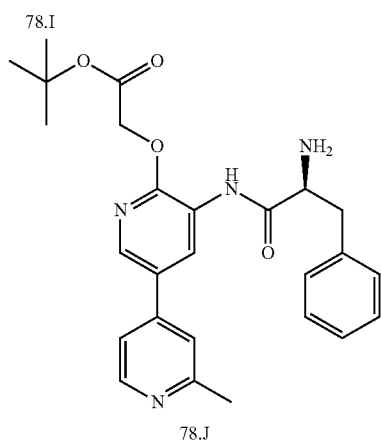

78.J tert-Butyl 2-(3-((S)-2-amino-3-phenylpropanamido)-5-(2-methylpyridin-4-yl)pyridin-2-yloxy)acetate (78.J)

To a flask with 78.I (220 mg, 0.55 mmol) was added 58 mg 10% Pd/C. The reaction was purged with hydrogen and stirred under hydrogen for 2.5 hrs. After filtering through a pad of celite, silica gel purification afforded 78.J, 200 mg (98%).

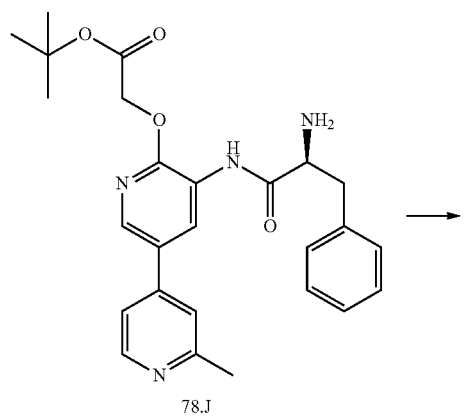

78.J

-continued

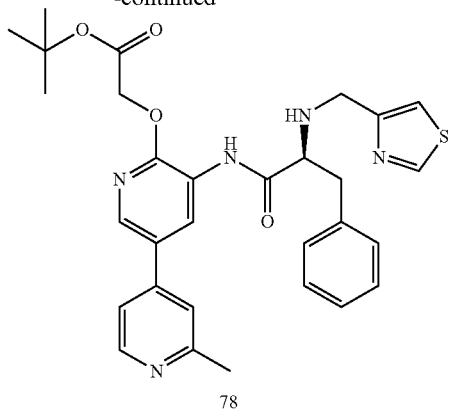

78 tert-Butyl 2-(5-(2-methylpyridin-4-yl)-3-((S)-3-phenyl-2-(thiazol-4-ylmethylamino)propanamido)pyridin-2-yloxy)acetate (78)

To a flask with tert-butyl 2-(3-((S)-2-amino-3-phenylpropanamido)-5-(2-methylpyridin-4-yl)pyridin-2-yloxy)acetate (78.J) (58 mg, 0.13 mmol) was added thiazole-4-carbaldehyde (15 mg, 0.13 mmol). Dichloromathane was added as the solvent. Then acetic acid, glacial (8 mL, 0.13 mmol) was added followed by sodium triacetoxyborohydride (80 mg, 0.38 mmol). The reaction was stirred at room temperature for 1 hour and worked up with EtOAc and saturated NaHCO3 solution. Reverse phase HPLC purification afforded compound 78 26 mg (37%). 1H NMR (400 MHz, MeOH) δ ppm 8.78-8.96 (m, 2H) 8.45 (d, J=5.48 Hz, 1H) 8.22 (d, J=2.35 Hz, 1H) 7.57 (s, 1H) 7.49 (dd, J=5.48, 1.56 Hz, 1H) 7.36 (d, J=1.96 Hz, 1H) 7.18-7.31 (m, 5H) 4.90 (d, J=3.13 Hz, 2H) 3.87-3.98 (m, 2H) 3.63 (dd, J=8.61, 5.09 Hz, 1H) 3.19 (dd, J=13.89, 4.89 Hz, 1H) 2.92 (dd, J=14.09, 8.61 Hz, 1H) 2.60 (s, 3H) 1.46 (s, 9H).

7.79 Examples 79 and 80

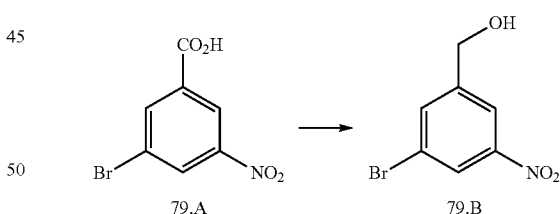

79.A      79.B

3-Bromo-5-nitrobenzaldehyde (79.B)

To a 0° C. suspension of 79.A (available from Aldrich) (4.00 g, 16.3 mmol) in THF (25 mL) under $N_2$ was added borane-dimethyl sulfide (available from Aldrich) (1.0 M, 65 mL) via additional funnel over 45 mins. After stirring at rt for 12 hr, the reaction solution was refluxed for 1.5 hrs, cooled to rt, and poured into saturated aqueous $NaHCO_3$ (25 mL). The mixture was extracted with EtOAc (3×30 mL) and the combined organic layers were washed with brine and dried over $MgSO_4$. After removal of organic solvent under reduced pressure, the crude product 79.B was directly carried to the next step (3.15 g, 84%).

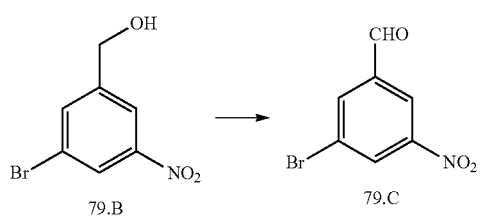 [SMILES: O=[N+]([O-])c1cc(Br)cc(CO)c1 ; O=Cc1cc(Br)cc([N+](=O)[O-])c1]

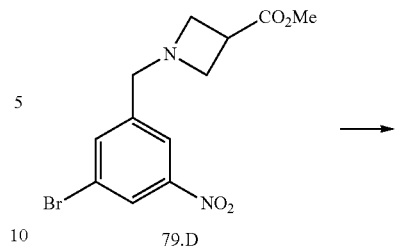

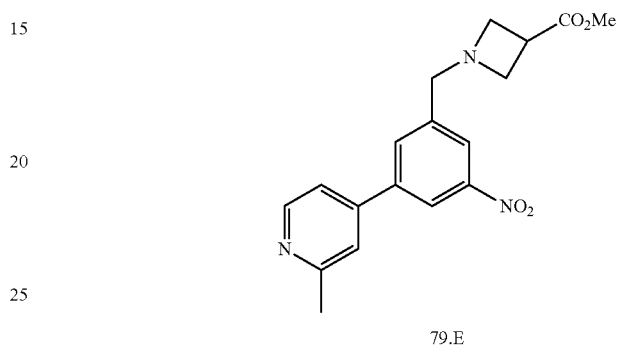

Methyl 1-(3-bromo-5-nitrobenzyl)azetidine-3-carboxylate (79.C)

To a rt suspension of pyridinium dichromate (available from Aldrich) (6.20 g, 16.0 mmol) in $CH_2Cl_2$ (22 mL) was added a solution of 79.B (3.15 g, 14.0 mmol) in $CH_2Cl_2$ (10 mL) drop wise over 10 mins. After stirring at rt for 64 hrs, to the reaction mixture was added celite. Solid was filtrated off, washed with EtOAc (4×15 mL), and the liquids were collected. After removal of organic solvents under reduced pressure, purification of the residue by flash chromatography on silica gel using 0-50 EtOAc/Hexanes for elution gave the title product 79.C as a yellow solid (2.5 g, 80%).

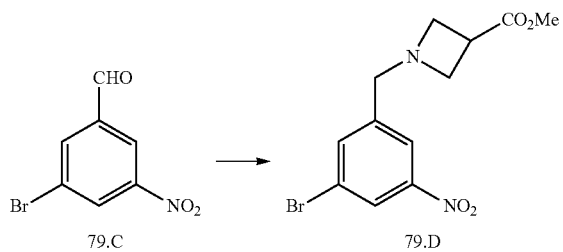 [SMILES: O=Cc1cc(Br)cc([N+](=O)[O-])c1 ; COC(=O)C1CN(Cc2cc(Br)cc([N+](=O)[O-])c2)C1]

Methyl 1-(3-bromo-5-nitrobenzyl)azetidine-3-carboxylate (79.D)

To a rt solution of 79.0 (2.01 g, 8.8 mmol) and methyl azetidine-3-carboxylate hydrochloride (available from Oakwood Products, Inc.) (1.98 g, 1.30 mmol) in 1,2-dichloroethane (10 mL) was added NaOAc (available from Aldrich) (710 mg, 8.7 mmol). After stirring at rt for 15 mins, to the reaction solution was added 5% HOAc/1,2-dichloroethane (150 μl) followed by sodium triacetoxyborohydride (4.61 g, 22.0 mmol). The resulting mixture was stirred at 60° C. for 35 mins, quenched with saturated aqueous $NaHCO_3$ (10 mL), diluted with water (30 mL) and extracted with 30% $^iPrOH/CHCl_3$ (3×30 mL). After removal of organic solvent under reduced pressure, purification of the residue by flash chromatography on silica gel using 0-55% EtOAc/Hexanes for elution gave the title product 79.D as pale yellow solid (2.61 g, 91%).

Methyl 1-(3-(2-methylpyridin-4-yl)-5-nitrobenzyl) azetidine-3-carboxylate (79.E)

To a rt solution of 79.D (2.42 g, 7.4 mmol) and 2-methylpyridin-4-ylboronic acid (available from CombiPhos Catalysts, Inc.) (2.52 g, 18.4 mmol) in DMF (22 mL) was added saturated aqueous $Na_2CO_3$ (5 mL) followed by bis(triphenylphosphine)palladium(ii) chloride (265 mg, 0.37 mmol) After being purged with $N_2$ for 15 mins, the mixture was stirred at 50° C. under $N_2$ atmosphere for 3.5 hrs. The reaction solution was cooled, diluted with water (35 mL), treated with acetic acid to pH=7, and extracted with EtOAc (3×30 mL). The combined organic layers were washed with water, brine dried over $MgSO_4$, and filtered. After removal of organic solvent under reduced pressure, purification of the residue by flash chromatography on silica gel using 0-6% MeOH/$CH_2Cl_2$ for elution gave the title product 79.E as pale yellow solid (1.51 g, 60%).

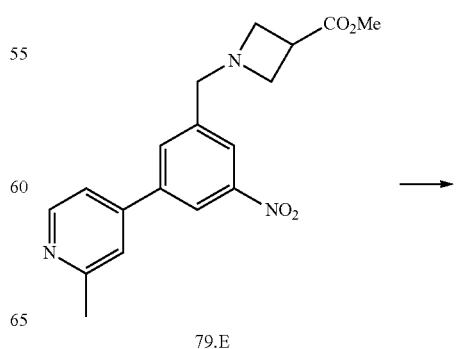

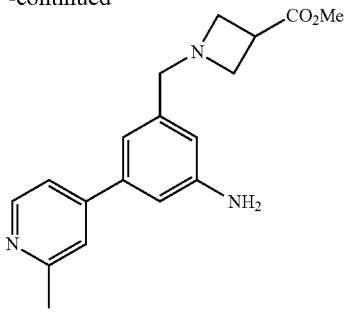

79.F

Methyl 1-(3-amino-5-(2-methylpyridin-4-yl)benzyl) azetidine-3-carboxylate (79.F)

This target intermediate was prepared starting from 79.E according the procedure described above for conversion of 51.B to 51.C. The crude product 79.F was carried to the next step without further purification (1.35 mg, 94%).

The following compounds were prepared starting from 79.F according to the methods described above for conversion of 4.A to 4, except that picolinaldehyde was used in reductive amination formation of 80.

TABLE 11

| Compound | R | Compound | R |
|---|---|---|---|
| 79 | thiazol-4-ylmethyl | 80 | pyridin-2-ylmethyl |

Methyl 1-((16S)-3-(2-methylpyridin-4-yl)-5-(S)-3-phenyl-2-(thiazol-4-ylmethylamino)propanamido) benzyl)azetidine-3-carboxylate (79)

MS ESI (positve.) m/e: 556.2 (M+H); 1H NMR (400 MHz, CHLOROFORM-d) δ ppm 9.61 (s, 1H) 8.63 (d, J=1.96 Hz, 1H), 8.45 (d, J=5.09 Hz, 1H) 7.90 (s, 1H), 7.44 (s, 1H), 7.33 (s, 1H), 7.16-7.29 (m, 5H), 7.11 (d, J=6.65 Hz, 2H), 6.91 (d, J=1.96 Hz, 2H), 4.04 (q, J=7.17 Hz, 2H), 3.71-3.91 (m, 2H), 3.69 (s, 3H), 3.61 (s, 2H), 3.39-3.58 (m, 3H), 3.16-3.38 (m, 1H), 2.67-2.88 (m, 2H), 2.45-2.63 (s, 3H).

Methyl 1-((16S)-3-(2-methylpyridin-4-yl)-5-((S)-3-phenyl-2-(pyridin-2-ylmethylamino)propanamido) benzyl)azetidine-3-carboxylate (80)

MS ESI (positve.) m/e: 550.3 (M+H), 1H NMR (400 MHz, CHLOROFORM-d) δ ppm 9.61 (s, 1H), 8.63 (d, J=1.96 Hz, 1H), 8.45 (d, J=5.09 Hz, 1H), 7.90 (s, 1H), 7.44 (s, 1H), 7.33 (s, 1H), 7.14-7.30 (m, 5H), 7.11 (d, J=6.65 Hz, 2H), 6.91 (d, J=1.96 Hz, 1H), 4.04 (q, J=7.17 Hz, 1H), 3.70-3.94 (m, 2H), 3.56-3.70 (m, 5H), 3.40-3.56 (m, 2H), 3.12-3.39 (m, 1H), 2.68-2.80 (m, 2H), 2.54 (s, 3H).

7.80 Example 81

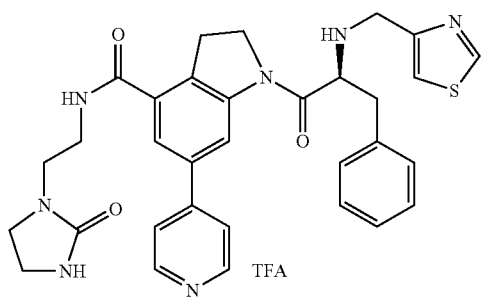 [SMILES: O=C(NCCN1CCNC1=O)c1cc(-c2ccncc2)cc2c1CCN2C(=O)[C@H](Cc1ccccc1)NCc1cscn1]

(S)—N-(2-(2-Oxoimidazolidin-1-yl)ethyl)-1-(3-phenyl-2-(thiazol-4-ylmethylamino)propanoyl)-6-(pyridin-4-yl)indoline-4-carboxamide (81)

The title compound was prepared from compound 60.A by methods analagous to those described in example 60. LCMS ESI (pos.) m/e: 596.1 (M+1).

7.81 Example 82

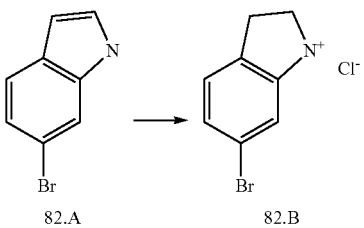 [SMILES: Brc1ccc2cc[nH]c2c1 ; Brc1ccc2c(c1)[NH2+]CC2 ; [Cl-]]

82.A → 82.B

6-Bromoindoline Hydrochloride (82.B)

6-Bromo-1H-indole (14.10 g, 72 mmol) was dissolved in ethanol (100 mL) and acetic acid (10 mL) and cooled to 0° C. Sodium cyanoborohydride (9.0 g, 144 mmol) was added slowly and allowed to warm to room temperature over five hours. LCMS indicated starting material remaining Another 1.0 equivalent of sodium cyanoborohydride was added and stirred overnight. Another 1.0 equivalent of sodium cyanoborohydride was added (4.0 equivalents total) and stirred for an additional three days. Concentrate the mixture (do not heat above 45° C.) to dryness and take up with ethyl acetate (400 mL) and extract with 1M sodium carbonate solution (2×250 mL). The impure product was then dissolved in ethyl acetate (200 mL) and 1M hydrochloric acid was added to the mixture (100 mL). The resulting white precipitate was then filtered and washed with hexanes to give the desired product with excellent purity as 6-bromoindoline hydrochloride (14.20 g, 84% yield) MS ESI (pos.) m/e: 197.9 (M+H).

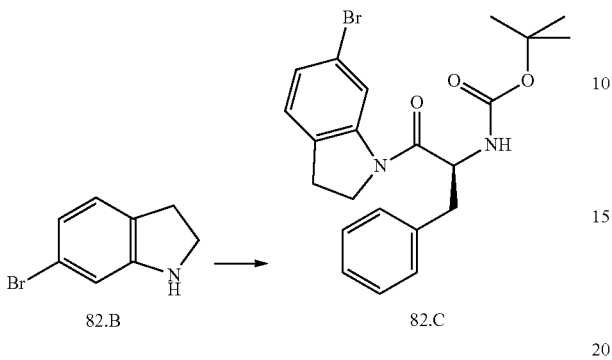

(S)-tert-Butyl 1-(6-bromoindolin-1-yl)-1-oxo-3-phenylpropan-2-ylcarbamate (82.C)

The 6-bromoindoline (1050 mg, 5.30 mmol), N—BOC-phenylalanine (1.41 g, 5.30 mmol), N-ethyl-N-isopropylpropan-2-amine (2.02 ml, 12.2 mmol) and 2-(1H-benzotriazol-1-yl)-1,1,3,3-tetramethyluronium hexafluorophosphate (2.41 g, 6.36 mmol) (HBTU) were dissolved in DMF. The reaction mixture was stirred for 2.5 days. The reaction was diluted with water and then extracted with ethyl acetate (2×150 mL). The combined organic layers were washed with 1M lithium chloride solution (2×70 mL) and brine (1×70 mL) and dried over magnesium sulfate. The crude product was then recrystallyzed using ethyl acetate:hexanes to give (S)-tert-butyl 1-(6-bromoindolin-1-yl)-1-oxo-3-phenylpropan-2-ylcarbamate (1.01 g, 42.8% yield). MS ESI (pos.) m/e: 445.1 (M+H).

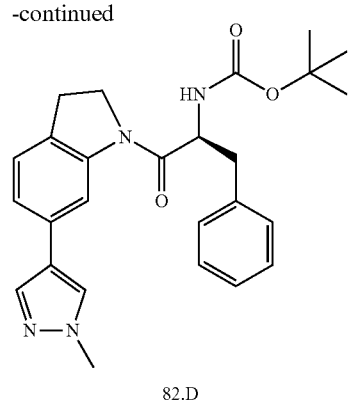

tert-Butyl (S)-1-(6-(1-methyl-1H-pyrazol-4-yl)indolin-1-yl)-1-oxo-3-phenylpropan-2-ylcarbamate (82.D)

To DMF (11 ml, 225 µmol) in a sealed tube flushed with nitrogen was added 1-methyl-4-(4,4,5,5-tetramethyl-1,3,2-dioxaborolan-2-yl)-1H-pyrazole (47 mg, 0.225 mmol), (S)-tert-butyl 1-(6-bromoindolin-1-yl)-1-oxo-3-phenylpropan-2-ylcarbamate (100 mg, 225 µmol), sodium carbonate solution (629 µl, 629 mmol), and 1,1'-dis(diphenylphosphino)ferrocene-palladium (II) dichloride dichloromethane complex (Pd(dppf)Cl$_2$) (9.2 mg, 11 µmol). The slurry was heated to 85° C. and stirred for three hours. LCMS indicated a trace of starting material remained. Another aliquot of Pd(dppf)Cl$_2$ (9.2 mg, 11 µmol) was added and the slurry stirred for an additional eight hours. The reaction was then allowed to cool to room temperature. The reaction was diluted with water and extracted with ethyl acetate (2×40 mL). The combined organic layers were washed with 1M lithium chloride solution (1×30 mL) and brine (1×30 mL) and dried over magnesium sulfate. The crude product was purified by medium pressure chromatography (silica, 0 to 60% ethyl acetate:hexanes) to give tert-butyl (S)-1-(6-(1-methyl-1H-pyrazol-4-yl)indolin-1-yl)-1-oxo-3-phenylpropan-2-ylcarbamate (67 mg, 67%). MS ESI (pos.) m/e: 447.3 (M+H).

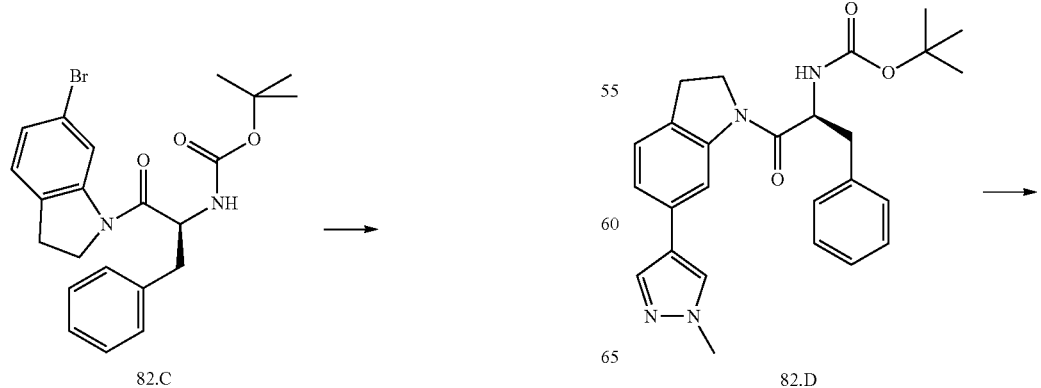

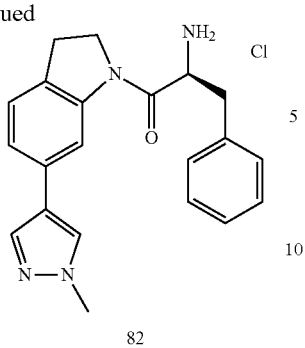

82

(2S)-2-Amino-1-(6-(1-methyl-1H-pyrazol-4-yl)indolin-1-yl)-3-phenylpropan-1-one hydrochloride (82)

Tert-butyl (S)-1-(6-(1-methyl-1H-pyrazol-4-yl)indolin-1-yl)-1-oxo-3-phenylpropan-2-ylcarbamate (60.0 mg, 134 µmol) was dissolved in dichloromethane (1.5 mL) and TFA (1.50 mL, 19 mmol) was added and the solution was stirred for three hours. The reaction mixture was then concentrated to dryness and then taken up in ethyl acetate and extracted and basified with saturated sodium bicarbonate solution. The organic layer was then concentrated and the residue was dissolved in ethyl acetate and 3.0 equivalents of 1M HCl in ether solution was added forming an off-white precipitate that was filtered and washed with hexanes to give (2S)-2-amino-1-(6-(1-methyl-1H-pyrazol-4-yl)indolin-1-yl)-3-phenylpropan-1-one hydrochloride 82. MS ESI (pos.) m/e: 347.2 (M+H).

7.82 Example 83

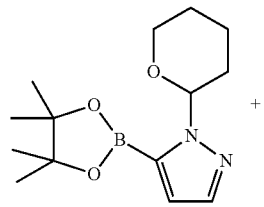

tert-Butyl (S)-1-oxo-3-phenyl-1-(6-(1-(tetrahydro-2H-pyran-2-yl)-1H-pyrazol-5-yl)indolin-1-yl)propan-2-ylcarbamate (83.A)

To DMF (1.1 ml) in a sealed tube flushed with nitrogen was added 1-(tetrahydro-2H-pyran-2-yl)-5-(4,4,5,5-tetramethyl-1,3,2-dioxaborolan-2-yl)-1H-pyrazole (62 mg, 230 µmol), (S)-tert-butyl 1-(6-bromoindolin-1-yl)-1-oxo-3-phenylpropan-2-ylcarbamate (100 mg, 230 µmol), 1M sodium carbonate solution (630 µl, 630 µmol), and 1,1'-dis(diphenylphosphino)ferrocene-palladium (II) dichloride dichloromethane complex (Pd(dppf)Cl$_2$) (9.2 mg, 11 µmol). The slurry was heated to 85° C. and stirred for three hours. A significant amount of starting material remained. Another portion of (Pd(dppf)Cl$_2$) (9.2 mg, 11 µmol) was added and the reaction was stirred for eight hours. The reaction was then allowed to cool to room temperature. The reaction was diluted with water and extracted with ethyl acetate (2×40 mL). The combined organic layers were washed with 1M lithium chloride solution (1×30 mL) and brine (1×30 mL) and dried over magnesium sulfate. The crude product was purified by medium pressure chromatography (silica, 0 to 60% ethyl acetate:hexanes) to give tert-butyl (S)-1-oxo-3-phenyl-1-(6-(1-(tetrahydro-2H-pyran-2-yl)-1H-pyrazol-5-yl)indolin-1-yl)propan-2-ylcarbamate (34 mg, 29% yield). MS ESI (pos.) m/e: 433.1 (M+H-THP).

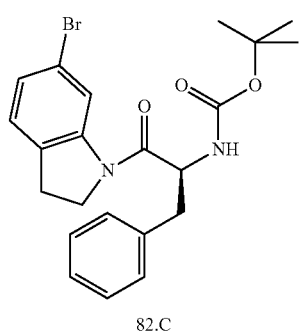

82.C

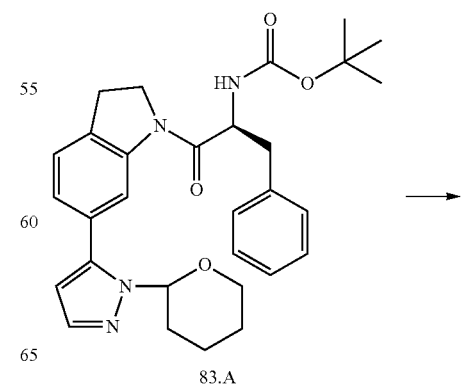

83.A

-continued

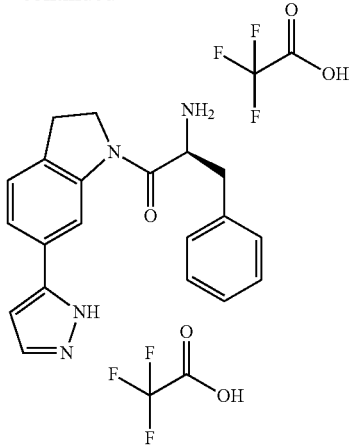

83

(2S)-1-(6-(1H-pyrazol-5-yl)indolin-1-yl)-2-amino-3-phenylpropan-1-one Ditrifluoroacetate (83)

The tert-butyl (S)-1-oxo-3-phenyl-1-(6-(1-(tetrahydro-2H-pyran-2-yl)-1H-pyrazol-5-yl)indolin-1-yl)propan-2-ylcarbamate (34.0 mg, 66 µmol) was dissolved in dichloromethane (1.0 mL) and TFA (1.00 mL, 13 mmol) was added and the solution was stirred for 2.5 hours. The reaction mixture was then concentrated and then purified by reverse phase chromatography (C18, 5 to 95% MeCN: H₂O+0.1% TFA) to give (2S)-1-(6-(1H-pyrazol-5-yl)indolin-1-yl)-2-amino-3-phenylpropan-1-one Ditrifluoroacetate (6.0 mg, 16% yield). MS ESI (pos.) m/e: 333.1 (M+H).

7.83 Example 84

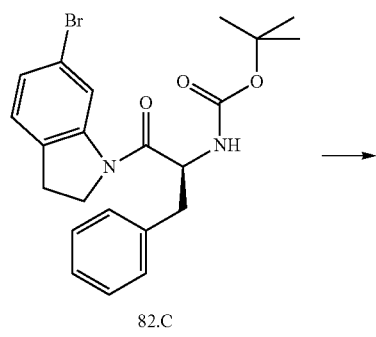

82.C

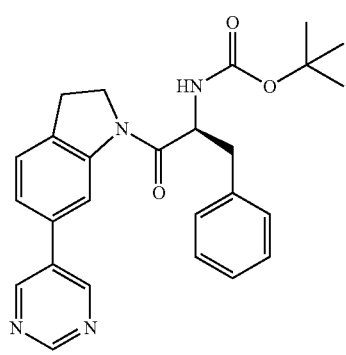

84.A

(S)-tert-Butyl 1-oxo-3-phenyl-1-(6-(pyrimidin-5-yl)indolin-1-yl)propan-2-ylcarbamate (84.A)

Pyrimidin-5-ylboronic acid (28 mg, 230 µmol), (S)-tert-butyl 1-(6-bromoindolin-1-yl)-1-oxo-3-phenylpropan-2-ylcarbamate (100 mg, 230 µmol), (Pd(dppf)Cl₂) (18 mg, 22 µmol) were dissolved in DMF (1.1 mL) and 1M sodium carbonate solution (630 µl, 630 µmol) was added. The resulting slurry was stirred in a sealed tube for one hour at 85° C., allowed to cool to room temperature and diluted with water. The mixture was extracted with ethyl acetate (2×50 mL). The organic layers were combined and washed with 1M lithium chloride solution (1×25 mL) and brine (1×25 mL) and dried over magnesium sulfate. The residue was purified by medium pressure chromatography (silica, 0 to 100% ethyl acetate:hexanes) to give (S)-tert-butyl 1-oxo-3-phenyl-1-(6-(pyrimidin-5-yl)indolin-1-yl)propan-2-ylcarbamate (74 mg, 74% yield). MS ESI (pos.) m/e: 445.1 (M+H).

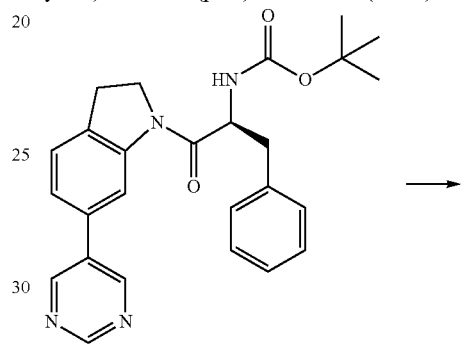

84.A

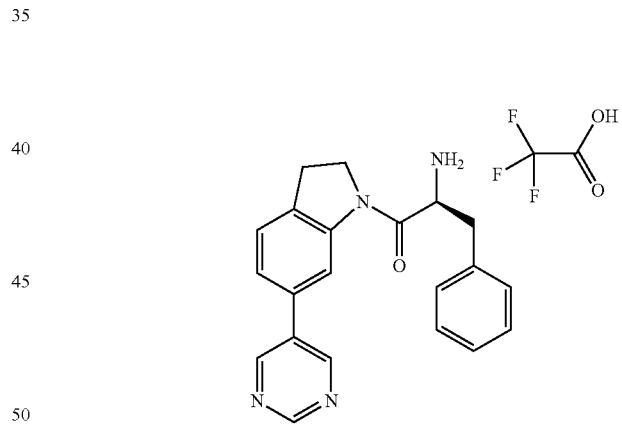

84.B

(S)-2-Amino-3-phenyl-1-(6-pyrimidin-5-yl-2,3-dihydro-indol-1-yl)-propan-1-one Trifluoroacetate (84.B)

The (S)-tert-butyl 1-oxo-3-phenyl-1-(6-(pyrimidin-5-yl)indolin-1-yl)propan-2-ylcarbamate (64 mg, 144 µmol) was dissolved in dichloromethane (1.0 mL) and TFA (1.0 mL, 13 mmol) was added. The resulting solution was stirred for three hours then concentrated. The residue was taken up in ethyl acetate and filtered and washed with hexanes to give the desired product (S)-2-amino-3-phenyl-1-(6-pyrimidin-5-yl-2,3-dihydro-indol-1-yl)-propan-1-one trifluoroacetate (50 mg, 76% yield) as the mono-trifluoroacetic acid salt. MS ESI (pos.) m/e: 345.1 (M+H).

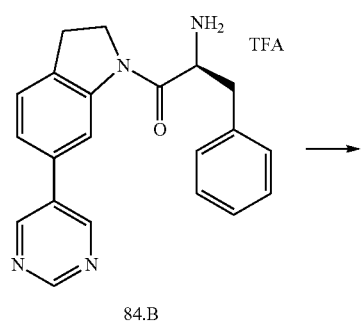

84.B

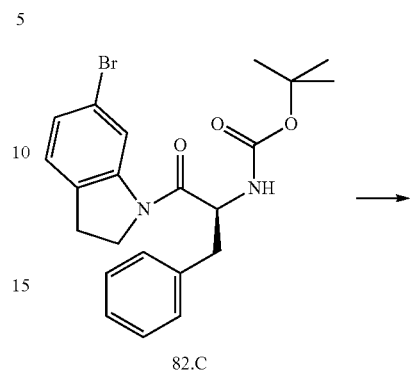

82.C

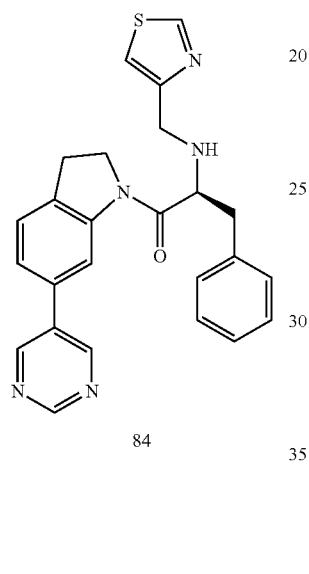

84

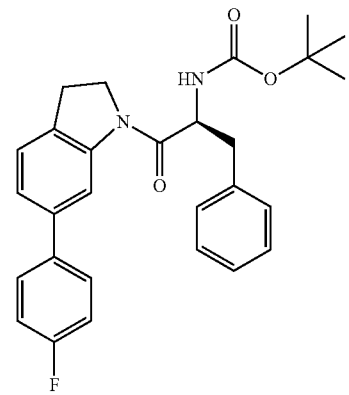

85.A (S)-3-Phenyl-1-(6-(pyrimidin-5-yl)indolin-1-yl)-2-(thiazol-4-ylmethylamino)propan-1-one (84)

The (S)-2-amino-3-phenyl-1-(6-(pyrimidin-5-yl)indolin-1-yl)propan-1-one (39.0 mg, 110 µmol) was dissolved in a DCE/THF mixture 1.5 mL. Thiazole-4-carbaldehyde (13 mg, 110 µmol), diisopropylethyl amine (20 µl, 110 µmol), and sodium triacetoxyborohydride (48 mg, 230 µmol) was added to the reaction mixture. The resulting solution was heated to 70° C. and stirred for three hours. LCMS indicated starting material was still present. 24 mg of sodium cyanoborohydride was added and the solution was stirred at 70° C. overnight to completion. The reaction mixture was diluted with dichloromethane and basified with saturated sodium bicarbonate. The layers were separated and the organic layer was dried over magnesium sulfate and concentrated under reduced pressure. The residue was then purified on an SCX column eluting with 0 to 2M ammonia in methanol solution to give impure product. This material was then purified by medium pressure chromatography (silica gel, 0 to 6.5% 2M ammonia in methanol: dichloromethane) to give the desired product (S)-3-phenyl-1-(6-(pyrimidin-5-yl)indolin-1-yl)-2-(thiazol-4-ylmethylamino)propan-1-one (16.6 mg, 33% yield). MS ESI (pos.) m/e: 442.1 (M+H).

7.84 Example 85

(S)-tert-Butyl 1-(6-(4-fluorophenyl)indolin-1-yl)-1-oxo-3-phenylpropan-2-ylcarbamate (85.A)

To DMF (1.1 mL) in a sealed tube flushed with nitrogen was added 4-fluorophenylboronic acid (31 mg, 230 µmol), (S)-tert-butyl 1-(6-bromoindolin-1-yl)-1-oxo-3-phenylpropan-2-ylcarbamate (100 mg, 230 µmol), 1M sodium carbonate solution (230 µl, 230 µmol), and Pd(dppf)Cl$_2$ (18 mg, 22 µmol). The slurry was heated to 85° C. and stirred for one hour. The reaction was then allowed to cool to room temperature and stirred overnight. The reaction was diluted with water and extracted with ethyl acetate (2×40 mL). The combined organic layers were washed with 1M lithium chloride solution (1×30 mL) and brine (1×30 mL) and dried over magnesium sulfate. The crude product was purified by medium pressure chromatography (silica, 0 to 30% ethyl acetate:hexanes) to give(S)-tert-butyl 1-(6-(4-fluorophenyl)indolin-1-yl)-1-oxo-3-phenylpropan-2-ylcarbamate (99 mg, 96% yield). MS ESI (pos.) m/e: 461.2 (M+H).

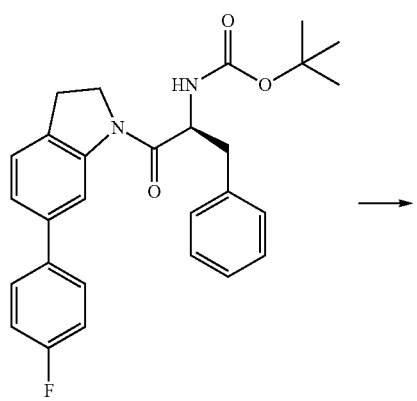

85.A

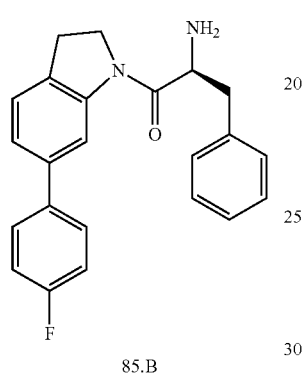

(S)-2-amino-1-(6-(4-fluorophenyl)indolin-1-yl)-3-phenylpropan-1-one (85.B)

The (S)-tert-butyl 1-(6-(4-fluorophenyl)indolin-1-yl)-1-oxo-3-phenylpropan-2-ylcarbamate (93.0 mg, 202 μmol) was dissolved in dichloromethane and TFA (1.0 mL, 13 mmol) was added. The resulting solution was stirred for three hours. The mixture was then concentrated and the residue was dissolved in ethyl acetate and extracted with saturated sodium bicarbonate (1×30 mL). The organic layer was then dried over magnesium sulfate and concentrated to dryness and the residue was again dissolved in ethyl acetate and 2.0 equivalents of 1M HCl in ether solution was added. A precipitate formed and the slurry was filtered and washed with hexanes to give (2S)-2-amino-1-(6-(4-fluorophenyl)indolin-1-yl)-3-phenylpropan-1-one hydrochloride (65 mg, 89% yield). MS ESI (pos.) m/e: 361.1 (M+H).

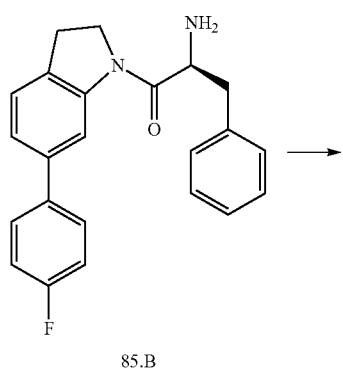

85.B

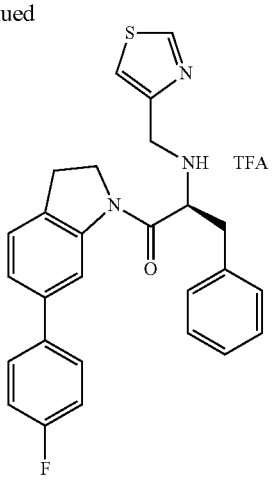

85

(S)-1-[6-(4-Fluoro-phenyl)-2,3-dihydro-indol-1-yl]-3-phenyl-2-[(thiazol-4-ylmethyl)-amino]-propan-1-one Trifluoroacetate (85)

The (S)-2-amino-3-phenyl-1-(6-(pyrimidin-5-yl)indolin-1-yl)propan-1-one (39.0 mg, 110 μmol) was dissolved in the DCE/THF mixture (1.5 mL). Thiazole-4-carbaldehyde (13 mg, 110 μmol), diisopropylethyl amine (20 μl, 110 μmol), and sodium triacetoxyborohydride (48 mg, 230 μmol) was added to the reaction mixture. The resulting solution was heated to 70° C. and stirred for three hours. LCMS indicated starting material was still present. 24 mg of sodium cyanoborohydride was added and the solution was stirred at 70° C. overnight to completion. The reaction mixture was diluted with dichloromethane and basified with saturated sodium bicarbonate. The layers were separated and the organic layer was dried over magnesium sulfate and concentrated under reduced pressure. The residue was then purified on an SCX column eluting with 0 to 2M ammonia in methanol solution to give impure product. This material was then purified by medium pressure chromatography (silica gel, 0 to 6.5% 2M ammonia in methanol: dichloromethane) to give the desired product (S)-3-phenyl-1-(6-(pyrimidin-5-yl)indolin-1-yl)-2-(thiazol-4-ylmethylamino)propan-1-one (16.6 mg, 33% yield). MS ESI (pos.) m/e: 458.2 (M+H).

7.85 Example 86

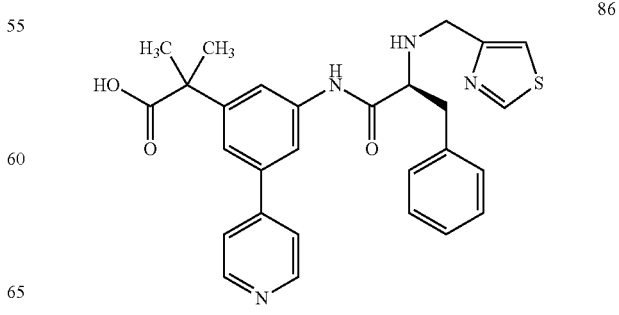

86

(S)-2-methyl-2-(3-(3-phenyl-2-(thiazol-4-ylmethylamino)propanamido)-5-(pyridin-4-yl)phenyl)propanoic acid (86)

The title compound was prepared following a modified version of the synthesis described above for 52.

7.86 Example 101

7.86.1 Example 101.1

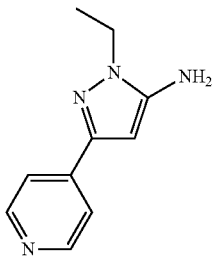

20.2.C

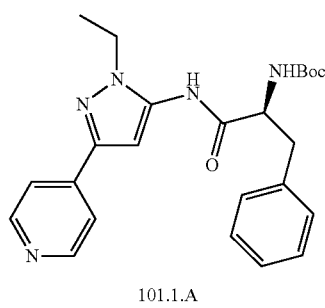

101.1.A

Tert-butyl (S)-1-(1-ethyl-3-(pyridin-4-yl)-1H-pyrazol-5-ylamino)-1-oxo-3-phenylpropan-2-ylcarbamate (101.1.A)

To a 25 ml flask was added 1-ethyl-3-(pyridin-4-yl)-1H-pyrazol-5-amine 20.2.0 (283 mg, 1.50 mmole), Boc-L-phenylalanine (439 mg, 1.65 mmole), EDC (375 mg, 1.95 mmole), 4-dimethylaminopyridine (202 mg, 1.65 mmole) and 5 ml of dichloromethane. The reaction was stirred at room temperature for 4 hours at which time the solvent was removed by rotary evaporation. The residue was suspended in ethyl acetate, and washed successively with saturated sodium bicarbonate, water and brine. The organic layer was dried over anhydrous sodium sulfate, and concentrated in vacuo. The crude product was purified by silica gel chromatography to give 101.1.A (568 mg, 87% yield) as colorless amorphous. 1H NMR (400 MHz, CDCl3) δ ppm 8.80 (brs, 1H), 8.56 (d, J=5.8 Hz, 2H), 7.64 (d, J=6.2 Hz, 2H), 7.65-7.63 (m, 5H), 6.68 (s, 1H), 5.32 (brs, 1H), 4.52 (dd, J=14.6, 7.3 Hz, 1H), 3.95 (q, J=7.2 Hz, 2H), 3.25-3.14 (m, 2H), 1.52 (s, 9H), 1.37 (t, J=7.4 Hz, 3H)

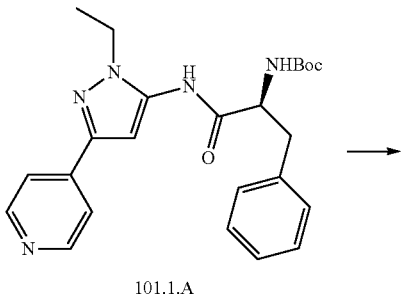

101.1.A

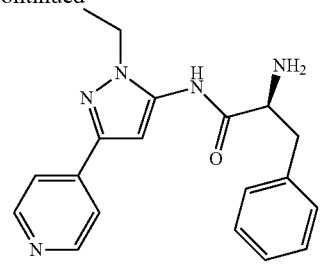

101.1.B (S)-2-Amino-N-(1-ethyl-3-(pyridin-4-yl)-1H-pyrazol-5-yl)-3-phenylpropanamide (101.1.B)

To a 25 ml flask was added tert-butyl (S)-1-(1-ethyl-3-(pyridin-4-yl)-1H-pyrazol-5-ylamino)-1-oxo-3-phenylpropan-2-ylcarbamate 101.1.A (568 mg, 1.30 mmole), 5 ml of 4N-hydrogen chloride solution in 1,4-dioxane, and 5 ml of 1,4-dioxane. The reaction was stirred at room temperature for 0.5 hours at which time the solvent was removed by rotary evaporation. The residue was suspended in ethyl acetate, and washed successively with saturated sodium bicarbonate, water and brine. The organic layer was dried over anhydrous sodium sulfate, and concentrated in vacuo to give 101.1.B (380 mg, 87% yield) as colorless syrup. 1H NMR (400 MHz, CDCl3) δ ppm 9.71 (s, 1H), 8.61 (d, J=5.8 Hz, 2H), 7.69 (d, J=6.2 Hz, 2H), 7.39-7.26 (m, 5H), 6.88 (s, 1H), 4.07 (q, J=7.2 Hz, 2H), 3.85 (dd, J=8.8, 4.1 Hz, 1H), 3.36 (dd, J=13.8, 4.1 Hz, 1H), 2.93 (dd, J=13.9, 8.8 Hz, 1H), 2.96 (brs, 2H), 1.45 (t, J=7.2 Hz, 3H).

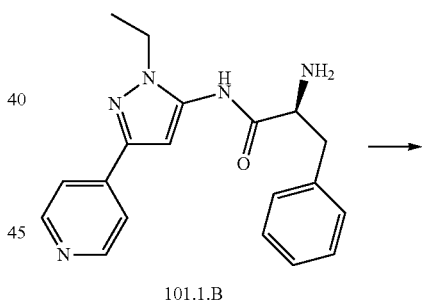

101.1.B

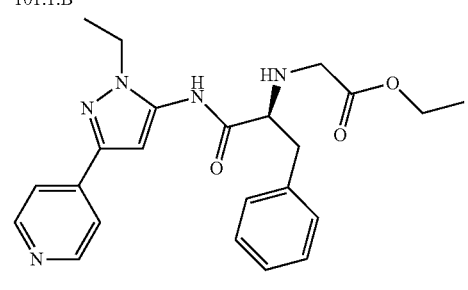

101.1.C

Ethyl 2-((S)-1-(1-ethyl-3-(pyridin-4-yl)-1H-pyrazol-5-ylamino)-1-oxo-3-phenylpropan-2-ylamino)acetate (101.1.C)

To a 25 ml flask was added (S)-2-amino-N-(1-ethyl-3-(pyridin-4-yl)-1H-pyrazol-5-yl)-3-phenylpropanamide 101.1.B (132 mg, 0.39 mmole), 3 ml of ethanol and 0.08 ml of triethylamine. The reaction mixture was cooled to 0° C., and then ethyl bromoacetate (48 µl, 0.43 mmole) was added to the mixture. The reaction was stirred at 50° C. for 1 hour and at room temperature overnight. After then, the solution was concentrated, and dissolved in ethyl acetate. The organic layer was washed with water and brine, and dried over anhydrous sodium sulfate. After concentration in vacuo, the residue was chromatographed on silica gel to give 101.1.C (45 mg, 27% yield) as colorless amorphous. 1H NMR (400 MHz, CDCl3) δ ppm 9.73 (s, 1H), 8.61 (d, J=5.9 Hz, 2H), 7.69 (d, J=6.3 Hz, 2H), 7.38-7.26 (m, 5H), 6.87 (s, 1H), 4.19-4.04 (m, 4H), 3.54 (dd, J=8.4, 4.5 Hz, 1H), 3.42 (d, J=17.6 Hz, 1H), 3.32 (d, J=17.6 Hz, 1H), 3.35 (dd, J=14.1, 4.5 Hz, 1H), 3.00 (dd, J=14.1, 8.2 Hz, 1H), 2.05 (brs, 1H), 1.43 (t, J=7.2 Hz, 3H), 1.24 (t, J=7.2 Hz, 3H).

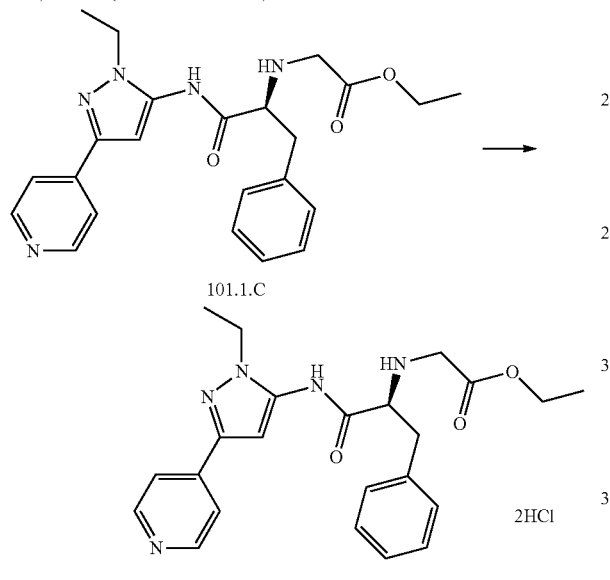

Ethyl 2-((S)-1-(1-ethyl-3-(pyridin-4-yl)-1H-pyrazol-5-ylamino)-1-oxo-3-phenylpropan-2-ylamino)acetate dihydrochloride (101.1)

To a 25 ml flask was added ethyl 2-((S)-1-(1-ethyl-3-(pyridin-4-yl)-1H-pyrazol-5-ylamino)-1-oxo-3-phenylpropan-2-ylamino)acetate 101.1.C (45 mg, 0.11 mmole), and 1 ml of 1,4-dioxane. To the solution, 1 ml of 4N-hydrogen chloride solution in 1,4-dioxane (4 mmol) was added at 0° C. After then, the solvent was removed by rotary evaporation. The crude product was dried under a high vacuum to give 101.1 (54 mg, 100% yield) as colorless amorphous. LCMS ESI (pos.) m/e: 423 (M+H).

7.86.2 Example 101.2

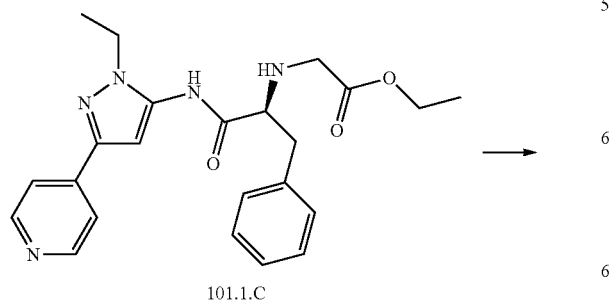

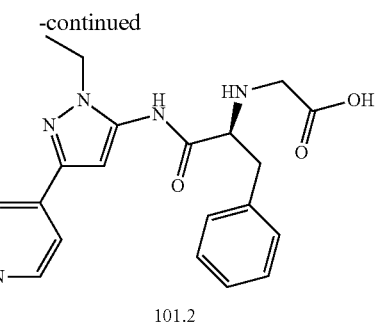

(S)-2-(1-(1-Ethyl-3-(pyridin-4-yl)-1H-pyrazol-5-ylamino)-1-oxo-3-phenylpropan-2-ylamino)acetic acid (101.2)

To a 25 ml flask was added ethyl 2-((S)-1-(1-ethyl-3-(pyridin-4-yl)-1H-pyrazol-5-ylamino)-1-oxo-3-phenylpropan-2-ylamino)acetate 101.1.C (105 mg, 0.78 mmole), 0.5 ml of 1N-sodium hydroxide solution and 1.5 ml of methanol. The mixture was stirred at room temperature for 1 hour and at 50° C. for 1 hour. After then, 0.25 ml of 2N-hydrogen chloride solution was added to neutralize. The solvent was removed by rotary evaporation. The crude product was purified by silica gel chromatography to give 101.2 (79 mg, 81% yield) as colorless powder. LCMS ESI (pos.) m/e: 394 (M+H); 1H NMR (400 MHz, DMSO-d6) δ ppm 8.57 (d, J=5.9 Hz, 2H), 7.72 (d, J=5.8 Hz, 2H), 7.34-7.22 (m, 5H), 6.79 (s, 1H), 3.89 (q, J=7.4 Hz, 2H), 3.66 (t, J=7.1 Hz, 1H), 3.30 (d, J=17.2 Hz, 1H), 3.24 (d, J=17.2 Hz, 1H), 3.04-2.93 (m, 2H), 1.24 (t, J=7.2 Hz, 3H).

7.86.3 Example 101.3

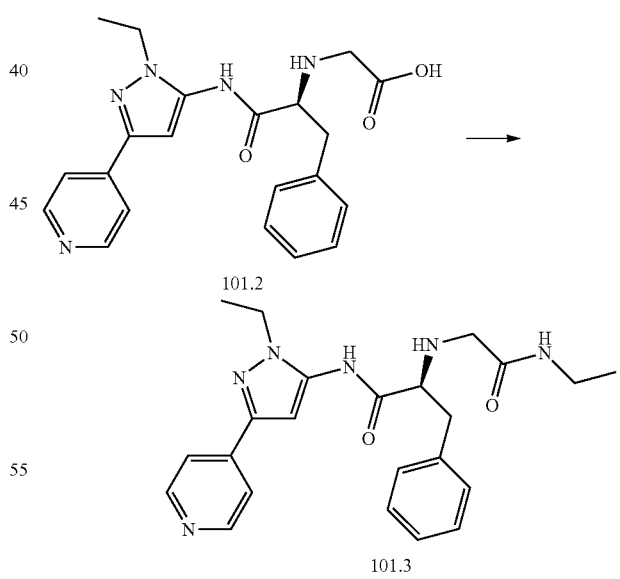

(S)—N-(1-Ethyl-3-(pyridin-4-yl)-1H-pyrazol-5-yl)-2-(ethylcarbamoylmethylamino)-3-phenylpropanamide (101.3)

To a 25 ml flask was added (S)-2-(1-(1-ethyl-3-(pyridin-4-yl)-1H-pyrazol-5-ylamino)-1-oxo-3-phenylpropan-2- ylamino)acetic acid 101.2 (138 mg, 0.35 mmole), 50 wt % propylphosphoric anhydride solution in ethyl acetate (251 μg, 0.42 mmole), 0.2 ml of triethylamine and 3 ml of acetonitrile. The reaction mixture was stirred at room temperature for 5.5 hours. The solution was diluted with ethyl acetate. The organic layer was washed with water and brine, and dried over anhydrous sodium sulfate. After concentration in vacuo, the residue was chromatographed on silica gel to give an intermediate (78 mg, 59% yield). LCMS ESI (pos.) m/e: 376 (M+H).

To a 25 ml flask was added the intermediate (78 mg, 0.21 mmole), 0.21 ml of 2M-ethylamine solution in THF and 1 ml of THF. The reaction mixture was stirred at 50° C. for 3 hours. After concentration in vacuo, the residue was chromatographed on silica gel to give 101.3 (84 mg, 96% yield) as colorless amorphous. LCMS ESI (pos.) m/e: 421 (M+H); $^1$H NMR (400 MHz, CDCl3) δ ppm 9.69 (s, 1H), 8.60 (d, J=5.9 Hz, 2H), 7.67 (d, J=5.9 Hz, 2H), 7.38-7.26 (m, 5H), 6.81 (s 1H), 5.87 (brs, 1H), 4.07 (q, J=7.1 Hz, 2H), 3.49 (dd, J=8.8, 4.7 Hz, 1H), 3.28-3.15 (m, 5H), 2.94 (dd, J=13.9, 8.8 Hz, 1H), 1.41 (t, J=7.2 Hz, 3H), 1.06 (t, J=7.2 Hz, 3H).

7.86.4 Example 101.4

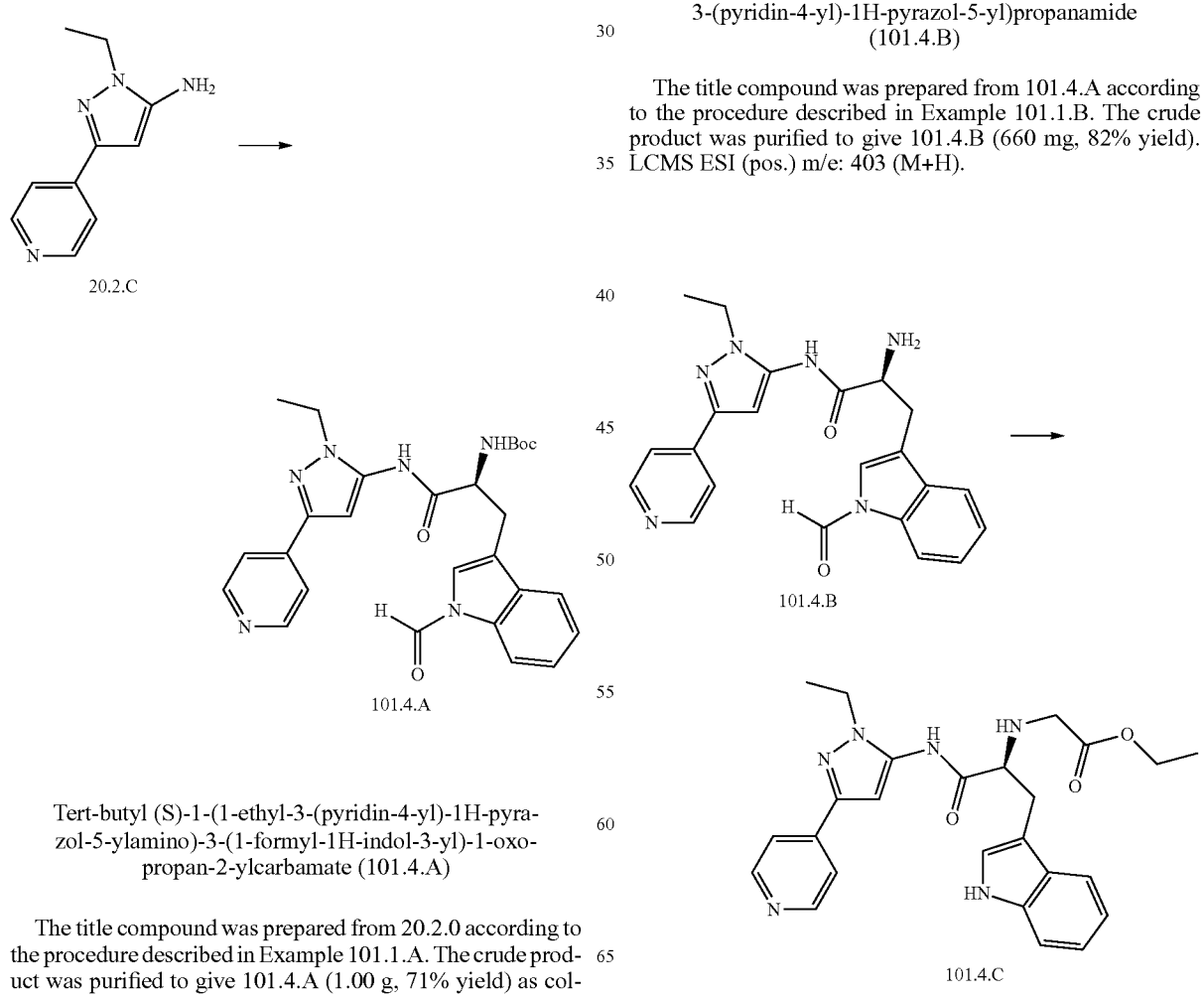

Tert-butyl (S)-1-(1-ethyl-3-(pyridin-4-yl)-1H-pyrazol-5-ylamino)-3-(1-formyl-1H-indol-3-yl)-1-oxopropan-2-ylcarbamate (101.4.A)

The title compound was prepared from 20.2.0 according to the procedure described in Example 101.1.A. The crude product was purified to give 101.4.A (1.00 g, 71% yield) as colorless powder.

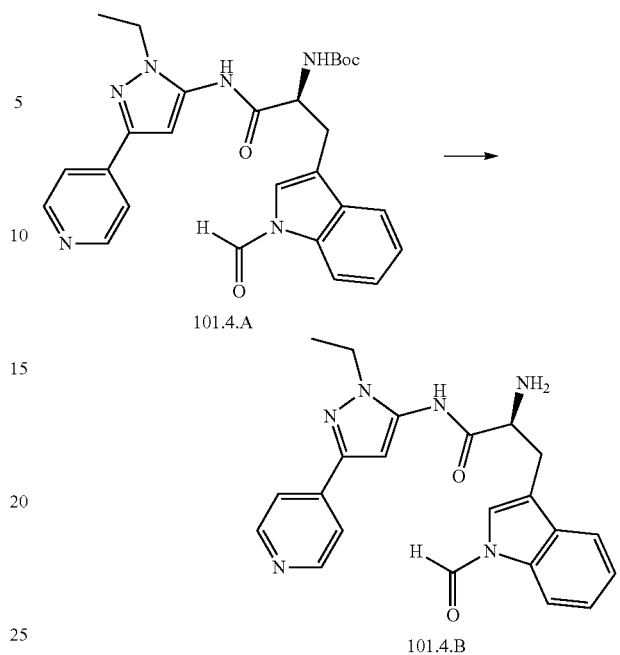

(S)-2-Amino-3-(1-formyl-1H-indol-3-yl)-N-(1-ethyl-3-(pyridin-4-yl)-1H-pyrazol-5-yl)propanamide (101.4.B)

The title compound was prepared from 101.4.A according to the procedure described in Example 101.1.B. The crude product was purified to give 101.4.B (660 mg, 82% yield). LCMS ESI (pos.) m/e: 403 (M+H).

Ethyl 2-((S)-1-(1-ethyl-3-(pyridin-4-yl)-1H-pyrazol-5-ylamino)-3-(1H-indol-3-yl)-1-oxopropan-2-ylamino)acetate (101.4.C)

The title compound was prepared from 101.4.B according to the procedure described in Example 101.1.C. The crude product was purified to give 101.4.0 (54 mg, 24% yield) as colorless crystals. 1H NMR (400 MHz, CDCl$_3$) δ ppm 9.73 (s, 1H), 8.61 (d, J=6.3 Hz, 2H), 8.24 (s, 1H), 7.69-7.68 (m, 3H), 7.41 (d, J=8.2 Hz, 1H), 7.24 (t, J=7.0 Hz, H), 7.17-7.13 (m, 2H), 6.85 (s, 1H), 4.16-3.99 (m, 4H), 3.62 (dd, J=7.6, 4.5 Hz, 1H), 3.48 (dd, J=14.1, 4.5 Hz, 1H), 3.43 (d, J=17.6 Hz, 1H), 3.37 (d, J=17.6 Hz, 1H), 3.24 (dd, J=14.1, 7.6 Hz, 1H), 1.37 (t, J=7.2 Hz, 3H), 1.22 (t, J=7.0 Hz, 3H).

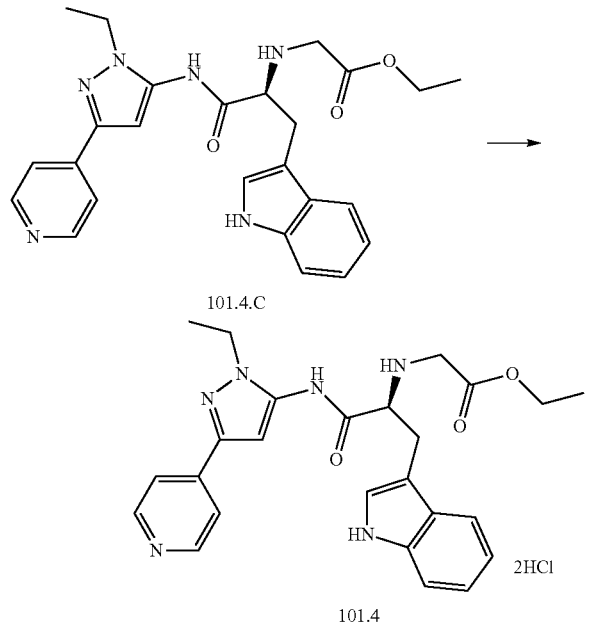

Ethyl 2-((S)-1-(1-ethyl-3-(pyridin-4-yl)-1H-pyrazol-5-ylamino)-3-(1H-indol-3-yl)-1-oxopropan-2-ylamino)acetate dihydrochloride (101.4)

The title compound was prepared from 101.4.C according to the procedure described in Example 101.1. The crude product was purified to give 101.4 (63 mg, 100% yield) as colorless crystals. LCMS ESI (pos.) m/e: 461 (M+H).

7.86.5 Example 101.5

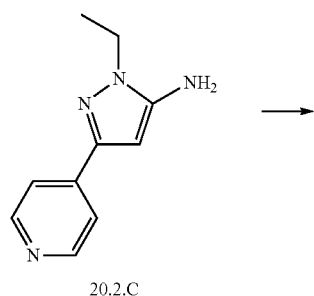

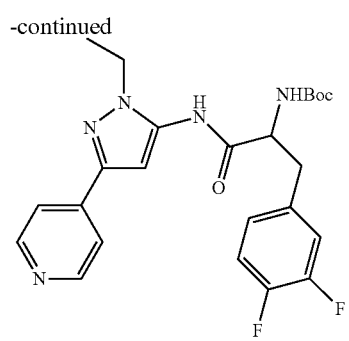

Tert-butyl (S)-1-(1-ethyl-3-(pyridin-4-yl)-1H-pyrazol-5-ylamino)-3-(3,4-difluorophenyl)-1-oxopropan-2-ylcarbamate (101.5.A)

The title compound was prepared from 20.2.0 and Boc-L-3,4-difluorophenylalanine according to the procedure described in Example 101.1.A. The crude product was purified to give 101.5.A (612 mg, 79% yield) as colorless powder. 1H NMR (400 MHz, CDCl3) δ ppm 9.06 (s, 1H), 8.58 (d, J=6.2 Hz, 2H), 7.65 (d, J=6.2 Hz, 2H), 7.16-7.09 (m, 2H), 7.00-6.98 (m, 1H), 6.72 (s, 1H), 5.27 (d, J=7.4 Hz, 1H), 4.46 (dd, J=14.8, 7.4 Hz, 1H), 4.03 (q, J=7.2 Hz, 2H), 3.23 (dd, J=14.3, 6.9 Hz, 1H), 3.09 (dd, J=14.3, 7.5 Hz, 1H), 1.46 (s, 9H), 1.42 (t, J=7.2 Hz, 3H).

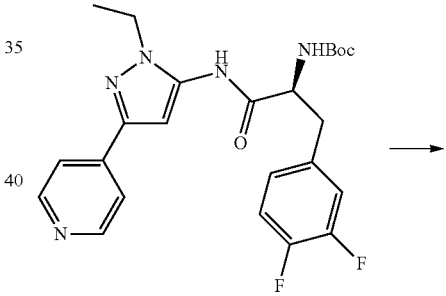

(S)-2-Amino-N-(1-ethyl-3-(pyridin-4-yl)-1H-pyrazol-5-yl)-3-(3,4-difluorophenyl)propanamide (101.5.B)

The title compound was prepared from 101.5.A according to the procedure described in Example 101.1.B. The crude product was purified to give 101.5.B (455 mg, 94% yield). 1H NMR (400 MHz, CDCl3) δ ppm 9.71 (brs, 1H), 8.60 (d, J=6.2 Hz, 2H), 7.68 (d, J=6.2 Hz, 2H), 7.18-7.07 (m, 2H), 6.99-6.96 (m, 1H), 6.85 (s, 1H), 4.07 (q, J=7.3 Hz, 2H), 3.81 (dd, J=8.3, 4.3 Hz, 1H), 3.28 (dd, J=14.0, 4.3 Hz, 1H), 3.28 (dd, J=14.0, 4.3 Hz, 1H,), 1.79 (brs, 2H), 1.46 (t, J=7.3 Hz, 3H).

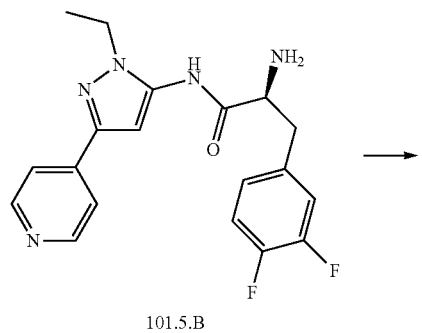

101.5.B

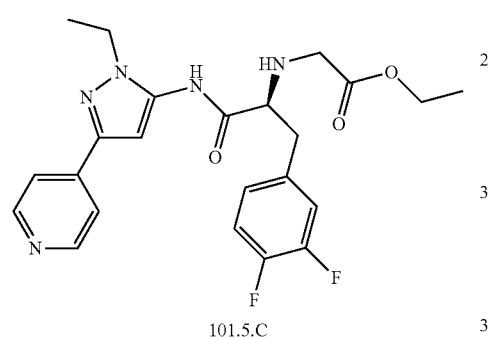

101.5.C

Ethyl 2-((S)-1-(1-ethyl-3-(pyridin-4-yl)-1H-pyrazol-5-ylamino)-3-(3,4-difluorophenyl)-1-oxopropan-2-ylamino)acetate (101.5.C)

The title compound was prepared from 101.5.B according to the procedure described in Example 101.1.C. The crude product was purified to give 101.5.0 (235 mg, 43% yield). 1H NMR (400 MHz, CDCl3) δ ppm 9.76 (s, 1H), 8.61 (d, J=6.3 Hz, 2H), 7.69 (d, J=6.3 Hz, 2H), 7.18-7.10 (m, 2H), 7.02-6.98 (m, 1H), 6.86 (s, 1H), 4.22-4.09 (m, 4H), 3.52 (dd, J=8.2, 4.5 Hz, 1H), 3.46 (d, J=17.6 Hz, 1H), 3.36 (d, J=17.6 Hz, 1H), 3.29 (dd, J=14.1, 4.5 Hz, 1H), 3.00 (dd, J=14.1, 8.2 Hz, 1H,), 1.45 (t, J=7.2 Hz, 3H), 1.26 (t, J=7.1 Hz, 3H).

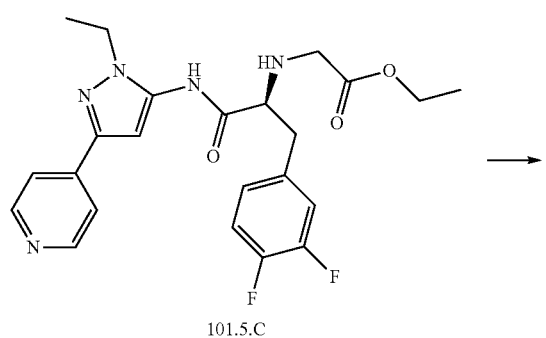

101.5.C

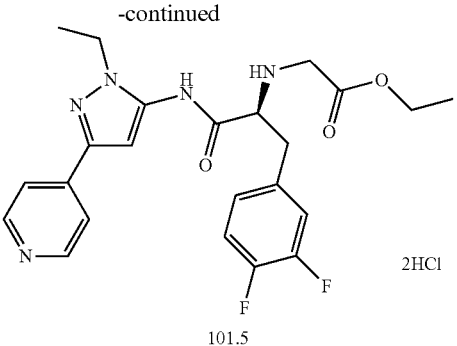

101.5

Ethyl 2-((S)-1-(1-ethyl-3-(pyridin-4-yl)-1H-pyrazol-5-ylamino)-3-(3,4-difluorophenyl)-1-oxopropan-2-ylamino)acetate dihydrochloride (101.5)

The title compound was prepared from 101.5.0 according to the procedure described in Example 101.1. The crude product was purified to give 101.5 (100 mg, 98% yield) as colorless amorphous. LCMS ESI (pos.) m/e: 531 (M+H).

7.86.6 Example 101.6

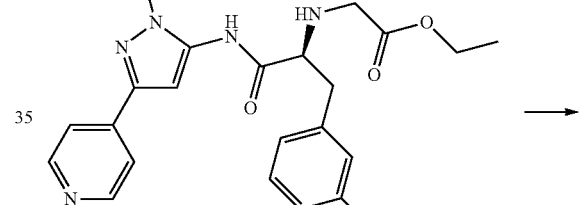

101.5.C

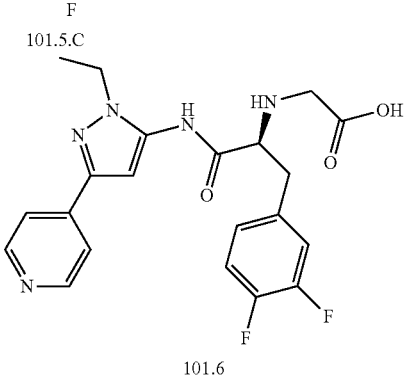

101.6

(S)-2-(1-(1-Ethyl-3-(pyridin-4-yl)-1H-pyrazol-5-ylamino)-3-(3,4-difluorophenyl)-1-oxopropan-2-ylamino)acetic acid (101.6)

The title compound was prepared from 101.5.0 according to the procedure described in Example 101.2. The crude product was purified to give 101.6 (125 mg, 91% yield) as colorless powder. LCMS ESI (pos.) m/e: 423 (M+H); 1H NMR (400 MHz, DMSO-d6) δ ppm 8.57 (d, J=5.8 Hz, 2H), 7.73 (d, J=5.9 Hz, 2H), 7.43-7.34 (m, 2H), 7.14-7.12 (m, 1H), 6.80 (s, 1H), 3.96 (q, J=7.0 Hz, 2H), 3.66 (dd, J=6.8, 6.9 Hz, 1H), 3.30 (d, J=17.6 Hz, 1H), 3.25 (d, J=17.2 Hz, 1H), 3.01 (dd, J=13.8, 6.5 Hz, 1H), 2.93 (dd, J=13.7, 6.9 Hz, 1H), 1.26 (t, J=7.2 Hz, 3H).

7.87 Example 102

7.87.1 Example 102.1

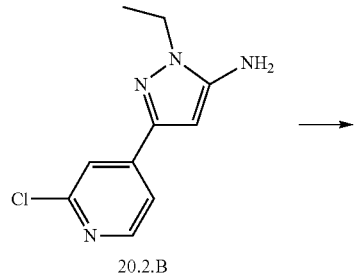

20.2.B

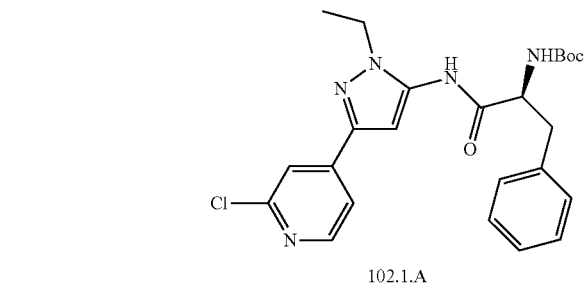

102.1.A

Tert-butyl (S)-1-(3-(2-chloropyridin-4-yl)-1-ethyl-1H-pyrazol-5-ylamino)-1-oxo-3-phenylpropan-2-ylcarbamate (102.1.A)

The title compound was prepared from 20.2.B according to the procedure described in Example 101.1.A. The crude product was purified to give 102.1.A (1.09 g, 76% yield) as colorless powder. 1H NMR (400 MHz, CDCl3) δ ppm 8.79 (brs, 1H), 8.32 (d, J=5.1 Hz, 1H), 7.68 (s, 1H), 7.53 (d, J=5.1 Hz, 1H), 7.35-7.22 (m, 5H), 6.65 (s, 1H), 5.36 (brs, 1H), 4.53 (dd, J=14.4, 7.5 Hz, 1H), 3.93 (q, J=7.2 Hz, 2H), 3.25-3.13 (m, 2H), 1.44 (s, 9H), 1.36 (t, J=7.2 Hz, 3H).

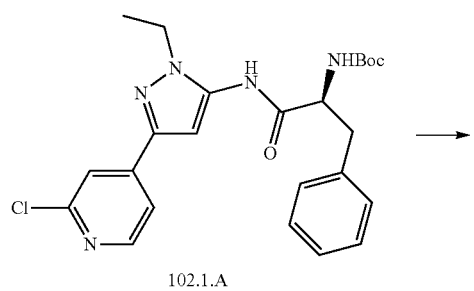

102.1.A

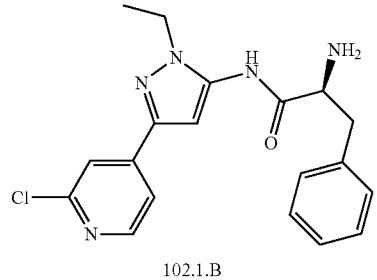

102.1.B

(S)-2-Amino-N-(3-(2-chloropyridin-4-yl)-1-ethyl-1H-pyrazol-5-yl)-3-phenylpropanamide (102.1.B)

The title compound was prepared from 102.1.A according to the procedure described in Example 101.1.B. The crude product was purified to give 102.1.B (794 mg, 93% yield) as colorless oil. 1H NMR (400 MHz, CDCl3) δ ppm 9.72 (s, 1H), 8.37 (d, J=5.1 Hz, 1H), 7.75 (d, J=0.8 Hz, 1H), 7.60 (dd, J=5.1, 0.8 Hz, 1H,), 7.38-7.25 (m, 5H), 6.87 (s, 1H), 4.06 (q, J=7.2 Hz, 2H), 3.85 (dd, J=8.8, 4.1 Hz, 1H), 3.35 (dd, J=13.8, 4.1 Hz, 1H), 2.93 (dd, J=13.8, 8.8 Hz, 1H), 1.64 (brs, 2H), 1.45 (t, J=7.4 Hz, 3H).

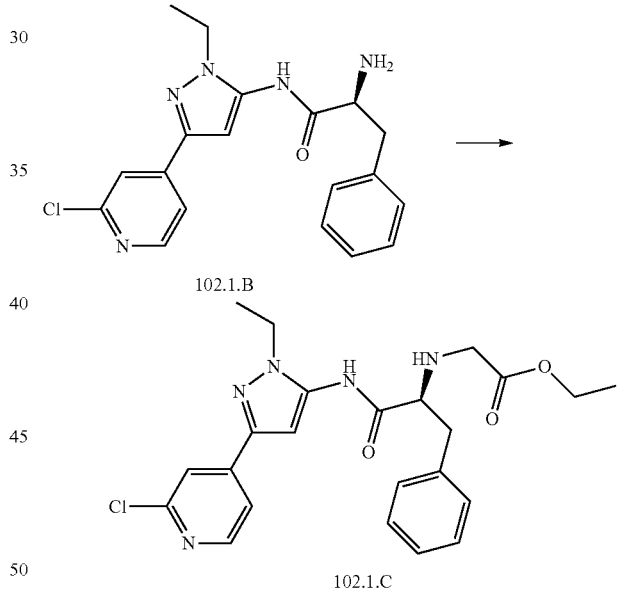

102.1.B 102.1.C

Ethyl 2-((S)-1-(3-(2-chloropyridin-4-yl)-1-ethyl-1H-pyrazol-5-ylamino)-1-oxo-3-phenylpropan-2-ylamino)acetate (102.1.C)

The title compound was prepared from 102.1.B according to the procedure described in Example 101.1.C. The crude product was purified to give 102.1.C (223 mg, 89% yield) as colorless powder. 1H NMR (400 MHz, CDCl$_3$) δ ppm 9.80 (s, 1H), 8.37 (d, J=5.1 Hz, 1H), 7.75 (d, J=1.6 Hz, 1H), 7.59 (dd, J=5.1, 1.6 Hz, 1H), 7.38-7.26 (m, 5H), 6.88 (s, 1H), 4.19-4.06 (m, 4H), 3.54 (dd, J=8.4, 4.5 Hz, 1H), 3.43 (d, J=17.6 Hz, 1H), 3.34 (dd, J=13.9, 4.5 Hz, 1H), 3.31 (d, J=17.6 Hz, 1H), 3.00 (dd, J=13.9, 8.4 Hz, 1H), 2.05 (brs, 1H), 1.43 (t, J=7.2 Hz, 3H), 1.24 (t, J=7.2 Hz, 3H).

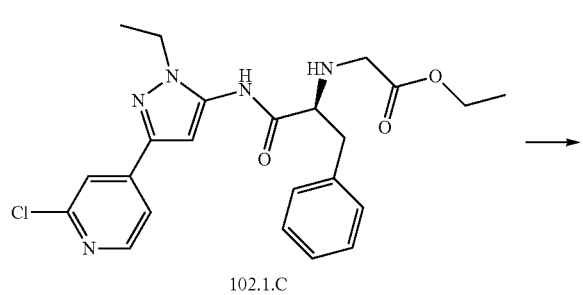

102.1.C

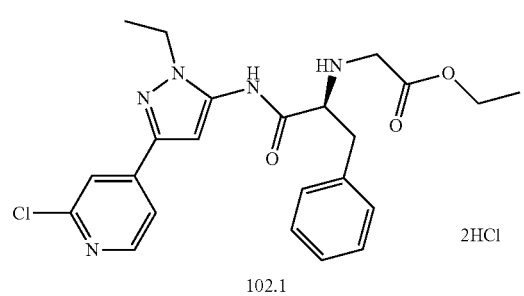

102.1 · 2HCl

Ethyl 2-((S)-1-(3-(2-chloropyridin-4-yl)-1-ethyl-1H-pyrazol-5-ylamino)-1-oxo-3-phenylpropan-2-ylamino)acetate dihydrochloride (102.1)

The title compound was prepared from 102.1.C according to the procedure described in Example 101.1. The crude product was purified to give 102.1 (80 mg, 95% yield) as colorless amorphous. LCMS ESI (pos.) m/e: 456 (M+H).

7.87.2 Example 102.2

102.1.C 102.2

(S)-2-(1-(3-(2-Chloropyridin-4-yl)-1-ethyl-1H-pyrazol-5-ylamino)-1-oxo-3-phenylpropan-2-ylamino)acetic acid (102.2)

The title compound was prepared from 102.1.C according to the procedure described in Example 101.2. The crude product was purified to give 102.2 (138 mg, 98% yield) as colorless powder. LCMS ESI (pos.) m/e: 428 (M+H); 1H NMR (400 MHz, DMSO-d6) δ ppm 8.40 (d, J=5.9 Hz, 1H), 7.82 (s, 1H), 7.76 (d, J=5.4 Hz, 1H), 7.34-7.23 (m, 5H), 6.89 (s, 1H), 3.88 (q, J=7.2 Hz, 2H), 3.66 (dd, J=7.1, 6.6 Hz, 1H), 3.29 (d, J=17.3 Hz, 1H), 3.24 (d, J=17.2 Hz, 1H), 3.01 (dd, J=13.7, 6.6 Hz, 1H), 2.94 (dd, J=13.7, 7.1 Hz, 1H), 1.24 (t, J=7.2 Hz, 3H).

7.88 Example 103

7.88.1 Example 103.1

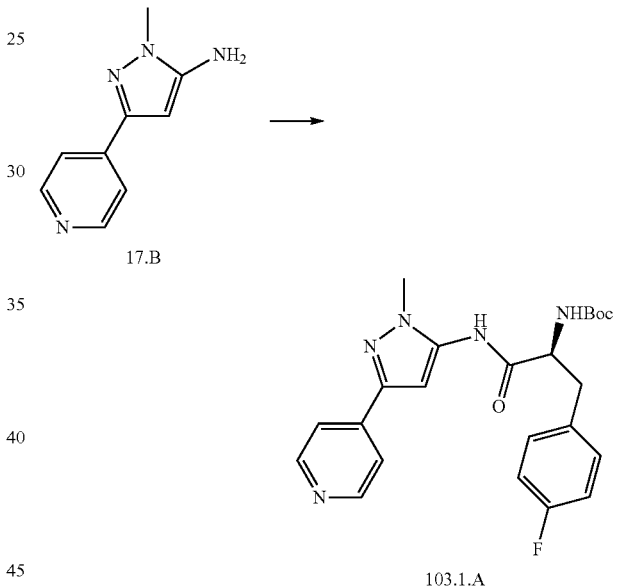

17.B 103.1.A

Tert-butyl (S)-3-(4-fluorophenyl)-1-(1-methyl-3-(pyridin-4-yl)-1H-pyrazol-5-ylamino)-1-oxopropan-2-ylcarbamate (103.1.A)

To a 100 ml flask was added 1-methyl-3-(pyridin-4-yl)-1H-pyrazol-5-amine 17.B (540 mg, 3.10 mmole), Boc-L-4-fluorophenylalanine (970 mg, 3.41 mmole), EDC (710 mg, 3.72 mmole), and 10 ml of pyridine. The reaction was stirred at room temperature for 5.5 hours at which time the solvent was removed by rotary evaporation. The residue was suspended in ethyl acetate, and washed successively with saturated sodium bicarbonate, water and brine. The organic layer was dried over anhydrous sodium sulfate, and concentrated in vacuo. The crude product was purified by silica gel chromatography to give 103.1.A (1.35 g, 99% yield) as colorless amorphous.

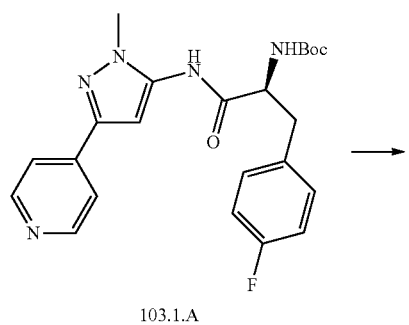

103.1.A

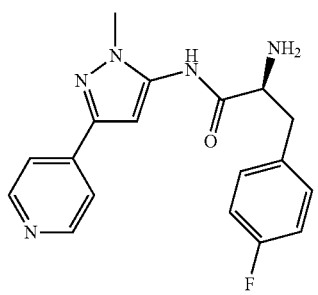

103.1.B (S)-2-Amino-3-(4-fluorophenyl)-N-(1-methyl-3-(pyridin-4-yl)-1H-pyrazol-5-yl)propanamide (103.1.B)

To a 100 ml flask was added tert-butyl (S)-3-(4-fluorophenyl)-1-(1-methyl-3-(pyridin-4-yl)-1H-pyrazol-5-ylamino)-1-oxopropan-2-ylcarbamate 103.1.A (1.35 g, 3.07 mmole), 18 ml of 4N-hydrogen chloride solution in 1,4-dioxane and 9 ml of 1,4-dioxane. The reaction was stirred at room temperature for 2 hours at which time the solvent was removed by rotary evaporation. The residue was suspended in ethyl acetate, and washed successively with saturated sodium bicarbonate, water and brine. The organic layer was dried over anhydrous sodium sulfate, and concentrated in vacuo to give 103.1.B (905 mg, 87% yield) as colorless crystals.

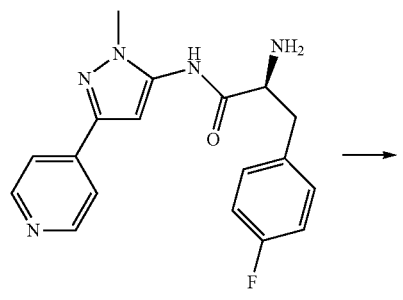

103.1.B

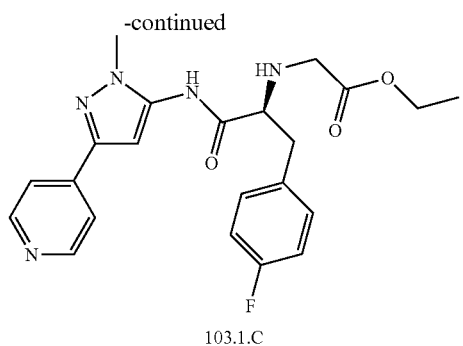

103.1.C

Ethyl 2-((S)-3-(4-fluorophenyl)-1-(1-methyl-3-(pyridin-4-yl)-1H-pyrazol-5-ylamino)-1-oxopropan-2-ylamino)acetate (103.1.C)

To a 100 ml flask was added (S)-2-amino-3-(4-fluorophenyl)-N-(1-methyl-3-(pyridin-4-yl)-1H-pyrazol-5-yl)propanamide 103.1.B (905 mg, 2.65 mmole), 5 ml of DMF and 0.69 ml of DIEA. The reaction mixture was cooled to 0° C., and then ethyl bromoacetate (0.49 g, 2.92 mmole) was added to the mixture. The reaction was stirred at room temperature overnight. After then, the solution was poured into saturated ammonium chloride, and extracted with ethyl acetate. The organic layer was washed with water and brine, and dried over anhydrous sodium sulfate. After concentration in vacuo, the residue was chromatographed on silica gel to give 103.1.C (552 mg, 49% yield) as orange syrup.

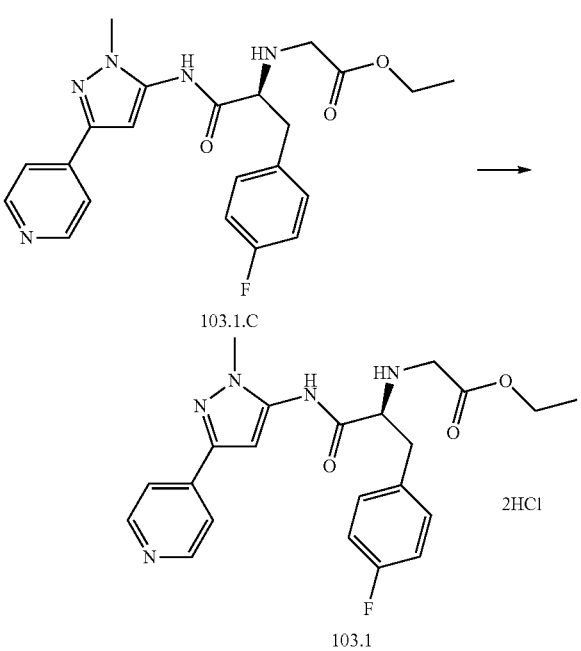

103.1.C 103.1

Ethyl 2-((S)-3-(4-fluorophenyl)-1-(1-methyl-3-(pyridin-4-yl)-1H-pyrazol-5-ylamino)-1-oxopropan-2-ylamino)acetate dihydrochloride (103.1)

To a 25 ml flask was added ethyl 2-((S)-3-(4-fluorophenyl)-1-(1-methyl-3-(pyridin-4-yl)-1H-pyrazol-5-ylamino)-

1-oxopropan-2-ylamino)acetate 103.1.C (199 mg, 0.47 mmole) and 1 ml of 1,4-dioxane. To the solution, 1 ml of 4N-hydrogen chloride solution in 1,4-dioxane (4 mmol) was added at 0° C. After then, the solvent was removed by rotary evaporation. The crude product was dried under a high vacuum to give 103.1 (221 mg, 95% yield) as colorless amorphous. LCMS ESI (pos.) m/e: 426 (M+H): 1H NMR (400 MHz, DMSO-d6) δ ppm 11.5 (brs, 1H), 8.86 (d, J=7.0 Hz, 2H), 8.33 (d, J=6.7 Hz, 2H), 7.42 (dd, J=8.6, 5.4 Hz, 2H), 7.20 (t, J=8.8 Hz, 2H), 7.15 (s, 1H), 4.65 (t, J=7.2 Hz, 1H), 4.01 (s, 2H), 3.74 (s, 3H), 3.62 (brs, 1H), 3.44 (q, J=7.0 Hz, 2H), 3.41 (dd, J=12.1, 6.6 Hz, 1H), 3.26 (dd, J=13.7, 8.6 Hz, 1H), 1.06 (t, J=6.8 Hz, 3H).

7.88.2 Example 103.2

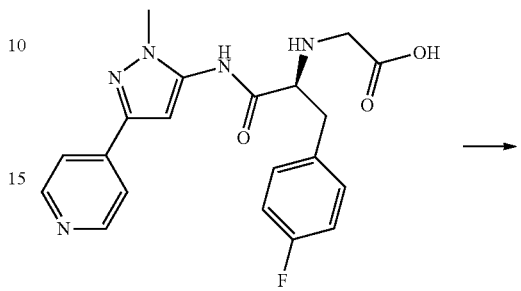

103.1.C

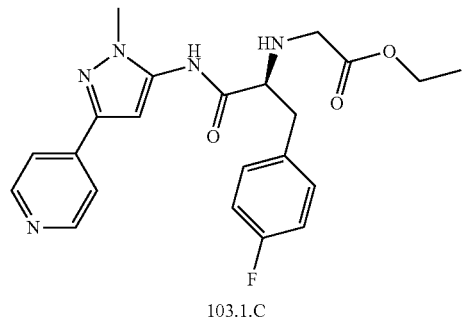

103.2

2-((S)-3-(4-Fluorophenyl)-1-(1-methyl-3-(pyridin-4-yl)-1H-pyrazol-5-ylamino)-1-oxopropan-2-ylamino) acetic acid (103.2)

To a 25 ml flask was added ethyl 2-((S)-3-(4-fluorophenyl)-1-(1-methyl-3-(pyridin-4-yl)-1H-pyrazol-5-ylamino)-1-oxopropan-2-ylamino)acetate 103.1.C (331 mg, 0.78 mmole), lithium hydroxide monohydrate (65.3 mg, 1.56 mmole), 1 ml of water and 6 ml of tetrahydrofuran. After 3 hours, 0.78 ml of 2N-hydrogen chloride solution was added to neutralize. The solvent was removed by rotary evaporation. The crude product was purified by silica gel chromatography to give 103.2 (268 mg, 87% yield) as colorless amorphous. LCMS ESI (pos.) m/e: 398 (M+H); 1H NMR (400 MHz, DMSO-d6) δ ppm 8.57 (d, J=5.5 Hz, 2H), 7.72 (d, J=6.3 Hz, 2H), 7.33 (dd, J=8.4, 5.7 Hz, 2H), 7.13 (t, J=8.8 Hz, 2H), 6.81 (s, 1H), 3.66 (s, 3H), 3.58 (t, J=6.8 Hz, 1H), 3.21 (d, J=16.9 Hz, 1H), 3.11 (d, J=17.2 Hz, 1H), 3.02 (dd, J=13.6, 5.9 Hz, 1H), 2.89 (dd, J=13.6, 7.9 Hz, 1H).

7.88.3 Example 103.3

103.2

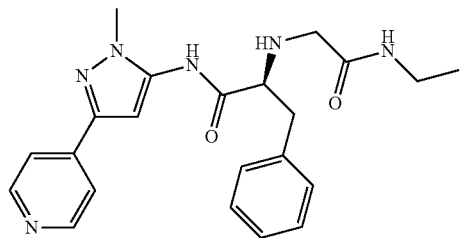

103.3

(S)-2-(Ethylcarbamoylmethylamino)-3-(4-fluorophenyl)-N-(1-methyl-3-(pyridin-4-yl)-1H-pyrazol-5-yl) propanamide (103.3)

To a 25 ml flask was added 2-((S)-3-(4-fluorophenyl)-1-(1-methyl-3-(pyridin-4-yl)-1H-pyrazol-5-ylamino)-1-oxopropan-2-ylamino)acetic acid 103.2 (145 mg, 0.36 mmole), 50% propylphosphoric anhydride in ethyl acetate (348 mg, 0.55 mmole), 0.2 ml of triethylamine and 3 ml of dichloromethane. After 20 min, ethylamine hydrochloride (60 mg, 0.73 mmole) was added to the mixture. The reaction was stirred at room temperature for 4 days. The solution was poured into saturated ammonium chloride, and extracted with ethyl acetate. The organic layer was washed with water and brine, and dried over anhydrous sodium sulfate. After concentration in vacuo, the residue was chromatographed on silica gel to give 103.3 (69 mg, 44% yield) as colorless amorphous. LCMS ESI (pos.) m/e: 425 (M+H); 1H NMR (400 MHz, DMSO-d6) δ ppm 9.91 (s, 1H), 8.58 (dd, J=17.9, 6.2 Hz, 2H), 7.63 (dd, J=19.5, 6.2 Hz, 2H), 7.25 (dd, J=9.2, 6.0 Hz, 2H), 7.05 (t, J=7.7 Hz, 2H), 6.82 (s, 1H), 5.79 (brs, 1H), 3.81 (s, 3H), 3.46 (dd, J=8.6, 4.7 Hz, 1H), 3.31-3.17 (m, 3H), 3.21 (d, J=2.8 Hz, 2H), 2.92 (dd, J=14.1, 8.6 Hz, 1H), 1.09 (t, J=7.2 Hz, 3H).

7.88.4 Example 103.4

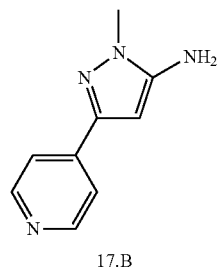

17.B

Tert-butyl (S)-3-(3,4-difluorophenyl)-1-(1-methyl-3-(pyridin-4-yl)-1H-pyrazol-5-ylamino)-1-oxopropan-2-ylcarbamate (103.4.A)

The title compound was prepared from Boc-L-3,4-difluorophenylalanine according to the procedure described in Example 103.1.A. The crude product was purified to give 103.4.A (1.20 g, 70% yield) as colorless powder. 1H NMR (400 MHz, CDCl3) δ ppm 9.09 (brs, 1H), 8.58 (d, J=6.2 Hz, 2H), 7.64 (d, J=6.2 Hz, 2H), 7.16-7.08 (m, 2H), 7.00-6.98 (m, 1H), 6.71 (s, 1H), 5.26 (d, J=7.4 Hz, 1H), 4.47 (q, J=7.5 Hz, 1H), 3.75 (s, 3H), 3.23 (dd, J=14.0, 7.0 Hz, 1H), 3.08 (dd, J=14.1, 7.4 Hz, 1H), 1.46 (s, 9H).

103.4.A 103.4.B

(S)-2-Amino-3-(3,4-difluorophenyl)-N-(1-methyl-3-(pyridin-4-yl)-1H-pyrazol-5-yl)propanamide (103.4.B)

The title compound was prepared from 103.4.A according to the procedure described in Example 103.1.B. The crude product was purified to give 103.4.B (794 mg, 93% yield) as colorless powder. 1H NMR (400 MHz, CDCl3) δ ppm 9.68 (brs, 1H), 8.62 (d, J=6.3 Hz, 2H), 7.67 (d, J=6.3 Hz, 2H), 7.19-7.08 (m, 2H), 7.00-6.97 (m, 1H), 6.84 (s, 1H), 3.81 (dd, J=8.6, 4.3 Hz, 1H), 3.81 (s, 3H), 3.30 (dd, J=14.1, 4.3 Hz, 1H), 2.93 (dd, J=14.1, 8.6 Hz, 1H), 1.65 (brs, 2H).

103.4.B

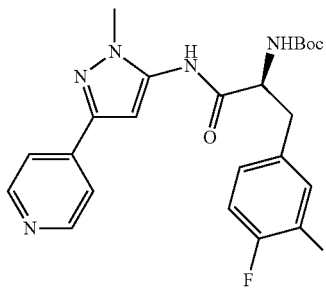

103.4.C

Ethyl 2-((S)-3-(3,4-difluorophenyl)-1-(1-methyl-3-(pyridin-4-yl)-1H-pyrazol-5-ylamino)-1-oxopropan-2-ylamino)acetate (103.4.C)

The title compound was prepared from 103.4.B according to the procedure described in Example 103.1.C. The crude product was purified to give 103.4.0 (527 mg, 54% yield) as colorless powder. 1H NMR (400 MHz, CDCl3) δ ppm 9.81 (s, 1H), 8.62 (d, J=6.2 Hz, 2H), 7.67 (d, J=6.3 Hz, 2H), 7.19-7.10 (m, 2H), 7.02-6.99 (m, 1H), 6.85 (s, 1H), 4.22-4.16 (m, 2H), 3.84 (s, 3H), 3.51 (dd, J=8.2, 4.3 Hz, 1H), 3.47 (d, J=17.6 Hz, 1H), 3.35 (d, J=17.6 Hz, 1H), 3.29 (dd, J=14.2, 4.5 Hz, 1H), 2.99 (dd, J=14.5, 8.2 Hz, 1H), 1.92 (brs, 1H), 1.26 (t, J=7.0 Hz, 3H).

103.4.C

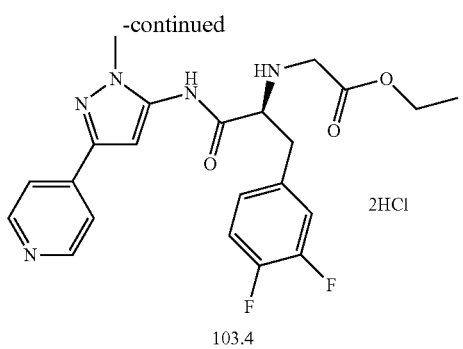

103.4

Ethyl 2-((S)-3-(3,4-difluorophenyl)-1-(1-methyl-3-(pyridin-4-yl)-1H-pyrazol-5-ylamino)-1-oxopropan-2-ylamino)acetate dihydrochloride (103.4)

The title compound was prepared from 103.4.C according to the procedure described in Example 103.1. The crude product was purified to give 103.4 (273 mg, 92% yield) as colorless amorphous. LCMS ESI (pos.) m/e: 444 (M+H).

7.88.5 Example 103.5

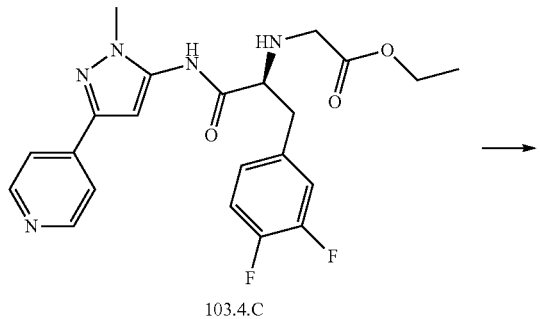

103.4.C

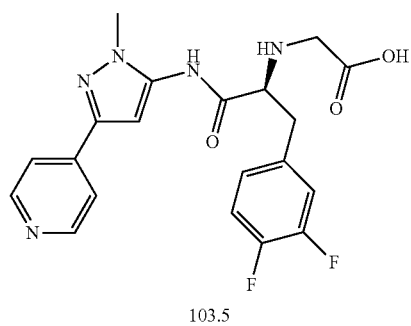

103.5

(S)-2-(3-(3,4-difluorophenyl)-1-(1-ethyl-3-(pyridin-4-yl)-1H-pyrazol-5-ylamino)-1-oxopropan-2-ylamino)acetic acid (103.5)

The title compound was prepared from 103.4.0 according to the procedure described in Example 103.2. The crude product was purified to give 103.5 (238 mg, 94% yield) as colorless powder. LCMS ESI (pos.) m/e: 416 (M+H); 1H NMR (400 MHz, DMSO-d6) δ ppm 8.57 (d, J=5.8 Hz, 2H), 7.72 (d, J=5.8 Hz, 2H), 7.43-7.34 (m, 2H), 7.15-7.14 (m, 1H), 6.81 (s, 1H), 3.67-3.63 (m, 4H), 3.29 (d, J=17.6 Hz, 1H), 3.25 (d, J=17.6 Hz, 1H), 3.02 (dd, J=13.7, 5.8 Hz, 1H), 2.91 (dd, J=13.7, 7.8 Hz, 1H).

7.89 Example 104

7.89.1 Example 104.1

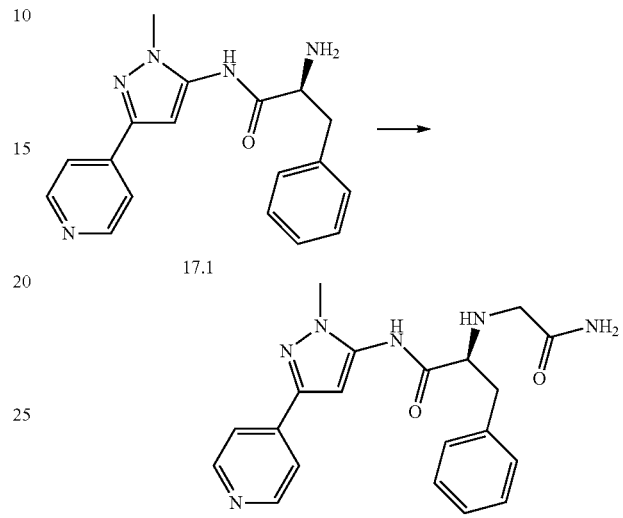

104.1

(S)-2-(Carbamoylmethylamino)-N-(1-methyl-3-(pyridin-4-yl)-1H-pyrazol-5-ylamino)-3-phenylpropanamide (104.1)

To a 25 ml flask was added (S)-2-amino-N-(1-methyl-3-(pyridin-4-yl)-1H-pyrazol-5-yl)-3-phenylpropanamide 17.1 (321 mg, 1.0 mmole), 2 ml of DMF and 0.26 ml of DIEA. The reaction mixture was cooled to 0° C., and then 2-bromoacetamide (152 mg, 1.1 mmole) was added to the mixture. The reaction was stirred at room temperature for 4 days. After then, the solvent was removed by rotary evaporation. The crude product was chromatographed on silica gel (eluent: dichloromethane/methanol=10/1). Then, the residue was chromatographed again on cosmosil (eluent: acetonitrile/water=¼) to give 104.1 (112 mg, 30% yield) as colorless amorphous. LCMS ESI (pos.) m/e: 379 (M+H); 1H NMR (400 MHz, DMSO-d6) δ ppm 9.76 (s, 1H), 8.60 (d, J=6.3 Hz, 2H), 7.67 (d, J=6.3 Hz, 2H), 7.38-7.28 (m, 5H), 6.82 (s, 1H), 5.90 (brs, 1H), 5.39 (brs, 1H), 3.79 (s, 3H), 3.56 (dd, J=8.6, 4.7 Hz, 1H), 3.34 (d, J=16.8 Hz, 1H), 3.30 (dd, J=14.6, 4.5 Hz, 1H), 3.26 (d, J=16.8 Hz, 1H), 2.96 (dd, J=13.9, 8.8 Hz, 1H).

7.89.2 Examples 104.2-104.7

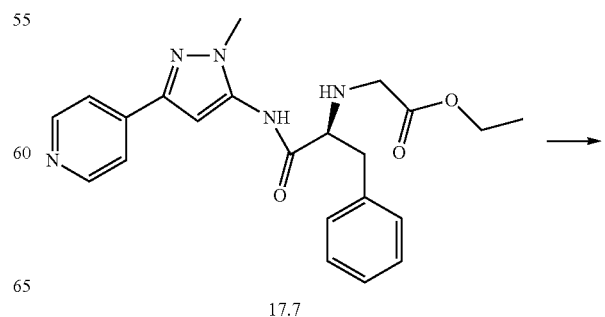

17.7

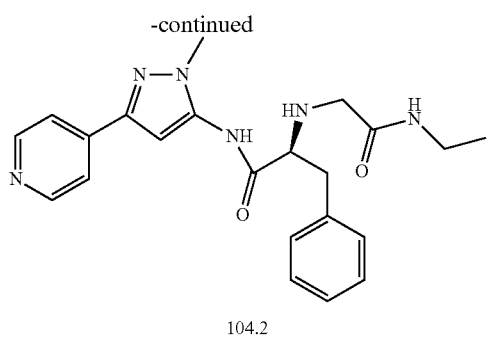

104.2

(S)-2-(Ethylcarbamoylmethylamino)-N-(1-methyl-3-(pyridin-4-yl)-1H-pyrazol-5-yl)-3-phenylpropanamide (104.2)

To a 25 ml flask was added ethylamine hydrochloride (245 mg, 3.00 mmole) and 7 ml of dichloromethane. Trimethylaluminum (1.0M in hexane, 6.0 ml, 6.0 mmole) was added to the solution at room temperature. After 10 min, a solution of ethyl 2-((S)-1-(1-methyl-3-(pyridin-4-yl)-1H-pyrazol-5-ylamino)-1-oxo-3-phenylpropan-2-ylamino)acetate 17.7 (408 mg, 1.00 mmole) in 3 ml of dichloromethane was added to the reaction mixture. The reaction was stirred at room temperature overnight. After then, the solution was poured into saturated ammonium chloride, and extracted with ethyl acetate. The organic layer was washed with water and brine, and dried over anhydrous sodium sulfate. After concentration in vacuo, the residue was chromatographed on silica gel to give 104.2 (283 mg, 70% yield) as colorless amorphous. LCMS ESI (pos.) m/e: 407 (M+H); 1H NMR (400 MHz, CDCl3) δ ppm 9.76 (s, 1H), 8.61 (d, J=6.3 Hz, 2H), 7.66 (d, J=6.2 Hz, 2H), 7.38-7.29 (m, 5H), 6.82 (s, 1H), 5.80 (brs, 1H), 3.79 (s, 3H), 3.49 (brs, 1H), 3.29-3.20 (m, 5H), 2.93 (dd, J=13.6, 8.9 Hz, 1H), 2.14 (brs, 1H), 1.07 (t, J=7.2 Hz, 3H).

The following compounds were prepared according to the procedure described herein for 104.2 preparation using appropriate amine

TABLE 1

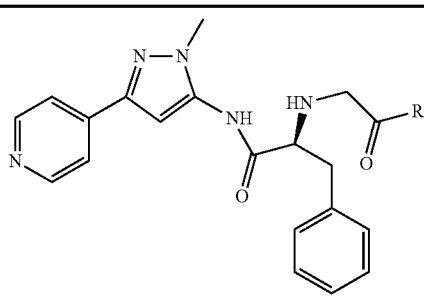

| Compound | R | Compound | R |
|---|---|---|---|
| 104.3 | —NHMe | 104.4 | —NMe₂ |
| 104.5 | —NHPr | 104.6 | —NHiPr |
| 104.7 | —NHcPr | | |

(S)—N-(1-Methyl-3-(pyridin-4-yl)-1H-pyrazol-5-yl)-2-(methylcarbamoylmethylamino)-3-phenylpropanamide (104.3)

LCMS ESI (pos.) m/e: 393 (M+H): 1H NMR (400 MHz, CDCl3) δ ppm 9.84 (s, 1H), 8.60 (d, J=6.3 Hz, 2H), 7.65 (d, J=6.3 Hz, 2H), 7.39-7.28 (m, 5H), 6.81 (s, 1H), 5.92 (d, J=5.1 Hz, 1H), 3.78 (s, 3H), 3.47 (dd, J=9.2, 4.5 Hz, 1H), 3.23 (dd, J=14.6, 5.2 Hz, 1H), 3.23 (d, J=15.6 Hz, 1H), 3.16 (d, J=16.4 Hz, 1H), 2.90 (dd, J=13.7, 9.0 Hz, 1H), 2.68 (d, J=5.1 Hz, 3H), 2.05 (brs, 1H).

(S)—N-(1-Methyl-3-(pyridin-4-yl)-1H-pyrazol-5-yl)-2-(dimethylcarbamoylmethylamino)-3-phenylpropanamide (104.4)

LCMS ESI (pos.) m/e: 407 (M+H): 1H NMR (400 MHz, CDCl3) δ ppm 10.2 (s, 1H), 8.61 (d, J=5.9 Hz, 2H), 7.67 (d, J=5.9 Hz, 2H), 7.68-7.66 (m, 5H), 6.88 (s, 1H), 3.79 (s, 3H), 3.53 (dd, J=8.2, 4.3 Hz, 1H), 3.41 (d, J=16.5 Hz, 1H), 3.33 (d, J=16.4 Hz, 1H), 3.35 (dd, J=13.9, 4.5 Hz, 1H), 3.00 (dd, J=13.9, 8.4 Hz, 1H), 2.96 (s, 3H), 2.86 (s, 3H), 2.28 (brs, 1H).

(S)—N-(1-Methyl-3-(pyridin-4-yl)-1H-pyrazol-5-yl)-3-phenyl-2-(propylcarbamoylmethylamino)propanamide (104.5)

LCMS ESI (pos.) m/e: 421 (M+H): 1H NMR (400 MHz, CDCl3) δ ppm 9.92 (s, 1H), 8.60 (d, J=5.9 Hz, 2H), 7.65 (d, J=5.9 Hz, 2H), 7.38-7.29 (m, 5H), 6.80 (s, 1H), 6.02 (brs, 1H), 3.76 (s, 3H), 3.47-3.46 (m, 1H), 3.25-3.13 (m, 4H), 3.03-2.98 (m, 1H), 2.91 (dd, J=13.8, 9.1 Hz, 1H), 2.19 (brs, 1H), 1.44-1.36 (m, 2H), 0.87 (t, J=7.4 Hz, 3H).

(S)-2-(Isopropylcarbamoylmethylamino)-N-(1-methyl-3-(pyridin-4-yl)-1H-pyrazol-5-yl)-3-phenylpropanamide (104.6)

LCMS ESI (pos.) m/e: 421 (M+H): 1H NMR (400 MHz, CDCl3) δ ppm 10.2 (s, 1H), 8.58 (d, J=5.9 Hz, 2H), 7.64 (d, J=6.2 Hz, 2H), 7.36-7.28 (m, 5H), 6.78 (s, 1H), 6.16 (d, J=7.8 Hz, 1H), 3.74 (s, 3H), 3.46 (dd, J=9.0, 4.6 Hz, 1H), 3.23 (d, J=16.4 Hz, 1H), 3.18 (dd, J=13.9, 4.9 Hz, 1H), 3.07 (d, J=16.9 Hz, 1H), 2.88 (dd, J=13.9, 9.2 Hz, 1H), 1.90 (brs, 1H), 1.07 (d, J=6.2 Hz, 3H), 0.96 (d, J=6.6 Hz, 3H).

(S)-2-(Cyclopropylcarbamoylmethylamino)-N-(1-methyl-3-(pyridin-4-yl)-1H-pyrazol-5-yl)-3-phenylpropanamide (104.7)

LCMS ESI (pos.) m/e: 419 (M+H): 1H NMR (400 MHz, CDCl3) δ ppm 9.65 (s, 1H), 8.61 (d, J=5.9 Hz, 2H), 7.66 (d, J=6.2 Hz, 2H), 7.37-7.28 (m, 5H), 6.88 (s, 1H), 5.93 (brs, 1H), 3.78 (s, 3H), 3.47 (brs, 1H), 3.26 (dd, J=13.9, 4.5 Hz, 1H), 3.19 (s, 2H), 2.93 (dd, J=13.9, 8.8 Hz, 1H), 2.66 (m, 1H), 2.05 (brs, 1H), 0.77-0.73 (m, 2H), 0.41-0.38 (m, 2H).

7.89.3 Example 104.8

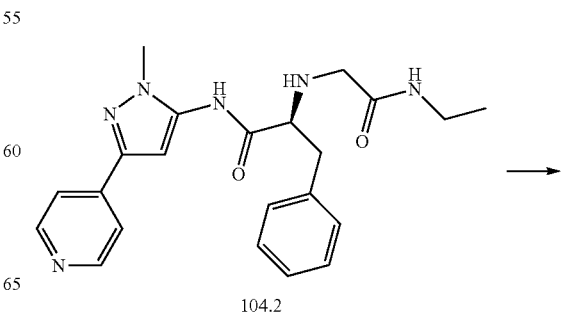

104.2

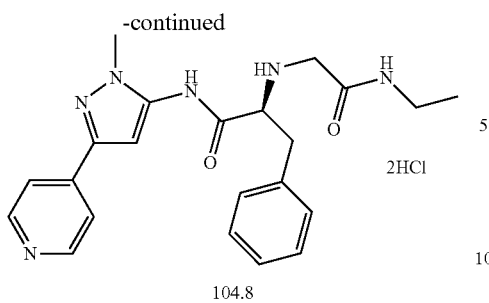

(S)-2-(Ethylcarbamoylmethylamino)-N-(1-methyl-3-(pyridin-4-yl)-1H-pyrazol-5-yl)-3-phenylpropanamide dihydrochloride (104.8)

The title compound was prepared from 104.2 according to the procedure described in Example 103.1. The crude product was purified to give 104.8 (206 mg, 100% yield) as colorless amorphous. LCMS ESI (pos.) m/e: 407 (M+H): 1H NMR (400 MHz, DMSO-d6) δ ppm 11.2 (s, 1H), 8.84 (d, J=6.7 Hz, 2H), 8.56 (t, J=5.7 Hz, 1H), 8.27 (d, J=6.7 Hz, 2H), 7.39-7.29 (m, 5H), 7.13 (s, 1H), 4.63 (dd, J=8.6, 6.3 Hz, 1H), 3.74 (s, 3H), 3.46 (q, J=8.4 Hz, 2H), 3.39 (dd, J=14.0, 6.2 Hz, 1H), 3.21 (dd, J=11.7, 7.8 Hz, 1H), 3.16 (dd, J=13.1, 6.9 Hz, 2H), 1.06 (t, J=7.2 Hz, 3H).

7.90 Example 105

7.90.1 Example 105.1

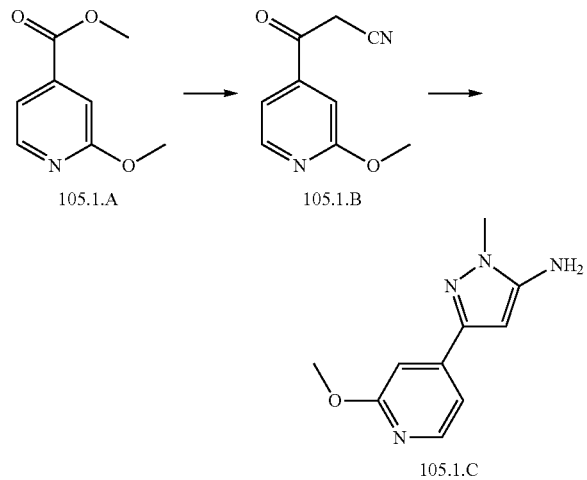

4-(2-Cyanoacetyl)-2-methoxypyridine (105.1.B)

To a 100 ml flask was added 30 ml of THF and acetonitrile (1.41 ml, 26.9 mmole). The mixture was cooled to −78° C. and then n-butyllithium (16.8 ml, 26.9 mmole, 1.6M solution in hexane) was added. The reaction was stirred for 30 minutes at which time 5 ml of a THF solution of methyl 2-methoxy-isonicotinate 105.1.A (1.50 g, 9.0 mmole) was added. After 3 hours at −78° C., the reaction mixture was quenched by 1.7 ml of acetic acid, and was warmed to room temperature. The solvent was removed by rotary evaporation and the crude was purified on a silica gel column to give 105.1.B (676 mg, 43% yield) as orange crystals.

5-Amino-3-(2-methoxypyridin-4-yl)-1-methyl-1H-pyrazol (105.1C)

To a 100 ml flask was added 4-(2-cyanoacetyl)-2-methoxy-pyridine 105.1.B, (676 mg, 3.84 mmole), methyl hydrazine (212 mg, 4.60 mmole) and 10 ml of ethanol. The reaction was stirred at reflux for 1.5 hours at which time the solvent was removed by rotary evaporation. The crude product was purified on a silica gel column to give 105.1.C (515 mg, 70% yield) as yellow crystals. 1H NMR (500 MHz, CDCl3) δ ppm 8.13 (d, J=5.4 Hz, 1H), 7.24 (d, J=5.3 Hz, 1H), 7.01 (s, 1H), 5.90 (s, 1H), 3.95 (s, 3H), 3.73 (s, 3H), 3.56 (brs, 2H).

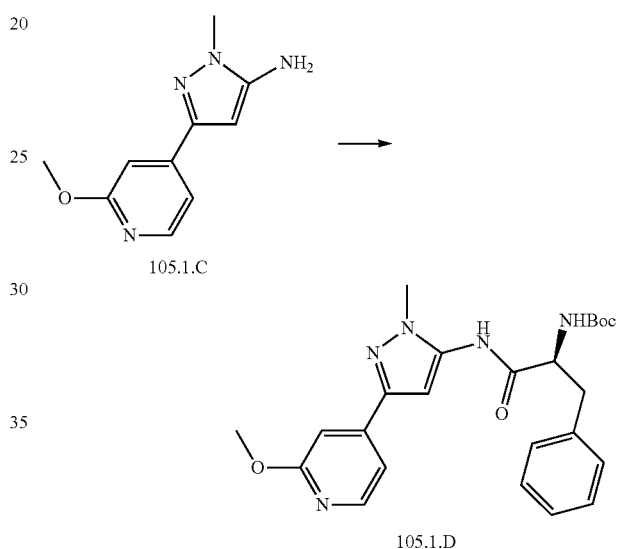

Tert-butyl (S)-1-(3-(2-methoxypyridin-4-yl)-1-methyl-1H-pyrazol-5-ylamino)-1-oxo-3-phenylpropan-2-ylcarbamate (105.1.D)

The title compound was prepared from 105.1.C according to the procedure described in Example 103.1.A. The crude product was purified to give 105.1.D (994 mg, 88% yield) as yellow amorphous.

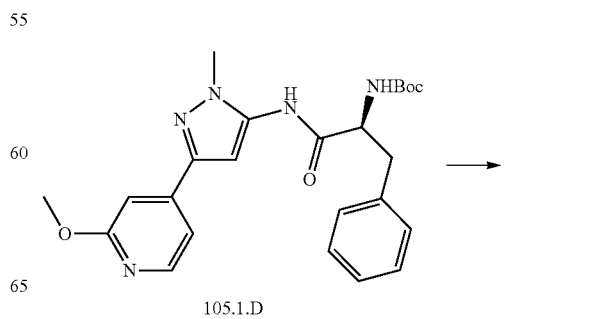

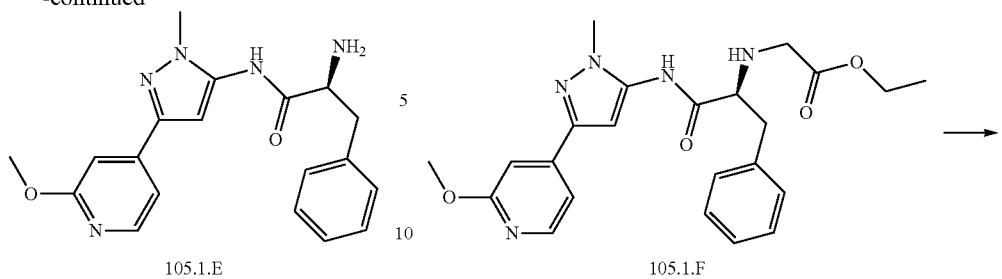

105.1.E

(S)-2-Amino-N-(3-(2-methoxypyridin-4-yl)-1-methyl-1H-pyrazol-5-yl)-3-phenylpropanamide (105.1.E)

To a 50 ml flask was added tert-butyl (S)-1-(3-(2-methoxypyridin-4-yl)-1-methyl-1H-pyrazol-5-ylamino)-1-oxo-3-phenylpropan-2-ylcarbamate 105.1.D (0.99 g, 2.19 mmole) and 20 ml of dichloromethane. To the solution, 5 ml of trifluoroacetic acid was added. The reaction was stirred at room temperature for 2.5 hours at which time the solvent was removed by rotary evaporation. The residue was suspended in ethyl acetate, and washed successively with saturated sodium bicarbonate, water and brine. The organic layer was dried over anhydrous sodium sulfate, and concentrated in vacuo to give 105.1.E (706 mg, 92% yield) as yellow solid.

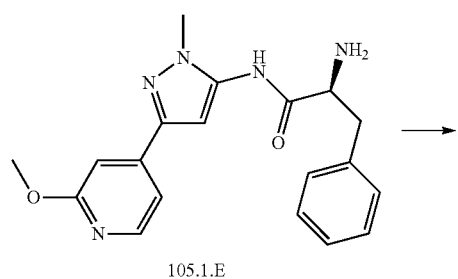

105.1.E

Ethyl 2-((S)-1-(3-(2-methoxypyridin-4-yl)-1-methyl-1H-pyrazol-5-ylamino)-1-oxo-3-phenylpropan-2-ylamino)acetate (105.1.F)

The title compound was prepared from 105.1.E according to the procedure described in Example 103.1.C. The crude product was purified to give 105.1.F (614 mg, 90% yield) as colorless crystals.

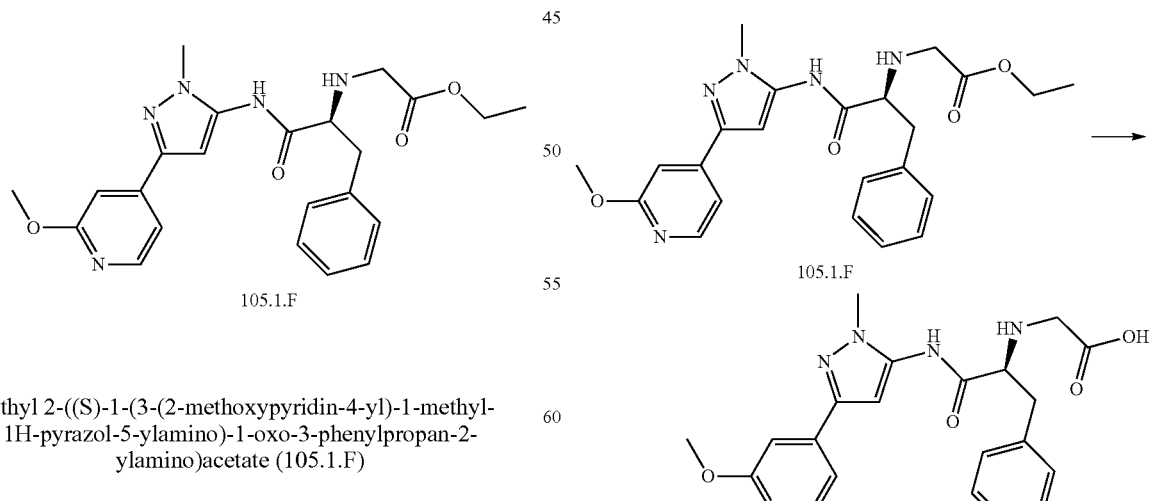

Ethyl 2-((S)-1-(3-(2-methoxypyridin-4-yl)-1-methyl-1H-pyrazol-5-ylamino)-1-oxo-3-phenylpropan-2-ylamino)acetate dihydrochloride (105.1.)

The title compound was prepared from 105.1.F according to the procedure described in Example 103.1. The crude product was purified to give 105.1 as yellow powder. LCMS ESI (pos.) m/e: 408.3 (M+H): 1H NMR (400 MHz, DMSO-d6) δ ppm 11.0 (s, 1H), 10.00 (brs, 1H), 8.19 (d, J=5.5 Hz, 1H), 7.40-7.29 (m, 6H), 7.15 (s, 1H), 6.79 (s, 1H), 4.57 (dd, J=8.4, 6.4 Hz, 1H), 4.03 (brs, 2H), 3.90 (s, 3H), 3.54 (s, 3H), 3.45 (q, J=5.2 Hz, 2H), 3.42 (dd, J=16.4, 6.6 Hz, 1H), 3.20 (dd, J=13.3, 8.6 Hz, 1H), 1.06 (t, J=7.1 Hz, 3H).

7.90.2 Example 105.2

(S)-2-(1-(3-(2-Methoxypyridin-4-yl)-1-methyl-1H-pyrazol-5-ylamino)-1-oxo-3-phenylpropan-2-ylamino)acetic acid (105.2)

The title compound was prepared from 105.1.G according to the procedure described in Example 103.2. The crude product was purified to give 105.2 as pale blue amorphous. LCMS ESI (pos.) m/e: 410 (M+H): 1H NMR (400 MHz, DMSO-d6) δ ppm 8.15 (d, J=5.5 Hz, 1H), 7.35-7.30 (m, 5H), 7.23 (d, J=4.3 Hz, 1H), 7.10 (s, 1H), 6.77 (s, 1H), 3.87 (s, 3H), 3.68 (brs, 1H), 3.68 (s, 3H), 3.16-2.89 (m, 4H).

7.91 Example 106

7.91.1 Example 106.1

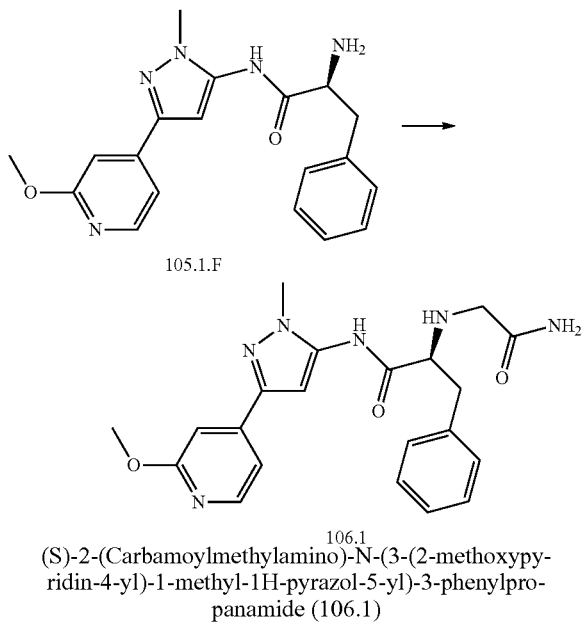

(S)-2-(Carbamoylmethylamino)-N-(3-(2-methoxypyridin-4-yl)-1-methyl-1H-pyrazol-5-yl)-3-phenylpropanamide (106.1)

The title compound was prepared from 105.1.F according to the procedure described in Example 104.1. The crude product was purified to give 106.1 (140 mg, 81% yield) as colorless crystals. LCMS ESI (pos.) m/e: 409 (M+H): 1H NMR (400 MHz, DMSO-d6) δ ppm 9.53 (s, 1H), 8.17 (d, J=5.5 Hz, 1H), 7.38-7.25 (m, 6H), 7.10 (s, 1H), 6.76 (s, 1H), 5.72 (brs, 1H), 5.31 (brs, 1H), 3.96 (s, 3H), 3.74 (s, 3H), 3.50 (dd, J=8.4, 4.9 Hz, 1H), 3.32 (d, J=16.5 Hz, 1H), 3.29 (dd, J=14.1, 5.9 Hz, 1H), 3.24 (d, J=16.8 Hz, 1H), 2.95 (dd, J=14.0, 8.6 Hz, 1H), 2.13 (brs, 1H).

7.91.2 Examples 106.2-106.4

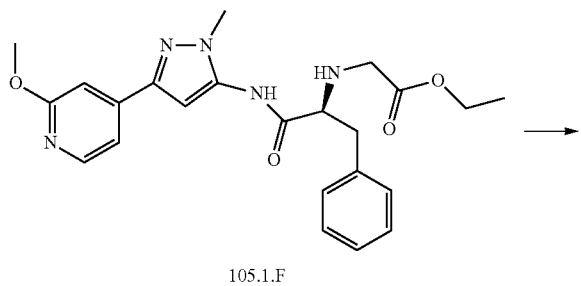

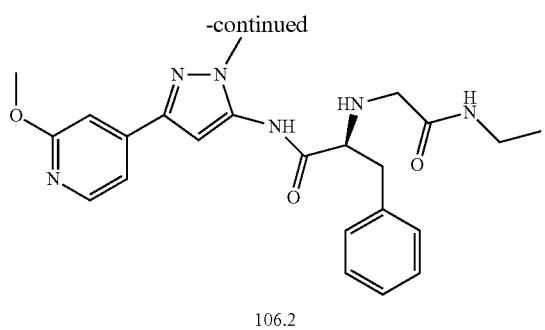

(S)-2-(Ethylcarbamoylmethylamino)-N-(3-(2-methoxypyridin-4-yl)-1-methyl-1H-pyrazol-5-yl)-3-phenylpropanamide (106.2)

The title compound was prepared from 105.1.F according to the procedure described in Example 104.2. The crude product was purified to give 106.2 (86 mg, 80% yield) as colorless crystals. LCMS ESI (pos.) m/e: 437 (M+H): 1H NMR (400 MHz, CDCl3) δ ppm 9.66 (s, 1H), 8.17 (d, J=5.5 Hz, 1H), 7.38-7.27 (m, 6H), 7.10 (s, 1H), 6.75 (s, 1H), 5.83 (brs, 1H), 3.96 (s, 3H), 3.76 (s, 3H), 3.47 (dd, J=8.5, 4.7 Hz, 1H), 3.29-3.12 (m, 5H), 2.92 (dd, J=13.9, 8.8 Hz, 1H), 2.15 (brs, 1H), 1.06 (t, J=7.2 Hz, 3H).

The following compounds were prepared according to the method described herein for 106.2 preparation using appropriate amine.

TABLE 2

| Compound | R | Compound | R |
|---|---|---|---|
| 106.3 | —N(CH2CH3)2 | 106.4 | —N(pyrrolidinyl) |

(S)-2-(Diethylcarbamoylmethylamino)-N-(3-(2-methoxypyridin-4-yl)-1-methyl-1H-pyrazol-5-yl)-3-phenylpropanamide (106.3)

1H NMR (400 MHz, CDCl3) δ ppm 10.1 (s, 1H,), 8.17 (d, J=5.5 Hz, 1H), 7.36-7.26 (m, 6H), 7.11 (s, 1H), 6.80 (s, 1H), 3.97 (s, 3H), 3.77 (s, 3H), 3.52 (dd, J=8.6, 4.3 Hz, 1H), 3.42-3.31 (m, 5H), 3.14 (q, J=7.0 Hz, 2H), 3.00 (dd, J=13.9, 8.4 Hz, 1H), 2.33 (brs, 1H), 1.11 (t, J=7.0 Hz, 6H).

(S)—N-(1-Methyl-3-(2-methoxypyridin-4-yl)-1H-pyrazol-5-yl)-3-phenyl-2-(pyrrolidin-1-ylcarbonylmethylamino)propanamide (106.4)

LCMS ESI (pos.) m/e: 463 (M+H): 1H NMR (400 MHz, CDCl3) δ ppm 10.2 (s, 1H), 8.17 (d, J=5.5 Hz, 1H), 7.36-7.26

(m, 6H), 7.11 (s, 1H), 6.82 (s, 1H), 3.97 (s, 3H), 3.79 (s, 3H), 3.54 (dd, J=8.2, 4.3 Hz, 1H), 3.46 (t, J=7.0 Hz, 2H), 3.36 (d, J=14.5 Hz, 1H), 3.35 (dd, J=14.3, 4.1 Hz, 1H), 3.25 (d, J=14.5 Hz, 1H), 3.22 (t, J=6.6 Hz, 2H), 2.99 (dd, J=13.9, 8.4 Hz, 1H), 2.25 (brs, 1H), 1.94 (quint, J=6.1 Hz, 2H), 1.85 (quint, J=6.1 Hz, 2H).

7.92 Example 107

7.92.1 Example 107.1

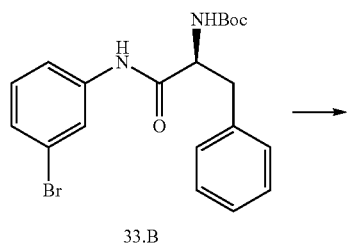

33.B (S)-2-Amino-N-(3-bromophenyl)-3-phenylpropanamide hydrochloride (107.1.A)

The title compound was prepared from 33.B according to the procedure described in Example 101.1.B. The crude product was purified to give 107.1.A (1.29 g, 93% yield) as colorless crystals. 1H NMR (400 MHz, DMSO-d6) δ ppm 10.9 (brs, 1H), 8.38 (brs, 2H), 7.87 (brs, 1H), 7.49 (brs, 1H), 7.36-7.26 (m, 5H), 4.22 (brs, 1H), 3.19 (dd, J=13.8, 6.0 Hz, 1H), 3.10 (dd, J=14.1, 7.8 Hz, 1H).

Ethyl 2-((S)-1-(3-bromophenylamino)-1-oxo-3-phenylpropan-2-ylamino)acetate (107.1.B)

The title compound was prepared from 107.1.A according to the procedure described in Example 101.1.C. The crude product was purified to give 107.1.B (870 mg, 93% yield). 1H NMR (400 MHz, CDCl3) δ ppm 9.43 (s, 1H), 7.87 (s, 1H), 7.52 (d, J=7.8 Hz, 1H), 7.37-7.18 (m, 7H), 4.17-4.10 (m, 2H), 3.47 (dd, J=9.2, 4.1 Hz, 1H), 3.32 (dd, J=13.9, 4.1 Hz, 1H), 3.32 (s 2H), 2.89 (dd, J=13.9, 9.1 Hz, 1H), 2.01 (brs, 1H), 1.22 (t, J=7.2 Hz, 3H).

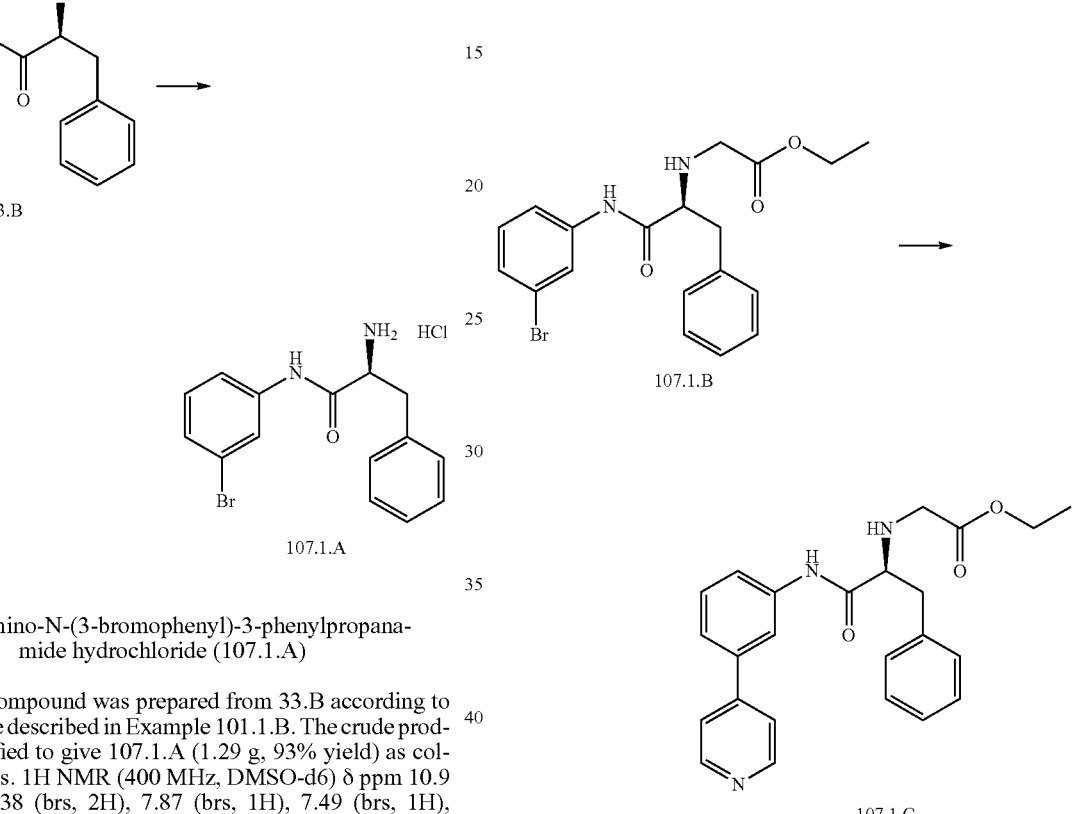

Ethyl 2-((S)-1-oxo-3-phenyl-1-(3-(pyridin-4-yl)phenylamino)propan-2-ylamino)acetate (107.1.C)

To a 25 ml of flask was added ethyl 2-((S)-1-(3-bromophenylamino)-1-oxo-3-phenylpropan-2-ylamino)acetate 107.1.B (165 mg, 0.41 mmole), pyridine-4-yl boronic acid (53 mg, 0.43 mmole), tetrakis(triphenylphosphine)palladium (94 mg, 0.081 mmole), potassium carbonate (112 mg, 0.81 mmole), 0.2 ml of water and 2 ml of N,N-dimethylacetamide. The reaction mixture was stirred at 80° C. for 5 hours. Then, the reaction mixture was diluted with ethyl acetate. The organic layer was washed with water and brine, and dried over anhydrous sodium sulfate. After concentration in vacuo, the residue was chromatographed on silica gel to give 107.1.C (26 mg, 16% yield). 1H NMR (400 MHz, CDCl3) δ ppm 9.53 (s, 1H), 8.67 (d, J=5.8 Hz, 2H), 8.01 (s, 1H), 7.70-7.27 (m, 10H), 4.17-4.10 (m, 2H), 3.50 (dd, J=9.0, 4.3 Hz, 1H), 3.36 (s, 2H,), 3.35 (dd, J=14.1, 4.3 Hz, 1H), 2.92 (dd, J=14.1, 9.0 Hz, 1H), 1.99 (brs, 1H), 1.22 (t, J=7.2 Hz, 3H).

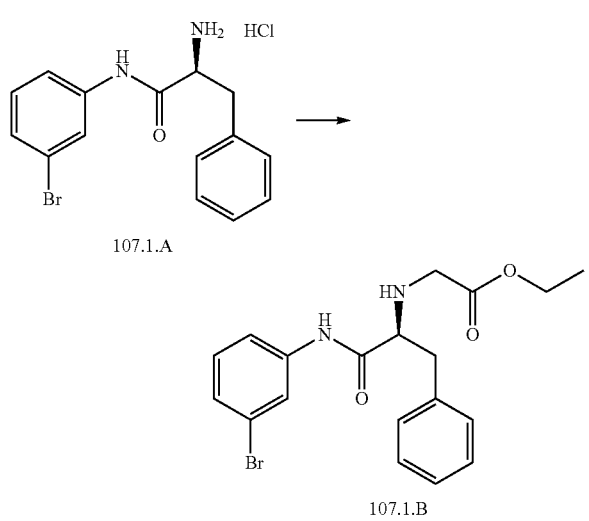

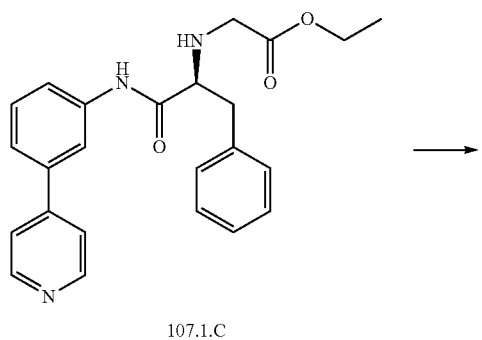

107.1.C

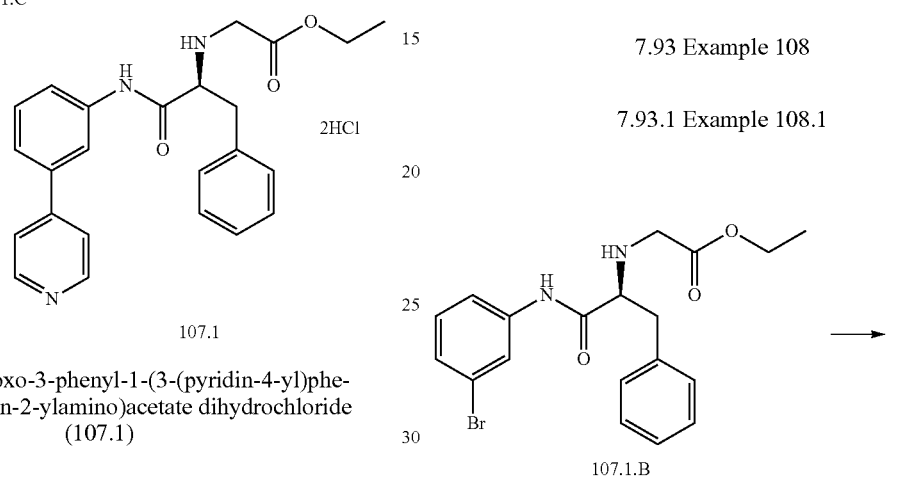

Ethyl 2-((S)-1-oxo-3-phenyl-1-(3-(pyridin-4-yl)phe-
nylamino)propan-2-ylamino)acetate dihydrochloride
(107.1)

The title compound was prepared from 107.1.C according to the procedure described in Example 101.1. The crude product was purified to give 107.1 (29 mg, 95% yield) as colorless amorphous. LCMS ESI (pos.) m/e: 404 (M+H).

7.92.2 Example 107.2

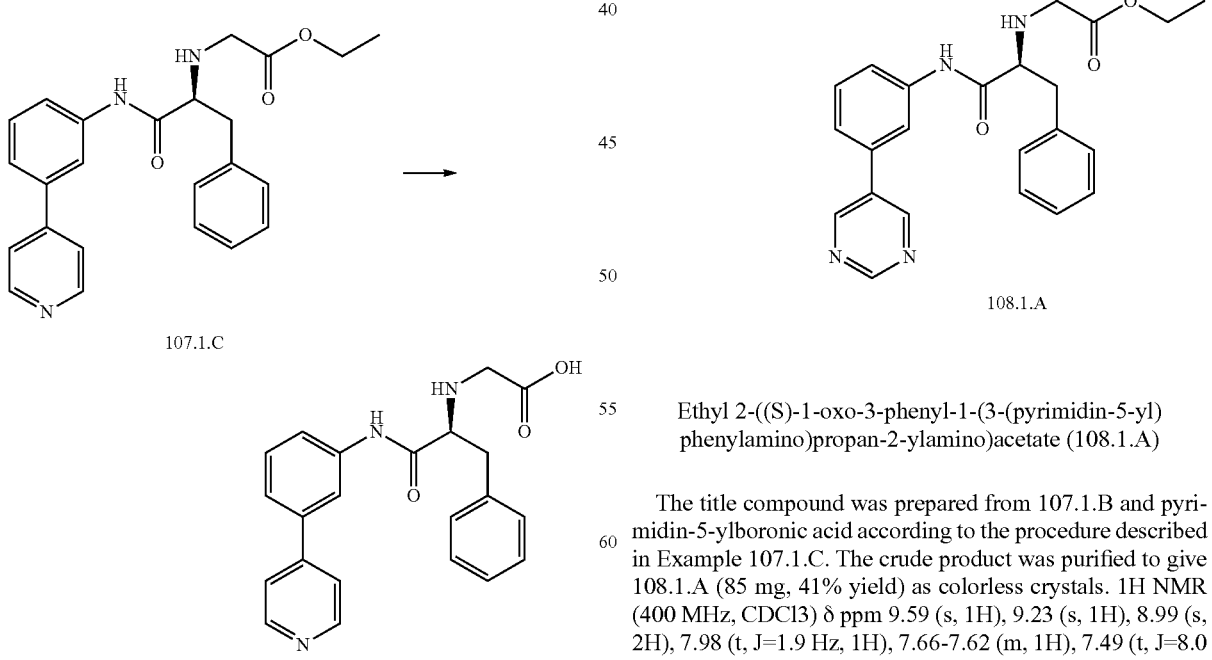

2-((S)-1-oxo-3-phenyl-1-(3-(pyridin-4-yl)pheny-
lamino)propan-2-ylamino)acetic acid (107.2)

The title compound was prepared from 107.1.C according to the procedure described in Example 101.2. The crude product was purified to give 107.2 (14 mg, 44% yield) as colorless amorphous. LCMS ESI (pos.) m/e: 376 (M+H): 1H NMR (400 MHz, DMSO-d6) δ ppm 10.24 (s, 1H), 8.66 (d, J=6.2 Hz, 2H), 8.01 (s, 1H), 7.69 (d, J=7.0 Hz, 1H), 7.64 (d, J=6.3 Hz, 2H), 7.50-7.44 (m, 2H), 7.31-7.28 (m, 4H), 7.22-7.18 (m, 1H), 3.56 (dd, J=7.0, 6.7 Hz, 2H), 3.23 (s, 2H), 3.04 (dd, J=13.7, 6.3 Hz, 1H), 2.90 (dd, J=13.5, 7.4 Hz, 1H).

7.93 Example 108

7.93.1 Example 108.1

Ethyl 2-((S)-1-oxo-3-phenyl-1-(3-(pyrimidin-5-yl)
phenylamino)propan-2-ylamino)acetate (108.1.A)

The title compound was prepared from 107.1.B and pyrimidin-5-ylboronic acid according to the procedure described in Example 107.1.C. The crude product was purified to give 108.1.A (85 mg, 41% yield) as colorless crystals. 1H NMR (400 MHz, CDCl3) δ ppm 9.59 (s, 1H), 9.23 (s, 1H), 8.99 (s, 2H), 7.98 (t, J=1.9 Hz, 1H), 7.66-7.62 (m, 1H), 7.49 (t, J=8.0 Hz, 1H), 7.37-7.27 (m, 6H), 4.17-4.12 (m, 2H), 3.51 (dd, J=9.1, 4.1 Hz, 1H), 3.36 (s, 2H), 3.35 (dd, J=14.1, 4.3 Hz, 1H), 2.92 (dd, J=14.1, 9.0 Hz, 1H), 1.22 (t, J=7.2 Hz, 3H).

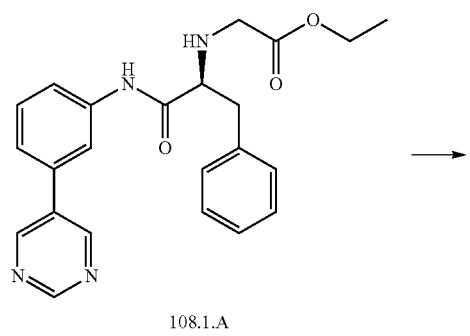

108.1.A

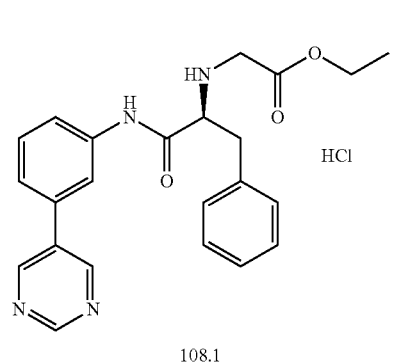

108.1

Ethyl 2-((S)-1-oxo-3-phenyl-1-(3-(pyrimidin-5-yl)phenylamino)propan-2-ylamino)acetate hydrochloride (108.1)

The title compound was prepared from 108.1.A according to the procedure described in Example 107.1. The crude product was purified to give 108.1 (30 mg, 98% yield) as light yellow amorphous. LCMS ESI (pos.) m/e: 405 (M+H).

7.93.2 Example 108.2

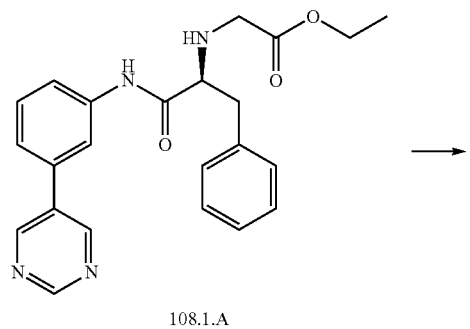

108.1.A

-continued

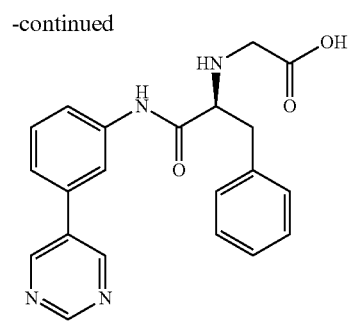

108.2

2-((S)-1-oxo-3-phenyl-1-(3-(pyrimidin-5-yl)phenylamino)propan-2-ylamino)acetic acid (108.2)

The title compound was prepared from 108.1.A according to the procedure described in Example 101.2. The crude product was purified to give 108.2 (45 mg, 83% yield) as light yellow amorphous. LCMS ESI (pos.) m/e: 377 (M+H): 1H NMR (400 MHz, DMSO-d6) δ ppm 10.21 (s, 1H), 9.21 (s, 1H), 9.08 (s, 2H), 7.94 (s, 1H), 7.75-7.72 (m, 1H), 7.50-7.48 (m, 2H), 7.31-7.28 (m, 4H), 7.22-7.19 (m, 1H), 3.57 (dd, J=7.4, 6.3 Hz, 1H), 3.23 (s, 2H), 3.05 (dd, J=13.7, 5.9 Hz, 1H), 2.90 (dd, J=13.5, 7.4 Hz, 1H).

7.94 Example 109

7.94.1 Example 109.1

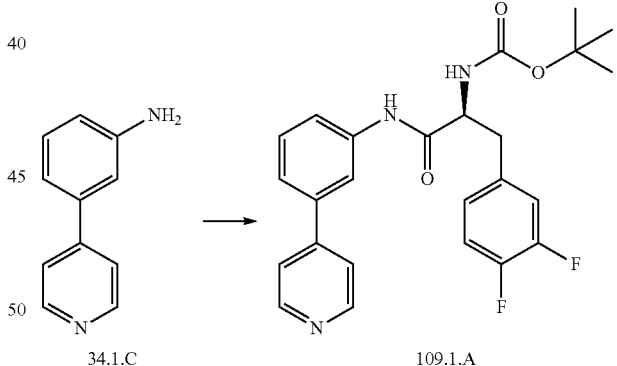

34.1.C        109.1.A

Tert-butyl (S)-3-(3,4-difluorophenyl)-1-oxo-1-(3-(pyridin-4-yl)phenylamino)propan-2-ylcarbamate (109.1.A)

The title compound was prepared from 34.1.C according to the procedure described in Example 101.1.A. The crude product was purified to give 109.1.A (436 mg, 89% yield) as colorless powder. 1H NMR (400 MHz, CDCl₃) δ ppm 8.96 (s, 1H), 8.60 (d, J=5.9 Hz, 2H), 7.77 (s, 1H), 7.43-7.39 (m, 3H), 7.29 (brs, 2H), 7.12-6.91 (m, 3H), 5.54 (d, J=8.2 Hz, 1H), 4.62 (d, J=5.8 Hz, 1H), 3.20 (dd, J=14.1, 6.2 Hz, 1H), 3.02 (dd, J=14.0, 7.9 Hz, 1H), 1.41 (s, 9H).

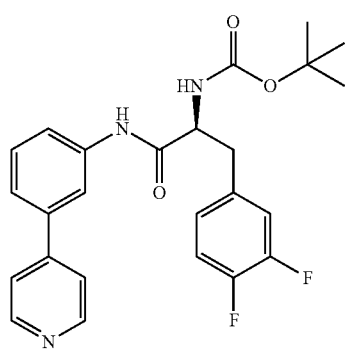

109.1.A

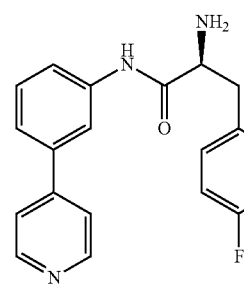

109.1.B

(S)-2-Amino-3-(3,4-difluorophenyl)-N-(3-(pyridin-4-yl)phenyl)propanamide (109.1.B)

The title compound was prepared from 109.1.A according to the procedure described in Example 101.1.B. The crude product was purified to give 109.1.B (316 mg, 93% yield). 1H NMR (400 MHz, CDCl3) δ ppm 9.60 (s, 1H), 8.66 (d, J=6.3 Hz, 2H), 7.99 (t, J=2.0 Hz, 1H), 7.62-7.58 (m, 1H), 7.53 (d, J=6.3 Hz, 2H), 7.46 (t, J=7.8 Hz, 1H), 7.41-7.38 (m, 1H), 7.16-7.07 (m, 2H), 7.00-6.96 (m, 1H), 3.75 (dd, J=9.0, 4.3 Hz, 1H), 3.31 (dd, J=14.0, 4.0 Hz, 1H), 2.86 (dd, J=14.1, 9.0 Hz, 1H), 1.73 (brs, 2H).

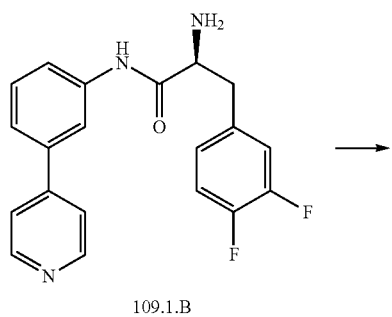

109.1.B

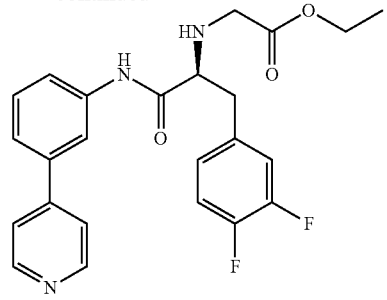

109.1.C

Ethyl 2-((S)-3-(3,4-difluorophenyl)-1-oxo-1-(3-(pyridin-4-yl)phenyl)propan-2-ylamino)acetate (109.1.C)

The title compound was prepared from 109.1.B according to the procedure described in Example 101.1.C. The crude product was purified to give 109.1.C (240 mg, 61% yield) as colorless crystals. 1H NMR (400 MHz, CDCl3) δ ppm 9.49 (s, 1H), 8.68 (d, J=5.5 Hz, 2H), 7.99 (s, 1H), 7.62 (d, J=7.8 Hz, 1H), 7.54 (d, J=5.5 Hz, 2H), 7.47 (t, J=7.8 Hz, 1H), 7.41 (d, J=6.7 Hz, 1H), 7.16-7.10 (m, 2H), 7.02-6.99 (m, 1H), 4.21-4.14 (m, 2H), 3.48 (dd, J=8.6, 4.3 Hz, 1H), 3.43 (d, J=17.6 Hz, 1H), 3.37 (d, J=17.6 Hz, 1H), 3.28 (dd, J=14.1, 4.3 Hz, 1H), 2.95 (dd, J=14.1, 8.6 Hz, 1H), 1.25 (t, J=6.6 Hz, 3H).

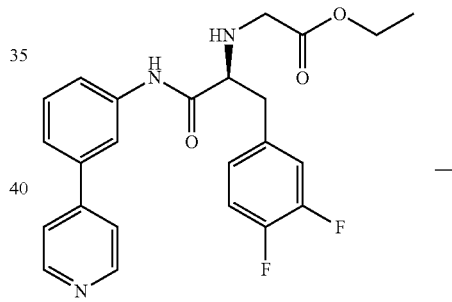

109.1.C

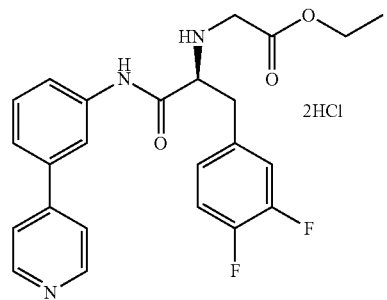

109.1

Ethyl 2-((S)-3-(3,4-difluorophenyl)-1-oxo-1-(3-(pyridin-4-yl)phenyl)propan-2-ylamino)acetate dihydrochloride (109.1)

The title compound was prepared from 109.1.C according to the procedure described in Example 101.1. The crude

7.94.2 Example 109.2

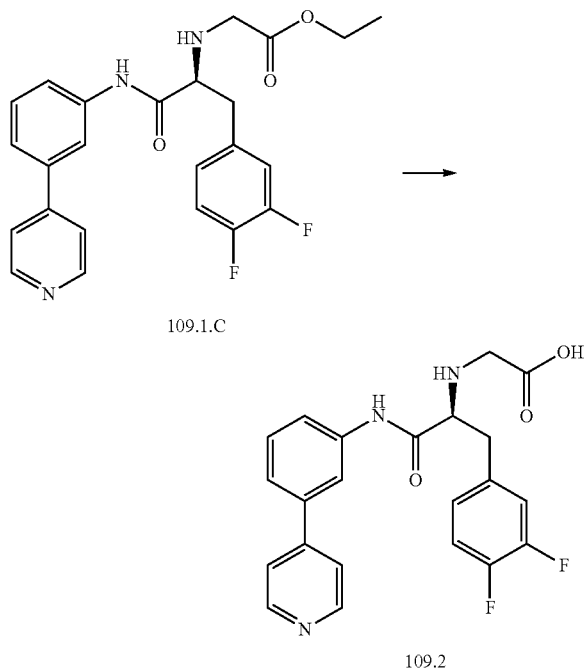

2-((S)-3-(3,4-Difluorophenyl)-1-oxo-1-(3-(pyridin-4-yl)phenylamino) propan-2-ylamino)acetic acid (109.2)

The title compound was prepared from 109.1.C according to the procedure described in Example 101.2. The crude product was purified to give 109.2 (75 mg, 59% yield) as colorless powder. LCMS ESI (pos.) m/e: 412 (M+H): ¹H NMR (400 MHz, DMSO-d6) δ ppm 10.25 (s, 1H), 8.66 (d, J=6.2 Hz, 2H), 8.01 (s, 1H), 7.68 (d, J=7.1 Hz, 1H), 7.64 (d, J=6.3 Hz, 2H), 7.51-7.45 (m, 2H), 7.41-7.29 (m, 2H), 7.13-7.11 (m, 1H), 3.56 (dd, J=7.7, 6.2 Hz, 1H), 3.24 (s, 2H), 3.02 (dd, J=13.5, 6.0 Hz, 1H), 2.89 (dd, J=13.3, 7.8 Hz, 1H).

7.95 Example 110

7.95.1 Example 110.1

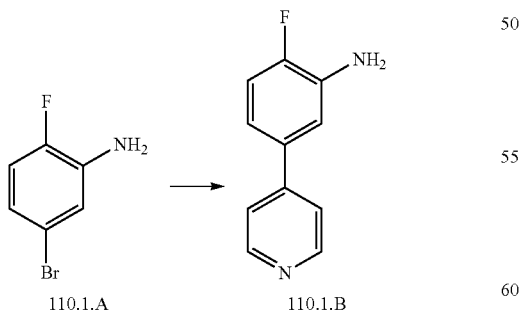

2-Fluoro-5-(pyridin-4-yl)aniline (110.1.B)

The title compound was prepared from 110.1.A according to the procedure described in Example 107.1.C. The crude product was purified to give 110.1.B (817 mg, 76% yield) as pale yellow solid. 1H NMR (400 MHz, CDCl₃) δ ppm 8.63 (d, J=6.3 Hz, 2H), 7.43 (d, J=6.3 Hz, 2H), 7.09 (dd, J=10.8, 8.4 Hz, 1H), 7.04 (dd, J=8.4, 2.2 Hz, 1H), 6.98-6.94 (m, 1H), 3.88 (brs, 2H).

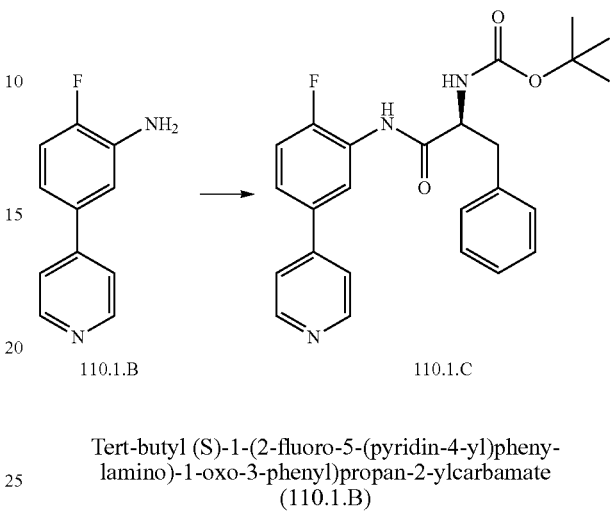

Tert-butyl (S)-1-(2-fluoro-5-(pyridin-4-yl)phenylamino)-1-oxo-3-phenyl)propan-2-ylcarbamate (110.1.B)

The title compound was prepared from 110.1.B according to the procedure described in Example 101.1.A. The crude product was purified to give 110.1.C (539 mg, 60% yield) as colorless powder. 1H NMR (400 MHz, CDCl3) δ ppm 8.66-8.64 (m, 3H), 8.37 (brs, 1H), 7.48 (d, J=5.8 Hz, 2H), 7.34-7.25 (m, 6H), 7.15 (dd, J=10.2, 8.6 Hz, 1H), 5.19 (d, J=5.1 Hz, 1H), 4.59 (s, 1H), 3.26-3.14 (m, 2H), 1.26 (s, 9H).

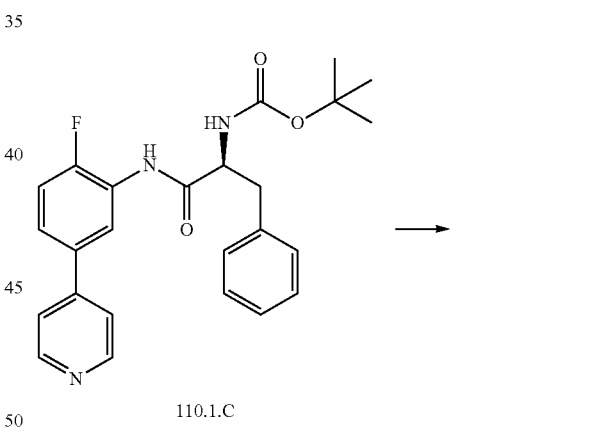

(S)-2-Amino-N-(2-fluoro-5-(pyridin-4-yl)phenyl)-3-phenylpropanamide (110.1.D)

The title compound was prepared from 110.1.C according to the procedure described in Example 101.1.B. The crude product was purified to give 110.1.D (337 mg, 81% yield). 1H NMR (400 MHz, CDCl3) δ ppm 9.96 (s, 1H), 8.84 (dd, J=7.4, 2.4 Hz, 1H), 8.66 (d, J=6.3 Hz, 2H), 7.53 (d, J=5.9 Hz, 2H), 7.38-7.25 (m, 6H), 7.21 (dd, J=10.4, 8.4 Hz, 1H), 3.80 (dd, J=9.7, 3.9 Hz, 1H), 3.42 (dd, J=13.7, 3.9 Hz, 1H), 2.82 (dd, J=13.8, 9.5 Hz, 1H), 1.68 (brs, 2H).

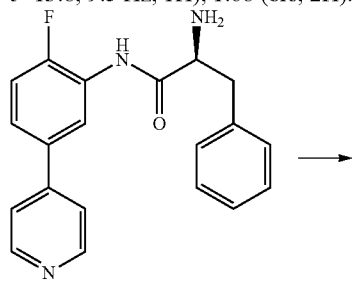

110.1.D

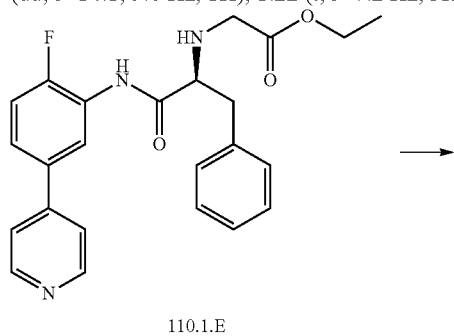

110.1.E

Ethyl 2-((S)-1-(2-fluoro-5-(pyridin-4-yl)phenylamino)-1-oxo-3-phenylpropan-2-ylamino)acetate (110.1.E)

The title compound was prepared from 110.1.D according to the procedure described in Example 101.1.C. The crude product was purified to give 110.1.E (184 mg, 43% yield). 1H NMR (400 MHz, CDCl3) δ ppm 9.64 (s, 1H), 8.77 (dd, J=7.4, 2.3 Hz, 1H), 8.67 (d, J=6.2 Hz, 2H), 7.53 (d, J=6.2 Hz, 2H), 7.37-7.27 (m, 6H), 7.21 (dd, J=10.2, 8.6 Hz, 1H), 4.16-4.10 (m, 2H), 3.54 (dd, J=9.0, 4.3 Hz, 1H), 3.44 (d, J=17.6 Hz, 1H), 3.34 (dd, J=14.3, 4.5 Hz, 1H), 3.30 (d, J=17.2 Hz, 1H), 2.95 (dd, J=14.1, 9.0 Hz, 1H), 1.22 (t, J=7.2 Hz, 3H).

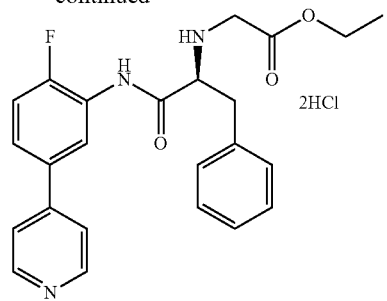

110.1

Ethyl 2-((S)-1-(2-fluoro-5-(pyridin-4-yl)phenylamino)-1-oxo-3-phenylpropan-2-ylamino)acetate dihydrochloride (110.1)

The title compound was prepared from 110.1.E according to the procedure described in Example 101.1. The crude product was purified to give 110.1 (70 mg, 96% yield) as light yellow solid.

7.95.2 Example 110.2

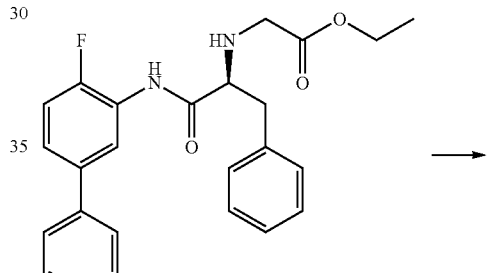

110.1.E

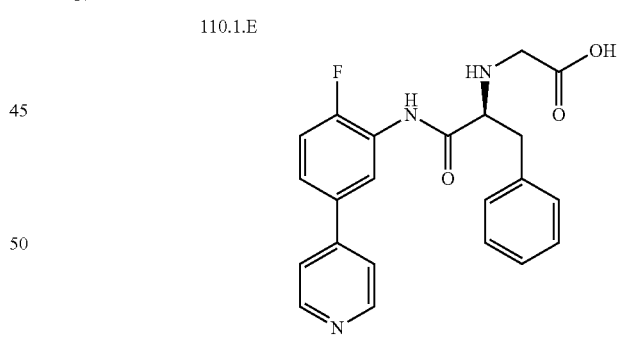

110.2

2-((S)-1-(2-fluoro-5-(pyridin-4-yl)phenylamino)-1-oxo-3-phenylpropan-2-ylamino)acetic acid (110.2)

The title compound was prepared from 110.1.E according to the procedure described in Example 101.2. The crude product was purified to give 110.2 (59 mg, 49% yield) as colorless solid. LCMS ESI (pos.) m/e: 394 (M+H): 1H NMR (400 MHz, DMSO-d6) δ ppm 10.0 (brs, 1H), 8.66 (d, J=6.2 Hz, 2H), 8.32 (dd, J=7.4, 2.4 Hz, 1H), 7.64 (d, J=6.2 Hz, 2H), 7.61-7.57 (m, 1H), 7.42 (dd, J=10.1, 8.6 Hz, 1H), 7.30-7.28

(m, 4H), 7.25-7.20 (m, 1H), 3.66 (dd, J=7.4, 5.9 Hz, 1H), 3.27 (d, J=17.2 Hz, 1H), 3.22 (d, J=17.2 Hz, 1H), 3.07 (dd, J=13.6, 5.9 Hz, 1H), 2.91 (dd, J=13.7, 7.8 Hz, 1H).

7.96 Example 111

The following example describes how compounds can be evaluated in a glucose-challenge animal model to identify in vivo active candidate drugs useful in treating diseases and conditions related to the regulation of insulin, e.g., type 2 diabetes.

B6D2F1 male mice (aged 6-20 weeks) are fasted for 4 hrs. Blood glucose levels are then determined by glucometer from blood expressed via a tail nick. Animals are pre-dosed with test article (10 mL/kg, PO, SC or IP) or vehicle (control group) and then at a pre-determined time relative to that required for the dosed test article to achieve systemic exposure, animals are challenged with glucose (2 g/10 mL/kg, PO). Glucose levels in whole blood samples from the animals are then determined by glucometer. Glucose clearance is then calculated from the glucose levels. Insulin levels are determined by ELISA in serum or plasma isolated from the blood samples.

Test articles that increase blood levels of insulin in response to glucose challenge to a level greater than that observed in the control group represent candidate drugs for use in treating diseases and conditions related to the regulation of insulin, e.g., type 2 diabetes.

Glucose Lowering Efficacy of Exemplary Compounds.

Following the protocol described above, groups of mice were treated with an exemplary compound (30 mg/10 mL/kg, SC) or vehicle (control group) (n=10 per group) and fifteen minutes later glucose (2 g/10 mL/kg, PO) was administered. FIG. 1 provides blood glucose levels measured in samples drawn from the mice at the times indicated (mean+SEM). In FIG. 1, glucose was administered at time=0. Data points indicated with # or * indicate statistically significant (p<0.05) differences in glucose levels observed in groups treated with an exemplary compound (35.1 or 86) versus control animals.

Results of an assay following the protocol above but where mice had been fasted overnight are provided in FIG. 2. Data points indicated with * indicate statistically significant differences in glucose levels observed in groups treated with exemplary compound 17.8 versus control animals.

These data demonstrate that compounds provided herein can, for example, lower glucose levels in vivo.

$ED_{50}$ Determination of an Exemplary Compound.

Following the protocol described above, groups of mice (n=5-6 animals per group) were treated with 0.3, 1, 3, 5, 10 or 30 mg/10 mL/kg exemplary compound 35.1 or vehicle. Fifteen minutes later glucose (2 g/10 mL/kg, PO) was administered. Blood samples were drawn at various time points before and up to 90 minutes after glucose administration. AUC values are calculated from plots of glucose levels to assess differences in observed glucose levels in treated and control groups, as provided in FIG. 3. In order to determine the $ED_{50}$ for glucose lowering efficacy, these data were plotted as provided in FIG. 4. These results demonstrated that the $ED_{50}$ for exemplary compound 35.1 was 0.4 mg/kg.

Glucose and Insulin Response in Glucose Challenged Mice.

Following the protocol described above, groups of mice (n=7 per group) were treated with 0.1, 0.3, 1, 3, 5, or 30 mg/10 mL/kg exemplary compound 35.1 or vehicle. Fifteen minutes later glucose (2 g/10 mL/kg, PO) was administered, and a blood sample was withdrawn 7.5 min after glucose administration. In vivo serum concentrations of 35.1 (termed "Exposure") were determined by liquid chromatography/mass spectrometry (LC/MS) for each of the groups. Concentrations of glucose and insulin in the blood samples were determined and plotted against the log Exposure of 35.1 for each group to determine $EC_{50}$ values. The $EC_{50}$ for potency in lowering glucose was 0.85 µM. FIG. 5 provides a plot of insulin concentrations versus log Exposure of 35.1. The calculated $EC_{50}$ for potency in increasing insulin concentrations was 0.29 µM. These data demonstrate that compounds provided herein can, for example, both lower blood glucose concentrations and increase blood insulin concentrations when administered in nanomolar concentrations to a subject.

7.97 Example 112

The following example describes an islet insulin secretion assay for evaluating compounds provided herein.

The pancreatic islets of Langerhans are isolated from 12-14 week old male C57BL/6 mice by collagenase digestion and histopaque fractionation as described in Gotoh et al., 1987, *Transplantation* 43:725-730. The isolated islets are cultured in RPMI 1640 medium plus 10% fetal bovine serum for 72 hours. For the assay, the islets are hand picked and each treatment group are tested with 8 replicates containing 2 islets. The islets are acclimated in 1.0 mL of Krebs-Ringer bicarbonate HEPES (KRBH) buffer plus 1.0 mM glucose, 0.1% (w/v) human serum albumin (HSA) for 1 hour. The islets are then transferred to 1.0 mL of KRBH assay buffer plus 16.7 mM glucose, 0.1% (w/v) HSA, and various concentrations of test compound. After one hour of treatment, to assess insulin secretion, supernatants are collected and concentrations of insulin in the supernatants are determined by an insulin ELISA method.

FIG. 6 provide representative results demonstrating that exemplary compounds 17.7 (FIG. 6A) and 35.1 (FIG. 6B) increase insulin secretion from islets when tested in an islet insulin secretion assay as described above. These results indicate that compounds as provided herein can, for example, be useful for treating diseases and conditions related to the regulation of insulin, e.g., type 2 diabetes.

7.98 Example 113

Table 12 provides exemplary compounds that were prepared and assessed, following protocols known to those of skilled in the art, for activation of intracellular inositol trisphosphate ($IP_3$) signaling pathways that lead to elevation of intracellular calcium concentration. $EC_{50}$ values provided in Table 12 were calculated from $IP_3$ concentration measurements in cells transfected with a human receptor found in pancreatic islet cells, inter alia. The receptor has been confirmed in the in vivo models described above.

TABLE 12

| Activation Assay Results | |
|---|---|
| Example Compound No. | Activity ($EC_{50}$)* |
| 1.1 | ++ |
| 1.2 | ++ |
| 1.3 | ++ |
| 1.4 | +++ |
| 1.5 | +++ |
| 1.6 | +++ |
| 2 | + |
| 3.1 | ++ |

TABLE 12-continued

Activation Assay Results

| Example Compound No. | Activity (EC$_{50}$)* |
|---|---|
| 3.2 | ++++ |
| 3.3 | ++ |
| 4 | ++ |
| 5.1 | + |
| 5.2 | +++ |
| 5.3 | +++ |
| 6 | ++ |
| 7 | +++ |
| 8.1 | ++++ |
| 8.2 | +++ |
| 9 | ++ |
| 10 | ++ |
| 11.1 | ++++ |
| 12 | +++ |
| 13 | ++++ |
| 14.1 | ++ |
| 14.2 | ++ |
| 14.3 | +++ |
| 15.1 | ++ |
| 15.2 | ++ |
| 16.1 | ++++ |
| 16.1.F | ++ |
| 16.2 | +++ |
| 17.2 | ++++ |
| 17.3 | +++ |
| 17.4 | ++++ |
| 17.5 | ++++ |
| 17.6 | ++ |
| 17.7 | +++ |
| 17.8 | +++ |
| 18.1 | ++++ |
| 18.2 | ++++ |
| 19.1 | ++ |
| 19.2 | ++ |
| 20.1 | ++++ |
| 20.2 | ++++ |
| 20.3 | + |
| 21.1 | ++++ |
| 21.2 | ++++ |
| 22 | +++ |
| 23.1 | ++++ |
| 23.2 | ++++ |
| 23.3 | ++ |
| 23.4 | +++ |
| 23.5 | ++++ |
| 23.6 | ++++ |
| 23.7 | ++++ |
| 23.8 | ++++ |
| 23.9 | ++++ |
| 23.10 | ++++ |
| 23.11 | +++ |
| 24 | ++++ |
| 25.1 | ++ |
| 25.2 | + |
| 26 | ++ |
| 27 | ++ |
| 28 | ++++ |
| 29 | +++ |
| 30 | +++ |
| 31.1 | ++++ |
| 31.2 | ++++ |
| 31.3 | ++++ |
| 31.4 | ++++ |
| 33 | ++ |
| 34.1 | ++ |
| 34.1.D | + |
| 34.2 | ++ |
| 34.3 | +++ |
| 34.4 | +++ |
| 34.5 | + |
| 34.6 | + |
| 34.7 | + |
| 34.8 | + |
| 34.10 | ++ |
| 34.11 | + |
| 34.12 | ++ |
| 34.13 | + |
| 34.14 | +++ |
| 34.15 | + |
| 34.16 | ++ |
| 34.17 | ++ |
| 34.18 | ++ |
| 34.19 | ++ |
| 34.20 | ++ |
| 34.21 | + |
| 35.1 | +++ |
| 35.2 | ++ |
| 35.3 | +++ |
| 35.4 | ++ |
| 35.5 | +++ |
| 35.6 | + |
| 36 | ++ |
| 37 | +++ |
| 38 | ++ |
| 39 | +++ |
| 40 | + |
| 41.1 | ++ |
| 41.2 | ++ |
| 41.3 | ++ |
| 41.4 | ++ |
| 41.5 | ++ |
| 41.6 | ++ |
| 42 | ++++ |
| 43.1 | ++ |
| 43.2 | +++ |
| 44 | ++ |
| 45.1 | + |
| 45.2 | ++ |
| 45.3 | ++ |
| 45.4 | + |
| 45.5 | ++ |
| 45.6 | +++ |
| 46 | +++ |
| 47 | +++ |
| 48 | ++ |
| 49.1 | + |
| 49.2 | ++ |
| 50 | ++ |
| 51.1 | +++ |
| 51.2 | +++ |
| 52 | ++ |
| 53 | ++ |
| 54.1 | ++ |
| 54.2 | ++ |
| 54.3 | +++ |
| 54.4 | +++ |
| 54.5 | +++ |
| 54.6 | +++ |
| 54.7 | +++ |
| 54.8 | ++ |
| 55 | ++ |
| 56 | +++ |
| 57 | +++ |
| 58 | ++++ |
| 59 | ++ |
| 60 | ++ |
| 61 | + |
| 62 | ++ |
| 63.1 | ++ |
| 63.2 | + |
| 64 | +++ |
| 65 | ++ |
| 66 | ++++ |
| 67 | +++ |
| 68 | ++ |
| 69 | +++ |
| 70 | +++ |
| 71 | +++ |

TABLE 12-continued

Activation Assay Results

| Example Compound No. | Activity (EC$_{50}$)* |
|---|---|
| 72 | +++ |
| 73 | ++ |
| 74 | ++ |
| 75 | ++ |
| 76 | ++ |
| 77 | ++ |
| 78 | ++++ |
| 79 | ++ |
| 80 | ++ |
| 81 | ++ |
| 82 | + |
| 83 | + |
| 84 | + |
| 85 | ++ |

*EC$_{50}$ values are within the ranges:

+ 10 µM > EC$_{50}$ ≥ 1 µM

++ 1 µM > EC$_{50}$ ≥ 0.1 µM

+++ 0.1 µM > EC$_{50}$ ≥ 0.05 µM

++++ 0.05 µM > EC$_{50}$

7.99 Example 114

Pharmacokinetics of compounds provided herein can used determined using routine methods known to those skilled in the art. For example, when administered (i.v.) at a dose of 0.5 mg/kg to rats, Clearance (Cl) and Volume of Distribution (V$_d$) values for determined to be as provided in Table 13.

TABLE 13

Pharmacokinetic Values for Exemplary Compounds

| Example Compound No. | Cl (L/h/kg) | Vd (L/kg) |
|---|---|---|
| 35.1 | 5.0 | 1.1 |
| 86 | 1.9 | 1.3 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

It is claimed:

1. A compound of formula V:

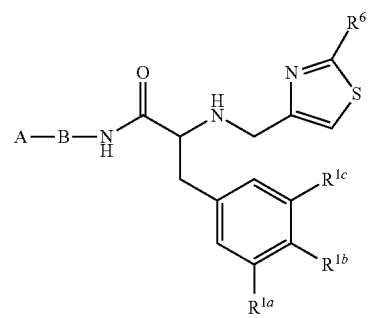

or pharmaceutically acceptable salt thereof, wherein

A is optionally substituted aryl, optionally substituted heteroaryl or optionally substituted heterocyclyl;

B is optionally substituted cycloalkyl, optionally substituted heterocyclyl, optionally substituted aryl or optionally substituted heteroaryl;

$R^{1a}$, $R^{1b}$ and $R^{1c}$ are each independently selected from —H, —Cl and —F; and $R^6$ is selected from amino or $(C_1-C_5)$alkyl.

2. A compound of formula VI:

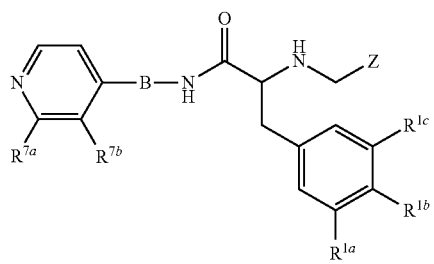

or pharmaceutically acceptable salt thereof, wherein

B is optionally substituted cycloalkyl, optionally substituted heterocyclyl, optionally substituted aryl or optionally substituted heteroaryl;

Z is amino, carboxy, optionally substituted alkyl, optionally substituted alkoxy, optionally substituted alkylamino, optionally substituted dialkylamino, optionally substituted cycloalkylamino, optionally substituted cycloalkyl, optionally substituted heterocyclyl, optionally substituted heteroaryl, —C(O)OR$^5$ or —C(O)NR$^9$R$^{10}$, wherein $R^5$ is $(C_1-C_5)$ alkyl; and $R^9$ and $R^{10}$ are independently selected from H and $(C_1-C_5)$ alkyl, or, optionally, $R^9$ and $R^{10}$ together with the nitrogen atom to which $R^9$ and $R^{10}$ are attached form a 5-membered ring;

$R^{1a}$, $R^{1b}$, $R^{1c}$ and $R^{7b}$ are each independently selected from —H, —Cl and —F; and $R^{7a}$ is selected from the group consisting of amino, monosubstituted amino, halo and optionally substituted $(C_1-C_5)$ alkyl.

3. A compound of formula VIII:

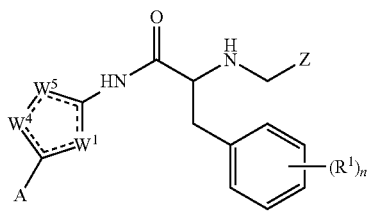

or pharmaceutically acceptable salt thereof, wherein
A is optionally substituted aryl, optionally substituted heteroaryl or optionally substituted heterocyclyl;
Z is amino, carboxy, optionally substituted alkyl, optionally substituted alkoxy, optionally substituted alkylamino, optionally substituted dialkylamino, optionally substituted cycloalkylamino, optionally substituted cycloalkyl, optionally substituted heterocyclyl, optionally substituted heteroaryl, —C(O)OR$^5$ or —C(O)NR$^9$R$^{10}$, wherein
R$^5$ is (C$_1$-C$_5$)alkyl; and
R$^9$ and R$^{10}$ are independently selected from H and (C$_1$-C$_5$) alkyl, or, optionally, R$^9$ and R$^{10}$ together with the nitrogen atom to which R$^9$ and R$^{10}$ are attached form a 5-membered ring;
each R$^1$ is independently halo;
subscript n is 0, 1, 2 or 3;
W$^1$ selected from the group consisting of —CH═, —N═, —NH—, —O— and —S—;
W$^4$ and W$^5$ are independently selected from —C(R$^8$)═, —C(O)—, —N═, —N(R$^8$)—, —O— and —S—, wherein
R$^8$ is selected from the group consisting of hydrogen, acyl, amino, carboxy, carboxyalkyl, halo, hydroxy, hydroxyalkyl, monosubstituted amino, optionally substituted (C$_1$-C$_5$)alkyl, optionally substituted (C$_1$-C$_5$)alkylamino, optionally substituted (C$_1$-C$_5$)alkoxy, optionally substituted heteroaryl, optionally substituted halo (C$_1$-C$_5$)alkyl, optionally substituted heterocyclyl and optionally substituted heterocyclylalkyl; and
each ═ bond is a single bond, double or π bond.

4. The compound of claim 3, wherein A is selected from the group consisting of optionally substituted phenyl, optionally substituted pyrazol-3-yl, optionally substituted pyrazol-4-yl, optionally substituted pyridine-4-yl and optionally substituted thiazol-5-yl.

5. The compound of claim 3, wherein Z is selected from the group consisting of pyridin-2-yl, thiazol-2-yl, thiazol-4-yl, pyrimidin-2-yl, pyrimidin-4-yl, imidazol-2-yl, imidazol-4-yl, 1,2,3-triazol-4-yl, pyrazol-3-yl, tetrazol-5-yl, pyrazin-2-yl, 1,2,4-triazol-3-yl and isooxazol-3-yl, each of which is optionally substituted.

6. The compound of claim 5, wherein R$^1$ is fluoro and subscript n is 0 or 1.

7. A compound or a pharmaceutically acceptable salt thereof, wherein the compound is selected from the group consisting of:
(S)-2-((2-aminothiazol-4-yl)methylamino)-3-phenyl-(5-(pyridin-4-yl)-1,3,4-thiadiazol-2-yl)propanamide,
(S)-3-phenyl-N-(5-(pyridin-4-yl)-1,3,4-thiadiazol-2-yl)-2-((S)-1-(thiazol-4-yl)ethylamino)propanamide,
(S)-3-phenyl-N-5-(pyridin-4-yl)-1,3,4-thiadiazol-2-yl)-2-(thiazol-4-ylmethylamino)propanamide,
(S)-3-(3-fluorophenyl)-N-(5-(pyridin-4-yl)-1,3,4-thiadiazol-2-yl)-2-(thiazol-4-ylmethylamino)propanamide,
(S)-3-Phenyl-N-(5-(pyridin-4-yl)-4H-1,2,4-triazol-3-yl)-2-(thiazol-4-ylmethylamino)propanamide,
(S)-3-(4-Chlorophenyl)-N-(3-(pyridin-4-yl)isoxazol-5-yl)-2-(thiazol-4-ylmethylamino)propanamide,
(S)-2-(3-(4-Fluorophenyl)-1-oxo-1-(3-(pyridin-4-yl)isoxazol-5-ylamino)propan-2-ylamino)acetic acid diTFA salt,
(S)-3-Phenyl-N-(3-(pyridin-4-yl)isoxazol-5-yl)-2-(thiazol-4-ylmethylamino)propanamide,
(S)-3-Phenyl-N-(2-(pyridin-4-yl)thiazol-4-yl)-2-(thiazol-4-ylmethylamino)propanamide,
(S)-tert-Butyl 1-oxo-3-phenyl-1-(2-(pyridin-4-yl)thiazol-4-ylamino)propan-2-ylcarbamate,
(S)-3-(4-Fluorophenyl)-N-(2-(pyridin-4-yl)thiazol-5-yl)-2-(thiazol-4-ylmethylamino)propanamide,
(S)-3-Phenyl-N-(2-(pyridin-4-yl)thiazol-5-yl)-2-(thiazol-4-ylmethylamino)-propanamide,
(2S)—N-(5-(1H-Pyrazol-5-yl)pyridin-3-yl)-3-phenyl-2-(thiazol-4-ylmethylamino)propanamide,
(S)-3-Phenyl-N-(3-(pyridin-4-yl)-1H-pyrazol-5-yl)-2-(thiazol-4-ylmethylamino)propanamide,
(2S)—N-(5-(2-methylamino)pyridine-4-yl)-1,3,4-thiadiazol-2-yl)-3-phenyl-2-(thiazol-4-ylmethylamino)propanamide,
(2S)-3-(4-fluorophenyl)-N-(5-(2-(methylamine)pyridine-4-yl)-1,3,4-thiadiazol-2-yl)-2-(thiazol-4-ylmethylamino)propanamide,
(2S)-3-(4-fluorophenyl)-N-(1-methyl-3-(2-(methylamino)pyrimidin-4-yl)-1H-pyrazol-5-yl)-2-(thiazol-4-ylmethylamino)propanamide,
(S)-3-phenyl-N-(4-(pyridin-4-yl)pyrimidin-2-yl)-2-(thiazol-4-ylmethylamino)propanamide,
(S)—N-(2-methoxy-5-(pyridin-4-yl)pyridin-3-yl)-3-phenyl-2-(1-(pyridin-2-yl)cyclopropylamino)propanamide,
(2S)—N-(3-(1H-pyrazol-3-yl)phenyl)-3-phenyl-2-(thiazol-4-ylmethylamino)propanamide,
(S)—N-(2-hydroxy-5-(pyridin-4-yl)phenyl)-3-phenyl-2-(thiazol-4-ylmethylamino)propanamide,
(2S)—N-(2-methoxy-5-(1H-pyrazol-3-yl)-3-phenyl-2-(1-(thiazol-4-yl)cyclopropylamino)propanamide,
(2S)—N-(2-methoxy-5-(1H-pyrazol-3-yl)pyridin-3-yl)-3-phenyl-2-(thiazol-4-ylmethylamino)propanamide,
(2S)—N-(2-methoxy-5-(1H-pyrazol-4-yl)pyridin-3-yl)-3-phenyl-2-(pyridin-2-ylmethylamino)propanamide,
(2S)-3-(4-Fluorophenyl)-N-(1-methyl-3-(2-methylpyridin-4-yl)-1H-pyrazol-5-yl)-2-(thiazol-4-ylmethylamino)propanamide,
2-((S)-3-(4-Fluorophenyl)-1-(1-methyl-3-(2-methylpyridin-4-yl)-1H-pyrazol-5-ylamino)-1-oxopropan-2-ylamino)acetic acid dihydrochloride,
(S-tert-Butyl 1-(1-methyl-3-(pyridin-4-yl)-1H-pyrazol-5-ylamino)-1-oxo-3-phenylpropan-2-ylcarbamate,
(S)—N-(1-Methyl-3-(pyridin-4-yl)-1H-pyrazol-5-yl)-3-phenyl-2-thiazol-4-ylmethylamino)propanamide,
(S)—N-(1-Methyl-3-(pyridin-4-yl)-1H-pyrazol-5-yl)-3-phenyl-2-(pyridin-2-ylmethylamino)propanamide,
(S)-2-((5-Fluoropyridin-2-yl)methylamino)-N-(1-methyl-3-(pyridin-4-yl)-1H-pyrazol-5-yl)-3-phenylpropanamide,
(S)-3-(4-Fluorophenyl)-N-(1-methyl-3-(pyridin-4-yl)-1H-pyrazol-5-yl)-2-(thiazol-4-ylmethylamino)propanamide,
(S)-2-(Cyclopropylmethylamino)-N-(1-methyl-3-(pyridin-4-yl)-1H-pyrazol-5-yl)-3-phenylpropanamide, (S)-Ethyl 2-(1-(1-methyl-3-(pyridin-4-yl)-1H-pyrazol-5-ylamino)-1-oxo-3-phenylpropan-2-ylamino)acetate dihydrochloride, (S)-2-(1-(1-Methyl-3-(pyridin-4-yl)-1H-pyrazol-5-ylamino)-1-oxo-3-phenylpropan-2-ylamino)acetic acid dihydrochloride, (2S)-3-(4-Fluorophenyl)-N-(3-(2-(methylamino)pyridin-4-yl)-1H-pyrazol-5-yl)-2-(thiazol-4-ylmethylamino)propanamide, (2S)-2-((1H-1,2,3-triazol-4-yl)methylamino)-3-(4-fluorophenyl)-N-(3-(2-(methylamino)pyridin-4-yl)-1H-pyrazol-5-yl)propanamide, (S)—N-(1-ethyl-3-(pyridine-4-yl)-1H-pyrazol-5-yl)-3-(4-fluorophenyl)-2-(thiazol-4-ylmethlamino)propanamide, (R)-2-((S)-1-(1-Ethyl-3-(pyridin-4-yl)-1H-pyrazol-5-ylamino)-1-oxo-3-phenylpropan-2-ylamino)propanoic acid, (2S)-3-(4-Fluorophenyl)-N-(3-(2-methylpyridin-4-yl)-1H-pyrazol-5-yl)-2-(thiazol-4-ylmethylamino)propanamide dihydrochloride, 2-((S)-3-(4-Fluorophenyl)-1-(3-(2-methylpyridin-4-yl)-1H-pyrazol-5-ylamino)-1-oxopropan-2-ylamino)acetic acid dihydrochloride, (2S)-3-(4-Fluorophenyl)-N-(4-methyl-2-(2-methylpyridin-4-yl)thiazol-5-yl)-2-(thiazol-4-ylmethylamino)propanamide, (2S)-2-((5-Fluoropyridin-2-yl)methylamino)-N-(1-methyl-3-(2-(methylamino)pyridin-4-yl)-1H-pyrazol-5-yl)-3-phenylpropanamide, (2S)-2-((1H-Pyrazol-3-yl)methylamino)-3-(4-fluorophenyl)-N-(1-methyl-3-(2-(methylamino)pyridin-4-yl)-1H-pyrazol-5-yl)propanamide, (2S)-2-(2-Ethoxyethylamino)-3-(4-fluorophenyl)-N-(1-methyl-3-(2-(methylamino)pyridin-4-yl)-1H-pyrazol-5-yl)propanamide, (2S)-3-(4-Fluorophenyl)-2-((1-methyl-1H-pyrazol-3-yl)methylamino)-N-(1-methyl-3-(2-(methylamino)pyridin4-yl)-1H-pyrazol-5-yl)propanamide, (2S)-3-(4-Fluorophenyl)-N-(1-methyl-3-(2-methylamino)pyridin-4-yl)-1H-pyrazol-5-yl)-2-(thiazol-4-ylmethylamino)propanamide, (2S)-3-(4-Fluorophenyl)-2-((5-fluoropyridin-2-yl)methylamino)-N-(1-methyl-3-(2-(methylamino)pyridin-4-yl)-1H-pyrazol-5-yl)propanamide, (2S)-2-((1H-1-1,2,3-triazol-4-yl)methylamino)-3-(4-fluorophenyl)-N-(1-methyl-3-(2-(methylamino)pyridin-4-yl)-1H-pyrazol-5-yl)propanamide, 2-((S)-3-(4-Fluorophenyl)-1-(1-methyl-3-(2-(methylamino)pyridin-4-yl)-1H-pyrazol-5-ylamino)-1-oxopropan-2-ylamino)acetic acid, 2-((S)-1-(1-Methyl-3-(2-(methylamino)pyridin-4-yl)-1H-pyrazol-5-ylamino)-1-oxo-3-phenylpropan-2-ylamino)acetic acid, (2S)—N-(1-methyl-3-(2-(methylamino)pyridin-4-yl)-1H-pyrazol-5-yl)-3-phenyl-2-(thiazol-4-ylmethylamino)propanamide, (2S)-2-((1H-tetrazol-5-yl)methylamino)-3-(4-fluorophenyl)-N-(1-methyl-3-(2-(methylamino)pyridin-4-yl)-1H-pyrazol-5-yl)propanamide, (S)-2-(1-Oxo-3-phenyl-1-(3-(pyridin-4-yl)-1-(2,2,2-trifluoroethyl)-1H-pyrazol-5-ylamino)propan-2-ylamino)acetic acid, (S)-3-(3Chlorophenyl)-N-(2-oxo-5-(pyridin-4-yl)-1,2-dihydropyridin-3-yl)-2-(thiazol-4-ylmethylamino)propanamide trifluoroacetate, (S)-2-(5-(3-Phenyl-2-(thiazol-4-ylmethylamino)propanamido)-3-(pyridin-4-yl)-1H-pyrazol-1-yl)acetic acid, (2S)—N-(3-(1-Methyl-1H-pyrazol-4-yl)phenyl)-3-phenyl-2-(thiazol-4-ylmethylamino)propanamide, (2S)—N-(1-ethyl-3-(2-methylpyridin-4-yl)-1H-pyrazol-5-yl)-3-(4-fluorophenyl)-2-(thiazol-4-ylmethylamino)propanamide dihydrochloride, (S)-2-(3-(4-Chlorophenyl)-1-(1-isopropyl-3-(pyridin-4-yl)-1H-pyrazol-5-ylamino)-1-oxopropan-2-ylamino)acetic acid, (2S)-3-(4-Fluorophenyl)-N-(1-(2-hydroxyethyl)-3-(2-(methylamino)pyridin-4-yl)-1H-pyrazol-5-yl)-2-(thiazol-4-ylmethylamino)propanamide, (2S)—N-(1-Ethyl-3-(2-(methylamino)pyridin-4-yl)-1H-pyrazol-5-yl)-3-(4-fluorophenyl)-2-(thiazol-4-ylmethylamino)propanamide, (2S)-2-((1H-1,2,3-triazol-4-yl)methylamino)-N-(1-ethyl-3-(2-(methylamino)pyridin-4-yl)-1H-pyrazol-5-yl)-3-(4-fluorophenyl)propanamide, (2S)—N-(1-Ethyl-3-(2-(methylamino)pyridin-4-yl)-1H-pyrazol-5-yl)-3-(4-fluorophenyl)-2-((5-fluoropyridin-2-yl)methylamino)propanamide, 2-((S)-1-(1-Ethyl-3-(2-(methylamino)pyridin-4-yl)-1H-pyrazol-5-ylamino)-3-(4-fluorophenyl)-1-oxopropan-2-ylamino)acetic acid, (S)—N-(1-Methyl-5-(pyridin-4-yl)-1H-pyrazol-3-yl)-3-phenyl-2-(thiazol-5-ylmethylamino)propanamide, (2S)—N-(3-(1H-Pyrazol-4-yl)phenyl)-3-phenyl-2-(thiazol-4-ylmethylamino)propanamide, (S)-3-Phenyl-N-(3-(pyridin-4-yl)phenyl)-2-(2-(tetrahydro-2H-pyran-4-yl)ethylamino)propanamide, (2S)-3-Phenyl-2-(1-(pyridin-2-yl)ethylamino)-N-(3-(pyridin-4-yl)phenyl)propanamide, (2S)-3-Phenyl-2-(1-(pyridin-2-yl)propylamino)-N-(3-(pyridin-4-yl)phenyl)propanamide, (R)-3-Phenyl-N-(3-(pyridin-4-yl)phenyl)-2-(thiazol-4-ylmethylamino)propanamide trifluoroacetate, (R)-3-Phenyl-N-(3-(pyridin-4-yl)phenyl)-2-(thiazol-5-ylmethylamino)propanamide trifluoroacetate, (R)-3-Phenyl-N-(3-(pyridin-4-yl)phenyl)-2-(thiazol-2-ylmethylamino)propanamide trifluoroacetate, (2S)-3-Phenyl-2-(1-(pyrazin-2-yl)ethylamino)-N-(3-(pyridin-4-yl)phenyl)propanamide, (2S)-3-Phenyl-N-(3-(pyridin-4-yl)phenyl)-2-((tetrahydrofuran-3-yl)methylamino)propanamide, (S)-2(Cyclopropylmethylamino)-3-(3-fluorophenyl)-N-(3-(pyridin-4-yl)phenyl)propanamide, (S)-2-(Isopropylamino)-3-phenyl-N-(3-(pyridin-4-yl)phenyl)propanamide, (S)-3-Phenyl-N-(3-(pyridin-4-yl)phenyl)-2-(thiazol-4-ylmethylamino)propanamide, (S)-2-(Oxazol-5-ylmethylamino)-3-phenyl-N-(3-(pyridin-4-yl)phenyl)propanamide, (S)-3-Phenyl-N-(3-(pyridin-4-yl)phenyl)-2-(thiazol-2-ylmethylamino)propanamide, (S)-3-Phenyl-N-(3-(pyridin-4-yl)phenyl)-2-(thiazol-5-ylmethylamino)propanamide, (S)-2-((2-Methylthiazol-5-yl)methylamino)-3-phenyl-N-(3-(pyridin-4-yl)phenyl)propanamide, (2S)-3-Phenyl-N-(3-(pyridin-4-yl)phenyl)-2-(1-(thiazol-4-yl)ethylamino)propanamide, (S)-tert-Butyl 2-(1-oxo-3-phenyl-1-(3-(pyridin-4-yl)phenylamino)propan-2-ylamino)acetate, (S)—N-Methyl-3-phenyl-N-(3-(pyridin-4-yl)phenyl)-2-(thiazol-4-ylmethylamino)propanamide, (S)-2-(1-Oxo-3-phenyl-1-(3-(pyridin-4-yl)phenylamino)propan-2-ylamino)acetic acid, (S)-2-((4-Methyl-4H-1,2,4-triazol-3-yl)methylamino)-3-phenyl-N-(3-(pyridin-4-yl)phenyl)propanamide,
(2S)—N-(3-(3-Fluoropyridin-4-yl)phenyl)-3-phenyl-2-(thiazol-4-ylmethylamino)propanamide,
(S)—N-(2-Oxo-5-(pyridin-4-yl)-1,2-dihydropyridin-3-yl)-3-phenyl-2-(1-(pyridin-2-yl)cyclopropylamino)propanamide,
(S)—N-(2-Methoxy-5-(pyridin-4-yl)pyridin-3-yl)-3-phenyl-2-((S)-1-(pyridin-2-yl)ethylamino)propanamide,
(S)—N-(2-Methoxy-5-(pyridin-4-yl)pyridin-3-yl)-2-(1-(2-methylthiazol-4-yl)cyclopropylamino)-3-phenyl-propanamide,
(S)-2-(Isoxazol-3-ylmethylamino)-N-(2-methoxy-5-(pyridin-4-yl)pyridin-3-yl)-3-phenylpropanamide,
(S)—N-(2-Methoxy-5-(pyridin-4-yl)pyridin-3-yl)-3-phenyl-2-(1-(pyrimidin-2-yl)cyclopropylamino))propanamide,
(2S)-2-Amino-N-(2-methoxy-5-(2-methylpyridin-4-yl)pyridin-3-yl)-3-phenylpropanamide,
(2S)—N-(3-(2-Aminopyridin-4-yl)phenyl)-3-phenyl-2-(thiazol-4-ylmethylamino)propanamide,
(S)—N-(4-Methoxy-3-(pyridin-4-yl)phenyl)-3-phenyl-2-(thiazol-4-ylmethylamino)propanamide1H,
(S)—N-(4-Methoxy-3-(pyridin-4-yl)phenyl)-3-phenyl-2-(thiazol-4-ylmethylamino)propanamide,
(2S)—N-(3-(2-methylpyridin-4-yl)phenyl)-3-phenyl-2-(thiazol-4-ylmethylamino)propanamide,
(S)—N-(3'-aminobiphenyl-3-yl)-3-phenyl-2-(thiazol-4-ylmethylamino)propanamide,
(2S)—N-(2-Methoxy-5-(2-methylpyridin-4-yl)pyridin-3-yl)-3-phenyl-2-(1-(pyridin-2-yl)cyclopropylamino)propanamide,
(S)—N-(2-Methoxy-5-(2-methylpyridin-4-yl)pyridin-3-yl)-3-phenyl-2-((S)-1-(pyridin-2-yl)ethylamino)propanamide,
(2S)—N-(2-Methoxy-5-(2-methylpyridin-4-yl)pyridin-3-yl)-3-phenyl-2-(pyridin-2-ylmethylamino)propanamide,
(2S)—N-(2-Methoxy-5-(2-methylpyridin-4-yl)pyridin-3-yl)-2-((1-methyl-1H-imidazol-4-yl)methylamino)-3-phenylpropanamide,
(2S)—N-(2-Methoxy-5-(2-methylpyridin-4-yl)pyridin-3-yl)-3-phenyl-2-(thiazol-4-ylmethylamino)propanamide,
(2S)—N-(2-Methoxy-6-(2-methylpyridin-4-yl)pyridin-3-yl)-3-phenyl-2-(thiazol-4-ylmethylamino)propanamide,
(2S)-3-(4-fluorophenyl)-N-(3-(2-(methylamino)pyridin-4-yl)-1-propyl-1H-pyrazol-5-yl)-2-(thiazol-4-ylmethylamino)propanamide,
(2S)-2-Amino-3-(4-fluorophenyl)-N-(1-isopropyl-3-(2-(methylamino)pyridin-4-yl)-1H-pyrazol-5-yl)propanamide,
(2S)-3-(4-Fluorophenyl)-N-(1-isopropyl-3-(2-methylamino)pyridin-4-yl)-1H-pyrazol-5-yl)-2-(thiazol-4-ylmethylamino)propanamide,
N-(4'-fluoro-1,1'-biphenyl-3-yl)-N-(1,3-thiazol-4-ylmethyl)-L-phenylalaninamide,
(S)-3-(2-Amino-3-phenylpropanamido)-5-(pyridin-4-yl)benzoic acid,
(S)-3-(3-Phenyl-2-(thiazol-5-ylmethylamino)propanamido)-5-(pyridin-4-yl)benzoic acid,
(S)-3-(3-Phenyl-2-(thiazol-2-ylmethylamino)propanamido)-5-(pyridin-4-yl)benzoic acid,
(S)-3-(2-((1H-Pyrazol-4-yl)methylamino)-3-phenylpropanamido)-5-(pyridin-4-yl)benzoic acid,
(S)-3-(2-((1H-Pyrazol-3-yl)methylamino)-3-phenylpropanamido)-5-(pyridin-4-yl)benzoic acid,
(S)-3-(3-Phenyl-2-(pyridin-2-ylmethylamino)propanamido)-5-(pyridin-4-yl)benzoic acid,
(2S)—N-(3-chloro-5-(2-methylpyridin-4-yl)phenyl)-3-phenyl-2-(pyridin-2-ylmethylamino)propanamide,
(S)-3-(3-phenyl-2-(thiazol-4-ylmethylamino)propanamido)-5-(pyridin-4-yl)benzamide,
N-(4'-fluoro-1,1'-biphenyl-3-yl)-N-(1,3-thiazol-4-ylmethyl)-L-phenylalaninamide,
3-((S)-2-Amino-3-(2,4-dichlorophenyl)propanamido)-5-(2-methylpyridin-4-yl)benzoic acid,
3-(2-Methylpyridin-4-yl)-5-((S)-3-phenyl-2-(thiazol-4-ylmethylamino)propanamido)benzoic acid,
3-(2-Methylpyridin-4-yl)-5-((S)-3-phenyl-2-(thiazol-4-ylmethylamino)propanamido)benzoic acid,
(S)-3-Phenyl-2-(pyridin-2-ylmethylamino)-1-(6-(pyridin-4-yl)indolin-1-yl)propan-1-one,
(2S)—N-(3-(2-Methylpyridin-4-yl)-5-(methylsulfonamido)phenyl)-3-phenyl-2-(thiazol-4-ylmethylamino)propanamide,
(2S)—N-(3-(2-Methylpyridin-4-yl)-5-(methylsulfonamido)phenyl)-3-phenyl-2-(pyridin-2-ylmethylamino)propanamide,
(S)-2,2-difluoro-2-(3-(3-phenyl-2-(thiazol-4-ylmethylamino)propanamido)-5-(pyridin-4-yl)phenyl)acetic acid,
(S)-1-(3-Phenyl-2-(thiazol-4-ylmethylamino)propanoyl)-6-(pyridin-4-yl)indoline-4-carbonitrile,
(S)-Methyl 1-(2-amino-3-phenylpropanoyl)-6-(pyridin-4-yl)indoline-4-carboxylate,
Methyl 1-((S)-3-phenyl-2-((S)-1-(pyridin-2-yl)ethylamino)propanoyl)-6-(pyridin-4-yl)indoline-4-carboxylate,
(S)-Methyl 1-(3-phenyl-2-(thiazol-4-ylmethylamino)propanoyl)-6-(pyridin-4-yl)indoline-4-carboxylate,
(S)-Methyl 1-(2-((1H-pyrazol-3-yl)methylamino)-3-phenylpropanoyl)-6-(pyridin-4-yl)indoline-4-carboxylate,
(S)-Methyl 1-(3-(4-fluorophenyl)-2-(thiazol-4-ylmethylamino)propanoyl)-6-(pyridin-4-yl)indoline-4-carboxylate,
(S)-Methyl 1-(2-((1H-pyrazol-3-yl)methylamino)-3-(4-fluorophenyl)propanoyl)-6-(pyridin-4-yl)indoline-4-carboxylate,
(S)-Methyl 1-(3-(4-fluorophenyl)-2-(pyridin-2-ylmethylamino)propanoyl)-6-(pyridin-4-yl)indoline-4-carboxylate,
Methyl 1-((S)-3-phenyl-2-((S)-1-(pyridin-2-yl)ethylamino)propanoyl)-6-(pyridin-4-yl)indoline-4-carboxylate,
(S)—N,N-Dimethyl-3-(3-phenyl-2-(thiazol-4-ylmethylamino)propanamido)-5-(pyridin-4-yl)benzamide,
(2S)-1-(6-(2-Methylpyridin-4-yl)indolin-1-yl)-3-phenyl-2-(thiazol-4-ylmethylamino)propan-1-one,
(S)-5-(1-(3-Phenyl-2-(thiazol-4-ylmethylamino)propanoyl)-6-(pyridin-4-yl)indolin-4-yl)-1,3,4-oxadiazol-2(3H)-one,
(S)-3-Phenyl-1-(6-(pyridin-4-yl)-4-(5-thioxo-4,5-dihydro-1,3,4-oxadiazol-2-yl)indolin-1-yl)-2-(thiazol-4-ylmethylamino)propan-1-one,
(2S)-2-Amino-1-(4-(5-amino-1,3,4-oxadiazol-2-yl)-6-(pyridin-4-yl)indolin-1-yl)-3-phenylpropan-1-one,
(S)-1-(3-Phenyl-2-(thiazol-4-ylmethylamino)propanoyl)-6-(pyridin-4-yl)indoline-4-carboxamide,
(2S)-1-(4-(2-Methyl-2H-1,2,4-triazol-3-yl)-6-(pyridin-4-yl)indolin-1-yl)-3-phenyl-2-(thiazol-4-ylmethylamino)propan-1-one, (S)—N-Methyl-1-(3-phenyl-2-(thiazol-4-ylmethylamino) propanoyl)-6-(pyridin-4-yl)indoline-4-carboxamide,
(S)-2-(3-(3-(4-Chlorophenyl)-2-(thiazol-4-ylmethylamino)propanamido)-5-(pyridin-4-yl)phenyl)-2-methylpropanoic acid,
Methyl 2-(4-(2-methylpyridin-4-yl)-2-((S)-3-phenyl-2-(thiazol-4-ylmethylamino)propanamido)phenoxy)acetate,
Methyl 2-(3-(2-methylpyridin-4-yl)-5-((S)-3-phenyl-2-(thiazol-4-ylmethylamino)propanamido)phenoxy)acetate,
(2S)-1-(6-(2-Methylpyridin-4-yl)-4-(5-thioxo-4,5-dihydro-1,3,4-oxadiazol-2-yl)indolin-1-yl)-3-phenyl-2-(thiazol-4-ylmethylamino)propan-1-one,
(2S)-1-(4-(5-Methyl-1,3,4-oxadiazol-2-yl)-6-(pyridin-4-yl)indolin-1-yl)-3-phenyl-2-(thiazol-4-ylmethylamino) propan-1-one,
(2S)-1-(4-(1,3,4-Oxadiazol-2-yl)-6-(pyridin-4-yl)indolin-1-yl)-3-phenyl-2-(thiazol-4-ylmethylamino)propan-1-one,
(2S)-1-(4-(5-Methyl-4H-1,2,4-triazol-3-yl)-6-(pyridin-4-yl)indolin-1-yl)-3-phenyl-2-(thiazol-4-ylmethylamino) propan-1-one,
(S)—N-(Cyclopropylmethyl)-3-(3-phenyl-2-(thiazol-4-ylmethylamino)propanamido)-5-(pyridin-4-yl)benzamide,
(S)—N-(2-Amino-2-oxoethyl)-1-(3-phenyl-2-(thiazol-4-ylmethylamino)propanoyl)-6-(pyridin-4-yl)indoline-4-carboxamide,
Methyl 6-(2-methylpyridine-4-yl)-1-((S)-3-phenyl-2-(pyridin-2-ylmethylamino)propanoyl)indoline-4-carboxylate,
(S)-tert-Butyl 3-(3-phenyl-2-(1-(pyridin-2-yl)cyclopropylamino)propanamido)-5-(pyridin-4-yl)benzoate,
(S)—N-(2-(dimethylamino)ethyl)-3-(3-phenyl-2-(thiazol-4-ylmethylamino)propanamido)-5-(pyridin-4-yl) benzamide bis trifluoroacetate salt,
(2S)—N-(2-(2-(Dimethylamino)ethoxy)-5-(2-methylpyridin-4-yl)phenyl)-3-phenyl-2(thiazol-4-ylmethylamino)propanamide trifluoroacetate,
(2S)—N-(3-(2-(Dimethylamino)ethoxy)-5-(2-methylpyridin-4-yl)phenyl)-3-phenyl-2-(pyridin-2-ylmethylamino)propanamide,
(S)-Methyl 2-(1-(3-phenyl-2-(thiazol-4-ylmethylamino) propanoyl)-6-(pyridin-4-yl)indoline-4-carboxamido) acetate,
tert-Butyl 2-(3-((S)-2-(benzyloxycarbonyl)-3-phenylpropanamido)-5-(2-methylpyridin-4-yl)pyridin-2-yloxy) acetate,
tert-Butyl 2-(5-(2-methylpyridin-4-yl)-3-((S)-3-phenyl-2-(thiazol-4-ylmethylamino)propanamido)pyridin-2-yloxy)acetate,
Methyl 1-((16S)-3-(2-methylpyridin-4-yl)-5-((S)-3-phenyl-2-(thiazol-4-ylmethylamino)propanamido)benzyl) azetidine-3-carboxylate,
Methyl 1-((16S)-3-(2-methylpyridin-4-yl)-5-((S)-3-phenyl-2-(pyridin-2-ylmethylamino)propanamido)benzyl) azetidine-3-carboxylate,
(S)—N-(2-(2-Oxoimidazolidin-1-yl)ethyl)-1-(3-phenyl-2-(thiazol-4-ylmethylamino)propanoyl)-6-(pyridin-4-yl)indoline-4-carboxamide,
(S)-tert-Butyl 1-oxo-3-phenyl-1-(6-(pyrimidin-5-yl)indolin-1-yl)propan-2-ylcarbamate,
(S)-3-Phenyl-1-(6-(pyrimidin-5-yl)indolin-1-yl)-2-(thiazol-4-ylmethylamino)propan-1-one,
(S)-1-[6-(4-Fluoro-phenyl)-2,3-dihydro-indol-1-yl]-3-phenyl-2-[(thiazol-4-ylmethyl)-amino]-propan-1-one Trifluoroacetate,
(S)-2-methyl-2-(3-(3-phenyl-2-(thiazol-4-ylmethylamino)propanamido)-5-(pyridin-4-yl)phenyl)propanoic acid,
Ethyl 2-((S)-1-(1-ethyl-3-(pyridin-4-yl)-1H-pyrazol-5-ylamino)-1-oxo-3-phenylpropan-2-ylamino)acetate dihydrochloride,
(S)-2-(1-(1-Ethyl-3-(pyridin-4-yl)-1H-pyrazol-5-ylamino)-1-oxo-3-phenylpropan-2-ylamino)acetic acid,
(S)—N-(1-Ethyl-3-(pyridin-4-yl)-1H-pyrazol-5-yl)-2-(ethylcarbamoylmethylamino)-3-phenylpropanamide,
Ethyl 2-((S)-1-(1-ethyl-3-(pyridin-4-yl)-1H-pyrazol-5-ylamino)-3-(1H-indol-3-yl)-1-oxopropan-2-ylamino) acetate dihydrochloride,
Ethyl 2-((S)-1-(1-ethyl-3-(pyridin-4-yl)-1H-pyrazol-5-ylamino)-3-(3,4-difluorophenyl)-1-oxopropan-2-ylamino)acetate dihydrochloride,
(S)-2-(1-(1-Ethyl-3-(pyridin-4-yl)-1H-pyrazol-5-ylamino)-3-(3,4-difluorophenyl)-1-oxopropan-2-ylamino)acetic acid,
Ethyl 2-((S)-1-(3-(2-chloropyridin-4-yl)-1-ethyl-1H-pyrazol-5-ylamino)-1-oxo-3-phenylpropan-2-ylamino) acetate dihydrochloride,
(S)-2-(1-(3-(2-Chloropyridin-4-yl)-1-ethyl-1H-pyrazol-5-ylamino)-1-oxo-3-phenylpropan-2-ylamino)acetic acid,
Ethyl 2-((S)-3-(4-fluorophenyl)-1-(1-methyl-3-(pyridin-4-yl)-1H-pyrazol-5-ylamino)-1-oxopropan-2-ylamino) acetate dihydrochloride,
2-((S)-3-(4-Fluorophenyl)-1-(1-methyl-3-(pyridin-4-yl)-1H-pyrazol-5-ylamino)-1-oxopropan-2-ylamino)acetic acid,
(S)-2-(Ethylcarbamoylmethylamino)-3-(4-fluorophenyl)-N-(1-methyl-3-(pyridin-4-yl)-1H-pyrazol-5-yl)propanamide,
Ethyl 2-((S)-3-(3,4-difluorophenyl)-1-(1-methyl-3-(pyridin-4-yl)-1H-pyrazol-5-ylamino)-1-oxopropan-2-ylamino)acetate dihydrochloride,
(S)-2-(3-(3,4-difluorophenyl)-1-(1-ethyl-3-(pyridin-4-yl)-1H-pyrazol-5-ylamino)-1-oxopropan-2-ylamino) acetic acid,
(S)-2-(Carbamoylmethylamino)-N-(1-methyl-3-(pyridin-4-yl)-1H-pyrazol-5-ylamino)-3-phenylpropanamide,
(S)-2-(Ethylcarbamoylmethylamino)-N-(1-methyl-3-(pyridin-4-yl)-1H-pyrazol-5-yl)-3-phenylpropanamide,
(S)—N-(1-Methyl-3-(pyridin-4-yl)-1H-pyrazol-5-yl)-2-(methylcarbamoylmethylamino)-3-phenylpropanamide,
(S)—N-(1-Methyl-3-(pyridin-4-yl)-1H-pyrazol-5-yl)-2-(dimethylcarbamoylmethylamino)-3-phenylpropanamide,
(S)—N-(1-Methyl-3-(pyridin-4-yl)-1H-pyrazol-5-yl)-3-phenyl-2-(propylcarbamoylmethylamino)propanamide,
(S)-2-(Isopropylcarbamoylmethylamino)-N-(1-methyl-3-(pyridin-4-yl)-1H-pyrazol-5-yl)-3-phenylpropanamide,
(S)-2-(Cyclopropylcarbamoylmethylamino)-N-(1-methyl-3-(pyridin-4-yl)-1H-pyrazol-5-yl)-3-phenylpropanamide,
(S)-2-(Ethylcarbamoylmethylamino)-N-(1-methyl-3-(pyridin-4-yl)-1H-pyrazol-5-yl)-3-phenylpropanamide dihydrochloride, Ethyl 2-((S)-1-(3-(2-methoxypyridin-4-yl)-1-methyl-1H-pyrazol-5-ylamino)-1-oxo-3-phenylpropan-2-ylamino)acetate dihydrochloride, (S)-2-(1-(3-(2-Methoxypyridin-4-yl)-1-methyl-1H-pyrazol-5-ylamino)-1-oxo-3-phenylpropan-2-ylamino)acetic acid, (S)-2-(Carbamoylmethylamino)-N-(3-(2-methoxypyridin-4-yl)-1-methyl-1H-pyrazol-5-yl)-3-phenylpropanamide, (S)-2-(Ethylcarbamoylmethylamino)-N-(3-(2-methoxypyridin-4-yl)-1-methyl-1H-pyrazol-5-yl)-3-phenylpropanamide, (S)-2-(Diethylcarbamoylmethylamino)-N-(3-(2-methoxypyridin-4-yl)-1-methyl-1H-pyrazol-5-yl)-3-phenylpropanamide, (S)—N-(1-Methyl-3-(2-methoxypyridin-4-yl)-1H-pyrazol-5-yl)-3-phenyl-2-(pyrrolidin-1-ylcarbonylmethylamino)propanamide, Ethyl 2-((S)-1-oxo-3-phenyl-1-(3-(pyridin-4-yl)phenylamino)propan-2-ylamino)acetate dihydrochloride, 2-((S)-3-(3,4-Difluorophenyl)-1-oxo-1-(3-(pyridin-4-yl)phenylamino)propan-2-ylamino)acetic acid, Ethyl 2-((S)-1-(2-fluoro-5-(pyridin-4-yl)phenylamino)-1-oxo-3-phenylpropan-2-ylamino)acetate dihydrochloride and 2-((S)-1-(2-fluoro-5-(pyridin-4-yl)phenylamino)-1-oxo-3-phenylpropan-2-ylamino)acetic acid.

8. A pharmaceutical composition comprising a pharmaceutically acceptable carrier or excipient and the compound as set forth in any of claims 1, 2, and 3.

9. A method for treating a disease or condition, or symptom thereof, wherein the disease or condition is selected from the group consisting of type 2 diabetes, diabetic ketoacidosis, hyperglycemia, diabetic neuropathy, obesity, metabolic syndrome, inflammation, asthma, psoriasis, arthritis, rheumatoid arthritis, inflammatory bowel disease, cancer and neurologic disorder, the method comprising administering to a subject having the disease or condition a therapeutically effective amount of a compound according to any of claims 1, 2 and 3.

* * * * *